United States Patent
Braun et al.

(10) Patent No.: US 9,090,600 B2
(45) Date of Patent: Jul. 28, 2015

(54) FUNGICIDAL 4-SUBSTITUTED-3-{PHENYL[(HETEROCYCLYLMETHOXY)IMINO]METHYL}-1,2,4-OXADIZOL-5(4H)-ONE DERIVATIVES

(75) Inventors: Christoph Braun, Dusseldorf (DE); Haruko Sawada, Langenfeld (DE); Helene Lachaise, Lyons (FR); Stephane Brunet, Saint-Andre-de-Corcy (FR); Philippe Rinolfi, Chatillon d'Azergues (FR); Christophe Dubost, Charbonnieres-les-Bains (FR); Pierre-Yves Coqueron, Lyons (FR); Simon Maechling, Lyons (FR); Anne-Sophie Rebstock, Lyons (FR); Ulrike Wachendorff-Neumann, Neuwied (DE)

(73) Assignee: BAYER INTELLECTUAL PROPERTY GMBH (DE)

( * ) Notice: Subject to any disclaimer, the term of this patent is extended or adjusted under 35 U.S.C. 154(b) by 0 days.

(21) Appl. No.: 14/344,579

(22) PCT Filed: Sep. 10, 2012

(86) PCT No.: PCT/EP2012/067596
§ 371 (c)(1),
(2), (4) Date: Mar. 12, 2014

(87) PCT Pub. No.: WO2013/037717
PCT Pub. Date: Mar. 21, 2013

(65) Prior Publication Data
US 2014/0349848 A1 Nov. 27, 2014

Related U.S. Application Data

(60) Provisional application No. 61/545,306, filed on Oct. 10, 2011.

(30) Foreign Application Priority Data

Sep. 12, 2011 (EP) .................... 11356012

(51) Int. Cl.
| | | |
|---|---|---|
| A01N 43/836 | (2006.01) | |
| C07D 417/12 | (2006.01) | |
| C07D 417/14 | (2006.01) | |
| C07D 413/12 | (2006.01) | |
| C07D 413/14 | (2006.01) | |
| C07D 277/40 | (2006.01) | |
| C07D 271/07 | (2006.01) | |
| C07D 213/75 | (2006.01) | |
| C07D 213/73 | (2006.01) | |
| C07D 213/74 | (2006.01) | |
| C07D 277/46 | (2006.01) | |
| C07D 277/48 | (2006.01) | |
| A01N 43/82 | (2006.01) | |
| C07D 231/16 | (2006.01) | |
| C07D 231/38 | (2006.01) | |
| A01N 55/00 | (2006.01) | |
| C07F 7/10 | (2006.01) | |
| C07F 7/08 | (2006.01) | |

(52) U.S. Cl.
CPC .............. *C07D 413/12* (2013.01); *A01N 43/82* (2013.01); *A01N 55/00* (2013.01); *C07D 213/73* (2013.01); *C07D 213/74* (2013.01); *C07D 213/75* (2013.01); *C07D 231/16* (2013.01); *C07D 231/38* (2013.01); *C07D 271/07* (2013.01); *C07D 277/40* (2013.01); *C07D 277/46* (2013.01); *C07D 277/48* (2013.01); *C07D 413/14* (2013.01); *C07D 417/12* (2013.01); *C07D 417/14* (2013.01); *C07F 7/0812* (2013.01); *C07F 7/10* (2013.01)

(58) Field of Classification Search
CPC .... A01N 43/82; C07D 417/12; C07D 417/14; C07D 413/12; C07D 413/14; C07D 277/40; C07D 271/07; C07D 213/75; C07D 213/73
See application file for complete search history.

(56) References Cited

U.S. PATENT DOCUMENTS

| | | | | |
|---|---|---|---|---|
| 6,340,697 | B1 | 1/2002 | Kobori et al. | 514/364 |
| 2011/0034445 | A1 | 2/2011 | Beier et al. | 514/224.2 |

FOREIGN PATENT DOCUMENTS

| | | |
|---|---|---|
| EP | 1038874 A1 | 9/2000 |
| EP | 1184382 A1 | 3/2002 |
| WO | WO 2009/130193 | 10/2009 |
| WO | WO 2009130193 A1 * | 10/2009 |
| WO | WO 2011/080254 | 7/2011 |

OTHER PUBLICATIONS

International Search Report issued Nov. 7, 2012 in corresponding International Application No. PCT/EP2012/067596.

* cited by examiner

Primary Examiner — Matthew Coughlin
(74) Attorney, Agent, or Firm — Ostrolenk Faber LLP

(57) ABSTRACT

The present invention provides fungicidal 4-substituted-3-{phenyl[(heterocyclylmethoxy)imino]methyl}-1,2,4-oxadiazol-5(4H)-one derivatives of formula (I)

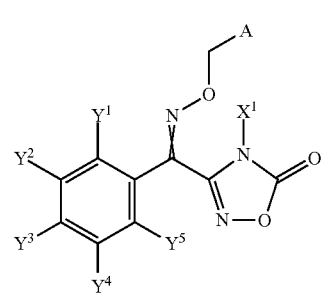

wherein A represents a pyridyl or thiazole group and X1, Y1 to Y5 represent independently different substituents.

21 Claims, No Drawings

FUNGICIDAL 4-SUBSTITUTED-3-{PHENYL [(HETEROCYCLYLMETHOXY)IMINO] METHYL}-1,2,4-OXADIZOL-5(4H)-ONE DERIVATIVES

CROSS-REFERENCE TO RELATED APPLICATION(S)

The present application is a 35 U.S.C. §371 national phase conversion of PCT/EP2012/067596 filed on Sep. 10, 2012, which claims priority of European Application No. 11356012.2 filed on Sep. 12, 2011 and U.S. Provisional Application No. 61/545,306 filed on Oct. 10, 2011. Applicants claim priority to each of the foregoing patent applications. The PCT International Application was published in the English language.

The present invention relates to 4-substituted-3-{phenyl [(heterocyclylmethoxy)imino]methyl}-1,2,4-oxadiazol-5 (4H)-one derivatives, their process of preparation, their use as fungicide active agents, particularly in the form of fungicide compositions, and methods for the control of phytopathogenic fungi, notably of plants, using these compounds or compositions.

In European patent application no 1184382, there are disclosed certain heterocyclyloxime derivatives of the following chemical structure:

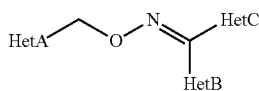

that are excluded from the scope of the present invention.

In world patent application WO2009/130193, there are disclosed certain hydroximoyl-heterocycles derivatives of the following chemical structure:

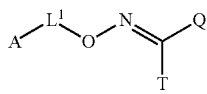

with

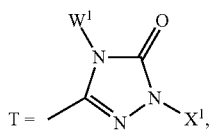

Q is a phenyl ring, L1 a methylene linker and A an heterocycle.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides 4-substituted-3-{phenyl[(heterocyclylmethoxy)imino]methyl}-1,2,4-oxadiazol-5(4H)-one derivatives of formula (I)

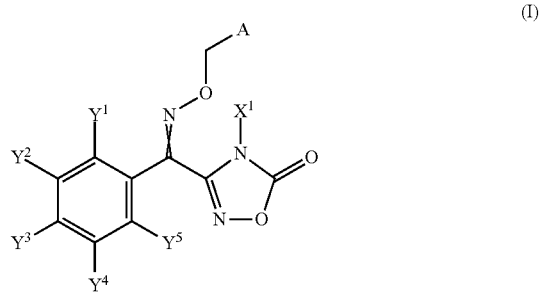

(I)

wherein $X^1$ represents a hydrogen atom, a formyl group, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_2$-$C_8$-alkynyl, substituted or non-substituted $C_1$-$C_8$-alkylcarbonyl;

A is selected in the list consisting of $A^1$ and $A^2$:

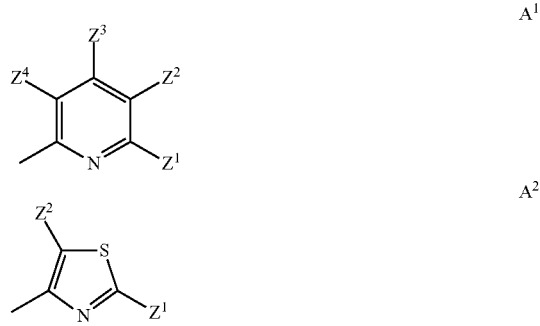

wherein $Z^1$ represents a hydrogen atom, a halogen atom, a nitro group, an amino group, an hydroxyamino group, a cyano group, a carboxylic acid group, substituted or non-substituted $C_1$-$C_8$-alkoxyamino group, substituted or non-substituted $C_1$-$C_8$-alkylaminosubstituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula QC(=U)NR$^a$ wherein Q represents a hydrogen atom, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_3$-$C_8$-cycloalkenyl, substituted or non-substituted $C_2$-$C_8$-alkynyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylamino, substituted or non-substituted $C_1$-$C_8$-alkylsulfenyl, substituted or non-substituted $C_2$-$C_8$-alkenylsulfenyl, substituted or non-substituted $C_2$-$C_8$-alkynylsulfenyl, substituted or non-substituted arylsulfenyl, substituted or non-substituted aryl, substituted or non-substituted heterocyclyl, substituted or non-substituted $C_5$-$C_{12}$-fused bicycloalkyl, substituted or non-substituted $C_5$-$C_{12}$-fused bicycloalkenyl, substituted or non-substituted $C_5$-$C_{12}$-benzofused carbocyclyl, substituted or non-substituted $C_5$-$C_{12}$-benzofused heterocyclyl, substituted or non-substituted cycloalkoxy; substituted or non-substituted cycloalkenyloxy, substituted or non-substituted aryloxy; substituted or non-substituted heterocyclyloxy, substituted or non-substituted $C_5$-$C_{12}$-fused bicycloalkoxy, substituted or non-substituted $C_5$-$C_{12}$-fused bicycloalkenyloxy, substituted or non-substituted $C_5$-$C_{12}$-benzofused carbocyclyloxy, substituted or non-substituted $C_5$-$C_{12}$-benzofused heterocyclyloxy;

U represents a oxygen atom or a sulfur atom;

$R^a$ represents a hydrogen atom, a hydroxy group, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_3$-$C_{10}$-cycloalkenyl, substituted or non-substituted $C_5$-$C_{12}$-fused bicycloalkyl, substituted or non-substituted $C_5$-$C_{12}$-fused bicycloalkenyl, substituted or non-substituted aryl, or substituted or non-substituted heterocyclyl, substituted or non-substituted $C_1$-$C_8$-alkylcarbonyl, substituted or non-substituted aryloxycarbonyl, substituted or non-substituted $C_1$-$C_8$-alkoxycarbonyl;

$Z^2$, $Z^3$ and $Z^4$ independently represent a hydrogen atom, a halogen atom, substituted or non-substituted $C_1$-$C_8$-alkyl, substituted or non-substituted $C_3$-$C_8$-cycloalkyl, a $C_2$-$C_8$-alkenyl, substituted or non-substituted $C_2$-$C_8$-alkynyl, substituted or non-substituted $C_1$-$C_8$-alkoxy;

$Y^1$ to $Y^5$ independently represent a hydrogen atom, a halogen atom, a nitro group, a a cyano group, a substituted or non-substituted carbaldehyde O—($C_1$-$C_8$-alkyl)oxime, a pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted phenoxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

as well as salts, N-oxides, metallic complexes and metalloidic complexes thereof or (E) and (Z) isomers and mixtures thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

Notably, the stereostructure of the oxime moiety present in the 4-substituted-3-{phenyl[(heterocyclylmethoxy)imino]methyl}-1,2,4-oxadiazol-5(4H)-one derivative of formula (I) includes (E) or (Z) isomer, and these stereoisomers form part of the present invention.

According to the invention, the following generic terms are generally used with the following meanings:

halogen means fluorine, chlorine, bromine or iodine;

heteroatom can be nitrogen, oxygen or sulfur;

unless indicated otherwise, a group or a substituent that is substituted according to the invention can be substituted by one or more of the following groups or atoms: a halogen atom, a nitro group, a hydroxy group, a cyano group, an amino group, a sulfenyl group, a pentafluoro-$\lambda^6$-sulfenyl group, a formyl group, a carbaldehyde O—($C_1$-$C_8$-alkyl)oxime, a formyloxy group, a formylamino group, a formylamino group, a (hydroxyimino)-$C_1$-$C_6$-alkyl group, a $C_1$-$C_8$-alkyl, a tri($C_1$-$C_8$-alkyl)silyl, $C_3$-$C_8$-cycloalkyl, $C_3$-$C_8$-cycloalkenyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfenyl, a $C_1$-$C_8$-halogenoalkylsulfenyl having 1 to 5 halogen atoms, a $C_2$-$C_8$-halogenoalkenyloxy having 1 to 5 halogen atoms, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, $C_1$-$C_8$-alkoxycarbonylamino, $C_1$-$C_8$-halogenoalkoxycarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, benzyloxy, benzylsulfenyl, benzylamino, phenoxy, phenylsulfenyl, or phenylamino, an aryl group, an heterocyclyl group; or a group or a substituent that is substituted according to the invention can be substituted in a way that substituting groups form together a substituted or non-substituted, saturated or partially saturated 3-, 4-, 5-, 6-, 7-, 8-, 9-, 10-, or 11-membered cycle, which can be a carbocycle or a heterocycle comprising up to 4 heteroatoms selected from the list consisting of N, O, and S the term "aryl" means phenyl or naphthyl;

the term "heterocyclyl" means fused or non-fused, saturated or unsaturated, 4-, 5-, 6-, 7-, 8-, 9-, 10-, 11- or 12-membered ring comprising up to 4 heteroatoms selected in the list consisting of N, O, S.

Preferred compounds of formula (I) according to the invention are those wherein $X^1$ represents a hydrogen atom, substituted or non-substituted $C_1$-$C_8$-alkyl, substituted or non-substituted $C_3$-$C_8$-cycloalkyl or a substituted or non-substituted $C_2$-$C_8$-alkenyl.

More preferred compounds of formula (I) according to the invention are those wherein $X^1$ represents a hydrogen atom, a methyl group, an ethyl group, a n-propyl group, an isopropyl group or a cyclopropyl group.

Even more preferred compounds of formula (I) according to the invention are those wherein $X^1$ represents a hydrogen atom or a methyl group.

Other preferred compounds of formula (I) according to the invention are those wherein A represents $A^1$.

Other preferred compounds of formula (I) according to the invention are those wherein $Z^1$ represents a hydrogen atom, a halogen atom, a nitro group, an amino group, an hydroxyamino group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula $QC(=U)NR^a$.

More preferred compounds of formula (I) according to the invention are those wherein $Z^1$ represents a hydrogen atom, a halogen atom, a nitro group, an amino group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, or a group of formula $QC(=U)NR^a$.

Even more preferred compounds of formula (I) according to the invention are those wherein $Z^1$ represents an amino group, or a group of formula $QC(=U)NR^a$.

When $Z^1$ represents a group of formula $QC(=U)NR^a$, other preferred compounds of formula (I) according to the invention are those wherein U represents an oxygen atom.

When $Z^1$ represents a group of formula $QC(=U)NR^a$, other preferred compounds of formula (I) according to the invention are those wherein $R^a$ represents a hydrogen atom, a hydroxy group, substituted or non-substituted $C_1$-$C_8$-alkyl, substituted or non-substituted $C_3$-$C_8$-cycloalkyl, substituted or non-substituted $C_1$-$C_8$-alkoxy.

When $Z^1$ represents a group of formula $QC(=U)NR^a$, more preferred compounds of formula (I) according to the invention are those wherein $R^a$ represents a hydrogen atom.

When $Z^1$ represents a group of formula $QC(=U)NR^a$, other preferred compounds of formula (I) according to the invention are those wherein Q represents a substituted or non-substituted $C_1$-$C_8$-alkyl, substituted or non-substituted $C_3$-$C_8$-cycloalkyl, substituted or non-substituted $C_2$-$C_8$-alkynyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylsulfenyl, substituted or non-substituted aryl, substituted or non-substituted heterocyclyl, substituted or non-substituted $C_3$-$C_8$-cycloalkoxy.

When $Z^1$ represents a group of formula $QC(=U)NR^a$, more preferred compounds of formula (I) according to the invention are those wherein Q represents a substituted or non-substituted $C_4$-$C_8$-alkyl, substituted or non-substituted $C_3$-$C_8$-cycloalkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl.

When $Z^1$ represents a group of formula $QC(=U)NR^a$, even more preferred compounds of formula (I) according to the invention are those wherein Q represents a substituted or non-substituted $C_4$-$C_8$-alkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted aryl, substituted or non-substituted heterocyclyl.

When $Z^1$ represents a group of formula $QC(=U)NR^a$, and when Q represents a substituted or non-substituted $C_4$-$C_8$-alkyl, substituted or non-substituted $C_3$-$C_8$-cycloalkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl, other preferred compounds of formula (I) according to the invention are those wherein substituents are chosen in the list of a halogen atom, a cyano group, a (hydroxyimino)-$C_1$-$C_6$-alkyl group, a $C_1$-$C_8$-alkyl, $C_3$-$C_8$-cycloalkyl, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkoxy, a $C_1$-$C_8$-alkylsulfenyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, benzyloxy, benzylsulfenyl, phenoxy, phenylsulfenyl, an aryl group or an heterocyclyl group, or wherein substituents form together a substituted or non-substituted, saturated or partially saturated 3-, 4-, 5-, 6-, 7-, 8-, 9-, 10-, or 11-membered cycle, which can be a carbocycle or a heterocycle comprising up to 4 heteroatoms selected from the list consisting of N, O, and S.

When $Z^1$ represents a group of formula $QC(=U)NR^a$, and when Q represents a substituted or non-substituted $C_4$-$C_8$-alkyl, substituted or non-substituted $C_3$-$C_8$-cycloalkyl, substituted or non-substituted $C_4$-$C_8$-alkynyl, substituted or non-substituted $C_4$-$C_8$-alkoxy, substituted or non-substituted $C_4$-$C_8$-alkenyloxy, substituted or non-substituted $C_4$-$C_8$-alkynyloxy, substituted or non-substituted $C_3$-$C_8$-alkylsulfenyl, substituted or non-substituted aryl, substituted or non-substituted heterocyclyl, more preferred compounds of formula (I) according to the invention are those wherein substituents are chosen in the list of a halogen atom, a cyano group, a (hydroxyimino)-$C_1$-$C_6$-alkyl group, a $C_1$-$C_8$-alkyl, $C_3$-$C_8$-cycloalkyl, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkoxy, a $C_1$-$C_8$-alkylsulfenyl, (benzyloxyimino)-$C_1$-$C_6$-alkyl, $C_1$-$C_8$-alkoxyalkyl, benzyloxy, phenoxy, an aryl group or an heterocyclyl group or wherein substituents form together a saturated or partially saturated 3-, 4-, 5-, 6-membered cycle, which can be a carbocycle or a heterocycle comprising up to 4 heteroatoms selected from the list consisting of N, O, and S.

Other preferred compounds of formula (I) according to the invention are those wherein $Z^2$, $Z^3$ and $Z^4$ independently represent a hydrogen atom, a halogen atom, substituted or non-substituted $C_1$-$C_8$-alkyl. More preferred compounds of formula (I) according to the invention are those wherein $Z^2$, $Z^3$ and $Z^4$ independently represent a hydrogen atom.

Other preferred compounds of formula (I) according to the invention are those wherein $Y^1$ to $Y^5$ independently represent a hydrogen atom, a halogen atom, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-alkoxy.

More preferred compounds of formula (I) according to the invention are those wherein $Y^1$ to $Y^5$ independently represent a hydrogen atom, a halogen atom, methyl, ethyl, isopropyl, isobutyl, tertbutyl, trifluoromethyl, difluoromethyl, allyl, ethynyl, propargyl, cyclopropyl, methoxy or trifluoromethoxy. Even more preferred compounds of formula (I) according to the invention are those wherein $Y^1$ to $Y^5$ independently represent a hydrogen atom or fluorine atom.

The above mentioned preferences with regard to the substituents of the compounds of formula (I) according to the invention can be combined in various manners. These combinations of preferred features thus provide sub-classes of compounds according to the invention. Examples of such sub-classes of preferred compounds according to the invention can combine:

preferred features of A with preferred features of one or more of $X^1$, $Y^1$ to $Y^5$ and $Z^1$ to $Z^4$;
preferred features of $X^1$ with preferred features of one or more of A, $Y^1$ to $Y^5$ and $Z^1$ to $Z^4$;
preferred features of $Y^1$ with preferred features of one or more of A, $X^1$, $Y^2$ to $Y^5$ and $Z^1$ to $Z^4$;
preferred features of $Y^2$ with preferred features of one or more of A, $X^1$, $Y^1$, $Y^3$ to $Y^5$ and $Z^1$ to $Z^4$;
preferred features of $Y^3$ with preferred features of one or more of A, $X^1$, $Y^1$, $Y^2$, $Y^4$, $Y^5$ and $Z^1$ to $Z^4$;
preferred features of $Y^4$ with preferred features of one or more of A, $X^1$, $Y^1$ to $Y^3$, $Y^5$ and $Z^1$ to $Z^4$;
preferred features of $Y^5$ with preferred features of one or more of A, $X^1$, $Y^1$ to $Y^4$ and $Z^1$ to $Z^4$;
preferred features of $Z^1$ with preferred features of one or more of $X^1$, $Y^1$ to $Y^5$, A and $Z^2$ to $Z^4$;
preferred features of $Z^2$ with preferred features of one or more of $X^1$, $Y^1$ to $Y^5$, A, $Z^1$ and $Z^3$ to $Z^4$;
preferred features of $Z^3$ with preferred features of one or more of $X^1$, $Y^1$ to $Y^5$, A, $Z^4$ and $Z^1$ to $Z^2$;
preferred features of $Z^4$ with preferred features of one or more of $X^1$, $Y^1$ to $Y^5$, A and $Z^1$ to $Z^3$;

In these combinations of preferred features of the substituents of the compounds according to the invention, the said preferred features can also be selected among the more preferred features of each of A, $X^1$, $Y^1$ to $Y^5$ and $Z^1$ so as to form most preferred subclasses of compounds according to the invention.

The present invention also relates to a process for the preparation of compounds of formula (I). Thus, according to a further aspect of the present invention, there is provided a process P1 for the preparation of compounds of formula (I) from compounds of formula (II), by a reaction of nucleophilic substitution on compounds of formula (III) to yield to a compound of formula (IV), according to known methods, optionally in the presence of a base, according to known methods; followed by the addition of hydroxylamine or an hydroxylamine salt on compounds of formula (IV) to yield to a compound of formula (V), optionally in the presence of a base, optionally in the presence of an acid, according to known methods; followed by a reaction of cyclization of compounds of formula (V) to yield to a compound of formula (Ia), with a phosgene equivalent, optionally in the presence of a base, according to known methods; followed by a reaction of alkylation of compounds of formula (Ia) to yield to a compound of formula (I), with an alkylating agent of formula $X^1$-LGa, optionally in the presence of a base, according to known methods.

In such a case there is provided a process P1 according to the invention and such a process P1 can be illustrated by the following reaction scheme:

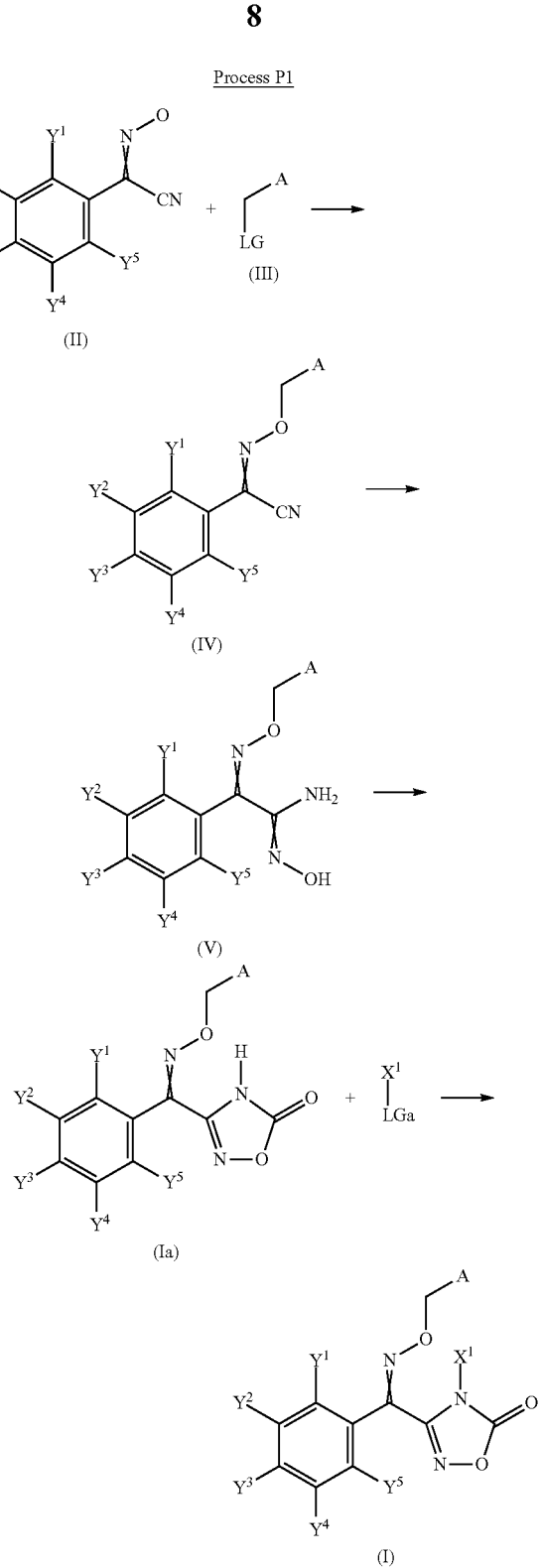

wherein $Y^1$, $Y^2$, $Y^3$, $Y^4$, $Y^5$, A and $X^1$ are as herein-defined and LG and LGa independently represent a leaving group. Suitable leaving groups can be selected in the list consisting of a halogen atom or other customary nucleofugal groups such as triflate, mesylate, or tosylate.

Suitable acids for the transformation of compounds of formula (IV) into compounds of formula (V) can be chosen as being a mineral acid such as hydrogen chloride and sulfuric acid, and an organic acid such as formic acid and acetic acid.

Suitable phosgene equivalent for the conversion of compounds of formula (V) into a compound of formula (I) can be chosen as being phosgene, diphosgene, triphosgene, carbonyl di-imidazole, a chlorformate derivative, such as ethyl chloroformate and 4-nitrophenoxy-chloroformate.

Compounds of formula (II) and (III) are commercially available or are easily accessible to the skilled worker in the art. Examples of preparation can be found in world patent application WO2009/130193. Compounds of formula $X^1$-LGa are commercially available.

According to the invention, there is provided a further process P2 for the preparation of compounds of formula (Ic) from compounds of formula (Ib).

For the compounds of formula (Ib) according to the invention if $Z^1$ represents —NHR$^a$, process P1 according to the invention can be completed by a further step comprising the additional modification of this group, notably by a reaction of acylation, alkoxycarbonylation, alkylaminocarbonylation, (thio)acylation, alkoxy(thio)carbonylation, alkylsuphenyl (thio)carbonylation or alkylamino(thio)carbonylation to yield to a compound of formula (Ic), according to known methods. In such a case there is provided a process P2 according to the invention and such a process P2 can be illustrated by the following reaction scheme:

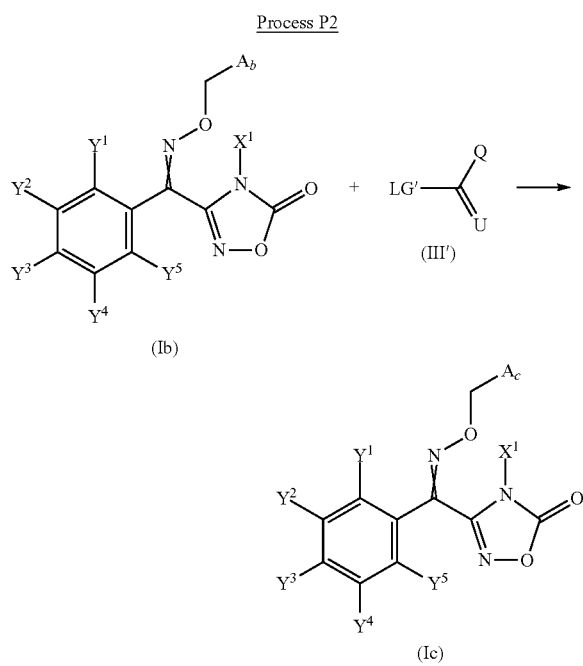

Wherein
$Y^1, Y^2, Y^3, Y^4, Y^5, X^1$, U, R$^a$ and Q are as herein-defined and A$_b$ represents A wherein $Z^1$ represents —NHR$^a$; A$_c$ represents A wherein $Z^1$ represents a group of formula QC(=U) NR$^a$ and LG' represents a leaving group.

Suitable leaving groups can be selected in the list consisting of a halogen atom or other customary nucleofugal groups such as alcoolate, hydroxide or cyanide.

According to the invention, there is provided a further process P3 for the preparation of compounds of formula (Ie) from compounds of formula (Id), by a reaction of nucleophilic substitution to yield to a compound of formula (Ie), according to known methods, optionally in the presence of a catalyst notably a transition metal catalyst, such as palladium salts or complexes for example palladium (II) chloride, palladium (II) acetate, tetrakis-(triphenylphosphine) palladium (0), bis-(triphenylphosphine) palladium dichloride (II), tris (dibenzylideneacetone) dipalladium(0), bis (dibenzylideneacetone) palladium(0) or 1,1'-bis (diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tart-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino) benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine) ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino) ferrocene, tris-(2,4-tart-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino) ferrocenyl]ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine, optionally in the presence of a base such as an inorganic or an organic base; preferably an alkaline earth metal or alkali metal hydride, hydroxide, amide, alcoholate, acetate, carbonate or hydrogen carbonate, such as sodium hydride, sodium amide, lithiium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amine, such as trimethylamine, triethylamine (TEA), tributylamine, N,N-dimethylaniline, N,N-dimethyl-benzylamine, N,N-di-isopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), according to known methods. In such a case there is provided a process P3 according to the invention and such a process P3 can be illustrated by the following reaction scheme:

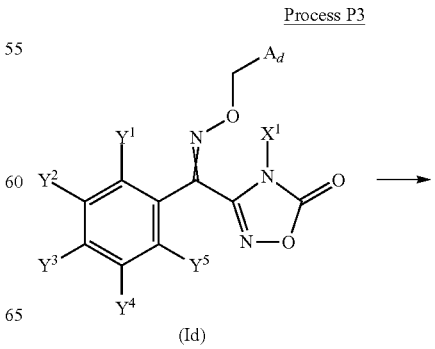

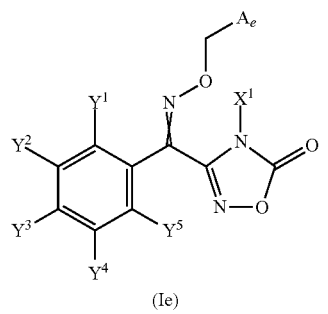

(Ie)

wherein
$Y^1, Y^2, Y^3, Y^4, Y^5$ and $X^1$ are as herein-defined and $A_d$ represents A wherein $Z^1$ represents a halogen atom; $A_e$ represents A wherein $Z^1$ represents an amino group, a cyano group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, or a group of formula QC(=O)NHR$^a$.

According to the invention, there is provided a further process P4 for the preparation of compounds of formula (Ig) from compounds of formula (If).

For the compounds of formula (If) according to the invention, $A_f$ represents A wherein $Z^1$ represents a group of formula QC(=O)NR$^a$, process P1 according to the invention can be completed by a further step comprising the additional modification of this group, notably by a reaction of thiocarbonylation in the presence of a thiocarbonylating agent such as 2,4-bis(4-methoxyphenyl)-1,3,2,4-dithiadiphosphetane 2,4-disulfide, phosphorus pentasulfide, sulfur to yield to a compound of formula (Ig), according to known methods. In such a case there is provided a process P4 according to the invention and such a process P4 can be illustrated by the following reaction scheme:

Process P4

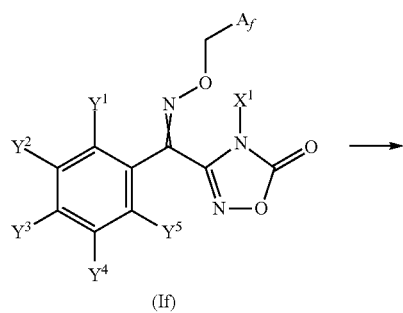

(If)

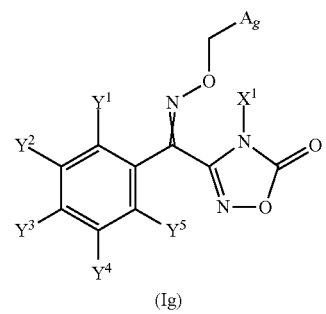

(Ig)

Wherein
$Y^1, Y^2, Y^3, Y^4, Y^5, X^1, R^a$ and Q are as herein-defined;
$A_f$ represents A wherein $Z^1$ represents a group of formula QC(=O)NR$^a$
and $A_g$ represents A wherein $Z^1$ represents a group of formula QC(=S)NR$^a$.

The present invention also relates to a process for the preparation of compounds of formula (I). Thus, according to a further aspect of the present invention, there is provided a process P5 for the preparation of compounds of formula (I) from compounds of formula (VI), by a reaction of oxidation compounds of formula (VI) in a presence of a suitable oxidizing agent to yield to a compound of compounds of formula (VII), followed by a condensation of compounds of formula (VIII), optionally under microwave irradiation, optionally in the presence of a dehydrating agent, such as molecular sieves, to yield to compounds of formula (I), according to known methods. In such a case there is provided a process P5, according to the invention and such a process P5 can be illustrated by the following reaction scheme:

Process P5

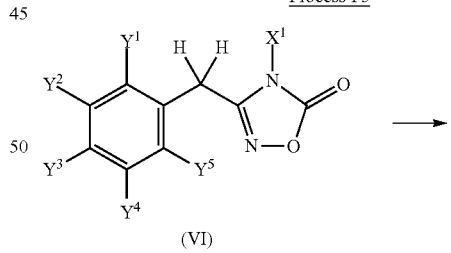

(VI)

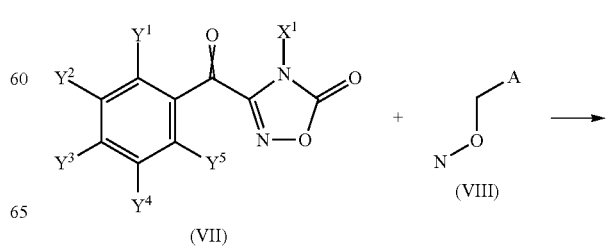

(VII)      (VIII)

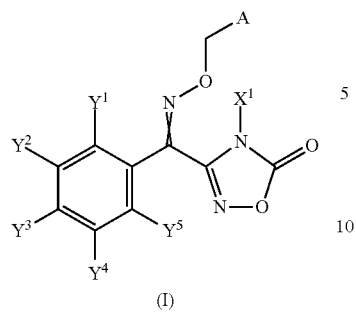

(I)

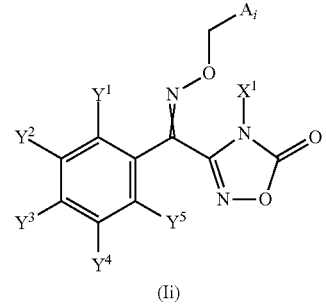

(Ii)

wherein $Y^1, Y^2, Y^3, Y^4, Y^5$, A and $X^1$ are as herein-defined.

Examples of oxidations at the methylene position between a phenyl ring and an heterocycle to yield an oxo substituent are known and can be found for example in Journal of the Chemical Society, Perkin Transactions 1: Organic and Bio-Organic Chemistry (1972-1999) (1982), (12), 2995-3006. Suitable oxidizing agents for carrying out the first step of process P5 according to the invention can be inorganic and organic peroxides such as hydrogen peroxide and benzoyl peroxide, metallic and metalloïdic oxides such as manganese (IV) oxide, chromium (VI) oxide, oxygen optionally in the presence of singlet oxygen activator, halogenating agents in an aqueous medium such as bleach.

Compounds of formula (VI) are easily accessible to the skilled worker in the art. Examples of preparation can be found in Annali di Chimica (Rome, Italy), (1963), 53(10), 1405-10

Examples of condensations of compounds of formula (VIII) with compounds of formula (VIII) can be found in world patent application WO2010/000841.

Compounds of formula (VIII) are easily accessible to the skilled worker in the art. Examples of preparation can be found in world patent application WO2010/000841.

According to the invention, there is provided a further process P6 for the preparation of compounds of formula (Ii) from compounds of formula (Ih), by a reaction of alkylation, according to known methods. In such a case there is provided a process P6 according to the invention and such a process P6 can be illustrated by the following reaction scheme:

Wherein $Y^1, Y^2, Y^3, Y^4, Y^5, X^1$ are as herein-defined $A_h$ represents A wherein $Z^1$ represents an amino, substituted or non-substituted $C_1$-$C_8$-alkylamino or a group of formula —NHC(=O)Q wherein Q is as herein defined $A_i$ represents A wherein $Z^1$ represents substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted heterocyclylamino, or a group of formula QC(=U)NR R represents optionally substituted $C_1$-$C_8$-alkyl, $C_2$-$C_8$-alkenyl, $C_2$-$C_8$-alkynyl, $C_3$-$C_{10}$-cycloalkyl, $C_3$-$C_{10}$-cycloalkenyl, $C_3$-$C_{10}$-fused bicycloalkyl, $C_5$-$C_{12}$-fused bicycloalkenyl LG" represents a leaving group.

Suitable leaving groups can be selected in the list consisting of a halogen atom or other customary nucleofugal groups such as alcoolate, hydroxide or cyanide.

According to the invention, there is provided a further process P7 for the preparation of compounds of formula (Ik) from compounds of formula (Il), by a reaction of deprotection, according to known methods. In such a case there is provided a process P7 according to the invention and such a process P7 can be illustrated by the following reaction scheme:

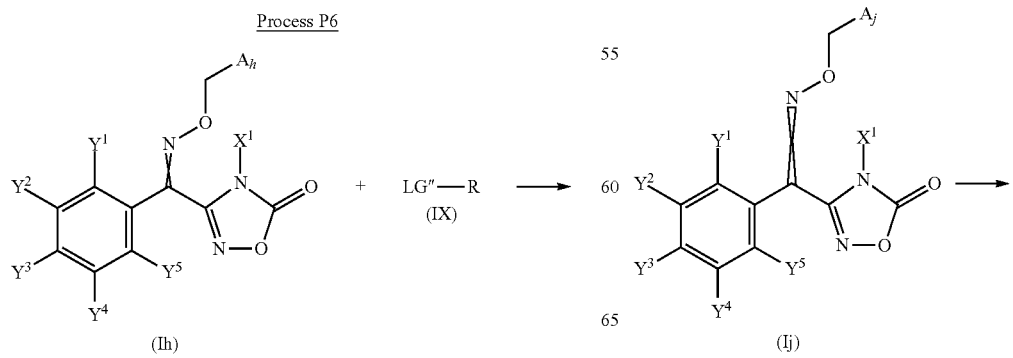

Process P6

(Ih) + LG"—R (IX) → (Ij)

Process P7

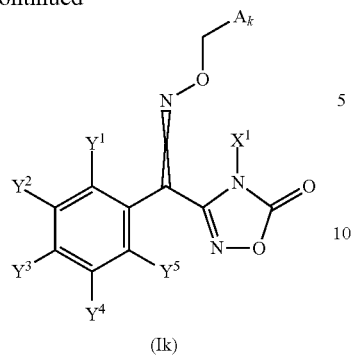

(Ik)

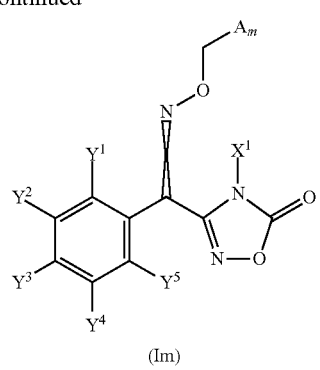

(Im)

Wherein

Y$^1$, Y$^2$, Y$^3$, Y$^4$, Y$^5$, X$^1$ are as herein-defined

A$_j$ represents A wherein Z$^1$ represents a group of formula Z$^1_a$-PG wherein Z$^1_a$ represents a substituted or non-substituted C$_1$-C$_8$-alkoxyamino, substituted or non-substituted C$_1$-C$_8$-alkylamino, a substituted or non-substituted C$_2$-C$_8$-alkenylamino, substituted or non-substituted C$_2$-C$_8$-alkynylamino, substituted or non-substituted C$_3$-C$_{10}$-cycloalkylamino, substituted or non-substituted C$_3$-C$_{10}$-cycloalkenylamino, substituted or non-substituted C$_5$-C$_{12}$-fused bicycloalkylamino, substituted or non-substituted C$_5$-C$_{12}$-fused bicycloalkenylamino, substituted or non-substituted di-C$_1$-C$_8$-alkylamino, substituted or non-substituted phenylamino, substituted or non-substituted heterocyclylamino and PG represents a protecting group such as a formyl group, C$_1$-C$_8$-alkylcarbonyl, C$_1$-C$_8$-alkoxycarbonyl, C$_1$-C$_8$-alkoxy-C$_1$-C$_2$-alkyl, tri(C$_1$-C$_8$-alkyl)silyl-C$_1$-C$_2$-alkyl, tri(C$_1$-C$_8$-alkyl)silyloxy-C$_1$-C$_2$-alkyl;

A$_k$ represents A wherein Z$^1$ represents Z$^1_a$;

Amino-protecting groups and related methods of cleavage thereof are known and can be found in T. W. Greene and P. G. M. Wuts, *Protective Group in Organic Chemistry*, 3$^{rd}$ ed., John Wiley & Sons.

According to the invention, there is provided a further process P8 for the preparation of compounds of formula (Im) from compounds of formula (Il), by a reaction of amino-reduction, in the presence of a reducing agent, such as hydrogen gas or an hydride derivative, in particular sodium cyanoborohydride, according to known methods. In such a case there is provided a process P8 according to the invention and such a process P8 can be illustrated by the following reaction scheme:

Process P8

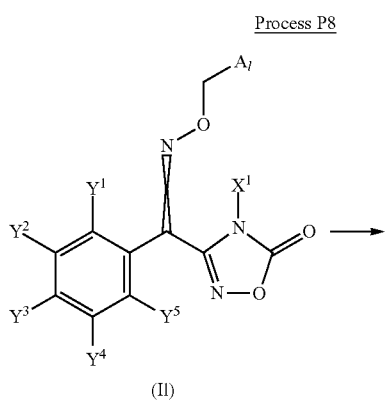

(Il)

Where

Y$^1$, Y$^2$, Y$^3$, Y$^4$, Y$^5$, X$^1$ are as herein-defined;

A$_l$ represents A wherein Z$^1$ represents an amino group, a substituted or non-substituted C$_1$-C$_8$-alkylamino;

A$_m$ represents A wherein Z$^1$ represents a substituted or non-substituted C$_1$-C$_8$-alkylamino, substituted or non-substituted di-C$_1$-C$_8$-alkylamino.

According to the invention, there is provided a further process P9 for the preparation of compounds of formula (Io) from compounds of formula (In) according to the following reaction scheme in either one or two steps.

Process P9

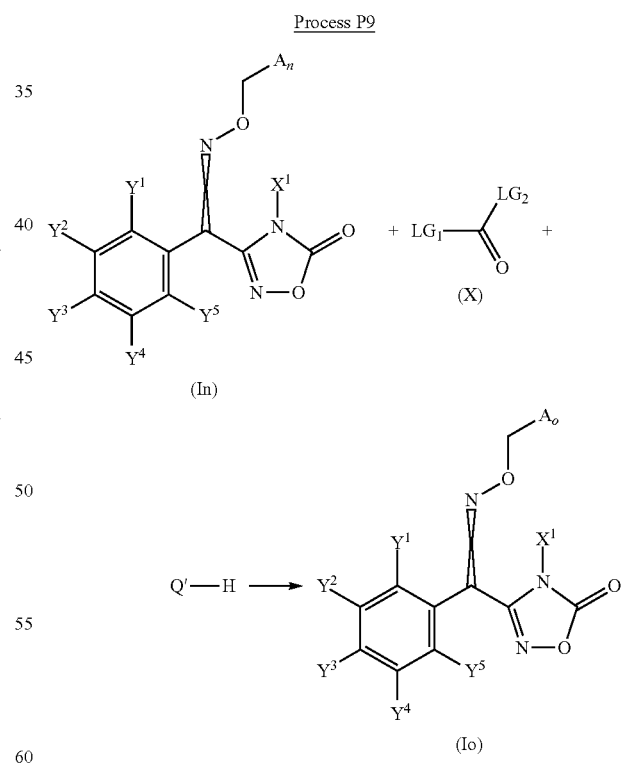

Wherein

Y$^1$, Y$^2$, Y$^3$, Y$^4$, Y$^5$, X$^1$, R$^a$ and Q are as herein-defined and A$_b$ represents A wherein Z$^1$ represents —NHR$^a$; A$_c$ represents A wherein Z$^1$ represents a group of formula QC(=U)NR$^a$ and LG' represents a leaving group.

Wherein $Y^1, Y^2, Y^3, Y^4, Y^5, X^1, R^a$ are as herein-defined;

$A_n$ represents A wherein $Z^1$ represents —$NHR^a$;

$A_o$ represents A wherein $Z^1$ represents $Q'C(=O)NR^a$ wherein Q' represents substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylsulfenyl, substituted or non-substituted $C_2$-$C_8$-alkenylsulfenyl, substituted or non-substituted $C_2$-$C_8$-alkynylsulfenyl, substituted or non-substituted arylsulfenyl, substituted or non-substituted cycloalkoxy; substituted or non-substituted cycloalkenyloxy, substituted or non-substituted aryloxy; substituted or non-substituted heterocyclyloxy, substituted or non-substituted $C_5$-$C_{12}$-fused bicycloalkoxy, substituted or non-substituted $C_5$-$C_{12}$-fused bicycloalkenyloxy, substituted or non-substituted $C_5$-$C_{12}$-benzofused carbocyclyloxy, substituted or non-substituted $C_5$-$C_{12}$-benzofused heterocyclyloxy;

$LG_1$ and $LG_2$ represent leaving groups

Suitable leaving groups can be selected in the list consisting of a halogen atom or other customary nucleofugal groups such as imidazole, halogenophenoxide or the likes.

According to the invention, processes P1 to P9 can be performed if appropriate in the presence of a solvent and if appropriate in the presence of a base.

According to the invention, processes P1 and P2 can be performed if appropriate in the presence of a catalyst. Suitable catalyst can be chosen as being 4-dimethyl-aminopyridine, 1-hydroxy-benzotriazole or dimethylformamide.

In case LG' represents a hydroxy group, the process P2 according to the present invention can be performed in the presence of condensing agent. Suitable condensing agent can be chosen as being acid halide former, such as phosgene, phosphorous tri-bro-mide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromo-tripyrrolidino-phosphonium-hexafluorophosphate.

Suitable solvents for carrying out processes P1 to P9 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulfoxides, such as dimethyl sulfoxide or sulfones, such as sulfolane.

Suitable bases for carrying out processes P1 to P9 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate and also tertiary amines, such as trimethylamine, triethylamine, diisopropylethylamine, tributylamine. N,N-dimethylaniline, pyridine, N-methylpiperidine. N,N-dimethylaminopyridine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

If carrying out processes P1 to P9, according to the invention, the reaction temperature can independently be varied within a relatively wide range. Generally, process P1 according to the invention is carried out at temperatures between −20° C. and 160° C.

Processes P1 to P9 according to the invention are generally independently carried out under atmospheric pressure. However, it is also possible to operate under elevated or reduced pressure.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that can still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesised.

The compounds of formula (IV) can be advantageously prepared according to the method described in WO2011/080254, hereby incorporated by reference.

In a further aspect, if A is as herein-described, the present invention relates to compounds of formula (V) useful as intermediate compounds or materials for the process of preparation according to the invention.

The present invention thus provides compounds of formula (V) wherein $Y^1, Y^2, Y^3, Y^4, Y^5$ and A are as herein-defined.

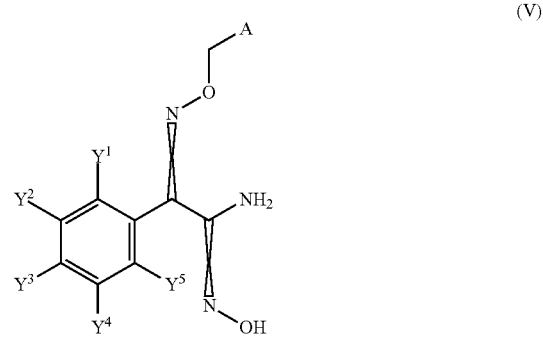

(V)

In a further aspect, if $X^1$ represents substituted or non-substituted $C_1$-$C_8$-alkyl, the present invention relates to compounds of formula (VII) useful as intermediate compounds or materials for the process of preparation according to the invention.

The present invention thus provides compounds of formula (VII) wherein $Y^1, Y^2, Y^3, Y^4, Y^5$ are as herein-defined and $X^1$ represents substituted or non-substituted $C_1$-$C_8$-alkyl.

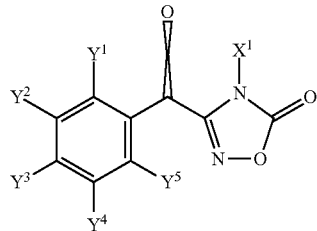

(VII)

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic organic or inorganic compound with which the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of polyoxyethylated alcohols or phenols, fatty acid esters of polyols and derivatives of the above compounds containing sulfate, sulfonate and phosphate functions. The presence of at least one surfactant is generally essential if the active compound and/or the inert support are water-insoluble and if the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention can contain from 0.05 to 99% by weight of active compound, preferably 10 to 70% by weight.

Compositions according to the invention can be used in various forms and formulations such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity. The mixtures with other fungicide compounds are particularly advantageous. The composition according to the invention comprising a mixture of a compound of formula (I) with a bactericide compound can also be particularly advantageous.

The formulations can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners, biologicals and/or semiochemicals.

The present invention further relates to the use of compounds of the formula (I) as herein defined for the control of phytopathogenic fungi.

The present invention further relates to the use of compounds of the formula (I) as herein defined for the treatment of transgenic plants.

The present invention further relates to the use of compounds of the formula (I) as herein defined for the treatment of seed and of seed of transgenic plants.

The present invention further relates to a process for producing compositions for controlling phytopathogenic harmful fungi, characterized in that derivatives of the formula (I) as herein defined are mixed with extenders and/or surfactants.

According to another object of the present invention, there is provided a method for controlling the phytopathogenic fungi of plants, crops or seeds, characterized in that an agronomically effective and substantially non-phytotoxic quantity of a pesticide composition according to the invention is applied as seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumice. Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to grow.

The expression "are applied to the plants to be treated" is understood to mean, for the purposes of the present invention, that the pesticide composition which is the subject of the invention can be applied by means of various methods of treatment such as:
- spraying onto the aerial parts of the said plants a liquid comprising one of the said compositions,
- dusting, the incorporation into the soil of granules or powders, spraying, around the said plants and in the case of trees injection or daubing,
- coating or film-coating the seeds of the said plants with the aid of a plant-protection mixture comprising one of the said compositions.

The method according to the invention can either be a curing, preventing or eradicating method. In this method, a composition used can be prepared beforehand by mixing the two or more active compounds according to the invention.

According to an alternative of such a method, it is also possible to apply simultaneously, successively or separately compounds (A) and (B) so as to have the conjugated (A)/(B) effects, of distinct compositions each containing one of the two or three active ingredients (A) or (B).

The dose of active compound usually applied in the method of treatment according to the invention is generally and advantageously
- for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;
- for seed treatment: from 2 to 200 g per 100 kilogram of seed, preferably from 3 to 150 g per 100 kilogram of seed;
- for soil treatment: from 0.1 to 10,000 g/ha, preferably from 1 to 5,000 g/ha.

The doses herein indicated are given as illustrative Examples of method according to the invention. A person skilled in the art will know how to adapt the application doses, notably according to the nature of the plant or crop to be treated.

Under specific conditions, for example according to the nature of the phytopathogenic fungus to be treated or controlled, a lower dose can offer adequate protection. Certain climatic conditions, resistance or other factors like the nature of the phytopathogenic fungi or the degree of infestation, for example, of the plants with these fungi, can require higher doses of combined active ingredients. The optimum dose usually depends on several factors, for example on the type of phytopathogenic fungus to be treated, on the type or level of development of the infested plant, on the density of vegetation or alternatively on the method of application.

Without it being limiting, the crop treated with the pesticide composition or combination according to the invention is, for example, grapevine, but this could be cereals, vegetables, lucerne, soybean, market garden crops, turf, wood, tree or horticultural plants.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

Among the plants that can be protected by the method according to the invention, mention can be made of cotton; flax; vine; fruit or vegetable crops such as *Rosaceae* sp. (for instance pip fruit such as apples and pears, but also stone fruit such as apricots, almonds and peaches). *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins). *Rubiaceae* sp., *Theaceae* sp., *Sterculiceae* sp., *Rutaceae* sp. (for instance lemons oranges and grapefruit); *Solanaceae* sp. (for instance tomatoes). *Liliaceae* sp., *Asteraceae* sp. (for instance lettuces). *Umbelliferae* sp., *Cruciferae* sp., *Chenopodiaceae* sp., *Cucurbitaceae* sp., *Papilionaceae* sp. (for instance peas). *Rosaceae* sp. (for instance strawberries); major crops such as *Graminae* sp. (for instance maize, lawn or cereals such as wheat, rice, barley and triticale). *Asteraceae* sp. (for instance sunflower). *Cruciferae* sp. (for instance colza). *Fabacae* sp. (for instance peanuts). *Papilionaceae* sp. (for instance soybean). *Solanaceae* sp. (for instance potatoes). *Chenopodiaceae* sp. (for instance beetroots); horticultural and forest crops; as well as genetically modified homologues of these crops.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (W0 1992/005251, WO 1995/009910, WO 1998/27806, WO 2005/002324, WO 2006/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai at al., Science (1983), 221, 370-371), the CP4 gene of the bacterium *Agrobacterium* sp. (Barry et al., Curr. Topics Plant Physiol. (1992), 7, 139-145), the genes encoding a Petunia EPSPS (Shah et al., Science (1986), 233, 478-481), a Tomato EPSPS (Gasser et al., J. Biol. Chem. (1988), 263, 4280-4289), or an *Eleusine* EPSPS (WO 2001/66704). It can also be a mutated EPSPS as described in for example EP-A0837044. WO 2000/066746, WO 2000/066747 or WO 2002/026995. Glyphosate-tolerant plants can also be obtained by expressing a gene that encodes a glyphosate oxido-reductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. No. 5,605,011, U.S. Pat. No. 5,378,824, U.S. Pat. No. 5,141,870, and U.S. Pat. No. 5,013,659. The production of sulfonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 1997/41218, for sugar beet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., Nat. Biotechnol. (2001), 19, 668-72; Schnepf et al., Applied Environm. Microbiol. (2006), 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:
- a. plants which contain a transgene capable of reducing the expression and/or the activity of poly(ADP-ribose)polymerase (PARP) gene in the plant cells or plants as described in WO 2000/004173 or WO2006/045633 or PCT/EP07/004142.
- b. plants which contain a stress tolerance enhancing transgene capable of reducing the expression and/or the activity of the PARG encoding genes of the plants or plants cells, as described e.g. in WO 2004/090140.
- c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO 2006/133827 or PCT/EP07/002,433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:
1) transgenic plants which synthesize a modified starch, which in its physical-chemical characteristics, in particular the amylase content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO99/58688, WO 1999/58690, WO 1999/58654, WO 2000/008184, WO 2000/008185, WO 2000/008175, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026, WO 1997/20936.
2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 1996/001904, WO 1996/021023, WO 1998/039460, and WO 1999/024593, plants producing alpha 1,4 glucans as disclosed in WO 1995/031553, US 2002/031826, U.S. Pat. No. 6,284,479, U.S. Pat. No. 5,712,107, WO 1997/047806, WO 1997/047807, WO 1997/047808 and WO 2000/014249, plants producing alpha-1,6 branched alpha-1,4-glucans, as disclosed in WO 2000/73422, plants producing alternan, as disclosed in WO 2000/047727, EP 06077301.7, U.S. Pat. No. 5,908,975 and EP 0728213,
3) transgenic plants which produce hyaluronan, as for example disclosed in WO 2006/032538, WO 2007/039314, WO 2007/039315, WO 2007/039316, JP 2006/304779, and WO 2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
- a) Plants, such as cotton plants, containing an altered form of cellulose synthase genes as described in WO 1998/000549
- b) Plants, such as cotton plants, containing an altered form of rsw2 or rsw3 homologous nucleic acids as described in WO2004/053219
- c) Plants, such as cotton plants, with increased expression of sucrose phosphate synthase as described in WO 2001/017333
- d) Plants, such as cotton plants, with increased expression of sucrose synthase as described in WO02/45485
- e) Plants, such as cotton plants, wherein the timing of the plasmodesmatal gating at the basis of the fiber cell is altered, e.g. through downregulation of fiberselective β 1,3-glucanase as described in WO2005/017157
- f) Plants, such as cotton plants, having fibers with altered reactivity, e.g. through the expression of N-acteylglucosaminetransferase gene including nodC and chitinsynthase genes as described in WO2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
b) Plants such as oilseed rape plants, producing oil having a low linolenic acid content as described in U.S. Pat. No. 6,270,828, U.S. Pat. No. 6,169,190 or U.S. Pat. No. 5,965,755
c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Application 61/135,230, WO 2009/068313 and WO 2010/006732.

Plants or plant cultivars (that can be obtained by plant biotechnology methods such as genetic engineering) which may also be treated according to the invention are plants, such as Tobacco plants, with altered post-translational protein modification patterns, for example as described in WO 2010/121818 and WO 2010/145846.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road, Riverdale, Md. 20737, USA), for instance on its internet site (URL http://www.aphis.usda.gov/brs/not_reg.html). On the filing date of this application the petitions for nonregulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp browse.aspx and http://www.agbios.com/dbase.php).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO 2006/128569); Event 1143-51B (cotton, insect control, not deposited, described in WO 2006/128570); Event 1445 (cotton, herbicide tolerance, not deposited, described in US-A 2002-120964 or WO 02/034946); Event 17053 (rice, herbicide tolerance, deposited as PTA-9843, described in WO 2010/117737); Event 17314 (rice, herbicide tolerance, deposited as PTA-9844, described in WO 2010/117735); Event 281-24-236 (cotton, insect control—herbicide tolerance, deposited as PTA-6233, described in WO 2005/103266 or US-A 2005-216969); Event 3006-210-23 (cotton, insect control-herbicide tolerance, deposited as PTA-6233, described in US-A 2007-143876 or WO 2005/103266); Event 3272 (corn, quality trait, deposited as PTA-9972, described in WO 2006/098952 or US-A 2006-230473); Event 40416 (corn, insect control-herbicide tolerance, deposited as ATCC PTA-11508, described in WO 2011/075593); Event 43A47 (corn, insect control-herbicide tolerance, deposited as ATCC PTA-11509, described in WO 2011/075595); Event 5307 (corn, insect control, deposited as ATCC PTA-9561, described in WO 2010/077816); Event ASR-368 (bent grass, herbicide tolerance, deposited as ATCC PTA-4816, described in US-A 2006-162007 or WO 2004/053062); Event B16 (corn, herbicide tolerance, not deposited, described in US-A 2003-126634); Event BPS-CV127-9 (soybean, herbicide tolerance, deposited as NCIMB No. 41603, described in WO 2010/080829); Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO 2006/128571); Event CE46-02A (cotton, insect control, not deposited, described in WO 2006/128572); Event COT102 (cotton, insect control, not deposited, described in US-A 2006-130175 or WO 2004/039986); Event COT202 (cotton, insect control, not deposited, described in US-A 2007-067868 or WO 2005/054479); Event COT203 (cotton, insect control, not deposited, described in WO 2005/054480); Event DAS40278 (corn, herbicide tolerance, deposited as ATCC PTA-10244, described in WO 2011/022469); Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO 2009/100188); Event DAS68416 (soybean, herbicide tolerance, deposited as ATCC PTA-10442, described in WO 2011/066384 or WO 2011/066360); Event DP-098140-6 (corn, herbicide tolerance, deposited as ATCC PTA-8296, described in US-A 2009-137395 or WO 2008/112019); Event DP-305423-1 (soybean, quality trait, not deposited, described in US-A 2008-312082 or WO 2008/054747); Event DP-32138-1 (corn, hybridization system, deposited as ATCC PTA-9158, described in US-A 2009-0210970 or WO 2009/103049); Event DP-356043-5 (soybean, herbicide tolerance, deposited as ATCC PTA-8287, described in US-A 2010-0184079 or WO 2008/002872); Event EE-1 (brinjal, insect control, not deposited, described in WO 2007/091277); Event F1117 (corn, herbicide tolerance, deposited as ATCC 209031, described in US-A 2006-059581 or WO 98/044140); Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control-herbicide tolerance, deposited as ATCC PTA-8398, described in WO 2008/151780); Event GHB614 (cotton, herbicide tolerance, deposited as ATCC PTA-6878, described in US-A 2010-050282 or WO 2007/017186); Event GJ11 (corn, herbicide tolerance, deposited as ATCC 209030, described in US-A 2005-188434 or WO 98/044140); Event GM RZ13 (sugar beet, virus resistance, deposited as NCIMB-41601, described in WO 2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO 2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO 03/013224 or US-A 2003-097687); Event LLRICE06 (rice, herbicide tolerance, deposited as ATCC-23352, described in U.S. Pat. No. 6,468,747 or WO 00/026345); Event LLRICE601 (rice, herbicide tolerance, deposited as ATCC PTA-2600, described in US-A 2008-2289060 or WO 00/026356); Event LY038 (corn, quality trait, deposited as ATCC PTA-5623, described in US-A 2007-028322 or WO 2005/061720); Event MIR162 (corn, insect control, deposited as PTA-8166, described in US-A 2009-300784 or WO 2007/142840); Event MIR604 (corn, insect control, not deposited, described in US-A 2008-167456 or WO 2005/103301); Event MON15985 (cotton, insect control, deposited as ATCC PTA-2516, described in US-A 2004-250317 or WO 02/100163); Event MON810 (corn, insect control, not deposited, described in US-A 2002-102582); Event MON863 (corn, insect control, deposited as ATCC PTA-2605, described in WO 2004/011601 or US-A 2006-095986); Event MON87427 (corn, pollination control, deposited as ATCC PTA-7899, described in WO 2011/062904); Event MON87460 (corn, stress tolerance, deposited as ATCC PTA-8910, described in WO 2009/111263 or US-A 2011-0138504); Event MON87701 (soybean, insect control, deposited as ATCC PTA-8194, described in US-A 2009-130071 or WO 2009/064652); Event MON87705 (soybean, quality trait-herbicide tolerance, deposited as ATCC PTA-9241, described in US-A 2010-0080887 or WO 2010/037016); Event MON87708 (soybean, herbicide tolerance, deposited as ATCC PTA9670, described in WO 2011/034704); Event MON87754 (soybean, quality trait, deposited as ATCC PTA-9385, described in WO 2010/024976); Event MON87769 (soybean, quality trait, deposited as ATCC PTA-8911, described in US-A 2011-0067141 or WO 2009/102873); Event MON88017 (corn, insect control-herbicide tolerance, deposited as ATCC PTA-5582, described in US-A 2008-028482 or WO 2005/059103); Event MON88913 (cotton, herbicide tolerance, deposited as ATCC PTA-4854, described in WO 2004/072235 or US-A 2006-059590); Event MON89034 (corn, insect control, deposited as ATCC PTA-7455, described in WO 2007/140256 or US-A 2008-260932); Event MON89788 (soybean, herbicide tolerance, deposited as ATCC PTA-6708, described in US-A 2006-282915 or WO 2006/130436); Event MS11 (oilseed rape, pollination control-herbicide tolerance, deposited as ATCC PTA-850 or PTA-2485, described in WO 01/031042); Event MS8 (oilseed rape, pollination control-herbicide tolerance, deposited as ATCC PTA-730, described in WO 01/041558 or US-A 2003-188347); Event NK603 (corn, herbicide tolerance, deposited as ATCC PTA-2478, described in US-A 2007-292854); Event PE-7 (rice, insect control, not deposited, described in WO 2008/114282); Event RF3 (oilseed rape, pollination control-herbicide tolerance, deposited as ATCC PTA-730, described in WO 01/041558 or US-A 2003-188347); Event RT73 (oilseed rape, herbicide tolerance, not deposited, described in WO 02/036831 or US-A 2008-070260); Event T227-1 (sugar beet, herbicide tolerance, not deposited, described in WO 02/44407 or US-A 2009-265817); Event T25 (corn, herbicide tolerance, not deposited, described in US-A 2001-029014 or WO 01/051654); Event T304-40 (cotton, insect control-herbicide tolerance, deposited as ATCC PTA-8171, described in US-A 2010-077501 or WO 2008/122406); Event T342-142 (cotton, insect control, not deposited, described in WO 2006/128568); Event TC1507 (corn, insect control-herbicide tolerance, not deposited, described in US-A 2005-039226 or WO 2004/099447); Event VIP1034 (corn, insect control-herbicide tolerance, deposited as ATCC PTA-3925, described in WO 03/052073), Event 32316 (corn, insect control-herbicide tolerance, deposited as PTA-11507, described in WO 2011/084632), Event 4114 (corn, insect control-herbicide tolerance, deposited as PTA-11506, described in WO 2011/084621).

The composition according to the invention can also be used against fungal diseases liable to grow on or inside timber. The term "timber" means all types of species of wood and all types of working of this wood intended for construction, for example solid wood, high-density wood, laminated wood and plywood. The method for treating timber according to the invention mainly consists in contacting one or more compounds according to the invention or a composition according to the invention; this includes for example direct application, spraying, dipping, injection or any other suitable means.

Among the diseases of plants or crops that can be controlled by the method according to the invention, mention can be made of:

Powdery mildew diseases such as:
Blumeria diseases, caused for example by *Blumeria graminis;*
Podosphaera diseases, caused for example by *Podosphaera leucotricha;*
Sphaerotheca diseases, caused for example by *Sphaerotheca fuliginea;*
Uncinula diseases, caused for example by *Uncinula necator;*
Rust diseases such as:
Gymnosporangium diseases, caused for example by *Gymnosporangium sabinae;*
Hemileia diseases, caused for example by *Hemileia vastatrix;*
Phakopsora diseases, caused for example by *Phakopsora pachyrhizi* or *Phakopsora meibomiae;*
Puccinia diseases, caused for example by *Puccinia recondita;*
Uromyces diseases, caused for example by *Uromyces appendiculatus;*
Oomycete diseases such as:
Bremia diseases, caused for example by *Bremia lactucae;*
Peronospora diseases, caused for example by *Peronospora pisi* or *P. brassicae;*
Phytophthora diseases, caused for example by *Phytophthora infestans;*
Plasmopara diseases, caused for example by *Plasmopara viticola;*
Pseudoperonospora diseases, caused for example by *Pseudoperonospora humuli* or *Pseudoperonospora cubensis;*

*Pythium* diseases, caused for example by *Pythium ultimum*;
Leafspot, leaf blotch and leaf blight diseases such as:
*Alternaria* diseases, caused for example by *Alternaria solani*;
*Cercospora* diseases, caused for example by *Cercospora beticola*;
*Cladiosporum* diseases, caused for example by *Cladiosporium cucumerinum*;
*Cochliobolus* diseases, caused for example by *Cochliobolus sativus*;
*Colletotrichum* diseases, caused for example by *Colletotrichum lindemuthanium*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawcettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;
*Leptosphaeria* diseases, caused for example by *Leptosphaeria maculans; Leptosphaeria nodorum*;
*Magnaporthe* diseases, caused for example by *Magnaporthe grisea*;
*Mycosphaerella* diseases, caused for example by *Mycosphaerella graminicola; Mycosphaerella arachidicola; Mycosphaerella fijiensis*;
*Phaeosphaeria* diseases, caused for example by *Phaeosphaeria nodorum*;
*Pyrenophora* diseases, caused for example by *Pyrenophora teres*;
*Ramularia* diseases, caused for example by *Ramularia collo-cygni*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incamata*;
*Venturia* diseases, caused for example by *Venturia inaequalis*;
Root and stem diseases such as:
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Tapesia* diseases, caused for example by *Tapesia acuformis*;
*Thielaviopsis* diseases, caused for example by *Thielaviopsis basicola*;
Ear and panicle diseases such as:
*Alternaria* diseases, caused for example by *Alternaria* spp.;
*Aspergillus* diseases, caused for example by *Aspergillus flavus*;
*Cladosporium* diseases, caused for example by *Cladosporium* spp.;
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;
Smut and bunt diseases such as:
*Sphacelotheca* diseases, caused for example by *Sphacelotheca reiliana*;
*Tilletia* diseases, caused for example by *Tilletia caries*;
*Urocystis* diseases, caused for example by *Urocystis occulta*;
*Ustilago* diseases, caused for example by *Ustilago nuda*;
Fruit rot and mould diseases such as:
*Aspergillus* diseases, caused for example by *Aspergillus flavus*;
*Botrytis* diseases, caused for example by *Botrytis cinerea*;
*Penicillium* diseases, caused for example by *Penicillium expansum*;
*Sclerotinia* diseases, caused for example by *Sclerotinia sclerotiorum*;
*Verticilium* diseases, caused for example by *Verticilium alboatrum*;
Seed and soilborne decay, mould, wilt, rot and damping-off diseases:
*Alternaria* diseases, caused for example by *Altemaria brassicicola*
*Aphanomyces* diseases, caused for example by *Aphanomyces euteiches*
*Ascochyta* diseases, caused for example by *Ascochyta lentis*
*Aspergillus* diseases, caused for example by *Aspergillus flavus*
*Cladosporium* diseases, caused for example by *Cladosporium herbarum*
*Cochliobolus* diseases, caused for example by *Cochliobolus sativus*
(Conidiaform: *Drechslera, Bipolaris* Syn: *Helminthosporium*);
*Colletotrichum* diseases, caused for example by *Colletotrichum coccodes*;
*Fusarium* diseases, caused for example by *Fusarium culmorum*;
*Gibberella* diseases, caused for example by *Gibberella zeae*;
*Macrophomina* diseases, caused for example by *Macrophomina phaseolina*
*Monographella* diseases, caused for example by *Monographella nivalis*;
*Penicillium* diseases, caused for example by *Penicillium expansum*
*Phoma* diseases, caused for example by *Phoma lingam*
*Phomopsis* diseases, caused for example by *Phomopsis sojae*;
*Phytophthora* diseases, caused for example by *Phytophthora cactorum*;
*Pyrenophora* diseases, caused for example by *Pyrenophora graminea*
*Pyricularia* diseases, caused for example by *Pyricularia oryzae*;
*Pythium* diseases, caused for example by *Pythium ultimum*;
*Rhizoctonia* diseases, caused for example by *Rhizoctonia solani*;
*Rhizopus* diseases, caused for example by *Rhizopus oryzae*
*Sclerotium* diseases, caused for example by *Sclerotium rolfsii*;

Septoria diseases, caused for example by *Septoria nodorum*;
Typhula diseases, caused for example by *Typhula incamata*;
Verticillium diseases, caused for example by *Verticillium dahliae*;
Canker, broom and dieback diseases such as:
Nectria diseases, caused for example by *Nectria galligena*;
Blight diseases such as:
Monilinia diseases, caused for example by *Monilinia laxa*;
Leaf blister or leaf curl diseases such as:
Taphrina diseases, caused for example by *Taphrina deformans*;
Decline diseases of wooden plants such as:
Esca diseases, caused for example by *Phaemoniella clamydospora*;
Eutypa dyeback, caused for example by *Eutypa lata*;
Dutch elm disease, caused for example by *Ceratocystsc ulmi*;
Diseases of flowers and Seeds such as:
Botrytis diseases, caused for example by *Botrytis cinerea*;
Diseases of tubers such as:
Rhizoctonia diseases, caused for example by *Rhizoctonia solani*
Helminthosporium diseases, caused for example by *Helminthosporium solani*.

The compounds according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The various aspects of the invention will now be illustrated with reference to the following table 1 of compound examples and the following preparation or efficacy examples.

The following table 1 illustrates in a non limiting manner examples of compounds according to the invention.

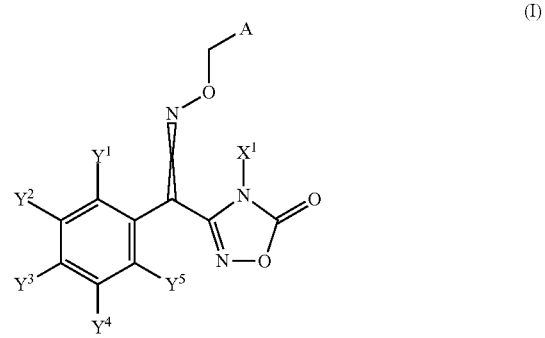

In table 1 we use the following abbreviations for specified claimed elements "A1" and "A2" of the generic structure (I) of the invention:

TABLE 1

| Ex-no | $Y^1$ | $Y^2$ | $Y^3$ | $Y^4$ | $Y^5$ | $X^1$ | A | $Z^1$ | $Z^2$ | $Z^3$ | $Z^4$ | Stereo | LogP |
|---|---|---|---|---|---|---|---|---|---|---|---|---|---|
| 1 | H | H | H | H | H | CH₃ | A1 | amino | H | H | H | Z | 1.14 [a] |
| 2 | H | H | H | H | H | CH₃ | A1 | [(pentyloxy)carbonyl]amino | H | H | H | Z | 4.44 [a] |
| 3 | H | H | H | H | H | CH₃ | A1 | [(but-3-yn-1-yloxy)carbonyl]amino | H | H | H | Z | 3.27 [a] |
| 4 | H | H | H | H | H | CH₃ | A2 | amino | H | | | Z | 1.54 [a] |
| 5 | H | H | H | H | H | CH₃ | A1 | [(2-cyclohexylethoxy)carbonyl]amino | H | H | H | Z | 5.27 [a] |
| 6 | H | H | H | H | H | CH₃ | A1 | [(pent-4-en-1-yloxy)carbonyl]amino | H | H | H | Z | 4.06 [a] |
| 7 | H | H | H | H | H | CH₃ | A1 | [(2-phenylethoxy)carbonyl]amino | H | H | H | Z | 4.15 [a] |
| 8 | H | H | H | H | H | CH₃ | A1 | heptanoylamino | H | H | H | Z | 4.3 [a] |
| 9 | H | H | H | H | H | CH₃ | A2 | heptanoylamino | H | | | Z | 4.13 [a] |
| 10 | H | H | H | H | H | CH₃ | A2 | (2,3-dihydro-1,4-benzodioxin-2-ylcarbonyl)amino | H | | | Z | 3.62 [a] |
| 11 | H | H | H | H | H | CH₃ | A2 | (3,4-dihydro-2H-chromen-2-ylcarbonyl)amino | H | | | Z | 3.94 [a] |
| 12 | H | H | H | H | H | CH₃ | A2 | [(pentyloxy)carbonyl]amino | H | | | Z | 4.11 [a] |
| 13 | H | H | H | H | H | CH₃ | A2 | pentanoylamino | H | | | Z | 3.37 [a] |
| 14 | H | H | H | H | H | CH₃ | A2 | (butoxycarbonyl)amino | H | | | Z | 3.73 [a] |
| 15 | H | H | H | H | H | CH₃ | A1 | pentanoylamino | H | H | H | Z | 3.51 [a] |
| 16 | H | H | H | H | H | CH₃ | A1 | [(cyclopentylmethoxy)carbonyl]amino | H | H | H | Z | 4.53 [a] |
| 17 | H | H | H | H | H | CH₃ | A1 | (3-fluorobenzoyl)amino | H | H | H | Z | 3.69 [a] |
| 18 | H | H | H | H | H | CH₃ | A1 | (butoxycarbonyl)amino | H | H | H | Z | 4.04 [a] |
| 19 | H | H | H | H | H | CH₃ | A2 | (2-phenoxypropanoyl)amino | H | | | Z | 3.71 [a] |
| 20 | H | H | H | H | H | CH₃ | A2 | (3-fluorobenzoyl)amino | H | | | Z | 3.6 [a] |
| 21 | H | H | H | H | H | CH₃ | A1 | (tert-butoxycarbonyl)amino | H | H | H | Z | 3.96 [a] |
| 22 | H | H | H | H | H | H | A1 | [(but-3-yn-1-yloxy)carbonyl]amino | H | H | H | Z | 3.09 [a] |
| 23 | H | H | H | H | H | H | A1 | amino | H | H | H | Z | 1.36 [a] |
| 24 | H | H | H | H | H | H | A2 | amino | H | | | Z | 1.58 [a] |
| 25 | H | H | H | H | H | CH₃ | A1 | amino | H | H | H | E | 1.14 [a] |
| 26 | H | H | H | H | H | CH₃ | A1 | [(pentyloxy)carbonyl]amino | H | H | H | E | 4.24 [a] |
| 27 | H | H | H | H | H | CH₃ | A2 | (2-fluorobenzoyl)amino | H | | | Z | 3.44 [a] |
| 28 | H | H | H | H | H | CH₃ | A2 | [(2-fluorophenoxy)acetyl]amino | H | | | Z | 3.51 [a] |
| 29 | H | H | H | H | H | CH₃ | A1 | [(2-chlorophenyl)acetyl]amino | H | H | H | Z | 3.76 [a] |
| 30 | H | CH₃ | H | H | H | CH₃ | A1 | amino | H | H | H | Z | 1.45 [a] |

TABLE 1-continued

| Ex-no | Y¹ | Y² | Y³ | Y⁴ | Y⁵ | X¹ | A | Z¹ | Z² | Z³ | Z⁴ | Stereo | LogP |
|---|---|---|---|---|---|---|---|---|---|---|---|---|---|
| 31 | H | H | H | H | H | CH₃ | A1 | [(2-methoxyphenoxy)acetyl]amino | H | H | H | Z | 3.8 [a] |
| 32 | H | H | H | H | H | CH₃ | A1 | octanoylamino | H | H | H | Z | 4.71 [a] |
| 33 | H | H | H | H | H | CH₃ | A1 | (propoxycarbonyl)amino | H | H | H | Z | 3.62 [a] |
| 34 | H | H | H | H | H | CH₃ | A1 | (4-chlorobutanoyl)amino | H | H | H | Z | 3.27 [a] |
| 35 | H | H | H | H | H | CH₃ | A1 | (cyclopropylcarbonyl)amino | H | H | H | Z | 2.92 [a] |
| 36 | H | methoxy | H | H | H | CH₃ | A1 | [(pentyloxy)carbonyl]amino | H | H | H | Z | 4.46 [a] |
| 37 | H | H | H | H | H | CH₃ | A1 | hept-6-ynoylamino | H | H | H | Z | 3.37 [a] |
| 38 | H | H | H | H | H | CH₃ | A2 | [(4-fluorophenoxy)acetyl]amino | H | | | Z | 3.53 [a] |
| 39 | H | H | H | H | H | CH₃ | A1 | {[(2-methylpent-4-yn-2-yl)oxy]carbonyl}amino | H | H | H | Z | 3.94 [a] |
| 40 | H | H | H | H | H | CH₃ | A1 | [(1-methylcyclohexyl)carbonyl]amino | H | H | H | Z | 4.36 [a] |
| 41 | H | H | CH₃ | H | H | CH₃ | A2 | [(pentyloxy)carbonyl]amino | H | | | Z | 4.41 [a] |
| 42 | H | fluoro | H | H | H | CH₃ | A1 | (3-fluorobenzoyl)amino | H | H | H | Z | 3.79 [a] |
| 43 | H | H | H | H | H | CH₃ | A1 | (1-phenylethyl)amino | H | H | H | Z | 2.86 [a] |
| 44 | H | H | H | H | H | CH₃ | A1 | (3-methoxybenzoyl)amino | H | H | H | Z | 3.62 [a] |
| 45 | H | H | H | H | H | CH₃ | A1 | {[(4-methylpentyl)oxy]carbonyl}amino | H | H | H | Z | 4.81 [a] |
| 46 | H | H | H | H | H | CH₃ | A1 | (diphenylacetyl)amino | H | H | H | Z | 4.48 [a] |
| 47 | H | H | H | H | H | CH₃ | A2 | [(3-methylbutoxy)carbonyl]amino | H | | | Z | 4.06 [a] |
| 48 | H | H | H | H | H | CH₃ | A1 | (3-ethoxypropanoyl)amino | H | H | H | Z | 2.96 [a] |
| 49 | H | H | H | H | H | CH₃ | A1 | {[2-(3-bromophenyl)ethoxy]carbonyl}amino | H | H | H | Z | 4.61 [a] |
| 50 | H | H | H | H | H | CH₃ | A2 | [2-(3-methoxyphenoxy)propanoyl]amino | H | | | Z | 3.71 [a] |
| 51 | H | H | H | H | H | CH₃ | A1 | [(3-methoxyphenoxy)acetyl]amino | H | H | H | Z | 3.73 [a] |
| 52 | H | H | H | H | H | CH₃ | A1 | acetylamino | H | H | H | Z | 2.44 [a] |
| 53 | H | H | H | H | H | CH₃ | A2 | [(hexyloxy)carbonyl]amino | H | | | Z | 4.51 [a] |
| 54 | H | H | H | H | H | CH₃ | A1 | (phenylcarbonyl)amino | H | H | H | Z | 3.51 [a] |
| 55 | H | H | H | H | H | CH₃ | A2 | [(4-bromophenoxy)acetyl]amino | H | | | Z | 3.94 [a] |
| 56 | H | H | H | H | H | CH₃ | A1 | {[(3-methylpentyl)oxy]carbonyl}amino | H | H | H | Z | 4.78 [a] |
| 57 | H | H | H | H | H | CH₃ | A2 | (2-chlorobenzoyl)amino | H | | | Z | 3.46 [a] |
| 58 | H | H | H | H | H | difluoromethyl | A1 | [(but-3-yn-1-yloxy)carbonyl]amino | H | H | H | Z | 3.64 [a] |
| 59 | H | H | H | H | H | CH₃ | A1 | (4,4-dimethylpentanoyl)amino | H | H | H | Z | 4.15 [a] |
| 60 | H | H | H | H | H | CH₃ | A1 | {[(1-phenylpropan-2-yl)oxy]carbonyl}amino | H | H | H | Z | 4.49 [a] |
| 61 | H | H | H | H | H | ethyl | A1 | [(cyclohexyloxy)carbonyl]amino | H | H | H | Z | 4.77 [a] |
| 62 | H | H | H | H | H | CH₃ | A1 | (3-cyclopropylpropanoyl)amino | H | H | H | Z | 3.51 [a] |
| 63 | H | H | H | H | H | CH₃ | A1 | (3-chloropropanoyl)amino | H | H | H | Z | 3.02 [a] |
| 64 | H | H | H | H | H | CH₃ | A1 | 2-(3-chlorophenoxy)propanoyl]amino | H | H | H | Z | 4.38 [a] |
| 65 | H | H | H | H | H | CH₃ | A1 | [(4-bromophenoxy)acetyl]amino | H | H | H | Z | 4.2 [a] |
| 66 | H | H | H | H | H | CH₃ | A1 | [(4-fluorophenoxy)acetyl]amino | H | H | H | Z | 3.73 [a] |
| 67 | H | H | H | H | H | CH₃ | A1 | 4-[5-(pyridinium-1-yl)pentanoyl]amino formate | H | H | H | Z | 1.67 [a] |
| 68 | H | H | H | H | H | CH₃ | A1 | [(1-phenylethoxy)carbonyl]amino | H | H | H | Z | 4.23 [a] |
| 69 | H | H | H | H | H | CH₃ | A1 | [2-(3-methoxyphenoxy)propanoyl]amino | H | H | H | Z | 3.97 [a] |
| 70 | H | H | H | H | H | cyanomethyl | A1 | [(but-3-yn-1-yloxy)carbonyl]amino | H | H | H | Z | 3.31 [a] |
| 71 | H | H | H | H | H | CH₃ | A1 | propanoylamino | H | H | H | Z | 2.77 [a] |
| 72 | H | H | H | H | H | CH₃ | A2 | [(2,2-dimethylpropoxy)carbonyl]amino | H | | | Z | 4.01 [a] |
| 73 | H | H | H | H | H | CH₃ | A1 | (5-bromopentanoyl)amino | H | H | H | Z | 3.59 [a] |
| 74 | H | H | H | H | H | CH₃ | A1 | (2-phenylethyl)amino | H | H | H | Z | 2.78 [a] |
| 75 | H | H | H | H | H | CH₃ | A2 | (phenoxycarbonyl)amino | H | | | Z | 3.48 [a] |
| 76 | H | H | H | H | H | CH₃ | A1 | [(2-methylphenoxy)acetyl]amino | H | H | H | Z | 4.17 [a] |
| 77 | H | H | H | H | H | CH₃ | A1 | (3-cyclohexylpropanoyl)amino | H | H | H | Z | 4.73 [a] |
| 78 | H | H | H | H | H | CH₃ | A1 | (bicyclo[2.2.1]hept-2-ylacetyl)amino | H | H | H | Z | 4.39 [a] |
| 79 | H | H | H | H | H | CH₃ | A1 | [(2-methyl-2-phenylpropoxy)carbonyl]amino | H | H | H | Z | 4.71 [a] |
| 80 | H | H | H | H | H | CH₃ | A2 | 2-(3-methylphenoxy)propanoyl]amino | H | | | Z | 3.99 [a] |
| 81 | H | H | H | H | H | CH₃ | A2 | (2-bromobenzoyl)amino | H | | | Z | 3.51 [a] |
| 82 | H | H | H | H | H | CH₃ | A2 | [2-(2-methylphenoxy)propanoyl]amino | H | | | Z | 4.12 [a] |
| 83 | H | fluoro | H | H | H | CH₃ | A1 | amino | H | H | H | Z | 1.34 [a] |
| 84 | H | H | H | H | H | CH₃ | A1 | (3-cyclopentylpropanoyl)amino | H | H | H | Z | 4.36 [a] |
| 85 | H | H | H | H | H | CH₃ | A1 | (3,4-dihydro-1H-isochromen-3-ylcarbonyl)amino | H | H | H | Z | 4.17 [a] |
| 86 | H | H | H | H | H | prop-2-yn-1-yl | A1 | [(but-3-yn-1-yloxy)carbonyl]amino | H | H | H | Z | 3.46 [a] |
| 87 | H | CH₃ | H | H | H | CH₃ | A1 | bis(tert-butoxycarbonyl)amino | H | H | H | Z | 4.77 [a] |
| 88 | H | H | H | H | H | ethyl | A1 | [(4-methoxyphenyl)acetyl]amino | H | H | H | Z | 3.7 [a] |
| 89 | H | H | H | H | H | CH₃ | A1 | {[2-(4-fluorophenyl)ethoxy]carbonyl}amino | H | H | H | Z | 4.19 [a] |
| 90 | H | H | H | H | chloro | CH₃ | A2 | amino | H | | | Z | 1.72 [a] |
| 91 | H | H | H | H | H | CH₃ | A2 | (2-methoxybenzoyl)amino | H | | | Z | 3.71 [a] |
| 92 | H | fluoro | H | H | H | CH₃ | A1 | [(but-3-yn-1-yloxy)carbonyl]amino | H | H | H | Z | 3.39 [a] |
| 93 | H | H | H | H | H | CH₃ | A1 | (2-butoxypropanoyl)amino | H | H | H | Z | 4.3 [a] |
| 94 | H | H | H | H | H | CH₃ | A1 | [(cyclopentyloxy)acetyl]amino | H | H | H | Z | 4.04 [a] |
| 95 | H | H | H | H | H | CH₃ | A1 | (5-methylhexanoyl)amino | H | H | H | Z | 4.25 [a] |
| 96 | H | H | H | H | H | H | A1 | amino | H | H | H | U | 1.2 [a] |
| 97 | fluoro | H | H | H | H | CH₃ | A1 | (tert-butoxycarbonyl)amino | H | H | H | Z | 3.92 [a] |
| 98 | H | H | H | H | H | CH₃ | A1 | nonanoylamino | H | H | H | Z | 5.11 [a] |
| 99 | H | H | H | H | H | CH₃ | A1 | oct-7-enoylamino | H | H | H | Z | 4.3 [a] |
| 100 | H | H | H | H | H | CH₃ | A2 | [(3-fluorophenoxy)acetyl]amino | H | | | Z | 3.58 [a] |
| 101 | H | methoxy | H | H | H | CH₃ | A1 | [(4-methoxyphenyl)acetyl]amino | H | H | H | Z | 3.51 [a] |
| 102 | H | H | H | H | H | CH₃ | A1 | (4-methylpentanoyl)amino | H | H | H | Z | 3.85 [a] |
| 103 | H | H | H | H | H | CH₃ | A2 | [(cyclopentyloxy)carbonyl]amino | H | | | Z | 3.76 [a] |
| 104 | H | H | H | H | H | ethyl | A1 | [(but-3-yn-1-yloxy)carbonyl]amino | H | H | H | Z | 3.51 [a] |
| 105 | H | H | H | H | H | CH₃ | A1 | [(3-chlorophenoxy)acetyl]amino | H | H | H | Z | 4.1 [a] |
| 106 | H | H | H | H | H | CH₃ | A1 | {[2-(2-chlorophenyl)ethoxy]carbonyl}amino | H | H | H | Z | 4.56 [a] |
| 107 | H | H | H | H | H | CH₃ | A1 | [(hexyloxy)carbonyl]amino | H | H | H | Z | 4.85 [a] |

TABLE 1-continued

| Ex-no | Y¹ | Y² | Y³ | Y⁴ | Y⁵ | X¹ | A | Z¹ | Z² | Z³ | Z⁴ | Stereo | LogP |
|---|---|---|---|---|---|---|---|---|---|---|---|---|---|
| 108 | H | methoxy | H | H | H | CH₃ | A1 | amino | H | H | H | Z | 1.32 [a] |
| 109 | H | H | H | H | H | CH₃ | A1 | [(prop-2-en-1-yloxy)carbonyl]amino | H | H | H | Z | 3.42 [a] |
| 110 | H | H | H | H | H | CH₃ | A1 | [(cyclopentyloxy)carbonyl]amino | H | H | H | Z | 4.09 [a] |
| 111 | H | H | H | H | H | CH₃ | A1 | hexanoylamino | H | H | H | Z | 3.89 [a] |
| 112 | H | methoxy | H | H | H | CH₃ | A1 | [(cyclohexyloxy)carbonyl]amino | H | H | H | Z | 4.49 [a] |
| 113 | H | H | H | H | H | CH₃ | A2 | [2-(2-bromophenoxy)propanoyl]amino | H | | | Z | 4.2 [a] |
| 114 | H | H | H | H | H | CH₃ | A1 | (2-fluorobenzoyl)amino | H | H | H | Z | 3.73 [a] |
| 115 | H | H | H | H | H | CH₃ | A1 | [2-(2-methoxyphenoxy)propanoyl]amino | H | H | H | Z | 4.15 [a] |
| 116 | H | H | H | H | H | CH₃ | A1 | (cyclohexylmethyl)amino | H | H | H | Z | 3.02 [a] |
| 117 | H | CH₃ | H | H | H | CH₃ | A1 | [(benzyloxy)carbonyl]amino | H | H | H | Z | 4.31 [a] |
| 118 | H | H | H | H | H | CH₃ | A1 | (cyclobutylcarbonyl)amino | H | H | H | Z | 3.27 [a] |
| 119 | H | H | H | H | H | CH₃ | A1 | {[(1-methoxy-1-oxopropan-2-yl)oxy]carbonyl}amino | H | H | H | Z | 3.17 [a] |
| 120 | H | H | H | H | H | CH₃ | A1 | {[(2-methylbutan-2-yl)oxy]carbonyl}amino | H | H | H | Z | 1.99 [a] |
| 121 | H | CH₃ | H | H | H | H | A1 | amino | H | H | H | U | 1.47 [a] |
| 122 | H | H | H | H | H | CH₃ | A1 | {[(5,5,5-trifluoropentyl)oxy]carbonyl}amino | H | H | H | Z | 4.06 [a] |
| 123 | H | H | H | H | H | CH₃ | A2 | [(2,4-dichlorophenoxy)acetyl]amino | H | | | Z | 4.23 [a] |
| 124 | H | H | H | H | H | CH₃ | A1 | (2-ethylbutanoyl)amino | H | H | H | Z | 3.71 [a] |
| 125 | H | H | H | H | H | CH₃ | A1 | [(2-fluorophenoxy)acetyl]amino | H | H | H | Z | 3.76 [a] |
| 126 | H | H | H | H | H | CH₃ | A2 | [2-(benzyloxy)propanoyl]amino | H | | | Z | 3.85 [a] |
| 127 | H | H | H | H | H | ethyl | A1 | [(pent-4-yn-2-yloxy)carbonyl]amino | H | H | H | Z | 3.81 [a] |
| 128 | H | H | H | H | H | CH₃ | A1 | [2-(3-methylphenoxy)propanoyl]amino | H | H | H | Z | 4.35 [a] |
| 129 | H | fluoro | H | H | H | H | A1 | amino | H | H | H | U | 1.35 [a] |
| 130 | H | H | H | H | H | ethyl | A1 | (2,3-dihydro-1,4-benzodioxin-2-ylcarbonyl)amino | H | H | H | Z | 4.14 [a] |
| 131 | H | methoxy | H | H | H | CH₃ | A1 | (tert-butoxycarbonyl)amino | H | H | H | Z | 3.99 [a] |
| 132 | H | H | H | H | H | CH₃ | A1 | (2-methylbutanoyl)amino | H | H | H | Z | 3.41 [a] |
| 133 | H | H | H | H | H | CH₃ | A1 | {[2-(2-methylphenyl)ethoxy]carbonyl}amino | H | H | H | Z | 4.51 [a] |
| 134 | H | H | H | H | H | CH₃ | A1 | 2-furoylamino | H | H | H | Z | 3.13 [a] |
| 135 | H | H | H | H | H | H | A1 | (tert-butoxycarbonyl)amino | H | H | H | Z | 3.76 [a] |
| 136 | H | H | H | H | H | CH₃ | A1 | {(2E)-2-(benzyloxy)imino]ethyl}amino | H | H | H | Z | 3.35 [a] |
| 137 | H | H | H | H | H | CH₃ | A1 | [(1-methylcyclopropyl)carbonyl]amino | H | H | H | Z | 3.31 [a] |
| 138 | H | H | H | H | H | CH₃ | A1 | (phenoxycarbonyl)amino | H | H | H | Z | 3.73 [a] |
| 139 | H | fluoro | H | H | H | CH₃ | A1 | (2,2-dimethylpropanoyl)amino | H | H | H | Z | 3.61 [a] |
| 140 | H | fluoro | H | H | H | CH₃ | A1 | pentanoylamino | H | H | H | Z | 3.61 [a] |
| 141 | H | methoxy | H | H | H | CH₃ | A1 | bis(tert-butoxycarbonyl)amino | H | H | H | Z | 4.44 [a] |
| 142 | H | CH₃ | H | H | H | CH₃ | A1 | (tert-butoxycarbonyl)amino | H | H | H | Z | 4.34 [a] |
| 143 | H | H | H | H | H | CH₃ | A2 | (3-iodobenzoyl)amino | H | | | Z | 4.19 [a] |
| 144 | H | H | H | H | H | CH₃ | A1 | (4-methylbenzoyl)amino | H | H | H | Z | 3.85 [a] |
| 145 | H | H | H | H | H | CH₃ | A1 | [(2-phenylpropoxy)carbonyl]amino | H | H | H | Z | 4.46 [a] |
| 146 | H | H | H | H | H | CH₃ | A1 | [(3S,5S,7S)-adamantan-1-ylacetyl]amino | H | H | H | Z | 5.08 [a] |
| 147 | H | H | H | H | H | CH₃ | A1 | (cyclohexylcarbonyl)amino | H | H | H | Z | 3.92 [a] |
| 148 | H | H | H | H | H | CH₃ | A1 | (2,2-dimethylpropanoyl)amino | H | H | H | Z | 3.48 [a] |
| 149 | H | methoxy | H | H | H | CH₃ | A1 | {[(4-methylpentan-2-yl)oxy]carbonyl}amino | H | H | H | Z | 4.72 [a] |
| 150 | H | fluoro | H | H | H | CH₃ | A2 | [(pentyloxy)carbonyl]amino | H | | | Z | 4.19 [a] |
| 151 | H | H | H | H | H | CH₃ | A1 | {[2-(3-methoxyphenyl)ethoxy]carbonyl}amino | H | H | H | Z | 4.11 [a] |
| 152 | H | H | H | H | H | ethyl | A1 | (tert-butoxycarbonyl)amino | H | H | H | Z | 4.26 [a] |
| 153 | H | H | H | H | H | CH₃ | A1 | (4-methylpent-3-enoyl)amino | H | H | H | Z | 3.59 [a] |
| 154 | H | H | H | H | H | CH₃ | A2 | (2,2-dimethylpropanoyl)amino | H | | | Z | 3.42 [a] |
| 155 | H | H | H | H | H | CH₃ | A2 | [2-(3-bromophenoxy)propanoyl]amino | H | | | Z | 4.17 [a] |
| 156 | H | H | H | H | H | CH₃ | A1 | [2-(benzyloxy)propanoyl]amino | H | H | H | Z | 4.15 [a] |
| 157 | H | H | methoxy | H | H | CH₃ | A1 | amino | H | H | H | Z | 1.35 [a] |
| 158 | H | H | H | H | H | CH₃ | A2 | (2-iodobenzoyl)amino | H | | | Z | 3.6 [a] |
| 159 | H | H | H | H | H | CH₃ | A2 | [(2-bromophenoxy)acetyl]amino | H | | | Z | 3.89 [a] |
| 160 | H | H | H | H | H | CH₃ | A2 | (2,2-dimethylhexanoyl)amino | H | | | Z | 4.48 [a] |
| 161 | H | H | fluoro | H | H | CH₃ | A1 | [(pentyloxy)carbonyl]amino | H | H | H | Z | 4.51 [a] |
| 162 | H | H | H | H | H | CH₃ | A1 | [(tert-butylsulfanyl)carbonyl]amino | H | H | H | Z | 4.39 [a] |
| 163 | H | H | H | H | H | CH₃ | A1 | hexylamino | H | H | H | Z | 2.64 [a] |
| 164 | H | H | H | H | H | CH₃ | A2 | [(4-chlorophenoxy)acetyl]amino | H | | | Z | 3.85 [a] |
| 165 | H | H | H | H | H | CH₃ | A1 | [(1-phenylcyclopropyl)carbonyl]amino | H | H | H | Z | 4.43 [a] |
| 166 | H | H | H | H | H | CH₃ | A1 | [3-(1-methylcyclopropyl)propanoyl]amino | H | H | H | Z | 3.87 [a] |
| 167 | H | H | H | H | H | CH₃ | A1 | hept-6-enoylamino | H | H | H | Z | 3.89 [a] |
| 168 | H | H | H | H | H | CH₃ | A1 | [(benzyloxy)carbonyl]amino | H | H | H | Z | 3.99 [a] |
| 169 | H | H | CH₃ | H | H | CH₃ | A2 | pentanoylamino | H | | | Z | 3.7 [a] |
| 170 | H | H | H | H | H | CH₃ | A1 | (3-methyl-2-furoyl)amino | H | H | H | Z | 3.71 [a] |
| 171 | H | H | H | H | H | CH₃ | A2 | [(2-methoxyphenoxy)acetyl]amino | H | | | Z | 3.55 [a] |
| 172 | H | H | H | H | H | ethyl | A1 | (2-methylpentanoyl)amino | H | H | H | Z | 4.06 [a] |
| 173 | H | H | H | H | H | CH₃ | A1 | (3,3-dimethylbutanoyl)amino | H | H | H | Z | 3.78 [a] |
| 174 | H | H | H | H | H | CH₃ | A1 | (4-iodobenzoyl)amino | H | H | H | Z | 4.29 [a] |
| 175 | H | H | H | H | H | CH₃ | A1 | {[2-(2-methoxyphenyl)ethoxy]carbonyl}amino | H | H | H | Z | 4.31 [a] |
| 176 | H | H | H | H | H | ethyl | A1 | pentanoylamino | H | H | H | Z | 3.76 [a] |
| 177 | H | H | H | H | H | CH₃ | A1 | isobutyrylamino | H | H | H | Z | 3.11 [a] |
| 178 | H | H | H | H | H | CH₃ | A1 | (2-chlorobenzoyl)amino | H | H | H | Z | 3.64 [a] |
| 179 | H | H | H | H | H | CH₃ | A1 | [2-(3-bromophenoxy)propanoyl]amino | H | H | H | Z | 4.46 [a] |
| 180 | H | H | H | H | H | CH₃ | A2 | (4-methylbenzoyl)amino | H | | | Z | 3.76 [a] |
| 181 | H | H | H | H | H | CH₃ | A1 | (2-methoxybenzoyl)amino | H | H | H | Z | 3.87 [a] |
| 182 | H | H | H | H | H | CH₃ | A1 | [(3-methylbutoxy)carbonyl]amino | H | H | H | Z | 4.39 [a] |
| 183 | H | H | H | H | H | CH₃ | A1 | (butoxycarbothioyl)amino | H | H | H | Z | 4.53 [a] |

TABLE 1-continued

| Ex-no | Y¹ | Y² | Y³ | Y⁴ | Y⁵ | X¹ | A | Z¹ | Z² | Z³ | Z⁴ | Stereo | LogP |
|---|---|---|---|---|---|---|---|---|---|---|---|---|---|
| 184 | H | H | H | H | H | CH₃ | A1 | [3-(2-methoxyphenyl)propanoyl]amino | H | H | H | z | 3.87 [a] |
| 185 | H | H | methoxy | H | H | CH₃ | A1 | {[(4-methylpentan-2-yl)oxy]carbonyl}amino | H | H | H | Z | 4.72 [a] |
| 186 | H | H | H | H | H | CH₃ | A1 | {[2-(2-fluorophenyl)ethoxy]carbonyl}amino | H | H | H | Z | 4.21 [a] |
| 187 | H | H | H | H | H | CH₃ | A1 | (4-bromobenzoyl)amino | H | H | H | Z | 4.14 [a] |
| 188 | H | H | H | H | H | CH₃ | A1 | [3-(methylsulfanyl)propanoyl]amino | H | H | H | Z | 3.09 [a] |
| 189 | H | H | H | H | H | CH₃ | A1 | [(2,2-dichloro-1-ethyl-3-methylcyclopropyl)carbonyl]amino | H | H | H | Z | 4.35 [a] |
| 190 | H | H | H | H | H | CH₃ | A1 | [(2,5-dimethoxyphenyl)acetyl]amino | H | H | H | Z | 3.6 [a] |
| 191 | H | H | methoxy | H | H | CH₃ | A1 | (trifluoroacetyl)amino | H | H | H | Z | 3.37 [a] |
| 192 | H | H | H | H | H | CH₃ | A1 | [(2-ethylbutoxy)carbonyl]amino | H | H | H | Z | 4.78 [a] |
| 193 | fluoro | H | H | H | H | H | A1 | (tert-butoxycarbonyl)amino | H | H | H | Z | 3.68 [a] |
| 194 | H | H | H | H | H | CH₃ | A2 | [(benzyloxy)acetyl]amino | H | | | Z | 3.6 [a] |
| 195 | H | H | H | H | H | CH₃ | A2 | [(cyclopentyloxy)acetyl]amino | H | | | Z | 3.73 [a] |
| 196 | H | H | H | H | H | CH₃ | A1 | [(4-chlorophenyl)acetyl]amino | H | H | H | Z | 3.92 [a] |
| 197 | H | H | H | H | H | CH₃ | A1 | diethylamino | H | H | H | Z | 2.63 [a] |
| 198 | H | H | H | H | H | CH₃ | A2 | hexanoylamino | H | | | Z | 3.76 [a] |
| 199 | H | H | H | H | H | CH₃ | A1 | {[(1-ethoxypropan-2-yl)oxy]carbonyl}amino | H | H | H | Z | 3.53 [a] |
| 200 | H | H | H | H | H | CH₃ | A1 | [(hexan-2-yloxy)carbonyl]amino | H | H | H | Z | 4.78 [a] |
| 201 | H | H | H | H | H | ethyl | A1 | [(benzyloxy)carbonyl]amino | H | H | H | Z | 4.24 [a] |
| 202 | H | H | H | H | H | CH₃ | A1 | (3,5-difluorobenzoyl)amino | H | H | H | Z | 3.92 [a] |
| 203 | H | fluoro | H | H | H | CH₃ | A2 | (phenylacetyl)amino | H | | | Z | 3.46 [a] |
| 204 | H | H | H | H | H | CH₃ | A1 | [2-(4-bromophenoxy)propanoyl]amino | H | H | H | Z | 4.46 [a] |
| 205 | H | H | H | H | H | CH₃ | A1 | [(4,4,4-trifluorobutoxy)carbonyl]amino | H | H | H | Z | 3.85 [a] |
| 206 | H | fluoro | H | H | H | CH₃ | A1 | (tert-butoxycarbonyl)amino | H | H | H | Z | 4.09 [a] |
| 207 | H | H | H | H | H | ethyl | A1 | [(hex-5-yn-2-yloxy)carbonyl]amino | H | H | H | Z | 4.04 [a] |
| 208 | H | H | H | H | H | CH₃ | A1 | (cyclohexylacetyl)amino | H | H | H | Z | 4.26 [a] |
| 209 | H | H | H | H | H | ethyl | A1 | amino | H | H | H | Z | 1.42 [a] |
| 210 | H | H | H | H | H | CH₃ | A1 | {[2-(3-methylphenyl)ethoxy]carbonyl}amino | H | H | H | Z | 4.53 [a] |
| 211 | H | methoxy | H | H | H | CH₃ | A1 | hexanoylamino | H | H | H | Z | 3.92 [a] |
| 212 | H | H | H | H | H | CH₃ | A2 | (3-methoxybenzoyl)amino | H | | | Z | 3.58 [a] |
| 213 | H | H | H | H | H | CH₃ | A2 | [(2-methylphenoxy)acetyl]amino | H | | | Z | 3.85 [a] |
| 214 | H | H | fluoro | H | H | H | A1 | (tert-butoxycarbonyl)amino | H | H | H | Z | 3.78 [a] |
| 215 | H | CH₃ | H | H | H | CH₃ | A1 | (butoxycarbonyl)amino | H | H | H | Z | 4.36 [a] |
| 216 | H | H | H | H | H | CH₃ | A2 | 2-(4-bromophenoxy)propanoyl]amino | H | | | Z | 4.17 [a] |
| 217 | H | H | H | H | H | CH₃ | A1 | (4-methoxybenzoyl)amino | H | H | H | Z | 3.53 [a] |
| 218 | H | H | H | H | H | CH₃ | A1 | [methoxy(phenyl)acetyl]amino | H | H | H | Z | 3.85 [a] |
| 219 | H | H | H | H | H | CH₃ | A2 | [2-(2-methoxyphenoxy)propanoyl]amino | H | | | Z | 3.89 [a] |
| 220 | H | H | H | H | H | CH₃ | A2 | [difluoro(phenoxy)acetyl]amino | H | | | Z | 3.89 [a] |
| 221 | H | H | H | H | H | CH₃ | A1 | (2,2-dimethylbutanoyl)amino | H | H | H | Z | 3.8 [a] |
| 222 | H | H | H | H | H | CH₃ | A1 | {1-(2,4-dichlorophenyl)cyclopropyl]carbonyl}amino | H | H | H | Z | 4.96 [a] |
| 223 | H | CH₃ | H | H | H | CH₃ | A1 | {[(4-methylpentan-2-yl)oxy]carbonyl}amino | H | H | H | Z | 5.05 [a] |
| 224 | H | CH₃ | H | H | H | CH₃ | A1 | [(pentyloxy)carbonyl]amino | H | H | H | Z | 4.78 [a] |
| 225 | H | H | H | H | H | CH₃ | A1 | [(2-methylpropoxy)carbonyl]amino | H | H | H | Z | 4.01 [a] |
| 226 | H | H | H | H | H | CH₃ | A1 | [(pent-4-yn-2-yloxy)carbonyl]amino | H | H | H | Z | 3.57 [a] |
| 227 | H | H | H | H | H | CH₃ | A1 | (3,4-dihydro-1H-isochromen-1-ylcarbonyl)amino | H | H | H | Z | 4.1 [a] |
| 228 | H | methoxy | H | H | H | CH₃ | A1 | [(but-3-yn-1-yloxy)carbonyl]amino | H | H | H | Z | 3.33 [a] |
| 229 | H | H | H | H | H | CH₃ | A2 | [(4-methylphenoxy)acetyl]amino | H | | | Z | 3.8 [a] |
| 230 | H | H | H | H | H | CH₃ | A1 | l-4-({[(1R,2R)-2-phenylcyclopropyl]carbonyl}amino) | H | H | H | Z | 4.04 [a] |
| 231 | H | H | H | H | H | CH₃ | A1 | [2-(2-chlorophenoxy)propanoyl]amino | H | H | H | Z | 4.41 [a] |
| 232 | H | H | H | H | H | CH₃ | A1 | (2-phenoxypropanoyl)amino | H | H | H | Z | 3.96 [a] |
| 233 | H | H | H | H | H | CH₃ | A1 | {[(2-methylpentan-2-yl)oxy]carbonyl}amino | H | H | H | Z | 4.77 [a] |
| 234 | H | fluoro | H | H | H | CH₃ | A2 | (2,3-dihydro-1,4-benzodioxin-2-ylcarbonyl)amino | H | | | Z | 3.7 [a] |
| 235 | H | H | H | H | H | CH₃ | A1 | (3,7-dimethyloct-6-enoyl)amino | H | H | H | Z | 4.88 [a] |
| 236 | H | H | H | H | H | CH₃ | A1 | (1-cyclohexylpropan-2-yl)amino | H | H | H | Z | 5.14 [a] |
| 237 | H | H | H | H | H | CH₃ | A1 | (3,3,3-trifluoropropanoyl)amino | H | H | H | Z | 3.19 [a] |
| 238 | H | H | H | H | H | CH₃ | A1 | {[2-(4-bromophenyl)ethoxy]carbonyl}amino | H | H | H | Z | 4.63 [a] |
| 239 | H | H | H | H | H | CH₃ | A2 | [(benzyloxy)carbonyl]amino | H | | | Z | 3.73 [a] |
| 240 | H | H | H | H | H | CH₃ | A1 | (butoxyacetyl)amino | H | H | H | Z | 3.97 [a] |
| 241 | H | H | H | H | H | CH₃ | A1 | {[(2-methylpropyl)sulfanyl]carbonyl}amino | H | H | H | Z | 4.39 [a] |
| 242 | H | H | H | H | H | CH₃ | A1 | [(but-3-yn-2-yloxy)carbonyl]amino | H | H | H | Z | 3.41 [a] |
| 243 | H | H | H | H | H | CH₃ | A1 | (2-bromobenzoyl)amino | H | H | H | Z | 3.67 [a] |
| 244 | H | H | H | H | H | CH₃ | A1 | (2-methylhexanoyl)amino | H | H | H | Z | 4.2 [a] |
| 245 | H | H | H | H | H | CH₃ | A1 | (4-chlorobenzoyl)amino | H | H | H | Z | 4.01 [a] |
| 246 | H | H | fluoro | H | H | CH₃ | A1 | (tert-butoxycarbonyl)amino | H | H | H | Z | 4.06 [a] |
| 247 | H | H | H | H | H | CH₃ | A1 | (5,5-dimethylhexanoyl)amino | H | H | H | Z | 4.53 [a] |
| 248 | H | H | H | H | H | CH₃ | A1 | (2-methylpentanoyl)amino | H | H | H | Z | 3.8 [a] |
| 249 | fluoro | fluoro | H | H | H | CH₃ | A1 | (tert-butoxycarbonyl)amino | H | H | H | E | 3.94 [a] |
| 250 | H | CH₃ | H | H | H | CH₃ | A1 | [(cyclohexyloxy)carbonyl]amino | H | H | H | Z | 4.82 [a] |
| 251 | H | H | H | H | H | CH₃ | A2 | (4-fluorobenzoyl)amino | H | | | Z | 3.55 [a] |
| 252 | H | H | CH₃ | H | H | CH₃ | A2 | (phenylacetyl)amino | H | | | Z | 3.65 [a] |
| 253 | H | H | H | H | H | CH₃ | A1 | (2-cyclohexylethyl)amino | H | H | H | Z | 2.96 [a] |
| 254 | fluoro | fluoro | H | H | H | CH₃ | A1 | (tert-butoxycarbonyl)amino | H | H | H | Z | 4.01 [a] |
| 255 | H | H | H | H | H | CH₃ | A1 | [(2,5-difluorophenyl)acetyl]amino | H | H | H | Z | 3.62 [a] |
| 256 | H | H | H | H | H | CH₃ | A1 | pent-4-enoylamino | H | H | H | Z | 3.25 [a] |
| 257 | H | H | H | H | H | CH₃ | A2 | (phenylcarbonyl)amino | H | | | Z | 3.44 [a] |
| 258 | H | H | fluoro | H | H | CH₃ | A1 | [(2-phenylethoxy)carbonyl]amino | H | H | H | Z | 4.24 [a] |

TABLE 1-continued

| Ex-no | Y¹ | Y² | Y³ | Y⁴ | Y⁵ | X¹ | A | Z¹ | Z² | Z³ | Z⁴ | Stereo | LogP |
|---|---|---|---|---|---|---|---|---|---|---|---|---|---|
| 259 | H | H | fluoro | H | H | CH₃ | A1 | amino | H | H | H | Z | 1.41 [a] |
| 260 | H | H | H | H | H | CH₃ | A1 | [2-(4-chlorophenoxy)propanoyl]amino | H | H | H | Z | 4.35 [a] |
| 261 | H | fluoro | H | H | H | CH₃ | A1 | bis(tert-butoxycarbonyl)amino | H | H | H | Z | 4.51 [a] |
| 262 | H | H | H | H | H | CH₃ | A2 | (2,4-dichlorobenzoyl)amino | H | | | Z | 3.94 [a] |
| 263 | H | H | H | H | H | CH₃ | A2 | (3,5-difluorobenzoyl)amino | H | | | Z | 3.8 [a] |
| 264 | H | H | H | H | H | CH₃ | A1 | (thiophen-2-ylacetyl)amino | H | H | H | Z | 3.42 [a] |
| 265 | H | H | H | H | H | CH₃ | A2 | (propoxycarbonyl)amino | H | | | Z | 3.35 [a] |
| 266 | H | H | H | H | H | CH₃ | A1 | butanoylamino | H | H | H | Z | 3.13 [a] |
| 267 | H | H | H | H | H | CH₃ | A1 | (4-cyclohexylbutanoyl)amino | H | H | H | Z | 5.14 [a] |
| 268 | H | H | H | H | H | CH₃ | A1 | [(6E)-8-methylnon-6-enoyl]amino | H | H | H | Z | 5.06 [a] |
| 269 | H | H | H | H | H | CH₃ | A1 | [(2-bromophenoxy)acetyl]amino | H | H | H | Z | 4.25 [a] |
| 270 | H | H | H | H | H | ethyl | A1 | [(2-phenylethoxy)carbonyl]amino | H | H | H | Z | 4.41 [a] |
| 271 | H | H | H | H | H | CH₃ | A2 | butanoylamino | H | | | Z | 3.02 [a] |
| 272 | H | CH₃ | H | H | H | CH₃ | A1 | [(2-phenylethoxy)carbonyl]amino | H | H | H | Z | 4.49 [a] |
| 273 | H | H | H | H | H | CH₃ | A1 | {[(4-methylpentan-2-yl)oxy]carbonyl}amino | H | H | H | Z | 4.68 [a] |
| 274 | H | H | H | H | H | CH₃ | A1 | [(2,4-dichlorophenoxy)acetyl]amino | H | H | H | Z | 4.61 [a] |
| 275 | H | H | H | H | H | CH₃ | A1 | [2-(2-bromophenoxy)propanoyl]amino | H | H | H | Z | 4.53 [a] |
| 276 | H | H | H | H | H | CH₃ | A2 | [2-(4-chlorophenoxy)propanoyl]amino | H | | | Z | 4.07 [a] |
| 277 | H | H | H | H | H | CH₃ | A1 | [4-(4-chloro-2-methylphenoxy)butanoyl]amino | H | H | H | Z | 4.73 [a] |
| 278 | H | H | H | H | H | CH₃ | A1 | [(benzyloxy)acetyl]amino | H | H | H | Z | 3.87 [a] |
| 279 | H | H | H | H | H | CH₃ | A1 | (tert-butoxycarbonyl)(2-cyclohexylethyl)amino | H | H | H | Z | 6.73 [a] |
| 280 | H | H | H | H | H | ethyl | A1 | (3-methylbutanoyl)amino | H | H | H | Z | 3.7 [a] |
| 281 | H | H | H | H | H | CH₃ | A1 | (3-iodobenzoyl)amino | H | H | H | Z | 4.31 [a] |
| 282 | H | H | H | H | H | CH₃ | A1 | [(pentan-2-yloxy)carbonyl]amino | H | H | H | Z | 4.36 [a] |
| 283 | H | H | H | H | H | CH₃ | A1 | (propoxycarbothioyl)amino | H | H | H | Z | 4.11 [a] |
| 284 | H | H | H | H | H | CH₃ | A1 | 2-ethylhexanoyl)amino | H | H | H | Z | 4.49 [a] |
| 285 | H | H | H | H | H | CH₃ | A1 | [(heptan-2-yloxy)carbonyl]amino | H | H | H | Z | 5.19 [a] |
| 286 | H | H | H | H | H | CH₃ | A2 | [(2-methylpropoxy)carbonyl]amino | H | | | Z | 3.71 [a] |
| 287 | H | H | H | H | H | CH₃ | A1 | [2-(4-methylphenoxy)propanoyl]amino | H | H | H | Z | 4.35 [a] |
| 288 | H | H | H | H | H | CH₃ | A1 | [(2-cyanoethoxy)carbonyl]amino | H | H | H | Z | 2.78 [a] |
| 289 | H | H | H | H | H | CH₃ | A2 | (3-bromobenzoyl)amino | H | | | Z | 4.04 [a] |
| 290 | H | methoxy | H | H | H | CH₃ | A1 | [(benzyloxy)carbonyl]amino | H | H | H | Z | 4.04 [a] |
| 291 | H | H | H | H | H | CH₃ | A1 | [(4-methyl-3,4-dihydro-1H-isochromen-3-yl)carbonyl]amino | H | H | H | Z | 4.35 [a] |
| 292 | H | H | H | H | H | CH₃ | A1 | {[(3-methylbutan-2-yl)oxy]carbonyl}amino | H | H | H | Z | 4.27 [a] |
| 293 | H | H | H | H | H | CH₃ | A1 | {[(4,4,5,5,5-pentafluoropentyl)oxy]carbonyl}amino | H | H | H | Z | 4.29 [a] |
| 294 | H | H | H | H | H | CH₃ | A1 | (2-phenoxybenzoyl)amino | H | H | H | Z | 4.76 [a] |
| 295 | H | fluoro | H | H | H | CH₃ | A1 | (butoxycarbonyl)amino | H | H | H | Z | 4.14 [a] |
| 296 | H | H | H | H | H | CH₃ | A1 | [(4-methylphenoxy)acetyl]amino | H | H | H | Z | 4.07 [a] |
| 297 | H | fluoro | H | H | H | CH₃ | A1 | [(2-phenylethoxy)carbonyl]amino | H | H | H | Z | 4.26 [a] |
| 298 | H | H | H | H | H | CH₃ | A1 | {[2-(2-bromophenyl)ethoxy]carbonyl}amino | H | H | H | Z | 4.66 [a] |
| 299 | H | CH₃ | H | H | H | CH₃ | A1 | (tert-butoxycarbonyl)(hexyl)amino | H | H | H | Z | 6.57 [a] |
| 300 | H | H | H | H | H | ethyl | A1 | [(pentyloxy)carbonyl]amino | H | H | H | Z | 4.72 [a] |
| 301 | H | H | H | H | H | CH₃ | A1 | [3-(4-fluorophenyl)propanoyl]amino | H | H | H | Z | 3.81 [a] |
| 302 | H | H | H | H | H | CH₃ | A1 | hex-5-ynoylamino | H | H | H | Z | 3.17 [a] |
| 303 | H | H | H | H | H | CH₃ | A1 | decanoylamino | H | H | H | Z | 5.54 [a] |
| 304 | H | H | H | H | H | CH₃ | A1 | acryloylamino | H | H | H | Z | 2.77 [a] |
| 305 | H | H | H | H | H | CH₃ | A1 | {[(3,3-dimethylbutan-2-yl)oxy]carbonyl}amino | H | H | H | Z | 4.56 [a] |
| 306 | H | H | H | H | H | CH₃ | A1 | {[(1,3-dichloropropan-2-yl)oxy]carbonyl}amino | H | H | H | Z | 3.83 [a] |
| 307 | H | H | H | H | H | CH₃ | A1 | [difluoro(phenoxy)acetyl]amino | H | H | H | Z | 4.08 [a] |
| 308 | H | H | CH₃ | H | H | H | A2 | amino | H | | | Z | 1.84 [a] |
| 309 | H | H | H | H | H | CH₃ | A1 | [(1-fluorocyclopropyl)carbonyl]amino | H | H | H | Z | 3.31 [a] |
| 310 | H | H | H | H | H | CH₃ | A1 | {[2-(4-methoxyphenyl)ethoxy]carbonyl}amino | H | H | H | Z | 4.08 [a] |
| 311 | H | H | H | H | H | CH₃ | A1 | [(3-fluorophenoxy)acetyl]amino | H | H | H | Z | 3.78 [a] |
| 312 | H | H | H | H | H | CH₃ | A2 | [2-(4-methylphenoxy)propanoyl]amino | H | | | Z | 4.02 [a] |
| 313 | H | H | H | H | H | CH₃ | A1 | (phenoxyacetyl)amino | H | H | H | Z | 3.73 [a] |
| 314 | H | H | H | H | H | CH₃ | A2 | [(3-bromophenoxy)acetyl]amino | H | | | Z | 3.94 [a] |
| 315 | H | H | H | H | H | CH₃ | A2 | (phenoxyacetyl)amino | H | | | Z | 3.51 [a] |
| 316 | H | H | H | H | H | CH₃ | A1 | (2,2-dimethylhexanoyl)amino | H | H | H | Z | 4.63 [a] |
| 317 | H | H | H | H | H | CH₃ | A1 | {[(2-methylbut-3-yn-2-yl)oxy]carbonyl}amino | H | H | H | Z | 3.6 [a] |
| 318 | H | H | H | H | H | CH₃ | A2 | [(3-methoxyphenoxy)acetyl]amino | H | | | Z | 3.53 [a] |
| 319 | H | H | CH₃ | H | H | CH₃ | A2 | (2-phenoxypropanoyl)amino | H | | | Z | 3.99 [a] |
| 320 | H | H | H | H | H | CH₃ | A1 | [(butylsulfanyl)carbonyl]amino | H | H | H | Z | 4.41 [a] |
| 321 | H | H | H | H | H | CH₃ | A2 | [2-(3-chlorophenoxy)propanoyl]amino | H | | | Z | 4.1 [a] |
| 322 | H | H | H | H | H | CH₃ | A2 | 2-phenoxybutanoyl)amino | H | | | Z | 3.99 [a] |
| 323 | H | H | H | H | H | CH₃ | A1 | (bicyclo[2.2.1]hept-5-en-2-ylcarbonyl)amino | H | H | H | Z | 3.68 [a] |
| 324 | H | H | fluoro | H | H | CH₃ | A1 | (3-phenylpropanoyl)amino | H | H | H | Z | 3.87 [a] |
| 325 | H | methoxy | H | H | H | CH₃ | A1 | [(2-phenylethoxy)carbonyl]amino | H | H | H | Z | 4.19 [a] |
| 326 | H | H | CH₃ | H | H | CH₃ | A2 | amino | H | | | Z | 1.82 [a] |
| 327 | H | H | H | H | H | CH₃ | A1 | (2,5-dimethylbenzoyl)amino | H | H | H | Z | 4.06 [a] |
| 328 | H | methoxy | H | H | H | CH₃ | A1 | (2-methylpentanoyl)amino | H | H | H | Z | 3.87 [a] |
| 329 | H | H | H | H | H | CH₃ | A1 | (3-phenoxybenzoyl)amino | H | H | H | Z | 4.61 [a] |
| 330 | H | H | H | H | H | CH₃ | A1 | bis[(4-fluorophenoxy)carbonyl]amino | H | H | H | Z | 4.2 [a] |
| 331 | H | H | H | H | H | CH₃ | A1 | (2-iodobenzoyl)amino | H | H | H | Z | 3.76 [a] |
| 332 | H | H | H | H | H | CH₃ | A1 | (2,4-dichlorobenzoyl)amino | H | H | H | Z | 4.14 [a] |
| 333 | H | H | methoxy | H | H | H | A1 | (tert-butoxycarbonyl)amino | H | H | H | Z | 3.69 [a] |
| 334 | H | H | H | H | H | CH₃ | A1 | [(3-methylphenoxy)acetyl]amino | H | H | H | Z | 4.07 [a] |

TABLE 1-continued

| Ex-no | Y¹ | Y² | Y³ | Y⁴ | Y⁵ | X¹ | A | Z¹ | Z² | Z³ | Z⁴ | Stereo | LogP |
|---|---|---|---|---|---|---|---|---|---|---|---|---|---|
| 335 | H | H | H | H | H | CH₃ | A1 | [(2-bromophenyl)acetyl]amino | H | H | H | Z | 3.85 [a] |
| 336 | H | H | H | H | H | CH₃ | A2 | (2,5-dimethylbenzoyl)amino | H | | | Z | 3.94 [a] |
| 337 | H | H | H | H | H | CH₃ | A1 | {[(2-methylpentyl)oxy]carbonyl}amino | H | H | H | Z | 4.83 [a] |
| 338 | H | fluoro | H | H | H | CH₃ | A2 | (2-phenoxypropanoyl)amino | H | | | Z | 3.76 [a] |
| 339 | H | H | CH₃ | H | H | CH₃ | A2 | [(cyclohexyloxy)carbonyl]amino | H | | | Z | 4.48 [a] |
| 340 | H | H | H | H | H | CH₃ | A1 | (3-methylbutanoyl)amino | H | H | H | Z | 3.44 [a] |
| 341 | H | H | H | H | H | CH₃ | A1 | (phenylacetyl)amino | H | H | H | Z | 3.53 [a] |
| 342 | H | H | H | H | H | CH₃ | A1 | [(prop-2-yn-1-yloxy)carbonyl]amino | H | H | H | Z | 3.13 [a] |
| 343 | H | CH₃ | H | H | H | CH₃ | A1 | [(but-3-yn-1-yloxy)carbonyl]amino | H | H | H | Z | 3.59 [a] |
| 344 | H | H | H | H | H | CH₃ | A1 | (3-methylbenzoyl)amino | H | H | H | Z | 3.87 [a] |
| 345 | H | H | H | H | H | CH₃ | A1 | (5-methyl-2-furoyl)amino | H | H | H | Z | 3.46 [a] |
| 346 | H | H | H | H | H | CH₃ | A1 | [3-(4-chlorophenyl)propanoyl]amino | H | H | H | Z | 4.17 [a] |
| 347 | H | H | H | H | H | CH₃ | A1 | (3-phenylpropanoyl)amino | H | H | H | Z | 3.78 [a] |
| 348 | H | H | H | H | H | CH₃ | A1 | (2,2,3,3,4,4,4-heptafluorobutanoyl)amino | H | H | H | Z | 4.17 [a] |
| 349 | H | H | H | H | H | CH₃ | A1 | {[2-(4-chlorophenyl)ethoxy]carbonyl}amino | H | H | H | Z | 4.53 [a] |
| 350 | H | H | H | H | H | CH₃ | A1 | [(2-methylbutoxy)carbonyl]amino | H | H | H | Z | 4.44 [a] |
| 351 | H | H | fluoro | H | H | CH₃ | A1 | [(cyclohexyloxy)carbonyl]amino | H | H | H | Z | 4.54 [a] |
| 352 | H | H | H | H | H | CH₃ | A1 | (3,4-dichlorobenzoyl)amino | H | H | H | Z | 4.54 [a] |
| 353 | H | H | H | H | H | CH₃ | A1 | {[(2-methylhexan-2-yl)oxy]carbonyl}amino | H | H | H | Z | 5.1 [a] |
| 354 | H | methoxy | H | H | H | H | A1 | amino | H | H | H | U | 1.29 [a] |
| 355 | H | CH₃ | H | H | H | CH₃ | A1 | hexanoylamino | H | H | H | Z | 4.24 [a] |
| 356 | H | H | H | H | H | CH₃ | A2 | [(3-methylphenoxy)acetyl]amino | H | | | Z | 3.8 [a] |
| 357 | H | H | H | H | H | CH₃ | A1 | (4-phenoxybenzoyl)amino | H | H | H | Z | 4.58 [a] |
| 358 | H | methoxy | H | H | H | CH₃ | A1 | pentanoylamino | H | H | H | Z | 3.55 [a] |
| 359 | H | H | H | H | H | CH₃ | A1 | {[2-(3-chlorophenyl)ethoxy]carbonyl}amino | H | H | H | Z | 4.51 [a] |
| 360 | H | H | CH₃ | H | H | CH₃ | A2 | formyl(methyl)amino | H | | | Z | 3.06 [a] |
| 361 | H | methoxy | H | H | H | CH₃ | A1 | (butoxycarbonyl)amino | H | H | H | Z | 4.06 [a] |
| 362 | H | methoxy | H | H | H | CH₃ | A1 | (3-methylbutanoyl)amino | H | H | H | Z | 3.46 [a] |
| 363 | H | H | H | H | H | CH₃ | A1 | [(but-3-en-1-yloxy)carbonyl]amino | H | H | H | Z | 3.71 [a] |
| 364 | H | H | H | H | H | CH₃ | A1 | (4-fluorobenzoyl)amino | H | H | H | Z | 3.62 [a] |
| 365 | H | H | H | H | H | CH₃ | A1 | (cyclopentylacetyl)amino | H | H | H | Z | 3.92 [a] |
| 366 | H | H | H | H | H | CH₃ | A2 | 2-(2-chlorophenoxy)propanoyl]amino | H | | | Z | 4.07 [a] |
| 367 | H | H | H | H | H | CH₃ | A1 | (2-acetoxy-2-methylpropanoyl)amino | H | H | H | Z | 3.15 [a] |
| 368 | H | H | H | H | H | CH₃ | A2 | [(3-chlorophenoxy)acetyl]amino | H | | | Z | 3.87 [a] |
| 369 | H | H | H | H | H | CH₃ | A1 | {[2-(4-methylphenyl)ethoxy]carbonyl}amino | H | H | H | Z | 4.53 [a] |
| 370 | H | fluoro | H | H | H | CH₃ | A2 | pentanoylamino | H | | | Z | 3.48 [a] |
| 371 | H | H | H | H | H | CH₃ | A1 | [(2,2-dichloro-1-isopropylcyclopropyl)carbonyl]amino | H | H | H | Z | 4.35 [a] |
| 372 | H | H | H | H | H | CH₃ | A1 | [(2,2-dimethylpropoxy)carbonyl]amino | H | H | H | Z | 4.36 [a] |
| 373 | H | H | H | H | H | CH₃ | A2 | (4-bromobenzoyl)amino | H | | | Z | 4.01 [a] |
| 374 | H | H | H | H | H | CH₃ | A1 | (6-bromohexanoyl)amino | H | H | H | Z | 3.85 [a] |
| 375 | H | H | H | H | H | CH₃ | A1 | [(4-methylphenyl)acetyl]amino | H | H | H | Z | 3.85 [a] |
| 376 | H | fluoro | H | H | H | CH₃ | A1 | hexanoylamino | H | H | H | Z | 3.99 [a] |
| 377 | H | H | H | H | H | CH₃ | A1 | (4-phenylbutanoyl)amino | H | H | H | Z | 4.04 [a] |
| 378 | H | H | H | H | H | CH₃ | A2 | (phenylacetyl)amino | H | | | Z | 3.37 [a] |
| 379 | H | H | H | H | H | CH₃ | A1 | (methoxyacetyl)amino | H | H | H | Z | 2.73 [a] |
| 380 | H | H | H | H | H | CH₃ | A1 | (3-bromobenzoyl)amino | H | H | H | Z | 4.16 [a] |
| 381 | H | H | H | H | H | CH₃ | A1 | (2-naphthylacetyl)amino | H | H | H | Z | 4.12 [a] |
| 382 | H | H | H | H | H | CH₃ | A1 | [(3-bromophenoxy)acetyl]amino | H | H | H | Z | 4.2 [a] |
| 383 | H | H | fluoro | H | H | CH₃ | A1 | {[(4-methylpentan-2-yl)oxy]carbonyl}amino | H | H | H | Z | 4.77 [a] |
| 384 | H | CH₃ | H | H | H | CH₃ | A1 | pentanoylamino | H | H | H | Z | 3.83 [a] |
| 385 | H | H | H | H | H | CH₃ | A1 | [(butylsulfanyl)carbothioyl]amino | H | H | H | Z | 4.8 [a] |
| 386 | H | H | H | H | H | CH₃ | A1 | (2-phenylbutanoyl)amino | H | H | H | Z | 4.23 [a] |
| 387 | H | CH₃ | H | H | H | CH₃ | A1 | (2,2-dimethylpropanoyl)amino | H | H | H | Z | 3.85 [a] |
| 388 | H | H | H | H | H | CH₃ | A1 | (cyclopentylcarbonyl)amino | H | H | H | Z | 3.62 [a] |
| 389 | H | H | H | H | H | CH₃ | A1 | (3-cyclobutylpropanoyl)amino | H | H | H | Z | 4.02 [a] |
| 390 | H | H | H | H | H | CH₃ | A1 | [2-(cyclopropylmethoxy)propanoyl]amino | H | H | H | Z | 3.78 [a] |
| 391 | H | CH₃ | H | H | H | CH₃ | A1 | (3-fluorobenzoyl)amino | H | H | H | Z | 3.99 [a] |
| 392 | H | H | CH₃ | H | H | CH₃ | A2 | (2,3-dihydro-1,4-benzodioxin-2-ylcarbonyl)amino | H | | | Z | 3.9 [a] |
| 393 | H | H | H | H | H | CH₃ | A2 | (4-methoxybenzoyl)amino | H | | | Z | 3.48 [a] |
| 394 | H | H | H | H | H | CH₃ | A2 | [(but-3-en-1-yloxy)carbonyl]amino | H | | | Z | 3.44 [a] |
| 395 | H | H | H | H | H | CH₃ | A1 | [(hex-5-yn-2-yloxy)carbonyl]amino | H | H | H | Z | 3.8 [a] |
| 396 | H | H | methoxy | H | H | CH₃ | A1 | (tert-butoxycarbonyl)amino | H | H | H | Z | 3.96 [a] |
| 397 | H | H | H | H | H | CH₃ | A1 | {[1-(4-methylphenyl)cyclopropyl]carbonyl}amino | H | H | H | Z | 4.76 [a] |
| 398 | H | H | H | H | H | CH₃ | A1 | [2-(2-methylphenoxy)propanoyl]amino | H | H | H | Z | 4.46 [a] |
| 399 | H | methoxy | H | H | H | CH₃ | A1 | (3-fluorobenzoyl)amino | H | H | H | Z | 3.72 [a] |
| 400 | H | H | H | H | H | CH₃ | A1 | [(2-ethoxyethoxy)carbonyl]amino | H | H | H | Z | 3.17 [a] |
| 401 | H | H | H | H | H | CH₃ | A1 | (3,4-dimethylbenzoyl)amino | H | H | H | Z | 4.16 [a] |
| 402 | H | H | H | H | H | CH₃ | A1 | [(4-chlorophenoxy)acetyl]amino | H | H | H | Z | 4.1 [a] |
| 403 | H | H | H | H | H | ethyl | A1 | (3-phenylpropanoyl)amino | H | H | H | Z | 4.01 [a] |
| 404 | H | H | H | H | H | CH₃ | A1 | (5-chloropentanoyl)amino | H | H | H | Z | 3.44 [a] |
| 405 | H | H | H | H | H | prop-2-en-1-yl | A1 | [(but-3-yn-1-yloxy)carbonyl]amino | H | H | H | Z | 3.61 [a] |
| 406 | H | fluoro | H | H | H | CH₃ | A1 | (pentyloxy)carbonyl]amino | H | H | H | Z | 4.53 [a] |
| 407 | H | methoxy | H | H | H | CH₃ | A1 | (2,2-dimethylpropanoyl)amino | H | H | H | Z | 3.55 [a] |
| 408 | H | H | H | H | H | CH₃ | A1 | [(3-cyclopentylpropoxy)carbonyl]amino | H | H | H | Z | 5.31 [a] |
| 409 | H | H | H | H | H | CH₃ | A1 | {[(2-methoxybenzyl)oxy]carbonyl}amino | H | H | H | Z | 4.06 [a] |
| 410 | H | H | H | H | H | CH₃ | A2 | (butoxycarbothioyl)amino | H | | | Z | 4.56 [a] |
| 411 | H | H | H | H | H | CH₃ | A1 | [(pyridin-4-ylmethoxy)carbonyl]amino | H | H | H | Z | 2.01 [a] |

TABLE 1-continued

| Ex-no | Y¹ | Y² | Y³ | Y⁴ | Y⁵ | X¹ | A | Z¹ | Z² | Z³ | Z⁴ | Stereo | LogP |
|---|---|---|---|---|---|---|---|---|---|---|---|---|---|
| 412 | H | H | H | H | H | CH₃ | A1 | {[(3-methyloxetan-3-yl)methoxy]carbonyl}amino | H | H | H | Z | 2.96 [a] |
| 413 | H | H | H | H | H | CH₃ | A1 | {[(2-chlorobenzyl)oxy]carbonyl}amino | H | H | H | Z | 4.34 [a] |
| 414 | H | H | H | H | H | CH₃ | A1 | [(but-2-yn-1-yloxy)carbonyl]amino | H | H | H | Z | 3.42 [a] |
| 415 | H | H | H | H | H | CH₃ | A1 | [(oct-2-yn-1-yloxy)carbonyl]amino | H | H | H | Z | 4.86 [a] |
| 416 | fluoro | fluoro | H | H | H | CH₃ | A1 | amino | H | H | H | E | 1.26 [a] |
| 417 | fluoro | fluoro | H | H | H | CH₃ | A1 | [(cyclohexyloxy)carbonyl]amino | H | H | H | Z | 4.46 [a] |
| 418 | H | H | H | H | H | CH₃ | A1 | [(hept-2-yn-1-yloxy)carbonyl]amino | H | H | H | Z | 4.51 [a] |
| 419 | H | H | H | H | H | CH₃ | A1 | [(heptyloxy)carbonyl]amino | H | H | H | Z | 5.25 [a] |
| 420 | fluoro | fluoro | H | H | H | CH₃ | A1 | pentanoylamino | H | H | H | Z | 3.55 [a] |
| 421 | H | H | H | H | H | CH₃ | A1 | (ethoxycarbonyl)amino | H | H | H | Z | 3.21 [a] |
| 422 | H | H | H | H | H | CH₃ | A1 | {[3-(trimethylsilyl)propoxy]carbonyl}amino | H | H | H | Z | 5.28 [a] |
| 423 | H | H | H | H | H | CH₃ | A1 | [(3,3-dimethylbutoxy)carbonyl]amino | H | H | H | Z | 4.68 [a] |
| 424 | H | H | H | H | H | CH₃ | A1 | {[3-chloro-2-(hydroxymethyl)-2-methylpropoxy]carbonyl}amino | H | H | H | Z | 3.19 [a] |
| 425 | H | H | H | H | H | CH₃ | A1 | [(4-methylphenoxy)carbonyl]amino | H | H | H | Z | 4.03 [a] |
| 426 | H | H | H | H | H | CH₃ | A1 | [(2-propylphenoxy)carbonyl]amino | H | H | H | Z | 4.54 [a] |
| 427 | H | H | H | H | H | CH₃ | A1 | [(propan-2-yloxy)carbonyl]amino | H | H | H | Z | 3.55 [a] |
| 428 | H | H | H | H | H | CH₃ | A1 | {[(2,6-dichlorobenzyl)oxy]carbonyl}amino | H | H | H | Z | 4.56 [a] |
| 429 | H | H | H | H | H | CH₃ | A1 | [(3-methoxybutoxy)carbonyl]amino | H | H | H | Z | 3.37 [a] |
| 430 | H | H | H | H | H | CH₃ | A1 | [(2-ethylphenoxy)carbonyl]amino | H | H | H | Z | 4.25 [a] |
| 431 | H | H | H | H | H | CH₃ | A1 | [(3-ethoxypropoxy)carbonyl]amino | H | H | H | Z | 3.44 [a] |
| 432 | H | H | H | H | H | CH₃ | A1 | {[(4-cyanobenzyl)oxy]carbonyl}amino | H | H | H | Z | 3.61 [a] |
| 433 | H | H | H | H | H | CH₃ | A1 | [(tetrahydro-2H-pyran-2-ylmethoxy)carbonyl]amino | H | H | H | Z | 3.5 [a] |
| 434 | H | H | H | H | H | CH₃ | A1 | [(pyridin-3-ylmethoxy)carbonyl]amino | H | H | H | Z | 2.17 [a] |
| 435 | H | H | H | H | H | CH₃ | A1 | [(3-ethylphenoxy)carbonyl]amino | H | H | H | Z | 4.34 [a] |
| 436 | H | H | H | H | H | CH₃ | A1 | [(pent-4-yn-1-yloxy)carbonyl]amino | H | H | H | Z | 3.51 [a] |
| 437 | H | H | H | H | H | CH₃ | A1 | [(pyridin-2-ylmethoxy)carbonyl]amino | H | H | H | Z | 2.64 [a] |
| 438 | H | H | H | H | H | CH₃ | A1 | [(2-cyclopropylethoxy)carbonyl]amino | H | H | H | Z | 4.01 [a] |
| 439 | H | H | H | H | H | CH₃ | A1 | {[2-(2-ethoxyethoxy)ethoxy]carbonyl}amino | H | H | H | Z | 3.13 [a] |
| 440 | H | H | H | H | H | CH₃ | A1 | {[(trimethylsilyl)methoxy]carbonyl}amino | H | H | H | Z | 4.53 [a] |
| 441 | H | H | H | H | H | CH₃ | A1 | {[(3-methoxybenzyl)oxy]carbonyl}amino | H | H | H | Z | 3.96 [a] |
| 442 | H | H | H | H | chloro | CH₃ | A2 | (2,3-dihydro-1,4-benzodioxin-2-ylcarbonyl)amino | H | | | Z | 3.73 [a] |
| 443 | H | H | H | H | H | CH₃ | A1 | ({[3-(trimethylsilyl)prop-2-yn-1-yl]oxy}carbonyl)amino | H | H | H | Z | 4.63 [a] |
| 444 | fluoro | H | H | H | H | CH₃ | A1 | [(pentyloxy)carbonyl]amino | H | H | H | Z | 4.34 [a] |
| 445 | H | H | H | H | H | CH₃ | A1 | {[(1,1,1-trichloro-2-methylpropan-2-yl)oxy]carbonyl}amino | H | H | H | Z | 4.91 [a] |
| 446 | H | H | H | H | H | CH₃ | A1 | {[(4-oxopentyl)oxy]carbonyl}amino | H | H | H | Z | 2.96 [a] |
| 447 | H | H | H | H | H | CH₃ | A1 | {[2-(2-chloroethoxy)ethoxy]carbonyl}amino | H | H | H | Z | 3.29 [a] |
| 448 | H | H | H | H | H | CH₃ | A1 | {[(4-methylpent-3-en-1-yl)oxy]carbonyl}amino | H | H | H | Z | 4.39 [a] |
| 449 | fluoro | H | H | H | H | CH₃ | A1 | (2-methylpentanoyl)amino | H | H | H | Z | 3.73 [a] |
| 450 | H | H | H | H | H | CH₃ | A1 | {[(4-methoxybenzyl)oxy]carbonyl}amino | H | H | H | Z | 3.92 [a] |
| 451 | H | H | H | H | H | CH₃ | A1 | [(2,4,4-trimethylpentyl)oxy)carbonyl}amino | H | H | H | Z | 5.39 [a] |
| 452 | H | H | H | H | H | CH₃ | A1 | [(hept-6-en-3-yn-1-yloxy)carbonyl]amino | H | H | H | Z | 4.01 [a] |
| 453 | H | H | H | H | H | CH₃ | A1 | {[(3Z)-hept-3-en-1-yloxy]carbonyl}amino | H | H | H | Z | 4.81 [a] |
| 454 | H | H | H | H | H | CH₃ | A1 | [(hex-5-en-1-yloxy)carbonyl]amino | H | H | H | Z | 4.39 [a] |
| 455 | H | H | H | H | H | CH₃ | A1 | [(hex-4-yn-2-yloxy)carbonyl]amino | H | H | H | Z | 3.89 [a] |
| 456 | H | H | H | H | H | CH₃ | A1 | [(2-phenoxyethoxy)carbonyl]amino | H | H | H | Z | 3.94 [a] |
| 457 | H | H | H | H | H | CH₃ | A1 | [(3-methoxy-3-methylbutoxy)carbonyl]amino | H | H | H | Z | 3.59 [a] |
| 458 | H | H | H | H | H | CH₃ | A1 | {[(3-methylbenzyl)oxy]carbonyl}amino | H | H | H | Z | 4.34 [a] |
| 459 | H | H | H | H | H | CH₃ | A1 | [(2-bromoethoxy)carbonyl]amino | H | H | H | Z | 3.42 [a] |
| 460 | fluoro | fluoro | H | H | H | H | A1 | (tert-butoxycarbonyl)amino | H | H | H | U | 3.76 [a] |
| 461 | H | H | H | H | H | CH₃ | A1 | [(2,2-dichloroethoxy)carbonyl]amino | H | H | H | Z | 3.74 [a] |
| 462 | H | H | H | H | H | CH₃ | A1 | l-4-[({[(1R,2S,5R)-2-isopropyl-5-methylcyclohexyl]oxy}carbonyl)amino] | H | H | H | Z | 5.9 [a] |
| 463 | H | H | H | H | H | CH₃ | A1 | {[(2-ethylhexyl)oxy]carbonyl}amino | H | H | H | Z | 5.54 [a] |
| 464 | fluoro | fluoro | H | H | H | CH₃ | A1 | hexanoylamino | H | H | H | Z | 3.92 [a] |
| 465 | H | H | H | H | H | CH₃ | A1 | [(octyloxy)carbonyl]amino | H | H | H | Z | 5.65 [a] |
| 466 | H | H | H | H | H | CH₃ | A1 | [(prop-1-en-2-yloxy)carbonyl]amino | H | H | H | Z | 3.37 [a] |
| 467 | H | H | H | H | H | CH₃ | A1 | [(4-propylphenoxy)carbonyl]amino | H | H | H | Z | 4.74 [a] |
| 468 | H | H | H | H | H | CH₃ | A1 | {[(3-phenylprop-2-yn-1-yl)oxy]carbonyl}amino | H | H | H | Z | 4.25 [a] |
| 469 | H | H | H | H | H | CH₃ | A1 | [(3-propylphenoxy)carbonyl]amino | H | H | H | Z | 4.72 [a] |
| 470 | H | H | H | H | H | CH₃ | A1 | [(mesityloxy)carbonyl]amino | H | H | H | Z | 4.56 [a] |
| 471 | H | H | H | H | H | CH₃ | A1 | {[2-(pyridin-2-yl)ethoxy]carbonyl}amino | H | H | H | Z | 2.07 [a] |
| 472 | H | H | H | H | H | CH₃ | A1 | [(3-(dimethylamino)propoxy]carbonyl}amino | H | H | H | Z | 1.88 [a] |
| 473 | H | H | H | H | H | CH₃ | A1 | [(cyclopropylmethoxy)carbonyl]amino | H | H | H | Z | 3.64 [a] |
| 474 | H | H | H | H | H | CH₃ | A1 | {[(2-oxo-1,3-dioxolan-4-yl)methoxy]carbonyl}amino | H | H | H | Z | 2.75 [a] |
| 475 | H | H | H | H | H | CH₃ | A1 | {[(1-cyclopropylpropan-2-yl)oxy]carbonyl}amino | H | H | H | Z | 4.32 [a] |
| 476 | H | H | H | H | H | CH₃ | A1 | 4-{[(4-nitrobenzyl)oxy]carbonyl}amino | H | H | H | Z | 3.83 [a] |
| 477 | H | H | H | H | H | CH₃ | A1 | {[(3-cyanobenzyl)oxy]carbonyl}amino | H | H | H | Z | 3.65 [a] |
| 478 | H | H | H | H | H | CH₃ | A1 | [(4-ethylphenoxy)carbonyl]amino | H | H | H | Z | 4.39 [a] |
| 479 | H | H | H | H | H | CH₃ | A1 | [(pent-4-en-2-yloxy)carbonyl]amino | H | H | H | Z | 4.01 [a] |
| 480 | fluoro | H | H | H | H | CH₃ | A1 | pentanoylamino | H | H | H | Z | 3.44 [a] |
| 481 | H | H | H | H | chloro | CH₃ | A2 | pentanoylamino | H | | | Z | 3.53 [a] |
| 482 | H | H | H | H | H | CH₃ | A1 | [(vinyloxy)carbonyl]amino | H | H | H | Z | 3.33 [a] |
| 483 | H | H | H | H | H | CH₃ | A1 | [(tetrahydrofuran-2-ylmethoxy)carbonyl]amino | H | H | H | Z | 3.11 [a] |
| 484 | H | H | H | H | H | CH₃ | A1 | [(hex-5-yn-1-yloxy)carbonyl]amino | H | H | H | Z | 3.78 [a] |

TABLE 1-continued

| Ex-no | Y¹ | Y² | Y³ | Y⁴ | Y⁵ | X¹ | A | Z¹ | Z² | Z³ | Z⁴ | Stereo | LogP |
|---|---|---|---|---|---|---|---|---|---|---|---|---|---|
| 485 | H | H | H | H | H | CH₃ | A1 | [(1-cyclohexylethoxy)carbonyl]amino | H | H | H | Z | 5.25 [a] |
| 486 | H | H | H | H | H | CH₃ | A1 | {[(6-chlorohexyl)oxy]carbonyl}amino | H | H | H | Z | 4.49 [a] |
| 487 | H | H | H | H | H | CH₃ | A1 | {[(2-methylbenzyl)oxy]carbonyl}amino | H | H | H | Z | 4.29 [a] |
| 488 | H | H | H | H | H | CH₃ | A1 | {[(4Z)-hept-4-en-1-yloxy]carbonyl}amino | H | H | H | Z | 4.78 [a] |
| 489 | H | H | H | H | H | CH₃ | A1 | [(3-methoxy-2,2-dimethyl-3-oxopropoxy)carbonyl]amino | H | H | H | Z | 3.65 [a] |
| 490 | H | H | H | H | H | CH₃ | A1 | {[2-(allyloxy)ethoxy]carbonyl}amino | H | H | H | Z | 3.37 [a] |
| 491 | H | H | H | H | H | CH₃ | A1 | [(3-methoxy-2-methyl-3-oxopropoxy)carbonyl]amino | H | H | H | Z | 3.33 [a] |
| 492 | H | H | H | H | H | CH₃ | A1 | [(4-isopropylphenoxy)carbonyl]amino | H | H | H | Z | 4.67 [a] |
| 493 | H | H | H | H | chloro | CH₃ | A2 | (2-phenoxypropanoyl)amino | H | | | Z | 3.81 [a] |
| 494 | H | H | H | H | H | CH₃ | A1 | [(2,6-dimethylphenoxy)carbonyl]amino | H | H | H | Z | 4.2 [a] |
| 495 | H | H | H | H | H | CH₃ | A1 | {[(2-fluorobenzyl)oxy]carbonyl}amino | H | H | H | Z | 4.01 [a] |
| 496 | H | H | H | H | H | CH₃ | A1 | {[2-(cyclohexyloxy)ethoxy]carbonyl}amino | H | H | H | Z | 4.31 [a] |
| 497 | H | H | H | H | H | CH₃ | A1 | {[3-(pyridin-3-yl)propoxy]carbonyl}amino | H | H | H | Z | 2.11 [a] |
| 498 | H | H | H | H | H | CH₃ | A1 | {[(3,5-dimethylbenzyl)oxy]carbonyl}amino | H | H | H | Z | 4.68 [a] |
| 499 | H | H | H | H | chloro | CH₃ | A2 | [(but-3-yn-1-yloxy)carbonyl]amino | H | | | Z | 3.19 [a] |
| 500 | H | H | H | H | H | CH₃ | A1 | [(2,2,2-trifluoroethoxy)carbonyl]amino | H | H | H | Z | 3.57 [a] |
| 501 | H | H | H | H | H | CH₃ | A1 | {[(3-fluorobenzyl)oxy]carbonyl}amino | H | H | H | Z | 4.01 [a] |
| 502 | H | H | H | H | H | CH₃ | A1 | [(1-cyclopentylethoxy)carbonyl]amino | H | H | H | Z | 4.82 [a] |
| 503 | H | H | H | H | H | CH₃ | A1 | [(pent-2-yn-1-yloxy)carbonyl]amino | H | H | H | Z | 3.78 [a] |
| 504 | H | H | H | H | H | CH₃ | A1 | {[(2-methylprop-2-en-1-yl)oxy]carbonyl}amino | H | H | H | Z | 3.73 [a] |
| 505 | H | H | H | H | H | CH₃ | A1 | {[(4Z)-hex-4-en-1-yloxy]carbonyl}amino | H | H | H | Z | 4.39 [a] |
| 506 | H | H | H | H | H | CH₃ | A1 | {[(5-methylhexyl)oxy]carbonyl}amino | H | H | H | Z | 5.17 [a] |
| 507 | H | H | H | H | H | CH₃ | A1 | {[(2E)-hex-2-en-1-yloxy]carbonyl}amino | H | H | H | Z | 4.56 [a] |
| 508 | fluoro | fluoro | H | H | H | CH₃ | A1 | amino | H | H | H | Z | 1.34 [a] |
| 509 | H | H | H | H | H | CH₃ | A1 | {[(4E)-hex-4-en-1-yloxy]carbonyl}amino | H | H | H | Z | 4.44 [a] |
| 510 | fluoro | H | H | H | H | CH₃ | A1 | amino | H | H | H | Z | 1.23 [a] |
| 511 | H | H | H | H | H | CH₃ | A1 | [(hept-3-yn-1-yloxy)carbonyl]amino | H | H | H | Z | 4.31 [a] |
| 512 | H | H | H | H | H | CH₃ | A2 | [(butylsulfanyl)carbothioyl]amino | H | | | Z | 4.81 [a] |
| 513 | fluoro | H | H | H | H | CH₃ | A1 | hexanoylamino | H | H | H | Z | 3.81 [a] |
| 514 | H | H | H | H | H | CH₃ | A1 | [(4-acetoxybutoxy)carbonyl]amino | H | H | H | Z | 3.35 [a] |
| 515 | H | H | H | H | H | CH₃ | A1 | {[2-(acryloyloxy)ethoxy]carbonyl}amino | H | H | H | Z | 3.21 [a] |
| 516 | H | H | H | H | H | CH₃ | A1 | {[3-(methylsulfanyl)propoxy]carbonyl}amino | H | H | H | Z | 3.68 [a] |
| 517 | H | H | H | H | H | CH₃ | A1 | l-4-[({[(1R,2S,5R)-2-isopropyl-5-methylcyclohexyl]oxy}carbonyl)amino] | H | H | H | Z | 5.9 [a] |
| 518 | H | H | H | H | H | CH₃ | A1 | [(2-chloroethoxy)carbonyl]amino | H | H | H | Z | 3.29 [a] |
| 519 | H | H | H | H | chloro | CH₃ | A2 | (butoxycarbonyl)amino | H | | | Z | 3.85 [a] |
| 520 | H | H | H | H | H | CH₃ | A1 | {[(3-ethyloxetan-3-yl)methoxy]carbonyl}amino | H | H | H | Z | 3.27 [a] |
| 521 | H | H | H | H | H | CH₃ | A1 | [(2-methylphenoxy)carbonyl]amino | H | H | H | Z | 3.96 [a] |
| 522 | H | H | H | H | H | CH₃ | A1 | {[(3E)-hex-3-en-1-yloxy]carbonyl}amino | H | H | H | Z | 4.46 [a] |
| 523 | H | H | H | H | H | CH₃ | A1 | [(3-cyclohexylpropoxy)carbonyl]amino | H | H | H | Z | 5.71 [a] |
| 524 | H | H | H | H | H | CH₃ | A1 | [(tetrahydrofuran-3-ylmethoxy)carbonyl]amino | H | H | H | Z | 2.98 [a] |
| 525 | fluoro | H | H | H | H | CH₃ | A1 | [(but-3-yn-1-yloxy)carbonyl]amino | H | H | H | Z | 3.21 [a] |
| 526 | H | H | H | H | H | CH₃ | A1 | [(cyclohex-3-en-1-ylmethoxy)carbonyl]amino | H | H | H | Z | 4.51 [a] |
| 527 | H | H | H | H | H | CH₃ | A1 | [(2-thienylmethoxy)carbonyl]amino | H | H | H | Z | 3.83 [a] |
| 528 | H | H | H | H | H | CH₃ | A1 | {[(4-fluorobenzyl)oxy]carbonyl}amino | H | H | H | Z | 3.99 [a] |
| 529 | H | H | H | H | H | CH₃ | A1 | [(1,3-dioxolan-4-ylmethoxy)carbonyl]amino | H | H | H | Z | 2.73 [a] |
| 530 | H | H | H | H | chloro | CH₃ | A2 | [(pentyloxy)carbonyl]amino | H | | | Z | 4.25 [a] |
| 531 | H | H | H | H | H | CH₃ | A1 | [(2-propoxyethoxy)carbonyl]amino | H | H | H | Z | 3.57 [a] |
| 532 | H | H | H | H | H | CH₃ | A1 | [(4-methoxyphenoxy)carbonyl]amino | H | H | H | Z | 3.69 [a] |
| 533 | H | H | H | H | H | CH₃ | A1 | [(2-cyclopentylethoxy)carbonyl]amino | H | H | H | Z | 4.9 [a] |
| 534 | fluoro | fluoro | H | H | H | CH₃ | A1 | [(but-3-yn-1-yloxy)carbonyl]amino | H | H | H | Z | 3.31 [a] |
| 535 | H | H | H | H | H | CH₃ | A1 | {[(2Z)-hex-2-en-1-yloxy]carbonyl}amino | H | H | H | Z | 4.53 [a] |
| 536 | H | H | H | H | H | CH₃ | A1 | [(2,2,2-trichloroethoxy)carbonyl]amino | H | H | H | Z | 4.15 [a] |
| 537 | H | H | H | H | H | CH₃ | A1 | {[2-(tetrahydro-2H-pyran-4-yl)ethoxy]carbonyl}amino | H | H | H | Z | 3.44 [a] |
| 538 | H | H | H | H | chloro | CH₃ | A2 | hexanoylamino | H | | | Z | 3.89 [a] |
| 539 | H | H | H | H | chloro | CH₃ | A2 | [(tert-butylsulfanyl)carbonyl]amino | H | | | Z | 4.04 [a] |
| 540 | H | H | H | H | H | CH₃ | A1 | {[(3Z)-hex-3-en-1-yloxy]carbonyl}amino | H | H | H | Z | 4.44 [a] |
| 541 | H | H | H | H | H | CH₃ | A1 | [(cyclohexylmethoxy)carbonyl]amino | H | H | H | Z | 4.88 [a] |
| 542 | H | H | H | H | H | CH₃ | A1 | {[2-(trimethylsilyl)ethoxy]carbonyl}amino | H | H | H | Z | 4.88 [a] |
| 543 | H | H | H | H | chloro | CH₃ | A2 | (phenylacetyl)amino | H | | | Z | 3.51 [a] |
| 544 | H | H | H | H | H | CH₃ | A1 | [(3-chloropropoxy)carbonyl]amino | H | H | H | Z | 3.6 [a] |
| 545 | H | H | H | H | H | CH₃ | A1 | [(2-isopropoxyethoxy)carbonyl]amino | H | H | H | Z | 3.44 [a] |
| 546 | H | H | H | H | H | CH₃ | A1 | {[(4-methylbenzyl)oxy]carbonyl}amino | H | H | H | Z | 4.31 [a] |
| 547 | H | H | H | H | H | CH₃ | A1 | (methoxycarbonyl)amino | H | H | H | Z | 2.84 [a] |
| 548 | H | H | H | H | H | CH₃ | A1 | [(pent-3-yn-1-yloxy)carbonyl]amino | H | H | H | Z | 3.58 [a] |
| 549 | H | H | H | H | H | CH₃ | A1 | [(3-cyclopropylpropoxy)carbonyl]amino | H | H | H | Z | 4.37 [a] |
| 550 | H | H | H | H | H | CH₃ | A1 | [(4-chlorobutoxy)carbonyl]amino | H | H | H | Z | 3.83 [a] |
| 551 | H | H | H | H | H | CH₃ | A1 | [(2-fluoroethoxy)carbonyl]amino | H | H | H | Z | 2.96 [a] |
| 552 | fluoro | H | H | H | H | CH₃ | A1 | (butoxycarbonyl)amino | H | H | H | Z | 3.92 [a] |
| 553 | H | H | H | H | H | CH₃ | A1 | [(3-isopropylphenoxy)carbonyl]amino | H | H | H | Z | 4.64 [a] |
| 554 | H | H | H | H | H | CH₃ | A1 | [(2-ethoxy-2-oxoethoxy)carbonyl]amino | H | H | H | Z | 3.21 [a] |

We describe the double bond geometry of the examples of table 1 as shown here:

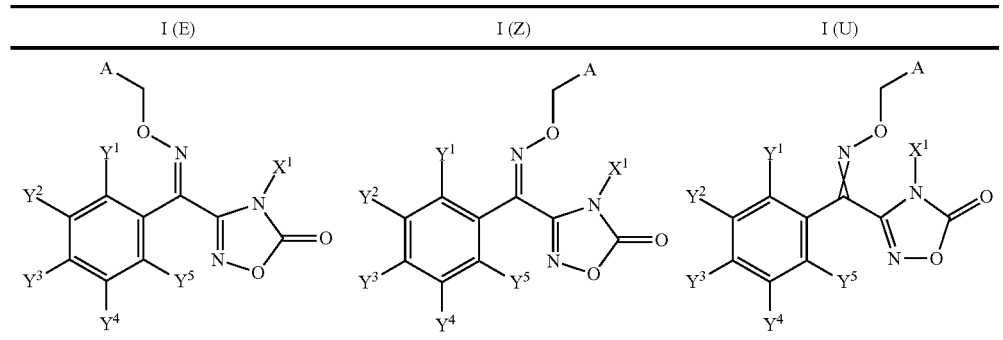

| I (E) | I (Z) | I (U) |

Measurement of log P values was performed according EEC directive 79/831 Annex V.A8 by HPLC (High Performance Liquid Chromatography) on reversed phase columns with the following methods: [a]Measurement of LC-MS was done at pH 2.7 with 0.1% formic acid in water and with acetonitrile (contains 0.1% formic acid) as eluent with a linear gradient from 10% acetonitrile to 95% acetonitrile. Calibration was done with not branched alkan2-ones (with 3 to 16 carbon atoms) with known log P-values (measurement of log P values using retention times with linear interpolation between successive alkanones). lambda-maX-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value-signal intensity pairs are semicolons as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$)

NMR Peak List Table 1

Example 1, Solvent: DMSO, Spectrometer: 499.93 MHz 7.7706 (0.59); 7.7438 (4.33); 7.7288 (4.77); 7.5449 (0.82); 7.5304 (2.27); 7.5160 (2.14); 7.4914 (3.65); 7.4760 (4.63); 7.4616 (1.97); 7.4219 (0.60); 7.4140 (1.79); 7.4072 (1.18); 7.3987 (2.87); 7.3831 (1.80); 6.5450 (2.86); 6.5306 (2.81); 6.4357 (2.85); 6.4192 (2.83); 6.0594 (6.23); 5.7816 (0.67); 5.2149 (9.25); 3.8061 (2.02); 3.4478 (3.34); 3.1218 (16.00); 2.5112 (0.36); 1.9897 (0.98); 1.1684 (0.52)

Example 2, Solvent: DMSO, Spectrometer: 499.93 MHz 10.1848 (2.68); 7.8340 (0.41); 7.8171 (2.04); 7.8092 (2.38); 7.8049 (4.86); 7.7925 (0.52); 7.7304 (2.61); 7.7200 (0.87); 7.7161 (3.25); 7.7132 (2.46); 7.5673 (0.55); 7.5649 (0.37); 7.5570 (0.44); 7.5526 (1.61); 7.5485 (0.57); 7.5404 (0.83); 7.5379 (1.32); 7.5354 (0.74); 7.5019 (2.27); 7.4992 (1.12); 7.4945 (0.53); 7.4890 (1.84); 7.4864 (3.15); 7.4752 (0.50); 7.4720 (1.29); 7.4701 (0.87); 7.1088 (1.26); 7.1041 (1.26); 7.0969 (1.13); 7.0922 (1.23); 5.3400 (6.66); 4.1044 (2.03); 4.0909 (4.22); 4.0775 (2.01); 3.9490 (1.03); 3.3400 (81.74); 3.3162 (1.90); 3.0753 (16.00); 2.5194 (2.79); 2.5159 (5.86); 2.5123 (8.04); 2.5086 (5.91); 2.5051 (2.84); 1.6318 (0.90); 1.6267 (0.73); 1.6181 (1.44); 1.6095 (0.75); 1.6044 (1.04); 1.5907 (0.33); 1.3485 (1.15); 1.3403 (1.83); 1.3343 (3.86); 1.3274 (2.69); 1.3199 (2.61); 1.3080 (0.47); 0.9041 (1.80); 0.8992 (1.09); 0.8901 (4.83); 0.8758 (1.55); 0.7455 (0.48); 0.7313 (0.97); 0.7167 (0.46)

Example 3, Solvent: DMSO, Spectrometer: 499.93 MHz 10.3221 (2.70); 7.8439 (0.69); 7.8271 (1.82); 7.8132 (2.25); 7.8065 (2.30); 7.8042 (2.59); 7.7899 (0.89); 7.7876 (0.69); 7.7313 (2.88); 7.7206 (0.96); 7.7168 (3.44); 7.7140 (2.62); 7.5687 (0.36); 7.5666 (0.59); 7.5643 (0.41); 7.5562 (0.49); 7.5518 (1.75); 7.5479 (0.61); 7.5395 (0.86); 7.5371 (1.36); 7.5348 (0.79); 7.5014 (2.47); 7.4859 (3.37); 7.4746 (0.61); 7.4715 (1.36); 7.1244 (1.53); 7.1222 (1.55); 7.1106 (1.49); 7.1084 (1.47); 5.3445 (6.98); 4.1960 (2.15); 4.1827 (4.65); 4.1693 (2.20); 4.0453 (0.95); 4.0310 (0.96); 4.0168 (0.33); 3.3394 (10.40); 3.3158 (0.46); 3.0794 (16.00); 2.9191 (1.40); 2.9138 (2.99); 2.9086 (1.44); 2.5789 (1.32); 2.5736 (1.41); 2.5656 (2.78); 2.5603 (2.73); 2.5522 (1.41); 2.5470 (1.27); 2.5192 (1.44); 2.5157 (2.92); 2.5122 (3.96); 2.5086 (2.93); 2.5052 (1.43); 1.9989 (4.08); 1.2525 (0.88); 1.2416 (0.43); 1.1980 (1.09); 1.1838 (2.15); 1.1695 (1.06); 0.8802 (0.51); 0.8666 (1.42); 0.8523 (0.63)

Example 4, Solvent: DMSO, Spectrometer: 499.93 MHz 7.7446 (3.01); 7.7343 (1.08); 7.7303 (3.49); 7.7274 (2.72); 7.5671 (0.40); 7.5648 (0.64); 7.5624 (0.51); 7.5550 (0.54); 7.5500 (1.77); 7.5458 (0.74); 7.5380 (1.00); 7.5355 (1.54); 7.5330 (0.99); 7.5076 (2.63); 7.4950 (1.98); 7.4922 (3.49); 7.4813 (0.74); 7.4781 (1.41); 7.4759 (0.98); 7.4708 (0.32); 7.0072 (3.79); 6.6393 (3.47); 5.1287 (6.93); 3.3423 (7.56); 3.0610 (16.00); 2.5195 (0.60); 2.5160 (1.19); 2.5124 (1.61); 2.5088 (1.24); 2.5055 (0.65); 1.9990 (1.19); 1.1984 (0.33); 1.1841 (0.64)

Example 5, Solvent: DMSO, Spectrometer: 400.13 MHz 10.1669 (3.24); 7.8318 (0.50); 7.8107 (2.28); 7.8007 (2.67); 7.7955 (5.24); 7.7800 (0.66); 7.7267 (2.91); 7.7088 (3.58); 7.7051 (2.67); 7.5666 (0.54); 7.5548 (0.45); 7.5483 (1.75); 7.5428 (0.62); 7.5301 (1.52); 7.4995 (2.65); 7.4803 (3.35); 7.4627 (1.30); 7.1047 (1.40); 7.0989 (1.39); 7.0899 (1.27); 7.0841 (1.35); 5.3335 (7.04); 4.1468 (1.93); 4.1298 (4.09); 4.1128 (2.01); 3.3279 (116.65); 3.0694 (16.00); 2.5155 (20.77); 2.5113 (40.74); 2.5069 (54.41); 2.5025 (40.18); 2.3339 (0.36); 1.7244 (1.24); 1.6879 (2.13); 1.6484 (1.50); 1.6310 (0.97); 1.6032 (0.68); 1.5377 (0.90); 1.5207 (2.62); 1.5036 (2.95); 1.4868 (1.20); 1.4125 (0.38); 1.4042 (0.46); 1.3960 (0.53); 1.3861 (0.55); 1.3781 (0.51); 1.3695 (0.50); 1.3613 (0.41); 1.2526 (0.44); 1.2221 (0.95); 1.1924 (1.39); 1.1656 (1.61); 1.1514 (0.63); 1.1439 (0.80); 1.1140 (0.48); 0.9629 (0.59); 0.9341 (1.29); 0.9043 (1.16); 0.8809 (0.48)

Example 6, Solvent: DMSO, Spectrometer: 400.13 MHz 10.1987 (3.02); 7.8363 (0.49); 7.8152 (2.33); 7.8063 (2.70); 7.8005 (5.45); 7.7855 (0.64); 7.7274 (2.92); 7.7095 (3.63); 7.7058 (2.67); 7.5662 (0.57); 7.5631 (0.41); 7.5543 (0.50); 7.5479 (1.77); 7.5423 (0.64); 7.5329 (1.08); 7.5297 (1.56); 7.5265 (0.90); 7.4995 (2.64); 7.4838 (1.99);

NMR Peak List Table 1

7.4803 (3.33); 7.4666 (0.69); 7.4627 (1.34); 7.4596 (0.86); 7.1087 (1.39); 7.1025 (1.38); 7.0941 (1.24); 7.0880 (1.33); 5.8795 (0.66); 5.8705 (0.38); 5.8631 (0.38); 5.8538 (0.97); 5.8369 (1.00); 5.8276 (0.43); 5.8202 (0.42); 5.8111 (0.78); 5.7947 (0.39); 5.7612 (1.46); 5.3376 (7.02); 5.0854 (0.55); 5.0814 (1.22); 5.0766 (1.29); 5.0726 (0.61); 5.0424 (0.95); 5.0337 (1.18); 5.0297 (0.58); 5.0055 (1.28); 5.0031 (1.17); 5.0006 (1.14); 4.9801 (1.20); 4.9775 (1.09); 4.9751 (1.07); 4.1127 (2.11); 4.0961 (4.43); 4.0796 (2.18); 3.3305 (40.52); 3.0706 (16.00); 2.5155 (7.99); 2.5112 (15.37); 2.5068 (20.26); 2.5024 (14.84); 2.1528 (0.71); 2.1352 (1.78); 2.1182 (1.83); 2.1159 (1.84); 2.0991 (0.87); 1.7438 (0.62); 1.7270 (1.73); 1.7079 (2.23); 1.6904 (1.66); 1.6733 (0.57)
Example 7, Solvent: DMSO, Spectrometer: 400.13 MHz 10.2520 (3.20); 7.8262 (0.66); 7.8052 (2.02); 7.7880 (3.89); 7.7829 (2.83); 7.7658 (0.83); 7.7279 (3.00); 7.7100 (3.67); 7.7063 (2.76); 5.5667 (0.56); 7.5636 (0.41); 7.5547 (0.48); 7.5483 (1.79); 7.5428 (0.66); 7.5332 (1.07); 7.5302 (1.56); 7.4998 (2.71); 7.4806 (3.42); 7.4669 (0.71); 7.4629 (1.37); 7.4599 (0.90); 7.3152 (9.49); 7.3043 (10.60); 7.2859 (0.54); 7.2827 (0.54); 7.2547 (0.43); 7.2454 (0.89); 7.2350 (1.32); 7.2241 (1.45); 7.2137 (0.79); 7.2021 (0.42); 7.1087 (1.55); 7.1049 (1.57); 7.0921 (1.47); 7.0883 (1.49); 5.7617 (5.40); 5.3363 (6.96); 4.3097 (1.95); 4.2925 (4.25); 4.2752 (2.06); 3.3342 (34.82); 3.0676 (16.00); 2.9561 (1.94); 2.9389 (3.94); 2.9217 (1.88); 2.5113 (12.99); 2.5069 (17.15); 2.5025 (12.65); 1.9933 (0.37)
Example 8, Solvent: DMSO, Spectrometer: 400.13 MHz 10.5083 (2.38); 8.0760 (1.44); 8.0553 (1.72); 7.8355 (1.33); 7.8161 (1.97); 7.7959 (1.24); 7.7279 (2.88); 7.7100 (3.57); 7.7063 (2.65); 7.5683 (0.55); 7.5651 (0.40); 7.5564 (0.47); 7.5500 (1.75); 7.5444 (0.63); 7.5349 (1.04); 7.5317 (1.52); 7.5007 (2.62); 7.4815 (3.32); 7.4677 (0.67); 7.4638 (1.32); 7.1445 (1.98); 7.1261 (1.92); 5.7617 (1.80); 5.3578 (6.81); 3.3305 (52.69); 3.0573 (16.00); 2.5155 (10.46); 2.5113 (20.34); 2.5069 (27.02); 2.5025 (19.91); 2.3963 (1.83); 2.3779 (3.38); 2.3594 (2.01); 1.5833 (0.93); 1.5670 (1.45); 1.5494 (1.15); 1.5310 (0.46); 1.2683 (6.34); 1.2651 (6.26); 0.8766 (1.79); 0.8598 (5.70); 0.8425 (2.16)
Example 9, Solvent: DMSO, Spectrometer: 400.13 MHz 12.1173 (2.55); 7.7390 (2.96); 7.7213 (3.56); 7.7176 (2.64); 7.5667 (0.50); 7.5636 (0.37); 7.5552 (0.41); 7.5483 (1.74); 7.5427 (0.60); 7.5335 (1.03); 7.5303 (1.57); 7.5051 (2.73); 7.4859 (3.34); 7.4724 (0.59); 7.4684 (1.25); 7.4650 (0.82); 7.2615 (4.30); 5.7612 (3.17); 5.3238 (6.70); 3.3346 (29.08); 3.0167 (16.00); 2.5111 (11.26); 2.5067 (14.95); 2.5024 (10.94); 2.4226 (1.84); 2.4042 (3.55); 2.3856 (2.02); 1.9928 (0.56); 1.5958 (0.97); 1.5790 (1.49); 1.5613 (1.14); 1.5430 (0.39); 1.2590 (6.75); 1.1781 (0.36); 0.8689 (1.89); 0.8599 (2.02); 0.8524 (5.93); 0.8351 (2.14)
Example 10, Solvent: DMSO, Spectrometer: 400.13 MHz 12.5590 (1.60); 7.7403 (2.99); 7.7225 (3.67); 7.7188 (2.71); 7.5698 (0.58); 7.5667 (0.43); 7.5582 (0.50); 7.5515 (1.82); 7.5457 (0.69); 7.5366 (1.17); 7.5334 (1.66); 7.5074 (2.81); 7.4883 (3.46); 7.4747 (1.75); 7.4707 (1.26); 7.4674 (0.92); 7.3697 (4.69); 7.0148 (1.41); 6.9960 (1.86); 6.9939 (1.79); 6.9214 (0.33); 6.9149 (0.79); 6.9073 (0.97); 6.9001 (1.09); 6.8926 (1.62); 6.8884 (0.78); 6.8804 (0.96); 6.8733 (2.00); 6.8624 (5.17); 6.8583 (3.48); 6.8473 (1.45); 6.8435 (1.38); 6.8320 (0.37); 6.8274 (0.40); 6.8236 (0.37); 5.7612 (5.24); 5.3492 (6.42); 5.1539 (1.22); 5.1452 (2.37); 5.1356 (1.29); 4.4359 (2.83); 4.4333 (2.89); 4.4258 (3.48); 4.4034 (0.38); 4.0429 (0.50); 4.0252 (0.50); 3.3306 (35.81); 3.2961 (0.61); 3.0174 (16.00); 2.5153 (10.91); 2.5112 (20.83); 2.5068 (27.33); 2.5024 (19.99); 1.9938 (2.16); 1.2405 (0.35); 1.1972 (0.60); 1.1794 (1.16); 1.1616 (0.60)
Example 11, Solvent: DMSO, Spectrometer: 400.13 MHz 12.3858 (1.35); 7.7445 (2.97); 7.7267 (3.64); 7.7230 (2.75); 7.5705 (0.54); 7.5676 (0.41); 7.5591 (0.46); 7.5522 (1.78); 7.5465 (0.67); 7.5374 (1.11); 7.5342 (1.65); 7.5089 (2.78); 7.4935 (1.99); 7.4898 (3.45); 7.4765 (0.75); 7.4723 (1.39); 7.4688 (0.97); 7.3613 (4.75); 7.1264 (0.72); 7.1081 (1.50); 7.0873 (1.38); 7.0804 (2.10); 7.0602 (2.42); 7.0391 (0.87); 6.8995 (2.03); 6.8791 (1.79); 6.8735 (1.39); 6.8549 (1.91); 6.8437 (0.76); 6.8409 (0.85); 6.8366 (1.03); 6.8339 (0.95); 6.8252 (0.93); 6.8226 (1.05); 6.8070 (1.35); 6.7868 (0.85); 5.3532 (6.46); 4.9141 (1.07); 4.9057 (1.24); 4.8938 (1.34); 4.8854 (1.16); 4.7823 (0.51); 4.7725 (0.59); 4.7660 (0.63); 4.7562 (0.53); 3.3355 (12.66); 3.3037 (0.88); 3.0259 (16.00); 2.8393 (0.37); 2.8332 (0.36); 2.8122 (0.70); 2.7920 (0.85); 2.7780 (0.65); 2.7664 (0.95); 2.7506 (0.33); 2.7264 (0.51); 2.7127 (1.04); 2.6981 (0.63); 2.6851 (0.42); 2.6713 (0.89); 2.6570 (0.64); 2.6377 (0.35); 2.5154 (9.57); 2.5113 (18.71); 2.5069 (24.93); 2.5025 (18.54); 2.2459 (0.49); 2.2373 (0.50); 2.2257 (0.53); 2.2173 (0.54); 2.2115 (0.77); 2.2029 (0.73); 2.1881 (0.42); 2.1535 (0.37); 2.1434 (0.39); 2.1393 (0.34); 2.1335 (0.37); 2.1294 (0.35); 2.1190 (0.51); 2.1045 (0.51); 2.0964 (0.73); 2.0828 (1.00); 2.0629 (1.15); 2.0478 (0.70); 2.0290 (0.42); 1.9938 (1.29); 1.1969 (0.35); 1.1791 (0.66); 1.1614 (0.34)
Example 12, Solvent: DMSO, Spectrometer: 400.13 MHz 11.7576 (2.06); 7.7345 (3.08); 7.7167 (3.65); 7.7130 (2.74); 7.5665 (0.55); 7.5633 (0.42); 7.5548 (0.49); 7.5481 (1.79); 7.5426 (0.64); 7.5301 (1.62); 7.5040 (2.81); 7.4849 (3.46); 7.4674 (1.30); 7.4639 (0.97); 7.5625 (2.56); 5.2861 (6.90); 4.1729 (0.33); 4.1617 (2.16); 4.1450 (4.50); 4.1283 (2.17); 3.3325 (76.53); 3.3085 (0.60); 3.0339 (16.00); 2.9930 (0.62); 2.5110 (32.54); 2.5067 (42.65); 2.5023 (31.20); 1.9936 (0.64); 1.6427 (1.23); 1.6256 (1.91); 1.6083 (1.33); 1.5910 (0.43); 1.3398 (1.29); 1.3306 (2.58); 1.3223 (4.17); 1.3130 (4.16); 1.3044 (2.61); 1.2388 (0.33); 1.1791 (0.38); 0.8967 (2.30); 0.8793 (6.15); 0.8616 (2.11)
Example 13, Solvent: DMSO, Spectrometer: 400.13 MHz 12.1083 (2.32); 7.7383 (2.90); 7.7255 (1.04); 7.7205 (3.51); 7.7167 (2.62); 7.5682 (0.54); 7.5567 (0.47); 7.5497 (1.76); 7.5441 (0.65); 7.5349 (1.06); 7.5318 (1.60); 7.5068 (2.76); 7.4914 (1.91); 7.4876 (3.36); 7.4742 (0.69); 7.4701 (1.31); 7.4667 (0.87); 7.2592 (4.09); 5.7579 (2.07); 5.3244 (6.84); 3.3214 (68.27); 3.3016 (1.27); 3.0191 (16.00); 2.5157 (9.34); 2.5115 (18.35); 2.5070 (24.67); 2.5026 (18.27); 2.4986 (9.55); 2.4320 (2.28); 2.4136 (3.88); 2.3949 (2.39); 1.9935 (0.74); 1.6087 (0.56); 1.5905 (1.62); 1.5717 (2.29); 1.5532 (1.76); 1.5342 (0.75); 1.3431 (0.37); 1.3244 (1.27); 1.3055 (2.11); 1.2868 (2.15); 1.2686 (1.36); 1.2505 (0.58); 1.2402 (0.40); 1.1802 (0.44); 0.8973 (4.48); 0.8790 (8.83); 0.8606 (3.98)
Example 14, Solvent: DMSO, Spectrometer: 400.13 MHz 11.7455 (1.91); 7.7336 (2.82); 7.7210 (1.05); 7.7159 (3.56); 7.7121 (2.61); 7.5665 (0.53); 7.5634 (0.40); 7.5550 (0.47); 7.5481 (1.75); 7.5424 (0.64); 7.5334 (1.07); 7.5301 (1.60); 7.5268 (0.91); 7.5045 (2.69); 7.4893 (1.90); 7.4854 (3.33); 7.4720 (0.69); 7.4679 (1.36); 7.4644 (1.02); 7.2529 (4.15); 5.7580 (2.45); 5.2874 (6.51); 4.1724 (2.20); 4.1558 (4.59); 4.1392 (2.30); 3.3209 (73.16); 3.0349 (16.00); 2.9949 (0.50); 2.5158 (9.29); 2.5114 (18.55); 2.5070 (25.08); 2.5025 (18.39); 2.4982 (9.44); 1.9936 (0.44); 1.6453 (0.50); 1.6283 (1.56); 1.6222 (0.70); 1.6108 (2.00); 1.5912 (1.74); 1.5746 (0.75); 1.4103 (0.35); 1.3917 (1.20); 1.3726 (1.96); 1.3538 (2.02); 1.3356 (1.25); 1.3173 (0.42); 0.9266 (4.37); 0.9082 (8.84); 0.8897 (3.94); 0.8633 (0.32)
Example 15, Solvent: DMSO, Spectrometer: 400.13 MHz 10.4985 (2.11); 8.0751 (1.44); 8.0545 (1.70); 7.8356 (1.29); 7.8161 (1.88); 7.7961 (1.20); 7.7272 (2.76); 7.7144 (0.97); 7.7094 (3.46); 7.7057 (2.61); 7.5692 (0.51); 7.5661 (0.38); 7.5572 (0.42); 7.5508 (1.67); 7.5453 (0.61); 7.5359 (0.96); 7.5327 (1.48); 7.5294 (0.88); 7.5021 (2.54); 7.4866 (1.78); 7.4829 (3.20); 7.4693 (0.63); 7.4653 (1.27); 7.4622 (0.83); 7.1441 (1.91); 7.1258 (1.81); 5.7585 (0.87); 5.3585 (6.77); 3.3210

NMR Peak List Table 1

(97.01); 3.0587 (16.00); 2.5160 (11.84); 2.5117 (24.12); 2.5072 (33.05); 2.5027 (24.80); 2.4984 (13.08); 2.4063 (2.03); 2.3880 (3.54); 2.3693 (2.20); 1.5971 (0.49); 1.5789 (1.43); 1.5601 (2.05); 1.5416 (1.57); 1.5228 (0.68); 1.3517 (0.34); 1.3331 (1.17); 1.3142 (1.91); 1.2955 (1.96); 1.2774 (1.24); 1.2593 (0.44); 0.9054 (4.07); 0.8872 (8.23); 0.8687 (3.69)
Example 16, Solvent: DMSO, Spectrometer: 400.13 MHz 10.1548 (2.83); 7.8327 (0.59); 7.8116 (2.03); 7.7959 (4.35); 7.7924 (3.17); 7.7759 (0.74); 7.7267 (2.82); 7.7138 (1.00); 7.7089 (3.49); 7.7052 (2.59); 7.5671 (0.53); 7.5641 (0.40); 7.5553 (0.44); 7.5487 (1.45); 7.5432 (0.60); 7.5338 (0.97); 7.5306 (1.49); 7.5273 (0.87); 7.5004 (2.57); 7.4849 (1.81); 7.4813 (3.23); 7.4677 (0.62); 7.4637 (1.29); 7.4606 (0.83); 7.1056 (1.39); 7.1010 (1.44); 7.0896 (1.30); 7.0850 (1.35); 5.7586 (1.43); 5.3364 (6.81); 3.9986 (4.32); 3.9809 (4.44); 3.3202 (133.08); 3.2974 (1.78); 3.2478 (0.43); 3.0711 (16.00); 2.5159 (16.66); 2.5115 (33.31); 2.5070 (45.25); 2.5026 (33.44); 2.4983 (17.30); 2.3338 (0.33); 2.2373 (0.37); 2.2185 (0.83); 2.2000 (1.13); 2.1813 (0.89); 2.1629 (0.42); 1.9939 (0.36); 1.7481 (0.34); 1.7322 (0.71); 1.7197 (0.96); 1.7006 (1.16); 1.6878 (0.84); 1.6717 (0.54); 1.6171 (0.72); 1.5969 (1.19); 1.5804 (1.17); 1.5547 (0.92); 1.5425 (0.64); 1.5349 (1.18); 1.5262 (1.00); 1.5159 (1.25); 1.4967 (0.78); 1.4864 (0.48); 1.3142 (0.44); 1.2981 (0.96); 1.2815 (1.16); 1.2673 (1.08); 1.2500 (1.00)
Example 17, Solvent: DMSO, Spectrometer: 400.13 MHz 10.9907 (2.47); 8.1662 (1.80); 8.1457 (2.17); 7.9407 (1.37); 7.9212 (2.03); 7.9011 (1.38); 7.8921 (1.50); 7.8726 (1.77); 7.8651 (1.14); 7.8590 (1.18); 7.8401 (0.94); 7.8343 (1.10); 7.8302 (0.84); 7.7407 (2.86); 7.7228 (3.51); 7.7191 (2.65); 7.5985 (0.63); 7.5838 (0.80); 7.5781 (1.34); 7.5725 (0.86); 7.5693 (0.72); 7.5635 (1.45); 7.5587 (1.32); 7.5541 (2.01); 7.5484 (0.85); 7.5439 (1.09); 7.5391 (1.19); 7.5359 (1.67); 7.5063 (2.71); 7.4871 (3.43); 7.4792 (1.15); 7.4771 (1.12); 7.4697 (1.87); 7.4564 (1.22); 7.4505 (1.11); 7.4345 (0.58); 7.4298 (0.53); 7.2525 (1.99); 7.2341 (1.92); 5.7583 (2.56); 5.4273 (6.85); 4.0440 (0.46); 4.0262 (0.48); 3.3216 (62.10); 3.2635 (0.45); 3.0866 (16.00); 2.5157 (11.88); 2.5115 (23.07); 2.5070 (30.83); 2.5026 (22.71); 2.4984 (11.72); 1.9935 (2.00); 1.1980 (0.55); 1.1802 (1.07); 1.1624 (0.54)
Example 18, Solvent: DMSO, Spectrometer: 400.13 MHz 10.1574 (2.74); 7.8335 (0.45); 7.8125 (2.33); 7.8044 (2.57); 7.7981 (5.52); 7.7835 (0.57); 7.7261 (2.75); 7.7133 (1.00); 7.7083 (3.46); 7.7046 (2.53); 7.5668 (0.53); 7.5551 (0.45); 7.5486 (1.70); 7.5430 (0.59); 7.5337 (0.99); 7.5304 (1.47); 7.5271 (0.83); 7.5002 (2.53); 7.4848 (1.79); 7.4811 (3.16); 7.4675 (0.61); 7.4635 (1.26); 7.4603 (0.77); 7.1058 (1.33); 7.0993 (1.33); 7.0916 (1.17); 7.0851 (1.27); 5.7586 (0.81); 5.3352 (6.89); 4.1135 (2.18); 4.0969 (4.56); 4.0803 (2.26); 3.3199 (123.98); 3.2974 (1.65); 3.2466 (0.43); 3.0700 (16.00); 2.5159 (16.11); 2.5115 (31.93); 2.5070 (43.10); 2.5025 (31.56); 2.4981 (16.17); 1.6332 (0.49); 1.6161 (1.46); 1.6098 (0.63); 1.5988 (1.89); 1.5793 (1.62); 1.5626 (0.70); 1.4204 (0.35); 1.4017 (1.17); 1.3826 (1.84); 1.3638 (1.87); 1.3457 (1.15); 1.3275 (0.38); 0.9319 (4.19); 0.9135 (8.44); 0.8951 (3.70)
Example 19, Solvent: DMSO, Spectrometer: 400.13 MHz 12.5294 (1.59); 7.7395 (2.96); 7.7217 (3.52); 7.7180 (2.62); 7.5699 (0.52); 7.5585 (0.41); 7.5515 (1.73); 7.5460 (0.60); 7.5336 (1.56); 7.5075 (2.73); 7.4884 (3.34); 7.4749 (0.59); 7.4709 (1.23); 7.4677 (0.83); 7.3325 (6.33); 7.3036 (1.94); 7.2821 (3.54); 7.2636 (2.48); 6.9614 (1.16); 6.9430 (2.09); 6.9213 (3.45); 6.9193 (3.62); 6.8995 (3.04); 6.8745 (0.67); 6.8547 (0.61); 5.7576 (7.18); 5.3414 (6.67); 5.0710 (0.48); 5.0546 (1.66); 5.0380 (1.67); 5.0215 (0.47); 4.8193 (0.35); 4.8023 (0.36); 4.0438 (0.43); 4.0260 (0.43); 3.3243 (31.22); 3.2976 (0.51); 3.0193 (16.00); 2.5112 (16.98); 2.5068 (22.43); 2.5025 (16.19); 1.9934 (1.84); 1.5537 (6.33); 1.5372 (6.27); 1.5084 (1.60); 1.4914 (1.55); 1.1977 (0.50); 1.1799 (0.97); 1.1621 (0.48)
Example 20, Solvent: DMSO, Spectrometer: 400.13 MHz 12.8184 (0.79); 7.9522 (1.39); 7.9328 (1.87); 7.9302 (2.03); 7.9232 (1.21); 7.9043 (0.92); 7.8986 (1.06); 7.8944 (0.81); 7.7505 (2.86); 7.7328 (3.50); 7.7291 (2.65); 7.6359 (0.58); 7.6213 (0.71); 7.6156 (1.16); 7.6010 (1.22); 7.5963 (0.95); 7.5813 (0.86); 7.5730 (0.69); 7.5698 (0.55); 7.5615 (0.51); 7.5545 (1.81); 7.5486 (0.75); 7.5399 (1.10); 7.5365 (1.69); 7.5332 (1.10); 7.5236 (0.96); 7.5124 (2.95); 7.4972 (2.81); 7.4935 (3.80); 7.4804 (1.23); 7.4759 (1.84); 7.4033 (4.13); 5.7585 (2.30); 5.3933 (6.38); 3.3207 (94.77); 3.0251 (16.00); 2.5159 (15.95); 2.5115 (31.24); 2.5070 (42.01); 2.5026 (31.01); 2.4983 (16.05); 1.9937 (1.08); 1.1804 (0.60); 1.1626 (0.32)
Example 21, Solvent: DMSO, Spectrometer: 400.13 MHz 9.8506 (1.17); 7.7812 (0.84); 7.7650 (1.91); 7.7608 (1.24); 7.7441 (0.38); 7.7251 (1.21); 7.7072 (1.45); 7.7036 (1.09); 7.5480 (0.72); 7.5297 (0.63); 7.4996 (1.08); 7.4804 (1.33); 7.4627 (0.54); 7.0797 (0.62); 7.0756 (0.64); 7.0635 (0.56); 7.0592 (0.56); 5.3201 (2.79); 3.3634 (296.68); 3.3409 (5.56); 3.0665 (6.33); 2.5114 (20.72); 2.5070 (27.49); 2.5027 (20.59); 1.9926 (0.59); 1.4657 (16.00); 1.3519 (0.95); 1.3258 (0.32); 1.3018 (0.57); 1.2479 (1.59); 1.1776 (0.35); 0.8776 (0.50); 0.8610 (1.44); 0.8434 (0.62)
Example 22, Solvent: DMSO, Spectrometer: 400.13 MHz 10.2809 (0.68); 7.9559 (2.45); 7.8012 (0.44); 7.7827 (0.45); 7.7542 (0.59); 7.5933 (0.62); 7.5763 (0.76); 7.5723 (0.62); 7.4749 (0.36); 7.4574 (0.44); 7.4426 (0.79); 7.4239 (0.71); 7.1464 (0.42); 7.1282 (0.38); 5.2491 (1.46); 4.1891 (0.53); 4.1724 (1.13); 4.1557 (0.53); 3.3545 (11.64); 2.9169 (0.49); 2.9104 (0.92); 2.9037 (0.73); 2.8939 (16.00); 2.7343 (13.95); 2.5721 (0.33); 2.5656 (0.35); 2.5554 (0.71); 2.5488 (0.69); 2.5386 (0.50); 2.5289 (0.66); 2.5107 (16.80); 2.5064 (22.26); 2.5022 (16.29)
Example 23, Solvent: DMSO, Spectrometer: 400.13 MHz 7.9573 (0.37); 7.8215 (0.44); 7.8010 (0.38); 7.7687 (0.36); 7.7571 (0.37); 7.7329 (0.39); 7.6427 (6.99); 7.6251 (8.28); 7.6214 (5.86); 7.5318 (1.42); 7.5134 (4.14); 7.5075 (1.62); 7.4956 (4.03); 7.4750 (6.92); 7.4628 (5.13); 7.4600 (5.35); 7.4559 (7.63); 7.4433 (5.44); 7.4389 (3.11); 7.4245 (2.90); 6.5712 (4.72); 6.5530 (4.29); 6.4382 (4.75); 6.4174 (4.44); 6.2342 (1.45); 5.3354 (0.74); 5.2840 (0.39); 5.2036 (16.00); 2.8945 (1.61); 2.7352 (1.36); 2.6755 (0.58); 2.5106 (89.93); 2.5064 (117.56); 2.5022 (87.81); 2.3332 (0.77); 2.0801 (0.45); 1.4661 (0.44); 1.3663 (0.51)
Example 25, Solvent: DMSO, Spectrometer: 499.93 MHz 7.6204 (1.43); 7.6161 (1.82); 7.6090 (2.12); 7.6011 (1.97); 7.5108 (4.24); 7.5065 (3.96); 7.4998 (2.44); 7.4899 (0.61); 7.3940 (1.02); 7.3787 (1.60); 7.3630 (1.08); 6.4882 (1.74); 6.4738 (1.68); 6.3819 (1.77); 6.3654 (1.72); 5.9978 (2.42); 5.9845 (0.70); 5.1329 (6.30); 3.3423 (16.00); 3.3187 (1.72); 3.2748 (12.78); 2.5150 (6.35); 2.5118 (8.32); 2.5085 (6.37); 1.9993 (0.40)
Example 26, Solvent: DMSO, Spectrometer: 499.93 MHz 10.1670 (6.78); 7.8170 (0.80); 7.8000 (5.62); 7.7954 (6.11); 7.7896 (11.23); 7.7790 (1.06); 7.6251 (3.99); 7.6211 (5.06); 7.6141 (5.59); 7.6060 (5.42); 7.5141 (11.08); 7.5103 (10.73); 7.5035 (6.79); 7.5009 (5.93); 7.4926 (1.69); 7.4851 (0.50); 7.0871 (0.47); 7.0764 (2.89); 7.0703 (3.01); 7.0660 (2.72); 7.0600 (2.76); 7.0495 (0.35); 5.2849 (16.00); 4.1004 (4.60); 4.0870 (9.35); 4.0736 (4.60); 3.9135 (0.57); 3.4056 (0.54); 3.4000 (0.48); 3.3947 (0.60); 3.3823 (0.34); 3.3455 (28.74); 3.3219 (1.33); 3.2412 (32.31); 2.5150 (6.09); 2.5118 (7.70); 2.5086 (5.87); 1.6258 (2.65); 1.6122 (4.01); 1.5986 (2.87); 1.5854 (0.93); 1.3570 (0.76); 1.3299 (9.83); 1.3229 (7.95); 1.3156 (6.59); 1.2430 (0.60); 0.9010 (4.82); 0.8873 (11.07); 0.8734 (4.09); 0.8477 (0.32)

NMR Peak List Table 1

Example 27, Solvent: DMSO, Spectrometer: 399.95 MHz 12.6614 (1.15); 7.7421 (2.97); 7.7381 (1.73); 7.7337 (1.65); 7.7297 (2.20); 7.7245 (3.73); 7.7208 (2.69); 7.7115 (0.81); 7.6590 (0.35); 7.6545 (0.35); 7.6457 (0.43); 7.6407 (0.79); 7.6381 (0.67); 7.6362 (0.65); 7.6339 (0.56); 7.6271 (0.63); 7.6227 (0.74); 7.6199 (0.81); 7.6151 (0.48); 7.6062 (0.45); 7.6018 (0.40); 7.5662 (0.49); 7.5630 (0.34); 7.5548 (0.38); 7.5479 (1.67); 7.5420 (0.55); 7.5332 (1.02); 7.5298 (1.56); 7.5263 (0.85); 7.5048 (2.60); 7.4896 (1.77); 7.4859 (3.17); 7.4725 (0.57); 7.4684 (1.28); 7.4649 (0.78); 7.3945 (5.01); 7.3703 (1.05); 7.3648 (1.42); 7.3624 (1.65); 7.3437 (2.87); 7.3248 (0.97); 7.3224 (0.86); 5.3703 (6.26); 3.3387 (88.38); 3.0367 (16.00); 2.8907 (2.15); 2.7323 (1.76); 2.7311 (1.75); 2.5253 (0.70); 2.5119 (12.90); 2.5076 (24.75); 2.5031 (32.03); 2.4985 (23.64); 2.4941 (11.72); −0.0002 (2.90)

Example 28, Solvent: DMSO, Spectrometer: 399.95 MHz 12.4655 (1.14); 7.9527 (0.99); 7.7392 (2.77); 7.7267 (0.81); 7.7216 (3.44); 7.7179 (2.52); 7.5665 (0.48); 7.5633 (0.32); 7.5551 (0.34); 7.5481 (1.66); 7.5423 (0.52); 7.5334 (0.94); 7.5301 (1.53); 7.5266 (0.81); 7.5045 (2.56); 7.4893 (1.64); 7.4855 (3.14); 7.4721 (0.49); 7.4680 (1.21); 7.4645 (0.73); 7.3366 (4.68); 7.2656 (0.68); 7.2628 (0.73); 7.2439 (0.97); 7.2364 (0.75); 7.2327 (0.77); 7.2161 (0.80); 7.2127 (0.84); 7.1310 (0.32); 7.1101 (1.28); 7.1067 (1.34); 7.1005 (1.10); 7.0930 (2.68); 7.0805 (1.09); 7.0759 (1.12); 7.0601 (0.40); 6.9975 (0.48); 6.9899 (0.48); 6.9859 (0.60); 6.9816 (0.71); 6.9773 (0.56); 6.9751 (0.51); 6.9682 (0.78); 6.9657 (0.70); 6.9632 (0.87); 6.9547 (0.32); 6.9481 (0.34); 5.3405 (6.14); 4.9435 (7.87); 3.3318 (62.16); 3.0274 (16.00); 2.8903 (7.39); 2.7317 (6.11); 2.7307 (5.95); 2.5248 (0.67); 2.5114 (13.19); 2.5070 (26.28); 2.5024 (34.60); 2.4978 (25.54); 2.4934 (12.50); −0.0002 (3.67)

Example 29, Solvent: DMSO, Spectrometer: 399.95 MHz 10.8476 (1.94); 8.0189 (0.92); 7.9981 (1.14); 7.9532 (1.08); 7.8446 (1.33); 7.8254 (1.80); 7.8051 (1.16); 7.7317 (2.58); 7.7278 (1.28); 7.7190 (0.82); 7.7139 (3.41); 7.7101 (2.40); 7.5687 (0.49); 7.5568 (0.36); 7.5504 (1.66); 7.5446 (0.51); 7.5354 (0.90); 7.5321 (1.43); 7.5287 (0.73); 7.5015 (2.41); 7.4981 (1.07); 7.4860 (1.69); 7.4823 (3.11); 7.4687 (0.51); 7.4646 (1.26); 7.4614 (0.75); 7.4499 (1.15); 7.4432 (0.66); 7.4381 (1.17); 7.4343 (0.98); 7.4269 (2.33); 7.4200 (0.92); 7.4165 (1.17); 7.4107 (0.71); 7.4044 (1.37); 7.3272 (0.45); 7.3154 (3.00); 7.3088 (1.57); 7.3044 (1.99); 7.3026 (1.89); 7.2984 (1.35); 7.2920 (2.28); 7.1682 (1.80); 7.1498 (1.74); 5.3814 (6.18); 3.9278 (6.08); 3.3309 (77.15); 3.0671 (16.00); 2.8905 (8.60); 2.7319 (7.04); 2.5250 (0.86); 2.5201 (1.35); 2.5116 (14.93); 2.5071 (29.35); 2.5025 (38.25); 2.4979 (27.55); 2.4934 (13.01); −0.0002 (7.72)

Example 30, Solvent: DMSO, Spectrometer: 400.13 MHz 7.9623 (2.56); 7.5454 (4.64); 7.5077 (2.36); 7.4103 (1.46); 7.3904 (3.38); 7.3590 (6.53); 6.5101 (2.80); 6.4923 (2.68); 6.3971 (2.78); 6.3764 (2.66); 6.0256 (7.00); 5.1800 (9.75); 3.3528 (4.97); 3.0867 (16.00); 2.8990 (10.92); 2.7401 (10.31); 2.5122 (33.53); 2.3438 (15.48); 1.3684 (0.34)

Example 31, Solvent: DMSO, Spectrometer: 399.95 MHz 10.4632 (2.02); 8.0550 (0.92); 8.0343 (1.16); 7.9530 (0.48); 7.8907 (1.24); 7.8714 (1.69); 7.8512 (1.08); 7.7316 (1.86); 7.7289 (2.49); 7.7250 (1.20); 7.7163 (0.73); 7.7111 (3.35); 7.7074 (2.31); 7.5666 (0.47); 7.5547 (0.35); 7.5483 (1.59); 7.5426 (0.46); 7.5334 (0.85); 7.5300 (1.40); 7.5266 (0.69); 7.4988 (2.28); 7.4953 (0.96); 7.4834 (1.56); 7.4796 (2.97); 7.4661 (0.46); 7.4620 (1.21); 7.4587 (0.68); 7.2092 (1.66); 7.1918 (1.59); 7.0301 (0.88); 7.0259 (0.69); 7.0100 (1.81); 7.0064 (1.26); 6.9842 (0.94); 6.9799 (2.12); 6.9755 (0.85); 6.9600 (3.36); 6.9556 (0.76); 6.9410 (0.94); 6.9369 (0.54); 6.8974 (1.18); 6.8932 (1.16); 6.8784 (0.97); 6.8741 (1.28); 6.8593 (0.54); 6.8552 (0.51); 5.3901 (5.77); 4.7685 (6.26); 3.8129 (15.55); 3.3339 (69.55); 3.0703 (16.00); 2.8906 (4.10); 2.7322 (3.23); 2.7310 (3.16); 2.5252 (0.57); 2.5204 (0.92); 2.5119 (11.58); 2.5074 (23.25); 2.5028 (30.71); 2.4981 (22.16); 2.4936 (10.43); −0.0002 (2.85)

Example 32, Solvent: DMSO, Spectrometer: 399.95 MHz 10.5046 (1.97); 8.0714 (1.21); 8.0507 (1.44); 7.8316 (1.26); 7.8123 (1.72); 7.7920 (1.17); 7.7263 (1.95); 7.7238 (2.53); 7.7199 (1.25); 7.7111 (0.79); 7.7060 (3.46); 7.7022 (2.34); 7.5642 (0.48); 7.5523 (0.36); 7.5459 (1.62); 7.5401 (0.48); 7.5309 (0.87); 7.5276 (1.41); 7.5242 (0.70); 7.4964 (2.38); 7.4930 (1.00); 7.4811 (1.63); 7.4773 (3.05); 7.4634 (0.67); 7.1398 (1.73); 7.1223 (1.69); 5.3535 (6.09); 3.3302 (50.68); 3.0535 (16.00); 2.5256 (0.54); 2.5207 (0.86); 2.5122 (10.08); 2.5077 (19.99); 2.5031 (26.30); 2.4985 (19.01); 2.4939 (8.99); 2.3905 (1.50); 2.3722 (2.83); 2.3536 (1.64); 1.5818 (0.77); 1.5641 (1.11); 1.5463 (0.74); 1.2705 (3.87); 1.2642 (4.45); 1.2541 (3.48); 1.2368 (1.95); 0.8754 (0.76); 0.8701 (1.75); 0.8624 (1.34); 0.8532 (5.74); 0.8356 (1.92); −0.0002 (6.01)

Example 33, Solvent: DMSO, Spectrometer: 399.95 MHz 10.1847 (2.26); 7.8318 (0.33); 7.8107 (2.37); 7.8045 (2.45); 7.7972 (5.68); 7.7836 (0.38); 7.7228 (2.60); 7.7190 (1.28); 7.7102 (0.77); 7.7051 (3.36); 7.7013 (2.32); 7.5624 (0.48); 7.5505 (0.36); 7.5440 (1.64); 7.5383 (0.49); 7.5291 (0.89); 7.5258 (1.43); 7.5224 (0.73); 7.4955 (2.41); 7.4921 (1.03); 7.4802 (1.66); 7.4764 (3.07); 7.4629 (0.48); 7.4588 (1.07); 7.1023 (1.29); 7.0950 (1.29); 7.0888 (1.06); 7.0815 (1.24); 5.3323 (6.65); 4.0624 (2.38); 4.0456 (5.06); 4.0289 (2.42); 3.3316 (57.81); 3.0663 (16.00); 2.8908 (2.35); 2.7322 (1.84); 2.7312 (1.85); 2.5254 (0.53); 2.5205 (0.81); 2.5120 (10.19); 2.5075 (20.50); 2.5029 (27.14); 2.4983 (19.73); 2.4938 (9.45); 1.6509 (1.17); 1.6337 (2.43); 1.6154 (2.49); 1.5982 (1.26); 0.9367 (4.25); 0.9183 (8.68); 0.8997 (3.83); −0.0002 (9.66)

Example 34, Solvent: DMSO, Spectrometer: 399.95 MHz 10.6207 (1.46); 10.5100 (0.68); 8.0663 (0.64); 8.0593 (0.96); 8.0456 (0.78); 8.0385 (1.14); 7.9533 (0.80); 7.9271 (0.69); 7.9082 (0.92); 7.8871 (0.68); 7.8441 (1.02); 7.8340 (0.57); 7.8247 (1.43); 7.8147 (0.71); 7.8046 (0.91); 7.7944 (0.43); 7.7548 (2.52); 7.7369 (3.27); 7.7332 (2.45); 7.7232 (2.85); 7.7053 (3.56); 7.7016 (2.53); 7.5895 (0.51); 7.5865 (0.32); 7.5769 (0.39); 7.5711 (1.62); 7.5655 (0.94); 7.5528 (1.58); 7.5471 (1.90); 7.5414 (0.54); 7.5318 (1.02); 7.5287 (1.53); 7.5254 (0.83); 7.5132 (2.27); 7.4977 (4.11); 7.4940 (3.92); 7.4790 (3.78); 7.4652 (0.59); 7.4613 (1.28); 7.4582 (0.75); 7.1532 (1.37); 7.1348 (1.37); 7.1217 (0.59); 6.9698 (0.93); 6.9412 (1.41); 6.9229 (1.13); 5.3831 (5.27); 5.3573 (5.56); 4.2783 (1.44); 4.2607 (2.68); 4.2431 (1.49); 3.6906 (1.84); 3.6740 (3.88); 3.6576 (1.90); 3.4255 (3.69); 3.4089 (8.93); 3.3836 (60.04); 3.2564 (0.33); 3.2516 (0.35); 3.2395 (0.33); 3.2334 (0.32); 3.0626 (16.00); 3.0570 (15.53); 2.8913 (4.82); 2.7316 (3.93); 2.6729 (0.42); 2.5715 (1.35); 2.5534 (2.62); 2.5449 (1.30); 2.5349 (1.99); 2.5310 (2.66); 2.5261 (1.54); 2.5127 (25.60); 2.5084 (49.26); 2.5038 (63.69); 2.4993 (46.36); 2.4949 (22.25); 2.4447 (1.04); 2.4382 (0.67); 2.4249 (2.44); 2.4201 (1.20); 2.4040 (1.62); 2.3306 (0.42); 2.1795 (0.34); 2.1618 (0.91); 2.1590 (0.59); 2.1419 (1.07); 2.1230 (0.71); 2.0522 (0.43); 2.0353 (1.34); 2.0175 (1.87); 2.0002 (1.21); 1.9828 (0.35); 1.7324 (0.48); 1.7141 (0.67); 1.6965 (0.49); 1.2345 (0.33); −0.0002 (4.61)

Example 35, Solvent: DMSO, Spectrometer: 399.95 MHz 10.8718 (2.00); 8.0528 (1.58); 8.0323 (1.90); 7.8250 (1.35); 7.8057 (1.88); 7.7855 (1.22); 7.7280 (2.71); 7.7243 (1.36); 7.7153 (0.85); 7.7102 (3.47); 7.7064 (2.56); 7.5663 (0.49); 7.5632 (0.32); 7.5545 (0.36); 7.5480 (1.68); 7.5424 (0.51); 7.5331 (0.91); 7.5298 (1.44); 7.5264 (0.75); 7.4999 (2.50); 7.4845 (1.70); 7.4808 (3.17); 7.4672 (0.49); 7.4631 (1.22); 7.4599 (0.70); 7.1412 (1.90); 7.1230 (1.83); 5.3661 (6.68); 3.3300 (61.03); 3.0561 (16.00); 2.8908 (2.33); 2.7318 (1.87); 2.5252 (0.58); 2.5119 (10.86); 2.5074 (21.30); 2.5029 (27.86); 2.4983 (20.28); 2.4938 (9.71); 2.0339 (0.48); 2.0293 (0.53); 2.0233 (0.42); 2.0162 (0.94); 2.0088 (0.39); 2.0030 (0.53); 1.9987 (0.53); 0.8757 (0.45); 0.8129 (4.44); 0.8057 (3.17); 0.7929 (2.42); 0.7862 (0.84); −0.0002 (4.96)

NMR Peak List Table 1

Example 36, Solvent: DMSO, Spectrometer: 400.13 MHz 10.2460 (0.33); 7.8570 (0.58); 5.3910 (0.69); 4.1415 (0.46); 3.8432 (1.77); 3.4129 (16.00); 3.1113 (1.64); 2.5736 (1.01); 2.5693 (2.12); 2.5648 (2.89); 2.5604 (2.08); 2.5560 (0.97); 1.3848 (0.40); 0.9402 (0.53)

Example 37, Solvent: DMSO, Spectrometer: 399.95 MHz 10.5318 (2.14); 8.0721 (1.28); 8.0515 (1.53); 7.8370 (1.30); 7.8177 (1.81); 7.7975 (1.19); 7.7260 (2.07); 7.7237 (2.64); 7.7199 (1.29); 7.7110 (0.84); 7.7059 (3.46); 7.7021 (2.42); 7.5647 (0.49); 7.5615 (0.32); 7.5528 (0.37); 7.5464 (1.67); 7.5407 (0.51); 7.5314 (0.90); 7.5281 (1.44); 7.5248 (0.73); 7.4974 (2.45); 7.4940 (1.08); 7.4820 (1.70); 7.4783 (3.14); 7.4646 (0.50); 7.4606 (1.23); 7.4574 (0.70); 7.1450 (1.82); 7.1266 (1.78); 5.3564 (6.32); 3.3326 (72.03); 3.0560 (16.00); 2.8909 (0.99); 2.7639 (1.41); 2.7572 (3.09); 2.7506 (1.43); 2.7321 (0.80); 2.5253 (0.68); 2.5121 (11.45); 2.5076 (22.26); 2.5030 (29.03); 2.4984 (21.05); 2.4939 (10.05); 2.4166 (1.58); 2.3984 (3.10); 2.3798 (1.72); 2.1999 (1.12); 2.1932 (1.17); 2.1821 (2.56); 2.1755 (2.49); 2.1646 (1.31); 2.1580 (1.20); 1.6938 (0.36); 1.6755 (1.08); 1.6567 (1.47); 1.6505 (0.82); 1.6378 (1.18); 1.6189 (0.49); 1.4968 (0.52); 1.4789 (1.36); 1.4654 (0.87); 1.4592 (1.53); 1.4479 (0.46); 1.4409 (1.10); −0.0002 (5.85)

Example 38, Solvent: DMSO, Spectrometer: 399.95 MHz 12.4201 (0.81); 7.9526 (1.01); 7.7385 (2.70); 7.7346 (1.31); 7.7261 (0.76); 7.7209 (3.49); 7.7171 (2.41); 7.5667 (0.47); 7.5553 (0.33); 7.5484 (1.67); 7.5425 (0.50); 7.5337 (0.91); 7.5303 (1.51); 7.5268 (0.77); 7.5047 (2.55); 7.5014 (1.08); 7.4896 (1.59); 7.4856 (3.10); 7.4724 (0.48); 7.4682 (1.22); 7.4647 (0.67); 7.3371 (4.84); 7.1550 (1.82); 7.1490 (0.60); 7.1378 (0.81); 7.1322 (3.25); 7.1280 (0.77); 7.1219 (0.34); 7.1168 (0.72); 7.1107 (2.55); 7.0018 (2.50); 6.9957 (0.79); 6.9909 (2.55); 6.9848 (1.20); 6.9788 (1.83); 6.9739 (0.69); 6.9678 (1.79); 5.3423 (5.97); 4.8284 (7.85); 3.3366 (94.01); 3.0211 (16.00); 2.8904 (8.13); 2.7319 (6.30); 2.7309 (6.69); 2.5252 (0.62); 2.5205 (0.97); 2.5119 (12.85); 2.5074 (25.82); 2.5028 (34.30); 2.4982 (24.98); 2.4937 (11.95); −0.0002 (1.87)

Example 39, Solvent: DMSO, Spectrometer: 300.16 MHz 10.0097 (2.45); 7.8064 (1.40); 7.7537 (3.31); 7.7417 (3.41); 7.7253 (3.44); 7.5382 (1.67); 7.5166 (2.48); 7.4949 (2.76); 7.1091 (1.48); 7.0870 (1.40); 5.3399 (5.03); 3.3558 (7.80); 3.3512 (7.52); 3.0891 (8.18); 3.0850 (8.18); 2.9282 (2.25); 2.8184 (4.78); 2.5210 (9.14); 1.5191 (16.00); 1.3792 (0.78); 1.2615 (1.92); 0.8795 (0.98)

Example 40, Solvent: DMSO, Spectrometer: 399.95 MHz 9.7892 (1.97); 8.0289 (1.61); 8.0091 (1.98); 7.8398 (1.33); 7.8207 (1.78); 7.8003 (1.20); 7.7243 (2.79); 7.7204 (1.43); 7.7115 (0.91); 7.7064 (3.71); 7.7027 (2.50); 7.5638 (0.52); 7.5606 (0.36); 7.5518 (0.40); 7.5455 (1.71); 7.5398 (0.55); 7.5305 (0.92); 7.5272 (1.47); 7.5239 (0.78); 7.4957 (2.58); 7.4923 (1.14); 7.4802 (1.80); 7.4765 (3.26); 7.4629 (0.52); 7.4588 (1.29); 7.4557 (0.73); 7.1532 (1.79); 7.1357 (1.71); 5.3794 (6.29); 3.3277 (50.30); 3.0878 (0.53); 3.0757 (16.00); 2.8908 (1.39); 2.7321 (1.09); 2.7312 (1.29); 2.5250 (0.66); 2.5117 (12.62); 2.5072 (24.96); 2.5026 (32.84); 2.4980 (23.92); 2.4935 (11.50); 2.1329 (0.75); 2.1212 (0.72); 2.1045 (0.76); 2.0921 (0.69); 1.5114 (0.71); 1.4957 (0.88); 1.4756 (1.03); 1.4525 (0.48); 1.4384 (0.46); 1.3871 (0.33); 1.3621 (0.73); 1.3517 (0.68); 1.3366 (0.97); 1.2984 (1.77); 1.2716 (1.59); 1.2531 (0.78); 1.2457 (0.85); 1.2378 (0.87); 1.1964 (11.91); 1.1791 (0.56); 1.0784 (1.14); 0.8758 (0.58); 0.8623 (0.36); 0.0080 (0.45); −0.0002 (12.32); −0.0085 (0.41)

Example 41, Solvent: DMSO, Spectrometer: 400.13 MHz 11.7635 (1.63); 7.6175 (3.88); 7.5970 (4.40); 7.3056 (3.82); 7.2853 (3.30); 7.2404 (4.71); 5.2588 (7.03); 4.1594 (2.19); 4.1427 (4.54); 4.1260 (2.21); 3.4666 (0.54); 3.4647 (0.51); 3.4155 (8.00); 3.3657 (567.17); 3.3160 (5.69); 3.0145 (16.00); 2.6798 (0.48); 2.6722 (0.36); 2.5618 (0.82); 2.5576 (1.04); 2.5532 (0.80); 2.5120 (62.60); 2.5078 (80.97); 2.5037 (60.79); 2.4624 (0.90); 2.4583 (0.98); 2.3518 (11.48); 2.3347 (0.83); 1.9934 (0.53); 1.6405 (1.26); 1.6235 (1.99); 1.6063 (1.44); 1.5902 (0.51); 1.3285 (2.73); 1.3204 (4.35); 1.3110 (4.54); 1.3023 (3.00); 1.2702 (0.89); 1.2482 (2.14); 1.1781 (0.32); 0.8955 (2.32); 0.8782 (7.02); 0.8705 (2.97); 0.8613 (4.37); 0.8439 (1.25)

Example 42, Solvent: DMSO, Spectrometer: 400.13 MHz 11.0254 (2.58); 8.1759 (1.76); 8.1554 (2.12); 7.9478 (1.32); 7.9283 (1.92); 7.9083 (1.24); 7.8924 (1.34); 7.8899 (1.11); 7.8729 (1.45); 7.8705 (1.66); 7.8610 (1.03); 7.8575 (0.71); 7.8421 (0.83); 7.8362 (0.96); 7.8320 (0.71); 7.6408 (0.66); 7.6367 (0.98); 7.6310 (0.91); 7.6199 (1.28); 7.6163 (1.45); 7.6113 (1.18); 7.6030 (2.24); 7.6008 (2.41); 7.5875 (0.76); 7.5819 (1.16); 7.5676 (1.38); 7.5624 (0.93); 7.5565 (0.92); 7.5501 (1.40); 7.5360 (1.28); 7.5309 (0.66); 7.5154 (0.61); 7.4861 (0.59); 7.4841 (0.62); 7.4795 (0.58); 7.4627 (1.00); 7.4573 (0.90); 7.4400 (0.81); 7.4371 (0.99); 7.4157 (0.94); 7.4120 (0.87); 7.3973 (0.43); 7.3948 (0.45); 7.3912 (0.42); 7.3887 (0.38); 7.2648 (1.94); 7.2466 (1.85); 5.4490 (6.50); 4.0438 (0.49); 4.0260 (0.50); 3.3947 (0.56); 3.3445 (30.39); 3.2944 (0.40); 3.0831 (16.00); 2.5647 (0.40); 2.5602 (0.50); 2.5323 (0.59); 2.5186 (12.69); 2.5143 (26.30); 2.5099 (35.79); 2.5054 (25.86); 2.5011 (12.23); 2.4644 (0.36); 2.4598 (0.39); 1.9965 (2.17); 1.2490 (0.82); 1.1987 (0.60); 1.1809 (1.16); 1.1631 (0.56); 0.8798 (0.37); 0.8631 (1.17); 0.8455 (0.46)

Example 43, Solvent: DMSO, Spectrometer: 400.13 MHz 7.7323 (2.93); 7.7195 (0.96); 7.7145 (3.65); 7.7108 (2.62); 7.5658 (0.54); 7.5627 (0.37); 7.5542 (0.45); 7.5475 (1.78); 7.5418 (0.57); 7.5327 (1.08); 7.5294 (1.59); 7.5261 (0.85); 7.5023 (2.72); 7.4870 (1.88); 7.4832 (3.39); 7.4697 (1.30); 7.4657 (1.73); 7.4623 (0.78); 7.3826 (1.70); 7.3779 (1.99); 7.3746 (2.56); 7.3615 (3.01); 7.3567 (3.52); 7.3439 (1.57); 7.2839 (1.87); 7.2796 (0.72); 7.2656 (3.56); 7.2463 (1.91); 7.1900 (1.24); 7.1870 (0.76); 7.1765 (0.61); 7.1718 (1.68); 7.1668 (0.48); 7.1536 (0.59); 7.0849 (1.44); 7.0648 (1.49); 6.4965 (2.07); 6.4788 (1.99); 6.4067 (1.60); 6.3858 (1.55); 5.1787 (6.38); 5.0182 (0.49); 5.0001 (0.70); 4.9823 (0.48); 3.3856 (0.80); 3.3356 (42.56); 3.3119 (0.34); 3.2856 (0.63); 2.9802 (16.00); 2.5186 (4.40); 2.5142 (8.84); 2.5097 (11.86); 2.5053 (8.48); 2.5009 (3.99); 1.9177 (0.32); 1.4203 (5.64); 1.4031 (5.60)

Example 44, Solvent: DMSO, Spectrometer: 399.95 MHz 10.8984 (2.13); 8.1729 (1.55); 8.1528 (1.85); 7.9531 (0.60); 7.9259 (1.20); 7.9065 (1.70); 7.8863 (1.11); 7.7360 (2.46); 7.7322 (1.21); 7.7235 (0.71); 7.7183 (3.19); 7.7146 (2.25); 7.6143 (1.14); 7.6119 (0.98); 7.5953 (3.17); 7.5888 (1.86); 7.5676 (0.46); 7.5558 (0.32); 7.5493 (1.55); 7.5436 (0.46); 7.5344 (0.84); 7.5311 (1.37); 7.5277 (0.69); 7.5013 (2.26); 7.4979 (0.98); 7.4859 (1.52); 7.4821 (2.90); 7.4685 (0.44); 7.4645 (1.15); 7.4612 (0.65); 7.4367 (1.07); 7.4165 (1.89); 7.3971 (1.13); 7.2329 (1.70); 7.2149 (1.65); 7.1635 (0.94); 7.1615 (1.01); 7.1571 (0.97); 7.1551 (0.93); 7.1430 (0.79); 7.1404 (0.80); 7.1370 (0.80); 7.1344 (0.73); 5.4218 (5.82); 3.8501 (16.00); 3.8030 (0.36); 3.3414 (75.06); 3.0860 (14.99); 2.8908 (4.68); 2.7323 (3.81); 2.7313 (3.75); 2.5257 (0.56); 2.5209 (0.89); 2.5124 (10.84); 2.5079 (21.59); 2.5034 (28.45); 2.4988 (20.65); 2.4943 (9.83); −0.0002 (2.50)

Example 45, Solvent: DMSO, Spectrometer: 399.95 MHz 10.1700 (2.41); 7.9533 (0.33); 7.8296 (0.37); 7.8086 (2.07); 7.8002 (2.23); 7.7940 (5.01); 7.7793 (0.42); 7.7250 (1.89); 7.7224 (2.42); 7.7186 (1.20); 7.7099 (0.75); 7.7047 (3.18); 7.7010 (2.23); 7.5626 (0.46); 7.5508 (0.35); 7.5443 (1.53); 7.5385 (0.47); 7.5294 (0.83); 7.5260 (1.34); 7.5226 (0.69); 7.4957 (2.25); 7.4923 (0.99); 7.4803 (1.55); 7.4766 (2.88); 7.4630 (0.44); 7.4589 (1.14); 7.4557 (0.64); 7.1023 (1.23); 7.0959 (1.22); 7.0879 (1.05); 7.0815 (1.16); 5.3309 (6.06); 4.0886 (1.69); 4.0718 (3.60); 4.0549 (1.71); 3.3454 (102.18); 3.0662 (14.92); 2.8915 (2.58); 2.7329 (2.10); 2.7317 (2.05); 2.5263 (0.57); 2.5130 (9.66); 2.5086 (19.08); 2.5040 (25.08); 2.4994 (18.29); 2.4948 (8.80); 1.6430 (0.43); 1.6259

NMR Peak List Table 1

(1.03); 1.6119 (0.85); 1.6067 (1.14); 1.5995 (0.86); 1.5861 (1.36); 1.5686 (1.08); 1.5515 (0.95); 1.5348 (0.80); 1.5182 (0.43); 1.2581 (1.01); 1.2450 (0.92); 1.2408 (1.40); 1.2381 (1.35); 1.2324 (0.97); 1.2283 (0.83); 1.2188 (1.38); 1.2013 (0.73); 0.8893 (0.94); 0.8808 (16.00); 0.8731 (1.37); 0.8643 (15.22); −0.0002 (1.46)
Example 46, Solvent: DMSO, Spectrometer: 399.95 MHz 11.0119 (1.84); 8.0896 (0.97); 8.0687 (1.17); 7.9529 (1.27); 7.8574 (1.18); 7.8381 (1.61); 7.8178 (1.08); 7.7108 (1.82); 7.7083 (2.40); 7.7045 (1.13); 7.6955 (0.72); 7.6905 (3.19); 7.6867 (2.22); 7.5581 (0.48); 7.5549 (0.32); 7.5459 (0.37); 7.5398 (1.54); 7.5342 (0.49); 7.5247 (0.81); 7.5214 (1.29); 7.5180 (0.65); 7.4867 (2.20); 7.4832 (0.91); 7.4712 (1.56); 7.4675 (2.88); 7.4538 (0.46); 7.4498 (1.17); 7.4467 (0.65); 7.3600 (0.94); 7.3575 (0.84); 7.3465 (16.00); 7.3391 (7.90); 7.3325 (7.19); 7.3258 (0.98); 7.3181 (1.80); 7.3142 (1.05); 7.3116 (1.13); 7.2767 (1.35); 7.2697 (1.65); 7.2631 (1.38); 7.2609 (1.35); 7.2550 (1.78); 7.2473 (0.99); 7.2413 (0.72); 7.2336 (0.47); 7.1685 (1.64); 7.1507 (1.59); 5.4111 (1.96); 5.3530 (5.42); 4.1499 (0.33); 4.1321 (0.33); 3.3723 (0.49); 3.3414 (160.75); 3.0220 (15.01); 2.8903 (10.82); 2.7319 (8.39); 2.7310 (8.34); 2.5255 (0.83); 2.5207 (1.35); 2.5122 (15.28); 2.5076 (30.21); 2.5030 (39.63); 2.4984 (28.45); 2.4939 (13.26); 1.1843 (0.35); 1.1666 (0.74); 1.1488 (0.36); −0.0002 (8.12)
Example 47, Solvent: DMSO, Spectrometer: 399.95 MHz 11.7568 (1.08); 7.7382 (0.48); 7.7303 (2.52); 7.7174 (1.00); 7.7123 (3.26); 7.7085 (2.27); 7.5623 (0.53); 7.5590 (0.36); 7.5508 (0.41); 7.5440 (1.80); 7.5381 (0.56); 7.5293 (1.03); 7.5259 (1.61); 7.5224 (0.80); 7.4998 (2.66); 7.4965 (1.17); 7.4847 (1.78); 7.4808 (3.32); 7.4674 (0.54); 7.4633 (1.30); 7.4597 (0.76); 7.2522 (3.78); 5.2823 (5.46); 4.1986 (1.61); 4.1815 (3.38); 4.1644 (1.62); 4.0909 (0.42); 4.0374 (0.33); 4.0220 (0.34); 3.9781 (0.34); 3.9613 (0.33); 3.3283 (60.16); 3.0484 (0.43); 3.0294 (13.57); 2.9949 (0.45); 2.8908 (2.32); 2.7321 (1.85); 2.7310 (1.78); 2.5250 (0.60); 2.5202 (1.00); 2.5117 (13.08); 2.5071 (26.34); 2.5025 (34.91); 2.4979 (25.44); 2.4934 (12.20); 1.6951 (0.60); 1.6782 (0.78); 1.6614 (0.69); 1.6447 (0.43); 1.5447 (1.01); 1.5277 (2.84); 1.5106 (2.51); 1.4933 (0.84); 1.4862 (0.37); 1.2348 (0.38); 1.1205 (0.57); 1.1053 (0.57); 0.9225 (0.69); 0.9097 (16.00); 0.8931 (15.47); 0.8788 (2.11); 0.8725 (1.79); 0.8603 (1.01); 0.8137 (0.96); 0.8064 (0.35); 0.7971 (0.92); 0.7900 (0.36); 0.0080 (0.40); −0.0002 (12.62); −0.0085 (0.42)
Example 48, Solvent: DMSO, Spectrometer: 399.95 MHz 10.5510 (1.98); 8.0744 (1.17); 8.0536 (1.40); 7.8447 (1.34); 7.8253 (1.81); 7.8052 (1.17); 7.7233 (2.71); 7.7196 (1.30); 7.7104 (0.82); 7.7055 (3.48); 7.7017 (2.39); 7.5639 (0.49); 7.5520 (0.36); 7.5455 (1.69); 7.5399 (0.48); 7.5306 (0.89); 7.5273 (1.42); 7.5240 (0.73); 7.4964 (2.50); 7.4808 (1.71); 7.4772 (3.18); 7.4635 (0.49); 7.4595 (1.22); 7.4564 (0.75); 7.1357 (1.74); 5.3768 (0.36); 5.3585 (6.41); 3.6536 (1.84); 3.6379 (4.14); 3.6223 (1.96); 3.4447 (1.40); 3.4272 (4.47); 3.4097 (4.54); 3.3922 (1.48); 3.3337 (93.21); 3.0551 (16.00); 2.8906 (1.56); 2.7311 (1.26); 2.6422 (1.75); 2.6266 (3.60); 2.6109 (1.65); 2.5252 (0.55); 2.5118 (11.81); 2.5074 (23.64); 2.5028 (31.28); 2.4982 (22.84); 2.4937 (10.97); 1.0934 (4.59); 1.0759 (9.31); 1.0584 (4.44); −0.0002 (5.00)
Example 49, Solvent: DMSO, Spectrometer: 399.95 MHz 10.2863 (2.97); 7.9533 (0.95); 7.8241 (0.78); 7.8031 (1.97); 7.7856 (2.37); 7.7725 (2.64); 7.7537 (1.10); 7.7217 (3.16); 7.7037 (3.78); 7.7001 (2.94); 7.6773 (0.33); 7.5623 (0.72); 7.5593 (0.63); 7.5446 (4.04); 7.5258 (1.82); 7.4949 (2.93); 7.4756 (3.65); 7.4579 (1.56); 7.4307 (1.31); 7.4111 (1.55); 7.3381 (1.16); 7.3189 (2.10); 7.2857 (2.27); 7.2664 (2.76); 7.2613 (1.04); 7.2466 (1.27); 7.1057 (1.74); 7.1035 (1.80); 7.0884 (1.71); 7.0861 (1.70); 5.3324 (7.17); 5.3085 (0.52); 4.3076 (1.89); 4.2910 (4.10); 4.2744 (2.04); 3.3303 (65.47); 3.3068 (4.07); 3.0606 (16.00); 3.0371 (0.88); 3.0206 (0.32); 3.0046 (0.32); 2.9542 (1.75); 2.9377 (3.46); 2.9213 (1.76); 2.8906 (6.69); 2.8670 (0.33); 2.7316 (5.59); 2.5112 (17.01); 2.5072 (30.80); 2.5027 (39.61); 2.4983 (29.86); 2.4795 (3.61); 1.2347 (0.39); 0.0075 (0.44); −0.0002 (6.95); −0.0082 (0.42)
Example 50, Solvent: DMSO, Spectrometer: 399.95 MHz 12.5452 (0.92); 7.9531 (0.69); 7.7390 (1.89); 7.7362 (2.54); 7.7323 (1.20); 7.7239 (0.75); 7.7187 (3.36); 7.7149 (2.29); 7.5664 (0.47); 7.5549 (0.33); 7.5481 (1.60); 7.5422 (0.48); 7.5334 (0.88); 7.5300 (1.44); 7.5264 (0.71); 7.5035 (2.35); 7.5001 (0.98); 7.4885 (1.53); 7.4845 (2.93); 7.4711 (0.46); 7.4670 (1.18); 7.4635 (0.64); 7.3334 (4.28); 7.1878 (0.92); 7.1675 (1.79); 7.1483 (0.76); 7.1463 (0.93); 6.5383 (0.76); 6.5358 (0.89); 6.5334 (0.98); 6.5309 (1.00); 6.5163 (0.79); 6.5118 (1.14); 6.5106 (1.09); 6.4930 (0.98); 6.4866 (2.77); 6.4834 (3.02); 6.4656 (1.11); 6.4598 (0.75); 5.3393 (5.31); 5.0533 (0.34); 5.0369 (1.31); 5.0204 (1.32); 5.0038 (0.34); 3.6961 (16.00); 3.3466 (81.44); 3.0198 (0.71); 3.0116 (15.09); 2.8909 (5.66); 2.7329 (4.46); 2.7317 (4.50); 2.5266 (0.40); 2.5217 (0.63); 2.5132 (8.04); 2.5087 (16.11); 2.5041 (21.24); 2.4994 (15.32); 2.4949 (7.20); 1.5351 (4.98); 1.5186 (4.92); −0.0002 (1.37)
Example 51, Solvent: DMSO, Spectrometer: 399.95 MHz 10.6093 (1.98); 8.0360 (0.78); 8.0154 (0.99); 7.9529 (0.47); 7.8853 (1.19); 7.8660 (1.63); 7.8458 (1.02); 7.7312 (1.80); 7.7287 (2.34); 7.7248 (1.12); 7.7160 (0.68); 7.7109 (3.10); 7.7071 (2.15); 7.5671 (0.44); 7.5488 (1.49); 7.5431 (0.43); 7.5338 (0.79); 7.5305 (1.29); 7.5271 (0.63); 7.4993 (2.15); 7.4958 (0.89); 7.4838 (1.48); 7.4801 (2.78); 7.4665 (0.42); 7.4624 (1.13); 7.4592 (0.61); 7.2131 (1.01); 7.2054 (1.79); 7.1976 (0.51); 7.1935 (1.04); 7.1885 (1.85); 7.1714 (1.26); 6.5619 (0.61); 6.5590 (0.94); 6.5572 (0.98); 6.5543 (1.15); 6.5382 (4.39); 6.5340 (3.31); 6.5272 (0.69); 6.5232 (1.17); 6.5201 (0.90); 6.5153 (0.44); 5.3850 (5.51); 4.7744 (5.49); 3.7264 (16.00); 3.3359 (75.79); 3.0697 (14.58); 2.8905 (3.90); 2.7320 (3.10); 2.7309 (3.03); 2.5253 (0.55); 2.5205 (0.87); 2.5119 (10.89); 2.5074 (21.83); 2.5028 (28.72); 2.4982 (20.67); 2.4937 (9.70); −0.0002 (2.40)
Example 52, Solvent: DMSO, Spectrometer: 399.95 MHz 10.5643 (1.54); 8.0510 (0.88); 8.0302 (1.05); 7.9531 (0.40); 7.8350 (1.27); 7.8157 (1.73); 7.7955 (1.16); 7.7264 (1.89); 7.7239 (2.51); 7.7200 (1.26); 7.7113 (0.78); 7.7061 (3.47); 7.7024 (2.31); 7.5651 (0.48); 7.5533 (0.35); 7.5468 (1.58); 7.5411 (0.47); 7.5319 (0.85); 7.5286 (1.40); 7.5251 (0.70); 7.4982 (2.36); 7.4947 (1.02); 7.4829 (1.58); 7.4791 (2.98); 7.4655 (0.46); 7.4614 (1.19); 7.4582 (0.66); 7.1454 (1.72); 7.1281 (1.65); 5.3545 (6.40); 3.3372 (100.07); 3.0527 (16.00); 2.8909 (3.30); 2.7322 (2.56); 2.7312 (2.58); 2.5257 (0.58); 2.5208 (0.94); 2.5123 (10.62); 2.5078 (21.02); 2.5032 (27.63); 2.4986 (19.95); 2.4941 (9.41); 2.0857 (14.04); 2.0777 (0.59); 1.2832 (0.34); 0.8757 (0.59); 0.8624 (0.34); −0.0002 (5.06)
Example 53, Solvent: DMSO, Spectrometer: 399.95 MHz 11.7519 (1.32); 7.7380 (0.41); 7.7325 (2.01); 7.7297 (2.63); 7.7258 (1.33); 7.7173 (0.93); 7.7121 (3.48); 7.7083 (2.41); 7.5624 (0.50); 7.5591 (0.34); 7.5509 (0.37); 7.5441 (1.71); 7.5382 (0.54); 7.5293 (0.98); 7.5259 (1.56); 7.5224 (0.79); 7.4998 (2.58); 7.4965 (1.15); 7.4848 (1.73); 7.4808 (3.20); 7.4674 (0.55); 7.4633 (1.31); 7.4598 (0.78); 7.2507 (4.08); 5.2821 (5.73); 4.1571 (1.77); 4.1404 (3.86); 4.1237 (1.81); 4.0502 (0.37); 3.3370 (86.57); 3.3043 (0.38); 3.0488 (0.33); 3.0295 (16.00); 3.0146 (0.37); 2.9877 (0.47); 2.8913 (0.81); 2.7326 (0.65); 2.7313 (0.62); 2.5257 (0.61); 2.5209 (1.02); 2.5124 (11.52); 2.5079 (22.88); 2.5033 (30.10); 2.4987 (21.78); 2.4942 (10.36); 1.6314 (1.02); 1.6143 (1.43); 1.5950 (1.25); 1.5781 (0.49); 1.3518 (0.70); 1.3353 (0.97); 1.3314 (0.95); 1.3223 (0.83); 1.3134 (1.16); 1.2903 (3.23); 1.2809 (2.75); 1.2740 (3.07); 1.2660 (1.70); 1.2563 (0.99); 1.2351 (0.45); 1.1207 (0.63); 1.1055 (0.61); 0.8872 (0.61); 0.8813 (1.73); 0.8643 (5.42); 0.8471 (1.72); 0.8205 (0.38); 0.0080 (0.34); −0.0002 (9.49)

-continued

NMR Peak List Table 1

Example 54, Solvent: DMSO, Spectrometer: 399.95 MHz 10.8752 (2.27); 8.1766 (1.70); 8.1563 (2.02); 8.0342 (2.65); 8.0211 (0.79); 8.0164 (3.14); 8.0128 (2.29); 7.9532 (0.73); 7.9258 (1.33); 7.9064 (1.86); 7.8862 (1.22); 7.7463 (0.35); 7.7381 (2.65); 7.7343 (1.30); 7.7254 (0.83); 7.7203 (3.41); 7.7164 (2.36); 7.6198 (0.34); 7.6167 (0.58); 7.6136 (0.34); 7.6037 (0.42); 7.5984 (1.65); 7.5933 (0.49); 7.5831 (0.76); 7.5800 (1.27); 7.5768 (0.69); 7.5678 (0.51); 7.5646 (0.36); 7.5559 (0.37); 7.5493 (1.73); 7.5437 (0.58); 7.5343 (1.33); 7.5306 (3.22); 7.5102 (3.39); 7.5018 (2.63); 7.4981 (1.28); 7.4922 (1.57); 7.4897 (1.24); 7.4866 (1.85); 7.4825 (3.17); 7.4690 (0.49); 7.4649 (1.22); 7.4617 (0.68); 7.2313 (1.86); 7.2131 (1.77); 5.4203 (6.48); 3.3357 (90.19); 3.0861 (16.00); 3.0220 (0.36); 2.8906 (5.67); 2.7315 (4.54); 2.5254 (0.57); 2.5121 (11.61); 2.5076 (23.03); 2.5030 (30.30); 2.4984 (21.97); 2.4939 (10.47); 0.0079 (0.38); −0.0002 (10.47)

Example 55, Solvent: DMSO, Spectrometer: 399.95 MHz 12.4362 (0.68); 7.9524 (1.44); 7.7380 (2.85); 7.7342 (1.42); 7.7203 (3.63); 7.7165 (2.58); 7.5670 (0.50); 7.5638 (0.34); 7.5556 (0.35); 7.5486 (1.84); 7.5428 (0.55); 7.5340 (0.99); 7.5306 (1.65); 7.5272 (0.85); 7.5050 (2.80); 7.4899 (1.79); 7.4858 (3.72); 7.4764 (4.26); 7.4708 (1.70); 7.4687 (1.70); 7.4650 (0.98); 7.4594 (1.36); 7.4538 (4.56); 7.4451 (0.42); 7.3375 (5.05); 6.9640 (0.40); 6.9553 (4.29); 6.9497 (1.30); 6.9382 (1.24); 6.9326 (4.04); 6.9239 (0.52); 5.3415 (6.44); 4.9711 (0.83); 4.8566 (7.26); 3.3437 (154.86); 3.0349 (2.07); 3.0231 (16.00); 3.0083 (0.42); 2.8908 (11.54); 2.7312 (9.32); 2.5257 (0.83); 2.5208 (1.37); 2.5123 (16.37); 2.5078 (32.60); 2.5033 (43.10); 2.4987 (31.36); 2.4942 (14.97); −0.0002 (1.53)

Example 56, Solvent: DMSO, Spectrometer: 399.95 MHz 10.1719 (2.73); 7.9534 (0.38); 7.8298 (0.35); 7.8088 (2.32); 7.8018 (2.45); 7.7949 (5.68); 7.7808 (0.42); 7.7247 (1.99); 7.7222 (2.56); 7.7183 (1.24); 7.7095 (0.78); 7.7044 (3.43); 7.7006 (2.37); 7.5624 (0.48); 7.5506 (0.36); 7.5441 (1.64); 7.5384 (0.48); 7.5292 (0.88); 7.5259 (1.41); 7.5225 (0.71); 7.4954 (2.38); 7.4920 (1.00); 7.4801 (1.64); 7.4763 (3.06); 7.4627 (0.47); 7.4587 (1.22); 7.4554 (0.67); 7.1020 (1.29); 7.0950 (1.27); 7.0882 (1.09); 7.0812 (1.23); 5.3304 (6.47); 4.1488 (0.95); 4.1424 (1.15); 4.1333 (1.24); 4.1299 (1.20); 4.1248 (2.03); 4.1153 (1.01); 4.1079 (0.85); 3.3424 (114.20); 3.0653 (16.00); 2.8915 (3.12); 2.7327 (2.47); 2.7318 (2.36); 2.5263 (0.49); 2.5214 (0.79); 2.5130 (9.87); 2.5084 (19.71); 2.5038 (26.01); 2.4992 (18.86); 2.4947 (8.98); 1.6653 (0.35); 1.6526 (0.68); 1.6334 (0.71); 1.6208 (0.57); 1.4904 (0.49); 1.4735 (0.58); 1.4588 (0.69); 1.4426 (0.85); 1.4272 (0.79); 1.4101 (0.63); 1.3907 (0.44); 1.3838 (0.42); 1.3702 (0.43); 1.3652 (0.46); 1.3509 (0.73); 1.3373 (0.54); 1.3318 (0.64); 1.3186 (0.50); 1.1993 (0.56); 1.1809 (0.89); 1.1654 (0.63); 1.1628 (0.70); 1.1473 (0.72); 1.1291 (0.46); 0.8923 (7.35); 0.8761 (7.67); 0.8715 (4.41); 0.8529 (8.39); 0.8344 (3.20); −0.0002 (1.69)

Example 57, Solvent: DMSO, Spectrometer: 399.95 MHz 12.7535 (1.68); 7.9525 (1.45); 7.7420 (2.08); 7.7392 (2.76); 7.7354 (1.45); 7.7267 (0.89); 7.7216 (3.48); 7.7179 (2.59); 7.6441 (1.18); 7.6411 (1.29); 7.6255 (1.55); 7.6220 (1.61); 7.5952 (0.64); 7.5922 (0.88); 7.5751 (2.18); 7.5722 (2.29); 7.5651 (1.69); 7.5610 (1.41); 7.5541 (0.53); 7.5472 (3.21); 7.5432 (1.86); 7.5324 (1.09); 7.5289 (1.86); 7.5231 (0.93); 7.5037 (2.59); 7.5005 (1.29); 7.4886 (1.81); 7.4846 (3.59); 7.4789 (1.79); 7.4713 (0.72); 7.4670 (1.75); 7.4640 (2.20); 7.4609 (1.68); 7.4461 (0.72); 7.4424 (0.68); 7.3992 (4.05); 5.3631 (6.03); 3.3442 (117.73); 3.0457 (16.00); 2.8909 (10.77); 2.7322 (9.09); 2.7308 (8.86); 2.5255 (0.68); 2.5121 (13.58); 2.5076 (26.45); 2.5031 (34.39); 2.4985 (25.53); 2.4941 (12.66); −0.0002 (1.25)

Example 58, Solvent: DMSO, Spectrometer: 400.13 MHz 10.3551 (0.43); 10.3115 (7.26); 8.3851 (0.33); 7.8845 (0.33); 7.8375 (2.37); 7.8176 (5.07); 7.8004 (10.27); 7.7837 (14.27); 7.7641 (2.76); 7.7411 (0.59); 7.7194 (0.39); 7.6537 (0.36); 7.6311 (1.91); 7.5722 (1.56); 7.5538 (4.13); 7.5356 (3.52); 7.5062 (6.33); 7.4897 (9.13); 7.4868 (9.11); 7.4686 (2.99); 7.3490 (2.16); 7.0658 (4.27); 7.0485 (4.20); 5.4362 (0.72); 5.3459 (16.00); 4.1885 (4.96); 4.1719 (10.50); 4.1553 (5.32); 4.0587 (0.57); 4.0402 (1.80); 4.0225 (1.70); 4.0046 (0.59); 3.4983 (1.04); 3.4907 (1.16); 3.3563 (2317.28); 3.3345 (45.91); 3.2320 (2.12); 3.1656 (0.62); 3.1409 (0.47); 2.9133 (3.25); 2.9069 (6.58); 2.9004 (3.36); 2.8852 (0.35); 2.6755 (1.96); 2.5706 (4.74); 2.5644 (5.28); 2.5541 (9.00); 2.5474 (9.66); 2.5371 (8.98); 2.5099 (258.76); 2.5063 (322.76); 2.3327 (2.37); 2.2491 (0.34); 2.2060 (0.33); 2.0761 (0.56); 1.9924 (7.15); 1.2839 (0.38); 1.2486 (1.45); 1.1947 (1.94); 1.1771 (3.72); 1.1597 (1.92); 0.8735 (0.54); 0.8609 (1.48); 0.8452 (0.66)

Example 59, Solvent: DMSO, Spectrometer: 399.95 MHz 10.5388 (0.75); 8.0594 (0.45); 8.0386 (0.54); 7.8303 (0.47); 7.8109 (0.66); 7.7907 (0.43); 7.7245 (0.97); 7.7208 (0.48); 7.7068 (1.25); 7.7030 (0.88); 7.5464 (0.61); 7.5315 (0.33); 7.5282 (0.52); 7.4973 (0.90); 7.4940 (0.39); 7.4818 (0.62); 7.4781 (1.15); 7.4605 (0.45); 7.1379 (0.67); 7.1202 (0.64); 5.3552 (2.34); 3.3292 (18.57); 3.0546 (5.87); 2.8908 (1.64); 2.7320 (1.30); 2.7312 (1.29); 2.5118 (4.25); 2.5073 (8.32); 2.5027 (10.90); 2.4981 (7.96); 2.4937 (3.84); 2.3834 (0.64); 2.3680 (0.42); 2.3632 (0.67); 2.3574 (0.40); 2.3426 (0.70); 1.5193 (0.79); 1.5043 (0.43); 1.4985 (0.70); 1.4938 (0.45); 1.4784 (0.71); 0.8796 (16.00); −0.0002 (2.86)

Example 60, Solvent: DMSO, Spectrometer: 399.95 MHz 10.1438 (2.72); 7.9531 (0.74); 7.8047 (0.76); 7.7837 (1.74); 7.7659 (1.99); 7.7503 (2.03); 7.7479 (2.29); 7.7295 (1.23); 7.7256 (2.45); 7.7228 (2.81); 7.7190 (1.38); 7.7101 (0.84); 7.7050 (3.53); 7.7012 (2.48); 7.5639 (0.49); 7.5608 (0.33); 7.5521 (0.36); 7.5456 (1.65); 7.5399 (0.53); 7.5307 (0.89); 7.5274 (1.45); 7.5240 (0.77); 7.4969 (2.52); 7.4936 (1.11); 7.4815 (1.70); 7.4777 (3.18); 7.4642 (0.52); 7.4601 (1.26); 7.4569 (0.73); 7.3101 (0.46); 7.3038 (0.33); 7.2930 (9.21); 7.2820 (8.50); 7.2638 (0.72); 7.2601 (0.83); 7.2449 (0.55); 7.2422 (0.72); 7.2205 (0.95); 7.2094 (1.08); 7.1984 (1.23); 7.1881 (0.72); 7.1849 (0.76); 7.1770 (0.36); 7.0919 (1.53); 7.0894 (1.59); 7.0743 (1.51); 7.0717 (1.48); 5.3278 (6.23); 5.0059 (0.52); 4.9908 (0.98); 4.9752 (0.97); 4.9584 (0.54); 3.3899 (0.38); 3.3485 (165.03); 3.0645 (16.00); 2.9281 (0.69); 2.9105 (0.55); 2.8909 (6.45); 2.8830 (0.37); 2.8765 (1.32); 2.8570 (1.29); 2.8427 (1.37); 2.8229 (0.57); 2.8087 (0.50); 2.7317 (4.89); 2.5263 (0.65); 2.5130 (12.58); 2.5085 (25.04); 2.5039 (32.97); 2.4993 (24.03); 2.4948 (11.56); 1.3012 (0.99); 1.2855 (0.98); 1.2321 (6.28); 1.2165 (6.11); −0.0002 (3.72)

Example 61, Solvent: DMSO, Spectrometer: 400.13 MHz 10.0934 (6.86); 7.8319 (1.42); 7.8110 (4.22); 7.7939 (6.37); 7.7908 (5.85); 7.7869 (5.91); 7.7696 (1.74); 7.7660 (1.14); 7.7264 (6.39); 7.7086 (7.84); 7.7049 (5.67); 7.5741 (1.13); 7.5711 (0.81); 7.5623 (1.04); 7.5558 (3.81); 7.5501 (1.31); 7.5409 (2.36); 7.5377 (3.40); 7.5345 (1.89); 7.5102 (5.90); 7.4947 (4.24); 7.4911 (7.16); 7.4775 (1.33); 7.4735 (2.74); 7.4703 (1.67); 7.0919 (3.36); 7.0884 (3.37); 7.0751 (3.21); 7.0716 (3.13); 5.7665 (4.63); 5.3415 (14.80); 4.6794 (1.01); 4.6671 (1.18); 4.6570 (1.86); 4.6476 (1.36); 4.6348 (0.92); 4.6254 (0.51); 3.5308 (1.95); 3.5127 (6.35); 3.4945 (6.46); 3.4764 (2.02); 3.3905 (1.14); 3.3406 (77.67); 3.3170 (0.72); 3.2904 (0.93); 2.5603 (0.43); 2.5558 (0.33); 2.5189 (12.38); 2.5147 (23.99); 2.5103 (31.66); 2.5059 (22.93); 2.5018 (11.08); 2.4647 (0.37); 2.4603 (0.42); 1.8689 (1.91); 1.8563 (2.21); 1.8423 (2.28); 1.7304 (1.91); 1.7221 (2.06); 1.7079 (2.22); 1.5236 (1.00); 1.5147 (1.06); 1.4936 (1.18); 1.4677 (1.05); 1.4594 (0.94); 1.4351 (2.23); 1.4106 (2.82); 1.3851 (2.90); 1.3719 (1.69); 1.3584 (2.54); 1.3327 (2.03); 1.3265 (2.22); 1.3007 (1.22); 1.2813 (1.02); 1.2507 (1.38); 1.2405 (1.27); 1.2271 (1.08); 1.2097 (0.64); 1.0652 (7.47); 1.0471 (16.00); 1.0289 (6.94)

NMR Peak List Table 1

Example 62, Solvent: DMSO, Spectrometer: 399.95 MHz 10.5328 (2.07); 8.0693 (1.32); 8.0486 (1.57); 7.8330 (1.31); 7.8136 (1.87); 7.7934 (1.20); 7.7231 (2.73); 7.7103 (0.86); 7.7053 (3.48); 7.7016 (2.44); 7.5649 (0.51); 7.5618 (0.33); 7.5530 (0.39); 7.5466 (1.69); 7.5410 (0.50); 7.5316 (0.93); 7.5284 (1.45); 7.5251 (0.74); 7.4975 (2.52); 7.4820 (1.78); 7.4783 (3.18); 7.4646 (0.51); 7.4606 (1.23); 7.4575 (0.70); 7.1408 (1.90); 7.1228 (1.81); 5.3557 (6.62); 3.3433 (112.40); 3.3109 (0.36); 3.0531 (16.00); 2.8912 (2.26); 2.7317 (1.85); 2.5260 (0.67); 2.5127 (11.48); 2.5083 (22.15); 2.5038 (28.70); 2.4992 (20.81); 2.4947 (9.94); 2.4795 (1.96); 2.4612 (2.90); 2.4422 (1.93); 1.5070 (0.98); 1.4890 (2.25); 1.4702 (2.27); 1.4523 (0.95); 0.7231 (0.43); 0.7173 (0.39); 0.7133 (0.34); 0.7054 (0.72); 0.6975 (0.35); 0.6929 (0.41); 0.6858 (0.47); 0.3938 (0.77); 0.3836 (2.14); 0.3794 (2.21); 0.3738 (0.95); 0.3696 (1.05); 0.3635 (2.15); 0.3593 (1.96); 0.3496 (0.76); 0.0611 (0.78); 0.0509 (2.30); 0.0475 (2.45); 0.0388 (2.25); 0.0353 (2.26); 0.0247 (0.62); −0.0002 (7.48)

Example 63, Solvent: DMSO, Spectrometer: 399.95 MHz 10.7229 (1.56); 8.3829 (0.46); 8.3620 (0.86); 8.3425 (0.72); 8.1789 (0.32); 8.1410 (0.89); 8.1381 (1.02); 8.1203 (1.17); 8.1168 (1.00); 8.0789 (0.75); 8.0583 (0.93); 7.9526 (0.74); 7.8660 (1.20); 7.8468 (1.58); 7.8266 (1.03); 7.8158 (0.33); 7.7972 (0.67); 7.7787 (0.45); 7.7418 (1.63); 7.7238 (4.26); 7.7048 (3.39); 7.7011 (2.36); 7.6486 (1.05); 7.6443 (0.96); 7.6280 (1.50); 7.6139 (0.47); 7.6095 (0.91); 7.6029 (0.45); 7.5997 (0.60); 7.5965 (0.48); 7.5870 (0.60); 7.5815 (1.82); 7.5763 (1.12); 7.5628 (2.00); 7.5524 (0.57); 7.5461 (1.90); 7.5403 (0.71); 7.5310 (1.15); 7.5276 (2.01); 7.5236 (2.14); 7.5025 (2.77); 7.4967 (2.92); 7.4886 (0.89); 7.4811 (3.37); 7.4774 (3.94); 7.4616 (3.04); 7.4481 (1.05); 7.4448 (1.04); 7.4401 (0.98); 7.4317 (0.53); 7.1885 (0.53); 7.1743 (1.79); 7.1567 (1.68); 7.0494 (0.33); 7.0316 (0.33); 6.4903 (0.70); 6.4782 (0.32); 6.4718 (0.72); 5.7781 (2.99); 5.3760 (1.33); 5.3658 (5.60); 4.7148 (0.79); 4.6973 (1.38); 4.6802 (0.92); 4.6669 (0.42); 4.6478 (0.39); 3.8819 (1.66); 3.8662 (3.52); 3.8506 (1.79); 3.3707 (8.60); 3.3284 (192.98); 3.0960 (10.49); 3.0593 (7.61); 3.0555 (16.00); 3.0523 (4.74); 3.0422 (1.91); 2.9579 (1.08); 2.9400 (1.91); 2.9263 (2.53); 2.9109 (3.38); 2.8950 (1.87); 2.8905 (6.69); 2.7503 (0.46); 2.7312 (5.05); 2.6802 (0.34); 2.6756 (0.73); 2.6710 (1.00); 2.6665 (0.70); 2.5244 (2.72); 2.5196 (4.18); 2.5111 (55.95); 2.5065 (113.37); 2.5019 (151.00); 2.4973 (109.61); 2.4928 (52.06); 2.3377 (0.37); 2.3333 (0.75); 2.3287 (1.02); 2.3241 (0.74); 2.3196 (0.35); 1.9090 (0.74); 1.2358 (1.11); 0.8539 (0.35); 0.0080 (1.83); −0.0002 (57.04); −0.0085 (1.68)

Example 64, Solvent: DMSO, Spectrometer: 399.95 MHz 10.8680 (2.25); 8.0124 (1.32); 7.9918 (1.74); 7.9532 (0.79); 7.8730 (1.39); 7.8537 (1.92); 7.8335 (1.16); 7.7274 (2.81); 7.7144 (0.88); 7.7095 (3.56); 7.7058 (2.55); 7.5678 (0.51); 7.5647 (0.33); 7.5557 (0.40); 7.5494 (1.73); 7.5439 (0.53); 7.5344 (0.94); 7.5312 (1.46); 7.5279 (0.77); 7.4985 (2.55); 7.4828 (1.85); 7.4793 (3.28); 7.4654 (0.55); 7.4616 (1.30); 7.4586 (0.76); 7.3313 (1.15); 7.3257 (0.32); 7.3101 (2.59); 7.2891 (1.61); 7.2088 (1.93); 7.1907 (1.86); 7.0128 (3.47); 7.0073 (2.68); 7.0021 (1.71); 6.9968 (1.43); 6.9952 (1.47); 6.9123 (1.06); 6.9101 (1.12); 6.9068 (1.02); 6.9047 (0.96); 6.8912 (1.04); 6.8897 (1.03); 6.8854 (0.99); 5.3897 (6.43); 5.1387 (0.34); 5.1226 (1.13); 5.1062 (1.14); 5.0899 (0.34); 3.3374 (98.89); 3.0642 (16.00); 2.8910 (6.17); 2.7317 (4.95); 2.5259 (0.74); 2.5124 (14.35); 2.5080 (27.93); 2.5035 (36.37); 2.4989 (26.54); 2.4945 (12.86); 1.5377 (5.80); 1.5213 (5.72); −0.0002 (2.08)

Example 65, Solvent: DMSO, Spectrometer: 399.95 MHz 10.6872 (2.25); 8.0182 (0.71); 7.9976 (0.92); 7.9527 (0.83); 7.8811 (1.33); 7.8619 (1.81); 7.8416 (1.11); 7.7279 (2.61); 7.7241 (1.26); 7.7152 (0.78); 7.7101 (3.42); 7.7064 (2.37); 7.5683 (0.49); 7.5564 (0.36); 7.5500 (1.64); 7.5443 (0.48); 7.5350 (0.87); 7.5317 (1.42); 7.5283 (0.71); 7.5005 (2.41); 7.4971 (1.04); 7.4849 (1.95); 7.4814 (3.29); 7.4756 (4.59); 7.4700 (1.42); 7.4637 (1.43); 7.4587 (1.65); 7.4530 (4.56); 7.4442 (0.39); 7.2039 (1.77); 7.1861 (1.68); 6.9528 (0.42); 6.9441 (4.29); 6.9385 (1.26); 6.9270 (1.22); 6.9215 (3.97); 6.9127 (0.33); 5.3821 (6.15); 4.8083 (5.61); 3.3429 (143.71); 3.3076 (0.38); 3.0661 (16.00); 2.8908 (6.80); 2.7319 (5.24); 2.7312 (5.34); 2.5258 (0.71); 2.5209 (1.16); 2.5124 (14.14); 2.5079 (28.18); 2.5033 (37.11); 2.4987 (26.84); 2.4942 (12.72); −0.0002 (0.63)

Example 66, Solvent: DMSO, Spectrometer: 399.95 MHz 10.6366 (2.23); 8.0298 (0.83); 8.0093 (1.06); 7.8832 (1.35); 7.8638 (1.84); 7.8436 (1.15); 7.7281 (2.63); 7.7243 (1.26); 7.7154 (0.76); 7.7103 (3.43); 7.7065 (2.38); 7.5681 (0.48); 7.5562 (0.35); 7.5497 (1.65); 7.5442 (0.47); 7.5348 (0.86); 7.5315 (1.41); 7.5282 (0.72); 7.5004 (2.42); 7.4970 (1.02); 7.4849 (1.63); 7.4812 (3.10); 7.4676 (0.47); 7.4635 (1.22); 7.4603 (0.69); 7.2047 (1.81); 7.1865 (1.72); 7.1554 (1.85); 7.1495 (0.60); 7.1383 (0.81); 7.1328 (3.23); 7.1285 (0.74); 7.1224 (0.33); 7.1173 (0.71); 7.1112 (2.49); 6.9915 (2.48); 6.9854 (0.79); 6.9805 (2.52); 6.9745 (1.19); 6.9685 (1.83); 6.9635 (0.69); 6.9576 (1.78); 5.3827 (6.30); 4.7789 (6.47); 3.3427 (116.03); 3.0663 (16.00); 2.8908 (0.57); 2.7314 (0.44); 2.5259 (0.59); 2.5211 (0.94); 2.5125 (12.03); 2.5080 (24.07); 2.5035 (31.81); 2.4988 (23.05); 2.4943 (10.95); −0.0002 (0.76)

Example 67, Solvent: DMSO, Spectrometer: 400.13 MHz 10.5993 (1.82); 9.1108 (1.66); 9.0962 (1.84); 8.6341 (0.47); 8.6147 (1.06); 8.5952 (0.64); 8.4425 (2.28); 8.1891 (1.06); 8.1707 (1.63); 8.1543 (1.14); 8.0594 (0.95); 8.0392 (1.18); 7.8476 (0.94); 7.8278 (1.38); 7.8079 (0.92); 7.7257 (2.11); 7.7078 (2.67); 7.7041 (2.13); 7.5766 (0.37); 7.5581 (1.35); 7.5399 (1.16); 7.5070 (1.93); 7.4877 (2.53); 7.4700 (1.04); 7.1633 (1.46); 7.1449 (1.45); 5.3555 (4.71); 4.6487 (0.94); 4.6306 (1.84); 4.6126 (1.04); 3.5220 (0.60); 3.4965 (1.34); 3.4471 (16.00); 3.3968 (911.69); 3.3470 (19.44); 3.2969 (2.10); 3.2676 (0.98); 3.2281 (0.66); 3.1869 (0.44); 3.1680 (0.34); 3.1020 (0.37); 3.0512 (11.93); 2.6848 (0.88); 2.6802 (1.19); 2.6756 (0.99); 2.6109 (0.34); 2.5660 (2.35); 2.5616 (3.07); 2.5571 (2.61); 2.5525 (2.00); 2.5333 (5.11); 2.5199 (65.47); 2.5156 (134.39); 2.5112 (183.81); 2.5067 (138.75); 2.5025 (71.95); 2.4707 (4.11); 2.4658 (3.82); 2.4611 (4.02); 2.4562 (3.69); 2.4530 (3.49); 2.4352 (1.51); 2.3425 (0.79); 2.3381 (1.09); 2.3336 (0.84); 1.9767 (0.71); 1.9569 (1.03); 1.9392 (0.80); 1.6144 (0.35); 1.5965 (0.84); 1.5778 (1.03); 1.5580 (0.75)

Example 68, Solvent: DMSO, Spectrometer: 400.13 MHz 10.3171 (2.77); 7.8219 (0.76); 7.8011 (1.72); 7.7834 (1.99); 7.7697 (2.19); 7.7672 (2.40); 7.7490 (1.03); 7.7275 (2.73); 7.7097 (3.44); 7.7060 (2.42); 7.5683 (0.53); 7.5567 (0.45); 7.5500 (1.72); 7.5444 (0.53); 7.5351 (0.97); 7.5318 (1.45); 7.5007 (2.52); 7.4852 (1.82); 7.4815 (3.19); 7.4638 (1.29); 7.4451 (1.37); 7.4413 (1.84); 7.4236 (3.52); 7.3981 (2.13); 7.3932 (0.69); 7.3801 (3.38); 7.3607 (1.53); 7.3220 (0.78); 7.3184 (1.21); 7.3148 (0.66); 7.3062 (0.56); 7.3005 (1.46); 7.2953 (0.29); 7.1078 (1.50); 7.1014 (1.50); 7.0903 (1.50); 7.0877 (1.42); 5.8544 (0.42); 5.8383 (1.42); 5.8218 (1.40); 5.8054 (0.40); 5.3399 (6.46); 3.3747 (0.40); 3.3249 (36.38); 3.3011 (1.86); 3.0722 (16.00); 2.6831 (0.66); 2.6786 (0.87); 2.6741 (0.64); 2.5638 (1.28); 2.5594 (1.69); 2.5547 (1.30); 2.5496 (0.86); 2.5184 (55.80); 2.5140 (109.68); 2.5095 (145.64); 2.5050 (103.32); 2.5006 (48.57); 2.4642 (1.44); 2.4597 (1.70); 2.4554 (1.26); 2.3409 (0.71); 2.3363 (0.91); 2.3319 (0.70); 1.5370 (6.04); 1.5206 (6.03)

Example 69, Solvent: DMSO, Spectrometer: 399.95 MHz 10.7919 (2.10); 8.0189 (1.20); 7.9983 (1.56); 7.9528 (0.58); 7.8679 (1.28); 7.8488 (1.77); 7.8284 (1.12); 7.7294 (2.04); 7.7268 (2.58); 7.7231 (1.28); 7.7142 (0.80); 7.7091 (3.40); 7.7054 (2.43); 7.5685 (0.48); 7.5565 (0.36); 7.5502 (1.60); 7.5445 (0.48); 7.5351 (0.87); 7.5318 (1.41); 7.5285 (0.71); 7.4997 (2.31); 7.4963 (1.02); 7.4841 (1.67); 7.4805 (3.03); 7.4669 (0.49); 7.4628 (1.21); 7.4596 (0.73); 7.2021 (1.76); 7.1880 (1.10); 7.1831 (2.00); 7.1680 (1.52); 7.1600 (0.34); 7.1457 (1.28); 6.5295 (0.71); 6.5259 (1.12); 6.5220 (1.10); 6.5005 (4.44); 6.4956 (2.89); 6.4894 (0.91); 6.4827 (1.25); 6.4772 (0.71); 5.3853 (5.82); 5.0648 (1.00); 5.0483 (1.01); 3.6978 (16.00); 3.3541 (114.20); 3.3508 (148.75);

NMR Peak List Table 1

3.0722 (0.65); 3.0627 (15.32); 2.8911 (4.53); 2.7326 (3.78); 2.7314 (3.60); 2.5265 (0.69); 2.5217 (1.11); 2.5131 (13.04); 2.5086 (25.87); 2.5040 (33.86); 2.4994 (24.65); 2.4950 (11.81); 1.5207 (5.12); 1.5043 (5.05); −0.0002 (0.57)
Example 70, Solvent: DMSO, Spectrometer: 400.13 MHz 10.2616 (6.41); 7.8384 (1.50); 7.8176 (3.85); 7.8000 (4.59); 7.7878 (5.39); 7.7694 (2.18); 7.7665 (2.07); 7.7568 (6.17); 7.7388 (7.21); 7.7352 (5.36); 7.5659 (1.06); 7.5538 (0.91); 7.5475 (3.51); 7.5421 (1.20); 7.5294 (3.02); 7.4987 (5.30); 7.4794 (6.77); 7.4617 (2.53); 7.1330 (3.40); 7.1179 (3.22); 5.3776 (13.62); 4.9879 (16.00); 4.1989 (4.31); 4.1823 (9.34); 4.1657 (4.39); 3.3284 (39.57); 2.9114 (2.84); 2.9049 (6.17); 2.8984 (3.00); 2.6755 (0.37); 2.5801 (2.62); 2.5735 (2.75); 2.5635 (5.52); 2.5569 (5.41); 2.5469 (3.10); 2.5403 (3.08); 2.5109 (49.01); 2.5066 (64.28); 2.5023 (46.96); 2.3333 (0.41); 2.3292 (0.32); 2.0798 (9.91)
Example 71, Solvent: DMSO, Spectrometer: 399.95 MHz 10.5020 (1.86); 8.0726 (1.33); 8.0519 (1.58); 7.8358 (1.32); 7.8165 (1.83); 7.7963 (1.21); 7.7264 (2.09); 7.7240 (2.64); 7.7202 (1.33); 7.7113 (0.82); 7.7062 (3.56); 7.7024 (2.42); 7.5648 (0.49); 7.5530 (0.36); 7.5465 (1.65); 7.5408 (0.50); 7.5315 (0.89); 7.5282 (1.42); 7.5249 (0.73); 7.4977 (2.44); 7.4944 (1.07); 7.4823 (1.68); 7.4786 (3.11); 7.4650 (0.48); 7.4609 (1.22); 7.4577 (0.69); 7.1399 (1.83); 7.1215 (1.78); 5.3540 (6.65); 3.3299 (59.74); 3.0539 (16.00); 2.8909 (2.02); 2.7321 (1.63); 2.5253 (0.57); 2.5120 (10.69); 2.5075 (21.11); 2.5029 (27.62); 2.4983 (20.03); 2.4939 (9.54); 2.4190 (1.06); 2.4001 (3.52); 2.3812 (3.61); 2.3624 (1.15); 1.2828 (0.35); 1.0758 (3.97); 1.0570 (8.37); 1.0381 (3.78); 0.8759 (0.59); 0.8625 (0.34); −0.0002 (5.22)
Example 72, Solvent: DMSO, Spectrometer: 399.95 MHz 11.7791 (0.48); 7.9532 (0.41); 7.7367 (0.88); 7.7340 (1.19); 7.7300 (0.60); 7.7216 (0.39); 7.7163 (1.56); 7.7125 (1.10); 7.5449 (0.78); 7.5303 (0.43); 7.5269 (0.70); 7.5234 (0.36); 7.5014 (1.14); 7.4980 (0.51); 7.4864 (0.74); 7.4824 (1.40); 7.4649 (0.56); 7.4613 (0.33); 7.2579 (1.81); 5.2897 (2.57); 3.8663 (3.73); 3.3298 (35.01); 3.0324 (7.32); 2.8910 (3.43); 2.7322 (2.69); 2.7313 (2.64); 2.5204 (0.41); 2.5118 (5.50); 2.5073 (11.12); 2.5027 (14.79); 2.4981 (10.79); 2.4936 (5.19); 0.9301 (16.00); 0.9054 (0.41); 0.7329 (1.03); −0.0002 (5.07)
Example 73, Solvent: DMSO, Spectrometer: 399.95 MHz 10.5533 (1.12); 10.5076 (0.32); 8.0711 (0.88); 8.0504 (1.04); 7.9531 (0.43); 7.9406 (0.34); 7.9208 (0.49); 7.9007 (0.37); 7.8411 (0.76); 7.8217 (1.10); 7.8016 (0.70); 7.7470 (1.25); 7.7287 (2.00); 7.7252 (2.79); 7.7053 (2.50); 7.7016 (1.79); 7.5750 (0.77); 7.5690 (0.40); 7.5653 (0.45); 7.5596 (0.52); 7.5564 (0.72); 7.5533 (0.61); 7.5470 (1.25); 7.5414 (0.90); 7.5318 (0.70); 7.5287 (1.08); 7.5253 (0.64); 7.5168 (1.12); 7.4977 (3.16); 7.4789 (2.78); 7.4650 (0.42); 7.4610 (0.88); 7.4579 (0.51); 7.1491 (1.03); 7.1312 (0.99); 7.1239 (0.37); 6.9620 (0.80); 6.9433 (1.07); 5.3809 (2.55); 5.3567 (4.46); 3.5688 (1.27); 3.5524 (2.55); 3.5358 (1.37); 3.5214 (0.33); 3.3933 (30.62); 3.0690 (0.47); 3.0549 (16.00); 2.8914 (2.58); 2.7321 (2.19); 2.5635 (1.27); 2.5496 (2.64); 2.5357 (1.55); 2.5260 (1.26); 2.5123 (18.66); 2.5081 (35.20); 2.5036 (45.00); 2.4991 (32.97); 2.4949 (16.23); 2.4520 (0.45); 2.4425 (0.90); 2.4348 (0.42); 2.4240 (1.82); 2.4062 (1.01); 2.3822 (0.49); 2.2189 (0.32); 2.2010 (0.56); 2.1823 (0.33); 1.8432 (0.54); 1.8265 (0.75); 1.8060 (0.75); 1.7894 (0.38); 1.7292 (0.35); 1.7109 (0.76); 1.6927 (0.80); 1.6741 (0.49); 1.5973 (0.42); 1.4284 (0.46); 1.4082 (0.44); 1.2374 (0.33); −0.0002 (2.87)
Example 74, Solvent: DMSO, Spectrometer: 400.13 MHz 7.7393 (2.83); 7.7213 (3.50); 7.7177 (2.51); 7.5588 (0.53); 7.5468 (0.45); 7.5405 (1.70); 7.5350 (0.56); 7.5253 (0.98); 7.5222 (1.45); 7.4896 (2.51); 7.4703 (3.27); 7.4526 (1.26); 7.4107 (1.21); 7.3925 (1.60); 7.3901 (1.55); 7.3719 (1.34); 7.2932 (0.91); 7.2749 (2.76); 7.2574 (3.45); 7.2413 (4.27); 7.2248 (1.60); 7.2087 (0.81); 7.2049 (0.96); 7.2001 (0.55); 7.1874 (1.45); 7.1810 (0.34); 7.1702 (0.48); 6.6962 (0.65); 6.6824 (1.29); 6.6685 (0.64); 6.5234 (2.00); 6.5057 (1.92); 6.4393 (1.98); 6.4185 (1.92); 5.7637 (2.15); 5.2300 (6.75); 3.4554 (0.83); 3.4394 (1.58); 3.4232 (1.48); 3.4193 (1.57); 3.4044 (0.93); 3.3765 (0.60); 3.3438 (155.57); 3.3200 (0.57); 3.0562 (16.00); 2.8373 (1.71); 2.8181 (2.42); 2.8003 (1.51); 2.5153 (15.94); 2.5113 (31.31); 2.5069 (41.19); 2.5025 (29.46)
Example 75, Solvent: DMSO, Spectrometer: 399.95 MHz 12.3671 (0.65); 9.3200 (0.57); 7.9528 (1.31); 7.7467 (2.02); 7.7441 (2.74); 7.7400 (1.43); 7.7346 (0.98); 7.7316 (1.14); 7.7265 (3.57); 7.7227 (2.60); 7.7173 (1.04); 7.7134 (0.72); 7.5699 (0.48); 7.5665 (0.33); 7.5586 (0.40); 7.5515 (1.69); 7.5455 (0.65); 7.5419 (0.57); 7.5369 (1.03); 7.5334 (1.56); 7.5299 (0.88); 7.5238 (0.51); 7.5087 (2.57); 7.5050 (1.31); 7.4938 (1.68); 7.4897 (3.18); 7.4855 (1.48); 7.4819 (1.48); 7.4765 (0.77); 7.4722 (1.44); 7.4683 (1.26); 7.4651 (2.00); 7.4603 (0.88); 7.4465 (2.69); 7.4303 (0.88); 7.4258 (2.30); 7.4199 (0.33); 7.3952 (0.42); 7.3921 (0.59); 7.3732 (0.35); 7.3355 (4.18); 7.3157 (1.19); 7.3131 (0.87); 7.2972 (1.19); 7.2813 (0.46); 7.2787 (0.76); 7.2759 (0.53); 7.2665 (2.44); 7.2636 (3.00); 7.2584 (0.82); 7.2448 (2.40); 7.2427 (1.94); 7.1751 (0.44); 7.1561 (0.46); 7.1534 (0.60); 7.1354 (0.48); 6.9953 (0.75); 6.7583 (0.99); 6.7556 (0.91); 6.7367 (0.95); 6.6282 (0.77); 5.3233 (5.58); 5.1160 (1.48); 3.3335 (41.99); 3.3310 (55.90); 3.0577 (16.00); 3.0481 (4.23); 3.0354 (0.50); 3.0175 (0.44); 2.8901 (10.70); 2.7317 (8.74); 2.7306 (8.34); 2.5247 (0.78); 2.5199 (1.27); 2.5113 (15.49); 2.5068 (30.92); 2.5022 (40.65); 2.4976 (29.35); 2.4931 (13.84); 0.0080 (0.36); −0.0002 (10.76)
Example 76, Solvent: DMSO, Spectrometer: 399.95 MHz 10.5782 (2.22); 8.0435 (0.84); 8.0229 (1.07); 7.8826 (1.33); 7.8633 (1.84); 7.8431 (1.13); 7.7276 (2.63); 7.7239 (1.28); 7.7149 (0.81); 7.7099 (3.44); 7.7061 (2.40); 7.7036 (0.49); 7.5557 (0.36); 7.5493 (1.65); 7.5436 (0.88); 7.5344 (0.92); 7.5310 (1.42); 7.5277 (0.72); 7.4998 (2.42); 7.4964 (1.03); 7.4843 (1.69); 7.4806 (3.11); 7.4670 (0.49); 7.4629 (1.23); 7.4597 (0.70); 7.2035 (1.81); 7.1853 (1.77); 7.1717 (1.12); 7.1525 (1.64); 7.1320 (1.18); 7.1120 (0.71); 7.1090 (0.60); 6.8792 (0.97); 6.8608 (1.70); 6.8450 (2.09); 6.8260 (1.47); 5.3814 (6.24); 4.8169 (6.31); 3.3473 (125.30); 3.0626 (16.00); 2.8906 (0.86); 2.7322 (0.69); 2.7312 (0.68); 2.5260 (0.56); 2.5126 (11.38); 2.5081 (22.51); 2.5035 (29.43); 2.4989 (21.30); 2.4944 (10.12); 2.2248 (10.54); −0.0002 (0.43)
Example 77, Solvent: DMSO, Spectrometer: 399.95 MHz 10.5111 (2.02); 8.0678 (1.23); 8.0471 (1.47); 7.8297 (1.26); 7.8105 (1.73); 7.7902 (1.19); 7.7235 (2.59); 7.7197 (1.29); 7.7108 (0.83); 7.7058 (3.52); 7.7020 (2.35); 7.5641 (0.49); 7.5522 (0.37); 7.5458 (1.63); 7.5401 (0.49); 7.5308 (0.87); 7.5275 (1.41); 7.5241 (0.71); 7.4963 (2.41); 7.4928 (1.02); 7.4809 (1.69); 7.4771 (3.07); 7.4635 (0.49); 7.4594 (1.23); 7.4562 (0.69); 7.1387 (1.76); 7.1211 (1.70); 5.3535 (6.08); 3.3290 (52.17); 3.0676 (0.35); 3.0535 (16.00); 2.8908 (2.53); 2.7322 (1.96); 2.7312 (1.99); 2.5252 (0.56); 2.5204 (0.95); 2.5119 (11.27); 2.5074 (22.37); 2.5028 (29.46); 2.4982 (21.31); 2.4937 (10.07); 2.4097 (1.50); 2.3910 (2.25); 2.3714 (1.63); 1.7077 (0.95); 1.6732 (1.93); 1.6378 (1.20); 1.6145 (0.63); 1.6107 (0.63); 1.5899 (0.46); 1.4985 (0.80); 1.4809 (1.64); 1.4611 (1.74); 1.4434 (0.86); 1.2341 (0.51); 1.2233 (0.48); 1.2146 (0.45); 1.1968 (0.93); 1.1923 (0.95); 1.1863 (1.02); 1.1685 (1.50); 1.1621 (1.26); 1.1507 (0.86); 1.1400 (1.27); 1.1205 (0.60); 1.1137 (0.38); 0.9076 (0.44); 0.8938 (0.47); 0.8760 (1.38); 0.8621 (0.67); 0.8563 (0.94); 0.8498 (0.93); −0.0002 (5.59)
Example 78, Solvent: DMSO, Spectrometer: 399.95 MHz 10.4942 (2.05); 8.0673 (1.38); 8.0466 (1.63); 7.9534 (0.69); 7.8251 (1.26); 7.8060 (1.85); 7.7856 (1.16); 7.7236 (2.98); 7.7108 (0.93); 7.7058 (3.91); 7.7021 (2.73); 7.5641 (0.55); 7.5610 (0.37); 7.5522 (0.41); 7.5458 (1.87); 7.5401 (0.57); 7.5308 (1.00); 7.5276 (1.62); 7.5243 (0.85); 7.4963 (2.80); 7.4808 (1.93); 7.4772 (3.56); 7.4635 (0.56); 7.4595 (1.39); 7.4563 (0.81); 7.1383 (1.91); 7.1198 (1.86); 5.3545 (7.06); 4.0446 (0.41); 4.0268 (0.42); 3.3291 (63.21); 3.0565 (16.00); 2.8909 (5.44); 2.7321 (4.37); 2.5252 (0.65); 2.5118 (13.63); 2.5074 (27.22); 2.5028

NMR Peak List Table 1

(36.02); 2.4982 (26.50); 2.4938 (12.92); 2.4656 (0.42); 2.4441 (0.48); 2.4299 (1.12); 2.4083 (1.54); 2.4021 (1.39); 2.3846 (1.43); 2.3664 (0.40); 2.3489 (0.50); 2.2552 (0.38); 2.2358 (0.52); 2.2202 (0.49); 2.2126 (0.37); 2.2012 (0.37); 2.1318 (1.14); 2.1213 (0.74); 2.0934 (1.22); 1.7405 (0.35); 1.7367 (0.33); 1.7184 (0.45); 1.7107 (0.59); 1.7000 (0.47); 1.5393 (0.35); 1.5318 (0.33); 1.5098 (0.52); 1.4804 (0.38); 1.4703 (0.61); 1.4617 (0.61); 1.4507 (0.55); 1.4409 (0.62); 1.4326 (0.49); 1.4228 (0.38); 1.3350 (0.96); 1.3115 (1.45); 1.2982 (0.81); 1.2832 (0.78); 1.2688 (0.42); 1.2440 (1.23); 1.2395 (1.35); 1.2213 (0.71); 1.2164 (0.71); 1.1836 (0.54); 1.1658 (1.05); 1.1552 (0.39); 1.1481 (0.89); 1.1393 (0.39); 1.1327 (0.48); 1.1279 (0.63); 1.1221 (0.62); 1.1165 (0.62); 1.1108 (0.44); 1.1052 (0.40); 1.0928 (0.35); 0.8757 (0.62); 0.8625 (0.38); 0.8570 (0.33); 0.7119 (0.48); 0.7064 (0.52); 0.6989 (0.51); 0.6930 (0.49); 0.6817 (0.47); 0.6762 (0.49); 0.6686 (0.50); 0.6632 (0.46); −0.0002 (7.35)
Example 79, Solvent: DMSO, Spectrometer: 399.95 MHz 10.2078 (2.01); 7.9530 (0.61); 7.8012 (0.70); 7.7805 (1.26); 7.7618 (1.18); 7.7227 (1.62); 7.7201 (2.12); 7.7163 (1.14); 7.7078 (1.92); 7.7024 (2.89); 7.6987 (2.01); 7.6880 (0.87); 7.5628 (0.39); 7.5445 (1.30); 7.5388 (0.43); 7.5295 (0.70); 7.5262 (1.13); 7.5228 (0.59); 7.4948 (1.93); 7.4914 (0.85); 7.4794 (1.37); 7.4756 (2.55); 7.4687 (1.72); 7.4653 (2.07); 7.4581 (1.24); 7.4546 (0.83); 7.4472 (2.45); 7.4445 (2.34); 7.4222 (0.36); 7.4195 (0.34); 7.3465 (0.38); 7.3371 (1.38); 7.3322 (0.53); 7.3186 (2.37); 7.3025 (0.63); 7.2985 (1.45); 7.2396 (0.46); 7.2227 (0.96); 7.2199 (1.41); 7.2101 (0.50); 7.2062 (0.54); 7.2018 (1.33); 7.1865 (0.34); 7.1836 (0.50); 7.0898 (1.35); 7.0730 (1.30); 5.3272 (4.75); 4.2948 (1.05); 4.1307 (5.89); 3.3440 (106.63); 3.0502 (12.46); 2.8907 (4.85); 2.7324 (3.83); 2.7313 (3.90); 2.5259 (0.53); 2.5211 (0.86); 2.5125 (9.60); 2.5080 (19.06); 2.5034 (25.11); 2.4988 (18.33); 2.4943 (8.79); 1.3430 (16.00); −0.0002 (1.31)
Example 80, Solvent: DMSO, Spectrometer: 399.95 MHz 12.5113 (0.77); 7.9531 (0.80); 7.7377 (2.09); 7.7352 (2.72); 7.7312 (1.30); 7.7226 (0.85); 7.7175 (3.57); 7.7137 (2.43); 7.5656 (0.50); 7.5624 (0.32); 7.5541 (0.35); 7.5473 (1.72); 7.5414 (0.51); 7.5325 (0.95); 7.5287 (0.76); 7.5024 (2.53); 7.4990 (1.07); 7.4873 (1.70); 7.4834 (3.18); 7.4699 (0.50); 7.4658 (1.27); 7.4624 (0.71); 7.3294 (4.53); 7.1646 (1.08); 7.1446 (2.02); 7.1241 (1.01); 6.7642 (1.30); 6.7463 (3.02); 6.6956 (1.00); 6.6895 (0.82); 6.6756 (0.78); 6.6719 (0.87); 5.3366 (5.85); 5.0461 (0.39); 5.0297 (1.47); 5.0131 (1.48); 4.9966 (0.40); 3.3407 (71.31); 3.0279 (0.40); 3.0092 (16.00); 2.8906 (6.59); 2.7323 (5.26); 2.7314 (5.08); 2.5259 (0.50); 2.5211 (0.81); 2.5125 (9.65); 2.5080 (19.21); 2.5034 (25.24); 2.4988 (18.23); 2.4943 (8.61); 2.2409 (9.78); 1.5310 (5.59); 1.5145 (5.54); −0.0002 (2.73)
Example 81, Solvent: DMSO, Spectrometer: 399.95 MHz 12.7334 (2.08); 7.9525 (1.68); 7.7397 (4.10); 7.7214 (5.10); 7.7179 (2.82); 7.6092 (1.18); 7.6045 (1.36); 7.5907 (1.65); 7.5860 (1.81); 7.5651 (0.49); 7.5620 (0.33); 7.5537 (0.36); 7.5467 (1.75); 7.5410 (0.52); 7.5287 (1.59); 7.5251 (0.93); 7.5225 (0.87); 7.5192 (0.87); 7.5036 (4.33); 7.5007 (2.84); 7.4847 (4.20); 7.4756 (1.50); 7.4706 (1.79); 7.4669 (1.44); 7.4634 (0.85); 7.4563 (1.45); 7.4515 (1.42); 7.4373 (0.58); 7.4327 (0.51); 7.3982 (4.18); 5.3621 (6.32); 3.3383 (108.95); 3.0483 (16.00); 2.8905 (13.02); 2.7314 (10.70); 2.5250 (0.66); 2.5116 (14.14); 2.5072 (28.01); 2.5026 (36.80); 2.4981 (26.89); 2.4937 (13.03); −0.0002 (4.70)
Example 82, Solvent: DMSO, Spectrometer: 399.95 MHz 12.5092 (1.00); 7.9529 (0.89); 7.7422 (0.32); 7.7365 (2.08); 7.7339 (2.67); 7.7299 (1.25); 7.7213 (0.83); 7.7162 (3.53); 7.7124 (2.38); 7.5655 (0.50); 7.5539 (0.35); 7.5472 (1.71); 7.5413 (0.49); 7.5324 (0.93); 7.5290 (1.52); 7.5255 (0.75); 7.5022 (2.50); 7.4988 (1.04); 7.4870 (1.67); 7.4831 (3.13); 7.4697 (0.49); 7.4656 (1.25); 7.4622 (0.77); 7.3383 (3.30); 7.3292 (4.54); 7.1636 (1.03); 7.1470 (1.10); 7.1452 (1.14); 7.1101 (0.49); 7.1069 (0.46); 7.0909 (1.05); 7.0711 (0.65); 7.0679 (0.57); 6.8576 (0.91); 6.8392 (1.54); 6.8224 (0.69); 6.8206 (0.68); 6.7567 (1.53); 6.7365 (1.38); 5.3340 (5.73); 5.0373 (0.38); 5.0208 (1.39); 5.0042 (1.40); 4.9877 (0.38); 3.3396 (95.93); 3.0194 (1.06); 3.0102 (16.00); 2.8904 (7.42); 2.7321 (5.68); 2.7311 (5.88); 2.5256 (0.51); 2.5208 (0.80); 2.5123 (10.61); 2.5077 (21.37); 2.5031 (28.27); 2.4985 (20.41); 2.4940 (9.65); 2.2170 (9.94); 1.5659 (5.54); 1.5494 (5.60); 1.5299 (0.37); −0.0002 (3.61)
Example 83, Solvent: DMSO, Spectrometer: 400.13 MHz 8.0123 (2.60); 7.6632 (3.98); 7.6419 (5.53); 7.6155 (0.94); 7.5975 (1.97); 7.5808 (1.80); 7.5641 (0.72); 7.4461 (3.86); 7.4264 (2.24); 6.5748 (2.81); 6.5571 (2.64); 6.4532 (2.79); 6.4325 (2.61); 6.0832 (6.83); 5.2576 (9.84); 3.4172 (4.30); 3.1433 (16.00); 2.9496 (10.68); 2.7900 (10.04); 2.7305 (0.36); 2.5619 (55.79); 2.3883 (0.36); 1.4182 (0.70); −0.0002 (1.16)
Example 84, Solvent: DMSO, Spectrometer: 399.95 MHz 10.5205 (1.96); 8.0698 (1.18); 8.0491 (1.40); 7.8298 (1.23); 7.8106 (1.67); 7.7903 (1.16); 7.7320 (0.32); 7.7265 (1.94); 7.7237 (2.55); 7.7198 (1.30); 7.7111 (0.83); 7.7060 (3.53); 7.7022 (2.37); 7.5641 (0.48); 7.5522 (1.50); 7.5458 (1.59); 7.5401 (0.50); 7.5309 (0.86); 7.5275 (1.41); 7.5241 (0.73); 7.4964 (2.39); 7.4930 (1.04); 7.4811 (1.64); 7.4773 (3.02); 7.4637 (0.50); 7.4596 (1.23); 7.4564 (0.69); 7.1387 (1.71); 7.1215 (1.64); 7.1201 (1.60); 5.3539 (5.96); 3.3295 (63.55); 3.0540 (16.00); 2.8911 (1.73); 2.7326 (1.37); 2.7313 (1.38); 2.5254 (0.58); 2.5206 (1.00); 2.5121 (11.09); 2.5076 (21.82); 2.5030 (28.61); 2.4984 (20.72); 2.4938 (9.82); 2.4106 (1.56); 2.3920 (2.27); 2.3727 (1.71); 1.7602 (0.38); 1.7429 (1.06); 1.7268 (1.48); 1.7123 (0.94); 1.6995 (0.67); 1.6087 (0.84); 1.5897 (1.60); 1.5716 (1.96); 1.5552 (1.24); 1.5403 (0.52); 1.5373 (0.49); 1.5268 (0.32); 1.5126 (0.39); 1.5082 (0.35); 1.4948 (0.49); 1.4855 (0.79); 1.4752 (0.81); 1.4693 (0.89); 1.4563 (0.79); 1.1065 (0.55); 1.0957 (0.72); 1.0904 (0.83); 1.0802 (0.69); 1.0756 (0.62); 1.0715 (0.62); 1.0645 (0.46); 1.0601 (0.44); 0.8759 (0.52); −0.0002 (5.65)
Example 85, Solvent: DMSO, Spectrometer: 399.95 MHz 10.0121 (2.29); 8.0825 (1.39); 8.0623 (1.78); 7.9530 (0.86); 7.9149 (1.28); 7.8955 (1.81); 7.8754 (1.10); 7.7325 (1.98); 7.7299 (2.61); 7.7260 (1.30); 7.7173 (0.84); 7.7121 (3.46); 7.7084 (2.42); 7.5666 (0.49); 7.5548 (0.37); 7.5483 (1.62); 7.5426 (0.50); 7.5334 (0.90); 7.5301 (1.44); 7.5267 (0.74); 7.4995 (2.40); 7.4961 (1.07); 7.4841 (1.68); 7.4804 (3.07); 7.4668 (0.51); 7.4627 (1.24); 7.4595 (0.71); 7.2181 (2.13); 7.2133 (1.27); 7.2066 (5.37); 7.1988 (5.01); 7.1838 (0.85); 7.1134 (0.82); 7.1057 (1.05); 7.0976 (0.61); 5.3889 (6.09); 4.9691 (0.85); 4.9313 (2.12); 4.8885 (1.60); 4.8510 (0.61); 4.4782 (0.93); 4.4658 (0.97); 4.4538 (1.23); 4.4414 (0.98); 3.3302 (71.52); 3.0854 (16.00); 3.0122 (1.27); 3.0018 (1.83); 2.9796 (0.89); 2.8902 (6.85); 2.7318 (5.35); 2.7306 (5.48); 2.5247 (0.62); 2.5114 (12.73); 2.5069 (24.95); 2.5023 (32.61); 2.4977 (23.73); 2.4931 (11.41); −0.0002 (7.97)
Example 86, Solvent: DMSO, Spectrometer: 400.13 MHz 10.2690 (7.09); 7.8414 (1.60); 7.8205 (4.46); 7.8032 (6.02); 7.7948 (6.83); 7.7768 (2.26); 7.6902 (7.09); 7.6722 (8.47); 7.6689 (6.85); 7.5582 (1.32); 7.5397 (4.13); 7.5218 (3.81); 7.4939 (6.61); 7.4746 (8.02); 7.4570 (3.23); 7.1412 (3.95); 7.1262 (3.78); 5.7626 (3.63); 5.3377 (16.00); 4.5315 (10.49); 4.5254 (10.88); 4.1988 (4.94); 4.1822 (10.57); 4.1655 (5.47); 4.1490 (0.77); 4.1330 (0.45); 4.0599 (0.34); 4.0422 (0.91); 4.0245 (0.91); 4.0068 (0.35); 3.3316 (33.70); 3.3251 (9.43); 3.3189 (4.52); 3.3080 (2.35); 2.9128 (3.20); 2.9063 (6.74); 2.8998 (3.70); 2.5808 (3.27); 2.5743 (3.63); 2.5643 (6.78); 2.5577 (6.87); 2.5476 (4.16); 2.5412 (3.91); 2.5106 (37.18); 2.5066 (48.53); 2.5026 (37.67); 2.3334 (0.40); 2.0789 (0.68); 1.9937 (3.66); 1.2820 (0.55); 1.2484 (2.52); 1.1966 (1.09); 1.1788 (1.97); 1.1610 (1.03); 0.8782 (1.00); 0.8620 (2.64); 0.8443 (1.22)
Example 87, Solvent: DMSO, Spectrometer: 300.16 MHz 7.9539 (0.50); 7.5448 (0.60); 7.4309 (0.48); 7.4056 (0.47); 7.3921 (0.55); 7.3742 (0.93); 7.3647 (0.87); 5.4238 (1.47); 3.3516 (3.48); 3.0694 (2.92); 2.5216 (16.27); 2.3428 (2.48); 1.3706 (16.00)

NMR Peak List Table 1

Example 88, Solvent: DMSO, Spectrometer: 400.13 MHz 10.7366 (1.91); 8.0323 (1.09); 8.0117 (1.32); 7.8379 (1.13); 7.8187 (1.56); 7.7984 (0.97); 7.7256 (2.28); 7.7127 (0.82); 7.7078 (2.91); 7.7040 (2.01); 7.5763 (0.43); 7.5645 (0.38); 7.5580 (1.42); 7.5524 (0.46); 7.5431 (0.83); 7.5399 (1.24); 7.5365 (0.65); 7.5103 (2.11); 7.4948 (1.51); 7.4911 (2.61); 7.4775 (0.45); 7.4735 (1.03); 7.4703 (0.58); 7.2722 (2.79); 7.2506 (3.04); 7.2434 (0.33); 7.1816 (0.54); 7.1599 (0.69); 7.1503 (1.63); 7.1319 (1.52); 6.8979 (0.52); 6.8908 (3.59); 6.8850 (1.46); 6.8740 (1.17); 6.8690 (3.18); 6.8620 (0.83); 5.3765 (5.28); 3.7503 (0.42); 3.7340 (3.41); 3.7251 (16.00); 3.6786 (0.33); 3.6353 (4.80); 3.4953 (0.76); 3.4848 (1.42); 3.4773 (2.39); 3.4591 (2.36); 3.4409 (0.74); 3.3414 (19.01); 2.6785 (0.33); 2.5640 (0.56); 2.5595 (0.75); 2.5551 (0.58); 2.5318 (1.59); 2.5183 (20.91); 2.5140 (41.52); 2.5095 (55.24); 2.5051 (39.23); 2.5007 (18.19); 2.4641 (0.47); 2.4597 (0.60); 2.4554 (0.44); 2.3364 (0.33); 1.9968 (0.89); 1.2524 (0.59); 1.1813 (0.48); 1.0367 (2.67); 1.0186 (5.93); 1.0004 (2.55); 0.8649 (0.80); 0.8473 (0.32)

Example 89, Solvent: DMSO, Spectrometer: 399.95 MHz 10.2546 (2.49); 8.1091 (0.37); 7.9531 (1.07); 7.8233 (0.70); 7.8024 (1.78); 7.7852 (2.22); 7.7778 (2.06); 7.7747 (2.28); 7.7570 (0.76); 7.7538 (0.54); 7.7225 (2.91); 7.7046 (3.72); 7.7009 (2.61); 7.6824 (0.43); 7.6644 (0.50); 7.6610 (0.39); 7.5692 (0.33); 7.5667 (0.35); 7.5633 (0.53); 7.5603 (0.37); 7.5514 (0.45); 7.5451 (1.74); 7.5395 (0.75); 7.5302 (1.15); 7.5268 (1.59); 7.5234 (0.89); 7.4961 (2.82); 7.4807 (1.96); 7.4770 (3.62); 7.4632 (0.87); 7.4593 (1.49); 7.4562 (0.94); 7.4517 (0.47); 7.4450 (0.50); 7.4401 (0.61); 7.4284 (0.62); 7.4243 (0.52); 7.3657 (1.64); 7.3607 (0.72); 7.3516 (1.85); 7.3441 (2.09); 7.3380 (0.87); 7.3357 (0.89); 7.3301 (1.87); 7.3219 (0.33); 7.3171 (0.61); 7.2944 (0.33); 7.2244 (1.73); 7.2224 (1.71); 7.2072 (3.30); 7.1431 (2.14); 7.1378 (0.69); 7.1266 (0.83); 7.1207 (3.52); 7.1149 (0.82); 7.1044 (1.90); 7.1019 (2.00); 7.0987 (2.07); 7.0881 (1.49); 7.0848 (1.40); 6.9748 (0.38); 6.0034 (0.44); 5.5348 (0.89); 5.3320 (6.39); 5.1790 (1.02); 4.2843 (1.67); 4.2674 (3.78); 4.2505 (1.72); 3.6701 (0.33); 3.3415 (169.96); 3.0881 (2.44); 3.0723 (0.52); 3.0617 (16.00); 3.0364 (2.41); 2.9409 (1.41); 2.9240 (2.85); 2.9071 (1.38); 2.8909 (8.40); 2.7322 (6.73); 2.7317 (6.68); 2.5258 (1.02); 2.5124 (18.10); 2.5080 (35.40); 2.5034 (46.36); 2.4988 (33.81); 2.4944 (16.26); −0.0002 (2.58)

Example 90, Solvent: DMSO, Spectrometer: 400.13 MHz 7.6966 (2.41); 7.6942 (4.34); 7.6916 (2.60); 7.6774 (3.33); 7.6761 (3.88); 7.6741 (3.72); 7.6224 (0.97); 7.6127 (8.36); 7.6101 (8.68); 7.6038 (6.46); 7.6025 (6.04); 7.5997 (5.69); 7.5960 (4.19); 7.5795 (0.81); 7.5759 (0.77); 7.5413 (0.58); 7.5300 (2.94); 7.5213 (2.60); 7.5168 (2.10); 7.5108 (2.69); 7.5082 (2.22); 7.5032 (2.14); 7.4968 (1.80); 7.4891 (1.58); 7.0336 (8.70); 6.6786 (8.90); 5.1662 (16.00); 4.0604 (0.42); 4.0426 (1.32); 4.0248 (1.35); 4.0070 (0.45); 3.4210 (0.35); 3.4000 (3.06); 3.3501 (236.52); 3.3278 (0.65); 3.3185 (0.35); 3.3154 (0.41); 3.3003 (2.76); 3.2516 (40.94); 3.2018 (0.44); 2.5626 (0.41); 2.5580 (0.56); 2.5535 (0.41); 2.5307 (0.71); 2.5172 (16.79); 2.5128 (34.61); 2.5082 (46.67); 2.5037 (32.85); 2.4993 (15.06); 2.4629 (0.40); 2.4584 (0.51); 2.4538 (0.37); 1.9946 (5.99); 1.2471 (0.47); 1.1970 (1.65); 1.1792 (3.31); 1.1614 (1.60); 0.8625 (0.70)

Example 91, Solvent: DMSO, Spectrometer: 399.95 MHz 11.9263 (2.25); 7.9528 (0.84); 7.7470 (1.98); 7.7442 (2.67); 7.7402 (1.31); 7.7318 (0.82); 7.7266 (3.45); 7.7228 (2.38); 7.6999 (1.37); 7.6955 (1.49); 7.6808 (1.52); 7.6764 (1.52); 7.5858 (0.78); 7.5813 (0.74); 7.5669 (1.36); 7.5647 (1.39); 7.5631 (1.41); 7.5604 (1.04); 7.5551 (0.42); 7.5472 (2.01); 7.5419 (1.33); 7.5334 (0.95); 7.5300 (1.53); 7.5264 (0.77); 7.5053 (2.50); 7.5019 (1.09); 7.4904 (1.59); 7.4864 (3.01); 7.4730 (0.50); 7.4689 (1.21); 7.4653 (0.70); 7.3504 (3.93); 7.2191 (1.82); 7.1988 (1.59); 7.1073 (1.02); 7.1053 (1.01); 7.0885 (1.78); 7.0866 (1.75); 7.0699 (0.91); 7.0678 (0.86); 5.3579 (5.97); 3.9100 (14.72); 3.3360 (72.19); 3.0555 (16.00); 2.8905 (6.69); 2.7320 (5.33); 2.7309 (5.35); 2.5251 (0.65); 2.5118 (11.62); 2.5073 (22.88); 2.5027 (29.89); 2.4981 (21.65); 2.4936 (10.27); −0.0002 (9.23)

Example 92, Solvent: DMSO, Spectrometer: 400.13 MHz 10.3314 (3.16); 7.8494 (0.63); 7.8284 (1.98); 7.8112 (3.98); 7.8062 (2.83); 7.7892 (0.73); 7.7853 (0.41); 7.6247 (0.70); 7.6206 (1.05); 7.6150 (0.98); 7.6063 (1.23); 7.6030 (0.98); 7.5999 (1.03); 7.5953 (1.27); 7.5893 (2.51); 7.5869 (2.39); 7.5637 (0.78); 7.5496 (0.87); 7.5435 (1.19); 7.5292 (1.23); 7.5240 (0.64); 7.5086 (0.55); 7.4328 (0.54); 7.4301 (0.60); 7.4266 (0.54); 7.4238 (0.52); 7.4090 (0.99); 7.4052 (0.87); 7.3905 (0.44); 7.3880 (0.46); 7.3847 (0.42); 7.3820 (0.37); 7.1326 (1.40); 7.1288 (1.51); 7.1122 (1.42); 5.7683 (0.62); 5.3615 (6.85); 4.1962 (2.13); 4.1796 (4.68); 4.1629 (2.17); 4.0438 (0.65); 4.0260 (0.66); 3.3444 (20.58); 3.0699 (16.00); 2.9229 (1.35); 2.9163 (3.03); 2.9097 (1.45); 2.5802 (1.26); 2.5736 (1.32); 2.5636 (2.87); 2.5569 (2.77); 2.5469 (1.34); 2.5403 (1.23); 2.5324 (0.51); 2.5186 (9.20); 2.5144 (18.80); 2.5100 (25.43); 2.5056 (18.47); 2.5015 (8.79); 1.9966 (2.83); 1.2490 (0.63); 1.1986 (0.76); 1.1808 (1.48); 1.1630 (0.73); 0.8634 (0.82); 0.8457 (0.34)

Example 93, Solvent: DMSO, Spectrometer: 399.95 MHz 10.5108 (2.23); 10.0297 (1.39); 8.0760 (1.54); 8.0726 (1.57); 8.0555 (1.80); 8.0520 (1.84); 7.8852 (0.85); 7.8659 (1.30); 7.8457 (0.79); 7.8327 (1.32); 7.8133 (1.96); 7.7931 (1.20); 7.7256 (4.21); 7.7061 (4.91); 7.5645 (0.50); 7.5525 (0.33); 7.5462 (2.74); 7.5407 (0.82); 7.5309 (1.63); 7.5279 (2.33); 7.4966 (4.18); 7.4774 (5.31); 7.4597 (2.05); 7.4569 (1.23); 7.1990 (1.27); 7.1804 (1.23); 7.1416 (1.99); 7.1231 (1.92); 5.8216 (0.60); 5.8128 (0.33); 5.8049 (0.32); 5.7959 (0.91); 5.7789 (0.95); 5.7699 (0.37); 5.7621 (0.36); 5.7532 (0.70); 5.7366 (0.34); 5.3750 (4.48); 5.3540 (6.90); 5.0233 (0.51); 5.0195 (1.08); 5.0144 (1.14); 5.0105 (0.53); 4.9804 (0.45); 4.9766 (0.98); 4.9715 (1.03); 4.9677 (0.47); 4.9429 (1.15); 4.9402 (1.08); 4.9375 (1.00); 4.9175 (1.09); 4.9148 (1.11); 4.9121 (1.06); 4.0893 (1.08); 3.4632 (0.38); 3.4566 (0.62); 3.4405 (1.75); 3.4246 (1.73); 3.4086 (0.64); 3.4019 (0.38); 3.3284 (64.05); 3.0753 (10.22); 3.0534 (16.00); 2.5253 (0.98); 2.5074 (35.87); 2.5029 (46.20); 2.4984 (34.05); 2.4942 (16.81); 2.3945 (1.65); 2.3761 (3.21); 2.3576 (1.79); 2.3297 (0.32); 2.0393 (0.63); 2.0222 (1.78); 2.0045 (1.81); 1.9867 (0.75); 1.6131 (0.41); 1.5945 (1.23); 1.5762 (1.75); 1.5577 (1.35); 1.5335 (0.84); 1.5166 (1.10); 1.5129 (1.05); 1.4956 (1.16); 1.4793 (0.48); 1.3849 (0.99); 1.3664 (2.14); 1.3477 (2.36); 1.3283 (1.70); 1.3168 (0.85); 1.3087 (1.55); 1.3014 (5.27); 1.2847 (5.18); 1.2697 (0.68); 1.2604 (0.72); 1.2347 (0.38); 0.8946 (2.74); 0.8763 (5.43); 0.8578 (2.34); 0.0078 (0.42); −0.0002 (11.40); −0.0085 (0.43)

Example 94, Solvent: DMSO, Spectrometer: 399.95 MHz 9.7653 (1.93); 8.0534 (1.29); 8.0329 (1.62); 7.8853 (1.31); 7.8659 (1.82); 7.8458 (1.13); 7.7271 (1.94); 7.7246 (2.52); 7.7207 (1.20); 7.7119 (0.79); 7.7068 (3.39); 7.7031 (2.32); 7.5641 (0.48); 7.5522 (0.35); 7.5458 (1.61); 7.5401 (0.46); 7.5308 (0.87); 7.5275 (1.39); 7.5241 (0.69); 7.4959 (2.35); 7.4925 (0.98); 7.4805 (1.64); 7.4767 (3.03); 7.4631 (0.48); 7.4591 (1.22); 7.4559 (0.66); 7.1944 (1.76); 7.1768 (1.65); 5.3740 (6.25); 4.0556 (8.70); 4.0391 (0.58); 4.0319 (0.73); 4.0266 (0.75); 4.0184 (0.75); 4.0140 (0.39); 3.3331 (71.93); 3.0795 (16.00); 3.0692 (0.50); 2.8909 (1.03); 2.7322 (0.81); 2.7313 (0.79); 2.5254 (0.57); 2.5206 (0.88); 2.5120 (11.07); 2.5075 (22.26); 2.5029 (29.43); 2.4983 (21.27); 2.4938 (10.06); 1.7085 (0.41); 1.7041 (0.47); 1.6908 (0.93); 1.6879 (0.97); 1.6729 (2.08); 1.6681 (2.39); 1.6626 (2.83); 1.6573 (2.42); 1.6548 (2.60); 1.6476 (1.03); 1.6424 (1.58); 1.6392 (1.47); 1.6234 (0.49); 1.6189 (0.46); 1.6146 (0.51); 1.5263 (0.33); 1.5183 (0.46); 1.5141 (0.64); 1.5071 (0.69); 1.5025 (0.98); 1.4995 (0.95); 1.4963 (1.01); 1.4922 (0.82); 1.4862 (0.71); 1.4767 (0.39); −0.0002 (2.96)

Example 95, Solvent: DMSO, Spectrometer: 399.95 MHz 10.5088 (2.07); 8.0749 (1.25); 8.0542 (1.48); 7.8323 (1.25); 7.8130 (1.74); 7.7928 (1.14); 7.7239 (2.57); 7.7201 (1.24); 7.7112 (0.85); 7.7061 (3.36); 7.7023 (2.31); 7.5642 (0.48); 7.5522 (0.37); 7.5458 (1.62); 7.5402 (0.47); 7.5309 (0.88); 7.5276 (1.39); 7.5243 (0.71); 7.4965 (2.37); 7.4811 (1.66); 7.4773 (3.03); 7.4637 (0.48); 7.4597 (1.19); 7.4565 (0.67); 7.1409 (1.78); 7.1231 (1.70); 5.3541 (6.16); 3.3284 (55.96); 3.0536

-continued

NMR Peak List Table 1

(15.38); 2.8909 (1.12); 2.7321 (0.88); 2.5252 (0.53); 2.5119 (10.97); 2.5074 (21.54); 2.5028 (28.23); 2.4982 (20.56); 2.4937 (9.88); 2.3775 (1.53); 2.3590 (3.07); 2.3404 (1.72); 1.6080 (0.40); 1.5890 (1.07); 1.5805 (0.58); 1.5758 (0.80); 1.5697 (1.41); 1.5627 (1.07); 1.5483 (1.36); 1.5302 (1.36); 1.5133 (0.85); 1.4966 (0.45); 1.1911 (1.03); 1.1740 (1.43); 1.1651 (0.81); 1.1615 (0.76); 1.1516 (1.48); 1.1344 (0.79); 0.8644 (16.00); 0.8478 (15.28); −0.0002 (7.59)
Example 96, Solvent: DMSO, Spectrometer: 400.13 MHz 7.6611 (6.58); 7.6574 (3.58); 7.6487 (2.26); 7.6436 (8.50); 7.6397 (6.42); 7.5529 (0.65); 7.5497 (1.18); 7.5465 (0.85); 7.5386 (0.99); 7.5314 (4.08); 7.5255 (1.43); 7.5169 (2.49); 7.5134 (3.82); 7.5100 (2.13); 7.4900 (8.69); 7.4701 (11.84); 7.4567 (1.82); 7.4520 (5.86); 6.5825 (4.46); 6.5648 (4.35); 6.4667 (4.64); 6.4462 (4.56); 6.4157 (0.33); 6.3951 (0.36); 6.3121 (0.68); 6.2256 (0.38); 5.7692 (0.38); 5.6971 (0.37); 5.6829 (0.39); 5.6382 (0.40); 5.6223 (0.40); 5.6026 (0.40); 5.2839 (0.36); 5.2331 (16.00); 5.1823 (0.33); 2.5661 (0.42); 2.5616 (0.63); 2.5571 (0.53); 2.5329 (0.85); 2.5193 (16.27); 2.5150 (34.12); 2.5105 (47.07); 2.5061 (35.41); 2.5019 (18.34); 2.4691 (0.91); 2.4642 (0.97); 2.4597 (1.00); 2.4553 (0.80)
Example 97, Solvent: DMSO, Spectrometer: 300.16 MHz 9.8567 (1.13); 7.7858 (0.94); 7.7766 (1.05); 7.7674 (2.28); 7.7308 (0.34); 7.7111 (0.55); 7.7051 (0.65); 7.6844 (0.35); 7.6792 (0.36); 7.6382 (0.36); 7.6187 (0.34); 7.6103 (0.41); 7.4006 (0.41); 7.3713 (0.80); 7.3655 (0.59); 7.3479 (0.81); 7.3454 (0.75); 7.3377 (0.45); 7.3230 (0.42); 7.3195 (0.34); 7.0981 (0.54); 7.0887 (0.56); 7.0799 (0.48); 7.0706 (0.54); 5.3503 (2.73); 3.3348 (10.70); 3.3146 (0.49); 3.1887 (6.24); 2.5158 (0.74); 2.5099 (1.54); 2.5039 (2.08); 2.4978 (1.52); 2.4920 (0.74); 1.9905 (1.26); 1.4664 (16.00); 1.1988 (0.34); 1.1751 (0.68); 1.1514 (0.33); −0.0002 (0.54)
Example 98, Solvent: DMSO, Spectrometer: 399.95 MHz 10.5038 (2.10); 8.0709 (1.23); 8.0503 (1.45); 7.8312 (1.27); 7.8120 (1.74); 7.7917 (1.18); 7.7261 (2.01); 7.7234 (2.66); 7.7196 (1.34); 7.7108 (0.89); 7.7057 (3.61); 7.7020 (2.40); 7.5639 (0.50); 7.5607 (0.33); 7.5520 (0.39); 7.5456 (1.63); 7.5399 (0.52); 7.5307 (0.91); 7.5273 (1.45); 7.5239 (0.75); 7.4961 (2.47); 7.4927 (1.08); 7.4807 (1.74); 7.4634 (0.53); 7.4593 (1.25); 7.4561 (0.71); 7.3393 (1.77); 7.1219 (1.68); 5.3532 (6.11); 3.3286 (57.15); 3.0536 (16.00); 2.5253 (0.63); 2.5120 (11.46); 2.5075 (22.17); 2.5029 (28.83); 2.4983 (20.85); 2.4938 (9.87); 2.3890 (1.45); 2.3706 (2.77); 2.3521 (1.59); 1.5794 (0.74); 1.5621 (1.09); 1.5449 (0.76); 1.2650 (4.90); 1.2575 (5.11); 1.2428 (4.42); 0.8756 (0.62); 0.8637 (1.94); 0.8472 (5.84); 0.8296 (2.02); −0.0002 (6.05)
Example 99, Solvent: DMSO, Spectrometer: 399.95 MHz 10.5108 (1.12); 10.0299 (2.22); 8.0771 (1.86); 8.0568 (2.26); 7.8852 (1.36); 7.8659 (2.03); 7.8457 (1.21); 7.8326 (0.68); 7.8133 (0.98); 7.7931 (0.61); 7.7259 (3.97); 7.7077 (4.53); 7.5647 (0.75); 7.5617 (0.49); 7.5526 (0.59); 7.5464 (2.53); 7.5409 (0.76); 7.5311 (1.47); 7.5281 (2.12); 7.5250 (1.11); 7.4966 (3.81); 7.4773 (4.87); 7.4634 (0.84); 7.4596 (1.06); 7.4287 (1.53); 7.1990 (1.99); 7.1805 (1.92); 7.1416 (1.01); 7.1230 (0.96); 5.7960 (0.46); 5.7790 (0.48); 7.5532 (0.35); 5.3750 (6.93); 5.3540 (3.50); 5.0195 (0.55); 5.0144 (0.57); 4.9767 (0.49); 4.9714 (0.51); 4.9429 (0.57); 4.9402 (0.53); 4.9376 (0.48); 4.9175 (0.55); 4.9148 (0.50); 4.9120 (0.45); 4.1225 (0.47); 4.1059 (1.68); 4.0893 (1.70); 4.0727 (0.47); 3.4633 (0.61); 3.4566 (0.98); 3.4405 (2.76); 3.4247 (2.72); 3.4087 (1.00); 3.4019 (0.63); 3.3280 (60.97); 3.0752 (16.00); 3.0533 (8.12); 2.5117 (17.95); 2.5074 (33.96); 2.5029 (43.62); 2.4984 (31.88); 2.4941 (15.63); 2.3945 (0.83); 2.3761 (1.61); 2.3576 (0.90); 2.0223 (0.88); 2.0045 (0.88); 1.9868 (0.37); 1.5946 (0.62); 1.5761 (0.87); 1.5578 (0.68); 1.5512 (0.53); 1.5476 (0.45); 1.5331 (1.19); 1.5167 (1.69); 1.5130 (1.60); 1.4957 (1.79); 1.4793 (0.75); 1.3845 (0.73); 1.3661 (1.90); 1.3472 (2.48); 1.3281 (2.14); 1.3094 (1.74); 1.3014 (7.15); 1.2848 (7.02); 1.2602 (0.41); 1.2347 (0.37); 0.8947 (4.30); 0.8854 (0.52); 0.8764 (8.53); 0.8579 (3.66); 0.0079 (0.44); −0.0002 (11.06); −0.0085 (0.42)
Example 100, Solvent: DMSO, Spectrometer: 399.95 MHz 12.4363 (1.13); 7.9530 (1.03); 7.7422 (2.09); 7.7397 (2.67); 7.7358 (1.27); 7.7272 (0.79); 7.7220 (3.47); 7.7182 (2.41); 7.5667 (0.47); 7.5553 (0.34); 7.5484 (1.69); 7.5425 (0.50); 7.5337 (0.94); 7.5303 (1.52); 7.5268 (0.74); 7.5048 (2.52); 7.5014 (1.07); 7.4897 (1.64); 7.4858 (3.14); 7.4723 (0.49); 7.4682 (1.23); 7.4647 (0.67); 7.3591 (0.68); 7.3419 (5.34); 7.3206 (1.46); 7.3179 (0.94); 7.3000 (0.72); 6.8902 (0.60); 6.8842 (1.30); 6.8782 (0.83); 6.8620 (0.56); 6.8561 (1.28); 6.8503 (0.87); 6.8344 (1.52); 6.8287 (1.55); 6.8230 (0.64); 6.8136 (1.21); 6.8077 (1.97); 6.8019 (0.97); 7.7866 (0.57); 7.7806 (0.47); 5.3455 (6.00); 4.8795 (7.70); 3.3316 (60.64); 3.0226 (16.00); 2.8905 (8.25); 2.7318 (6.79); 2.5249 (0.61); 2.5199 (1.00); 2.5115 (12.85); 2.5071 (25.50); 2.5025 (33.42); 2.4979 (24.14); 2.4934 (11.42); −0.0002 (3.58)
Example 101, Solvent: DMSO, Spectrometer: 300.16 MHz 10.7469 (2.01); 8.0501 (1.22); 8.0225 (1.59); 7.8555 (1.13); 7.8297 (1.58); 7.8028 (0.98); 7.4420 (0.86); 7.4156 (2.00); 7.3889 (1.62); 7.2982 (1.74); 7.2878 (2.96); 7.2721 (1.43); 7.2673 (1.58); 7.2585 (4.15); 7.2491 (2.27); 7.2438 (1.36); 7.1721 (1.72); 7.1601 (1.18); 7.1493 (1.96); 7.1348 (0.90); 7.1268 (0.84); 6.9187 (0.43); 6.9090 (3.60); 6.9024 (1.25); 6.8868 (1.07); 6.8802 (3.15); 5.7792 (10.93); 5.3829 (5.06); 3.8221 (0.32); 3.8006 (14.08); 3.7764 (0.65); 3.7715 (0.47); 3.7393 (16.00); 3.6481 (5.03); 3.3457 (19.77); 3.0509 (12.47); 2.5332 (4.56); 2.5275 (9.68); 2.5215 (13.43); 2.5155 (9.90); 2.5097 (4.84); 2.0090 (0.55); 1.3760 (1.22); 1.2529 (0.35); 1.1941 (0.33)
Example 102, Solvent: DMSO, Spectrometer: 399.95 MHz 10.5242 (2.13); 8.0679 (1.37); 8.0472 (1.63); 7.8307 (1.34); 7.8114 (1.94); 7.7912 (1.22); 7.7241 (2.75); 7.7111 (0.90); 7.7062 (3.50); 7.7025 (2.47); 7.5645 (0.49); 7.5614 (0.32); 7.5526 (0.38); 7.5462 (1.71); 7.5406 (0.51); 7.5312 (0.95); 7.5280 (1.45); 7.5247 (0.76); 7.4971 (2.53); 7.4815 (1.78); 7.4779 (3.24); 7.4642 (0.51); 7.4602 (1.26); 7.4571 (0.76); 7.1399 (1.95); 7.1217 (1.87); 5.3548 (6.82); 3.3292 (42.97); 3.0730 (0.32); 3.0546 (16.00); 2.8909 (1.93); 2.7319 (1.57); 2.5252 (0.57); 2.5118 (11.07); 2.5074 (21.63); 2.5029 (28.29); 2.4983 (20.72); 2.4939 (10.11); 2.4089 (1.88); 2.3900 (2.51); 2.3714 (1.87); 1.5491 (0.55); 1.5323 (0.76); 1.5164 (0.78); 1.4985 (1.41); 1.4795 (2.01); 1.4614 (1.88); 1.4455 (0.59); 0.8855 (15.29); 0.8696 (14.75); −0.0002 (6.94)
Example 103, Solvent: DMSO, Spectrometer: 399.95 MHz 11.6620 (1.02); 7.9532 (1.10); 7.7277 (2.89); 7.7100 (3.52); 7.7063 (2.55); 7.5612 (0.50); 7.5582 (0.33); 7.5497 (0.38); 7.5430 (1.74); 7.5371 (0.53); 7.5280 (1.04); 7.5248 (1.55); 7.5216 (0.82); 7.4989 (2.68); 7.4798 (3.33); 7.4622 (1.04); 7.4588 (0.79); 7.2416 (4.49); 5.2743 (6.55); 5.1458 (0.56); 5.1370 (0.72); 5.1313 (1.01); 5.1252 (0.71); 5.1167 (0.57); 3.3296 (47.71); 3.0365 (16.00); 2.8909 (7.86); 2.7321 (6.63); 2.5113 (13.57); 2.5071 (25.86); 2.5026 (33.34); 2.4981 (24.40); 2.4939 (11.91); 1.8996 (0.48); 1.8832 (1.00); 1.8717 (1.05); 1.8505 (0.60); 1.8449 (0.54); 1.7182 (0.46); 1.7032 (1.18); 1.6959 (1.56); 1.6925 (1.61); 1.6833 (2.22); 1.6735 (2.37); 1.6562 (1.08); 1.6320 (0.42); 1.6069 (0.36); 1.5959 (0.69); 1.5853 (0.68); 1.5704 (1.26); 1.5457 (0.35); 0.0080 (0.35); −0.0002 (9.28)
Example 104, Solvent: DMSO, Spectrometer: 400.13 MHz 10.2939 (6.31); 7.8558 (0.51); 7.8440 (1.72); 7.8357 (0.89); 7.8230 (4.05); 7.8168 (0.98); 7.8054 (4.73); 7.7926 (4.97); 7.7902 (5.55); 7.7720 (2.13); 7.7215 (6.33); 7.7090 (2.34); 7.7038 (7.73); 7.7000 (5.45); 7.6175 (0.64); 7.5968 (0.54); 7.5713 (1.20); 7.5596 (1.05); 7.5530 (4.07); 7.5472 (1.42); 7.5380 (2.43); 7.5349 (3.51); 7.5073 (6.06); 7.4915 (4.68); 7.4882 (7.26); 7.4705 (2.77); 7.4674 (1.61); 7.2332 (0.54); 7.2143 (0.52); 7.1100 (3.45); 7.1076 (3.49); 7.0925 (3.45); 7.0899 (3.28); 5.7602 (11.54); 5.4179 (1.98); 5.3443 (14.61); 5.2751 (0.43); 4.2022 (0.88); 4.1917 (4.86); 4.1865 (2.38); 4.1750 (10.43); 4.1584 (4.82); 3.9159 (0.66); 3.8980 (0.66); 3.5263 (1.92); 3.5082 (6.28); 3.4900 (6.44); 3.4775

NMR Peak List Table 1

(1.40); 3.4719 (2.08); 3.4596 (0.99); 3.4413 (0.36); 3.3443 (713.81); 3.3210 (3.83); 3.3024 (0.58); 2.9067 (3.20); 2.9001 (6.96); 2.8935 (3.66); 2.8869 (1.01); 2.8805 (0.47); 2.6802 (0.44); 2.6757 (0.64); 2.6713 (0.41); 2.5730 (2.91); 2.5665 (3.13); 2.5564 (6.33); 2.5498 (6.37); 2.5397 (3.91); 2.5331 (4.11); 2.5154 (39.34); 2.5111 (78.78); 2.5067 (105.05); 2.5023 (74.78); 2.4980 (35.14); 2.2377 (0.50); 2.3334 (0.65); 2.3289 (0.47); 2.0901 (2.66); 2.0782 (0.62); 1.9929 (1.19); 1.4235 (0.61); 1.2382 (0.57); 1.1961 (0.35); 1.1784 (0.67); 1.1606 (0.37); 1.1448 (0.84); 1.1275 (1.87); 1.1100 (0.80); 1.0675 (1.39); 1.0599 (7.31); 1.0495 (3.20); 1.0418 (16.00); 1.0314 (1.91); 1.0237 (6.94)
Example 105, Solvent: DMSO, Spectrometer: 399.95 MHz 10.6888 (2.29); 8.0230 (0.81); 8.0023 (1.05); 7.8853 (1.37); 7.8660 (1.90); 7.8458 (1.14); 7.7286 (2.72); 7.7157 (0.85); 7.7107 (3.53); 7.7070 (2.50); 7.5677 (0.49); 7.5558 (0.38); 7.5494 (1.72); 7.5437 (0.50); 7.5344 (0.92); 7.5311 (1.45); 7.5278 (0.74); 7.5000 (2.48); 7.4845 (1.77); 7.4808 (3.23); 7.4671 (0.52); 7.4631 (1.26); 7.4599 (0.72); 7.3445 (1.36); 7.3241 (2.63); 7.3037 (1.70); 7.2095 (1.86); 7.1910 (1.80); 7.0664 (1.30); 7.0612 (2.44); 7.0556 (1.80); 7.0393 (1.31); 7.0376 (1.14); 7.0347 (1.06); 7.0329 (0.93); 7.0196 (1.14); 7.0178 (1.14); 7.0149 (1.00); 7.0131 (0.84); 6.9594 (1.17); 6.9577 (1.14); 6.9533 (1.08); 6.9384 (1.06); 6.9323 (0.99); 5.3865 (6.45); 4.8441 (6.17); 3.3480 (144.23); 3.2984 (0.34); 3.0694 (16.00); 2.8911 (0.45); 2.7324 (0.35); 2.5262 (0.72); 2.5128 (13.63); 2.5084 (26.69); 2.5038 (34.77); 2.4993 (25.25); 2.4948 (12.15); −0.0002 (0.43)
Example 106, Solvent: DMSO, Spectrometer: 399.95 MHz 10.2417 (2.97); 7.9536 (0.95); 7.8241 (0.68); 7.8032 (1.80); 7.7858 (2.31); 7.7775 (2.45); 7.7751 (2.42); 7.7569 (0.88); 7.7227 (2.89); 7.7047 (3.55); 7.7012 (2.48); 7.5630 (0.52); 7.5447 (1.70); 7.5394 (0.58); 7.5294 (1.13); 7.5267 (1.45); 7.4963 (2.60); 7.4769 (3.29); 7.4588 (1.64); 7.4539 (2.05); 7.4494 (2.24); 7.4435 (1.60); 7.4357 (2.21); 7.4307 (2.78); 7.4263 (1.72); 7.3234 (0.47); 7.3192 (0.61); 7.3050 (1.71); 7.3008 (1.58); 7.2944 (1.78); 7.2881 (2.65); 7.2825 (1.34); 7.2758 (1.44); 7.2708 (1.31); 7.2576 (0.62); 7.2524 (0.35); 7.2423 (0.38); 7.1068 (1.69); 7.1043 (1.56); 7.0896 (1.64); 7.0872 (1.47); 5.3307 (6.73); 4.3338 (1.79); 4.3167 (3.86); 4.2997 (1.85); 3.3359 (83.87); 3.0961 (1.82); 3.0791 (3.82); 3.0628 (16.00); 2.8910 (6.51); 2.7320 (5.63); 2.5076 (32.88); 2.5032 (39.64); 2.4988 (28.69); 2.4947 (14.33); 1.2352 (0.39); 0.0003 (5.61); −0.0002 (5.65)
Example 107, Solvent: DMSO, Spectrometer: 399.95 MHz 10.1721 (2.46); 7.8286 (0.36); 7.8075 (2.24); 7.8003 (2.37); 7.7935 (5.60); 7.7793 (0.43); 7.7306 (0.33); 7.7250 (2.01); 7.7223 (2.61); 7.7185 (1.27); 7.7098 (0.80); 7.7046 (3.45); 7.7009 (2.39); 7.5616 (0.49); 7.5497 (0.38); 7.5433 (1.63); 7.5376 (0.49); 7.5284 (0.91); 7.5250 (1.44); 7.5216 (0.73); 7.4945 (2.40); 7.4911 (1.03); 7.4792 (1.69); 7.4754 (3.30); 7.4619 (0.50); 7.4578 (1.26); 7.4546 (0.69); 7.1006 (1.28); 7.0937 (1.26); 7.0866 (1.07); 7.0798 (1.21); 5.3301 (6.35); 4.0971 (1.77); 4.0804 (3.85); 4.0637 (1.82); 3.3283 (53.91); 3.0652 (16.00); 3.0545 (0.62); 2.5253 (0.57); 2.5205 (0.90); 2.5119 (11.11); 2.5074 (22.32); 2.5028 (29.56); 2.4982 (21.54); 2.4937 (10.36); 1.6184 (1.00); 1.6011 (1.41); 1.5818 (1.25); 1.5650 (0.47); 1.3629 (0.66); 1.3457 (0.90); 1.3334 (0.74); 1.3245 (0.96); 1.3098 (0.94); 1.2964 (2.73); 1.2872 (2.45); 1.2798 (2.81); 1.2710 (1.46); 1.2618 (0.93); 1.2345 (0.37); 0.8922 (0.61); 0.8869 (1.63); 0.8698 (5.16); 0.8595 (0.97); 0.8526 (1.69); −0.0002 (9.40)
Example 108, Solvent: DMSO, Spectrometer: 400.13 MHz 7.9621 (1.63); 7.4051 (3.60); 7.3952 (3.49); 7.3888 (3.48); 7.2892 (2.92); 7.2696 (2.25); 7.2481 (4.22); 7.1363 (2.57); 7.1160 (2.18); 6.5182 (2.73); 6.5005 (2.58); 6.4004 (2.72); 6.3798 (2.56); 6.0273 (6.83); 5.9367 (0.32); 5.2248 (0.33); 5.1887 (9.33); 5.0260 (0.42); 3.7964 (16.00); 3.7671 (1.28); 3.3492 (7.06); 3.0848 (15.07); 2.8992 (6.82); 2.7403 (6.47); 2.5119 (33.94); 1.9999 (0.81); 1.3674 (2.15); 1.2435 (0.54); 1.2014 (0.33); 1.1841 (0.55)
Example 109, Solvent: DMSO, Spectrometer: 399.95 MHz 10.3271 (3.10); 7.8427 (0.59); 7.8217 (2.51); 7.8111 (3.15); 7.8063 (5.43); 7.7907 (0.61); 7.7233 (3.28); 7.7050 (3.80); 7.7016 (2.83); 7.5629 (0.61); 7.5446 (1.89); 7.5391 (0.74); 7.5264 (1.63); 7.4964 (3.03); 7.4770 (3.60); 7.4594 (1.33); 7.1163 (1.58); 7.1106 (1.55); 7.1013 (1.43); 7.0957 (1.45); 6.0095 (0.33); 5.9963 (0.68); 5.9833 (0.68); 5.9700 (0.83); 5.9533 (0.85); 5.9402 (0.77); 5.9270 (0.81); 5.9139 (0.39); 5.3939 (1.55); 5.3897 (1.55); 5.3507 (2.00); 5.3495 (1.97); 5.3397 (8.04); 5.2409 (1.51); 5.2371 (1.45); 5.2146 (1.37); 5.2109 (1.32); 4.6268 (3.53); 4.6137 (3.35); 3.3417 (129.08); 3.0661 (16.00); 2.8909 (1.92); 2.7314 (1.69); 2.5077 (26.43); 2.5035 (32.92); 2.4992 (25.05)
Example 110, Solvent: DMSO, Spectrometer: 399.95 MHz 10.0548 (2.57); 7.9532 (0.61); 7.8197 (0.51); 7.8038 (0.33); 7.7987 (1.99); 7.7830 (3.68); 7.7808 (3.18); 7.7646 (0.58); 7.7302 (0.33); 7.7247 (1.94); 7.7220 (2.61); 7.7182 (1.27); 7.7094 (0.79); 7.7043 (3.41); 7.7005 (2.75); 7.5617 (0.48); 7.5499 (0.36); 7.5434 (1.61); 7.5377 (0.48); 7.5285 (0.87); 7.5252 (1.43); 7.5217 (0.72); 7.4949 (2.40); 7.4915 (1.04); 7.4796 (1.62); 7.4758 (3.05); 7.4622 (0.47); 7.4581 (1.20); 7.4549 (0.67); 7.0923 (1.33); 7.0873 (1.33); 7.0766 (1.19); 7.0715 (1.26); 5.3225 (6.45); 5.0982 (0.54); 5.0902 (0.65); 5.0831 (0.91); 5.0762 (0.62); 5.0681 (0.50); 3.3296 (49.98); 3.0659 (16.00); 2.8907 (4.97); 2.7320 (3.82); 2.7311 (3.98); 2.5252 (0.63); 2.5203 (0.96); 2.5118 (10.77); 2.5073 (21.36); 2.5027 (28.12); 2.4981 (20.42); 2.4936 (9.73); 1.8855 (0.35); 1.8780 (0.43); 1.8663 (0.87); 1.8495 (0.80); 1.8362 (0.63); 1.8309 (0.55); 1.8225 (0.52); 1.7047 (0.59); 1.6833 (2.80); 1.6742 (1.66); 1.6689 (1.26); 1.6630 (1.06); 1.6539 (0.96); 1.6440 (0.57); 1.6363 (0.54); 1.5916 (0.45); 1.5826 (0.56); 1.5764 (0.64); 1.5611 (1.08); 1.5571 (0.89); 1.5509 (1.03); −0.0002 (7.45)
Example 111, Solvent: DMSO, Spectrometer: 400.13 MHz 10.5173 (3.55); 8.0818 (2.07); 8.0610 (2.40); 7.8400 (1.49); 7.8204 (2.59); 7.8006 (1.35); 7.7321 (4.08); 7.7130 (4.68); 7.5713 (0.69); 7.5537 (2.02); 7.5358 (1.92); 7.5048 (3.39); 7.4858 (4.32); 7.4672 (1.60); 7.1487 (2.67); 7.1301 (2.55); 5.3622 (9.11); 4.0634 (0.77); 4.0458 (2.29); 4.0280 (2.34); 4.0104 (0.78); 3.5757 (1.57); 3.3373 (54.92); 3.0616 (16.00); 2.5108 (37.34); 2.3989 (2.30); 2.3805 (4.60); 2.3622 (2.55); 1.9970 (9.33); 1.6150 (0.58); 1.5967 (1.91); 1.5789 (2.76); 1.5616 (1.95); 1.5447 (0.63); 1.3107 (1.68); 1.2872 (4.54); 1.2794 (4.48); 1.2001 (2.47); 1.1823 (4.81); 1.1646 (2.43); 0.8870 (3.49); 0.8708 (7.31); 0.8535 (3.47)
Example 112, Solvent: DMSO, Spectrometer: 400.13 MHz 10.1208 (2.89); 7.8322 (0.46); 7.8112 (1.96); 7.7990 (2.44); 7.7954 (3.87); 7.7783 (0.52); 7.4212 (1.03); 7.4012 (2.17); 7.3812 (1.57); 7.2836 (1.41); 7.2802 (1.23); 7.2667 (0.77); 7.2630 (1.17); 7.2609 (0.94); 7.2455 (1.25); 7.2396 (1.91); 7.2354 (1.30); 7.1432 (1.08); 7.1414 (1.11); 7.1368 (0.98); 7.1351 (0.95); 7.1226 (0.95); 7.1207 (0.92); 7.1163 (0.93); 7.0998 (1.28); 7.0945 (1.26); 7.0843 (1.15); 7.0791 (1.19); 5.7679 (0.34); 5.3315 (5.87); 4.6766 (0.39); 4.6635 (0.43); 4.6541 (0.70); 4.6446 (0.51); 4.6316 (0.34); 3.7886 (16.00); 3.4026 (2.53); 3.3527 (178.70); 3.3291 (0.82); 3.3028 (1.97); 3.0577 (14.67); 2.5595 (0.42); 2.5185 (11.43); 2.5141 (23.24); 2.5096 (31.23); 2.5051 (22.06); 2.5007 (10.07); 2.4597 (0.33); 1.8754 (0.69); 1.8619 (0.81); 1.8498 (0.83); 1.7325 (0.70); 1.7239 (0.75); 1.7097 (0.81); 1.7018 (0.74); 1.5284 (0.36); 1.5177 (0.38); 1.4971 (0.42); 1.4340 (0.80); 1.4088 (1.05); 1.3845 (1.17); 1.3585 (0.94); 1.3330 (0.71); 1.3263 (0.79); 1.3005 (0.41); 1.2779 (0.34); 1.2490 (0.53); 1.2223 (0.32)
Example 113, Solvent: DMSO, Spectrometer: 399.95 MHz 12.5540 (0.80); 7.9538 (0.81); 7.7433 (1.98); 7.7404 (2.71); 7.7364 (1.31); 7.7280 (0.79); 7.7228 (3.57); 7.7190 (2.45); 7.6150 (1.60); 7.6111 (1.69); 7.5955 (1.74); 7.5915 (1.73); 7.5675 (0.49); 7.5561 (0.35); 7.5492 (1.69); 7.5433 (0.50); 7.5345 (0.94); 7.5311 (1.55); 7.5276 (0.77); 7.5052 (2.53); 7.5018 (1.07); 7.4902 (1.59); 7.4862 (3.09); 7.4729 (0.48); 7.4687 (1.26); 7.4652 (0.69); 7.3483 (4.70); 7.3229 (0.76); 7.3189

NMR Peak List Table 1

(0.76); 7.3043 (1.04); 7.3020 (1.20); 7.3006 (1.18); 7.2983 (1.03); 7.2837 (0.98); 7.2796 (0.92); 6.9421 (1.20); 6.9394 (1.71); 6.9307 (1.25); 6.9274 (0.83); 6.9212 (1.20); 6.9184 (1.52); 6.9117 (1.75); 6.9084 (1.26); 6.8926 (0.93); 6.8893 (0.75); 5.3443 (5.56); 5.1249 (0.37); 5.1085 (1.38); 5.0919 (1.38); 5.0754 (0.37); 3.3375 (33.52); 3.0312 (16.00); 2.8906 (6.70); 2.7329 (5.32); 2.7316 (5.38); 2.5217 (0.49); 2.5131 (6.08); 2.5086 (12.24); 2.5040 (16.21); 2.4994 (11.72); 2.4948 (5.51); 1.5957 (5.55); 1.5792 (5.51); −0.0002 (3.65)
Example 114, Solvent: DMSO, Spectrometer: 399.95 MHz 10.8702 (1.70); 8.1751 (1.42); 8.1545 (1.70); 7.9528 (0.63); 7.9350 (1.32); 7.9154 (1.92); 7.8954 (1.21); 7.7304 (2.73); 7.7267 (1.39); 7.7174 (0.88); 7.7126 (3.87); 7.7090 (3.07); 7.6955 (1.19); 7.6910 (1.34); 7.6763 (0.74); 7.6721 (0.75); 7.6099 (0.35); 7.6053 (0.36); 7.5965 (0.39); 7.5916 (0.77); 7.5889 (0.59); 7.5872 (0.60); 7.5847 (0.51); 7.5767 (0.64); 7.5736 (0.64); 7.5707 (0.85); 7.5652 (0.83); 7.5616 (0.43); 7.5571 (0.53); 7.5528 (0.75); 7.5464 (1.70); 7.5408 (0.51); 7.5315 (0.93); 7.5282 (1.48); 7.5249 (0.76); 7.4981 (2.54); 7.4827 (1.70); 7.4790 (3.20); 7.4654 (0.50); 7.4614 (1.27); 7.4582 (0.74); 7.3500 (0.97); 7.3305 (1.97); 7.3254 (1.16); 7.3230 (0.38); 7.3137 (1.91); 7.3117 (1.78); 7.3044 (0.84); 7.3022 (0.81); 7.2951 (1.00); 7.2927 (0.81); 7.2431 (1.90); 7.2246 (1.80); 5.3929 (6.33); 3.3399 (89.26); 3.0941 (16.00); 3.0812 (0.41); 2.8906 (4.90); 2.7311 (3.99); 2.5255 (0.57); 2.5206 (0.91); 2.5121 (11.45); 2.5077 (22.91); 2.5031 (30.33); 2.4985 (22.07); 2.4940 (10.54); −0.0002 (1.99)
Example 115, Solvent: DMSO, Spectrometer: 399.95 MHz 10.5535 (2.14); 8.0453 (1.37); 8.0248 (1.75); 7.9533 (0.58); 7.8791 (1.33); 7.8597 (1.83); 7.8396 (1.15); 7.7277 (2.65); 7.7239 (1.28); 7.7149 (0.79); 7.7098 (3.48); 7.7061 (2.42); 7.5674 (0.50); 7.5554 (0.37); 7.5490 (1.69); 7.5434 (0.49); 7.5341 (0.87); 7.5308 (1.43); 7.5274 (0.72); 7.4986 (2.43); 7.4952 (1.03); 7.4831 (1.67); 7.4794 (3.16); 7.4657 (0.48); 7.4617 (1.25); 7.4585 (0.70); 7.2046 (1.82); 7.1866 (1.74); 7.0277 (0.86); 7.0235 (0.93); 7.0075 (1.89); 7.0037 (1.74); 6.9928 (1.10); 6.9892 (1.35); 6.9793 (1.11); 6.9733 (1.45); 6.9696 (1.93); 6.9605 (1.74); 6.9565 (1.00); 6.9409 (0.80); 6.9370 (0.55); 6.8791 (1.07); 6.8750 (1.06); 6.8600 (1.42); 6.8559 (1.24); 6.8409 (0.58); 6.8369 (0.54); 5.3912 (6.09); 4.9657 (0.34); 4.9492 (1.22); 4.9325 (1.22); 4.9160 (0.35); 3.8202 (15.07); 3.3287 (41.87); 3.0620 (16.00); 2.8905 (4.85); 2.7313 (3.79); 2.5251 (0.62); 2.5202 (1.01); 2.5117 (12.12); 2.5072 (24.14); 2.5026 (31.85); 2.4980 (23.10); 2.4935 (10.99); 1.5534 (5.69); 1.5368 (5.65); 0.0080 (0.39); −0.0002 (11.88); −0.0086 (0.37)
Example 116, Solvent: DMSO, Spectrometer: 400.13 MHz 7.7403 (2.64); 7.7225 (3.27); 7.7188 (2.39); 7.5620 (0.53); 7.5503 (0.45); 7.5436 (1.64); 7.5379 (0.62); 7.5288 (1.03); 7.5256 (1.49); 7.4993 (2.51); 7.4803 (3.04); 7.4627 (1.21); 7.4594 (0.75); 7.3734 (1.12); 7.3354 (0.37); 7.3527 (1.43); 7.3347 (1.25); 6.5737 (0.68); 6.5594 (1.25); 6.5454 (0.68); 6.4757 (1.88); 6.4583 (1.83); 6.4262 (1.83); 6.4052 (1.78); 5.7631 (6.38); 5.1946 (6.31); 3.3269 (28.63); 3.3037 (0.54); 3.2732 (0.40); 3.0709 (16.00); 3.0541 (2.95); 3.0380 (1.79); 2.6757 (0.35); 2.5154 (22.73); 2.5112 (44.61); 2.5068 (59.64); 2.5024 (44.34); 2.3336 (0.48); 2.3289 (0.37); 1.7372 (1.18); 1.7049 (1.27); 1.6654 (1.03); 1.6368 (1.42); 1.6109 (0.90); 1.5936 (0.69); 1.5153 (0.46); 1.5035 (0.48); 1.4961 (0.57); 1.4872 (0.68); 1.4780 (0.58); 1.4693 (0.50); 1.4594 (0.43); 1.1809 (0.82); 1.1503 (1.56); 1.1275 (1.24); 1.0996 (0.36); 1.0938 (0.43); 0.9326 (0.53); 0.9028 (1.13); 0.8731 (1.01); 0.8453 (0.49)
Example 117, Solvent: DMSO, Spectrometer: 400.13 MHz 10.3747 (3.00); 7.8516 (0.37); 7.8305 (2.52); 7.8245 (2.72); 7.8171 (5.74); 7.8036 (0.56); 7.5368 (2.33); 7.5220 (0.84); 7.5175 (0.74); 7.5125 (1.13); 7.5092 (1.16); 7.4998 (1.07); 7.4953 (0.82); 7.4443 (1.06); 7.4399 (1.48); 7.4232 (3.85); 7.4197 (3.53); 7.4154 (3.05); 7.4132 (2.99); 7.4078 (1.06); 7.3959 (3.95); 7.3913 (1.75); 7.3807 (1.43); 7.3767 (1.95); 7.3698 (2.93); 7.3685 (2.95); 7.3564 (4.77); 7.3457 (1.15); 7.3386 (1.55); 7.3308 (0.60); 7.3252 (0.51); 7.3212 (0.61); 7.3172 (0.41); 7.1149 (1.34); 7.1074 (1.36); 7.1015 (1.21); 7.0941 (1.31); 5.7646 (0.50); 5.3358 (6.92); 5.2055 (0.43); 5.1880 (7.58); 3.3664 (0.62); 3.3287 (11.77); 3.0586 (16.00); 2.5611 (0.48); 2.5569 (0.47); 2.5187 (10.61); 2.5143 (20.78); 2.5099 (27.63); 2.5054 (20.12); 2.5011 (10.23); 2.4685 (0.75); 2.4639 (0.79); 2.4593 (0.79); 2.3378 (11.35)
Example 118, Solvent: DMSO, Spectrometer: 399.95 MHz 10.3719 (1.81); 8.0936 (0.97); 8.0729 (1.16); 7.9533 (0.46); 7.8377 (1.27); 7.8184 (1.73); 7.7982 (1.18); 7.7229 (2.03); 7.7203 (2.60); 7.7164 (1.24); 7.7074 (0.96); 7.7025 (3.46); 7.6987 (2.34); 7.5633 (0.50); 7.5514 (0.37); 7.5450 (1.70); 7.5393 (0.50); 7.5300 (0.89); 7.5267 (1.42); 7.5233 (0.71); 7.4956 (2.45); 7.4922 (1.03); 7.4803 (1.68); 7.4765 (3.14); 7.4629 (0.48); 7.4588 (1.25); 7.4556 (0.68); 7.1366 (1.73); 7.1356 (1.73); 7.1181 (1.67); 5.3482 (6.18); 3.3881 (0.63); 3.3675 (0.98); 3.3450 (1.22); 3.3310 (66.49); 3.0506 (16.00); 2.8910 (3.83); 2.7323 (3.00); 2.7314 (2.94); 2.5255 (0.56); 2.5207 (0.90); 2.5122 (10.83); 2.5076 (21.65); 2.5030 (28.64); 2.4984 (20.76); 2.4939 (9.81); 2.2280 (0.76); 2.2225 (0.64); 2.2043 (1.00); 2.1990 (1.29); 2.1826 (0.80); 2.1775 (1.17); 2.1550 (0.38); 2.1276 (0.33); 2.1207 (0.40); 2.1183 (0.41); 2.1060 (0.79); 2.0975 (1.04); 2.0908 (0.64); 2.0847 (0.68); 2.0758 (0.97); 2.0684 (0.57); 1.9514 (0.37); 1.9467 (0.32); 1.9286 (0.60); 1.9248 (0.61); 1.9076 (0.35); 1.9021 (0.83); 1.8808 (0.44); 1.7988 (0.53); 1.7880 (0.34); 1.7850 (0.33); 1.7746 (0.41); 0.8759 (0.50); 0.8627 (0.36); −0.0002 (5.96)
Example 119, Solvent: DMSO, Spectrometer: 400.13 MHz 10.5103 (2.58); 7.8458 (0.89); 7.8253 (1.65); 7.8065 (1.51); 7.7503 (2.13); 7.7316 (3.58); 7.7193 (0.88); 7.7142 (3.30); 7.7105 (2.35); 7.5702 (0.47); 7.5583 (0.38); 7.5519 (1.61); 7.5462 (0.50); 7.5369 (0.91); 7.5337 (1.41); 7.5303 (0.74); 7.5036 (2.38); 7.4882 (1.66); 7.4845 (3.00); 7.4709 (0.49); 7.4669 (1.16); 7.4637 (0.68); 7.1399 (1.70); 7.1225 (1.85); 5.7646 (5.66); 5.3509 (6.05); 5.0796 (0.47); 5.0621 (1.86); 5.0444 (1.88); 5.0268 (0.48); 3.6946 (16.00); 3.3260 (15.16); 3.0829 (15.38); 2.5596 (0.41); 2.5319 (0.63); 2.5186 (12.09); 2.5142 (24.34); 2.5097 (32.66); 2.5052 (23.20); 2.5008 (10.83); 2.4598 (0.39); 1.9969 (0.93); 1.4619 (6.33); 1.4443 (6.26); 1.2544 (0.44); 1.1828 (0.51); 0.8664 (0.63)
Example 120, Solvent: DMSO, Spectrometer: 400.13 MHz 9.8770 (1.66); 7.8031 (0.40); 7.7821 (1.16); 7.7651 (1.72); 7.7622 (1.52); 7.7582 (1.65); 7.7411 (0.55); 7.7369 (0.47); 7.7305 (1.28); 7.7277 (1.67); 7.7238 (0.88); 7.7152 (0.59); 7.7100 (2.21); 7.7063 (1.58); 7.5501 (1.04); 7.5444 (0.34); 7.5352 (0.60); 7.5318 (0.95); 7.5284 (0.52); 7.5012 (1.52); 7.4978 (0.72); 7.4859 (1.07); 7.4821 (1.97); 7.4686 (0.35); 7.4645 (0.83); 7.4613 (0.47); 7.0799 (0.87); 7.0761 (0.90); 7.0631 (0.85); 7.0593 (0.85); 5.3253 (3.92); 3.4053 (5.47); 3.3907 (0.44); 3.3555 (386.71); 3.3239 (2.18); 3.3057 (4.68); 3.0672 (10.54); 2.5628 (0.42); 2.5584 (0.60); 2.5538 (0.45); 2.5309 (1.03); 2.5262 (1.65); 2.5175 (16.50); 2.5131 (34.24); 2.5085 (47.05); 2.5040 (34.35); 2.4995 (17.21); 2.4634 (0.82); 2.4588 (0.82); 2.4543 (0.62); 1.7964 (0.40); 1.7779 (1.36); 1.7591 (1.45); 1.7407 (0.49); 1.4327 (16.00); 1.2515 (0.87); 0.9126 (1.76); 0.8941 (4.06); 0.8753 (1.92); 0.8632 (1.53); 0.8455 (0.60)
Example 121, Solvent: DMSO, Spectrometer: 400.13 MHz 7.4804 (1.87); 7.4654 (5.40); 7.4431 (3.13); 7.4300 (2.24); 7.3773 (0.81); 7.3582 (3.18); 7.3431 (5.61); 6.5698 (2.81); 6.5518 (2.73); 6.4592 (2.87); 6.4384 (2.79); 6.2730 (0.68); 5.2206 (9.93); 4.6025 (1.13); 2.8986 (0.33); 2.5108 (35.19); 2.3426 (16.00); 1.3680 (0.35)
Example 122, Solvent: DMSO, Spectrometer: 400.13 MHz 10.2685 (2.98); 7.8412 (0.42); 7.8202 (2.15); 7.8110 (2.41); 7.8053 (5.21); 7.7901 (0.50); 7.7290 (2.66); 7.7163 (0.88); 7.7113 (3.45); 7.7076 (2.43); 7.5675 (0.49); 7.5643 (0.33); 7.5556 (0.42); 7.5492 (1.67); 7.5435 (0.51); 7.5342 (0.92); 7.5309 (1.45); 7.5276 (0.75); 7.5000 (2.45); 7.4845 (1.76); 7.4808 (3.12); 7.4672 (0.53); 7.4632 (1.24); 7.4600 (0.73); 7.1118 (1.30); 7.1057 (1.29); 7.0972 (1.15); 7.0911 (1.24); 5.7661

NMR Peak List Table 1

(6.09); 5.3394 (6.38); 4.1390 (1.65); 4.1236 (3.56); 4.1078 (1.74); 3.3408 (21.83); 3.0678 (16.00); 2.5575 (0.36); 2.5300 (0.64); 2.5252 (1.07); 2.5165 (11.30); 2.5121 (22.87); 2.5076 (30.60); 2.5031 (21.66); 2.4987 (10.00); 2.4578 (0.36); 2.3548 (0.75); 2.3437 (0.49); 2.3348 (0.89); 2.3299 (0.74); 2.3257 (0.93); 2.3152 (0.88); 2.3061 (0.73); 2.2969 (0.41); 2.2862 (0.77); 1.9944 (0.92); 1.7148 (0.82); 1.6975 (1.24); 1.6794 (1.22); 1.6638 (0.52); 1.6264 (0.57); 1.6072 (1.12); 1.5987 (0.69); 1.5893 (1.26); 1.5748 (0.59); 1.5673 (0.74); 1.1788 (0.50); 0.8619 (0.38)
Example 123, Solvent: DMSO, Spectrometer: 399.95 MHz 12.4657 (0.52); 7.7435 (1.98); 7.7407 (2.78); 7.7368 (1.34); 7.7284 (0.81); 7.7231 (3.56); 7.7193 (2.46); 7.6096 (3.22); 7.6031 (3.36); 7.5674 (0.49); 7.5642 (0.32); 7.5560 (0.35); 7.5491 (1.71); 7.5432 (0.52); 7.5344 (0.94); 7.5310 (1.58); 7.5275 (0.80); 7.5055 (2.62); 7.5022 (1.13); 7.4906 (1.60); 7.4865 (3.12); 7.4732 (0.49); 7.4691 (1.27); 7.4655 (0.71); 7.3681 (1.67); 7.3616 (1.59); 7.3458 (2.41); 7.3415 (5.22); 7.1019 (2.86); 7.0795 (2.44); 5.3418 (5.76); 5.0032 (6.64); 3.3373 (39.41); 3.0341 (16.00); 2.8904 (0.58); 2.7325 (0.45); 2.7313 (0.48); 2.5260 (0.37); 2.5213 (0.58); 2.5126 (7.10); 2.5081 (14.27); 2.5035 (18.89); 2.4989 (13.65); 2.4944 (6.45); −0.0002 (4.18)
Example 124, Solvent: DMSO, Spectrometer: 399.95 MHz 10.5358 (1.87); 8.1245 (1.44); 8.1040 (1.68); 7.9540 (0.34); 7.8403 (1.29); 7.8211 (1.78); 7.8008 (1.23); 7.7331 (0.32); 7.7251 (2.68); 7.7212 (1.36); 7.7124 (0.83); 7.7072 (3.64); 7.7035 (2.46); 7.5646 (0.49); 7.5614 (0.32); 7.5526 (0.37); 7.5463 (1.68); 7.5406 (0.53); 7.5313 (0.89); 7.5280 (1.43); 7.5246 (0.75); 7.4964 (2.51); 7.4930 (1.08); 7.4814 (1.73); 7.4773 (3.21); 7.4636 (0.50); 7.4596 (1.28); 7.4564 (0.71); 7.1509 (1.79); 7.1326 (1.76); 5.3651 (6.25); 3.3307 (55.19); 3.0885 (0.43); 3.0570 (16.00); 2.8913 (2.78); 2.7326 (2.23); 2.5257 (0.55); 2.5209 (0.89); 2.5124 (10.97); 2.5079 (21.87); 2.5033 (28.84); 2.4987 (20.95); 2.4942 (10.00); 2.4785 (0.51); 2.4675 (0.56); 2.4557 (0.78); 2.4435 (0.53); 2.4331 (0.42); 1.5830 (0.57); 1.5644 (0.75); 1.5604 (0.65); 1.5494 (1.04); 1.5419 (0.73); 1.5308 (1.10); 1.5270 (1.06); 1.5083 (0.92); 1.4565 (0.86); 1.4435 (1.04); 1.4380 (1.00); 1.4248 (1.29); 1.4101 (0.65); 1.4049 (0.78); 1.3916 (0.57); 1.2831 (0.40); 0.8761 (0.72); 0.8625 (0.55); 0.8497 (6.16); 0.8312 (13.00); 0.8126 (5.44); −0.0002 (6.14)
Example 125, Solvent: DMSO, Spectrometer: 399.95 MHz 10.6838 (2.13); 8.0275 (0.70); 8.0071 (0.89); 7.9529 (0.51); 7.8836 (1.34); 7.8643 (1.83); 7.8441 (1.13); 7.7280 (2.62); 7.7242 (1.26); 7.7153 (0.76); 7.7103 (3.39); 7.7065 (2.35); 7.5672 (0.47); 7.5553 (0.35); 7.5488 (1.63); 7.5432 (0.47); 7.5339 (0.86); 7.5306 (1.41); 7.5273 (0.71); 7.4996 (2.39); 7.4962 (1.02); 7.4842 (1.62); 7.4804 (3.08); 7.4668 (0.47); 7.4628 (1.21); 7.4596 (0.68); 7.2637 (0.65); 7.2605 (0.68); 7.2418 (0.90); 7.2344 (0.71); 7.2306 (0.73); 7.2140 (0.86); 7.2070 (1.85); 7.1882 (1.71); 7.1166 (1.23); 7.1131 (1.25); 7.1062 (1.07); 7.0992 (2.47); 7.0861 (1.08); 7.0815 (1.08); 7.0656 (0.40); 6.9913 (0.47); 6.9838 (0.46); 6.9797 (0.52); 6.9753 (0.74); 6.9710 (0.51); 6.9688 (0.47); 6.9620 (0.72); 6.9595 (0.61); 6.9568 (0.81); 6.9417 (0.34); 5.3838 (6.25); 4.8919 (5.88); 3.3422 (120.00); 3.0701 (16.00); 2.8908 (4.16); 2.7314 (3.25); 2.5258 (0.59); 2.5209 (0.96); 2.5125 (12.14); 2.5080 (24.22); 2.5034 (32.04); 2.4988 (23.30); 2.4943 (11.11); −0.0002 (0.47)
Example 126, Solvent: DMSO, Spectrometer: 399.95 MHz 12.2345 (1.79); 7.9531 (0.65); 7.7473 (0.32); 7.7416 (2.17); 7.7390 (2.79); 7.7350 (1.36); 7.7265 (0.85); 7.7213 (3.63); 7.7175 (2.55); 7.5658 (0.50); 7.5626 (0.34); 7.5544 (0.37); 7.5475 (1.77); 7.5416 (0.54); 7.5328 (0.99); 7.5294 (1.57); 7.5259 (0.79); 7.5039 (2.61); 7.5005 (1.12); 7.4889 (1.73); 7.4849 (3.27); 7.4715 (0.51); 7.4674 (1.27); 7.4638 (0.72); 7.3688 (0.58); 7.3548 (8.10); 7.3484 (3.98); 7.3392 (5.49); 7.3374 (5.17); 7.3256 (0.54); 7.3220 (0.68); 7.3198 (0.76); 7.3011 (0.72); 7.2948 (0.86); 7.2880 (1.73); 7.2835 (0.57); 7.2793 (0.48); 7.2704 (0.45); 7.2651 (0.33); 5.3402 (6.12); 4.8146 (0.33); 4.5665 (1.64); 4.5370 (2.66); 4.4470 (2.69); 4.4175 (1.75); 4.2618 (0.44); 4.2452 (1.72); 4.2284 (1.75); 4.2118 (0.45); 3.3318 (62.61); 3.0271 (16.00); 2.8906 (5.33); 2.7319 (4.34); 2.5251 (0.72); 2.5201 (1.16); 2.5117 (13.47); 2.5072 (26.54); 2.5026 (34.66); 2.4980 (25.07); 2.4935 (11.92); 2.2691 (0.44); 1.3627 (6.04); 1.3460 (5.97); −0.0002 (4.02)
Example 127, Solvent: DMSO, Spectrometer: 400.13 MHz 10.2000 (6.98); 7.8389 (1.87); 7.8181 (4.15); 7.8002 (4.53); 7.7817 (5.60); 7.7629 (2.39); 7.7251 (6.61); 7.7073 (7.91); 7.7036 (5.68); 7.5740 (1.19); 7.5708 (0.90); 7.5621 (1.14); 7.5556 (3.97); 7.5500 (1.39); 7.5406 (2.48); 7.5376 (3.46); 7.5099 (6.02); 7.4907 (7.25); 7.4731 (2.66); 7.4700 (1.61); 7.1049 (3.87); 7.1031 (3.86); 7.0873 (3.71); 5.4189 (0.40); 5.3416 (14.90); 4.9351 (0.33); 4.9193 (1.53); 4.9040 (3.12); 4.8886 (3.12); 4.8733 (1.46); 5.3367 (2.01); 3.5187 (6.44); 3.5005 (6.54); 3.4824 (2.13); 3.4615 (5.44); 3.4113 (5.44); 3.3608 (562.41); 3.3260 (0.72); 3.3101 (8.40); 3.2614 (0.35); 2.9312 (3.09); 2.9247 (6.61); 2.9182 (3.06); 2.6840 (0.50); 2.6792 (0.64); 2.6749 (0.47); 2.5607 (1.30); 2.5565 (1.25); 2.5340 (7.87); 2.5278 (11.07); 2.5189 (47.05); 2.5147 (84.48); 2.5104 (107.33); 2.5060 (77.67); 2.4686 (0.81); 2.4641 (1.25); 2.4596 (1.62); 2.4551 (1.28); 2.3416 (0.54); 2.3373 (0.67); 2.3327 (0.48); 1.9964 (1.24); 1.3706 (1.15); 1.3167 (15.46); 1.3010 (15.61); 1.2836 (1.00); 1.2656 (0.90); 1.2502 (1.98); 1.1986 (0.44); 1.1808 (0.70); 1.1630 (0.37); 1.1258 (0.38); 1.0638 (7.30); 1.0458 (16.00); 1.0276 (7.04); 0.8805 (0.81); 0.8640 (2.18); 0.8463 (0.88)
Example 128, Solvent: DMSO, Spectrometer: 399.95 MHz 10.7155 (2.03); 8.0201 (1.22); 7.9995 (1.58); 7.9531 (0.49); 7.8666 (1.32); 7.8474 (1.76); 7.8271 (1.13); 7.7281 (1.97); 7.7256 (2.53); 7.7217 (1.20); 7.7129 (0.76); 7.7078 (3.40); 7.7040 (2.35); 7.5673 (0.49); 7.5553 (0.35); 7.5490 (1.63); 7.5433 (0.47); 7.5340 (0.85); 7.5306 (1.40); 7.5272 (0.69); 7.4980 (2.33); 7.4946 (0.96); 7.4825 (1.64); 7.4788 (3.05); 7.4652 (0.47); 7.4611 (1.23); 7.4580 (0.68); 7.1982 (1.73); 7.1806 (1.68); 7.1660 (0.97); 7.1456 (2.10); 7.1255 (1.31); 6.7582 (2.69); 6.7413 (1.17); 6.7141 (0.88); 6.6937 (0.85); 6.6877 (0.71); 5.3827 (5.91); 5.0545 (1.06); 5.0380 (1.07); 3.3429 (107.22); 3.0573 (16.00); 2.8908 (4.15); 2.7323 (3.24); 2.7313 (3.21); 2.5260 (0.57); 2.5212 (0.93); 2.5126 (12.24); 2.5081 (24.48); 2.5035 (32.21); 2.4989 (23.19); 2.4944 (10.92); 2.2430 (9.37); 1.5184 (5.42); 1.5019 (5.40); −0.0002 (1.29)
Example 129, Solvent: DMSO, Spectrometer: 400.13 MHz 7.6045 (0.61); 7.5849 (2.48); 7.5672 (8.15); 7.5630 (8.02); 7.5548 (9.54); 7.5335 (4.79); 7.5141 (2.65); 7.4570 (1.82); 7.4342 (2.49); 7.4185 (1.32); 6.6476 (4.56); 6.6296 (4.37); 6.5329 (4.74); 6.5120 (4.57); 6.3970 (0.74); 6.3109 (0.40); 5.3044 (16.00); 5.1127 (0.42); 5.0351 (0.33); 4.7538 (1.76); 4.5189 (0.41); 4.4872 (0.34); 2.9502 (0.66); 2.7909 (0.62); 2.5626 (54.18); 2.3891 (0.36); 1.4191 (0.50); −0.0002 (2.62)
Example 130, Solvent: DMSO, Spectrometer: 400.13 MHz 10.6899 (5.67); 8.0245 (2.42); 8.0039 (3.35); 7.9045 (3.07); 7.8853 (4.11); 7.8650 (2.50); 7.7289 (5.97); 7.7252 (2.97); 7.7162 (1.84); 7.7112 (7.77); 7.7074 (5.51); 7.5829 (0.57); 7.5800 (1.08); 7.5768 (0.71); 7.5682 (0.82); 7.5616 (3.73); 7.5559 (1.15); 7.5467 (2.06); 7.5434 (3.29); 7.5400 (1.72); 7.5145 (5.55); 7.4992 (3.66); 7.4954 (6.95); 7.4819 (1.09); 7.4778 (2.68); 7.4746 (1.56); 7.2215 (4.06); 7.2037 (3.89); 7.0153 (2.78); 7.0110 (2.28); 7.0073 (1.43); 6.9983 (1.32); 6.9944 (5.05); 6.9904 (2.48); 6.9860 (0.80); 6.9096 (1.34); 6.9030 (1.64); 6.8933 (2.64); 6.8871 (4.18); 6.8820 (2.67); 6.8693 (9.15); 6.8657 (6.94); 6.8610 (4.65); 6.8495 (3.54); 6.8455 (0.95); 6.8371 (0.71); 6.8295 (0.67); 6.8255 (0.57); 5.3987 (13.52); 5.0934 (1.73); 5.0857 (2.23); 5.0819 (2.46); 5.0744 (1.78); 4.4509 (0.98); 4.4434 (1.16); 4.4215 (3.90); 4.4141 (3.74); 4.4071 (3.72); 4.3949 (3.44); 4.3776 (1.05); 4.3656 (1.10); 4.0433 (0.55); 4.0255 (0.55); 3.5160 (1.76); 3.4979 (5.98); 3.4797 (6.13); 3.4622 (2.17); 3.4131 (7.23); 3.3948 (0.59); 3.3824 (1.27); 3.3630 (703.91); 3.3279 (1.21); 3.3203 (1.10); 3.3134 (6.00); 2.6835 (0.40); 2.6789 (0.57); 2.6745 (0.41); 2.5645 (0.76); 2.5600 (0.98); 2.5555 (0.64); 2.5323 (1.32); 2.5276 (2.19); 2.5188 (33.47); 2.5144 (71.25); 2.5099 (97.99); 2.5054 (70.26); 2.5010 (32.73); 2.4647 (0.92); 2.4603 (1.04); 2.4559 (0.75); 2.3413 (0.47); 2.3367 (0.65); 2.3323 (0.46); 1.9958 (2.57); 1.3751 (0.35); 1.2514 (0.98); 1.1981 (0.72); 1.1803 (1.39); 1.1624 (0.67); 1.0707 (6.92); 1.0527 (16.00); 1.0344 (6.79); 0.8803 (0.46); 0.8635 (1.48); 0.8459 (0.57)

NMR Peak List Table 1

Example 131, Solvent: DMSO, Spectrometer: 400.13 MHz 9.8705 (1.10); 7.7857 (0.75); 7.7701 (1.59); 7.7666 (1.14); 7.4220 (0.40); 7.4020 (0.87); 7.3820 (0.66); 7.2838 (0.56); 7.2814 (0.50); 7.2642 (0.47); 7.2621 (0.38); 7.2465 (0.61); 7.2407 (0.78); 7.2365 (0.54); 7.1422 (0.46); 7.1374 (0.47); 7.1234 (0.39); 7.1214 (0.41); 7.1170 (0.43); 7.0818 (0.53); 7.0772 (0.54); 7.0659 (0.49); 7.0612 (0.51); 5.3238 (2.45); 3.7901 (6.40); 3.7597 (0.86); 3.3412 (4.16); 3.0542 (5.92); 2.5596 (0.38); 2.5318 (0.39); 2.5182 (9.59); 2.5139 (19.99); 2.5094 (27.16); 2.5050 (19.46); 2.5006 (9.11); 2.4638 (0.36); 2.4592 (0.49); 2.4546 (0.36); 1.4692 (16.00); 1.3642 (2.08)

Example 132, Solvent: DMSO, Spectrometer: 399.95 MHz 10.5084 (1.89); 8.0977 (1.47); 8.0771 (1.73); 7.9534 (0.51); 7.8376 (1.28); 7.8183 (1.78); 7.7981 (1.20); 7.7242 (2.60); 7.7204 (1.26); 7.7115 (0.79); 7.7064 (3.42); 7.7027 (2.37); 7.5651 (0.48); 7.5632 (0.50); 7.5600 (0.32); 7.5513 (0.38); 7.5448 (1.69); 7.5392 (0.51); 7.5300 (0.91); 7.5266 (1.46); 7.5232 (0.75); 7.4961 (2.48); 7.4928 (1.06); 7.4807 (1.71); 7.4770 (3.17); 7.4634 (0.50); 7.4593 (1.26); 7.4561 (0.48); 7.4606 (1.22); 7.4575 (0.68); 7.1466 (1.79); 7.1289 (1.74); 5.3609 (6.34); 3.3353 (90.78); 3.0575 (16.00); 2.8911 (4.14); 2.7323 (3.28); 2.6169 (0.38); 2.6002 (0.62); 2.5815 (0.65); 2.5645 (0.43); 2.5258 (0.58); 2.5124 (11.50); 2.5079 (22.88); 2.5033 (30.06); 2.4987 (21.84); 2.4942 (10.42); 1.6265 (0.39); 1.6076 (0.56); 1.5929 (0.60); 1.5879 (0.49); 1.5739 (0.72); 1.5543 (0.52); 1.4098 (0.44); 1.3949 (0.61); 1.3914 (0.54); 1.3764 (0.84); 1.3614 (0.42); 1.3579 (0.55); 1.3430 (0.35); 1.0670 (6.48); 1.0500 (6.37); 0.8591 (3.34); 0.8406 (7.10); 0.8221 (2.95); −0.0002 (3.50)

Example 133, Solvent: DMSO, Spectrometer: 399.95 MHz 10.2555 (2.88); 7.9531 (0.76); 7.8280 (0.44); 7.8069 (2.11); 7.7965 (2.37); 7.7915 (4.71); 7.7756 (0.51); 7.7315 (0.33); 7.7259 (2.06); 7.7234 (2.70); 7.7195 (1.31); 7.7107 (0.85); 7.7056 (3.55); 7.7019 (2.45); 7.5632 (0.50); 7.5600 (0.32); 7.5513 (0.38); 7.5448 (1.69); 7.5392 (0.51); 7.5300 (0.91); 7.5266 (1.46); 7.5232 (0.75); 7.4961 (2.48); 7.4928 (1.06); 7.4807 (1.71); 7.4770 (3.17); 7.4634 (0.50); 7.4593 (1.26); 7.4561 (0.71); 7.2626 (0.99); 7.2462 (1.42); 7.2345 (0.83); 7.2249 (1.11); 7.2124 (1.27); 7.1728 (0.56); 7.1672 (0.56); 7.1604 (1.25); 7.1500 (1.89); 7.1427 (0.74); 7.1365 (2.59); 7.1339 (2.60); 7.1288 (1.07); 7.1246 (2.62); 7.1186 (0.97); 7.1123 (1.83); 7.1086 (1.48); 7.1028 (1.38); 7.0936 (1.21); 7.0878 (1.28); 5.3338 (6.42); 4.3817 (0.48); 4.2754 (1.63); 4.2574 (3.43); 4.2394 (1.57); 3.3352 (98.43); 3.0632 (16.00); 3.0034 (0.39); 2.9546 (1.54); 2.9366 (3.11); 2.9187 (1.46); 2.8904 (6.13); 2.7320 (4.83); 2.7312 (4.79); 2.5252 (0.65); 2.5119 (12.06); 2.5074 (23.69); 2.5028 (30.99); 2.4982 (22.39); 2.4937 (10.61); 2.3295 (0.32); 2.3147 (12.20); 2.3068 (1.71); −0.0002 (3.96)

Example 134, Solvent: DMSO, Spectrometer: 399.95 MHz 10.6679 (2.32); 8.1176 (1.76); 8.0970 (2.18); 7.9559 (2.46); 7.9543 (2.55); 7.9518 (2.58); 7.9093 (1.35); 7.8900 (1.98); 7.8698 (1.21); 7.7338 (2.71); 7.7208 (0.88); 7.7158 (3.43); 7.7121 (2.48); 7.6437 (2.27); 7.6348 (2.35); 7.5669 (0.49); 7.5550 (0.38); 7.5486 (1.70); 7.5430 (0.50); 7.5336 (0.94); 7.5304 (1.44); 7.5272 (0.76); 7.5003 (2.49); 7.4846 (1.77); 7.4810 (3.22); 7.4673 (0.52); 7.4633 (1.23); 7.4602 (0.73); 7.2176 (1.98); 7.1991 (1.92); 6.7062 (1.85); 6.7020 (1.84); 6.6974 (1.83); 6.6931 (1.77); 5.4100 (6.80); 3.3312 (65.24); 3.0741 (16.00); 2.8911 (0.91); 2.7321 (0.72); 2.5253 (0.67); 2.5119 (13.07); 2.5076 (25.52); 2.5030 (33.26); 2.4985 (24.41); 2.4941 (11.98); −0.0002 (5.84)

Example 135, Solvent: DMSO, Spectrometer: 400.13 MHz 9.7994 (1.17); 7.9562 (0.46); 7.7879 (0.36); 7.7672 (0.81); 7.7492 (0.90); 7.7326 (1.08); 7.7138 (0.48); 7.6212 (1.23); 7.6039 (1.49); 7.6000 (1.17); 7.4966 (0.72); 7.4822 (0.54); 7.4789 (0.74); 7.4606 (1.25); 7.4417 (1.39); 7.4245 (0.53); 7.4207 (0.36); 7.1002 (0.73); 7.0834 (0.68); 5.2749 (2.71); 2.8902 (2.75); 2.7331 (2.41); 2.5106 (1.90); 2.5063 (2.63); 2.5021 (2.11); 1.4645 (16.00)

Example 136, Solvent: DMSO, Spectrometer: 400.13 MHz 7.7386 (7.06); 7.7194 (7.83); 7.5623 (1.43); 7.5440 (3.55); 7.5268 (3.76); 7.4980 (6.64); 7.4791 (7.19); 7.4584 (3.89); 7.4491 (2.27); 7.4371 (2.93); 7.4295 (3.06); 7.4180 (1.98); 7.4101 (1.94); 7.3781 (9.20); 7.3675 (8.11); 7.3352 (13.24); 7.3215 (2.70); 7.3138 (2.77); 7.2998 (2.34); 7.0484 (0.99); 7.0341 (1.89); 7.0195 (0.95); 6.9628 (1.01); 6.9490 (1.96); 6.9344 (0.99); 6.7934 (1.31); 6.7841 (2.50); 6.7748 (1.34); 6.5917 (2.68); 6.5833 (3.05); 6.5748 (2.80); 6.5661 (2.71); 6.4748 (2.59); 6.4548 (2.97); 6.4406 (2.08); 5.7694 (4.38); 5.2201 (9.46); 5.2111 (8.76); 5.1866 (0.43); 5.1027 (8.78); 5.0127 (9.99); 4.1298 (2.33); 4.1182 (3.52); 4.1069 (2.32); 3.9865 (2.39); 3.9731 (4.39); 3.9595 (2.38); 3.3566 (261.77); 3.0785 (16.00); 3.0673 (14.86); 2.6802 (0.64); 2.5109 (112.20); 2.3375 (0.71); 1.9968 (0.47); 1.2410 (1.10); 1.1970 (0.52); 1.1808 (0.42)

Example 137, Solvent: DMSO, Spectrometer: 399.95 MHz 9.5609 (1.79); 7.9684 (1.41); 7.9489 (1.96); 7.8400 (1.34); 7.8209 (1.73); 7.8005 (1.10); 7.7295 (1.84); 7.7268 (2.44); 7.7229 (1.15); 7.7142 (0.72); 7.7091 (3.30); 7.7053 (2.26); 7.5658 (0.46); 7.5539 (0.33); 7.5475 (1.56); 7.5418 (0.45); 7.5326 (0.83); 7.5292 (1.37); 7.5258 (0.68); 7.4984 (2.27); 7.4950 (0.94); 7.4831 (1.54); 7.4793 (2.95); 7.4658 (0.45); 7.4617 (1.19); 7.4584 (0.65); 7.1598 (1.66); 7.1425 (1.61); 5.3806 (6.19); 3.3343 (88.20); 3.0852 (16.00); 2.8907 (0.83); 2.7320 (0.65); 2.7310 (0.64); 2.5252 (0.49); 2.5204 (0.83); 2.5119 (10.80); 2.5073 (21.58); 2.5027 (28.42); 2.4981 (20.44); 2.4935 (9.57); 1.4156 (10.91); 1.1357 (0.90); 1.1262 (2.74); 1.1193 (2.82); 1.1102 (0.97); 0.6700 (1.20); 0.6606 (3.75); 0.6536 (3.64); 0.6438 (1.02); −0.0002 (4.44)

Example, 138, Solvent: DMSO, Spectrometer: 399.95 MHz 9.3214 (4.34); 7.9528 (0.64); 7.8496 (0.82); 7.8288 (1.76); 7.8212 (0.36); 7.8107 (2.04); 7.7894 (1.01); 7.7689 (0.50); 7.7356 (0.75); 7.7272 (3.86); 7.7143 (1.32); 7.7092 (4.15); 7.7061 (3.82); 7.5502 (0.73); 7.5466 (0.64); 7.5390 (1.03); 7.5317 (1.96); 7.5255 (0.93); 7.5214 (0.88); 7.5167 (1.07); 7.5133 (1.47); 7.5101 (0.86); 7.5043 (0.51); 7.4953 (1.42); 7.4917 (0.70); 7.4852 (0.75); 7.4798 (1.52); 7.4753 (3.64); 7.4585 (2.46); 7.4551 (3.67); 7.4412 (0.57); 7.4372 (1.40); 7.4346 (1.10); 7.4021 (0.63); 7.3839 (0.77); 7.3816 (0.78); 7.3634 (0.67); 7.2262 (0.56); 7.1755 (1.67); 7.1702 (0.53); 7.1564 (1.81); 7.1539 (2.14); 7.1411 (0.58); 7.1359 (1.67); 7.1106 (1.67); 7.0906 (1.59); 6.7768 (0.75); 6.7742 (0.60); 6.7586 (3.42); 6.7560 (3.28); 6.7370 (3.18); 6.5114 (0.86); 6.4936 (0.82); 6.3910 (0.88); 6.3707 (0.84); 6.0040 (1.40); 5.3782 (0.80); 5.3568 (5.89); 5.3350 (0.50); 5.1786 (3.26); 3.6697 (0.72); 3.3651 (0.33); 3.3346 (122.05); 3.0915 (2.64); 3.0877 (8.10); 3.0806 (1.02); 3.0724 (16.00); 3.0607 (1.07); 2.9337 (0.41); 2.8904 (5.29); 2.7312 (4.16); 2.6719 (0.33); 2.5251 (0.95); 2.5203 (1.57); 2.5118 (19.46); 2.5073 (38.76); 2.5027 (51.18); 2.4981 (37.17); 2.4936 (17.78); 2.3295 (0.33); 1.2343 (0.35); −0.0002 (6.98)

Example 139, Solvent: DMSO, Spectrometer: 400.13 MHz 9.8766 (0.82); 8.0302 (0.60); 8.0096 (0.74); 7.8519 (0.47); 7.8325 (0.65); 7.8124 (0.41); 7.6227 (0.35); 7.6169 (0.33); 7.6073 (0.42); 7.6020 (0.38); 7.5973 (0.42); 7.5909 (0.79); 7.5877 (0.75); 7.5458 (0.40); 7.5314 (0.42); 7.4130 (0.32); 7.1691 (0.67); 7.1508 (0.63); 5.7692 (0.38); 5.4057 (2.29); 3.3933 (0.38); 3.3440 (19.84); 3.0759 (5.46); 2.5592 (0.39); 2.5321 (0.47); 2.5186 (7.96); 2.5144 (16.08); 2.5099 (21.64); 2.5055 (15.59); 2.5012 (7.37); 2.4607 (0.32); 1.2391 (16.00)

Example 140, Solvent: DMSO, Spectrometer: 400.13 MHz 10.5354 (2.37); 8.0859 (1.40); 8.0651 (1.66); 7.8428 (1.32); 7.8234 (1.94); 7.8033 (1.23); 7.6261 (0.71); 7.6221 (1.05); 7.6166 (0.99); 7.6071 (1.24); 7.6035 (1.11); 7.6015 (1.13); 7.5969 (1.29); 7.5905 (2.43); 7.5876 (2.31); 7.5656 (0.79); 7.5515 (0.87); 7.5455 (1.19); 7.5311 (1.25); 7.5261 (0.64); 7.5105 (0.56); 7.4358 (0.56); 7.4331 (0.62); 7.4296 (0.57); 7.4267 (0.53); 7.4118 (1.00); 7.4082 (0.89); 7.3936 (0.45); 7.3909

NMR Peak List Table 1

(0.47); 7.3875 (0.43); 7.3849 (0.38); 7.1570 (2.00); 7.1388 (1.90); 5.7688 (0.56); 5.3810 (6.74); 3.4004 (0.34); 3.3503 (27.17); 3.0553 (16.00); 2.5186 (7.86); 2.5145 (15.63); 2.5101 (20.87); 2.5057 (15.18); 2.4070 (1.91); 2.3887 (3.50); 2.3701 (2.06); 1.5946 (0.49); 1.5764 (1.45); 1.5577 (2.04); 1.5392 (1.53); 1.5202 (0.60); 1.3689 (0.44); 1.3480 (0.33); 1.3294 (1.18); 1.3105 (1.90); 1.2918 (1.90); 1.2736 (1.13); 1.2555 (0.34); 0.9042 (4.19); 0.8859 (8.38); 0.8675 (3.52)
Example 141, Solvent: DMSO, Spectrometer: 400.13 MHz 8.0012 (0.53); 7.9817 (0.34); 7.4837 (0.42); 7.4665 (0.55); 7.4474 (0.51); 7.4389 (0.48); 7.4274 (0.40); 7.4191 (0.45); 7.3333 (0.33); 7.3321 (0.34); 7.3009 (0.40); 7.2951 (0.47); 7.2910 (0.32); 5.8270 (3.36); 5.4783 (1.27); 3.8397 (3.61); 3.4023 (0.92); 3.1102 (3.32); 2.5841 (0.35); 2.5753 (3.05); 2.5709 (6.29); 2.5664 (8.57); 2.5619 (6.29); 2.5575 (3.16); 1.4626 (0.32); 1.4540 (0.53); 1.4277 (0.56); 1.4127 (16.00)
Example 142, Solvent: DMSO, Spectrometer: 300.16 MHz 9.9207 (1.35); 7.8411 (0.82); 7.8200 (1.98); 7.5956 (1.21); 7.5715 (0.53); 7.5558 (0.46); 7.4284 (1.27); 7.4118 (1.51); 7.1316 (0.58); 7.1251 (0.56); 7.1112 (0.54); 7.1049 (0.54); 5.3722 (2.91); 3.3955 (6.45); 3.1134 (5.84); 2.5655 (25.41); 2.3954 (4.77); 1.5257 (16.00)
Example 143, Solvent: DMSO, Spectrometer: 399.95 MHz 12.8077 (1.19); 8.4458 (1.46); 8.4417 (2.61); 8.4376 (1.47); 8.0836 (0.87); 8.0811 (1.17); 8.0771 (0.91); 8.0641 (0.97); 8.0615 (1.19); 8.0601 (1.17); 8.0574 (0.94); 8.0075 (0.87); 8.0050 (1.09); 8.0012 (0.84); 7.9879 (0.96); 7.9852 (1.13); 7.9841 (1.15); 7.9817 (0.86); 7.9533 (0.35); 7.7500 (1.92); 7.7472 (2.58); 7.7432 (1.25); 7.7349 (0.77); 7.7297 (3.37); 7.7259 (2.36); 7.5685 (0.46); 7.5501 (1.63); 7.5442 (0.49); 7.5355 (0.91); 7.5321 (1.50); 7.5285 (0.75); 7.5078 (2.44); 7.5044 (1.05); 7.4929 (1.53); 7.4889 (3.00); 7.4755 (0.48); 7.4713 (1.23); 7.4677 (0.71); 7.3930 (3.28); 7.3685 (1.40); 7.3489 (2.57); 7.3293 (1.27); 5.3839 (5.38); 3.3336 (58.22); 3.0204 (16.00); 2.8913 (2.75); 2.7326 (2.25); 2.7314 (2.13); 2.5259 (0.59); 2.5210 (0.97); 2.5125 (12.27); 2.5080 (24.58); 2.5034 (32.37); 2.4988 (23.49); 2.4942 (11.18); −0.0002 (6.97)
Example 144, Solvent: DMSO, Spectrometer: 399.95 MHz 10.7760 (2.24); 8.1665 (1.64); 8.1460 (1.99); 7.9514 (3.83); 7.9307 (3.59); 7.9126 (1.28); 7.8932 (1.80); 7.8730 (1.17); 7.7392 (2.03); 7.7368 (2.57); 7.7330 (1.24); 7.7242 (0.77); 7.7190 (3.36); 7.7153 (2.37); 7.5669 (0.47); 7.5551 (0.34); 7.5486 (1.65); 7.5428 (0.48); 7.5336 (0.88); 7.5303 (1.44); 7.5269 (0.72); 7.5005 (2.40); 7.4972 (1.03); 7.4852 (1.63); 7.4814 (3.09); 7.4679 (0.47); 7.4638 (1.22); 7.4605 (0.69); 7.3221 (2.78); 7.3022 (2.64); 7.2180 (1.81); 7.1996 (1.76); 5.4154 (6.26); 3.3274 (26.08); 3.0820 (16.00); 2.8906 (5.83); 2.7320 (4.83); 2.7309 (4.48); 2.5249 (0.62); 2.5200 (0.95); 2.5115 (11.35); 2.5070 (22.54); 2.5024 (29.51); 2.4978 (21.28); 2.4933 (10.05); 2.3820 (9.07); 0.0080 (0.39); −0.0002 (11.73); −0.0085 (0.35)
Example 145, Solvent: DMSO, Spectrometer: 399.95 MHz 10.2168 (2.70); 7.9531 (1.06); 7.8111 (0.84); 7.7903 (1.73); 7.7721 (1.81); 7.7448 (2.06); 7.7213 (3.16); 7.7082 (0.87); 7.7033 (3.55); 7.6995 (2.49); 7.5627 (0.50); 7.5597 (0.33); 7.5508 (0.38); 7.5443 (1.72); 7.5388 (0.52); 7.5294 (0.93); 7.5262 (1.48); 7.5229 (0.77); 7.4952 (2.56); 7.4797 (1.74); 7.4760 (3.26); 7.4624 (0.51); 7.4584 (1.27); 7.4553 (0.73); 7.3365 (0.59); 7.3230 (10.19); 7.3156 (4.69); 7.3091 (4.05); 7.2942 (0.40); 7.2883 (0.61); 7.2473 (0.38); 7.2388 (0.87); 7.2319 (0.95); 7.2251 (1.17); 7.2172 (0.97); 7.2100 (0.63); 7.2031 (0.48); 7.0974 (1.68); 7.0958 (1.71); 7.0795 (1.65); 7.0778 (1.59); 5.3271 (6.50); 4.2373 (0.82); 4.2206 (0.85); 4.2107 (1.50); 4.1939 (1.60); 4.1628 (1.50); 4.1452 (1.50); 4.1363 (0.84); 4.1185 (0.84); 3.3406 (110.56); 3.1332 (0.56); 3.1158 (1.17); 3.0985 (1.16); 3.0811 (0.62); 3.0707 (0.48); 3.0575 (16.00); 2.8906 (8.37); 2.7315 (6.74); 2.5256 (0.61); 2.5123 (11.84); 2.5078 (23.42); 2.5032 (30.78); 2.4987 (22.39); 2.4942 (10.74); 1.2814 (6.61); 1.2638 (6.42); 1.2341 (0.38); −0.0002 (2.62)
Example 146, Solvent: DMSO, Spectrometer: 399.95 MHz 10.3818 (2.06); 8.0962 (1.40); 8.0757 (1.65); 7.9536 (0.91); 7.8276 (1.26); 7.8084 (1.74); 7.7881 (1.21); 7.7257 (2.07); 7.7233 (2.63); 7.7195 (1.31); 7.7105 (0.82); 7.7055 (3.58); 7.7017 (2.45); 7.5629 (0.49); 7.5509 (0.36); 7.5446 (1.67); 7.5389 (0.53); 7.5296 (0.87); 7.5262 (1.43); 7.5228 (0.73); 7.4943 (2.46); 7.4909 (1.05); 7.4789 (1.70); 7.4752 (3.19); 7.4616 (0.51); 7.4575 (1.28); 7.4543 (0.72); 7.1423 (1.77); 7.1247 (1.72); 5.3537 (6.07); 4.0414 (0.85); 4.0236 (0.86); 3.3487 (80.54); 3.3529 (16.00); 2.8912 (7.65); 2.7324 (6.12); 2.7314 (5.78); 2.5254 (0.58); 2.5206 (0.91); 2.5121 (11.85); 2.5076 (23.77); 2.5030 (31.40); 2.4984 (22.77); 2.4938 (10.80); 2.1529 (5.48); 2.0176 (1.69); 1.9178 (2.86); 1.6667 (1.21); 1.6366 (2.71); 1.6109 (7.81); 1.6055 (7.95); 1.5610 (2.66); 1.2831 (0.33); 1.2352 (0.33); 1.1917 (0.93); 1.1739 (1.88); 1.1561 (0.91); 0.8758 (0.58); 0.8625 (0.33); −0.0002 (6.70)
Example 147, Solvent: DMSO, Spectrometer: 399.95 MHz 11.9704 (0.36); 10.4304 (2.10); 8.0659 (1.50); 8.0454 (1.81); 7.9529 (0.46); 7.8238 (1.30); 7.8045 (1.86); 7.7843 (1.20); 7.7229 (2.66); 7.7100 (0.84); 7.7050 (3.49); 7.7012 (2.46); 7.5644 (0.48); 7.5526 (0.38); 7.5461 (1.72); 7.5405 (0.50); 7.5312 (0.91); 7.5279 (1.45); 7.5246 (0.77); 7.4971 (2.47); 7.4815 (1.76); 7.4779 (3.20); 7.4642 (0.54); 7.4601 (1.28); 7.4571 (0.72); 7.1333 (1.90); 7.1150 (1.84); 5.3533 (6.54); 3.3413 (110.17); 3.0575 (16.00); 2.8912 (3.64); 2.7322 (2.97); 2.5260 (0.93); 2.5125 (13.33); 2.5081 (25.98); 2.5035 (33.74); 2.4989 (24.85); 2.4945 (12.02); 2.4717 (0.56); 2.1829 (0.57); 2.1739 (0.42); 1.7926 (1.41); 1.7734 (1.25); 1.7574 (1.49); 1.7363 (0.78); 1.7133 (1.18); 1.6766 (0.48); 1.6692 (0.67); 1.6595 (0.74); 1.6472 (1.22); 1.6404 (1.12); 1.5845 (0.37); 1.5584 (0.35); 1.4195 (0.37); 1.3890 (1.02); 1.3595 (1.21); 1.3345 (1.05); 1.2999 (0.93); 1.2800 (1.00); 1.2561 (1.61); 1.2328 (1.38); 1.2257 (1.87); 1.1971 (1.71); 1.1755 (0.81); 1.1456 (0.56)
Example 148, Solvent: DMSO, Spectrometer: 400.13 MHz 9.8673 (1.22); 8.0280 (0.79); 8.0071 (0.99); 7.8490 (0.51); 7.8296 (0.88); 7.8096 (0.45); 7.7332 (1.37); 7.7139 (1.59); 7.5537 (0.67); 7.5359 (0.65); 7.5048 (1.14); 7.4857 (1.46); 7.4668 (0.56); 7.1608 (0.90); 7.1422 (0.87); 5.3883 (3.07); 4.0449 (0.84); 4.0271 (0.85); 3.3422 (15.57); 3.0829 (5.43); 2.5104 (12.92); 1.9970 (3.42); 1.2408 (16.00); 1.2104 (0.39); 1.1994 (0.97); 1.1816 (1.80); 1.1638 (0.91)
Example 149, Solvent: DMSO, Spectrometer: 400.13 MHz 10.1013 (2.94); 7.8300 (0.34); 7.8089 (2.20); 7.8021 (2.37); 7.7952 (5.34); 7.7811 (0.55); 7.4210 (1.01); 7.4010 (2.16); 7.3810 (1.59); 7.2843 (1.41); 7.2829 (1.43); 7.2806 (1.29); 7.2674 (0.81); 7.2635 (1.23); 7.2612 (1.01); 7.2457 (1.01); 7.2398 (1.98); 7.2356 (1.44); 7.1433 (1.06); 7.1413 (1.12); 7.1369 (1.02); 7.1350 (0.99); 7.1227 (0.99); 7.1206 (0.97); 7.1162 (1.03); 7.1144 (0.97); 7.1009 (1.29); 7.0939 (1.29); 7.0872 (1.14); 7.0802 (1.26); 5.7687 (0.43); 5.3307 (5.86); 4.9258 (0.42); 4.9130 (0.56); 4.9102 (0.56); 4.9042 (0.55); 4.8976 (0.57); 4.8916 (0.58); 4.8890 (0.58); 4.8762 (0.46); 3.7889 (16.00); 3.7665 (0.33); 3.3998 (0.86); 3.3496 (73.70); 3.3263 (1.03); 3.2994 (0.68); 3.0617 (14.72); 2.5189 (7.09); 2.5145 (14.73); 2.5100 (20.22); 2.5055 (14.96); 2.5011 (7.60); 2.4646 (0.38); 2.4604 (0.36); 1.6952 (0.45); 1.6763 (0.57); 1.6596 (0.56); 1.6432 (0.36); 1.5914 (0.50); 1.5767 (0.41); 1.5700 (0.53); 1.5569 (0.83); 1.5424 (0.58); 1.5357 (0.68); 1.5210 (0.53); 1.3563 (0.60); 1.3439 (0.67); 1.3361 (0.58); 1.3229 (0.90); 1.3096 (0.50); 1.3017 (0.50); 1.2893 (0.45); 1.2349 (6.21); 1.2193 (6.25); 0.9022 (8.57); 0.9003 (8.65); 0.8857 (8.73); 0.8840 (8.67)
Example 150, Solvent: DMSO, Spectrometer: 400.13 MHz 11.7624 (1.72); 7.6204 (1.22); 7.6135 (1.44); 7.6094 (1.46); 7.5993 (1.11); 7.5894 (3.38); 7.5669 (0.91); 7.5528 (0.99); 7.5467 (1.29); 7.5324 (1.29); 7.5277 (0.82); 7.5116 (0.57); 7.4290 (0.71); 7.4263 (0.71); 7.4230 (0.65); 7.4201 (0.60); 7.4055 (1.11); 7.4010 (0.99); 7.3868 (0.51);

NMR Peak List Table 1

7.3834 (0.54); 7.3781 (0.42); 7.2771 (4.69); 5.3063 (6.66); 4.1630 (2.10); 4.1463 (4.45); 4.1296 (2.18); 3.8448 (0.41); 3.4517 (0.41); 3.4024 (4.01); 3.3520 (239.49); 3.3008 (3.74); 3.0281 (16.00); 2.5629 (0.48); 2.5584 (0.73); 2.5541 (0.67); 2.5165 (16.72); 2.5125 (32.52); 2.5081 (43.23); 2.5037 (32.17); 2.4663 (0.80); 2.4614 (0.88); 2.4568 (1.02); 2.4523 (0.93); 1.9939 (0.36); 1.6609 (0.34); 1.6434 (1.15); 1.6262 (1.84); 1.6090 (1.32); 1.5917 (0.48); 1.3403 (1.18); 1.3309 (2.37); 1.3225 (4.01); 1.3132 (4.03); 1.3043 (2.69); 1.2956 (1.44); 1.2706 (0.71); 1.2614 (0.79); 1.2477 (1.74); 0.8969 (2.16); 0.8795 (6.51); 0.8618 (3.91); 0.8443 (1.16)
Example 151, Solvent: DMSO, Spectrometer: 399.95 MHz 10.2568 (1.94); 8.1284 (0.84); 8.1089 (1.79); 8.0894 (1.18); 7.9532 (1.46); 7.9072 (1.50); 7.8877 (1.31); 7.8226 (0.43); 7.8016 (1.32); 7.7844 (2.46); 7.7789 (1.82); 7.7618 (0.63); 7.7224 (2.04); 7.7045 (2.68); 7.7009 (1.95); 7.6827 (2.12); 7.6646 (2.48); 7.6613 (1.94); 7.6533 (0.41); 7.5888 (1.38); 7.5700 (1.41); 7.5630 (0.54); 7.5598 (0.47); 7.5498 (0.81); 7.5448 (1.43); 7.5386 (0.70); 7.5305 (1.83); 7.5265 (1.57); 7.5126 (1.12); 7.4958 (2.01); 7.4801 (1.54); 7.4765 (2.51); 7.4631 (0.58); 7.4583 (1.15); 7.4558 (0.79); 7.4437 (1.80); 7.4240 (2.38); 7.4096 (0.72); 7.4055 (1.15); 7.2472 (0.39); 7.2327 (1.41); 7.2243 (8.72); 7.2226 (8.67); 7.2072 (16.00); 7.1951 (2.36); 7.1928 (2.31); 7.1048 (1.03); 7.1010 (1.04); 7.0882 (1.09); 7.0844 (1.03); 6.8776 (2.47); 6.8743 (2.20); 6.8584 (1.24); 6.8007 (0.73); 6.7966 (0.75); 6.7921 (0.63); 6.7797 (0.80); 6.7734 (0.69); 5.5347 (4.39); 5.5234 (0.68); 5.3310 (4.64); 5.3194 (0.69); 4.3017 (1.16); 4.2846 (2.66); 4.2675 (1.36); 3.7328 (12.41); 3.7208 (1.23); 3.3357 (173.12); 3.3243 (22.80); 3.0879 (0.74); 3.0615 (11.06); 3.0496 (1.42); 3.0363 (11.02); 3.0244 (1.26); 2.9232 (1.11); 2.9060 (2.41); 2.8905 (11.62); 2.8787 (1.31); 2.7311 (0.81); 2.7192 (0.91); 2.6720 (0.39); 2.5117 (24.10); 2.5074 (45.12); 2.5028 (58.63); 2.4983 (44.65); 2.4939 (25.55); 2.3297 (0.36); 1.2353 (0.39); −0.0002 (3.12)
Example 152, Solvent: DMSO, Spectrometer: 400.13 MHz 9.8500 (1.17); 7.7865 (0.75); 7.7690 (0.88); 7.7565 (1.08); 7.7379 (0.50); 7.7277 (1.20); 7.7097 (1.42); 7.7060 (1.09); 7.5572 (0.69); 7.5392 (0.62); 7.5115 (1.08); 7.4923 (1.32); 7.4742 (0.63); 7.4723 (0.63); 7.4608 (0.39); 7.4494 (0.48); 7.4380 (0.45); 7.3483 (0.41); 7.3268 (0.57); 7.0734 (0.64); 7.0712 (0.66); 7.0562 (0.63); 7.0539 (0.62); 5.3333 (2.74); 3.5265 (0.35); 3.5084 (1.15); 3.4902 (1.19); 3.4722 (0.39); 3.3453 (22.18); 3.3219 (0.40); 2.5150 (8.47); 2.5107 (11.39); 2.5064 (8.66); 1.9976 (0.71); 1.4671 (16.00); 1.1820 (0.37); 1.0658 (1.28); 1.0478 (2.81); 1.0296 (1.29)
Example 153, Solvent: DMSO, Spectrometer: 399.95 MHz 10.6140 (0.42); 10.5013 (1.85); 8.1623 (0.34); 8.1414 (0.40); 8.0435 (1.35); 8.0227 (1.52); 7.9531 (0.49); 7.8376 (1.51); 7.8182 (1.83); 7.7983 (1.11); 7.7252 (2.66); 7.7230 (2.94); 7.7050 (3.90); 7.7013 (2.08); 7.5680 (0.33); 7.5651 (0.59); 7.5620 (0.39); 7.5532 (0.44); 7.5467 (2.08); 7.5411 (0.61); 7.5318 (1.09); 7.5285 (1.74); 7.5252 (0.89); 7.4979 (3.00); 7.4821 (2.09); 7.4786 (3.83); 7.4649 (0.59); 7.4609 (1.45); 7.4578 (0.82); 7.1591 (0.46); 7.1479 (1.80); 7.1299 (1.69); 5.3662 (1.69); 5.3578 (6.59); 5.3316 (0.36); 5.3282 (0.46); 5.3247 (0.42); 5.3136 (0.72); 5.3102 (0.90); 5.3067 (0.70); 5.2956 (0.39); 5.2922 (0.44); 5.2889 (0.33); 3.3428 (149.21); 3.1358 (1.85); 3.1178 (1.81); 3.0690 (0.34); 3.0561 (16.00); 2.8912 (3.85); 2.7321 (3.12); 2.5357 (0.39); 2.5258 (0.83); 2.5126 (14.94); 2.5081 (29.45); 2.5036 (38.64); 2.4990 (28.03); 2.4945 (13.33); 1.7118 (0.83); 1.6998 (6.01); 1.6979 (5.93); 1.6335 (6.78); 1.5716 (0.89); 1.2939 (1.08); 1.0457 (2.97); 1.0288 (2.90); −0.0002 (4.84)
Example 154, Solvent: DMSO, Spectrometer: 400.13 MHz 11.8962 (1.28); 7.7434 (1.36); 7.7246 (1.52); 7.5551 (0.66); 7.5374 (0.68); 7.5120 (1.16); 7.4928 (1.43); 7.4746 (0.54); 7.2893 (1.70); 5.3425 (2.96); 3.3434 (23.50); 3.0088 (5.43); 2.5109 (19.23); 1.2319 (16.00)
Example 155, Solvent: DMSO, Spectrometer: 399.95 MHz 12.5650 (1.08); 7.9538 (0.99); 7.7368 (2.77); 7.7329 (1.34); 7.7241 (0.85); 7.7191 (3.52); 7.7153 (2.44); 7.5658 (0.49); 7.5543 (0.36); 7.5474 (1.71); 7.5416 (0.51); 7.5327 (0.96); 7.5293 (1.53); 7.5259 (0.77); 7.5029 (2.58); 7.4995 (1.11); 7.4877 (1.71); 7.4838 (3.20); 7.4703 (0.51); 7.4663 (1.26); 7.4628 (0.74); 7.3463 (4.44); 7.2683 (0.96); 7.2485 (2.03); 7.2276 (1.27); 7.1611 (1.14); 7.1564 (3.43); 7.1530 (4.31); 7.1368 (1.05); 7.1349 (1.09); 7.1327 (0.87); 6.9486 (1.01); 6.9440 (1.17); 6.9403 (0.95); 6.9276 (0.96); 6.9258 (0.97); 6.9215 (0.97); 6.9197 (0.88); 5.3438 (5.92); 5.1215 (0.40); 5.1050 (1.46); 5.0885 (1.47); 5.0721 (0.39); 3.3355 (43.51); 3.0149 (16.00); 2.8911 (7.80); 2.7329 (6.23); 2.7319 (6.31); 2.5263 (0.48); 2.5130 (8.25); 2.5085 (16.33); 2.5039 (21.44); 2.4993 (15.57); 2.4948 (7.44); 1.5457 (5.67); 1.5292 (5.62); −0.0002 (3.37)
Example 156, Solvent: DMSO, Spectrometer: 399.95 MHz 10.2194 (2.13); 8.0945 (1.45); 8.0744 (1.77); 7.8905 (1.26); 7.8711 (1.77); 7.8510 (1.13); 7.7273 (1.91); 7.7246 (2.59); 7.7208 (1.24); 7.7119 (0.80); 7.7069 (3.44); 7.7031 (2.36); 7.5659 (0.49); 7.5539 (0.37); 7.5476 (1.62); 7.5419 (0.48); 7.5326 (0.86); 7.5293 (1.41); 7.5259 (0.72); 7.4971 (2.37); 7.4936 (1.01); 7.4816 (1.63); 7.4779 (3.06); 7.4643 (0.48); 7.4602 (1.23); 7.4571 (0.70); 7.3823 (0.60); 7.3674 (7.84); 7.3618 (3.51); 7.3530 (2.93); 7.3513 (3.54); 7.3458 (0.67); 7.3369 (0.52); 7.3336 (0.70); 7.3314 (0.82); 7.3117 (0.67); 7.3058 (0.87); 7.2985 (0.72); 7.2899 (0.82); 7.2803 (0.38); 7.2750 (0.33); 7.2003 (1.75); 7.1828 (1.68); 5.3733 (6.02); 4.5879 (1.41); 4.5586 (2.66); 4.4973 (2.65); 4.4680 (1.48); 4.2677 (0.40); 4.2512 (1.53); 4.2345 (1.55); 4.2179 (0.42); 3.3374 (102.65); 3.0625 (16.00); 2.8906 (1.22); 2.7321 (0.92); 2.7311 (0.96); 2.5255 (0.57); 2.5208 (0.91); 2.5122 (11.80); 2.5077 (23.81); 2.5031 (31.59); 2.4984 (23.00); 2.4939 (11.00); 1.3643 (5.95); 1.3476 (5.91); −0.0002 (1.54)
Example 157, Solvent: DMSO, Spectrometer: 400.13 MHz 7.8410 (0.48); 7.8218 (0.77); 7.8019 (0.57); 7.6923 (0.55); 7.6851 (3.99); 7.6802 (1.34); 7.6677 (1.45); 7.6628 (4.40); 7.6554 (0.54); 7.0545 (0.53); 7.0471 (4.16); 7.0422 (1.32); 7.0296 (1.29); 7.0248 (3.89); 7.0172 (0.46); 6.8597 (1.73); 6.8415 (1.42); 5.2972 (5.30); 3.8208 (16.00); 3.7716 (0.47); 3.6367 (0.75); 3.6188 (0.71); 3.0550 (0.56); 3.0434 (15.06); 2.5183 (7.32); 2.5142 (15.39); 2.5098 (21.16); 2.5054 (15.45); 1.2602 (0.34); 1.2444 (0.39)
Example 158, Solvent: DMSO, Spectrometer: 399.95 MHz 12.6738 (2.31); 7.9545 (3.14); 7.9353 (1.86); 7.7430 (1.97); 7.7404 (2.69); 7.7364 (1.29); 7.7279 (0.80); 7.7227 (3.49); 7.7189 (2.40); 7.5644 (0.47); 7.5530 (0.35); 7.5460 (1.68); 7.5401 (0.54); 7.5312 (1.33); 7.5280 (1.73); 7.5244 (1.06); 7.5183 (3.77); 7.5115 (2.42); 7.5029 (4.15); 7.4879 (1.66); 7.4839 (3.45); 7.4706 (0.52); 7.4664 (1.26); 7.4628 (0.71); 7.3942 (3.61); 7.2815 (0.90); 7.2743 (0.90); 7.2661 (0.77); 7.2617 (0.93); 7.2588 (0.88); 7.2548 (0.88); 7.2459 (0.73); 7.2389 (0.73); 5.3636 (5.71); 3.3280 (66.85); 3.0512 (16.00); 2.8901 (13.73); 2.7310 (10.63); 2.7305 (10.71); 2.5242 (0.78); 2.5193 (1.22); 2.5108 (14.68); 2.5063 (29.26); 2.5017 (38.58); 2.4971 (27.93); 2.4926 (13.22); 0.0079 (0.34); −0.0002 (9.89)
Example 159, Solvent: DMSO, Spectrometer: 399.95 MHz 12.4204 (0.90); 7.7407 (3.17); 7.7229 (3.69); 7.7193 (2.84); 7.6158 (1.59); 7.6119 (1.72); 7.5961 (1.73); 7.5922 (1.77); 7.5674 (0.52); 7.5559 (0.38); 7.5488 (1.87); 7.5434 (0.59); 7.5311 (1.65); 7.5058 (2.97); 7.4864 (3.56); 7.4691 (1.29); 7.4660 (0.85); 7.3402 (5.55); 7.3197 (1.49); 7.3023 (0.98); 7.2985 (0.96); 7.0249 (1.83); 7.0066 (1.50); 7.0041 (1.59); 6.9432 (0.97); 6.9403 (1.00); 6.9238 (1.69); 6.9214 (1.65); 6.9051 (0.86); 6.9021 (0.84); 5.3429 (6.98); 4.9715 (7.89); 3.3432 (128.35); 3.0349 (16.00); 3.0233 (1.12); 2.5075 (28.50); 2.5030 (37.51); 2.4986 (28.09); 2.4944 (14.15); 2.2229 (0.46); −0.0002 (1.60)

NMR Peak List Table 1

Example 160, Solvent: DMSO, Spectrometer: 399.95 MHz 11.8369 (1.56); 7.7378 (1.60); 7.7349 (2.16); 7.7309 (1.01); 7.7226 (0.64); 7.7173 (2.88); 7.7136 (1.93); 7.5647 (0.40); 7.5465 (1.37); 7.5405 (0.40); 7.5317 (0.76); 7.5283 (1.26); 7.5247 (0.61); 7.5019 (2.03); 7.4985 (0.83); 7.4870 (1.30); 7.4830 (2.50); 7.4696 (0.39); 7.4655 (1.03); 7.4619 (0.54); 7.2695 (3.52); 5.3364 (4.71); 3.3293 (35.22); 2.9884 (13.82); 2.8909 (1.97); 2.7324 (1.59); 2.7311 (1.56); 2.5253 (0.45); 2.5206 (0.70); 2.5120 (9.18); 2.5074 (18.49); 2.5028 (24.47); 2.4981 (17.64); 2.4936 (8.27); 1.6349 (0.85); 1.6150 (0.75); 1.6052 (0.61); 1.5935 (1.00); 1.2519 (0.49); 1.2336 (1.26); 1.2150 (1.41); 1.1966 (1.13); 1.1830 (16.00); 1.1212 (0.34); 1.1095 (0.42); 1.1017 (0.70); 1.0936 (0.58); 1.0831 (0.72); 1.0742 (0.56); 1.0664 (0.41); 1.0608 (0.46); 0.8419 (2.99); 0.8239 (6.18); 0.8055 (2.43); −0.0002 (8.03)

Example 161, Solvent: CDCl3, Spectrometer: 300.16 MHz 7.9406 (2.10); 7.9128 (2.66); 7.7328 (1.48); 7.7061 (2.57); 7.6756 (2.97); 7.6512 (2.98); 7.6464 (3.09); 7.6288 (2.56); 7.3615 (2.79); 7.2652 (6.26); 7.1386 (2.32); 7.1116 (4.45); 7.0842 (2.21); 7.0246 (2.66); 7.0000 (2.47); 5.2881 (10.14); 4.2019 (2.57); 4.1799 (5.23); 4.1577 (2.69); 3.1032 (16.00); 2.0111 (5.35); 1.7072 (1.74); 1.6858 (2.72); 1.6644 (2.07); 1.6327 (10.56); 1.3657 (5.67); 1.3562 (5.80); 1.2538 (0.45); 0.9358 (2.93); 0.9175 (6.36); −0.0002 (2.29)

Example 162, Solvent: DMSO, Spectrometer: 400.13 MHz 10.7979 (1.40); 7.8362 (1.62); 7.8338 (1.77); 7.8180 (1.00); 7.7270 (1.29); 7.7141 (0.41); 7.7092 (1.65); 7.7055 (1.18); 7.5504 (0.79); 7.5354 (0.43); 7.5322 (0.68); 7.5289 (0.37); 7.5008 (1.19); 7.4853 (0.83); 7.4816 (1.51); 7.4639 (0.65); 7.4608 (0.41); 7.1546 (0.64); 7.1497 (0.61); 7.1387 (0.63); 7.1338 (0.62); 5.7666 (2.26); 5.3476 (3.10); 3.3401 (13.01); 3.0584 (7.68); 2.5301 (0.33); 2.5165 (7.09); 2.5122 (14.63); 2.5077 (19.78); 2.5032 (14.18); 2.4989 (6.70); 2.4701 (0.32); 1.4799 (16.00); 1.4489 (0.54)

Example 163, Solvent: DMSO, Spectrometer: 400.13 MHz 7.7383 (2.71); 7.7257 (0.99); 7.7206 (3.40); 7.7168 (2.51); 7.5614 (0.51); 7.5582 (0.38); 7.5499 (0.42); 7.5431 (1.67); 7.5373 (0.61); 7.5283 (1.02); 7.5250 (1.54); 7.5216 (0.88); 7.4989 (2.58); 7.4836 (1.78); 7.4798 (1.39); 7.4664 (0.63); 7.4623 (1.28); 7.4589 (0.81); 7.3854 (1.22); 7.3673 (1.53); 7.3646 (1.53); 7.3466 (1.35); 6.5468 (0.66); 6.5332 (1.27); 6.5195 (0.71); 6.4895 (1.95); 6.4719 (1.90); 6.4059 (1.90); 6.3852 (1.87); 5.7595 (1.92); 5.2000 (6.69); 3.3207 (26.40); 3.2065 (0.92); 3.1892 (1.85); 3.1747 (1.86); 3.1575 (0.98); 3.0772 (16.00); 3.0516 (0.47); 2.5157 (7.56); 2.5113 (14.94); 2.5068 (20.08); 2.5023 (14.74); 2.4980 (7.57); 1.5122 (0.93); 1.4943 (1.51); 1.4769 (1.25); 1.4582 (0.55); 1.3430 (0.33); 1.3252 (0.87); 1.3042 (1.36); 1.2973 (1.36); 1.2867 (1.80); 1.2827 (1.83); 1.2711 (2.95); 1.2650 (4.03); 1.2586 (2.86); 0.8750 (1.85); 0.8582 (5.67); 0.8408 (2.18)

Example 164, Solvent: DMSO, Spectrometer: 399.95 MHz 12.4389 (1.06); 7.9528 (1.21); 7.7388 (2.70); 7.7348 (1.29); 7.7262 (0.79); 7.7211 (3.47); 7.7172 (2.40); 7.5668 (0.48); 7.5554 (0.35); 7.5484 (1.69); 7.5425 (0.50); 7.5337 (0.93); 7.5303 (1.51); 7.5269 (1.06); 7.5047 (2.54); 7.5014 (1.08); 7.4896 (1.62); 7.4857 (3.14); 7.4723 (0.48); 7.4681 (1.23); 7.4646 (0.68); 7.3645 (0.37); 7.3555 (4.27); 7.3499 (1.34); 7.3384 (5.86); 7.3329 (4.92); 7.3240 (0.44); 7.0133 (0.44); 7.0044 (4.67); 6.9987 (1.31); 6.9874 (1.24); 6.9818 (4.12); 6.9728 (0.33); 5.3422 (5.94); 4.8586 (7.30); 3.3327 (63.87); 3.0226 (16.00); 2.8904 (9.87); 2.7317 (7.82); 2.7309 (7.72); 2.5249 (0.72); 2.5201 (1.13); 2.5116 (13.74); 2.5071 (27.47); 2.5025 (36.24); 2.4979 (26.26); 2.4934 (12.45); −0.0002 (3.18)

Example 165, Solvent: DMSO, Spectrometer: 399.95 MHz 8.2664 (2.30); 8.0307 (1.57); 8.0107 (1.97); 7.9530 (0.67); 7.8574 (1.31); 7.8380 (1.80); 7.8179 (1.14); 7.6823 (2.54); 7.6785 (1.23); 7.6696 (0.77); 7.6645 (3.45); 7.6608 (2.39); 7.5610 (0.50); 7.5488 (0.38); 7.5426 (1.63); 7.5371 (0.50); 7.5247 (2.61); 7.5214 (2.96); 7.5165 (0.73); 7.5043 (3.21); 7.5015 (2.76); 7.4945 (0.67); 7.4889 (2.41); 7.4854 (1.00); 7.4732 (1.70); 7.4696 (3.11); 7.4518 (2.07); 7.4501 (2.19); 7.4324 (3.32); 7.4284 (1.43); 7.4170 (0.90); 7.4135 (1.79); 7.3907 (0.78); 7.3871 (1.42); 7.3836 (0.77); 7.3753 (0.51); 7.3690 (1.60); 7.3624 (0.32); 7.3510 (0.47); 7.1435 (1.78); 7.1257 (1.70); 5.2672 (6.28); 3.3380 (136.98); 2.9697 (16.00); 2.8908 (5.49); 2.7313 (4.41); 2.5256 (0.64); 2.5208 (1.02); 2.5122 (13.67); 2.5077 (27.43); 2.5031 (36.24); 2.4985 (26.25); 2.4940 (12.46); 1.5356 (1.14); 1.5253 (3.03); 1.5180 (3.27); 1.5084 (1.26); 1.1924 (1.32); 1.1826 (3.22); 1.1753 (3.11); 1.1648 (1.11); −0.0002 (4.98)

Example 166, Solvent: DMSO, Spectrometer: 399.95 MHz 10.5501 (2.03); 8.0599 (1.22); 8.0393 (1.45); 7.9534 (0.44); 7.8305 (1.29); 7.8112 (1.76); 7.7910 (1.16); 7.7266 (2.05); 7.7241 (2.63); 7.7202 (1.31); 7.7114 (0.89); 7.7063 (3.47); 7.7025 (2.39); 7.5647 (0.49); 7.5615 (0.32); 7.5528 (0.38); 7.5464 (1.65); 7.5407 (0.50); 7.5315 (0.93); 7.5281 (1.43); 7.5247 (0.74); 7.4971 (2.42); 7.4938 (1.06); 7.4817 (1.73); 7.4780 (3.09); 7.4644 (0.51); 7.4603 (1.25); 7.4571 (0.72); 7.1395 (1.79); 7.1220 (1.72); 5.3563 (6.32); 3.3289 (56.12); 3.0729 (0.34); 3.0531 (16.00); 2.8908 (3.54); 2.7321 (2.78); 2.7311 (2.79); 2.5252 (0.66); 2.5119 (11.40); 2.5074 (22.31); 2.5028 (29.21); 2.4982 (21.28); 2.4937 (10.21); 2.4667 (1.73); 2.4507 (1.38); 2.4472 (1.93); 2.4426 (1.27); 2.4273 (1.81); 1.5443 (1.77); 1.5289 (1.28); 1.5243 (1.88); 1.5049 (1.63); 1.0161 (12.01); 0.3017 (0.81); 0.2870 (3.12); 0.2784 (1.31); 0.2105 (1.59); 0.2019 (3.43); 0.1979 (2.76); 0.1869 (0.94); −0.0002 (7.31)

Example 167, Solvent: DMSO, Spectrometer: 399.95 MHz 10.5191 (2.06); 8.0722 (1.29); 8.0515 (1.54); 7.8334 (1.30); 7.8141 (1.82); 7.7938 (1.19); 7.7237 (2.64); 7.7199 (1.26); 7.7110 (0.85); 7.7059 (3.48); 7.7022 (2.41); 7.5646 (0.49); 7.5527 (0.37); 7.5463 (0.92); 7.5406 (0.49); 7.5313 (0.92); 7.5280 (1.44); 7.5246 (0.75); 7.4970 (2.44); 7.4936 (1.04); 7.4815 (1.70); 7.4778 (3.15); 7.4643 (0.50); 7.4602 (1.25); 7.4570 (0.73); 7.1424 (1.83); 7.1241 (1.78); 5.8288 (0.61); 5.8200 (0.32); 5.8032 (0.93); 5.7861 (0.96); 5.7771 (0.36); 5.7693 (0.36); 5.7605 (0.72); 5.7438 (0.35); 5.3547 (6.44); 5.0386 (0.46); 5.0347 (1.07); 5.0294 (1.17); 5.0255 (0.52); 4.9957 (0.42); 4.9918 (0.97); 4.9865 (1.05); 4.9825 (0.47); 4.9614 (0.58); 4.9587 (1.12); 4.9559 (0.99); 4.9533 (0.96); 4.9504 (0.47); 4.9360 (0.56); 4.9332 (1.06); 4.9305 (0.94); 4.9278 (0.90); 4.9249 (0.44); 3.3316 (55.34); 3.0536 (16.00); 2.5255 (0.49); 2.5122 (10.21); 2.5077 (20.28); 2.5031 (26.66); 2.4985 (19.39); 2.4940 (9.34); 2.4075 (1.65); 2.3892 (3.19); 2.3707 (1.80); 2.0637 (0.63); 2.0459 (1.61); 2.0278 (1.67); 2.0101 (0.71); 1.6166 (0.38); 1.5984 (1.10); 1.5796 (1.50); 1.5606 (1.21); 1.5416 (0.52); 1.4055 (0.53); 1.3860 (1.32); 1.3740 (0.71); 1.3678 (1.66); 1.3485 (1.02); 1.3303 (0.34); −0.0002 (6.33)

Example 168, Solvent: DMSO, Spectrometer: 400.13 MHz 10.3988 (3.23); 7.8325 (2.66); 7.8280 (2.70); 7.8199 (5.62); 7.8070 (0.37); 7.7283 (2.85); 7.7104 (3.50); 7.7067 (2.57); 7.5678 (0.49); 7.5556 (0.39); 7.5494 (1.74); 7.5440 (0.55); 7.5343 (0.95); 7.5313 (1.46); 7.5001 (2.59); 7.4808 (3.30); 7.4670 (0.58); 7.4631 (1.27); 7.4434 (0.94); 7.4387 (1.38); 7.4221 (3.80); 7.4186 (3.57); 7.4155 (3.08); 7.4131 (3.06); 7.4077 (0.72); 7.3956 (3.66); 7.3913 (1.23); 7.3766 (1.50); 7.3598 (0.81); 7.3554 (1.28); 7.3507 (0.64); 7.3455 (0.54); 7.3383 (1.27); 7.3213 (0.41); 7.1244 (1.33); 7.1162 (1.38); 7.1119 (1.20); 7.1036 (1.28); 5.3428 (7.01); 5.1856 (7.82); 3.4027 (0.64); 3.4003 (0.81); 3.3515 (109.79); 3.3027 (0.64); 3.2998 (0.47); 3.0703 (16.00); 2.5586 (0.43); 2.5319 (0.81); 2.5182 (17.55); 2.5141 (35.67); 2.5097 (48.03); 2.5054 (34.89); 2.4613 (0.41); 2.4576 (0.36); 1.9966 (0.63); 1.2515 (0.57); 1.1808 (0.33); 0.8643 (0.76)

NMR Peak List Table 1

Example 169, Solvent: DMSO, Spectrometer: 400.13 MHz 12.1300 (1.69); 7.6226 (3.42); 7.6020 (3.93); 7.3078 (3.21); 7.2876 (2.83); 7.2488 (4.77); 5.2968 (6.30); 3.4115 (4.99); 3.3986 (0.39); 3.3615 (311.04); 3.3119 (1.57); 3.2615 (0.34); 2.9987 (16.00); 2.5622 (0.56); 2.5577 (0.71); 2.5533 (0.52); 2.5301 (0.86); 2.5164 (17.19); 2.5122 (34.56); 2.5078 (46.09); 2.5033 (33.23); 2.4992 (15.91); 2.4585 (0.33); 2.4287 (2.01); 2.4104 (3.66); 2.3916 (2.19); 2.3530 (9.91); 2.3347 (0.47); 2.3301 (0.34); 1.9936 (0.47); 1.6039 (0.49); 1.5856 (1.45); 1.5669 (2.00); 1.5483 (1.52); 1.5294 (0.60); 1.3376 (0.32); 1.3191 (1.18); 1.3002 (1.99); 1.2815 (2.12); 1.2632 (1.48); 1.2453 (1.39); 0.8946 (4.19); 0.8763 (8.85); 0.8609 (2.45); 0.8580 (3.91); 0.8438 (0.71)

Example 170, Solvent: DMSO, Spectrometer: 399.95 MHz 9.8542 (2.06); 8.0824 (1.56); 8.0624 (1.96); 7.9536 (0.38); 7.9015 (1.29); 7.8821 (1.84); 7.8620 (1.14); 7.7978 (2.41); 7.7937 (2.42); 7.7383 (1.95); 7.7359 (2.53); 7.7320 (1.25); 7.7232 (0.83); 7.7181 (3.37); 7.7143 (2.36); 7.5659 (0.48); 7.5541 (0.36); 7.5476 (1.64); 7.5418 (0.50); 7.5327 (0.90); 7.5293 (1.44); 7.5259 (0.75); 7.4993 (2.41); 7.4959 (1.08); 7.4840 (1.62); 7.4801 (3.09); 7.4666 (0.49); 7.4625 (1.23); 7.4592 (0.70); 7.2092 (1.76); 7.1914 (1.71); 6.6034 (2.47); 6.5995 (2.48); 5.3974 (6.35); 3.3312 (63.44); 3.0917 (16.00); 2.8911 (3.05); 2.7324 (2.43); 2.7314 (2.38); 2.5254 (0.60); 2.5206 (0.94); 2.5121 (11.56); 2.5076 (23.08); 2.5030 (30.37); 2.4984 (22.06); 2.4939 (10.54); 2.3490 (12.91); 2.2917 (0.43); 1.2864 (0.50); 0.8757 (0.49); −0.0002 (7.45)

Example 171, Solvent: DMSO, Spectrometer: 399.95 MHz 12.3285 (0.78); 7.9532 (0.64); 7.7436 (1.99); 7.7411 (2.68); 7.7371 (1.32); 7.7286 (0.79); 7.7235 (3.42); 7.7196 (2.40); 7.5665 (0.48); 7.5551 (0.34); 7.5481 (1.69); 7.5422 (0.50); 7.5335 (0.93); 7.5301 (1.53); 7.5266 (0.77); 7.5049 (2.55); 7.5016 (1.09); 7.4898 (1.60); 7.4858 (3.10); 7.4725 (0.48); 7.4683 (1.22); 7.4648 (0.68); 7.3320 (4.62); 7.0182 (0.93); 7.0143 (1.06); 6.9981 (1.90); 6.9943 (1.82); 6.9657 (0.88); 6.9613 (0.98); 6.9480 (1.19); 6.9437 (1.46); 6.9264 (1.19); 6.9235 (1.48); 6.9061 (2.27); 6.9019 (1.50); 6.8777 (1.37); 6.8737 (1.33); 6.8599 (1.04); 6.8564 (1.15); 6.8537 (0.76); 6.8399 (0.48); 6.8359 (0.48); 5.3424 (5.87); 4.8205 (7.49); 3.7826 (16.00); 3.3351 (33.96); 3.0278 (15.32); 3.0143 (0.35); 2.8899 (5.11); 2.7319 (4.05); 2.7310 (4.09); 2.5253 (0.33); 2.5205 (0.52); 2.5120 (6.64); 2.5075 (13.33); 2.5029 (17.62); 2.4983 (12.81); 2.4938 (6.12); −0.0002 (3.49)

Example 172, Solvent: DMSO, Spectrometer: 400.13 MHz 10.5339 (4.60); 8.1018 (3.12); 8.0812 (3.70); 7.8447 (2.73); 7.8254 (3.85); 7.8052 (2.65); 7.7302 (5.81); 7.7175 (2.02); 7.7124 (7.41); 7.7087 (5.49); 7.6920 (0.36); 7.5781 (1.04); 7.5750 (0.78); 7.5664 (0.88); 7.5597 (3.15); 7.5541 (1.30); 7.5449 (2.12); 7.5416 (3.23); 7.5383 (1.88); 7.5128 (5.44); 7.4974 (3.73); 7.4937 (6.78); 7.4802 (1.29); 7.4761 (2.70); 7.4729 (1.68); 7.1465 (3.95); 7.1288 (3.77); 5.3725 (13.34); 5.3456 (0.42); 3.5039 (1.80); 3.4858 (5.88); 3.4676 (6.08); 3.4494 (1.97); 3.3912 (0.65); 3.3409 (43.04); 3.2907 (0.61); 2.7173 (0.66); 2.6973 (1.20); 2.6836 (1.59); 2.6798 (1.72); 2.6665 (0.88); 2.5696 (0.40); 2.5652 (0.88); 2.5608 (1.23); 2.5562 (0.91); 2.5516 (0.50); 2.5328 (1.90); 2.5193 (33.14); 2.5150 (69.27); 2.5105 (95.86); 2.5060 (71.93); 2.5016 (37.19); 2.4697 (1.83); 2.4650 (1.90); 2.4605 (1.93); 2.4559 (1.48); 2.3420 (0.50); 2.3374 (0.65); 2.3329 (0.49); 1.6154 (0.48); 1.6040 (0.62); 1.5956 (1.03); 1.5916 (0.90); 1.5815 (1.09); 1.5751 (1.27); 1.5699 (0.96); 1.5603 (1.26); 1.5394 (0.55); 1.3744 (0.48); 1.3451 (0.43); 1.3314 (0.93); 1.3193 (1.27); 1.3133 (0.94); 1.3063 (1.87); 1.2930 (2.04); 1.2870 (2.27); 1.2724 (3.51); 1.2619 (2.10); 1.2537 (3.00); 1.2384 (3.01); 1.2255 (1.23); 1.2207 (1.30); 1.2136 (0.94); 1.1807 (0.33); 1.1033 (0.37); 1.0903 (0.42); 1.0700 (13.27); 1.0582 (9.12); 1.0530 (15.18); 1.0403 (16.00); 1.0220 (7.07); 0.9902 (0.47); 0.8832 (6.32); 0.8653 (12.63); 0.8474 (5.25); 0.8151 (0.38)

Example 173, Solvent: DMSO, Spectrometer: 399.95 MHz 10.4268 (0.85); 8.0973 (0.65); 8.0770 (0.77); 7.8320 (0.59); 7.8127 (0.78); 7.7924 (0.55); 7.7253 (0.86); 7.7226 (1.15); 7.7186 (0.54); 7.7100 (0.33); 7.7048 (1.57); 7.7011 (1.07); 7.5453 (0.75); 7.5303 (0.39); 7.5270 (0.66); 7.5235 (0.32); 7.4953 (1.08); 7.4918 (0.44); 7.4800 (0.73); 7.4762 (1.40); 7.4585 (0.58); 7.1465 (0.78); 7.1452 (0.79); 7.1280 (0.76); 7.1266 (0.73); 5.3564 (2.81); 3.3292 (22.20); 3.0495 (7.72); 2.8909 (2.42); 2.7323 (1.92); 2.7311 (1.89); 2.5206 (0.38); 2.5120 (5.12); 2.5075 (10.41); 2.5028 (13.85); 2.4982 (10.00); 2.4936 (4.73); 2.2811 (3.18); 1.0017 (16.00); −0.0002 (0.61)

Example 174, Solvent: DMSO, Spectrometer: 399.95 MHz 11.0174 (0.49); 10.9652 (2.77); 8.3621 (0.52); 8.3585 (0.37); 8.1522 (1.93); 8.1315 (2.48); 8.1187 (0.63); 7.9520 (1.28); 7.9233 (1.46); 7.9025 (5.11); 7.8812 (5.99); 7.8682 (1.35); 7.7992 (4.69); 7.7947 (2.16); 7.7826 (1.87); 7.7780 (3.76); 7.7644 (0.81); 7.7328 (3.18); 7.7150 (4.28); 7.7114 (3.40); 7.5664 (0.57); 7.5545 (0.53); 7.5480 (2.03); 7.5425 (0.92); 7.5299 (1.94); 7.5480 (2.99); 7.4997 (2.99); 7.4804 (4.14); 7.4668 (1.49); 7.4629 (1.94); 7.3170 (0.51); 7.2339 (2.11); 7.2155 (2.23); 7.2036 (0.54); 5.4129 (7.30); 5.4004 (2.02); 3.3336 (259.50); 3.3254 (85.59); 3.2568 (0.38); 3.0748 (16.00); 3.0613 (3.35); 2.8906 (8.49); 2.8772 (1.53); 2.7508 (0.32); 2.7311 (7.17); 2.7175 (1.42); 2.6760 (0.42); 2.6715 (0.61); 2.6669 (0.52); 2.5244 (1.68); 2.5111 (31.96); 2.5068 (67.85); 2.5023 (96.64); 2.4978 (83.97); 2.4934 (59.44); 2.3335 (0.48); 2.3291 (0.67); 2.3245 (0.59); 1.2341 (0.71); 0.0080 (0.55); −0.0002 (16.64); −0.0084 (2.01); −0.0139 (2.74)

Example 175, Solvent: DMSO, Spectrometer: 399.95 MHz 10.1866 (2.65); 7.9531 (0.97); 7.8234 (0.52); 7.8024 (1.91); 7.7867 (3.90); 7.7836 (2.80); 7.7670 (0.56); 7.7226 (2.65); 7.7188 (1.31); 7.7098 (0.80); 7.7048 (3.41); 7.7010 (2.41); 7.5633 (0.48); 7.5515 (0.36); 7.5393 (0.49); 7.5300 (0.88); 7.5267 (1.43); 7.5234 (0.75); 7.4963 (2.45); 7.4809 (1.66); 7.4771 (3.12); 7.4635 (0.49); 7.4595 (1.22); 7.4563 (0.70); 7.2432 (0.55); 7.2390 (0.75); 7.2192 (3.18); 7.2006 (2.92); 7.1029 (1.35); 7.0982 (1.36); 7.0869 (1.23); 7.0822 (1.30); 6.9777 (1.59); 6.9580 (1.43); 6.9009 (0.95); 6.8985 (0.93); 6.8824 (1.72); 6.8802 (1.57); 6.8640 (0.79); 6.8616 (0.75); 5.3288 (6.32); 4.2549 (1.61); 4.2373 (3.54); 4.2196 (1.69); 3.7772 (16.00); 3.3389 (97.25); 3.0633 (15.72); 2.9347 (1.51); 2.9171 (3.04); 2.8995 (1.52); 2.8906 (7.73); 2.7322 (6.02); 2.7313 (6.13); 2.5256 (0.56); 2.5122 (11.48); 2.5077 (22.92); 2.5031 (30.26); 2.4985 (22.17); 2.4940 (10.74); −0.0002 (2.39)

Example 176, Solvent: DMSO, Spectrometer: 400.13 MHz 10.5325 (4.18); 8.0778 (2.47); 8.0571 (2.95); 7.8416 (2.45); 7.8222 (3.52); 7.8021 (2.27); 7.7285 (5.15); 7.7157 (1.61); 7.7108 (6.55); 7.7070 (4.71); 7.5773 (0.91); 7.5741 (0.62); 7.5654 (0.75); 7.5589 (3.16); 7.5532 (1.07); 7.5440 (1.83); 7.5407 (2.80); 7.5375 (1.51); 7.5121 (4.79); 7.4967 (3.19); 7.4930 (5.96); 7.4794 (0.96); 7.4754 (2.26); 7.4721 (1.34); 7.1384 (3.59); 7.1205 (3.43); 5.3672 (12.41); 3.5051 (1.58); 3.4870 (5.34); 3.4688 (5.44); 3.4507 (1.66); 3.3929 (0.46); 3.3429 (38.50); 3.2931 (0.40); 2.6832 (0.41); 2.6787 (0.55); 2.6742 (0.40); 2.5641 (0.83); 2.5597 (1.13); 2.5553 (0.83); 2.5321 (1.45); 2.5185 (33.63); 2.5142 (70.52); 2.5097 (96.23); 2.5052 (69.78); 2.5009 (33.26); 2.4688 (0.65); 2.4644 (0.94); 2.4599 (1.16); 2.4554 (0.91); 2.4056 (3.54); 2.3873 (6.46); 2.3686 (3.85); 2.3410 (0.52); 2.3366 (0.71); 2.3321 (0.52); 1.5944 (0.88); 1.5762 (2.64); 1.5575 (3.67); 1.5391 (2.77); 1.5201 (1.13); 1.3728 (0.33); 1.3474 (0.61); 1.3288 (2.14); 1.3099 (3.42); 1.2911 (3.47); 1.2729 (2.15); 1.2548 (0.78); 1.2408 (0.39); 1.0603 (6.03); 1.0423 (13.70); 1.0240 (5.88); 0.9037 (7.83); 0.8854 (16.00); 0.8670 (6.78); 0.8512 (0.34)

Example 177, Solvent: DMSO, Spectrometer: 399.95 MHz 10.4940 (1.73); 8.0791 (1.46); 8.0588 (1.73); 7.8363 (1.30); 7.8170 (1.73); 7.7968 (1.18); 7.7266 (1.92); 7.7243 (2.52); 7.7204 (1.19); 7.7116 (0.75); 7.7065 (3.35); 7.7026 (2.29); 7.5652 (0.48); 7.5533 (0.35); 7.5468 (1.62); 7.5411 (0.46); 7.5319 (0.85); 7.5286 (1.39); 7.5252 (0.69);

NMR Peak List Table 1

7.4978 (2.35); 7.4944 (0.97); 7.4825 (1.58); 7.4787 (3.02); 7.4651 (0.46); 7.4611 (1.20); 7.4578 (0.65); 7.1433 (1.74); 7.1257 (1.68); 5.3595 (6.26); 3.3326 (58.89); 3.0590 (16.00); 2.8910 (1.13); 2.7735 (0.82); 2.7564 (1.15); 2.7393 (0.88); 2.7322 (0.95); 2.7223 (0.33); 2.5257 (0.50); 2.5208 (0.83); 2.5123 (9.61); 2.5078 (19.11); 2.5032 (25.17); 2.4986 (18.15); 2.4940 (8.58); 1.0854 (13.94); 1.0684 (13.71); 1.0488 (0.41); −0.0002 (0.91)
Example 178, Solvent: DMSO, Spectrometer: 399.95 MHz 11.1105 (2.12); 8.1675 (0.51); 8.1474 (0.58); 7.9532 (0.83); 7.9310 (1.18); 7.9115 (1.71); 7.8914 (1.06); 7.7368 (0.39); 7.7312 (2.06); 7.7284 (2.75); 7.7246 (1.48); 7.7159 (0.85); 7.7108 (3.55); 7.7070 (2.57); 7.5710 (1.12); 7.5671 (1.41); 7.5609 (0.50); 7.5524 (1.88); 7.5458 (2.62); 7.5406 (1.50); 7.5309 (1.41); 7.5274 (2.18); 7.5241 (2.81); 7.5212 (2.24); 7.5057 (1.23); 7.5014 (1.68); 7.4967 (2.69); 7.4933 (1.30); 7.4877 (1.92); 7.4816 (2.44); 7.4776 (3.38); 7.4678 (1.11); 7.4635 (1.23); 7.4599 (1.43); 7.4567 (0.80); 7.4411 (1.38); 7.4374 (1.30); 7.4227 (1.64); 7.4191 (1.67); 7.4044 (0.68); 7.4008 (0.62); 7.2419 (1.69); 7.2234 (1.60); 5.3769 (4.33); 3.3314 (18.88); 3.0797 (16.00); 3.0662 (0.84); 3.0592 (0.39); 2.8902 (6.68); 2.7320 (5.26); 2.7308 (5.21); 2.5251 (0.50); 2.5203 (0.77); 2.5117 (9.24); 2.5072 (18.61); 2.5026 (24.66); 2.4980 (17.91); 2.4934 (8.52); 1.2347 (0.46); 0.9274 (0.36); 0.9106 (0.36); −0.0002 (6.89)
Example 179, Solvent: DMSO, Spectrometer: 399.95 MHz 10.8683 (2.02); 8.0121 (1.14); 7.9916 (1.50); 7.9531 (0.80); 7.8734 (1.31); 7.8542 (1.74); 7.8339 (1.11); 7.7296 (1.95); 7.7271 (2.56); 7.7232 (1.23); 7.7144 (0.76); 7.7093 (3.42); 7.7055 (2.38); 7.5673 (0.49); 7.5554 (0.35); 7.5491 (1.64); 7.5434 (0.48); 7.5340 (0.85); 7.5307 (1.42); 7.5273 (0.72); 7.4982 (2.36); 7.4947 (0.99); 7.4827 (1.68); 7.4790 (3.08); 7.4653 (0.49); 7.4613 (1.27); 7.4581 (0.70); 7.2691 (0.77); 7.2488 (1.95); 7.2318 (0.43); 7.2276 (1.43); 7.2089 (1.74); 7.1914 (1.68); 7.1453 (3.72); 7.1413 (4.09); 7.1375 (1.20); 7.1265 (1.03); 7.1245 (1.07); 7.1223 (0.79); 7.1201 (0.60); 6.9514 (0.95); 6.9471 (1.32); 6.9429 (0.89); 6.9303 (0.89); 6.9283 (0.88); 6.9242 (0.89); 6.9223 (0.79); 5.3899 (5.81); 5.1185 (0.97); 5.1021 (0.98); 3.3336 (96.07); 3.0642 (16.00); 2.8909 (6.73); 2.7324 (5.27); 2.7313 (5.16); 2.5257 (0.66); 2.5209 (1.02); 2.5123 (13.79); 2.5077 (27.87); 2.5031 (36.97); 2.4985 (26.80); 2.4940 (12.70); 1.5333 (5.24); 1.5169 (5.22); −0.0002 (3.65)
Example 180, Solvent: DMSO, Spectrometer: 399.95 MHz 12.6387 (1.10); 8.0024 (3.31); 7.9817 (3.46); 7.9534 (1.30); 7.7464 (2.73); 7.7424 (1.31); 7.7339 (0.75); 7.7288 (3.40); 7.7249 (2.36); 7.5674 (0.46); 7.5561 (0.33); 7.5490 (1.67); 7.5431 (0.50); 7.5345 (0.92); 7.5310 (1.54); 7.5275 (0.78); 7.5068 (2.57); 7.5035 (1.10); 7.4918 (1.57); 7.4878 (3.11); 7.4745 (0.47); 7.4703 (1.22); 7.4667 (0.72); 7.3618 (4.47); 7.3566 (2.93); 7.3363 (2.54); 5.3801 (5.76); 3.3299 (37.79); 3.0182 (16.00); 2.8906 (10.49); 2.7313 (8.46); 2.5253 (0.56); 2.5205 (0.87); 2.5120 (10.77); 2.5075 (21.56); 2.5029 (28.46); 2.4983 (20.56); 2.4938 (9.71); 2.3857 (8.82); −0.0002 (7.41)
Example 181, Solvent: DMSO, Spectrometer: 399.95 MHz 10.4711 (2.24); 8.2403 (1.27); 8.2197 (1.46); 7.9535 (0.44); 7.9239 (1.22); 7.9043 (1.82); 7.8968 (1.39); 7.8923 (1.45); 7.8844 (1.25); 7.8775 (1.48); 7.8730 (1.42); 7.7447 (1.95); 7.7421 (2.54); 7.7381 (1.21); 7.7295 (0.81); 7.7244 (3.40); 7.7206 (2.31); 7.5964 (0.73); 7.5919 (0.72); 7.5781 (0.95); 7.5753 (1.12); 7.5739 (1.08); 7.5708 (1.07); 7.5668 (0.57); 7.5635 (0.38); 7.5572 (1.05); 7.5526 (1.08); 7.5485 (1.67); 7.5427 (0.49); 7.5336 (0.90); 7.5302 (1.45); 7.5268 (0.72); 7.5016 (2.35); 7.4981 (0.99); 7.4864 (1.59); 7.4825 (3.02); 7.4690 (0.48); 7.4649 (1.22); 7.4615 (0.67); 7.2578 (1.68); 7.2377 (1.50); 7.2228 (1.74); 7.2043 (1.69); 7.1388 (0.99); 7.1366 (0.95); 7.1198 (1.64); 7.1183 (1.58); 7.1013 (0.90); 7.0991 (0.83); 5.4054 (6.07); 3.9637 (13.31); 3.3374 (70.18); 3.1119 (16.00); 2.8910 (3.66); 2.7326 (2.89); 2.7316 (2.80); 2.5260 (0.49); 2.5212 (0.79); 2.5126 (9.51); 2.5081 (18.83); 2.5035 (24.63); 2.4989 (17.69); 2.4944 (8.33); −0.0002 (3.28)
Example 182, Solvent: DMSO, Spectrometer: 399.95 MHz 10.1856 (0.61); 10.1708 (2.08); 7.8299 (0.39); 7.8088 (2.07); 7.8008 (1.98); 7.7943 (5.27); 7.7799 (0.39); 7.7219 (2.53); 7.7086 (0.83); 7.7038 (3.15); 7.7000 (2.27); 7.5625 (0.48); 7.5507 (0.37); 7.5442 (1.69); 7.5386 (0.50); 7.5293 (0.89); 7.5260 (1.43); 7.5227 (0.74); 7.4957 (2.45); 7.4801 (1.70); 7.4764 (3.15); 7.4627 (0.50); 7.4587 (1.21); 7.4555 (0.69); 7.1015 (1.27); 7.0948 (1.08); 7.0870 (1.13); 7.0808 (1.20); 5.3296 (5.58); 4.1394 (1.64); 4.1223 (3.47); 4.1053 (1.70); 3.9744 (0.34); 3.9590 (0.35); 3.9160 (0.35); 3.8994 (0.35); 3.3428 (190.68); 3.0647 (16.00); 2.8912 (0.69); 2.7321 (0.56); 2.5257 (0.80); 2.5124 (16.78); 2.5079 (33.61); 2.5033 (44.43); 2.4987 (32.45); 2.4943 (15.78); 1.7102 (0.62); 1.6935 (0.82); 1.6767 (0.71); 1.6601 (0.40); 1.5327 (0.98); 1.5156 (2.85); 1.4985 (2.56); 1.4814 (0.80); 1.2348 (0.32); 0.9270 (0.58); 0.9146 (15.37); 0.8980 (14.95); 0.8892 (1.21); 0.8826 (1.81); 0.8725 (0.88); 0.8639 (0.71); −0.0002 (5.02)
Example 183, Solvent: DMSO, Spectrometer: 400.13 MHz 11.4550 (1.75); 7.9097 (0.81); 7.8897 (1.65); 7.8706 (1.15); 7.7324 (2.64); 7.7197 (0.87); 7.7146 (3.39); 7.7109 (2.39); 7.5698 (0.50); 7.5667 (0.34); 7.5578 (0.39); 7.5516 (1.64); 7.5459 (0.50); 7.5366 (0.89); 7.5333 (1.40); 7.5300 (0.73); 7.5010 (2.35); 7.4854 (1.69); 7.4818 (3.05); 7.4681 (0.49); 7.4641 (1.20); 7.4610 (0.69); 7.2522 (1.52); 7.2320 (1.44); 5.3849 (6.33); 4.4679 (1.79); 4.4515 (3.80); 4.4352 (1.82); 3.3999 (2.05); 3.3497 (219.89); 3.3000 (1.99); 3.0666 (16.00); 2.6767 (0.38); 2.5624 (0.48); 3.5580 (0.61); 2.5535 (0.42); 2.5302 (1.07); 2.5254 (1.80); 2.5167 (22.34); 2.5123 (45.93); 2.5078 (61.94); 2.5033 (44.09); 2.4989 (20.54); 2.4671 (0.41); 2.4627 (0.57); 2.4581 (0.65); 2.4536 (0.42); 2.3346 (0.38); 1.7159 (0.45); 1.6992 (1.32); 1.6923 (0.50); 1.6814 (1.62); 1.6619 (1.41); 1.6455 (0.56); 1.4150 (0.94); 1.3961 (1.55); 1.3773 (1.55); 1.3590 (0.90); 0.9199 (3.53); 0.9015 (7.19); 0.8829 (3.09)
Example 184, Solvent: DMSO, Spectrometer: 399.95 MHz 10.5439 (1.97); 8.0731 (1.14); 8.0525 (1.36); 7.9531 (0.35); 7.8385 (1.18); 7.8193 (1.58); 7.7990 (1.10); 7.7241 (1.82); 7.7215 (2.39); 7.7176 (1.17); 7.7088 (0.75); 7.7037 (3.21); 7.7000 (2.23); 7.5641 (0.46); 7.5522 (0.34); 7.5458 (1.53); 7.5401 (0.46); 7.5309 (0.80); 7.5275 (1.33); 7.5241 (0.66); 7.4964 (2.23); 7.4929 (0.95); 7.4810 (1.50); 7.4772 (2.86); 7.4637 (0.44); 7.4596 (1.16); 7.4564 (0.63); 7.1985 (0.52); 7.1941 (0.72); 7.1784 (0.84); 7.1743 (1.30); 7.1678 (1.35); 7.1639 (0.95); 7.1602 (0.69); 7.1556 (1.16); 7.1489 (1.55); 7.1438 (2.16); 7.1247 (1.57); 6.9539 (1.59); 6.9336 (1.43); 6.8677 (0.97); 6.8652 (0.85); 6.8492 (1.72); 6.8467 (1.47); 6.8308 (0.79); 6.8282 (0.68); 5.3494 (5.50); 4.0439 (0.51); 4.0261 (0.52); 3.7797 (16.00); 3.3330 (71.39); 3.0469 (15.02); 2.8904 (3.02); 2.8664 (1.01); 2.8485 (1.83); 2.8280 (1.46); 2.8011 (0.32); 2.7321 (2.37); 2.7310 (2.30); 2.6673 (1.68); 2.6506 (1.16); 2.6466 (2.01); 2.6285 (1.02); 2.5461 (0.35); 2.5257 (0.87); 2.5205 (0.88); 2.5119 (10.15); 2.5074 (20.41); 2.5027 (26.76); 2.4981 (19.33); 2.4936 (9.10); 1.1700 (0.58); 1.1522 (1.22); 1.1345 (0.56); 0.8757 (0.43); −0.0002 (5.23)
Example 185, Solvent: CDCl3, Spectrometer: 300.16 MHz 7.9283 (2.16); 7.9007 (2.74); 7.7163 (1.49); 7.6905 (2.60); 7.6646 (1.29); 7.5846 (4.48); 7.5581 (4.95); 7.2637 (7.93); 7.0223 (2.69); 6.9980 (2.54); 6.9266 (5.31); 6.9007 (4.85); 6.7759 (0.57); 5.3056 (0.37); 5.2570 (10.02); 5.1202 (0.33); 5.0276 (0.79); 5.0079 (1.48); 4.9879 (1.42); 4.9693 (0.79); 3.8411 (16.00); 3.2810 (0.32); 3.0929 (15.51); 1.7320 (0.47); 1.7110 (0.96); 1.6882 (1.31); 1.6508 (1.63); 1.6204 (4.25); 1.5870 (1.42); 1.5647 (0.73); 1.3395 (1.47); 1.3167 (1.80); 1.2930 (9.08); 1.2726 (8.98); 0.9350 (15.38); 0.9144 (14.64); −0.0002 (4.37)
Example 186, Solvent: DMSO, Spectrometer: 399.95 MHz 10.2345 (2.80); 7.9531 (0.71); 7.8221 (0.75); 7.8011 (1.81); 7.7836 (2.16); 7.7726 (2.19); 7.7703 (2.28); 7.7520 (0.86); 7.7220 (2.79); 7.7040 (3.52); 7.7003 (2.46); 7.5624 (0.52); 7.5594 (0.35); 7.5504 (0.42); 7.5441 (1.74); 7.5385 (0.54); 7.5290 (0.99); 7.5259 (1.47); 7.5226 (0.75); 7.4952 (2.57); 7.4795 (1.87); 7.4760 (3.27); 7.4622 (0.54); 7.4583 (1.25); 7.4552 (0.72); 7.4225 (0.67); 7.4184 (0.65); 7.4035 (1.22); 7.3990

| NMR Peak List Table 1 |
|---|
| (1.26); 7.3833 (0.68); 7.3800 (0.70); 7.3034 (0.37); 7.2987 (0.77); 7.2840 (0.75); 7.2783 (0.92); 7.2739 (0.52); 7.2645 (0.51); 7.2602 (0.43); 7.2240 (0.42); 7.2070 (0.75); 7.1870 (1.03); 7.1664 (2.07); 7.1500 (1.89); 7.1475 (1.62); 7.1433 (0.86); 7.1316 (0.81); 7.1289 (0.65); 7.1048 (1.62); 7.1022 (1.59); 7.0873 (1.57); 7.0847 (1.47); 5.3288 (6.75); 4.3161 (3.90); 4.2992 (3.90); 4.2823 (1.81); 3.3288 (77.85); 3.0613 (16.00); 3.0360 (0.56); 2.9986 (1.39); 2.9818 (2.76); 2.9650 (1.29); 2.8906 (5.36); 2.7317 (4.48); 2.5113 (19.22); 2.5069 (35.97); 2.5024 (45.95); 2.4978 (33.18); 2.4935 (15.90); 1.2349 (0.43); 0.0079 (0.47); −0.0002 (10.29); −0.0085 (0.33) Example 187, Solvent: DMSO, Spectrometer: 399.95 MHz |
| 10.9980 (2.26); 8.1570 (1.59); 8.1370 (1.93); 7.9746 (0.46); 7.9685 (3.76); 7.9636 (1.22); 7.9520 (2.11); 7.9469 (4.65); 7.9408 (0.60); 7.9287 (1.28); 7.9094 (1.76); 7.8891 (1.15); 7.7352 (2.97); 7.7302 (5.32); 7.7251 (1.54); 7.7173 (3.55); 7.7135 (3.43); 7.7085 (3.88); 7.7023 (0.45); 7.5675 (0.48); 7.5557 (0.35); 7.5492 (1.63); 7.5434 (0.48); 7.5343 (0.86); 7.5309 (1.42); 7.5275 (0.70); 7.5008 (2.38); 7.4973 (1.01); 7.4854 (1.61); 7.4816 (3.06); 7.4681 (0.47); 7.4640 (1.22); 7.4607 (0.68); 7.2402 (1.74); 7.2219 (1.69); 5.4168 (6.02); 3.3313 (54.91); 3.0774 (16.00); 2.8908 (7.50); 2.7321 (6.14); 2.7311 (5.80); 2.5252 (0.66); 2.5204 (1.09); 2.5119 (12.91); 2.5074 (25.67); 2.5028 (33.69); 2.4982 (24.28); 2.4936 (11.37); 0.0080 (0.32); −0.0002 (9.68) Example 188, Solvent: DMSO, Spectrometer: 399.95 MHz |
| 10.6228 (1.66); 8.0751 (0.94); 8.0544 (1.13); 7.9527 (0.34); 7.8495 (1.04); 7.8300 (1.49); 7.8099 (0.95); 7.7229 (2.22); 7.7101 (0.72); 7.7052 (2.81); 7.7015 (2.00); 7.5646 (0.40); 7.5462 (1.33); 7.5406 (0.42); 7.5313 (0.73); 7.5280 (1.17); 7.5247 (0.64); 7.4971 (2.06); 7.4816 (1.43); 7.4779 (2.59); 7.4644 (0.45); 7.4603 (1.02); 7.4572 (0.62); 7.1583 (1.54); 7.1398 (1.45); 5.3617 (5.31); 3.3370 (87.40); 3.0555 (12.82); 2.8905 (2.63); 2.7445 (0.65); 2.7306 (3.30); 2.7289 (3.34); 2.7171 (3.13); 2.7095 (2.99); 2.6982 (2.32); 2.6821 (0.62); 2.6721 (0.42); 2.5252 (0.62); 2.5117 (10.99); 2.5074 (21.33); 2.5028 (27.84); 2.4983 (20.51); 2.4938 (10.05); 2.0764 (16.00); −0.0002 (2.01) Example 189, Solvent: DMSO, Spectrometer: 399.95 MHz |
| 11.1037 (1.84); 8.0165 (1.21); 7.9960 (1.59); 7.9531 (1.28); 7.8721 (1.31); 7.8530 (1.73); 7.8326 (1.15); 7.7282 (2.05); 7.7255 (2.60); 7.7216 (1.30); 7.7129 (0.89); 7.7077 (3.59); 7.7040 (2.47); 7.5647 (0.52); 7.5615 (0.32); 7.5527 (0.38); 7.5464 (1.67); 7.5408 (0.50); 7.5314 (0.89); 7.5281 (1.45); 7.5247 (0.74); 7.4953 (2.39); 7.4918 (1.01); 7.4799 (1.69); 7.4761 (3.12); 7.4625 (0.50); 7.4584 (1.27); 7.4553 (0.70); 7.1973 (1.70); 7.1799 (1.65); 5.3952 (5.72); 3.3590 (0.49); 3.3334 (125.04); 3.0610 (16.00); 2.8911 (10.61); 2.7322 (8.55); 2.7310 (8.21); 2.5253 (0.85); 2.5205 (1.37); 2.5120 (16.39); 2.5075 (32.58); 2.5028 (42.74); 2.4982 (30.83); 2.4937 (14.55); 2.4377 (0.45); 2.4190 (0.62); 2.4008 (0.64); 2.3823 (0.49); 2.2072 (0.39); 2.1911 (1.52); 2.1747 (1.58); 2.1584 (0.40); 1.4256 (0.51); 1.4069 (0.72); 1.3887 (0.73); 1.3702 (0.61); 1.2832 (0.45); 1.1985 (6.18); 1.1822 (5.98); 0.8909 (2.37); 0.8724 (5.19); 0.8626 (0.89); 0.8536 (2.23); 0.0080 (0.43); −0.0002 (12.63); −0.0085 (0.36) Example 190, Solvent: DMSO, Spectrometer: 399.95 MHz |
| 10.5608 (1.34); 8.0228 (0.72); 8.0021 (0.89); 7.9528 (0.38); 7.8316 (0.76); 7.8122 (1.10); 7.7920 (0.69); 7.7302 (1.64); 7.7124 (2.01); 7.7087 (1.45); 7.5489 (0.97); 7.5436 (0.32); 7.5340 (0.53); 7.5309 (0.83); 7.5277 (0.47); 7.5005 (1.48); 7.4847 (1.03); 7.4813 (1.85); 7.4636 (0.69); 7.4606 (0.43); 7.1509 (1.12); 7.1325 (1.07); 6.8993 (1.12); 6.8772 (1.75); 6.8389 (1.14); 6.8314 (1.58); 6.8066 (1.21); 6.7989 (0.76); 6.7846 (0.72); 6.7769 (0.52); 5.3707 (3.71); 3.6870 (16.00); 3.5449 (0.32); 3.3313 (39.68); 3.0634 (8.83); 2.8898 (2.88); 2.7309 (2.40); 2.5110 (7.31); 2.5067 (13.78); 2.5022 (17.78); 2.4977 (13.04); 2.4933 (6.37); 1.1676 (0.35); −0.0002 (3.10) Example 191, Solvent: DMSO, Spectrometer: 499.93 MHz |
| 12.1460 (2.13); 8.0017 (0.91); 7.9855 (2.03); 7.9703 (1.79); 7.9417 (2.55); 7.9255 (1.40); 7.7986 (0.34); 7.7938 (0.42); 7.6739 (4.00); 7.6699 (2.08); 7.6561 (4.45); 7.3455 (1.98); 7.3308 (1.92); 7.0396 (4.23); 7.0218 (4.19); 5.7761 (3.49); 5.3920 (6.96); 5.3772 (0.52); 5.2861 (0.72); 3.8283 (0.81); 3.8147 (16.00); 3.3674 (5.04); 3.3439 (0.35); 3.1634 (0.42); 3.0586 (15.02); 2.5170 (2.29); 2.5137 (3.03); 2.5104 (2.41); 1.9994 (0.56); 1.2582 (0.59); 1.2457 (0.67); 1.2342 (0.58); 1.2218 (0.52); 0.8992 (0.72); 0.8879 (0.71); 0.8862 (0.72) Example 192, Solvent: DMSO, Spectrometer: 399.95 MHz |
| 10.1742 (2.55); 7.9535 (0.41); 7.8300 (0.54); 7.8090 (1.93); 7.7933 (4.11); 7.7896 (2.83); 7.7732 (0.60); 7.7260 (1.98); 7.7233 (2.58); 7.7195 (1.26); 7.7108 (0.78); 7.7056 (3.39); 7.7019 (2.37); 7.5632 (0.49); 7.5513 (0.36); 7.5449 (1.63); 7.5391 (0.49); 7.5300 (0.88); 7.5266 (1.43); 7.5232 (0.73); 7.4962 (2.40); 7.4928 (1.03); 7.4809 (1.64); 7.4771 (3.06); 7.4635 (0.47); 7.4595 (1.22); 7.4562 (0.68); 7.1022 (1.35); 7.0975 (1.36); 7.0861 (1.24); 7.0815 (1.28); 5.3340 (6.35); 4.0253 (4.21); 4.0105 (4.19); 3.3444 (106.79); 3.3202 (0.53); 3.0655 (16.00); 2.8915 (3.26); 2.7329 (2.64); 2.7317 (2.60); 2.5264 (0.50); 2.5216 (0.82); 2.5131 (9.27); 2.5086 (19.27); 2.5040 (25.37); 2.4994 (18.43); 2.4948 (8.78); 1.5324 (0.68); 1.5169 (1.01); 1.5013 (0.84); 1.4858 (0.41); 1.3872 (0.69); 1.3779 (0.56); 1.3682 (1.83); 1.3595 (1.77); 1.3495 (2.08); 1.3419 (2.25); 1.3336 (1.60); 1.3247 (1.84); 1.3149 (0.57); 1.3067 (0.76); 0.8918 (6.94); 0.8827 (0.78); 0.8733 (14.45); 0.8545 (5.92); −0.0002 (1.59) Example 193, Solvent: DMSO, Spectrometer: 400.13 MHz |
| 9.8075 (1.18); 7.8067 (0.34); 7.7858 (0.74); 7.7676 (0.77); 7.7440 (0.93); 7.7250 (0.43); 7.6041 (0.34); 7.5968 (0.55); 7.5913 (0.40); 7.5840 (0.43); 7.5770 (0.75); 7.5580 (0.36); 7.3637 (0.39); 7.3434 (0.40); 7.3361 (0.53); 7.3329 (0.66); 7.3142 (1.09); 7.2951 (0.38); 7.2926 (0.33); 7.1170 (0.69); 7.1003 (0.64); 5.3220 (2.56); 3.3496 (6.90); 2.5169 (3.21); 2.5126 (6.45); 2.5081 (8.62); 2.5037 (6.15); 2.4994 (2.89); 1.4659 (16.00); 1.3779 (0.32) Example 194, Solvent: DMSO, Spectrometer: 399.95 MHz |
| 12.1539 (1.39); 7.7436 (0.41); 7.7375 (1.92); 7.7348 (2.58); 7.7308 (1.30); 7.7224 (0.96); 7.7172 (3.36); 7.7134 (2.30); 7.5640 (0.50); 7.5608 (0.34); 7.5527 (0.38); 7.5457 (1.64); 7.5398 (0.52); 7.5310 (1.00); 7.5275 (1.52); 7.5241 (0.76); 7.5018 (2.48); 7.4984 (1.72); 7.4868 (1.72); 7.4828 (3.05); 7.4695 (0.57); 7.4653 (1.22); 7.4618 (0.68); 7.3763 (7.33); 7.3708 (3.59); 7.3602 (3.85); 7.3533 (3.47); 7.3461 (1.39); 7.3429 (1.36); 7.3404 (1.38); 7.3198 (3.36); 7.3085 (0.92); 7.2970 (1.17); 7.2847 (0.33); 5.4850 (0.46); 5.3745 (0.36); 5.3310 (4.73); 5.1949 (0.66); 5.1861 (0.60); 5.1812 (0.78); 4.9241 (1.28); 4.9149 (1.23); 4.9102 (0.96); 4.9057 (1.15); 4.8977 (1.97); 4.8879 (0.35); 4.8592 (0.62); 4.8455 (0.58); 4.8349 (0.77); 4.7813 (1.01); 4.5853 (6.58); 4.5680 (2.97); 4.5464 (0.58); 4.2871 (2.56); 4.2709 (0.78); 4.2462 (6.50); 4.1258 (0.96); 4.1098 (0.95); 3.8443 (0.78); 3.6800 (2.12); 3.3842 (0.41); 3.3326 (338.47); 3.0557 (0.36); 3.0468 (0.32); 3.0156 (16.00); 2.8903 (0.99); 2.7304 (0.77); 2.6800 (0.32); 2.6756 (0.70); 2.6711 (0.96); 2.6664 (0.68); 2.5244 (2.76); 2.5196 (4.50); 2.5110 (56.29); 2.5065 (112.47); 2.5019 (148.17); 2.4973 (107.53); 2.4928 (51.23); 2.3377 (0.36); 2.3333 (0.74); 2.3287 (0.99); 2.3242 (0.72); 2.3197 (0.36); 1.2352 (0.66); 0.0080 (0.97); −0.0002 (29.69); −0.0086 (0.88) Example 195, Solvent: DMSO, Spectrometer: 399.95 MHz |
| 11.9972 (1.78); 7.9529 (0.44); 7.7372 (1.98); 7.7347 (2.59); 7.7307 (1.25); 7.7222 (0.80); 7.7170 (3.40); 7.7132 (2.33); 7.5641 (0.46); 7.5527 (0.34); 7.5458 (1.66); 7.5399 (0.49); 7.5311 (0.92); 7.5277 (1.48); 7.5242 (0.74); 7.5018 (2.47); 7.4985 (1.05); 7.4868 (1.61); 7.4828 (3.05); 7.4694 (0.48); 7.4653 (1.20); 7.4618 (0.66); 7.3106 (4.44); 5.3305 (6.05); 4.1165 (9.21); 4.0002 (0.65); 3.9902 (0.90); 3.9804 (0.78); 3.3322 (59.45); 3.0125 (16.00); 2.8908 (3.55); 2.7320 (2.85); 2.7310 (2.79); 2.5251 (0.57); 2.5117 (11.15); 2.5072 (22.21); 2.5026 (29.22); 2.4980 (21.22); 2.4935 (10.14); 1.6846 (0.35); 1.6746 (0.78); 1.6707 (0.89); 1.6578 (2.44); 1.6550 (2.68); 1.6490 (3.72); 1.6465 (3.44); 1.6385 (4.46); 1.6298 (1.54); 1.6187 (0.74); 1.6075 (0.55); 1.6028 (0.52); 1.4829 (1.01); 1.4761 (1.08); 1.4665 (0.90); 0.0080 (0.33); −0.0002 (10.02) |

NMR Peak List Table 1

Example 196, Solvent: DMSO, Spectrometer: 399.95 MHz 10.8301 (1.89); 8.0235 (1.08); 8.0028 (1.34); 7.9533 (0.96); 7.8389 (1.29); 7.8197 (1.72); 7.7993 (1.14); 7.7256 (1.93); 7.7231 (2.55); 7.7192 (1.20); 7.7104 (0.77); 7.7053 (3.41); 7.7015 (2.34); 7.5655 (0.49); 7.5536 (0.36); 7.5472 (1.63); 7.5415 (0.48); 7.5322 (0.86); 7.5289 (1.40); 7.5255 (0.69); 7.4972 (2.36); 7.4938 (0.98); 7.4818 (1.62); 7.4781 (3.04); 7.4644 (0.47); 7.4604 (1.22); 7.4572 (0.67); 7.3943 (0.94); 7.3926 (0.74); 7.3874 (0.54); 7.3790 (0.90); 7.3722 (7.83); 7.3690 (2.87); 7.3644 (6.62); 7.3575 (0.74); 7.3490 (0.45); 7.3422 (0.88); 7.1637 (1.72); 7.1463 (1.66); 5.3697 (5.94); 3.7272 (5.85); 3.3342 (102.59); 3.0507 (16.00); 2.8907 (8.08); 2.7321 (6.25); 2.7311 (6.24); 2.5255 (0.68); 2.5207 (1.08); 2.5122 (13.38); 2.5076 (26.78); 2.5030 (35.23); 2.4984 (25.41); 2.4938 (11.94); −0.0002 (5.23)

Example 197, Solvent: DMSO, Spectrometer: 499.93 MHz 7.7531 (2.74); 7.7426 (0.97); 7.7387 (3.35); 7.7358 (2.51); 7.5661 (0.54); 7.5637 (0.38); 7.5561 (0.44); 7.5514 (1.70); 7.5472 (0.66); 7.5390 (1.14); 7.5368 (1.54); 7.5343 (0.91); 7.5244 (0.43); 7.5060 (2.59); 7.5029 (2.05); 7.4904 (3.82); 7.4796 (0.97); 7.4762 (1.65); 7.4739 (1.33); 7.4713 (1.47); 7.3695 (0.33); 7.3009 (0.60); 7.2960 (0.34); 7.2920 (0.74); 7.2847 (0.62); 7.1964 (0.41); 6.5446 (1.64); 6.5402 (2.15); 6.5263 (2.97); 5.7777 (2.34); 5.2802 (0.36); 5.2431 (6.80); 3.9093 (0.44); 3.7593 (1.82); 3.6223 (0.46); 3.6209 (0.46); 3.4938 (1.50); 3.4798 (4.87); 3.4658 (5.01); 3.4519 (1.70); 3.3664 (2.18); 3.3406 (0.69); 3.0694 (16.00); 3.0540 (0.46); 3.0210 (0.67); 2.5204 (1.77); 2.5171 (3.78); 2.5136 (5.21); 2.5100 (3.94); 2.5067 (2.01); 2.3165 (1.95); 2.2189 (0.71); 1.6012 (0.53); 1.4713 (0.51); 1.4334 (0.97); 1.2419 (0.47); 1.0913 (5.78); 1.0774 (13.03); 1.0634 (5.98)

Example 198, Solvent: DMSO, Spectrometer: 400.13 MHz 12.1310 (3.72); 7.7440 (4.00); 7.7247 (4.54); 7.5710 (0.65); 7.5531 (1.97); 7.5354 (1.98); 7.5100 (3.43); 7.4909 (4.23); 7.4724 (1.53); 7.2682 (5.13); 5.3276 (8.77); 4.0450 (0.91); 4.0271 (0.91); 3.3442 (36.64); 3.0208 (16.00); 2.5109 (29.55); 2.4248 (2.36); 2.4065 (4.70); 2.3881 (2.63); 1.9971 (3.67); 1.6264 (0.57); 1.6080 (1.91); 1.5902 (2.77); 1.5725 (1.95); 1.5551 (0.63); 1.3164 (0.70); 1.3013 (1.67); 1.2772 (4.42); 1.2699 (4.39); 1.2406 (1.32); 1.1996 (1.03); 1.1818 (1.92); 1.1640 (0.99); 1.1305 (0.56); 1.1154 (0.55); 0.8807 (3.55); 0.8646 (7.48); 0.8471 (3.55)

Example 199, Solvent: DMSO, Spectrometer: 400.13 MHz 10.2386 (3.75); 7.8908 (0.59); 7.8698 (2.25); 7.8535 (5.80); 7.8338 (0.76); 7.7875 (3.92); 7.7688 (4.45); 7.6246 (0.65); 7.6068 (1.98); 7.5890 (1.85); 7.5583 (3.28); 7.5391 (4.18); 7.5208 (1.54); 7.1635 (2.05); 7.1473 (1.94); 5.8248 (3.93); 5.3893 (8.72); 5.0345 (0.71); 5.0193 (1.26); 5.0073 (1.31); 4.9917 (0.76); 3.5848 (0.76); 3.5613 (1.84); 3.5439 (2.34); 3.5280 (4.17); 3.5098 (4.87); 3.4924 (1.20); 3.4863 (1.02); 3.3996 (33.79); 3.3760 (2.77); 3.1356 (16.00); 2.5664 (53.52); 2.3924 (0.33); 1.2763 (7.71); 1.2602 (7.72); 1.1786 (4.44); 1.1611 (8.80); 1.1437 (4.38); −0.0002 (0.32)

Example 200, Solvent: DMSO, Spectrometer: 399.95 MHz 10.0669 (2.72); 7.9531 (0.43); 7.8220 (0.42); 7.8009 (2.26); 7.7921 (2.46); 7.7862 (5.44); 7.7712 (0.51); 7.7224 (2.73); 7.7186 (1.39); 7.7097 (0.86); 7.7046 (3.50); 7.7009 (2.49); 7.5625 (0.51); 7.5593 (0.34); 7.5506 (0.38); 7.5441 (1.66); 7.5384 (0.53); 7.5292 (0.91); 7.5259 (1.47); 7.5225 (0.79); 7.4957 (2.51); 7.4924 (1.15); 7.4803 (1.70); 7.4765 (3.17); 7.4630 (0.52); 7.4589 (1.25); 7.4557 (0.73); 7.0955 (1.33); 7.0893 (1.34); 7.0810 (1.17); 7.0748 (1.30); 5.3256 (6.60); 4.8229 (0.50); 4.8045 (0.50); 4.7906 (0.83); 4.7751 (0.51); 3.3495 (128.02); 3.0714 (16.00); 2.8916 (3.46); 2.7321 (2.77); 2.5266 (0.61); 2.5134 (10.19); 2.5089 (20.15); 2.5043 (26.68); 2.4998 (19.80); 2.4953 (9.87); 1.5837 (0.40); 1.5731 (0.52); 1.5645 (0.45); 1.5596 (0.43); 1.5548 (0.51); 1.5393 (0.62); 1.5248 (0.57); 1.5183 (0.44); 1.5046 (0.40); 1.3356 (0.55); 1.3080 (1.81); 1.2994 (2.11); 1.2965 (2.07); 1.2850 (1.55); 1.2719 (0.77); 1.2598 (0.36); 1.2534 (0.33); 1.2303 (6.88); 1.2147 (6.76); 0.8885 (1.66); 0.8715 (3.87); 0.8536 (1.45); −0.0002 (0.79)

Example 201, Solvent: DMSO, Spectrometer: 400.13 MHz 10.3873 (6.45); 7.8543 (1.01); 7.8332 (4.47); 7.8216 (5.37); 7.8174 (9.45); 7.8009 (1.23); 7.7953 (0.41); 7.7250 (5.85); 7.7123 (1.79); 7.7072 (7.41); 7.7035 (5.23); 7.5769 (0.64); 7.5738 (1.12); 7.5706 (0.83); 7.5619 (0.96); 7.5554 (3.69); 7.5497 (1.21); 7.5406 (2.12); 7.5373 (3.23); 7.5339 (1.73); 7.5087 (5.41); 7.4934 (3.70); 7.4896 (6.72); 7.4761 (1.15); 7.4720 (2.75); 7.4687 (1.67); 7.4404 (2.11); 7.4358 (2.89); 7.4192 (7.93); 7.4152 (7.60); 7.4135 (7.36); 7.4107 (6.78); 7.4052 (1.46); 7.3934 (7.72); 7.3889 (2.42); 7.3785 (1.83); 7.3742 (2.89); 7.3582 (1.70); 7.3537 (2.67); 7.3487 (1.41); 7.3439 (1.17); 7.3365 (2.54); 7.3291 (0.96); 7.3238 (0.83); 7.3171 (1.39); 7.1149 (2.86); 7.1095 (2.85); 7.0996 (2.59); 7.0942 (2.75); 5.3506 (13.87); 5.1862 (16.00); 4.5052 (0.38); 4.4907 (0.37); 3.5221 (1.78); 3.5040 (6.02); 3.4858 (6.14); 3.4676 (1.85); 3.3953 (2.45); 3.3454 (152.36); 3.3218 (1.12); 3.2955 (1.14); 3.2696 (0.38); 3.2689 (0.38); 3.2646 (0.74); 3.2600 (1.00); 3.2556 (0.73); 2.5511 (0.37); 2.5325 (0.86); 2.5191 (22.11); 2.5147 (46.04); 2.5102 (62.64); 2.5057 (44.54); 2.5013 (20.50); 2.4602 (0.44); 2.4558 (0.38); 2.3369 (0.38); 1.9972 (1.37); 1.3708 (1.12); 1.3237 (0.55); 1.2407 (0.43); 1.1994 (0.42); 1.1817 (0.76); 1.1639 (0.38); 1.0551 (6.72); 1.0370 (15.39); 1.0187 (6.58)

Example 202, Solvent: DMSO, Spectrometer: 399.95 MHz 11.0982 (2.23); 8.1505 (1.59); 8.1306 (1.94); 7.9528 (0.93); 7.9484 (1.54); 7.9289 (1.82); 7.9087 (1.18); 7.7624 (1.46); 7.7567 (1.82); 7.7440 (1.37); 7.7412 (2.11); 7.7380 (3.00); 7.7355 (3.97); 7.7315 (1.56); 7.7229 (0.91); 7.7176 (3.43); 7.7138 (2.37); 7.5689 (0.48); 7.5657 (0.33); 7.5574 (0.69); 7.5508 (2.02); 7.5452 (0.73); 7.5353 (1.52); 7.5323 (1.77); 7.5290 (1.92); 7.5233 (0.86); 7.5121 (0.51); 7.5020 (2.55); 7.4867 (1.60); 7.4829 (3.07); 7.4694 (0.48); 7.4653 (1.23); 7.4620 (0.70); 7.2632 (1.78); 7.2454 (1.72); 5.4248 (6.10); 3.3442 (100.27); 3.0943 (0.34); 3.0785 (16.00); 2.8913 (6.97); 2.7324 (5.33); 2.7317 (5.39); 2.5263 (0.62); 2.5215 (0.99); 2.5130 (11.94); 2.5085 (23.82); 2.5039 (31.41); 2.4993 (22.74); 2.4947 (10.77); −0.0002 (1.22)

Example 203, Solvent: DMSO, Spectrometer: 400.13 MHz 12.4298 (2.41); 7.6250 (1.17); 7.6181 (1.35); 7.6141 (1.40); 7.6040 (1.01); 7.5940 (3.31); 7.5687 (0.82); 7.5546 (0.92); 7.5485 (1.27); 7.5342 (1.22); 7.5295 (0.81); 7.5134 (0.53); 7.4305 (0.62); 7.4278 (0.68); 7.4244 (0.64); 7.4217 (0.59); 7.4069 (1.11); 7.4027 (1.00); 7.3883 (0.52); 7.3828 (0.57); 7.3510 (0.51); 7.3468 (0.37); 7.3314 (3.65); 7.3262 (4.10); 7.3179 (13.37); 7.3034 (5.07); 7.2906 (0.37); 7.2780 (0.90); 7.2713 (0.94); 7.2689 (0.99); 7.2601 (0.81); 7.2565 (0.95); 7.2518 (0.68); 7.2420 (0.47); 5.7615 (4.82); 5.3522 (6.66); 4.0419 (0.68); 4.0241 (0.70); 3.7558 (8.04); 3.4034 (3.90); 3.3532 (198.24); 3.3033 (2.75); 3.0161 (16.00); 2.5626 (0.48); 2.5580 (0.65); 2.5534 (0.51); 2.5488 (0.36); 2.5122 (27.53); 2.5078 (36.26); 2.5035 (26.37); 2.4625 (0.39); 2.4579 (0.46); 1.9936 (2.97); 1.2468 (0.42); 1.1964 (0.81); 1.1786 (1.57); 1.1608 (0.77); 0.8615 (0.51)

Example 204, Solvent: DMSO, Spectrometer: 399.95 MHz 10.8413 (2.18); 8.0076 (1.27); 7.9870 (1.66); 7.9530 (0.92); 7.8670 (1.37); 7.8477 (1.84); 7.8274 (1.15); 7.7281 (2.70); 7.7243 (1.32); 7.7153 (0.79); 7.7103 (3.45); 7.7065 (2.42); 7.5697 (0.49); 7.5665 (0.32); 7.5576 (0.37); 7.5512 (1.66); 7.5456 (0.50); 7.5363 (0.87); 7.5330 (1.43); 7.5297 (0.74); 7.5012 (2.46); 7.4979 (1.09); 7.4857 (1.69); 7.4820 (3.19); 7.4718 (0.53); 7.4632 (4.80); 7.4577 (1.35); 7.4460 (1.27); 7.4405 (4.44); 7.4318 (0.38); 7.2020 (1.83); 7.1841 (1.73); 6.9056 (0.43); 6.8969 (4.17); 6.8914 (1.24); 6.8798 (1.20); 6.8743 (3.92); 6.8656 (0.33); 5.3842 (6.11); 5.0686 (1.07); 5.0521 (1.07); 3.3370 (109.81); 3.0613 (16.00); 2.8907 (7.63); 2.7313 (6.04); 2.5256 (0.74); 2.5123 (14.64); 2.5078 (29.08); 2.5032 (38.29); 2.4986 (27.75); 2.4941 (13.21); 1.5345 (5.46); 1.5181 (5.42); −0.0002 (2.46)

NMR Peak List Table 1

Example 205, Solvent: DMSO, Spectrometer: 400.13 MHz 10.2539 (2.80); 7.8468 (0.61); 7.8258 (1.79); 7.8087 (2.72); 7.8062 (2.48); 7.8021 (2.53); 7.7850 (0.72); 7.7811 (0.46); 7.7309 (1.95); 7.7284 (2.59); 7.7246 (1.32); 7.7158 (0.79); 7.7106 (3.35); 7.7069 (2.41); 7.5683 (0.48); 7.5652 (0.33); 7.5565 (0.38); 7.5501 (1.60); 7.5444 (0.49); 7.5351 (0.88); 7.5318 (1.44); 7.5284 (0.76); 7.5012 (2.40); 7.4979 (1.11); 7.4858 (1.63); 7.4821 (3.03); 7.4685 (0.48); 7.4644 (1.19); 7.4612 (0.69); 7.1199 (1.35); 7.1161 (1.41); 7.1031 (1.29); 7.0993 (1.32); 5.7629 (5.65); 5.3423 (6.20); 4.1663 (1.39); 4.1503 (2.90); 4.1344 (1.43); 3.4009 (2.36); 3.3509 (182.55); 3.3235 (0.34); 3.3010 (1.74); 3.0681 (16.00); 2.5583 (0.38); 2.5307 (0.42); 2.5259 (0.71); 2.5173 (9.78); 2.5128 (20.52); 2.5083 (28.08); 2.5038 (20.19); 2.4994 (9.50); 2.4590 (0.42); 2.4316 (0.70); 2.4170 (0.49); 2.4119 (0.70); 2.4027 (0.88); 2.3911 (0.88); 2.3830 (0.71); 2.3742 (0.50); 2.3625 (0.76); 2.3340 (0.37); 1.8789 (0.44); 1.8630 (1.09); 1.8478 (0.92); 1.8426 (1.08); 1.8232 (1.04); 1.8071 (0.38)

Example 206, Solvent: CDCl3, Spectrometer: 300.16 MHz 7.9142 (1.19); 7.8866 (1.56); 7.7097 (1.08); 7.6839 (1.47); 7.6570 (0.91); 7.4591 (0.71); 7.4531 (0.81); 7.4458 (0.66); 7.4349 (0.44); 7.4262 (0.66); 7.4204 (0.84); 7.4161 (0.95); 7.4092 (1.09); 7.3916 (0.96); 7.3833 (1.04); 7.3753 (1.26); 7.3697 (2.24); 7.3668 (2.31); 7.3494 (0.46); 7.3447 (0.58); 7.2622 (13.27); 7.2093 (0.48); 7.2037 (0.55); 7.2010 (0.58); 7.1959 (0.54); 7.1818 (1.16); 7.1740 (1.97); 7.1593 (0.69); 7.1505 (0.70); 7.1425 (0.38); 7.0029 (1.55); 6.9786 (1.46); 5.3012 (2.73); 5.2941 (7.16); 3.1072 (0.41); 3.0941 (16.00); 1.5679 (0.47); 1.5257 (41.12); 1.4635 (0.34); 1.4433 (8.40); −0.0002 (7.32)

Example 207, Solvent: DMSO, Spectrometer: 400.13 MHz 10.1215 (6.72); 7.8362 (1.44); 7.8152 (4.05); 7.7981 (5.62); 7.7940 (5.07); 7.7903 (5.55); 7.7730 (1.72); 7.7694 (1.12); 7.7248 (6.08); 7.7209 (3.06); 7.7121 (1.93); 7.7070 (7.83); 7.7033 (5.52); 7.5771 (0.61); 7.5741 (1.08); 7.5709 (0.73); 7.5623 (0.89); 7.5557 (3.78); 7.5500 (1.15); 7.5409 (2.15); 7.5376 (3.34); 7.5342 (1.75); 7.5100 (5.71); 7.4948 (3.76); 7.4909 (7.02); 7.4775 (1.12); 7.4734 (2.70); 7.4700 (1.55); 7.0981 (3.21); 7.0946 (3.22); 7.0812 (3.06); 7.0776 (2.98); 5.3434 (13.84); 4.8874 (0.98); 4.8720 (1.46); 4.8583 (1.41); 4.8547 (1.50); 4.8394 (1.01); 3.5303 (1.75); 3.5122 (6.02); 3.4940 (6.13); 3.4759 (1.90); 3.4628 (8.00); 3.3926 (0.68); 3.3623 (579.30); 3.3382 (1.37); 3.3297 (0.78); 3.3253 (0.75); 3.3123 (6.40); 2.8081 (2.87); 2.8015 (6.71); 2.7949 (2.94); 2.6835 (0.34); 2.6790 (0.50); 2.6744 (0.35); 2.5689 (0.36); 2.5645 (0.75); 2.5600 (1.03); 2.5555 (0.74); 2.5509 (0.37); 2.5323 (1.30); 2.5275 (2.21); 2.5188 (29.41); 2.5144 (61.47); 2.5099 (83.77); 2.5054 (59.95); 2.5011 (27.90); 2.4691 (0.57); 2.4645 (0.81); 2.4600 (0.99); 2.4554 (0.72); 2.3414 (0.40); 2.3368 (0.55); 2.3323 (0.42); 2.2867 (1.91); 2.2801 (2.07); 2.2678 (4.04); 2.2614 (3.84); 2.2501 (2.37); 2.2436 (2.18); 1.7945 (0.62); 1.7773 (1.26); 1.7596 (2.65); 1.7510 (0.87); 1.7415 (2.98); 1.7241 (2.67); 1.7046 (1.15); 1.6904 (0.48); 1.3029 (0.41); 1.2929 (0.39); 1.2869 (0.52); 1.2585 (14.74); 1.2429 (15.24); 1.0647 (7.01); 1.0466 (16.00); 1.0284 (6.85); 0.8798 (0.69); 0.8630 (2.19); 0.8454 (0.86)

Example 208, Solvent: DMSO, Spectrometer: 399.95 MHz 10.4914 (1.95); 8.0795 (1.27); 8.0589 (1.49); 7.9534 (0.57); 7.8298 (1.25); 7.8106 (1.73); 7.7902 (1.19); 7.7256 (1.98); 7.7230 (2.57); 7.7192 (1.25); 7.7104 (0.82); 7.7053 (3.47); 7.7015 (2.34); 7.5640 (0.49); 7.5521 (0.37); 7.5457 (1.63); 7.5400 (0.48); 7.5307 (0.88); 7.5274 (1.42); 7.5240 (0.70); 7.4961 (2.40); 7.4926 (1.00); 7.4807 (1.68); 7.4770 (3.06); 7.4634 (0.49); 7.4593 (1.23); 7.4561 (0.67); 7.1404 (1.73); 7.1230 (1.69); 5.3542 (6.07); 3.3300 (53.86); 3.0544 (16.00); 2.8910 (4.71); 2.7324 (3.77); 2.7313 (3.66); 2.5255 (0.57); 2.5206 (0.96); 2.5121 (10.93); 2.5076 (21.56); 2.5030 (28.24); 2.4984 (20.40); 2.4939 (9.59); 2.2748 (3.13); 2.2572 (3.26); 1.7590 (0.35); 1.7501 (0.45); 1.7418 (0.38); 1.7319 (0.32); 1.6732 (1.45); 1.6665 (1.45); 1.6415 (1.86); 1.5830 (0.45); 1.2343 (0.68); 1.2257 (0.72); 1.2014 (0.76); 1.1946 (0.91); 1.1636 (0.87); 1.1335 (0.51); 1.1032 (0.35); 1.0019 (0.38); 0.9960 (0.45); 0.9671 (0.99); 0.9405 (0.81); 0.8758 (0.44); −0.0002 (5.71)

Example 210, Solvent: DMSO, Spectrometer: 399.95 MHz 10.2465 (2.58); 7.9533 (0.56); 7.8237 (0.58); 7.8067 (0.53); 7.8026 (1.81); 7.7856 (3.42); 7.7803 (2.40); 7.7634 (0.64); 7.7593 (0.35); 7.7305 (0.32); 7.7250 (1.97); 7.7223 (2.58); 7.7185 (1.27); 7.7098 (0.81); 7.7046 (3.42); 7.7009 (2.39); 7.5626 (0.48); 7.5507 (0.37); 7.5443 (1.63); 7.5386 (0.50); 7.5293 (0.88); 7.5260 (1.42); 7.5226 (0.73); 7.4951 (2.38); 7.4917 (1.04); 7.4798 (1.66); 7.4760 (3.07); 7.4624 (0.49); 7.4584 (1.23); 7.4551 (0.69); 7.2617 (1.60); 7.2454 (1.83); 7.2098 (0.35); 7.2040 (0.83); 7.1851 (2.07); 7.1664 (1.43); 7.1162 (1.95); 7.1055 (1.55); 7.1013 (1.67); 7.0928 (1.72); 7.0890 (2.12); 7.0848 (1.62); 7.0741 (0.95); 7.0387 (1.16); 7.0200 (0.90); 5.3317 (6.15); 4.4018 (0.68); 4.3848 (0.32); 4.2879 (1.61); 4.2705 (3.66); 4.2531 (1.67); 3.3314 (67.99); 3.0619 (16.00); 2.9517 (0.48); 2.9070 (1.42); 2.8902 (7.30); 2.8724 (1.34); 2.7321 (3.71); 2.7309 (3.66); 2.5250 (0.65); 2.5201 (1.10); 2.5117 (11.88); 2.5072 (23.41); 2.5025 (30.75); 2.4979 (22.38); 2.4934 (10.71); 2.2922 (1.58); 2.2788 (10.11); −0.0002 (6.38)

Example 211, Solvent: DMSO, Spectrometer: 400.13 MHz 10.5300 (2.16); 8.0820 (1.25); 8.0613 (1.47); 7.8411 (1.22); 7.8217 (1.74); 7.8016 (1.11); 7.4233 (1.03); 7.4034 (2.19); 7.3833 (1.59); 7.2856 (1.43); 7.2833 (1.28); 7.2661 (1.17); 7.2639 (0.98); 7.2455 (1.54); 7.2395 (1.39); 7.2354 (2.84); 7.1463 (2.84); 7.1400 (1.14); 7.1382 (1.10); 7.1268 (2.18); 7.1193 (0.92); 5.3602 (5.94); 3.7893 (16.00); 3.3436 (40.59); 3.0438 (14.80); 2.5610 (0.36); 2.5321 (1.09); 2.5187 (16.41); 2.5143 (33.34); 2.5099 (45.01); 2.5054 (32.39); 2.5011 (15.25); 2.4608 (0.40); 2.3960 (1.63); 2.3776 (3.06); 2.3591 (1.76); 1.6129 (0.36); 1.5943 (1.09); 1.5759 (1.51); 1.5581 (1.05); 1.5397 (0.35); 1.3252 (0.38); 1.3092 (0.85); 1.2925 (1.70); 1.2850 (2.49); 1.2777 (2.12); 1.2677 (1.76); 1.2575 (1.37); 1.2472 (0.90); 0.8864 (2.49); 0.8694 (6.22); 0.8516 (2.57)

Example 212, Solvent: DMSO, Spectrometer: 399.95 MHz 12.7329 (1.22); 7.9533 (1.66); 7.7494 (1.84); 7.7465 (2.48); 7.7425 (1.20); 7.7342 (0.74); 7.7290 (3.27); 7.7252 (2.24); 7.6770 (1.30); 7.6745 (1.29); 7.6713 (1.59); 7.6670 (1.88); 7.6652 (1.78); 7.6608 (2.96); 7.6587 (1.90); 7.5685 (0.44); 7.5502 (1.55); 7.5442 (0.47); 7.5356 (0.88); 7.5321 (1.45); 7.5286 (0.72); 7.5079 (2.34); 7.5045 (1.00); 7.4930 (1.48); 7.4889 (2.85); 7.4720 (2.20); 7.4678 (0.80); 7.4624 (0.34); 7.4520 (2.53); 7.4315 (1.35); 7.3830 (3.66); 7.2063 (0.90); 7.2041 (0.98); 7.2000 (0.92); 7.1978 (0.89); 7.1857 (0.79); 7.1832 (0.78); 7.1796 (0.81); 7.1771 (0.72); 5.3863 (5.28); 3.8427 (16.00); 3.3389 (84.95); 3.0183 (15.32); 2.8912 (13.52); 2.7326 (10.94); 2.7314 (10.57); 2.5260 (0.60); 2.5212 (0.97); 2.5126 (11.52); 2.5081 (22.90); 2.5035 (30.01); 2.4989 (21.67); 2.4943 (10.22); −0.0002 (5.68)

Example 213, Solvent: DMSO, Spectrometer: 399.95 MHz 12.4033 (1.18); 7.9526 (1.06); 7.7378 (2.75); 7.7339 (1.35); 7.7253 (0.81); 7.7202 (3.49); 7.7164 (2.47); 7.5661 (0.49); 7.5629 (0.33); 7.5546 (0.35); 7.5477 (1.68); 7.5419 (0.51); 7.5330 (0.94); 7.5297 (1.52); 7.5262 (0.78); 7.5038 (2.55); 7.5006 (1.14); 7.4886 (1.66); 7.4848 (3.17); 7.4714 (0.50); 7.4673 (1.22); 7.4638 (0.70); 7.3316 (4.68); 7.1725 (1.12); 7.1543 (1.28); 7.1436 (0.59); 7.1407 (0.51); 7.1244 (1.16); 7.1045 (0.72); 7.1014 (0.62); 6.8819 (0.97); 6.8636 (1.65); 6.8466 (0.74); 6.8450 (0.74); 6.8173 (1.68); 6.7970 (1.50); 5.3395 (6.05); 4.8670 (7.56); 3.3370 (92.18); 3.0230 (16.00); 2.8901 (8.26); 2.7317 (6.57); 2.7308 (6.65); 2.5249 (0.64); 2.5115 (13.25); 2.5071 (26.45); 2.5025 (34.92); 2.4979 (25.57); 2.4934 (12.40); 2.2229 (10.86); −0.0002 (2.10)

Example 214, Solvent: DMSO, Spectrometer: 300.16 MHz 9.8147 (0.73); 8.1638 (0.91); 7.8000 (0.36); 7.7861 (0.35); 7.7719 (0.62); 7.7626 (0.45); 7.7487 (0.78); 7.7326 (0.75); 7.7087 (0.33); 7.6790 (0.62); 7.6607 (0.76); 7.6492 (0.75); 7.6382 (0.36); 7.6311 (0.69); 7.3100 (0.73); 7.2803 (1.54); 7.2737 (2.64); 7.2706 (2.35); 7.2509 (0.63);

NMR Peak List Table 1

7.1221 (0.49); 7.1190 (0.49); 7.0993 (0.41); 5.2502 (1.74); 5.1466 (0.34); 4.0590 (0.32); 4.0353 (0.33); 2.5332 (0.71); 2.5274 (1.48); 2.5215 (2.02); 2.5155 (1.48); 2.5098 (0.72); 2.0079 (1.37); 1.4982 (1.79); 1.4791 (16.00); 1.3561 (0.34); 1.2163 (0.37); 1.1926 (0.73); 1.1688 (0.36)
Example 215, Solvent: DMSO, Spectrometer: 400.13 MHz 10.2011 (3.15); 7.8365 (0.44); 7.8155 (2.34); 7.8071 (2.56); 7.8010 (5.59); 7.7862 (0.48); 7.5384 (2.33); 7.5234 (0.69); 7.5189 (0.59); 7.5143 (0.99); 7.5111 (1.03); 7.5017 (0.95); 7.3894 (0.34); 7.3699 (2.52); 7.3580 (3.35); 7.3560 (3.24); 7.0972 (1.36); 7.0908 (1.34); 7.0829 (1.18); 7.0765 (1.29); 5.7684 (0.63); 5.3282 (6.96); 4.1125 (2.20); 4.0959 (4.67); 4.0793 (2.24); 3.4034 (2.72); 3.3533 (187.35); 3.3261 (0.66); 3.3033 (2.15); 3.0728 (0.40); 3.0584 (16.00); 2.6788 (0.36); 2.5643 (0.55); 2.5598 (0.76); 2.5553 (0.54); 2.5320 (0.95); 2.5183 (21.78); 2.5142 (44.85); 2.5098 (60.71); 2.5054 (44.01); 2.4688 (0.41); 2.4643 (0.59); 2.4598 (0.70); 2.4552 (0.51); 2.3375 (11.57); 1.6317 (0.47); 1.6147 (1.51); 1.6083 (0.56); 1.5973 (1.94); 1.5776 (1.60); 1.5609 (0.66); 1.4187 (0.34); 1.4000 (1.17); 1.3810 (1.87); 1.3622 (1.88); 1.3440 (1.11); 1.3258 (0.33); 0.9317 (4.32); 0.9134 (8.71); 0.8949 (3.74)
Example 216, Solvent: DMSO, Spectrometer: 399.95 MHz 12.5582 (1.05); 7.9544 (1.11); 7.7470 (0.32); 7.7413 (2.15); 7.7387 (2.76); 7.7347 (1.32); 7.7262 (0.86); 7.7210 (3.62); 7.7172 (2.52); 7.5674 (0.49); 7.5560 (0.36); 7.5491 (1.76); 7.5432 (0.51); 7.5344 (0.97); 7.5310 (1.57); 7.5275 (0.78); 7.5049 (2.60); 7.5016 (1.11); 7.4899 (1.71); 7.4859 (3.25); 7.4721 (0.83); 7.4683 (1.54); 7.4629 (4.55); 7.4574 (1.28); 7.4458 (1.34); 7.4403 (4.55); 7.4316 (0.41); 7.3404 (4.75); 6.9039 (0.43); 6.8952 (4.38); 6.8896 (1.27); 6.8781 (1.27); 6.8725 (4.02); 6.8638 (0.35); 5.3399 (5.85); 5.0656 (0.39); 5.0491 (1.47); 5.0325 (1.49); 5.0160 (0.40); 3.3352 (22.31); 3.0226 (16.00); 3.0128 (0.57); 2.8912 (8.97); 2.7333 (7.30); 2.5220 (0.50); 2.5135 (6.25); 2.5090 (12.45); 2.5044 (16.32); 2.4998 (11.74); 2.4953 (5.52); 1.5486 (5.61); 1.5321 (5.54); −0.0002 (6.50)
Example 217, Solvent: DMSO, Spectrometer: 399.95 MHz 10.7035 (2.17); 8.1584 (1.52); 8.1385 (1.80); 8.0607 (0.41); 8.0534 (3.55); 8.0483 (1.09); 8.0362 (1.12); 8.0310 (3.79); 8.0237 (0.39); 7.9032 (2.27); 7.8982 (0.43); 7.8814 (2.19); 7.8633 (1.17); 7.7391 (1.86); 7.7365 (2.49); 7.7326 (1.22); 7.7239 (0.74); 7.7188 (3.28); 7.7150 (2.28); 7.5676 (0.47); 7.5558 (0.34); 7.5493 (1.59); 7.5436 (0.49); 7.5344 (0.85); 7.5310 (1.40); 7.5276 (0.72); 7.5015 (2.31); 7.4981 (1.00); 7.4862 (1.56); 7.4824 (2.94); 7.4689 (0.47); 7.4648 (1.19); 7.4615 (0.66); 7.3845 (0.61); 7.3625 (0.68); 7.2064 (1.66); 7.1889 (1.60); 7.0537 (0.41); 7.0465 (3.74); 7.0413 (1.12); 7.0350 (0.33); 7.0281 (2.08); 7.0241 (3.79); 7.0167 (0.40); 7.0109 (0.36); 7.0057 (1.09); 6.9765 (0.68); 6.9545 (0.58); 5.4143 (5.66); 3.8499 (0.99); 3.8405 (16.00); 3.8284 (0.59); 3.8236 (5.06); 3.7995 (0.60); 3.7894 (2.83); 3.3430 (69.40); 3.0831 (15.12); 2.9456 (2.95); 2.8910 (2.46); 2.7848 (0.45); 2.7498 (0.58); 2.7325 (1.96); 2.7313 (1.94); 2.5261 (0.61); 2.5213 (0.96); 2.5127 (12.40); 2.5082 (24.80); 2.5036 (32.75); 2.4990 (23.81); 2.4945 (11.31); −0.0002 (2.77)
Example 218, Solvent: DMSO, Spectrometer: 399.95 MHz 10.4625 (2.01); 8.0034 (1.43); 7.9831 (1.88); 7.9533 (0.39); 7.8580 (1.31); 7.8387 (1.79); 7.8185 (1.11); 7.7185 (2.58); 7.7147 (1.24); 7.7058 (0.86); 7.7007 (3.40); 7.6969 (2.40); 7.5632 (0.49); 7.5511 (0.36); 7.5449 (1.63); 7.5393 (0.48); 7.5299 (0.86); 7.5266 (1.40); 7.5232 (0.72); 7.5071 (1.65); 7.5030 (2.25); 7.4932 (2.71); 7.4896 (2.35); 7.4861 (2.95); 7.4836 (2.50); 7.4778 (1.97); 7.4741 (3.20); 7.4605 (0.51); 7.4564 (1.26); 7.4533 (0.72); 7.3952 (0.80); 7.3909 (1.14); 7.3864 (0.48); 7.3738 (3.05); 7.3698 (1.30); 7.3554 (2.17); 7.3495 (0.42); 7.3454 (0.89); 7.3416 (1.60); 7.3378 (0.87); 7.3309 (0.47); 7.3241 (1.43); 7.3059 (0.37); 7.1874 (1.78); 7.1696 (1.70); 5.3745 (6.07); 5.0204 (3.59); 3.3353 (28.56); 3.3316 (77.85); 3.2150 (0.44); 3.0702 (0.39); 3.0548 (16.00); 2.8903 (3.14); 2.7319 (2.49); 2.7309 (2.46); 2.5251 (0.63); 2.5203 (1.02); 2.5118 (13.84); 2.5073 (27.81); 2.5027 (36.70); 2.4981 (26.57); 2.4935 (12.61); 0.0079 (0.46); −0.0002 (13.90); −0.0086 (0.42)
Example 219, Solvent: DMSO, Spectrometer: 399.95 MHz 12.3592 (1.32); 7.9533 (0.68); 7.7409 (1.96); 7.7382 (2.70); 7.7343 (1.37); 7.7258 (0.85); 7.7206 (3.52); 7.7168 (2.52); 7.5664 (0.50); 7.5631 (0.33); 7.5549 (0.36); 7.5480 (1.71); 7.5422 (0.55); 7.5334 (0.96); 7.5299 (1.57); 7.5264 (0.83); 7.5038 (2.57); 7.5005 (1.17); 7.4888 (1.66); 7.4848 (3.19); 7.4714 (0.58); 7.4673 (1.33); 7.4638 (0.78); 7.3323 (4.48); 7.0164 (0.90); 7.0128 (1.01); 6.9962 (1.87); 6.9925 (1.84); 6.9649 (0.89); 6.9599 (1.00); 6.9477 (1.11); 6.9428 (1.33); 6.9275 (0.64); 6.9226 (0.78); 6.8840 (0.56); 6.8792 (0.83); 6.8640 (2.19); 6.8592 (1.79); 6.8513 (1.54); 6.8476 (1.51); 6.8341 (1.13); 6.8304 (1.24); 6.8141 (0.47); 6.8102 (0.56); 5.3384 (5.74); 4.9686 (0.39); 4.9521 (1.50); 4.9354 (1.53); 4.9188 (0.43); 3.7803 (15.50); 3.3322 (39.87); 3.0186 (16.00); 2.8903 (5.50); 2.7322 (4.29); 2.7310 (4.44); 2.5254 (0.43); 2.5206 (0.68); 2.5120 (8.09); 2.5075 (16.53); 2.5029 (22.20); 2.4983 (16.46); 2.4938 (8.35); 1.5410 (5.49); 1.5244 (5.58); −0.0002 (4.39)
Example 220, Solvent: DMSO, Spectrometer: 400.13 MHz 7.7516 (2.80); 7.7338 (3.40); 7.7300 (2.55); 7.5760 (0.59); 7.5729 (0.47); 7.5645 (0.53); 7.5576 (1.83); 7.5519 (0.74); 7.5428 (1.18); 7.5396 (1.71); 7.5363 (1.09); 7.5131 (3.48); 7.5098 (2.53); 7.4980 (2.72); 7.4941 (4.04); 7.4868 (1.96); 7.4809 (1.58); 7.4765 (2.09); 7.4665 (2.66); 7.4470 (2.14); 7.3462 (2.33); 7.3286 (2.42); 5.7603 (5.19); 5.3835 (3.93); 4.0432 (0.38); 4.0253 (0.38); 3.3241 (11.73); 3.2913 (0.73); 3.0156 (16.00); 2.5157 (10.03); 2.5114 (19.41); 2.5069 (25.78); 2.5025 (18.91); 2.4982 (9.74); 1.9934 (1.62); 1.2390 (0.35); 1.1972 (0.47); 1.1794 (0.87); 1.1616 (0.44)
Example 221, Solvent: DMSO, Spectrometer: 399.95 MHz 9.7726 (1.32); 8.0140 (1.09); 7.9940 (1.36); 7.8377 (0.93); 7.8186 (1.24); 7.7982 (0.83); 7.7246 (1.90); 7.7207 (0.96); 7.7120 (0.61); 7.7068 (2.55); 7.7030 (1.73); 7.5640 (0.34); 7.5457 (1.16); 7.5400 (0.39); 7.5308 (0.62); 7.5274 (1.00); 7.5241 (0.54); 7.4960 (1.77); 7.4927 (0.77); 7.4806 (1.22); 7.4769 (2.26); 7.4633 (0.36); 7.4592 (0.90); 7.4560 (0.51); 7.1523 (1.24); 7.1347 (1.19); 5.3791 (4.39); 3.3293 (39.08); 3.0881 (0.67); 3.0728 (10.99); 2.8909 (1.10); 2.7321 (0.82); 2.7314 (0.83); 2.5252 (0.36); 2.5204 (0.60); 2.5119 (7.76); 2.5074 (15.47); 2.5028 (20.42); 2.4982 (14.82); 2.4937 (7.08); 1.6926 (0.46); 1.6739 (1.57); 1.6552 (1.66); 1.6367 (0.54); 1.2342 (0.41); 1.1827 (16.00); 0.8759 (0.37); 0.7918 (1.95); 0.7734 (4.41); 0.7546 (1.80); −0.0002 (5.77)
Example 222, Solvent: DMSO, Spectrometer: 399.95 MHz 8.5738 (2.41); 7.9525 (1.26); 7.9479 (1.67); 7.9270 (2.16); 7.8491 (1.43); 7.8301 (1.83); 7.8097 (1.07); 7.6954 (2.56); 7.6917 (1.25); 7.6822 (3.74); 7.6772 (5.94); 7.6741 (2.68); 7.6205 (2.37); 7.5997 (3.24); 7.5790 (1.50); 7.5497 (0.38); 7.5436 (1.66); 7.5380 (0.48); 7.5285 (0.88); 7.5252 (1.38); 7.5219 (0.68); 7.4951 (2.62); 7.4901 (3.70); 7.4744 (3.09); 7.4716 (3.48); 7.4692 (2.48); 7.4579 (0.52); 7.4539 (1.24); 7.4508 (0.69); 7.1560 (1.77); 7.1376 (1.72); 5.3008 (6.18); 3.3416 (164.31); 3.0054 (16.00); 2.8912 (9.12); 2.7323 (7.55); 2.5258 (0.81); 2.5209 (1.29); 2.5124 (15.83); 2.5079 (31.43); 2.5033 (41.17); 2.4987 (29.73); 2.4942 (14.01); 1.6912 (0.88); 1.6804 (2.43); 1.6730 (2.57); 1.6628 (0.91); 1.2167 (1.03); 1.2064 (2.45); 1.1990 (2.45); 1.1883 (0.87); −0.0002 (4.60)
Example 223, Solvent: DMSO, Spectrometer: 400.13 MHz 10.0714 (2.63); 7.8267 (0.37); 7.8057 (2.13); 7.7975 (2.44); 7.7913 (5.42); 7.7766 (0.48); 7.5376 (2.16); 7.5222 (0.62); 7.5175 (0.54); 7.5136 (0.92); 7.5102 (0.98); 7.5046 (0.59); 7.5008 (0.90); 7.4962 (0.66); 7.3885 (0.33); 7.3694 (2.27); 7.3634 (1.53); 7.3575 (3.16); 7.3550 (3.12); 7.0922 (1.26); 7.0856 (1.22); 7.0779 (1.12); 7.0714 (1.20); 5.7640 (3.25); 5.3237 (6.55); 4.9274 (0.43); 4.9146 (0.58); 4.9121 (0.58); 4.9061 (0.55); 4.8993 (0.56); 4.8933 (0.59); 4.8780 (0.44); 3.3275 (11.77); 3.3047 (0.75); 3.0654 (16.00); 2.5322 (0.33); 2.5187 (7.70); 2.5143 (15.83); 2.5098 (21.48); 2.5053 (15.33); 2.5008 (7.18); 2.3394 (10.43); 1.6989 (0.49); 1.6803 (0.60); 1.6636 (0.57); 1.6472 (0.36); 1.5939 (0.54); 1.5791

NMR Peak List Table 1

(0.43); 1.5725 (0.56); 1.5592 (0.89); 1.5448 (0.60); 1.5382 (0.70); 1.5234 (0.54); 1.3592 (0.64); 1.3469 (0.71); 1.3391 (0.60); 1.3259 (0.94); 1.3126 (0.53); 1.3048 (0.55); 1.2923 (0.52); 1.2477 (0.81); 1.2371 (6.90); 1.2216 (6.73); 0.9042 (9.66); 0.9030 (9.64); 0.8876 (9.68); 0.8652 (0.97); 0.8475 (0.40)
Example 224, Solvent: DMSO, Spectrometer: 400.13 MHz 10.1980 (3.39); 7.8358 (0.41); 7.8147 (2.34); 7.8062 (2.58); 7.8002 (5.62); 7.7854 (0.50); 7.5391 (2.45); 7.5237 (0.72); 7.5147 (1.02); 7.5115 (1.07); 7.5019 (1.01); 7.3891 (0.34); 7.3697 (2.62); 7.3573 (3.50); 7.0973 (1.39); 7.0910 (1.36); 7.0829 (1.22); 7.0766 (1.33); 5.7683 (4.33); 5.3284 (7.17); 4.1036 (2.10); 4.0868 (4.54); 4.0701 (2.17); 3.4000 (1.14); 3.3497 (84.51); 3.3260 (0.53); 3.2994 (1.10); 3.0734 (0.39); 3.0591 (16.00); 2.5646 (0.34); 2.5601 (0.45); 2.5319 (0.57); 2.5141 (30.36); 2.5097 (41.01); 2.5054 (29.94); 2.4686 (0.34); 2.4639 (0.48); 2.4595 (0.56); 2.4550 (0.38); 2.3375 (11.99); 1.9964 (0.43); 1.6310 (1.02); 1.6137 (1.65); 1.5967 (1.19); 1.5796 (0.38); 1.3485 (1.17); 1.3380 (2.06); 1.3307 (4.06); 1.3216 (3.23); 1.3127 (2.74); 1.2510 (0.54); 0.9036 (2.02); 0.8863 (5.30); 0.8686 (1.84); 0.8643 (1.22); 0.8462 (0.38)
Example 225, Solvent: DMSO, Spectrometer: 399.95 MHz 10.1956 (2.22); 7.8322 (0.50); 7.8112 (1.95); 7.7954 (3.65); 7.7935 (3.12); 7.7773 (0.55); 7.7256 (2.01); 7.7229 (2.56); 7.7191 (1.23); 7.7104 (0.83); 7.7052 (3.34); 7.7015 (2.26); 7.5628 (0.49); 7.5510 (0.39); 7.5445 (1.63); 7.5387 (0.49); 7.5296 (0.90); 7.5262 (1.42); 7.5228 (0.72); 7.4959 (2.39); 7.4925 (1.00); 7.4806 (1.70); 7.4768 (3.04); 7.4633 (0.51); 7.4591 (1.21); 7.4559 (0.65); 7.1031 (1.30); 7.0981 (1.30); 7.0874 (1.19); 7.0824 (1.22); 5.3352 (6.27); 3.8862 (4.75); 3.8695 (4.79); 3.3373 (121.73); 3.0652 (16.00); 2.8909 (2.35); 2.7322 (1.87); 2.7312 (1.83); 2.5254 (0.77); 2.5121 (14.62); 2.5076 (29.05); 2.5030 (38.16); 2.4984 (27.63); 2.4938 (13.18); 1.9416 (0.40); 1.9248 (0.83); 1.9081 (1.06); 1.8913 (0.85); 1.8746 (0.43); 1.2347 (0.32); 0.9272 (14.67); 0.9104 (14.23); 0.8980 (0.66); −0.0002 (6.10)
Example 226, Solvent: DMSO, Spectrometer: 400.13 MHz 10.2218 (3.02); 7.8377 (0.71); 7.8167 (1.86); 7.7995 (2.39); 7.7932 (2.26); 7.7901 (2.53); 7.7724 (0.83); 7.7692 (0.58); 7.7302 (2.78); 7.7171 (0.84); 7.7122 (3.46); 7.7085 (2.45); 7.5686 (0.50); 7.5656 (0.32); 7.5566 (0.40); 7.5503 (1.73); 7.5447 (0.53); 7.5353 (0.95); 7.5321 (1.45); 7.5289 (0.75); 7.5016 (2.50); 7.4859 (1.73); 7.4823 (3.19); 7.4686 (0.45); 7.4647 (1.20); 7.4616 (0.70); 7.1152 (1.49); 7.1120 (1.51); 7.0981 (1.44); 7.0949 (1.40); 5.7683 (0.91); 5.3344 (6.56); 4.9204 (0.64); 4.9051 (1.36); 4.8896 (1.37); 4.8743 (0.63); 3.4000 (1.26); 3.3505 (106.77); 3.3008 (1.03); 3.0791 (16.00); 2.9380 (1.30); 2.9314 (3.01); 2.9249 (1.33); 2.5636 (0.42); 2.5591 (0.59); 2.5546 (0.47); 2.5499 (0.35); 2.5375 (2.16); 2.5314 (2.82); 2.5183 (17.62); 2.5142 (34.59); 2.5097 (45.30); 2.5052 (32.26); 2.5009 (15.00); 2.4645 (0.37); 2.4599 (0.48); 2.4556 (0.38); 1.3707 (0.74); 1.3200 (6.79); 1.3042 (6.76)
Example 227, Solvent: DMSO, Spectrometer: 399.95 MHz 10.3769 (2.12); 8.0203 (1.54); 8.0001 (2.07); 7.9530 (0.94); 7.8853 (1.40); 7.8659 (1.92); 7.8458 (1.15); 7.7280 (2.72); 7.7151 (0.85); 7.7101 (3.50); 7.7063 (2.50); 7.5663 (0.50); 7.5631 (0.33); 7.5543 (0.38); 7.5479 (1.73); 7.5423 (0.51); 7.5329 (0.91); 7.5297 (1.46); 7.5264 (0.77); 7.4980 (2.53); 7.4824 (1.75); 7.4788 (3.27); 7.4651 (0.54); 7.4611 (1.29); 7.4580 (0.74); 7.3286 (0.71); 7.3242 (0.87); 7.3064 (1.40); 7.2330 (0.75); 7.2286 (0.63); 7.2166 (2.17); 7.2123 (3.66); 7.2078 (2.41); 7.2021 (2.00); 7.1943 (3.30); 7.1863 (0.89); 7.1709 (0.38); 5.4621 (2.62); 5.3902 (6.51); 4.3243 (0.42); 4.3113 (0.77); 4.2972 (0.89); 4.2828 (0.88); 4.2702 (0.49); 3.9033 (0.48); 3.8924 (0.66); 3.8846 (0.59); 3.8744 (0.88); 3.8645 (0.55); 3.8567 (0.57); 3.8458 (0.46); 3.3316 (69.84); 3.0853 (0.63); 3.0755 (16.00); 2.9850 (0.34); 2.9798 (0.33); 2.9566 (0.44); 2.9434 (0.54); 2.9387 (0.53); 2.9261 (0.38); 2.8903 (7.59); 2.8083 (0.40); 2.7962 (0.71); 2.7836 (0.44); 2.7549 (0.48); 2.7313 (6.08); 2.5248 (0.66); 2.5115 (13.88); 2.5070 (27.45); 2.5024 (36.12); 2.4978 (26.26); 2.4934 (12.61); −0.0002 (8.08)
Example 228, Solvent: DMSO, Spectrometer: 400.13 MHz 10.3312 (2.87); 7.8479 (0.61); 7.8269 (1.78); 7.8098 (2.61); 7.8066 (2.36); 7.8027 (2.46); 7.7855 (0.71); 7.7818 (0.44); 7.4213 (1.02); 7.4013 (2.19); 7.3813 (1.58); 7.2835 (1.46); 7.2813 (1.28); 7.2640 (1.21); 7.2619 (1.00); 7.2465 (1.57); 7.2407 (1.98); 7.2365 (1.36); 7.1432 (1.10); 7.1415 (1.15); 7.1369 (1.03); 7.1352 (0.99); 7.1227 (2.32); 7.1200 (2.09); 7.1060 (1.36); 7.1023 (1.31); 5.7685 (0.68); 5.3409 (5.98); 4.1955 (1.97); 4.1789 (4.28); 4.1622 (1.97); 3.7894 (16.00); 3.3943 (0.40); 3.3449 (25.89); 3.0753 (0.38); 3.0602 (14.66); 2.9234 (1.30); 2.9168 (2.93); 2.9102 (1.37); 2.5796 (1.18); 2.5729 (1.25); 2.5630 (2.80); 2.5563 (2.68); 2.5463 (1.26); 2.5396 (1.16); 2.5322 (0.65); 2.5186 (9.84); 2.5143 (19.78); 2.5099 (26.44); 2.5054 (18.87); 2.5011 (8.77); 2.4605 (0.33)
Example 229, Solvent: DMSO, Spectrometer: 399.95 MHz 12.3982 (0.67); 7.9527 (0.74); 7.7410 (2.02); 7.7384 (2.73); 7.7344 (1.32); 7.7260 (0.80); 7.7208 (3.54); 7.7170 (2.45); 7.5667 (0.50); 7.5634 (0.33); 7.5553 (0.35); 7.5483 (1.74); 7.5425 (0.52); 7.5337 (0.95); 7.5303 (1.58); 7.5268 (0.78); 7.5048 (2.58); 7.5013 (1.09); 7.4897 (1.64); 7.4857 (3.18); 7.4724 (0.49); 7.4682 (1.26); 7.4647 (0.69); 7.3301 (4.81); 7.1016 (2.47); 7.0812 (2.92); 6.8624 (0.45); 6.8550 (3.93); 6.8498 (1.19); 6.8384 (1.10); 6.8334 (3.31); 5.3406 (5.96); 4.7940 (7.63); 3.6954 (0.43); 3.3486 (86.86); 3.0357 (0.38); 3.0206 (16.00); 3.0111 (0.61); 2.8904 (6.12); 2.7322 (4.75); 2.7312 (4.80); 2.5261 (0.45); 2.5213 (0.71); 2.5127 (8.80); 2.5082 (17.65); 2.5036 (23.41); 2.4990 (16.97); 2.4944 (8.04); 2.2230 (10.05); −0.0002 (1.03)
Example 230, Solvent: DMSO, Spectrometer: 399.95 MHz 10.9090 (2.21); 8.0883 (1.25); 8.0676 (1.49); 7.8495 (1.30); 7.8301 (1.82); 7.8100 (1.21); 7.7200 (2.78); 7.7162 (1.39); 7.7070 (0.93); 7.7022 (3.52); 7.6984 (2.50); 7.5604 (0.50); 7.5573 (0.33); 7.5484 (0.38); 7.5419 (1.68); 7.5364 (0.51); 7.5271 (0.91); 7.5238 (1.45); 7.5205 (0.76); 7.4927 (2.53); 7.4772 (1.75); 7.4735 (3.21); 7.4599 (0.51); 7.4558 (1.25); 7.4527 (0.73); 7.3123 (1.16); 7.2942 (3.15); 7.2753 (2.45); 7.2162 (1.18); 7.2132 (0.91); 7.1978 (1.71); 7.1927 (0.63); 7.1817 (2.96); 7.1784 (3.48); 7.1607 (2.43); 7.1520 (2.10); 7.1328 (1.81); 5.3541 (6.10); 3.3297 (58.71); 3.0519 (16.00); 2.8903 (1.67); 2.7311 (1.34); 2.5248 (0.69); 2.5135 (12.61); 2.5070 (24.94); 2.5025 (32.88); 2.4979 (24.08); 2.4934 (11.66); 2.4261 (0.35); 2.4161 (0.60); 2.4105 (0.54); 2.4004 (0.80); 2.3935 (0.94); 2.3892 (0.84); 2.3775 (1.29); 2.3694 (0.71); 2.3565 (0.66); 1.5034 (0.51); 1.4929 (0.72); 1.4904 (0.69); 1.4804 (0.96); 1.4705 (0.67); 1.4678 (0.69); 1.4574 (0.52); 1.3763 (0.56); 1.3660 (0.62); 1.3602 (0.69); 1.3559 (0.80); 1.3502 (0.74); 1.3460 (0.60); 1.3399 (0.68); 1.3297 (0.48); 0.8756 (0.43); −0.0002 (6.50)
Example 231, Solvent: DMSO, Spectrometer: 399.95 MHz 10.7963 (2.26); 8.0278 (1.31); 8.0071 (1.72); 7.9529 (0.79); 7.8784 (1.37); 7.8590 (1.92); 7.8389 (1.17); 7.7282 (2.93); 7.7245 (1.59); 7.7104 (3.62); 7.7067 (2.63); 7.5691 (0.52); 7.5660 (0.37); 7.5570 (0.41); 7.5505 (1.74); 7.5452 (0.57); 7.5357 (0.96); 7.5325 (1.52); 7.5293 (0.84); 7.5006 (2.64); 7.4851 (1.91); 7.4814 (3.34); 7.4613 (2.30); 7.4575 (1.90); 7.4416 (1.73); 7.4377 (1.73); 7.2908 (0.73); 7.2868 (0.73); 7.2700 (1.27); 7.2685 (1.29); 7.2663 (1.15); 7.2514 (0.99); 7.2474 (0.93); 7.2101 (1.99); 7.1916 (1.89); 7.0172 (1.50); 7.0144 (1.78); 6.9963 (1.41); 6.9935 (1.50); 6.9875 (1.16); 6.9843 (0.97); 6.9681 (1.66); 6.9652 (1.45); 6.9492 (0.86); 6.9460 (0.79); 5.3872 (6.51); 5.1665 (0.33); 5.1503 (1.11); 5.1337 (1.11); 5.1174 (0.35); 5.1337 (1.11); 3.3803 (0.39); 3.3414 (130.53); 3.0658 (16.00); 3.0355 (0.46); 2.8907 (6.04); 2.7314 (5.07); 2.5258 (0.73); 2.5123 (14.56); 2.5080 (28.22); 2.5035 (36.82); 2.4989 (27.18); 2.4945 (13.39); 1.5828 (5.84); 1.5664 (5.80); −0.0002 (1.18)
Example 232, Solvent: DMSO, Spectrometer: 399.95 MHz 10.7787 (1.95); 8.0189 (1.31); 7.9983 (1.69); 7.9532 (0.55); 7.8653 (1.35); 7.8461 (1.83); 7.8258 (1.16); 7.7272 (2.57); 7.7234 (1.25); 7.7145 (0.74); 7.7094 (3.36); 7.7057 (2.40); 7.5689 (0.48); 7.5569 (0.35); 7.5506 (1.66); 7.5449 (0.47); 7.5356 (0.85); 7.5323 (1.41); 7.5289 (0.72);

NMR Peak List Table 1

7.5003 (2.42); 7.4970 (1.03); 7.4848 (1.62); 7.4811 (3.12); 7.4675 (0.47); 7.4635 (1.23); 7.4603 (0.70); 7.2993 (1.74); 7.2941 (0.64); 7.2795 (2.38); 7.2775 (2.63); 7.2642 (0.73); 7.2592 (2.22); 7.1981 (1.82); 7.1803 (1.74); 6.9484 (0.98); 6.9463 (0.76); 6.9304 (2.22); 6.9270 (3.58); 6.9243 (3.02); 6.9093 (1.68); 6.9048 (3.02); 5.3845 (6.13); 5.0939 (0.33); 5.0770 (1.15); 5.0605 (1.16); 5.0441 (0.33); 3.3446 (117.32); 3.0603 (16.00); 2.8909 (4.49); 2.7323 (3.65); 2.7313 (3.50); 2.5261 (0.52); 2.5214 (0.82); 2.5128 (11.33); 2.5083 (23.02); 2.5037 (30.58); 2.4991 (22.28); 2.4946 (10.69); 1.5360 (5.77); 1.5196 (5.72); −0.0002 (0.43)
Example 233, Solvent: DMSO, Spectrometer: 400.13 MHz 9.8433 (1.76); 7.8017 (0.42); 7.7807 (1.17); 7.7635 (1.52); 7.7578 (1.37); 7.7544 (1.57); 7.7368 (0.69); 7.7329 (1.58); 7.7303 (1.75); 7.7264 (0.84); 7.7177 (0.51); 7.7125 (2.21); 7.7088 (1.56); 7.5515 (1.08); 7.5458 (0.33); 7.5366 (0.58); 7.5332 (0.95); 7.5299 (0.48); 7.5030 (1.56); 7.4997 (0.69); 7.4876 (1.05); 7.4839 (1.99); 7.4662 (0.78); 7.4630 (0.45); 7.0807 (0.91); 7.0773 (0.93); 7.0637 (0.88); 7.0603 (0.87); 5.7638 (0.90); 5.3261 (4.14); 3.3823 (0.95); 3.3324 (57.48); 3.3086 (0.49); 3.2824 (0.64); 3.0700 (10.61); 2.5275 (0.43); 2.5189 (6.42); 2.5144 (13.43); 2.5099 (18.41); 2.5054 (13.05); 2.5009 (6.05); 1.7497 (0.75); 1.7375 (0.59); 1.7292 (0.73); 1.7186 (0.63); 1.7080 (0.96); 1.4418 (16.00); 1.4017 (0.48); 1.3916 (0.52); 1.3827 (0.66); 1.3716 (1.01); 1.3611 (0.63); 1.3542 (0.40); 1.3419 (0.43); 0.9098 (1.87); 0.8917 (3.99); 0.8732 (1.65)
Example 234, Solvent: DMSO, Spectrometer: 400.13 MHz 12.5653 (1.63); 7.6272 (1.07); 7.6216 (1.06); 7.6183 (0.95); 7.6151 (1.26); 7.6116 (0.90); 7.6064 (0.94); 7.5956 (2.93); 7.5705 (0.78); 7.5564 (0.88); 7.5503 (1.17); 7.5360 (1.22); 7.5309 (0.70); 7.5152 (0.52); 7.4333 (0.58); 7.4306 (0.62); 7.4271 (0.56); 7.4243 (0.54); 7.4096 (1.04); 7.4050 (0.96); 7.3916 (4.93); 7.0153 (1.26); 6.9969 (1.68); 6.9946 (1.59); 6.9161 (0.66); 6.9085 (0.87); 6.9015 (0.93); 6.8938 (1.45); 6.8896 (0.57); 6.8817 (0.73); 6.8746 (1.81); 6.8634 (4.76); 6.8593 (2.94); 6.8484 (1.09); 6.8444 (0.87); 5.7631 (5.16); 5.3684 (5.98); 5.1570 (1.07); 5.1486 (1.99); 5.1388 (1.10); 4.4380 (2.18); 4.4330 (2.40); 4.4277 (2.64); 3.3982 (3.66); 3.3484 (263.44); 3.2987 (2.86); 3.0116 (16.00); 2.6771 (0.37); 2.5622 (0.63); 2.5578 (0.87); 2.5533 (0.67); 2.5486 (0.42); 2.5303 (1.19); 2.5168 (23.67); 2.5125 (47.68); 2.5081 (63.56); 2.5037 (45.37); 2.4994 (21.41); 2.4630 (0.55); 2.4585 (0.70); 2.4539 (0.50); 2.3350 (0.37)
Example 235, Solvent: DMSO, Spectrometer: 399.95 MHz 10.5169 (2.26); 8.0834 (1.34); 8.0627 (1.59); 7.8340 (1.29); 7.8147 (1.83); 7.7945 (1.19); 7.7230 (2.73); 7.7101 (0.89); 7.7051 (3.54); 7.7014 (2.49); 7.5638 (0.51); 7.5607 (0.33); 7.5519 (0.39); 7.5455 (1.69); 7.5399 (0.52); 7.5305 (0.92); 7.5272 (1.45); 7.5239 (0.75); 7.4957 (2.49); 7.4801 (1.78); 7.4765 (3.19); 7.4628 (0.52); 7.4588 (1.25); 7.4557 (0.72); 7.1443 (1.87); 7.1264 (1.80); 5.3554 (6.40); 5.0926 (0.44); 5.0895 (0.38); 5.0780 (0.74); 5.0747 (0.89); 5.0603 (0.39); 5.0572 (0.44); 3.3279 (52.28); 3.3058 (1.01); 2.5251 (0.72); 2.5118 (12.64); 2.5073 (24.46); 2.5028 (31.75); 2.4982 (23.07); 2.4937 (11.05); 2.3968 (0.66); 2.3814 (0.71); 2.3618 (0.95); 2.3463 (1.02); 2.2453 (0.94); 2.2253 (1.06); 2.2104 (0.64); 2.1902 (0.73); 1.9797 (0.75); 1.9619 (1.27); 1.9440 (1.28); 1.9270 (0.84); 1.9093 (0.43); 1.6557 (0.55); 1.6297 (6.45); 1.5525 (7.37); 1.3547 (0.33); 1.3376 (0.44); 1.3332 (0.36); 1.3208 (0.49); 1.3150 (0.44); 1.3068 (0.36); 1.2996 (0.41); 1.1983 (0.48); 1.1857 (0.51); 1.1785 (0.43); 1.1718 (0.32); 1.1637 (0.48); 0.9019 (5.82); 0.8853 (5.69); 0.0079 (0.36); −0.0002 (8.83)
Example 236, Solvent: CDCl3, Spectrometer: 300.16 MHz 7.6688 (4.49); 7.6461 (5.37); 7.4378 (7.28); 7.4124 (7.11); 7.3906 (3.09); 7.2619 (12.61); 6.5633 (2.62); 6.5419 (2.50); 6.3065 (2.64); 6.2784 (2.51); 5.2285 (10.11); 4.4256 (1.25); 3.7686 (1.43); 3.1067 (16.00); 2.0868 (0.99); 1.7385 (3.38); 1.6955 (5.73); 1.6524 (4.11); 1.4633 (1.09); 1.4367 (2.16); 1.4101 (2.73); 1.3263 (1.92); 1.2933 (2.12); 1.2537 (2.36); 1.2075 (2.41); 1.1744 (12.09); 1.1557 (10.90); 0.9880 (0.76); 0.9493 (1.94); 0.9057 (2.30); 0.8694 (1.58); −0.0002 (8.47)
Example 237, Solvent: DMSO, Spectrometer: 399.95 MHz 10.9450 (1.79); 8.0365 (0.79); 8.0157 (1.02); 7.9532 (0.86); 7.9012 (1.37); 7.8819 (1.86); 7.8617 (1.11); 7.7234 (2.67); 7.7197 (1.31); 7.7106 (0.79); 7.7056 (3.43); 7.7018 (2.42); 7.5661 (0.48); 7.5541 (0.35); 7.5477 (1.63); 7.5421 (0.49); 7.5327 (0.86); 7.5295 (1.40); 7.5261 (0.74); 7.4977 (2.43); 7.4822 (1.67); 7.4785 (3.12); 7.4649 (0.48); 7.4609 (1.21); 7.4578 (0.71); 7.2230 (1.81); 7.2048 (1.73); 5.3795 (6.53); 3.6620 (0.59); 3.6342 (1.83); 3.6063 (1.88); 3.5784 (0.64); 3.3291 (63.12); 3.0552 (16.00); 2.8907 (6.74); 2.7312 (5.41); 2.5251 (0.64); 2.5117 (12.44); 2.5072 (24.80); 2.5027 (32.66); 2.4981 (23.87); 2.4936 (11.50); 0.0080 (0.36); −0.0002 (10.95); −0.0085 (0.34)
Example 238, Solvent: DMSO, Spectrometer: 399.95 MHz 10.2540 (2.69); 7.9534 (0.87); 7.8225 (0.71); 7.8015 (1.78); 7.7841 (2.12); 7.7740 (2.08); 7.7714 (2.26); 7.7533 (0.82); 7.7504 (0.62); 7.7227 (2.70); 7.7099 (0.85); 7.7049 (3.49); 7.7011 (2.48); 7.5631 (0.51); 7.5392 (0.52); 7.5299 (1.91); 7.5266 (1.51); 7.5233 (0.77); 7.4991 (4.62); 7.4958 (3.54); 7.4781 (6.63); 7.4631 (0.53); 7.4590 (1.26); 7.4558 (0.73); 7.2932 (4.02); 7.2767 (1.37); 7.2722 (3.31); 7.2602 (0.56); 7.2438 (0.49); 7.1047 (1.54); 7.1018 (1.53); 7.0873 (1.51); 7.0844 (1.44); 5.3312 (6.46); 4.2908 (1.61); 4.2741 (3.64); 4.2575 (1.66); 3.3302 (61.62); 3.0610 (16.00); 2.9281 (1.43); 2.9115 (2.95); 2.8907 (7.28); 2.7320 (5.51); 2.5252 (0.69); 2.5203 (1.10); 2.5118 (13.33); 2.5073 (26.35); 2.5028 (34.64); 2.4982 (25.35); 2.4937 (12.29); 1.2348 (0.35); −0.0002 (7.26)
Example 239, Solvent: DMSO, Spectrometer: 399.95 MHz 11.9040 (0.97); 7.9531 (0.94); 7.7274 (2.91); 7.7146 (0.91); 7.7096 (3.62); 7.7058 (2.54); 7.5600 (0.51); 7.5570 (0.33); 7.5486 (0.41); 7.5417 (1.78); 7.5360 (0.53); 7.5269 (1.04); 7.5237 (1.56); 7.5203 (0.80); 7.4973 (2.67); 7.4819 (1.89); 7.4781 (3.33); 7.4646 (0.59); 7.4606 (1.30); 7.4571 (0.81); 7.4380 (0.67); 7.4328 (1.09); 7.4264 (0.64); 7.4159 (4.82); 7.4127 (5.70); 7.3966 (3.78); 7.3915 (1.18); 7.3817 (1.87); 7.3773 (1.49); 7.3713 (1.12); 7.3661 (1.38); 7.3596 (0.79); 7.3494 (1.08); 7.2723 (4.67); 5.2853 (6.47); 5.2229 (8.16); 5.1615 (0.81); 3.3291 (51.70); 3.0358 (0.47); 3.0245 (16.00); 2.8903 (7.20); 2.7315 (5.92); 2.5245 (0.76); 2.5112 (13.86); 2.5068 (26.69); 2.5023 (34.48); 2.4977 (24.97); 2.4933 (11.96); 0.0078 (0.44); −0.0002 (11.95); −0.0085 (0.41)
Example 240, Solvent: DMSO, Spectrometer: 399.95 MHz 9.9471 (2.07); 8.0542 (1.28); 8.0335 (1.59); 7.8817 (1.33); 7.8623 (1.94); 7.8422 (1.14); 7.7245 (2.73); 7.7067 (3.47); 7.7030 (2.51); 7.5643 (0.51); 7.5611 (0.34); 7.5523 (0.38); 7.5460 (1.68); 7.5403 (0.54); 7.5310 (0.95); 7.5277 (1.46); 7.5244 (0.79); 7.4962 (2.52); 7.4806 (1.84); 7.4770 (3.22); 7.4633 (0.54); 7.4593 (1.26); 7.4563 (0.76); 7.1730 (1.82); 5.3689 (6.74); 4.0933 (8.50); 3.3292 (45.74); 3.0719 (16.00); 2.5251 (0.59); 2.5117 (11.15); 2.5073 (21.82); 2.5028 (28.55); 2.4982 (21.20); 2.4939 (10.54); 1.5736 (0.45); 1.5563 (1.48); 1.5500 (0.55); 1.5397 (1.95); 1.5199 (1.60); 1.5036 (0.68); 1.3975 (0.36); 1.3791 (1.22); 1.3599 (1.86); 1.3410 (1.85); 1.3231 (1.07); 0.9122 (4.40); 0.8938 (8.76); 0.8753 (3.72); −0.0002 (6.95)
Example 241, Solvent: DMSO, Spectrometer: 400.13 MHz 11.0140 (2.97); 7.8384 (4.05); 7.8278 (4.28); 7.7290 (2.77); 7.7111 (3.50); 7.7074 (2.47); 7.5694 (0.51); 7.5573 (0.43); 7.5511 (1.72); 7.5455 (0.54); 7.5360 (0.97); 7.5328 (1.47); 7.5013 (2.53); 7.4857 (1.86); 7.4822 (3.20); 7.4645 (1.38); 7.1630 (1.30); 7.1526 (2.13); 7.1421 (1.21); 5.3565 (6.72); 3.3941 (2.10); 3.3443 (171.35); 3.2941 (1.27); 3.0619 (16.00); 2.7990 (4.33); 2.7824 (4.46); 2.6813 (0.43); 2.6768 (0.57); 2.6724 (0.42); 2.5619 (0.91); 2.5575 (1.22); 2.5531 (0.95); 2.5300 (2.04); 2.5164 (37.35); 2.5122 (74.24); 2.5077 (98.29); 2.5033 (70.37); 2.4991 (33.42); 2.4575 (0.92); 2.3391 (0.46); 2.3346 (0.62); 2.3301 (0.45); 1.9948 (0.65); 1.8223 (0.43); 1.8056 (0.89); 1.7889 (1.12); 1.7723 (0.88); 1.7557 (0.46); 1.2508 (1.44); 1.1793 (0.36); 0.9545 (15.44); 0.9379 (14.90); 0.8796 (0.72); 0.8630 (2.05); 0.8454 (0.82)

NMR Peak List Table 1

Example 242, Solvent: DMSO, Spectrometer: 400.13 MHz 10.3887 (3.15); 7.8550 (0.86); 7.8342 (1.87); 7.8162 (2.05); 7.7966 (2.48); 7.7948 (2.52); 7.7760 (1.23); 7.7282 (2.99); 7.7104 (3.74); 7.7067 (2.70); 7.5669 (0.57); 7.5639 (0.42); 7.5549 (0.54); 7.5487 (1.82); 7.5431 (0.67); 7.5336 (1.15); 7.5305 (1.62); 7.5272 (0.92); 7.5000 (2.72); 7.4843 (2.16); 7.4809 (3.42); 7.4670 (0.76); 7.4632 (1.41); 7.4601 (0.87); 7.1345 (1.79); 7.1168 (1.76); 5.4326 (0.42); 5.4274 (0.42); 5.4159 (1.21); 5.4107 (1.23); 5.3992 (1.28); 5.3939 (1.27); 5.3824 (0.50); 5.3771 (0.46); 5.3418 (6.76); 3.5850 (3.39); 3.5798 (3.32); 3.3971 (1.47); 3.3474 (119.76); 3.2970 (1.75); 3.0759 (16.00); 2.5573 (0.96); 2.5531 (0.92); 2.5160 (20.07); 2.5121 (37.07); 2.5077 (47.62); 2.5033 (34.71); 2.4669 (1.05); 2.4619 (1.10); 2.4575 (1.10); 1.4870 (7.01); 1.4702 (7.01)

Example 243, Solvent: DMSO, Spectrometer: 399.95 MHz 11.0967 (2.79); 8.1639 (0.70); 8.1437 (0.81); 7.9529 (1.48); 7.9305 (1.31); 7.9110 (2.06); 7.8911 (1.16); 7.7277 (3.18); 7.7097 (3.91); 7.7062 (3.10); 7.6940 (1.91); 7.6920 (1.87); 7.6743 (2.06); 7.6722 (1.98); 7.5647 (0.57); 7.5464 (1.96); 7.5386 (1.44); 7.5335 (1.77); 7.5319 (1.78); 7.5283 (1.98); 7.5250 (1.41); 7.5197 (2.13); 7.5155 (2.11); 7.4974 (2.92); 7.4786 (4.49); 7.4634 (2.81); 7.4607 (3.30); 7.4449 (1.16); 7.4423 (1.04); 7.4186 (1.26); 7.4140 (1.24); 7.3991 (1.53); 7.3950 (1.49); 7.3804 (0.71); 7.3760 (0.64); 7.2413 (2.07); 7.2226 (1.98); 5.3754 (5.29); 3.3476 (114.40); 3.0811 (16.00); 2.8913 (9.58); 2.7324 (8.25); 2.5081 (34.57); 2.5037 (43.87); 2.4993 (33.49); 0.0004 (1.58)

Example 244, Solvent: DMSO, Spectrometer: 399.95 MHz 10.5103 (2.00); 8.0958 (1.42); 8.0752 (1.70); 7.8354 (1.27); 7.8162 (1.79); 7.7959 (1.18); 7.7275 (2.12); 7.7251 (2.63); 7.7214 (1.29); 7.7124 (0.85); 7.7073 (3.45); 7.7036 (2.42); 7.5647 (0.50); 7.5615 (0.32); 7.5527 (0.38); 7.5464 (1.68); 7.5407 (0.51); 7.5314 (0.91); 7.5281 (1.45); 7.5247 (0.74); 7.4967 (2.44); 7.4933 (1.08); 7.4812 (1.74); 7.4775 (1.34); 7.4639 (0.50); 7.4598 (1.26); 7.4566 (0.71); 7.1478 (1.80); 7.1293 (1.75); 5.3607 (6.17); 3.3304 (51.56); 3.0569 (16.00); 2.8913 (2.07); 2.7326 (1.71); 2.7316 (1.59); 2.6846 (0.33); 2.6713 (0.58); 2.6677 (0.64); 2.6491 (0.56); 2.6326 (0.37); 2.5256 (0.59); 2.5124 (10.74); 2.5079 (21.06); 2.5033 (27.53); 2.4987 (19.99); 2.4942 (9.54); 1.6099 (0.33); 1.5995 (0.35); 1.5872 (0.44); 1.5781 (0.42); 1.5653 (0.36); 1.3496 (0.35); 1.3367 (0.45); 1.3236 (0.56); 1.3051 (0.59); 1.2898 (0.92); 1.2785 (0.91); 1.2718 (1.20); 1.2549 (1.30); 1.2459 (1.04); 1.2354 (1.03); 1.2217 (0.82); 1.2152 (0.61); 1.2044 (0.54); 1.1962 (0.43); 1.1881 (0.47); 1.1733 (0.35); 1.0670 (5.83); 1.0500 (5.71); 0.8578 (2.10); 0.8528 (1.20); 0.8406 (4.59); 0.8225 (2.41); −0.0002 (8.32)

Example 245, Solvent: DMSO, Spectrometer: 400.13 MHz 10.9988 (2.86); 8.1622 (1.92); 8.1415 (2.35); 8.0503 (4.12); 8.0457 (1.56); 8.0332 (1.65); 8.0288 (4.52); 7.9336 (1.40); 7.9142 (2.11); 7.8942 (1.28); 7.7393 (2.94); 7.7213 (3.60); 7.7176 (2.71); 7.5949 (4.60); 7.5904 (1.65); 7.5734 (4.59); 7.5601 (0.66); 7.5536 (1.93); 7.5480 (0.76); 7.5353 (1.64); 7.5054 (2.70); 7.4861 (3.43); 7.4684 (1.34); 7.2443 (2.11); 7.2257 (2.05); 5.7612 (6.52); 5.4213 (7.01); 4.0422 (0.33); 4.0246 (0.35); 3.3685 (1.08); 3.3365 (221.52); 3.2583 (0.71); 3.0816 (16.00); 2.6758 (0.34); 2.5112 (43.36); 2.5068 (57.28); 2.5025 (42.19); 2.3337 (0.39); 1.9934 (1.44); 1.2382 (0.42); 1.1967 (0.40); 1.1790 (0.76); 1.1612 (0.40)

Example 246, Solvent: DMSO, Spectrometer: 400.13 MHz 9.8610 (1.10); 7.8194 (0.75); 7.8141 (0.34); 7.8059 (0.88); 7.7970 (0.84); 7.7887 (0.44); 7.7831 (1.42); 7.7696 (1.10); 7.7668 (1.53); 7.3587 (0.78); 7.3366 (1.43); 7.3144 (0.71); 7.0800 (0.51); 7.0749 (0.51); 7.0645 (0.49); 7.0594 (0.49); 5.3185 (2.53); 3.5596 (0.87); 3.4011 (0.37); 3.3516 (32.11); 3.0680 (5.99); 2.5186 (2.03); 2.5142 (4.23); 2.5098 (5.74); 2.5053 (4.09); 2.5009 (1.88); 1.9957 (0.47); 1.5107 (1.98); 1.4682 (16.00); 1.3330 (0.37)

Example 247, Solvent: DMSO, Spectrometer: 399.95 MHz 10.5085 (0.85); 8.0766 (0.49); 8.0559 (0.58); 7.8330 (0.50); 7.8136 (0.70); 7.7935 (0.46); 7.7240 (1.04); 7.7111 (0.35); 7.7061 (1.35); 7.7024 (0.95); 7.5458 (0.66); 7.5308 (0.35); 7.5275 (0.56); 7.4964 (0.97); 7.4809 (0.68); 7.4772 (1.23); 7.4595 (0.48); 7.1416 (0.72); 7.1235 (0.69); 5.3540 (2.48); 3.3285 (24.24); 3.0542 (6.16); 2.8910 (1.65); 2.7320 (1.33); 2.5118 (4.89); 2.5074 (9.68); 2.5028 (12.76); 2.4982 (9.38); 2.4938 (4.60); 2.3677 (0.59); 2.3494 (1.23); 2.3308 (0.71); 1.5627 (0.37); 1.5435 (0.40); 1.5403 (0.41); 1.5309 (0.33); 1.5206 (0.40); 1.1837 (0.76); 1.1733 (0.44); 1.1633 (0.44); 1.1604 (0.45); 1.1525 (0.41); 1.1410 (0.61); 0.8623 (16.00); −0.0002 (3.48)

Example 248, Solvent: DMSO, Spectrometer: 399.95 MHz 10.5134 (2.17); 8.0921 (1.60); 8.0715 (1.88); 7.8348 (1.33); 7.8153 (1.96); 7.7952 (1.26); 7.7243 (2.91); 7.7114 (0.95); 7.7064 (3.73); 7.7028 (2.63); 7.5650 (0.51); 7.5619 (0.36); 7.5529 (0.40); 7.5466 (1.72); 7.5410 (0.57); 7.5316 (0.94); 7.5284 (1.48); 7.5252 (0.83); 7.4972 (2.69); 7.4815 (1.85); 7.4779 (3.35); 7.4642 (0.53); 7.4603 (1.27); 7.4573 (0.78); 7.1461 (2.00); 7.1276 (1.90); 5.3601 (6.80); 3.3344 (89.79); 3.0882 (0.49); 3.0572 (16.00); 2.8911 (1.68); 2.7316 (1.43); 2.7087 (0.35); 2.6892 (0.60); 2.6725 (0.79); 2.6579 (0.40); 2.5121 (13.08); 2.5078 (25.41); 2.5033 (33.14); 2.4987 (24.36); 2.4944 (11.93); 1.5898 (0.51); 1.5852 (0.43); 1.5755 (0.53); 1.5692 (0.61); 1.5639 (0.43); 1.5543 (0.60); 1.3273 (0.48); 1.3148 (0.63); 1.3019 (0.92); 1.2826 (1.32); 1.2684 (1.74); 1.2577 (0.88); 1.2491 (1.38); 1.2339 (1.28); 1.2207 (0.45); 1.2161 (0.50); 1.2088 (0.34); 1.0653 (6.44); 1.0483 (6.34); 0.8939 (0.36); 0.8785 (3.29); 0.8607 (6.20); 0.8428 (2.44); −0.0002 (5.41)

Example 249, Solvent: DMSO, Spectrometer: 400.13 MHz 9.8213 (1.22); 7.7724 (0.82); 7.7568 (1.83); 7.6494 (0.32); 7.3888 (0.69); 7.3835 (0.80); 7.3760 (1.13); 7.3667 (0.78); 7.0218 (0.59); 7.0175 (0.58); 7.0059 (0.55); 7.0015 (0.55); 5.7640 (2.62); 5.3195 (2.87); 3.3401 (6.83); 3.3237 (6.22); 2.5124 (0.98); 2.5081 (1.27); 2.5039 (0.93); 1.4639 (16.00)

Example 250, Solvent: DMSO, Spectrometer: 400.13 MHz 10.0917 (2.65); 7.8295 (0.49); 7.8085 (1.97); 7.7927 (4.08); 7.7746 (0.63); 7.5387 (2.38); 7.5231 (0.70); 7.5145 (1.00); 7.5110 (1.06); 7.5015 (1.00); 7.4972 (0.75); 7.3893 (0.36); 7.3701 (2.46); 7.3640 (1.77); 7.3580 (3.41); 7.3557 (3.30); 7.0915 (1.40); 7.0866 (1.35); 7.0759 (1.29); 7.0710 (1.30); 5.7642 (4.65); 5.3254 (6.89); 4.6816 (0.44); 4.6690 (0.33); 4.6590 (0.83); 4.6495 (0.61); 4.6366 (0.41); 3.3277 (10.72); 3.3053 (0.96); 3.0626 (16.00); 2.5185 (9.24); 2.5142 (18.30); 2.5098 (24.34); 2.5054 (17.56); 2.5012 (8.48); 2.3398 (11.18); 1.8755 (0.86); 1.8628 (0.98); 1.8494 (1.02); 1.7352 (0.85); 1.7269 (0.92); 1.7121 (1.00); 1.5277 (0.44); 1.5175 (0.47); 1.4974 (0.52); 1.4711 (0.43); 1.4632 (0.40); 1.4391 (1.00); 1.4143 (1.27); 1.3887 (1.27); 1.3616 (1.14); 1.3359 (0.90); 1.3296 (0.97); 1.3116 (0.40); 1.3038 (0.53); 1.2830 (0.47); 1.2533 (0.80); 0.8655 (0.36)

Example 251, Solvent: DMSO, Spectrometer: 399.95 MHz 12.7560 (0.76); 8.1825 (1.92); 8.1772 (0.82); 8.1689 (2.16); 8.1656 (1.14); 8.1602 (2.17); 8.1521 (0.87); 8.1466 (1.97); 7.9535 (1.88); 7.7488 (2.02); 7.7462 (2.70); 7.7422 (1.34); 7.7338 (0.84); 7.7286 (3.47); 7.7247 (2.44); 7.5689 (0.47); 7.5576 (0.34); 7.5505 (1.66); 7.5446 (0.52); 7.5359 (0.94); 7.5325 (1.53); 7.5290 (0.79); 7.5082 (2.52); 7.5048 (1.13); 7.4932 (1.63); 7.4892 (3.11); 7.4759 (0.52); 7.4717 (1.23); 7.4681 (0.73); 7.4076 (1.98); 7.4024 (0.69); 7.3849 (5.55); 7.3684 (0.71); 7.3632 (1.90); 5.3844 (5.92); 3.3476 (122.79); 3.0193 (16.00); 2.8918 (14.81); 2.7330 (11.98); 2.5269 (0.67); 2.5136 (12.10); 2.5091 (23.58); 2.5045 (30.73); 2.4999 (22.31); 2.4954 (10.72); −0.0002 (1.49)

NMR Peak List Table 1

Example 252, Solvent: DMSO, Spectrometer: 400.13 MHz 12.4342 (2.00); 7.6225 (3.81); 7.6020 (4.37); 7.3495 (0.58); 7.3451 (0.47); 7.3298 (4.03); 7.3240 (4.71); 7.3162 (14.21); 7.3074 (5.07); 7.2870 (3.71); 7.2772 (1.63); 7.2672 (6.35); 7.2557 (1.44); 7.2512 (1.07); 7.2419 (0.83); 7.2344 (0.41); 5.3051 (7.02); 3.7517 (8.42); 3.5607 (1.00); 3.4211 (3.15); 3.3715 (269.39); 3.3219 (2.90); 3.0017 (16.00); 2.5572 (0.56); 2.5120 (34.30); 2.5077 (43.77); 2.5036 (32.56); 2.4582 (0.55); 2.3524 (11.36); 1.9931 (0.71); 1.2476 (0.82); 1.1775 (0.37); 0.8772 (0.35); 0.8606 (0.95); 0.8429 (0.40)

Example 253, Solvent: DMSO, Spectrometer: 400.13 MHz 7.7389 (2.92); 7.7211 (3.54); 7.7173 (2.65); 7.5620 (0.56); 7.5588 (0.43); 7.5503 (0.49); 7.5436 (1.77); 7.5379 (0.68); 7.5288 (1.08); 7.5255 (1.60); 7.4986 (2.75); 7.4832 (1.93); 7.4795 (3.36); 7.4659 (0.69); 7.4619 (1.34); 7.4586 (0.89); 7.3839 (1.23); 7.3657 (1.59); 7.3632 (1.60); 7.3451 (1.37); 6.5154 (0.75); 6.5021 (1.44); 6.4870 (2.65); 6.4691 (2.05); 6.3994 (2.02); 6.3787 (1.97); 5.7616 (1.11); 5.1994 (6.87); 3.3396 (118.89); 3.2708 (0.67); 3.2506 (0.44); 3.2314 (1.07); 3.2146 (1.87); 3.1992 (1.83); 3.1821 (1.04); 3.0738 (16.00); 3.0481 (0.42); 2.5158 (11.06); 2.5116 (21.74); 2.5072 (29.16); 2.5028 (21.84); 1.7043 (1.28); 1.6690 (1.94); 1.6248 (1.72); 1.5917 (0.78); 1.4442 (0.43); 1.4240 (0.81); 1.4072 (1.97); 1.3886 (2.16); 1.3716 (1.33); 1.3634 (0.65); 1.3410 (0.49); 1.3329 (0.58); 1.3253 (0.56); 1.3162 (0.61); 1.3073 (0.56); 1.2990 (0.49); 1.2898 (0.44); 1.2803 (0.33); 1.2390 (0.50); 1.2303 (0.43); 1.1985 (0.95); 1.1688 (1.44); 1.1466 (1.69); 1.1261 (0.88); 1.0957 (0.50); 0.9179 (0.61); 0.8891 (1.28); 0.8609 (1.22); 0.8373 (0.49)

Example 254, Solvent: DMSO, Spectrometer: 400.13 MHz 9.8576 (1.05); 7.7899 (0.86); 7.7808 (0.98); 7.7751 (2.20); 7.5367 (0.39); 7.5328 (0.43); 7.0999 (0.53); 7.0938 (0.54); 7.0854 (0.48); 7.0792 (0.54); 5.7642 (3.14); 5.3711 (2.61); 3.3398 (7.33); 3.1915 (6.87); 2.5176 (0.35); 2.5131 (0.76); 2.5086 (1.07); 2.5041 (0.79); 2.4996 (0.40); 1.4703 (16.00)

Example 255, Solvent: DMSO, Spectrometer: 399.95 MHz 10.8720 (1.81); 8.0114 (0.77); 7.9907 (0.97); 7.9537 (0.52); 7.8515 (1.29); 7.8323 (1.71); 7.8119 (1.13); 7.7329 (1.93); 7.7301 (2.57); 7.7262 (1.29); 7.7176 (0.83); 7.7124 (3.41); 7.7087 (2.43); 7.5678 (0.49); 7.5646 (0.32); 7.5559 (0.36); 7.5495 (1.61); 7.5437 (0.51); 7.5346 (0.86); 7.5312 (1.42); 7.5278 (0.74); 7.5005 (2.37); 7.4971 (1.10); 7.4852 (1.60); 7.4814 (3.01); 7.4679 (0.47); 7.4638 (1.21); 7.4605 (0.69); 7.2920 (0.46); 7.2840 (0.55); 7.2776 (0.56); 7.2695 (0.98); 7.2615 (0.63); 7.2559 (0.92); 7.2455 (0.79); 7.2339 (1.15); 7.2222 (1.13); 7.2112 (0.77); 7.1995 (0.76); 7.1839 (0.60); 7.1761 (2.23); 7.1640 (0.82); 7.1590 (1.89); 7.1574 (1.95); 7.1457 (0.48); 5.3814 (5.89); 4.1094 (0.35); 4.0916 (0.35); 3.8350 (3.84); 3.7363 (0.35); 3.7328 (0.35); 3.3305 (59.82); 3.2301 (0.36); 3.0667 (16.00); 3.0574 (0.36); 2.8909 (4.28); 2.7325 (3.42); 2.7312 (3.33); 2.5256 (0.69); 2.5208 (1.11); 2.5123 (11.54); 2.5078 (22.78); 2.5031 (29.97); 2.4985 (21.65); 2.4940 (10.19); 1.2029 (0.40); 1.1851 (0.83); 1.1673 (0.39); 0.8761 (0.50); −0.0002 (7.11)

Example 256, Solvent: DMSO, Spectrometer: 399.95 MHz 10.5588 (1.92); 8.0692 (1.21); 8.0485 (1.45); 7.8364 (1.30); 7.8171 (1.80); 7.7969 (1.20); 7.7262 (2.15); 7.7241 (2.67); 7.7112 (0.85); 7.7062 (3.58); 7.7024 (2.41); 7.5647 (0.49); 7.5528 (0.37); 7.5464 (1.67); 7.5406 (0.51); 7.5314 (0.91); 7.5281 (1.42); 7.5248 (0.73); 7.4973 (2.50); 7.4819 (1.74); 7.4782 (3.15); 7.4646 (0.50); 7.4605 (1.24); 7.4573 (0.68); 7.1464 (1.79); 7.1280 (1.75); 5.8644 (0.63); 5.8549 (0.33); 5.8485 (0.32); 5.8386 (0.87); 5.8217 (0.87); 5.8119 (0.36); 5.8055 (0.37); 5.7959 (0.04); 5.7799 (0.45); 5.3561 (6.42); 5.0796 (0.48); 5.0755 (1.20); 5.0709 (1.22); 5.0668 (0.48); 5.0366 (0.43); 5.0325 (1.08); 5.0279 (1.09); 5.0238 (0.43); 4.9832 (0.55); 4.9801 (1.14); 4.9779 (0.90); 4.9753 (1.00); 4.9723 (0.46); 4.9576 (0.52); 4.9545 (1.08); 4.9523 (0.85); 4.9498 (0.95); 4.9467 (0.42); 3.3290 (56.17); 3.2234 (0.36); 3.0878 (0.60); 3.0535 (16.00); 2.8908 (0.51); 2.7320 (0.42); 2.5252 (0.64); 2.5118 (12.37); 2.5073 (22.99); 2.5027 (29.47); 2.4981 (21.39); 2.4934 (12.11); 2.4732 (2.16); 2.3493 (0.70); 2.3335 (1.76); 2.3301 (1.78); 2.3172 (1.20); 2.3140 (1.54); 2.2975 (0.45); 0.8758 (0.48); −0.0002 (4.83)

Example 257, Solvent: DMSO, Spectrometer: 399.95 MHz 12.7279 (1.12); 8.0919 (2.68); 8.0786 (0.91); 8.0740 (3.13); 8.0705 (2.35); 7.9533 (1.19); 7.7499 (2.15); 7.7474 (2.71); 7.7434 (1.32); 7.7349 (0.91); 7.7297 (3.52); 7.7259 (2.47); 7.6618 (0.34); 7.6589 (0.57); 7.6559 (0.35); 7.6454 (0.48); 7.6406 (1.62); 7.6357 (0.53); 7.6250 (0.78); 7.6220 (1.22); 7.6189 (0.67); 7.5652 (2.44); 7.5580 (0.66); 7.5499 (2.75); 7.5453 (3.65); 7.5360 (1.22); 7.5324 (1.96); 7.5275 (1.71); 7.5086 (2.58); 7.5053 (1.14); 7.4937 (1.71); 7.4896 (3.16); 7.4763 (0.54); 7.4721 (1.26); 7.4685 (0.76); 7.3803 (4.21); 5.3865 (6.20); 3.3487 (150.38); 3.3096 (0.39); 3.0226 (16.00); 2.8916 (9.19); 2.7329 (7.61); 2.5267 (0.71); 2.5133 (12.92); 2.5089 (24.83); 2.5043 (31.99); 2.4997 (23.15); 2.4953 (11.06); −0.0002 (0.54)

Example 258, Solvent: CDCl3, Spectrometer: 300.16 MHz 7.9129 (1.78); 7.8851 (2.27); 7.7253 (1.47); 7.6987 (2.54); 7.6693 (3.25); 7.6447 (3.33); 7.6240 (2.67); 7.3467 (4.08); 7.3191 (3.66); 7.2968 (4.19); 7.2573 (12.26); 7.2301 (3.45); 7.1347 (2.37); 7.1087 (4.54); 7.0814 (2.29); 7.0233 (2.66); 6.9986 (2.51); 5.2777 (10.06); 4.4296 (2.48); 4.4069 (5.17); 4.3840 (2.68); 3.0953 (16.00); 3.0239 (2.57); 3.0012 (4.99); 2.9786 (2.43); 2.0084 (2.01); 1.6038 (6.29); 1.2541 (0.52); −0.0002 (3.01)

Example 259, Solvent: DMSO, Spectrometer: 400.13 MHz 7.8120 (1.89); 7.8066 (0.85); 7.7985 (2.10); 7.7932 (1.15); 7.7895 (2.11); 7.7815 (0.87); 7.7761 (1.92); 7.3987 (1.28); 7.3804 (1.66); 7.3783 (1.62); 7.3599 (1.42); 7.3477 (2.07); 7.3424 (0.74); 7.3255 (3.68); 7.3207 (0.88); 7.3086 (0.65); 7.3033 (1.83); 6.5061 (1.83); 6.4886 (1.76); 6.3893 (1.87); 6.3693 (1.81); 6.0030 (2.81); 5.7558 (11.12); 5.1716 (6.65); 4.9644 (0.41); 3.4636 (2.31); 3.3258 (9.38); 3.3020 (0.35); 3.1338 (0.43); 3.0837 (16.00); 3.0284 (0.43); 2.5097 (1.31); 2.5053 (2.76); 2.5007 (3.79); 2.4963 (2.70); 2.4919 (1.26); 1.5326 (2.59)

Example 260, Solvent: DMSO, Spectrometer: 399.95 MHz 10.8357 (2.17); 8.0093 (1.23); 7.9887 (1.63); 7.9531 (0.80); 7.8678 (1.35); 7.8486 (1.80); 7.8283 (1.14); 7.7300 (1.97); 7.7275 (2.60); 7.7237 (1.26); 7.7149 (0.79); 7.7098 (3.45); 7.7060 (2.40); 7.5698 (0.49); 7.5579 (0.36); 7.5515 (1.65); 7.5459 (0.49); 7.5365 (0.87); 7.5332 (1.42); 7.5299 (0.73); 7.5015 (2.40); 7.4980 (1.01); 7.4860 (1.69); 7.4823 (3.10); 7.4687 (0.50); 7.4646 (1.24); 7.4614 (0.70); 7.3514 (0.36); 7.3425 (4.16); 7.3369 (1.23); 7.3255 (1.31); 7.3199 (4.66); 7.3109 (0.40); 7.2029 (1.76); 7.1852 (1.71); 6.9558 (0.42); 6.9469 (4.37); 6.9413 (1.26); 6.9299 (1.19); 6.9243 (3.92); 6.9154 (0.32); 5.3843 (5.98); 5.0701 (1.07); 5.0536 (1.08); 3.3514 (102.16); 3.3486 (139.13); 3.0611 (16.00); 2.8914 (6.58); 2.7327 (5.16); 2.7319 (5.05); 2.5266 (0.64); 2.5133 (13.11); 2.5088 (25.99); 2.5042 (34.16); 2.4996 (24.71); 2.4951 (11.70); 1.5354 (5.41); 1.5190 (5.40); −0.0002 (0.56)

Example 261, Solvent: DMSO, Spectrometer: 400.13 MHz 8.0043 (0.53); 7.9848 (0.33); 7.6324 (0.57); 7.4997 (0.41); 7.4808 (0.48); 7.4447 (0.51); 7.4255 (0.41); 5.8276 (1.62); 5.5018 (1.32); 3.4021 (1.07); 3.1184 (3.35); 2.5758 (4.24); 2.5714 (8.61); 2.5669 (11.56); 2.5624 (8.20); 2.5580 (3.77); 1.5267 (0.57); 1.4096 (16.00)

NMR Peak List Table 1

Example 262, Solvent: DMSO, Spectrometer: 399.95 MHz 12.8129 (1.57); 7.9526 (1.61); 7.7914 (2.80); 7.7865 (2.81); 7.7412 (2.05); 7.7386 (2.70); 7.7346 (1.31); 7.7262 (0.93); 7.7210 (3.51); 7.7171 (2.39); 7.6968 (2.46); 7.6761 (3.42); 7.5797 (2.16); 7.5747 (2.02); 7.5684 (0.38); 7.5651 (0.59); 7.5590 (1.64); 7.5539 (1.85); 7.5468 (1.72); 7.5410 (0.51); 7.5321 (0.98); 7.5288 (1.53); 7.5253 (0.77); 7.5030 (2.53); 7.4996 (1.07); 7.4879 (1.74); 7.4840 (3.13); 7.4705 (0.54); 7.4664 (1.28); 7.4629 (0.75); 7.4112 (4.10); 5.3639 (5.70); 3.3327 (57.92); 3.3298 (86.16); 3.0374 (16.00); 3.0161 (0.56); 2.8905 (13.13); 2.7315 (10.22); 2.7308 (10.22); 2.5246 (0.96); 2.5198 (1.45); 2.5113 (18.55); 2.5068 (36.83); 2.5022 (48.25); 2.4976 (34.97); 2.4930 (16.60); 0.0079 (0.40); −0.0002 (12.51); −0.0085 (0.40)

Example 263, Solvent: DMSO, Spectrometer: 399.95 MHz 12.8993 (0.93); 7.8246 (1.47); 7.8192 (1.89); 7.8040 (1.90); 7.7986 (1.52); 7.7462 (2.83); 7.7423 (1.48); 7.7336 (0.90); 7.7285 (3.53); 7.7247 (2.56); 7.6126 (0.33); 7.6068 (0.54); 7.5898 (0.68); 7.5841 (1.07); 7.5785 (0.62); 7.5691 (0.71); 7.5613 (0.67); 7.5582 (0.61); 7.5510 (1.79); 7.5452 (0.57); 7.5363 (0.99); 7.5330 (1.58); 7.5295 (0.87); 7.5083 (2.63); 7.4932 (1.69); 7.4893 (3.22); 7.4759 (0.55); 7.4718 (1.26); 7.4683 (0.75); 7.4245 (3.48); 5.3912 (6.09); 3.3462 (66.87); 3.3416 (98.96); 3.0178 (16.00); 2.8915 (0.44); 2.7322 (0.36); 2.5263 (0.57); 2.5129 (12.95); 2.5085 (25.78); 2.5040 (34.03); 2.4994 (25.26); 2.4950 (12.64); −0.0002 (8.68); −0.0085 (0.33)

Example 264, Solvent: DMSO, Spectrometer: 399.95 MHz 10.8225 (1.89); 8.0438 (1.01); 8.0231 (1.23); 7.9530 (0.55); 7.8547 (1.32); 7.8354 (1.82); 7.8152 (1.18); 7.7230 (2.64); 7.7192 (1.31); 7.7103 (0.83); 7.7052 (3.52); 7.7015 (2.39); 7.5641 (0.49); 7.5609 (0.32); 7.5522 (0.37); 7.5458 (1.67); 7.5401 (0.50); 7.5308 (0.88); 7.5275 (1.43); 7.5242 (0.73); 7.4962 (2.50); 7.4929 (1.11); 7.4808 (1.67); 7.4770 (3.15); 7.4634 (0.49); 7.4594 (1.24); 7.4562 (0.69); 7.3918 (1.71); 7.3881 (1.77); 7.3794 (1.79); 7.3757 (1.82); 7.1740 (1.80); 7.1560 (1.78); 6.9915 (0.93); 6.9864 (2.04); 6.9830 (1.86); 6.9796 (3.14); 6.9708 (1.01); 6.9671 (2.25); 6.9585 (1.10); 5.3715 (6.28); 3.9564 (5.70); 3.3300 (63.32); 3.2185 (0.68); 3.0543 (16.00); 2.8902 (4.49); 2.7317 (3.51); 2.7309 (3.56); 2.5249 (0.63); 2.5201 (0.99); 2.5116 (11.97); 2.5071 (23.85); 2.5025 (31.51); 2.4979 (22.91); 2.4934 (10.95); 0.8757 (0.44); −0.0002 (7.55)

Example 265, Solvent: DMSO, Spectrometer: 399.95 MHz 11.7658 (1.42); 7.9531 (0.62); 7.7302 (2.85); 7.7263 (1.44); 7.7174 (1.11); 7.7126 (3.67); 7.7088 (2.49); 7.5624 (0.53); 7.5592 (0.37); 7.5508 (0.42); 7.5440 (1.76); 7.5382 (0.58); 7.5292 (1.07); 7.5259 (1.61); 7.5225 (0.70); 7.4848 (1.93); 7.4810 (3.48); 7.4676 (0.62); 7.4634 (1.37); 7.4599 (0.85); 7.2523 (4.15); 5.3572 (0.43); 5.2833 (6.24); 4.1472 (0.63); 4.1312 (0.39); 4.1221 (2.32); 4.1053 (4.91); 4.0886 (2.37); 3.3301 (65.71); 3.0486 (0.70); 3.0299 (16.00); 2.9910 (0.99); 2.8907 (4.72); 2.7321 (3.83); 2.7311 (3.80); 2.5250 (0.70); 2.5117 (13.28); 2.5072 (26.01); 2.5026 (34.09); 2.4981 (24.95); 2.4936 (12.17); 1.6644 (1.22); 1.6472 (2.50); 1.6289 (2.58); 1.6117 (1.30); 1.5937 (0.32); 1.2349 (0.38); 1.1211 (0.61); 1.1058 (0.60); 0.9307 (4.55); 0.9123 (8.73); 0.8937 (3.88); 0.8028 (0.50); 0.7844 (1.04); 0.7658 (0.45); 0.0080 (0.38); −0.0002 (9.93); −0.0085 (0.33)

Example 266, Solvent: DMSO, Spectrometer: 399.95 MHz 10.5110 (1.78); 8.0783 (1.26); 8.0577 (1.49); 7.8342 (1.26); 7.8150 (1.72); 7.7947 (1.16); 7.7263 (1.91); 7.7238 (2.51); 7.7199 (1.21); 7.7112 (0.74); 7.7060 (3.33); 7.7023 (2.30); 7.5647 (0.47); 7.5528 (0.35); 7.5463 (1.60); 7.5406 (0.47); 7.5314 (0.85); 7.5281 (1.39); 7.5246 (0.70); 7.4973 (2.34); 7.4938 (1.00); 7.4819 (1.59); 7.4781 (3.01); 7.4646 (0.46); 7.4605 (1.20); 7.4573 (0.66); 7.1409 (1.74); 7.1235 (1.68); 5.3553 (6.25); 3.3290 (47.50); 3.0544 (16.00); 2.8908 (0.96); 2.7321 (0.75); 2.7311 (0.74); 2.5252 (0.56); 2.5204 (0.88); 2.5119 (10.17); 2.5074 (20.26); 2.5028 (26.71); 2.4982 (19.34); 2.4937 (9.17); 2.3781 (1.98); 2.3599 (3.85); 2.3416 (2.19); 1.6185 (1.28); 1.6001 (2.48); 1.5817 (2.46); 1.5634 (1.29); 0.9106 (4.18); 0.8922 (8.59); 0.8736 (3.79); −0.0002 (7.17)

Example 267, Solvent: DMSO, Spectrometer: 399.95 MHz 10.5028 (2.08); 8.0700 (1.21); 8.0493 (1.45); 7.9534 (0.39); 7.8304 (1.26); 7.8112 (1.73); 7.7909 (1.16); 7.7314 (0.32); 7.7257 (1.96); 7.7232 (2.58); 7.7194 (1.25); 7.7106 (0.80); 7.7055 (3.40); 7.7017 (2.36); 7.5637 (0.48); 7.5518 (0.35); 7.5454 (1.62); 7.5397 (0.49); 7.5305 (0.87); 7.5272 (1.41); 7.5237 (0.72); 7.4958 (2.39); 7.4924 (1.03); 7.4804 (1.65); 7.4766 (3.07); 7.4631 (0.48); 7.4590 (1.22); 7.4558 (0.68); 7.1392 (1.76); 7.1215 (1.69); 5.3524 (6.09); 3.3277 (54.17); 3.0520 (16.00); 2.8908 (3.16); 2.7321 (2.47); 2.7311 (2.47); 2.5250 (0.71); 2.5117 (12.59); 2.5072 (24.78); 2.5026 (32.57); 2.4980 (23.61); 2.4935 (11.26); 2.3682 (1.40); 2.3498 (2.77); 2.3311 (1.64); 1.6865 (0.99); 1.6576 (1.98); 1.6362 (0.94); 1.6282 (1.15); 1.6127 (1.04); 1.5935 (1.32); 1.5746 (1.59); 1.5557 (0.98); 1.5369 (0.37); 1.2339 (0.58); 1.2191 (0.45); 1.2073 (0.81); 1.1991 (1.06); 1.1871 (1.49); 1.1753 (1.92); 1.1682 (2.47); 1.1488 (1.75); 1.1384 (1.38); 1.1225 (0.41); 1.1160 (0.56); 1.1098 (0.41); 1.0854 (0.37); 0.8776 (0.44); 0.8487 (0.88); 0.8221 (0.82); 0.0080 (0.35); −0.0002 (9.29)

Example 268, Solvent: DMSO, Spectrometer: 399.95 MHz 10.5090 (1.95); 8.0719 (1.29); 8.0512 (1.54); 7.8323 (1.29); 7.8129 (1.81); 7.7928 (1.20); 7.7231 (2.74); 7.7194 (1.36); 7.7105 (0.83); 7.7054 (3.62); 7.7016 (2.45); 7.5642 (0.50); 7.5610 (0.32); 7.5523 (0.38); 7.5458 (1.70); 7.5403 (0.50); 7.5310 (0.89); 7.5276 (1.46); 7.5243 (0.75); 7.4964 (2.54); 7.4931 (1.07); 7.4809 (1.71); 7.4772 (3.21); 7.4636 (0.49); 7.4596 (1.26); 7.4564 (0.71); 7.1407 (1.86); 7.1225 (1.78); 5.4108 (0.42); 5.3970 (0.36); 5.3722 (1.59); 5.3543 (6.98); 5.3425 (1.86); 5.3037 (0.40); 5.3309 (61.84); 3.0544 (15.69); 2.5257 (0.52); 2.5123 (9.90); 2.5078 (19.67); 2.5032 (25.99); 2.4986 (18.86); 2.4941 (8.99); 2.3961 (1.36); 2.3881 (0.66); 2.3779 (2.62); 2.3594 (1.42); 2.2293 (0.47); 2.2126 (0.72); 2.1962 (0.66); 2.1803 (0.40); 1.9840 (0.57); 1.9671 (1.27); 1.9514 (1.43); 1.9333 (0.76); 1.5991 (0.43); 1.5809 (1.05); 1.5620 (1.35); 1.5431 (1.03); 1.5245 (0.40); 1.3616 (0.47); 1.3423 (1.15); 1.3304 (0.77); 1.3239 (1.47); 1.3046 (0.97); 1.2858 (0.52); 0.9309 (16.00); 0.9140 (15.65); 0.8974 (2.18); 0.8808 (2.11); 0.8758 (0.68); 0.8623 (0.34); −0.0002 (4.98)

Example 269, Solvent: DMSO, Spectrometer: 399.95 MHz 10.5931 (2.29); 8.0375 (0.71); 8.0168 (0.91); 7.8905 (1.34); 7.8712 (1.86); 7.8510 (1.15); 7.7298 (2.70); 7.7260 (1.34); 7.7170 (0.83); 7.7120 (3.50); 7.7082 (2.49); 7.6176 (1.63); 7.6137 (1.68); 7.5979 (1.77); 7.5940 (1.73); 7.5684 (0.50); 7.5564 (0.37); 7.5500 (1.70); 7.5444 (0.50); 7.5351 (0.92); 7.5318 (1.47); 7.5284 (0.75); 7.5010 (2.47); 7.4976 (1.08); 7.4855 (1.70); 7.4818 (3.20); 7.4681 (0.52); 7.4641 (1.27); 7.4609 (0.72); 7.3529 (0.73); 7.3489 (0.73); 7.3341 (1.08); 7.3319 (1.25); 7.3284 (1.04); 7.3137 (0.96); 7.3097 (0.90); 7.2140 (1.82); 7.1956 (1.75); 7.0479 (1.50); 7.0448 (1.61); 7.0271 (1.37); 7.0240 (1.34); 6.9440 (1.01); 6.9407 (0.92); 6.9248 (1.54); 6.9218 (1.48); 6.9058 (0.86); 6.9025 (0.78); 5.3871 (6.33); 4.9188 (5.58); 3.3532 (60.00); 3.3473 (97.95); 3.0723 (16.00); 2.8909 (0.53); 2.7323 (0.35); 2.5261 (0.64); 2.5128 (12.51); 2.5083 (24.48); 2.5038 (31.93); 2.4992 (23.20); 2.4947 (11.08); −0.0002 (2.55)

Example 270, Solvent: DMSO, Spectrometer: 400.13 MHz 10.2536 (4.91); 7.8306 (1.24); 7.8097 (2.96); 7.7922 (3.54); 7.7818 (3.38); 7.7790 (3.75); 7.7611 (1.42); 7.7581 (1.12); 7.7247 (4.46); 7.7208 (2.20); 7.7120 (1.48); 7.7069 (5.89); 7.7032 (4.08); 7.5784 (0.45); 7.5752 (0.81); 7.5720 (0.55); 7.5635 (0.64); 7.5569 (2.82); 7.5511 (0.86); 7.5421 (1.61); 7.5387 (2.50); 7.5353 (1.30); 7.5105 (4.22); 7.4952 (2.79); 7.4914 (5.22); 7.4779 (0.82); 7.4738 (2.04); 7.4704 (1.14); 7.3147 (16.00); 7.3037 (15.02); 7.2946 (0.69); 7.2901 (0.42); 7.2849 (0.47); 7.2820 (0.53); 7.2560 (0.44); 7.2465 (1.26); 7.2360 (1.87); 7.2252 (1.99); 7.2149 (1.08); 7.2034 (0.48); 7.1002 (2.50); 7.0973 (2.55); 7.0828 (2.42); 7.0799 (2.35); 5.3435 (10.41); 4.3087 (2.93); 4.2915 (6.69); 4.2743

NMR Peak List Table 1

(3.04); 4.0612 (0.38); 4.0434 (1.16); 4.0256 (1.17); 4.0078 (0.39); 3.5201 (1.32); 3.5020 (4.61); 3.4839 (4.65); 3.4655 (1.48); 3.4124 (9.03); 3.4045 (0.68); 3.3977 (0.59); 3.3625 (697.57); 3.3126 (8.07); 3.3005 (0.40); 3.2629 (0.33); 2.9537 (2.84); 2.9365 (6.03); 2.9193 (2.75); 2.6835 (0.42); 2.6789 (0.57); 2.6744 (0.42); 2.5688 (0.33); 2.5643 (0.78); 2.5552 (0.49); 2.5509 (0.49); 2.5323 (1.56); 2.5275 (2.67); 2.5189 (34.24); 2.5144 (71.95); 2.5099 (98.33); 2.5054 (69.91); 2.5009 (32.16); 2.4691 (0.51); 2.4645 (0.86); 2.4599 (1.17); 2.4555 (0.90); 2.4509 (0.51); 2.3413 (0.45); 2.3368 (0.62); 2.3321 (0.45); 1.9958 (5.24); 1.3701 (0.42); 1.2841 (0.40); 1.2510 (1.87); 1.1982 (1.46); 1.1804 (2.85); 1.1626 (1.39); 1.0513 (5.25); 1.0332 (12.20); 1.0150 (5.20); 0.8804 (0.89); 0.8637 (2.97); 0.8461 (1.12)
Example 271, Solvent: DMSO, Spectrometer: 399.95 MHz 12.1189 (1.60); 7.9530 (0.48); 7.7432 (0.33); 7.7374 (2.09); 7.7347 (2.76); 7.7306 (1.39); 7.7223 (0.86); 7.7171 (3.63); 7.7132 (2.53); 7.5640 (0.50); 7.5607 (0.35); 7.5526 (0.36); 7.5456 (1.68); 7.5398 (0.56); 7.5310 (0.95); 7.5276 (1.58); 7.5240 (0.88); 7.5021 (2.62); 7.4988 (1.18); 7.4871 (1.68); 7.4831 (3.19); 7.4698 (0.52); 7.4657 (1.27); 7.4621 (0.72); 7.2601 (3.80); 5.3202 (5.95); 5.1159 (0.52); 3.3307 (65.87); 3.0484 (1.43); 3.0298 (0.62); 3.0139 (16.00); 2.8907 (3.98); 2.7320 (3.13); 2.7310 (3.10); 2.5251 (0.64); 2.5202 (1.04); 2.5118 (12.70); 2.5073 (25.38); 2.5026 (33.45); 2.4980 (24.20); 2.4935 (11.50); 2.4042 (2.10); 2.3859 (4.07); 2.3764 (0.36); 2.3675 (2.31); 2.1760 (0.67); 2.1579 (0.36); 1.6315 (1.32); 1.6130 (2.55); 1.5946 (2.52); 1.5762 (1.32); 1.5169 (0.35); 1.4985 (0.35); 1.2350 (0.41); 1.1237 (0.50); 1.1084 (0.49); 0.9055 (4.24); 0.8940 (0.95); 0.8870 (8.75); 0.8758 (1.29); 0.8685 (3.89); 0.8573 (0.53); 0.0080 (0.38); −0.0002 (11.42); −0.0085 (0.35)
Example 272, Solvent: DMSO, Spectrometer: 400.13 MHz 10.2748 (3.08); 7.8288 (0.62); 7.8077 (1.84); 7.7907 (2.76); 7.7879 (2.33); 7.7839 (2.42); 7.7666 (0.68); 7.7630 (0.42); 7.5396 (2.16); 7.5241 (0.64); 7.5201 (0.56); 7.5152 (0.95); 7.5119 (1.00); 7.5065 (0.59); 7.5024 (0.90); 7.4979 (0.69); 7.3698 (2.38); 7.3642 (1.56); 7.3581 (3.33); 7.3557 (3.19); 7.3182 (9.42); 7.3072 (10.44); 7.2977 (0.47); 7.2484 (1.13); 7.2271 (1.24); 7.2169 (0.59); 7.2151 (0.59); 7.1003 (1.43); 7.0967 (1.44); 7.0835 (1.36); 7.0798 (1.36); 5.7683 (4.36); 5.3294 (6.25); 4.3091 (1.77); 4.2919 (3.97); 4.2746 (1.82); 3.4037 (0.97); 3.3535 (85.62); 3.3034 (0.84); 3.0561 (16.00); 2.9567 (1.70); 2.9394 (3.60); 2.9223 (1.63); 2.5598 (0.36); 2.5321 (0.51); 2.5273 (0.83); 2.5186 (10.78); 2.5142 (22.44); 2.5097 (30.45); 2.5052 (21.69); 2.5008 (10.00); 2.3376 (10.61); 1.9962 (0.32); 0.8633 (0.38)
Example 273, Solvent: DMSO, Spectrometer: 400.13 MHz 10.0964 (3.37); 7.8268 (0.34); 7.8057 (2.55); 7.7996 (2.71); 7.7923 (5.67); 7.7786 (0.49); 7.7281 (2.96); 7.7102 (3.59); 7.7066 (2.67); 7.5665 (0.51); 7.5545 (0.42); 7.5481 (1.76); 7.5427 (0.58); 7.5330 (1.00); 7.5300 (1.53); 7.4993 (2.67); 7.4801 (3.37); 7.4663 (0.60); 7.4624 (1.28); 7.0999 (1.37); 7.0926 (1.37); 7.0866 (1.21); 7.0792 (1.31); 5.7660 (9.16); 5.3293 (7.08); 4.9239 (0.48); 4.9086 (0.67); 4.9026 (0.63); 4.8958 (0.64); 4.8896 (0.68); 4.8744 (0.48); 3.3938 (0.69); 3.3441 (47.37); 3.2945 (0.46); 3.0757 (16.00); 2.5620 (0.35); 2.5575 (0.45); 2.5530 (0.33); 2.5121 (25.17); 2.5077 (33.19); 2.5034 (24.22); 2.4584 (0.34); 1.6934 (0.55); 1.6756 (0.68); 1.6582 (0.64); 1.6419 (0.40); 1.5897 (0.56); 1.5748 (0.46); 1.5682 (0.60); 1.5549 (0.96); 1.5406 (0.64); 1.5340 (0.74); 1.5192 (0.57); 1.3542 (0.67); 1.3419 (0.75); 1.3341 (0.65); 1.3209 (1.04); 1.3076 (0.57); 1.2998 (0.59); 1.2872 (0.57); 1.2329 (7.05); 1.2174 (6.90); 0.8989 (10.42); 0.8828 (10.36); 0.8617 (0.94); 0.8441 (0.40)
Example 274, Solvent: DMSO, Spectrometer: 399.95 MHz 10.7019 (2.04); 8.0143 (0.53); 7.9939 (0.68); 7.9532 (0.96); 7.8834 (1.41); 7.8645 (1.82); 7.8439 (1.19); 7.7312 (1.94); 7.7285 (2.56); 7.7247 (1.23); 7.7160 (0.76); 7.7108 (3.44); 7.7071 (2.38); 7.6072 (3.15); 7.6007 (3.32); 7.5674 (0.48); 7.5555 (0.35); 7.5491 (1.63); 7.5434 (0.48); 7.5342 (0.87); 7.5308 (1.41); 7.5274 (0.72); 7.4996 (2.34); 7.4962 (0.99); 7.4842 (1.60); 7.4805 (3.04); 7.4669 (0.47); 7.4628 (1.22); 7.4596 (0.67); 7.3777 (1.54); 7.3713 (1.43); 7.3555 (1.80); 7.3490 (1.73); 7.2103 (1.70); 7.1917 (1.63); 7.1000 (2.67); 7.0776 (2.29); 5.3832 (5.95); 4.9497 (4.55); 3.3282 (37.74); 3.0682 (16.00); 2.8906 (7.85); 2.7319 (6.15); 2.7310 (6.09); 2.5250 (0.63); 2.5202 (0.97); 2.5117 (12.73); 2.5071 (25.54); 2.5025 (33.71); 2.4979 (24.41); 2.4934 (11.58); −0.0002 (8.34)
Example 275, Solvent: DMSO, Spectrometer: 399.95 MHz 10.7688 (2.18); 8.0309 (1.21); 8.0102 (1.60); 7.9528 (0.76); 7.8802 (1.31); 7.8607 (1.81); 7.8406 (1.14); 7.7282 (2.70); 7.7246 (1.38); 7.7156 (0.77); 7.7105 (3.43); 7.7068 (2.51); 7.6133 (1.57); 7.6094 (1.68); 7.5936 (1.72); 7.5896 (1.73); 7.5690 (0.50); 7.5659 (0.34); 7.5570 (0.36); 7.5507 (1.64); 7.5451 (0.50); 7.5357 (0.86); 7.5324 (1.44); 7.5291 (0.78); 7.5005 (2.47); 7.4851 (1.65); 7.4813 (3.15); 7.4677 (0.49); 7.4637 (1.25); 7.4606 (0.76); 7.3333 (0.70); 7.3293 (0.73); 7.3145 (1.01); 7.3125 (1.22); 7.3109 (1.23); 7.3088 (1.10); 7.2941 (0.92); 7.2901 (0.90); 7.2107 (1.86); 7.1920 (1.77); 6.9906 (1.36); 6.9877 (1.60); 6.9697 (1.29); 6.9668 (1.36); 6.9256 (0.92); 6.9223 (0.90); 6.9062 (1.47); 6.9035 (1.44); 6.8874 (0.84); 6.8841 (0.79); 5.3872 (6.09); 5.1467 (1.03); 5.1302 (1.04); 3.3399 (123.75); 3.0660 (16.00); 2.8908 (5.95); 2.7322 (4.63); 2.7311 (4.93); 2.5258 (0.64); 2.5210 (1.07); 2.5124 (13.90); 2.5079 (28.05); 2.5033 (37.22); 2.4987 (27.34); 2.4942 (13.33); 1.5824 (5.61); 1.5660 (5.59); −0.0002 (1.61)
Example 276, Solvent: DMSO, Spectrometer: 399.95 MHz 12.5560 (0.64); 7.9537 (0.82); 7.7374 (2.70); 7.7335 (1.28); 7.7249 (0.79); 7.7197 (3.48); 7.7159 (2.39); 7.5677 (0.48); 7.5562 (0.35); 7.5493 (1.71); 7.5435 (0.50); 7.5346 (0.94); 7.5312 (1.53); 7.5277 (0.77); 7.5050 (2.54); 7.5016 (1.06); 7.4899 (1.64); 7.4859 (3.15); 7.4725 (0.49); 7.4684 (1.25); 7.4649 (0.68); 7.3508 (0.43); 7.3414 (6.02); 7.3404 (5.91); 7.3249 (1.35); 7.3193 (4.72); 7.3104 (0.42); 6.9532 (0.42); 6.9443 (4.51); 6.9387 (1.29); 6.9273 (1.23); 6.9217 (4.04); 6.9127 (0.34); 5.3386 (5.77); 5.0657 (0.38); 5.0492 (1.46); 5.0326 (1.48); 5.0161 (0.39); 3.3457 (65.65); 3.0206 (16.00); 2.8912 (6.84); 2.7330 (5.35); 2.7321 (5.33); 2.5269 (0.41); 2.5221 (0.63); 2.5136 (7.99); 2.5091 (16.01); 2.5045 (21.12); 2.4999 (15.25); 2.4953 (7.19); 1.5480 (5.56); 1.5314 (5.56); −0.0002 (1.60)
Example 277, Solvent: DMSO, Spectrometer: 399.95 MHz 10.6096 (2.19); 8.0826 (1.14); 8.0618 (1.37); 7.9528 (0.54); 7.8409 (1.25); 7.8215 (1.73); 7.8013 (1.16); 7.7213 (2.00); 7.7189 (2.60); 7.7151 (1.25); 7.7062 (0.86); 7.7011 (3.43); 7.6974 (2.44); 7.5647 (0.49); 7.5527 (0.37); 7.5464 (1.64); 7.5407 (0.51); 7.5314 (0.87); 7.5281 (1.42); 7.5247 (0.72); 7.4962 (2.43); 7.4929 (1.04); 7.4808 (1.67); 7.4770 (3.10); 7.4634 (0.49); 7.4594 (1.23); 7.4562 (0.68); 7.1677 (3.79); 7.1664 (3.80); 7.1476 (2.84); 7.1283 (1.73); 6.9328 (1.44); 6.9284 (1.09); 6.9099 (1.23); 5.3488 (6.06); 4.0675 (0.65); 4.0497 (0.65); 4.0080 (1.45); 3.9927 (3.37); 3.9776 (2.00); 3.9627 (0.33); 3.3890 (0.38); 3.3452 (212.55); 3.3105 (0.40); 3.0430 (16.00); 2.8912 (4.40); 2.7324 (3.41); 2.7316 (3.45); 2.6095 (1.27); 2.5913 (2.79); 2.5733 (1.45); 2.5261 (0.99); 2.5213 (1.58); 2.5128 (17.45); 2.5083 (34.25); 2.5037 (44.75); 2.4991 (32.26); 2.4946 (15.19); 2.4704 (0.69); 2.4523 (0.36); 2.1263 (1.67); 2.1070 (10.62); 2.0661 (0.37); 2.0495 (1.13); 2.0329 (1.74); 2.0160 (1.10); 1.9995 (0.51); 1.9820 (0.35); 1.1884 (0.73); 1.1706 (1.50); 1.1528 (0.72); −0.0002 (3.49)
Example 278, Solvent: DMSO, Spectrometer: 399.95 MHz 10.1336 (1.96); 8.0664 (1.00); 8.0457 (1.26); 7.9513 (0.33); 7.8853 (1.24); 7.8659 (1.71); 7.8459 (1.15); 7.7246 (2.19); 7.7221 (2.73); 7.7180 (1.51); 7.7142 (0.65); 7.7089 (1.35); 7.7043 (3.69); 7.7005 (2.37); 7.5649 (0.50); 7.5616 (0.33); 7.5528 (0.42); 7.5466 (1.70); 7.5408 (0.57); 7.5315 (1.18); 7.5282 (1.48); 7.5249 (0.82); 7.4962 (2.41); 7.4927 (1.05); 7.4808 (1.86); 7.4770 (3.30); 7.4635 (0.63); 7.4593 (1.50); 7.4559 (1.13); 7.4002 (0.58); 7.3855 (7.73); 7.3797 (3.53); 7.3714 (2.95); 7.3696 (3.46); 7.3640 (0.65); 7.3553 (0.54); 7.3520 (0.70); 7.3498 (0.81); 7.3310 (0.68); 7.3248 (0.93); 7.3179 (0.78); 7.3090 (0.84); 7.3001 (0.46); 7.2945 (0.34); 7.1994 (0.35); 7.1902 (1.72); 7.1726 (1.65); 7.1104 (0.40); 5.4143 (0.33); 5.3643 (6.06); 5.3563 (1.29); 5.2003 (0.33); 4.6039 (8.29); 4.1870 (7.38); 3.3359 (181.12); 3.3008 (0.45); 3.0859 (0.55); 3.0808 (1.06); 3.0716 (2.84); 3.0582 (16.00); 2.9841 (0.85); 2.8906 (2.19); 2.7318 (1.71); 2.7307 (1.65); 2.6762 (0.32); 2.6716 (0.45); 2.6670

NMR Peak List Table 1

(0.33); 2.5484 (0.34); 2.5343 (0.39); 2.5250 (1.32); 2.5201 (2.11); 2.5117 (26.87); 2.5071 (53.88); 2.5025 (71.21); 2.4979 (51.70); 2.4934 (24.61); 2.3822 (0.50); 2.3338 (0.35); 2.3292 (0.47); 2.3247 (0.34); 1.2349 (0.42); 0.0079 (0.69); −0.0002 (21.52); −0.0085 (0.66)
Example 280, Solvent: DMSO, Spectrometer: 400.13 MHz 10.5230 (2.44); 8.0938 (1.50); 8.0731 (1.78); 7.8439 (1.38); 7.8244 (2.03); 7.8043 (1.29); 7.7289 (2.98); 7.7111 (3.71); 7.7074 (2.72); 7.5768 (0.52); 7.5738 (0.37); 7.5651 (0.44); 7.5585 (1.80); 7.5529 (0.59); 7.5435 (1.08); 7.5404 (1.59); 7.5119 (2.76); 7.4963 (1.92); 7.4927 (3.41); 7.4791 (0.59); 7.4751 (1.29); 7.4720 (0.80); 7.1436 (2.08); 7.1254 (1.99); 5.3696 (7.11); 3.5033 (0.91); 3.4852 (3.04); 3.4670 (3.10); 3.4489 (0.96); 3.3413 (12.46); 2.5602 (0.35); 2.5324 (0.52); 2.5186 (11.43); 2.5145 (23.19); 2.5101 (31.21); 2.5057 (22.84); 2.4646 (0.39); 2.4601 (0.46); 2.4556 (0.33); 2.2822 (3.82); 2.2643 (4.64); 2.1022 (0.46); 2.0853 (0.83); 2.0684 (0.98); 2.0513 (0.77); 2.0341 (0.41); 1.0578 (3.39); 1.0397 (7.59); 1.0215 (3.33); 0.9258 (16.00); 0.9091 (15.75); 0.8953 (0.76); 0.8759 (0.34)
Example 281, Solvent: DMSO, Spectrometer: 399.95 MHz 11.0200 (2.46); 8.3677 (1.55); 8.3636 (2.85); 8.3595 (1.59); 8.1509 (1.72); 8.1305 (2.07); 8.0224 (0.91); 8.0198 (1.25); 8.0161 (0.96); 8.0028 (1.00); 8.0000 (1.28); 7.9965 (0.99); 7.9676 (1.01); 7.9649 (1.26); 7.9612 (1.03); 7.9533 (1.19); 7.9482 (1.33); 7.9443 (1.35); 7.9417 (0.99); 7.9289 (1.34); 7.9095 (1.89); 7.8893 (1.20); 7.7370 (2.65); 7.7242 (0.78); 7.7191 (3.38); 7.7153 (2.38); 7.5677 (0.48); 7.5559 (0.35); 7.5493 (1.69); 7.5437 (0.48); 7.5344 (0.88); 7.5312 (1.44); 7.5278 (0.73); 7.5015 (2.46); 7.4861 (1.65); 7.4823 (3.14); 7.4688 (0.48); 7.4647 (1.22); 7.4615 (0.68); 7.3370 (1.49); 7.3174 (2.77); 7.2978 (1.35); 7.2416 (1.89); 7.2232 (1.81); 5.4172 (6.36); 3.3294 (54.36); 3.0805 (16.00); 2.8908 (8.70); 2.7319 (7.06); 2.5250 (0.74); 2.5118 (13.92); 2.5073 (27.85); 2.5027 (36.77); 2.4981 (26.76); 2.4936 (12.83); 0.0080 (0.38); −0.0002 (11.62); −0.0085 (0.35)
Example 282, Solvent: DMSO, Spectrometer: 400.13 MHz 10.0952 (3.12); 7.8296 (0.38); 7.8084 (2.33); 7.8011 (2.52); 7.7944 (5.57); 7.7801 (0.48); 7.7305 (2.80); 7.7175 (0.87); 7.7126 (3.46); 7.7089 (2.53); 7.5694 (0.50); 7.5664 (0.34); 7.5575 (0.38); 7.5511 (1.71); 7.5456 (0.52); 7.5360 (0.93); 7.5329 (1.47); 7.5024 (2.53); 7.4867 (1.76); 7.4832 (3.22); 7.4695 (0.51); 7.4655 (1.21); 7.4625 (0.73); 7.1017 (1.33); 7.7094 (1.20); 7.0877 (1.16); 7.0810 (1.27); 5.7679 (0.50); 5.3323 (6.88); 4.8468 (0.51); 4.8312 (0.81); 4.8146 (0.82); 4.7991 (0.52); 3.4002 (1.35); 3.3506 (114.16); 3.3011 (1.16); 3.0779 (16.00); 2.5599 (0.44); 2.5554 (0.36); 2.5327 (0.62); 2.5190 (13.97); 2.5148 (28.89); 2.5104 (39.28); 2.5060 (28.69); 2.5019 (13.86); 2.4655 (0.34); 2.4610 (0.45); 2.4565 (0.37); 1.9969 (0.77); 1.5931 (0.52); 1.5889 (0.34); 1.5787 (0.44); 1.5745 (0.45); 1.5693 (0.69); 1.5603 (0.45); 1.5550 (0.54); 1.5507 (0.51); 1.5361 (0.69); 1.5193 (0.54); 1.5130 (0.44); 1.5053 (0.52); 1.4993 (0.65); 1.4835 (0.66); 1.4633 (0.34); 1.3874 (0.66); 1.3708 (0.99); 1.3540 (1.17); 1.3476 (0.93); 1.3362 (0.80); 1.3311 (0.84); 1.3193 (0.34); 1.3133 (0.54); 1.2355 (7.10); 1.2198 (7.05); 1.1814 (0.45); 0.9132 (3.75); 0.8949 (7.77); 0.8766 (3.27)
Example 283, Solvent: DMSO, Spectrometer: 400.13 MHz 11.4597 (1.60); 7.9113 (0.78); 7.8913 (1.69); 7.8723 (1.17); 7.7326 (2.70); 7.7198 (0.86); 7.7148 (3.40); 7.7111 (2.45); 7.5694 (0.49); 7.5663 (0.33); 7.5574 (0.38); 7.5511 (1.66); 7.5455 (0.51); 7.5360 (0.89); 7.5328 (1.43); 7.5296 (0.77); 7.5009 (2.42); 7.4854 (1.71); 7.4818 (3.12); 7.4681 (0.50); 7.4641 (1.21); 7.4610 (0.72); 7.2536 (1.56); 7.2332 (1.50); 5.7642 (6.38); 5.3885 (6.64); 4.4197 (2.03); 4.4033 (4.31); 4.3868 (2.06); 3.3963 (1.56); 3.3463 (92.86); 3.2958 (0.99); 3.0685 (16.00); 2.5577 (0.46); 2.5532 (0.38); 2.5301 (0.55); 2.5166 (10.67); 2.5122 (21.77); 2.5077 (29.27); 2.5033 (20.86); 2.4990 (9.75); 1.7398 (1.09); 1.7229 (2.25); 1.7047 (2.31); 1.6877 (1.16); 0.9557 (3.48); 0.9373 (7.16); 0.9187 (3.18)
Example 284, Solvent: DMSO, Spectrometer: 399.95 MHz 10.5363 (2.05); 8.1219 (1.42); 8.1013 (1.65); 7.8375 (1.30); 7.8182 (1.79); 7.7979 (1.24); 7.7335 (0.33); 7.7254 (2.71); 7.7216 (1.38); 7.7128 (0.87); 7.7076 (3.63); 7.7039 (2.48); 7.5641 (0.50); 7.5609 (0.33); 7.5521 (0.38); 7.5457 (1.68); 7.5401 (0.52); 7.5307 (0.88); 7.5274 (1.43); 7.5241 (0.75); 7.4955 (2.51); 7.4920 (1.10); 7.4800 (1.70); 7.4762 (3.21); 7.4626 (0.49); 7.4586 (1.26); 7.4554 (0.71); 7.1502 (1.83); 7.1323 (1.77); 5.3644 (6.20); 3.3298 (63.56); 3.2303 (0.37); 3.0552 (16.00); 2.8911 (1.33); 2.7316 (1.05); 2.5431 (0.40); 2.5316 (0.63); 2.5254 (0.90); 2.5205 (1.60); 2.5122 (12.11); 2.5078 (23.99); 2.5032 (31.50); 2.4985 (23.15); 2.4940 (11.22); 1.5746 (0.50); 1.5575 (0.66); 1.5519 (0.59); 1.5413 (0.89); 1.5347 (0.68); 1.5233 (0.78); 1.5194 (0.75); 1.5010 (0.54); 1.4484 (0.42); 1.4353 (0.52); 1.4299 (0.50); 1.4164 (0.65); 1.4019 (0.51); 1.3969 (0.51); 1.3892 (0.49); 1.3835 (0.47); 1.3770 (0.52); 1.3645 (0.60); 1.3523 (0.52); 1.3436 (0.37); 1.3317 (0.46); 1.3193 (0.32); 1.3068 (0.41); 1.3001 (0.47); 1.2817 (1.02); 1.2632 (1.34); 1.2451 (1.38); 1.2287 (1.07); 1.2220 (0.79); 1.2059 (0.95); 1.1933 (0.56); 1.1888 (0.51); 1.1739 (0.49); 1.1624 (0.36); 0.8759 (0.71); 0.8624 (0.55); 0.8568 (0.68); 0.8470 (4.95); 0.8291 (10.76); 0.8108 (5.01); −0.0002 (5.59)
Example 285, Solvent: DMSO, Spectrometer: 399.95 MHz 10.0705 (2.77); 7.9536 (0.36); 7.8216 (0.41); 7.8005 (2.24); 7.7921 (2.44); 7.7860 (5.46); 7.7711 (0.49); 7.7226 (2.67); 7.7187 (1.30); 7.7098 (0.84); 7.7048 (3.49); 7.7010 (2.43); 7.5621 (0.50); 7.5503 (0.37); 7.5438 (1.67); 7.5381 (0.49); 7.5289 (0.91); 7.5256 (1.45); 7.5222 (0.74); 7.4951 (2.47); 7.4919 (1.05); 7.4797 (1.72); 7.4760 (3.15); 7.4624 (0.51); 7.4583 (1.24); 7.4551 (0.70); 7.0950 (1.33); 7.0886 (1.32); 7.0806 (1.15); 7.0742 (1.26); 5.3254 (6.53); 4.8215 (0.47); 4.8062 (0.78); 4.7738 (0.38); 3.3407 (96.03); 3.0703 (16.00); 2.8915 (2.89); 2.7327 (2.25); 2.7320 (2.25); 2.5262 (0.53); 2.5213 (0.88); 2.5129 (10.07); 2.5085 (19.85); 2.5039 (26.06); 2.4993 (18.98); 2.4948 (9.12); 1.5881 (0.36); 1.5747 (0.42); 1.5658 (0.48); 1.5564 (0.42); 1.5509 (0.51); 1.5322 (0.59); 1.5152 (0.44); 1.5066 (0.54); 1.4929 (0.46); 1.3536 (0.50); 1.3363 (0.71); 1.3321 (0.72); 1.3193 (0.78); 1.3149 (0.81); 1.3045 (0.94); 1.2950 (1.34); 1.2863 (1.61); 1.2797 (2.04); 1.2703 (3.01); 1.2541 (1.61); 1.2431 (0.80); 1.2287 (6.76); 1.2130 (6.55); 0.8749 (1.76); 0.8582 (5.20); 0.8411 (1.83); −0.0002 (4.73)
Example 286, Solvent: DMSO, Spectrometer: 399.95 MHz 11.7750 (1.35); 7.9533 (0.60); 7.7398 (0.37); 7.7340 (2.02); 7.7314 (2.73); 7.7275 (1.36); 7.7189 (0.84); 7.7138 (3.47); 7.7100 (2.46); 7.5626 (0.51); 7.5594 (0.34); 7.5512 (0.38); 7.5443 (1.73); 7.5384 (0.52); 7.5296 (0.99); 7.5262 (1.55); 7.5227 (0.77); 7.5004 (2.57); 7.4971 (1.18); 7.4854 (1.72); 7.4814 (3.18); 7.4680 (0.52); 7.4639 (1.26); 7.4603 (0.76); 7.2548 (3.95); 5.3572 (0.33); 5.2852 (5.91); 3.9704 (0.55); 3.9495 (4.69); 3.9327 (4.70); 3.3295 (58.14); 3.0320 (16.00); 3.0231 (0.61); 3.0055 (0.91); 2.8909 (4.96); 2.7322 (3.94); 2.7313 (3.79); 2.5251 (0.61); 2.5203 (1.00); 2.5118 (11.94); 2.5073 (23.81); 2.5027 (31.39); 2.4981 (22.76); 2.4936 (10.82); 1.9567 (0.44); 1.9399 (0.86); 1.9231 (1.11); 1.9063 (0.90); 1.8896 (0.45); 1.2350 (0.33); 1.1216 (0.52); 1.1064 (0.51); 0.9226 (15.33); 0.9058 (14.86); 0.8933 (0.33); 0.7691 (1.58); 0.7522 (1.53); 0.0079 (0.35); −0.0002 (10.48); −0.0085 (0.32)
Example 287, Solvent: DMSO, Spectrometer: 399.95 MHz 10.7077 (2.17); 8.0144 (1.38); 7.9939 (1.80); 7.9534 (0.62); 7.8623 (1.36); 7.8430 (1.89); 7.8227 (1.15); 7.7275 (2.71); 7.7146 (0.94); 7.7097 (3.53); 7.7060 (2.49); 7.5683 (0.51); 7.5651 (0.34); 7.5562 (0.42); 7.5500 (1.70); 7.5444 (0.52); 7.5350 (0.95); 7.5317 (1.46); 7.5284 (0.75); 7.4994 (2.48); 7.4838 (1.86); 7.4802 (3.21); 7.4665 (0.56); 7.4624 (1.28); 7.4594 (0.74); 7.1953 (1.87); 7.1770 (1.81); 7.0770 (2.58); 7.0565 (3.04); 6.8270 (0.55); 6.8201 (3.88); 6.8154 (1.29); 6.8032 (1.28); 6.7986 (3.28); 6.7914 (0.35); 5.3807 (6.32); 5.0371 (0.35); 5.0208 (1.21); 5.0043 (1.22); 4.9881 (0.35); 3.3311 (69.44); 3.0567 (16.00); 2.8905 (4.81); 2.7320 (3.89); 2.5250 (0.77); 2.5117 (14.21); 2.5073 (26.90); 2.5027 (34.43); 2.4981 (24.82); 2.4937 (11.83); 2.1976 (10.16); 1.5119 (5.69); 1.4954 (5.63); −0.0002 (4.65)

NMR Peak List Table 1

Example 288, Solvent: DMSO, Spectrometer: 399.95 MHz 10.4500 (2.47); 7.9533 (1.17); 7.8545 (0.85); 7.8337 (1.78); 7.8155 (1.90); 7.7901 (2.36); 7.7711 (1.12); 7.7244 (2.84); 7.7115 (0.89); 7.7066 (3.55); 7.7028 (2.54); 7.5624 (0.51); 7.5593 (0.34); 7.5506 (0.39); 7.5441 (1.74); 7.5385 (0.54); 7.5291 (0.96); 7.5259 (1.49); 7.5226 (0.80); 7.4958 (2.63); 7.4802 (1.83); 7.4766 (3.33); 7.4629 (0.53); 7.4589 (1.28); 7.4558 (0.74); 7.1345 (1.71); 7.1328 (1.71); 7.1166 (1.68); 7.1148 (1.58); 5.3445 (6.69); 4.3068 (2.26); 4.2918 (4.59); 4.2767 (2.35); 3.3322 (55.35); 3.0881 (0.45); 3.0698 (16.00); 2.9408 (2.44); 2.9257 (4.72); 2.9107 (2.35); 2.8907 (8.90); 2.7315 (7.16); 2.5252 (0.58); 2.5119 (10.49); 2.5074 (20.47); 2.5029 (26.75); 2.4983 (19.59); 2.4939 (9.53); −0.0002 (4.03)

Example 289, Solvent: DMSO, Spectrometer: 399.95 MHz 12.8382 (0.82); 8.2864 (1.50); 8.2819 (2.62); 8.2774 (1.51); 8.0804 (0.90); 8.0778 (1.16); 8.0741 (0.90); 8.0608 (1.00); 8.0571 (1.22); 8.0545 (0.94); 7.9532 (0.46); 7.8530 (0.83); 7.8508 (0.95); 7.8482 (0.90); 7.8461 (0.82); 7.8330 (0.96); 7.8308 (1.03); 7.8282 (1.05); 7.8261 (0.89); 7.7496 (1.91); 7.7471 (2.60); 7.7431 (1.26); 7.7346 (0.77); 7.7295 (3.35); 7.7256 (2.30); 7.5686 (0.46); 7.5574 (0.33); 7.5503 (1.64); 7.5443 (0.51); 7.5327 (2.72); 7.5288 (0.89); 7.5134 (3.05); 7.5080 (2.62); 7.5046 (1.13); 7.4934 (2.73); 7.4890 (3.11); 7.4757 (0.49); 7.4715 (1.23); 7.4679 (0.72); 7.3997 (3.42); 5.3866 (5.58); 3.3426 (101.07); 3.0219 (16.00); 2.8915 (3.90); 2.7329 (3.01); 2.7320 (3.03); 2.5265 (0.57); 2.5217 (0.91); 2.5132 (11.98); 2.5086 (24.12); 2.5040 (31.99); 2.4994 (23.20); 2.4949 (11.01); −0.0002 (3.13)

Example 290, Solvent: DMSO, Spectrometer: 400.13 MHz 10.3988 (2.83); 7.8336 (2.30); 7.8287 (2.35); 7.8207 (5.19); 7.8077 (0.34); 7.4434 (0.79); 7.4388 (1.18); 7.4220 (3.44); 7.4190 (3.83); 7.4157 (2.78); 7.4131 (2.79); 7.4076 (0.68); 7.3984 (3.61); 7.3958 (3.68); 7.3913 (1.19); 7.3792 (2.33); 7.3602 (0.72); 7.3557 (1.14); 7.3508 (0.57); 7.3459 (0.51); 7.3384 (1.09); 7.3215 (0.37); 7.2813 (1.35); 7.2790 (1.22); 7.2656 (0.72); 7.2618 (1.13); 7.2596 (0.95); 7.2437 (1.47); 7.2377 (1.88); 7.2336 (1.31); 7.1422 (1.05); 7.1403 (1.12); 7.1360 (1.09); 7.1341 (0.98); 7.1226 (1.64); 7.1154 (2.04); 7.1027 (1.16); 5.7688 (7.76); 5.3422 (5.76); 5.1856 (6.65); 3.7858 (16.00); 3.4000 (1.19); 3.3500 (96.57); 3.3264 (0.61); 3.3000 (0.91); 3.0634 (0.62); 3.0542 (14.52); 2.5599 (0.33); 2.5187 (9.19); 2.5143 (19.51); 2.5098 (26.74); 2.5053 (19.07); 2.5009 (8.79); 1.9968 (0.40)

Example 291, Solvent: DMSO, Spectrometer: 399.95 MHz 10.5535 (2.45); 8.0774 (1.51); 8.0567 (1.87); 7.9531 (1.07); 7.8944 (1.41); 7.8749 (2.05); 7.8549 (1.20); 7.7282 (2.93); 7.7103 (3.67); 7.7066 (2.68); 7.5666 (0.53); 7.5636 (0.36); 7.5546 (0.42); 7.5483 (1.81); 7.5428 (0.42); 7.5331 (1.02); 7.5301 (1.54); 7.5269 (0.85); 7.4990 (2.71); 7.4798 (3.47); 7.4659 (0.58); 7.4621 (1.33); 7.4591 (0.82); 7.3608 (1.26); 7.3418 (1.65); 7.2478 (0.66); 7.2297 (1.44); 7.2120 (2.96); 7.1941 (2.57); 7.1785 (1.52); 7.1614 (0.69); 7.0748 (1.56); 7.0567 (1.15); 5.3861 (6.82); 4.9128 (0.91); 4.8752 (2.31); 4.8329 (2.03); 4.7953 (0.79); 4.1945 (1.83); 4.1732 (1.91); 3.3299 (76.90); 3.2517 (0.66); 3.2333 (0.92); 3.2148 (0.63); 3.0958 (0.46); 3.0854 (0.44); 3.0703 (16.00); 2.8904 (7.84); 2.7317 (6.48); 2.5246 (0.89); 2.5113 (15.64); 2.5069 (30.26); 2.5024 (39.50); 2.4979 (29.41); 2.4936 (14.76); 1.2661 (6.42); 1.2488 (6.34); 1.2353 (0.43); −0.0002 (8.21)

Example 292, Solvent: DMSO, Spectrometer: 400.13 MHz 10.0906 (2.91); 7.8316 (0.45); 7.8106 (2.16); 7.8001 (2.59); 7.7951 (4.96); 7.7795 (0.62); 7.7311 (2.80); 7.7181 (0.96); 7.7132 (3.48); 7.7096 (2.55); 7.5696 (0.51); 7.5665 (0.36); 7.5578 (0.42); 7.5513 (1.71); 7.5457 (0.55); 7.5363 (0.97); 7.5331 (1.51); 7.5299 (0.83); 7.5029 (2.57); 7.4873 (1.82); 7.4837 (3.22); 7.4701 (0.55); 7.4661 (1.22); 7.4630 (0.76); 7.1024 (1.36); 7.0967 (1.35); 7.0874 (1.22); 7.0817 (1.29); 5.7644 (2.15); 5.3389 (6.96); 4.6343 (1.09); 4.6189 (1.59); 4.6034 (1.10); 3.3258 (8.17); 3.3019 (0.51); 3.0752 (16.00); 2.5643 (0.36); 2.5598 (0.50); 2.5553 (0.37); 2.5184 (10.46); 2.5141 (20.80); 2.5097 (27.75); 2.5052 (20.12); 2.5011 (9.73); 1.9967 (0.88); 1.8155 (0.55); 1.7987 (0.87); 1.7834 (0.90); 1.7666 (0.60); 1.2867 (0.39); 1.2527 (1.85); 1.2003 (0.46); 1.1879 (7.34); 1.1720 (7.27); 0.9252 (6.99); 0.9176 (7.32); 0.9083 (7.07); 0.9007 (6.78); 0.8824 (0.96); 0.8657 (2.52); 0.8481 (1.04)

Example 293, Solvent: DMSO, Spectrometer: 400.13 MHz 10.2789 (3.15); 7.8438 (0.62); 7.8228 (1.93); 7.8054 (3.57); 7.8002 (2.69); 7.7832 (0.75); 7.7793 (0.42); 7.7257 (2.84); 7.7078 (3.51); 7.7041 (2.48); 7.5642 (0.52); 7.5610 (0.35); 7.5520 (0.42); 7.5457 (1.74); 7.5402 (0.52); 7.5307 (0.93); 7.5275 (1.46); 7.4965 (2.61); 7.4809 (1.82); 7.4773 (3.26); 7.4636 (0.54); 7.4596 (1.24); 7.4567 (0.74); 7.1155 (1.45); 7.1117 (1.47); 7.0989 (1.36); 7.0951 (1.37); 5.3380 (6.63); 4.1862 (1.65); 4.1705 (3.40); 4.1547 (1.67); 3.3866 (0.40); 3.3374 (24.34); 3.2878 (0.41); 3.0613 (16.00); 2.5124 (2.45); 2.5081 (4.96); 2.5036 (6.66); 2.4992 (4.73); 2.4950 (2.19); 2.4122 (0.34); 2.3838 (0.60); 2.3638 (0.66); 2.3425 (0.65); 2.3154 (0.35); 1.9055 (0.43); 1.8899 (1.05); 1.8748 (1.00); 1.8663 (1.06); 1.8497 (0.95); 1.8339 (0.36); −0.0002 (3.50)

Example 294, Solvent: DMSO, Spectrometer: 399.95 MHz 10.6890 (2.49); 8.1522 (0.93); 8.1315 (1.09); 7.8916 (1.25); 7.8721 (1.85); 7.8520 (1.16); 7.8050 (1.30); 7.8008 (1.38); 7.7857 (1.46); 7.7815 (1.41); 7.7131 (2.66); 7.7003 (0.83); 7.6952 (3.45); 7.6916 (2.47); 7.5588 (0.53); 7.5557 (0.33); 7.5466 (0.41); 7.5406 (1.71); 7.5349 (0.52); 7.5224 (2.03); 7.5186 (1.47); 7.5043 (1.15); 7.5021 (1.24); 7.5001 (1.26); 7.4979 (1.10); 7.4869 (2.60); 7.4837 (2.02); 7.4794 (1.19); 7.4712 (1.81); 7.4677 (3.23); 7.4540 (0.53); 7.4499 (1.28); 7.4469 (0.76); 7.4106 (1.68); 7.4054 (0.66); 7.3918 (2.78); 7.3893 (2.68); 7.3753 (0.88); 7.3706 (2.30); 7.2762 (1.04); 7.2738 (1.03); 7.2572 (1.72); 7.2551 (1.89); 7.2386 (0.87); 7.2362 (0.84); 7.2005 (1.89); 7.1871 (2.58); 7.1822 (1.99); 7.1687 (1.87); 7.1525 (0.51); 7.1501 (0.83); 7.1476 (0.52); 7.1309 (2.34); 7.1286 (2.70); 7.1093 (2.38); 6.9056 (1.77); 6.9041 (1.75); 6.8849 (1.69); 5.3532 (5.98); 3.3296 (46.78); 3.0321 (16.00); 2.8901 (1.73); 2.7318 (1.42); 2.7307 (1.38); 2.5249 (0.61); 2.5200 (0.95); 2.5115 (11.41); 2.5070 (22.62); 2.5024 (29.74); 2.4978 (21.66); 2.4933 (10.40); −0.0002 (7.59)

Example 295, Solvent: DMSO, Spectrometer: 400.13 MHz 10.2021 (3.03); 7.8194 (2.48); 7.8139 (2.57); 7.8063 (5.69); 7.7929 (0.38); 7.6238 (0.66); 7.6198 (0.99); 7.6141 (0.93); 7.6087 (0.73); 7.6054 (1.17); 7.6020 (0.92); 7.5989 (0.96); 7.5945 (1.23); 7.5884 (2.44); 7.5859 (2.27); 7.5638 (0.76); 7.5496 (0.85); 7.5436 (1.15); 7.5292 (1.21); 7.5239 (0.60); 7.5086 (0.53); 7.4333 (0.52); 7.4305 (0.58); 7.4271 (0.53); 7.4241 (0.49); 7.4093 (0.93); 7.4053 (0.81); 7.3911 (0.42); 7.3883 (0.43); 7.3850 (0.40); 7.3822 (0.34); 7.1167 (1.31); 7.1091 (1.31); 7.0960 (1.26); 5.7681 (4.69); 5.3569 (6.73); 4.1129 (2.13); 4.0963 (4.54); 4.0797 (2.17); 3.4003 (0.73); 3.3503 (83.72); 3.3005 (0.85); 3.0656 (16.00); 2.5321 (0.53); 2.5185 (12.25); 2.5142 (25.77); 2.5097 (35.14); 2.5053 (25.40); 2.5009 (11.99); 2.4642 (0.35); 2.4599 (0.42); 1.6318 (0.45); 1.6147 (1.42); 1.6084 (0.53); 1.5974 (1.82); 1.5777 (1.54); 1.5611 (0.62); 1.4181 (0.32); 1.3996 (1.13); 1.3805 (1.78); 1.3616 (1.80); 1.3435 (1.07); 0.9310 (4.22); 0.9127 (8.61); 0.8941 (3.62)

Example 296, Solvent: DMSO, Spectrometer: 399.95 MHz 10.5653 (2.11); 8.0322 (0.93); 8.0114 (1.20); 7.9526 (0.57); 7.8814 (1.32); 7.8622 (1.82); 7.8419 (1.12); 7.7279 (2.60); 7.7241 (1.26); 7.7152 (0.80); 7.7101 (3.42); 7.7064 (2.39); 7.5680 (0.49); 7.5560 (0.37); 7.5497 (1.65); 7.5439 (0.49); 7.5347 (0.88); 7.5314 (1.42); 7.5280 (0.72); 7.5001 (2.40); 7.4967 (1.02); 7.4847 (1.67); 7.4809 (3.11); 7.4673 (0.49); 7.4633 (1.23); 7.4601 (0.69); 7.2018 (1.78); 7.1835 (1.74); 7.1030 (2.47); 7.0826 (2.95); 6.8616 (0.47); 6.8542 (3.89); 6.8491 (1.20); 6.8377 (1.13); 6.8327 (3.27); 5.3810 (6.19); 4.7431 (6.57); 3.3497 (123.82); 3.0655 (16.00); 2.8907 (4.55); 2.7323 (3.65); 2.7313 (3.54); 2.5260 (0.60); 2.5128 (11.48); 2.5083 (22.74); 2.5037 (29.82); 2.4991 (21.60); 2.4946 (10.25); 2.2250 (10.15); −0.0002 (2.80)

NMR Peak List Table 1

Example 297, Solvent: DMSO, Spectrometer: 400.13 MHz 7.3734 (0.52); 7.3625 (0.62); 5.8215 (0.71); 5.4128 (0.36); 3.4142 (16.00); 3.1179 (0.93); 2.5748 (0.94); 2.5704 (1.97); 2.5659 (2.68); 2.5614 (1.90); 2.5570 (0.88)

Example 298, Solvent: DMSO, Spectrometer: 399.95 MHz 10.2484 (2.39); 7.9534 (0.83); 7.8248 (0.61); 7.8038 (1.65); 7.7867 (2.12); 7.7805 (1.88); 7.7772 (2.09); 7.7597 (0.68); 7.7563 (0.46); 7.7251 (1.89); 7.7226 (2.41); 7.7187 (1.18); 7.7099 (0.77); 7.7048 (3.20); 7.7011 (2.24); 7.6211 (1.42); 7.6182 (1.43); 7.6011 (1.55); 7.5982 (1.49); 7.5628 (0.46); 7.5509 (0.35); 7.5445 (1.55); 7.5388 (0.47); 7.5296 (0.84); 7.5262 (1.35); 7.5228 (0.69); 7.4956 (2.24); 7.4922 (0.97); 7.4802 (1.55); 7.4765 (2.89); 7.4629 (0.48); 7.4588 (1.19); 7.4556 (0.70); 7.4476 (0.99); 7.4433 (1.04); 7.4285 (1.51); 7.4243 (1.46); 7.3636 (0.83); 7.3606 (0.84); 7.3451 (1.48); 7.3421 (1.40); 7.3263 (0.74); 7.3232 (0.69); 7.2615 (0.42); 7.2452 (0.46); 7.2151 (0.84); 7.2107 (0.83); 7.1956 (1.11); 7.1918 (1.06); 7.1768 (0.62); 7.1724 (0.58); 7.1076 (1.33); 7.1042 (1.34); 7.0905 (1.29); 7.0870 (1.25); 5.3310 (5.73); 4.3271 (1.48); 4.3099 (3.37); 4.2927 (1.54); 3.3297 (54.92); 3.0986 (1.40); 3.0814 (2.94); 3.0634 (16.00); 2.8907 (6.64); 2.7322 (5.40); 2.7310 (5.22); 2.5252 (0.66); 2.5118 (11.96); 2.5073 (23.52); 2.5027 (30.86); 2.4981 (22.42); 2.4936 (10.72); −0.0002 (7.07)

Example 300, Solvent: DMSO, Spectrometer: 400.13 MHz 10.1755 (6.27); 7.8379 (1.21); 7.8168 (4.35); 7.8011 (9.36); 7.7974 (6.41); 7.7874 (0.39); 7.7810 (1.42); 7.7763 (0.68); 7.7288 (4.42); 7.7264 (5.89); 7.7224 (2.90); 7.7138 (1.80); 7.7087 (7.61); 7.7049 (5.26); 7.5779 (0.59); 7.5748 (1.08); 7.5716 (0.75); 7.5631 (0.92); 7.5565 (3.72); 7.5507 (1.19); 7.5417 (2.13); 7.5383 (3.32); 7.5349 (1.70); 7.5105 (5.53); 7.5071 (2.44); 7.4953 (3.67); 7.4914 (6.78); 7.4779 (1.12); 7.4738 (2.70); 7.4705 (1.53); 7.0992 (3.00); 7.0946 (3.03); 7.0831 (2.78); 7.0785 (2.83); 5.3451 (14.17); 4.1046 (4.42); 4.0879 (9.60); 4.0712 (4.48); 3.5266 (1.80); 3.5085 (6.12); 3.4903 (6.24); 3.4722 (1.91); 3.4170 (0.98); 3.3670 (69.16); 3.3169 (0.75); 2.5647 (0.39); 2.5602 (0.58); 2.5557 (0.41); 2.5325 (0.90); 2.5191 (16.36); 2.5147 (33.99); 2.5102 (46.37); 2.5056 (32.84); 2.5012 (15.09); 2.4644 (0.37); 2.4600 (0.49); 2.4557 (0.37); 1.6470 (0.54); 1.6293 (1.98); 1.6121 (3.17); 1.5949 (2.25); 1.5778 (0.71); 1.3719 (1.55); 1.3653 (0.56); 1.3477 (2.42); 1.3444 (2.31); 1.3372 (4.03); 1.3296 (8.24); 1.3207 (6.12); 1.3116 (5.42); 1.2783 (0.39); 1.2413 (0.56); 1.0620 (6.97); 1.0439 (16.00); 1.0256 (6.73); 0.9020 (4.14); 0.8958 (2.36); 0.8887 (3.98); 0.8846 (11.41); 0.8728 (2.50); 0.8667 (3.29); 0.8535 (0.33)

Example 301, Solvent: DMSO, Spectrometer: 399.95 MHz 10.5817 (2.01); 8.0676 (1.09); 8.0469 (1.31); 7.9533 (0.61); 7.8393 (1.24); 7.8200 (1.68); 7.7997 (1.13); 7.7234 (1.93); 7.7207 (2.49); 7.7168 (1.18); 7.7080 (0.75); 7.7029 (3.37); 7.6992 (2.32); 7.5640 (0.48); 7.5521 (0.35); 7.5457 (1.60); 7.5400 (0.47); 7.5308 (0.84); 7.5274 (1.39); 7.5240 (0.69); 7.4957 (2.34); 7.4922 (0.98); 7.4803 (1.60); 7.4765 (3.03); 7.4629 (0.47); 7.4588 (1.22); 7.4556 (0.67); 7.2924 (1.43); 7.2870 (0.61); 7.2783 (1.68); 7.2706 (1.96); 7.2621 (0.73); 7.2566 (1.76); 7.1448 (1.71); 7.1259 (1.76); 7.1173 (2.20); 7.1118 (0.63); 7.1008 (0.73); 7.0949 (3.46); 7.0889 (0.72); 7.0779 (0.59); 7.0726 (1.70); 5.3495 (5.92); 3.3272 (45.85); 3.0539 (0.44); 3.0439 (16.00); 2.9030 (0.99); 2.8904 (5.61); 2.8848 (2.09); 2.8648 (1.47); 2.7318 (4.10); 2.7308 (3.99); 2.7112 (1.68); 2.6911 (2.30); 2.6724 (1.23); 2.5250 (0.71); 2.5202 (1.11); 2.5115 (13.41); 2.5070 (26.81); 2.5024 (35.26); 2.4978 (25.40); 2.4932 (11.99); 0.0080 (0.42); −0.0002 (12.90); −0.0085 (0.38)

Example 302, Solvent: DMSO, Spectrometer: 399.95 MHz 10.5751 (1.95); 8.0622 (1.18); 8.0415 (1.42); 7.8378 (1.28); 7.8186 (1.79); 7.7983 (1.19); 7.7239 (2.63); 7.7201 (1.30); 7.7112 (0.81); 7.7061 (3.53); 7.7023 (2.40); 7.5646 (0.48); 7.5527 (0.37); 7.5463 (1.68); 7.5406 (0.49); 7.5314 (0.89); 7.5280 (1.44); 7.5247 (0.73); 7.4975 (2.46); 7.4941 (1.05); 7.4821 (1.68); 7.4784 (3.15); 7.4648 (0.49); 7.4607 (1.24); 7.4575 (0.69); 7.1459 (1.79); 7.1275 (1.75); 5.3552 (6.34); 3.3313 (57.75); 3.0564 (16.00); 2.8909 (0.69); 2.8048 (1.11); 2.7982 (2.33); 2.7916 (1.11); 2.7322 (0.57); 2.5253 (0.64); 2.5205 (1.04); 2.5120 (11.23); 2.5075 (22.90); 2.5029 (28.76); 2.4983 (20.75); 2.4938 (10.21); 2.4883 (4.07); 2.4697 (1.89); 2.2215 (1.06); 2.2149 (1.11); 2.2035 (2.52); 2.1969 (2.46); 2.1858 (1.30); 2.1792 (1.22); 1.7808 (0.50); 1.7628 (1.78); 1.7446 (2.56); 1.7265 (1.66); 1.7082 (0.39); 0.8758 (0.46); −0.0002 (5.54)

Example 303, Solvent: DMSO, Spectrometer: 399.95 MHz 10.5034 (2.10); 8.0708 (1.22); 8.0501 (1.45); 7.8310 (1.27); 7.8118 (1.75); 7.7914 (1.20); 7.7258 (2.01); 7.7234 (2.56); 7.7195 (1.26); 7.7106 (0.79); 7.7055 (3.50); 7.7017 (2.38); 7.5638 (0.49); 7.5520 (0.36); 7.5456 (1.65); 7.5399 (0.48); 7.5306 (0.87); 7.5273 (1.41); 7.5239 (0.71); 7.4961 (2.41); 7.4927 (1.01); 7.4807 (1.65); 7.4769 (3.08); 7.4633 (0.48); 7.4593 (1.23); 7.4560 (0.67); 7.1401 (1.75); 7.1217 (1.72); 5.3530 (6.14); 3.3298 (59.04); 3.0538 (16.00); 2.5255 (0.55); 2.5207 (0.98); 2.5122 (10.97); 2.5076 (21.92); 2.5030 (28.82); 2.4984 (20.84); 2.4939 (9.85); 2.3883 (1.42); 2.3699 (2.74); 2.3515 (1.55); 1.5786 (0.72); 1.5611 (1.06); 1.5439 (0.73); 1.2645 (4.43); 1.2525 (4.67); 1.2380 (7.50); 0.8757 (0.48); 0.8610 (1.82); 0.8441 (5.76); 0.8267 (1.94); −0.0002 (6.01)

Example 304, Solvent: DMSO, Spectrometer: 400.13 MHz 10.8355 (2.01); 8.1896 (1.63); 8.1692 (1.88); 7.8924 (1.28); 7.8729 (1.87); 7.8529 (1.22); 7.7345 (2.69); 7.7216 (0.91); 7.7167 (3.42); 7.7130 (2.45); 7.5740 (0.51); 7.5709 (0.35); 7.5620 (0.41); 7.5556 (1.64); 7.5500 (0.55); 7.5407 (0.94); 7.5374 (1.45); 7.5341 (0.78); 7.5063 (2.45); 7.4909 (1.73); 7.4872 (3.13); 7.4735 (0.55); 7.4695 (1.23); 7.4664 (0.72); 7.1973 (1.87); 7.1792 (1.78); 6.6584 (0.92); 6.6330 (1.09); 6.6159 (1.36); 6.5904 (1.30); 6.3429 (1.55); 6.3382 (1.57); 6.3004 (1.18); 6.2956 (1.16); 5.8106 (1.49); 5.8059 (1.27); 5.7853 (1.24); 5.7805 (1.38); 5.3846 (6.54); 3.4060 (4.17); 3.4030 (0.76); 3.3548 (290.02); 3.3064 (2.05); 3.3037 (2.28); 3.0602 (16.00); 2.6799 (0.45); 2.6755 (0.35); 2.5713 (0.43); 2.5668 (0.73); 2.5623 (0.90); 2.5577 (0.61); 2.5333 (1.13); 2.5197 (25.85); 2.5153 (54.79); 2.5109 (75.93); 2.5064 (57.01); 2.5020 (29.30); 2.4643 (1.40); 2.4599 (1.19); 2.3424 (0.35); 2.3378 (0.48); 2.3332 (0.37); 2.0844 (1.74)

Example 305, Solvent: DMSO, Spectrometer: 400.13 MHz 10.1303 (1.45); 7.8128 (0.98); 7.8011 (1.25); 7.7970 (2.15); 7.7299 (1.32); 7.7120 (1.62); 7.7083 (1.19); 7.5496 (0.79); 7.5345 (0.45); 7.5314 (0.69); 7.5007 (1.20); 7.4849 (0.88); 7.4815 (1.51); 7.4639 (0.60); 7.1003 (0.64); 7.0950 (0.63); 7.0851 (0.58); 7.0797 (0.61); 5.3422 (3.17); 4.5504 (0.86); 4.5343 (0.87); 3.4017 (0.75); 3.3517 (60.76); 3.3007 (0.38); 3.0662 (7.33); 2.5121 (12.87); 2.5077 (17.01); 2.5034 (12.34); 1.1513 (3.30); 1.1352 (3.28); 0.9115 (16.00)

Example 306, Solvent: DMSO, Spectrometer: 400.13 MHz 10.4951 (2.75); 7.8642 (0.94); 7.8437 (1.78); 7.8249 (1.67); 7.7724 (2.22); 7.7523 (1.40); 7.7318 (2.74); 7.7189 (0.93); 7.7139 (3.47); 7.7102 (2.47); 7.5692 (0.51); 7.5660 (0.38); 7.5574 (0.42); 7.5509 (1.74); 7.5452 (0.54); 7.5359 (0.95); 7.5327 (1.47); 7.5294 (0.77); 7.5024 (2.51); 7.4869 (1.75); 7.4833 (3.18); 7.4697 (0.53); 7.4656 (1.24); 7.4625 (0.75); 7.1503 (1.82); 7.1326 (1.75); 5.7642 (5.61); 5.3520 (6.47); 5.2171 (0.63); 5.2130 (0.74); 5.2020 (1.22); 5.1979 (0.64); 5.1909 (0.70); 5.1866 (0.76); 4.0461 (0.40); 4.0283 (0.40); 3.9591 (1.44); 3.9480 (1.61); 3.9294 (3.60); 3.9185 (3.17); 3.8929 (3.27); 3.8774 (3.29); 3.8632 (1.54); 3.8478 (1.49); 3.3268 (10.91); 3.0843 (16.00); 2.5319 (0.47); 2.5186 (9.15); 2.5142 (18.42); 2.5097 (24.73); 2.5053 (17.65); 2.5009 (8.30); 1.9968 (1.70); 1.3740 (0.87); 1.2540 (0.46); 1.2004 (0.47); 1.1826 (0.90); 1.1648 (0.44); 0.8658 (0.64)

NMR Peak List Table 1

Example 307, Solvent: DMSO, Spectrometer: 400.13 MHz 11.7662 (2.02); 7.9923 (0.70); 7.9716 (2.06); 7.9544 (3.68); 7.9488 (2.77); 7.9322 (0.83); 7.7339 (2.77); 7.7160 (3.50); 7.7123 (2.60); 7.5723 (0.59); 7.5693 (0.44); 7.5604 (0.52); 7.5541 (1.76); 7.5484 (0.66); 7.5391 (1.04); 7.5358 (1.54); 7.5326 (0.92); 7.5039 (2.87); 7.4999 (2.41); 7.4942 (1.14); 7.4844 (4.11); 7.4788 (3.45); 7.4666 (1.94); 7.4600 (3.02); 7.4060 (3.23); 7.3866 (1.99); 7.3629 (0.96); 7.3601 (1.32); 7.3419 (2.03); 7.3372 (1.99); 7.3332 (1.68); 7.3267 (0.82); 7.3203 (1.75); 7.3163 (1.45); 5.7616 (1.24); 5.4392 (6.75); 3.3368 (242.25); 3.2532 (0.67); 3.2134 (0.36); 3.0760 (16.00); 2.6760 (0.42); 2.6712 (0.35); 2.5157 (22.45); 2.5113 (44.00); 2.5069 (58.73); 2.5024 (42.83); 2.4982 (21.79); 2.3380 (0.36); 2.3339 (0.46); 2.3291 (0.35); 1.9936 (0.48); 1.2393 (0.34)

Example 308, Solvent: DMSO, Spectrometer: 400.13 MHz 8.4946 (0.35); 7.9608 (0.78); 7.5519 (5.07); 7.5313 (5.95); 7.2961 (5.25); 7.2760 (4.82); 7.0021 (3.34); 6.9834 (1.17); 6.9611 (0.58); 6.7589 (0.48); 6.7475 (0.48); 6.7362 (0.37); 6.7248 (0.36); 6.5653 (5.42); 5.2835 (0.60); 5.0766 (8.67); 3.1224 (0.36); 3.1101 (0.68); 3.1043 (1.12); 3.0860 (1.13); 3.0677 (0.42); 2.9646 (0.46); 2.9424 (0.59); 2.8976 (5.66); 2.7391 (4.59); 2.7380 (4.66); 2.5603 (0.41); 2.5557 (0.43); 2.5509 (0.42); 2.5331 (0.36); 2.5283 (0.65); 2.5194 (13.51); 2.5151 (29.37); 2.5106 (40.95); 2.5061 (30.28); 2.5018 (14.89); 2.4699 (0.46); 2.4652 (0.59); 2.4607 (0.70); 2.4562 (0.56); 2.4275 (0.36); 2.3926 (0.37); 2.3519 (16.00); 2.3206 (0.44); 2.3026 (0.40); 1.2036 (1.64); 1.1854 (3.50); 1.1672 (1.64)

Example 309, Solvent: DMSO, Spectrometer: 399.95 MHz 10.3176 (1.10); 7.9596 (0.98); 7.9575 (1.12); 7.9391 (2.11); 7.9369 (1.93); 7.9072 (1.61); 7.8887 (1.76); 7.8681 (0.91); 7.7338 (1.85); 7.7311 (2.43); 7.7272 (1.22); 7.7185 (0.80); 7.7134 (3.35); 7.7096 (2.29); 7.5668 (0.87); 7.5550 (0.35); 7.5485 (1.58); 7.5428 (0.48); 7.5336 (0.85); 7.5302 (1.41); 7.5268 (0.70); 7.5044 (0.48); 7.4992 (2.31); 7.4957 (1.02); 7.4839 (1.57); 7.4801 (2.97); 7.4665 (0.46); 7.4624 (1.21); 7.4592 (0.67); 7.2448 (1.48); 7.2426 (1.52); 7.2265 (1.48); 7.2243 (1.42); 5.4005 (6.19); 3.3294 (55.22); 3.0910 (0.33); 3.0797 (16.00); 3.0660 (0.33); 2.8907 (2.20); 2.7320 (1.76); 2.7308 (1.72); 2.5249 (0.59); 2.5201 (0.98); 2.5116 (10.84); 2.5071 (21.47); 2.5025 (28.28); 2.4978 (20.42); 2.4933 (9.62); 1.4784 (0.34); 1.4674 (0.47); 1.4617 (0.90); 1.4543 (1.07); 1.4427 (0.67); 1.4338 (0.37); 1.4165 (0.84); 1.4104 (1.10); 1.4085 (1.14); 1.3983 (0.82); 1.3868 (0.36); 1.3685 (0.70); 1.3573 (1.37); 1.3479 (1.50); 1.3366 (1.20); 1.3342 (1.17); 1.3289 (0.93); 1.3108 (0.36); 0.8756 (0.43); −0.0002 (5.94)

Example 310, Solvent: DMSO, Spectrometer: 399.95 MHz 10.2343 (1.95); 8.1087 (0.50); 8.0893 (0.32); 7.9529 (1.04); 7.9064 (0.39); 7.8876 (0.32); 7.8227 (0.48); 7.8017 (1.47); 7.7847 (2.76); 7.7794 (1.93); 7.7624 (0.53); 7.7226 (2.31); 7.7048 (3.01); 7.7011 (2.12); 7.6822 (0.56); 7.6642 (0.64); 7.6608 (0.50); 7.5892 (0.36); 7.5695 (0.37); 7.5630 (0.43); 7.5510 (0.37); 7.5447 (1.39); 7.5391 (0.63); 7.5299 (0.99); 7.5264 (1.34); 7.5229 (0.73); 7.4958 (2.30); 7.4924 (0.98); 7.4805 (1.57); 7.4767 (2.96); 7.4630 (0.78); 7.4590 (1.26); 7.4558 (0.70); 7.4442 (0.58); 7.4398 (0.66); 7.4280 (0.69); 7.4239 (0.64); 7.4030 (0.34); 7.3382 (0.46); 7.3170 (0.57); 7.2332 (0.38); 7.2250 (3.92); 7.2219 (2.99); 7.2068 (5.84); 7.1038 (1.10); 7.0998 (1.12); 7.0872 (1.05); 7.0832 (1.05); 6.9745 (0.36); 6.8804 (0.36); 6.8730 (3.25); 6.8678 (0.97); 6.8565 (0.94); 6.8513 (2.89); 6.0032 (0.41); 5.5344 (1.14); 5.3314 (4.96); 5.1786 (0.99); 4.2520 (1.21); 4.2346 (2.78); 4.2173 (1.26); 3.7187 (16.00); 3.3402 (147.09); 3.0878 (2.53); 3.0642 (13.07); 3.0361 (3.25); 2.8906 (8.67); 2.8806 (1.16); 2.8632 (2.24); 2.8460 (1.04); 2.7322 (6.81); 2.7310 (6.82); 2.5255 (0.81); 2.5207 (1.32); 2.5122 (16.89); 2.5077 (33.74); 2.5031 (44.53); 2.4984 (32.34); 2.4939 (15.43); −0.0002 (2.35)

Example 311, Solvent: DMSO, Spectrometer: 399.95 MHz 10.6801 (2.05); 8.0262 (0.75); 8.0054 (0.97); 7.9533 (0.54); 7.8844 (1.30); 7.8652 (1.73); 7.8449 (1.09); 7.7320 (1.88); 7.7293 (2.50); 7.7255 (1.19); 7.7167 (0.73); 7.7116 (3.35); 7.7079 (2.31); 7.5674 (0.47); 7.5555 (0.34); 7.5491 (1.59); 7.5434 (0.46); 7.5341 (0.84); 7.5308 (1.39); 7.5274 (0.69); 7.4996 (2.30); 7.4961 (0.96); 7.4842 (1.56); 7.4805 (2.97); 7.4669 (0.46); 7.4628 (1.20); 7.4596 (0.66); 7.3586 (0.64); 7.3378 (1.37); 7.3200 (1.26); 7.3173 (0.91); 7.2997 (0.59); 7.2070 (1.66); 7.1896 (1.61); 6.8686 (0.56); 6.8626 (1.23); 6.8567 (0.83); 6.8404 (0.46); 6.8346 (1.14); 6.8263 (1.20); 6.8241 (1.70); 6.8208 (1.28); 6.8182 (1.05); 6.8154 (0.70); 6.8034 (1.29); 6.7997 (1.72); 6.7976 (1.56); 6.7945 (1.01); 6.7790 (0.55); 6.7772 (0.50); 6.7730 (0.42); 6.7713 (0.37); 5.3863 (5.92); 4.8317 (6.00); 3.3310 (56.17); 3.0697 (16.00); 2.8905 (4.50); 2.7320 (3.56); 2.7309 (3.46); 2.5252 (0.59); 2.5204 (0.93); 2.5118 (11.75); 2.5073 (23.51); 2.5027 (30.97); 2.4980 (22.33); 2.4935 (10.51); −0.0002 (6.98)

Example 312, Solvent: DMSO, Spectrometer: 399.95 MHz 12.4977 (1.07); 7.9530 (0.84); 7.7382 (1.90); 7.7354 (2.59); 7.7315 (1.23); 7.7230 (0.79); 7.7178 (3.43); 7.7140 (2.30); 7.5662 (0.47); 7.5547 (0.35); 7.5479 (1.64); 7.5420 (0.48); 7.5331 (0.90); 7.5297 (1.49); 7.5262 (0.73); 7.5031 (2.44); 7.4997 (1.01); 7.4880 (1.58); 7.4840 (3.01); 7.4707 (0.47); 7.4665 (1.22); 7.4630 (0.66); 7.3252 (4.43); 7.0772 (2.42); 7.0568 (2.80); 6.8137 (0.44); 6.8064 (3.66); 6.8014 (1.12); 6.7898 (1.08); 6.7849 (3.15); 5.3337 (5.52); 5.0082 (0.37); 4.9917 (1.44); 4.9751 (1.46); 4.9586 (0.37); 3.3371 (72.07); 3.0111 (16.00); 2.8904 (6.99); 2.7322 (5.42); 2.7310 (5.57); 2.5255 (0.52); 2.5207 (0.86); 2.5122 (10.05); 2.5077 (19.96); 2.5031 (26.22); 2.4985 (18.83); 2.4939 (8.79); 2.1960 (9.43); 1.5253 (5.41); 1.5088 (5.36); −0.0002 (3.46)

Example 313, Solvent: DMSO, Spectrometer: 399.95 MHz 10.6270 (2.08); 8.0373 (0.90); 8.0167 (1.13); 7.9533 (0.58); 7.8838 (1.37); 7.8645 (1.85); 7.8443 (1.15); 7.7954 (0.39); 7.7303 (2.72); 7.7265 (1.56); 7.7176 (0.93); 7.7124 (3.49); 7.7086 (2.54); 7.5679 (0.51); 7.5647 (0.36); 7.5560 (0.40); 7.5496 (1.74); 7.5439 (0.69); 7.5346 (0.94); 7.5313 (1.53); 7.5279 (0.87); 7.5004 (2.59); 7.4970 (1.36); 7.4850 (1.77); 7.4812 (3.38); 7.4677 (0.56); 7.4636 (1.34); 7.4603 (0.84); 7.3224 (1.90); 7.3158 (0.54); 7.3026 (2.47); 7.2999 (2.29); 7.2896 (0.98); 7.2822 (2.23); 7.2042 (1.83); 7.1864 (1.74); 6.9787 (1.01); 6.9764 (0.98); 6.9660 (2.78); 6.9635 (3.38); 6.9597 (3.35); 6.9494 (1.08); 6.9429 (4.65); 6.9359 (0.32); 5.3856 (6.31); 5.3362 (0.58); 4.7944 (6.74); 3.8868 (0.36); 3.8701 (0.37); 3.3346 (65.65); 3.0692 (16.00); 3.0596 (0.58); 2.8903 (4.69); 2.7319 (3.67); 2.5255 (0.56); 2.5206 (0.90); 2.5121 (9.87); 2.5076 (19.62); 2.5030 (25.88); 2.4984 (18.88); 2.4939 (9.15); 1.2343 (0.56); 0.9274 (1.14); 0.9142 (0.37); 0.9106 (1.13); −0.0002 (5.70)

Example 314, Solvent: DMSO, Spectrometer: 399.95 MHz 12.4317 (0.74); 7.9526 (1.20); 7.7390 (2.69); 7.7351 (1.30); 7.7266 (0.77); 7.7214 (3.45); 7.7176 (2.40); 7.5666 (0.47); 7.5552 (0.34); 7.5482 (1.66); 7.5423 (0.50); 7.5335 (0.92); 7.5301 (1.51); 7.5267 (0.76); 7.5046 (2.51); 7.5012 (1.07); 7.4895 (1.58); 7.4855 (3.09); 7.4722 (0.47); 7.4681 (1.21); 7.4645 (0.68); 7.3430 (4.60); 7.2834 (1.19); 7.2632 (2.64); 7.2428 (2.00); 7.2274 (1.42); 7.2223 (2.18); 7.2168 (1.66); 7.1772 (1.24); 7.1751 (1.50); 7.1730 (1.24); 7.1708 (1.12); 7.1575 (0.88); 7.1554 (0.93); 7.1532 (0.89); 7.1510 (0.72); 7.0102 (1.04); 7.0082 (1.11); 7.0040 (1.05); 7.0021 (1.00); 6.9894 (0.93); 6.9875 (0.92); 6.9832 (0.93); 6.9813 (0.86); 5.3457 (5.76); 4.8880 (7.21); 3.3347 (91.17); 3.0214 (16.00); 2.8904 (9.66); 2.7318 (7.62); 2.7308 (7.75); 2.5251 (0.80); 2.5202 (1.21); 2.5117 (14.62); 2.5072 (29.20); 2.5026 (38.58); 2.4980 (28.01); 2.4935 (13.36); −0.0002 (3.21)

Example 315, Solvent: DMSO, Spectrometer: 399.95 MHz 12.4292 (1.10); 7.9524 (0.91); 7.7415 (1.96); 7.7389 (2.67); 7.7350 (1.31); 7.7265 (0.85); 7.7213 (3.46); 7.7175 (2.41); 7.5667 (0.49); 7.5635 (0.34); 7.5553 (0.35); 7.5483 (1.67); 7.5425 (0.53); 7.5337 (0.92); 7.5303 (1.53); 7.5268 (0.79); 7.5048 (2.53); 7.5014 (1.15); 7.4898 (1.63);

-continued

NMR Peak List Table 1

7.4858 (3.13); 7.4724 (0.52); 7.4683 (1.24); 7.4647 (0.71); 7.3352 (4.68); 7.3280 (0.42); 7.3212 (1.97); 7.3156 (0.68); 7.3087 (0.50); 7.2989 (2.61); 7.2927 (0.37); 7.2872 (0.74); 7.2811 (2.16); 6.9835 (1.01); 6.9813 (0.90); 6.9667 (4.14); 6.9515 (1.30); 6.9461 (5.18); 5.3429 (5.92); 4.8426 (8.14); 4.8334 (0.55); 3.3374 (135.09); 3.3008 (0.33); 3.0224 (16.00); 2.8902 (7.54); 2.7316 (5.86); 2.7307 (5.95); 2.5248 (0.78); 2.5116 (14.77); 2.5071 (29.36); 2.5025 (38.78); 2.4979 (28.33); 2.4934 (13.71); 1.2348 (0.34); 1.1312 (0.55); 1.1160 (0.54); 0.0080 (0.37); −0.0002 (10.08)
Example 316, Solvent: DMSO, Spectrometer: 399.95 MHz 9.7797 (1.56); 8.0154 (1.22); 7.9956 (1.55); 7.8351 (1.07); 7.8160 (1.38); 7.7955 (0.95); 7.7281 (1.63); 7.7256 (2.08); 7.7218 (0.98); 7.7130 (0.64); 7.7079 (2.76); 7.7041 (1.91); 7.5637 (0.40); 7.5454 (1.33); 7.5397 (0.39); 7.5304 (0.69); 7.5271 (1.15); 7.5237 (0.58); 7.4951 (1.93); 7.4917 (0.83); 7.4796 (1.32); 7.4759 (2.50); 7.4623 (0.38); 7.4582 (1.00); 7.4551 (0.56); 7.1526 (1.38); 7.1350 (1.34); 5.3778 (4.99); 3.3271 (28.80); 3.1371 (0.50); 3.0675 (12.85); 2.5252 (0.48); 2.5204 (0.75); 2.5119 (3.19); 2.5073 (18.30); 2.5027 (24.18); 2.4981 (17.49); 2.4935 (8.27); 1.6465 (0.87); 1.6259 (0.76); 1.6175 (0.62); 1.6054 (1.01); 1.2727 (0.40); 1.2534 (0.96); 1.2353 (1.45); 1.2179 (0.87); 1.1885 (16.00); 1.1730 (1.20); 1.1623 (0.77); 1.1555 (0.63); 1.1440 (0.73); 1.1360 (0.58); 1.1287 (0.42); 1.1217 (0.45); 0.8557 (2.82); 0.8379 (5.68); 0.8196 (2.37); −0.0002 (9.76)
Example 317, Solvent: DMSO, Spectrometer: 400.13 MHz 10.1338 (1.76); 7.8350 (0.51); 7.8142 (1.18); 7.7964 (1.33); 7.7795 (1.74); 7.7609 (0.75); 7.7317 (1.99); 7.7138 (2.40); 7.7102 (1.83); 7.5702 (0.34); 7.5584 (0.33); 7.5518 (1.17); 7.5465 (0.46); 7.5337 (1.03); 7.5038 (1.79); 7.4846 (2.24); 7.4670 (0.89); 7.1163 (1.11); 7.1003 (1.09); 5.7646 (4.79); 5.3393 (4.53); 3.5385 (3.49); 3.3282 (12.06); 3.3043 (1.20); 3.0957 (0.40); 3.0742 (10.25); 2.5146 (14.75); 2.5102 (19.75); 2.5059 (15.03); 2.4650 (0.47); 2.4605 (0.46); 1.9972 (0.51); 1.6757 (16.00); 1.6259 (0.32); 1.3742 (0.56)
Example 318, Solvent: DMSO, Spectrometer: 399.95 MHz 12.4153 (0.70); 7.9530 (0.69); 7.7402 (2.57); 7.7363 (1.28); 7.7277 (0.77); 7.7226 (3.27); 7.7188 (2.30); 7.5665 (0.45); 7.5551 (0.32); 7.5481 (1.60); 7.5423 (0.49); 7.5335 (0.89); 7.5301 (1.46); 7.5266 (0.75); 7.5047 (2.23); 7.5014 (1.08); 7.4897 (1.54); 7.4857 (2.97); 7.4723 (0.47); 7.4682 (1.17); 7.4647 (0.67); 7.3372 (4.45); 7.2124 (1.11); 7.1936 (1.02); 7.1889 (1.27); 7.1761 (0.39); 7.1704 (1.14); 6.5674 (0.60); 6.5630 (1.09); 6.5598 (1.25); 6.5517 (0.54); 6.5452 (4.82); 6.5414 (5.79); 6.5253 (1.07); 6.5213 (1.17); 6.5174 (0.58); 5.3454 (5.49); 4.8238 (6.77); 3.7825 (0.48); 3.7233 (16.00); 3.3357 (39.45); 3.0205 (14.29); 2.8899 (5.54); 2.7318 (4.27); 2.7309 (4.41); 2.5253 (0.35); 2.5204 (0.56); 2.5120 (6.85); 2.5075 (13.71); 2.5029 (18.17); 2.4983 (13.29); 2.4938 (6.42); −0.0002 (3.59)
Example 319, Solvent: DMSO, Spectrometer: 400.13 MHz 7.6252 (3.43); 7.6045 (3.97); 7.3099 (7.22); 7.3018 (2.61); 7.2960 (1.28); 7.2885 (3.34); 7.2832 (3.38); 7.2801 (2.98); 7.2662 (0.90); 7.2615 (2.31); 7.2557 (0.33); 7.2066 (0.49); 7.2041 (0.49); 7.1855 (0.37); 6.9577 (1.05); 6.9393 (1.89); 6.9207 (1.50); 6.9166 (2.90); 6.9143 (3.19); 6.8946 (2.91); 6.8224 (0.61); 6.8025 (0.49); 5.3124 (5.92); 5.0675 (0.41); 5.0511 (1.47); 5.0345 (1.48); 5.0181 (0.41); 3.3657 (19.18); 3.0017 (16.00); 2.5578 (0.36); 2.5303 (0.59); 2.5168 (11.86); 2.5124 (24.30); 2.5080 (32.65); 2.5035 (23.38); 2.4992 (11.02); 2.4580 (0.36); 2.3543 (9.77); 2.3350 (0.34); 1.9942 (0.85); 1.5485 (5.79); 1.5319 (5.78); 1.4177 (0.87); 1.4009 (0.86); 1.2493 (1.28); 1.1785 (0.47); 0.8785 (0.58); 0.8617 (1.87); 0.8441 (0.74)
Example 320, Solvent: DMSO, Spectrometer: 400.13 MHz 10.9991 (2.97); 7.8393 (4.30); 7.8291 (3.79); 7.7294 (2.72); 7.7165 (0.96); 7.7115 (3.51); 7.7078 (2.54); 7.5691 (0.50); 7.5659 (0.35); 7.5571 (0.41); 7.5508 (1.72); 7.5452 (0.57); 7.5358 (0.98); 7.5325 (1.49); 7.5293 (0.81); 7.5013 (2.52); 7.4857 (1.83); 7.4821 (3.24); 7.4683 (0.66); 7.4644 (1.42); 7.4613 (0.90); 7.1624 (1.29); 7.1518 (2.06); 7.1415 (1.55); 7.5665 (4.47); 5.3558 (6.58); 3.3905 (0.41); 3.3403 (28.15); 3.2898 (0.38); 3.0603 (16.00); 2.8748 (1.96); 2.8568 (3.37); 2.8386 (2.06); 2.5624 (0.42); 2.5580 (0.59); 2.5536 (0.45); 2.5300 (1.29); 2.5166 (15.51); 2.5122 (31.16); 2.5078 (41.93); 2.5033 (30.56); 2.4990 (15.36); 2.4668 (0.80); 2.4620 (0.80); 2.4574 (0.81); 2.4529 (0.60); 1.9948 (0.57); 1.5845 (0.44); 1.5670 (1.20); 1.5483 (1.96); 1.5426 (1.04); 1.5310 (1.48); 1.5112 (0.67); 1.4100 (0.35); 1.3916 (1.16); 1.3726 (1.78); 1.3536 (1.74); 1.3359 (1.04); 1.3178 (0.34); 1.1792 (0.32); 0.9091 (4.22); 0.9016 (0.56); 0.8908 (8.65); 0.8724 (3.76); 0.8626 (0.53)
Example 321, Solvent: DMSO, Spectrometer: 399.95 MHz 12.5670 (0.86); 7.9540 (0.93); 7.7375 (2.93); 7.7337 (1.42); 7.7247 (0.85); 7.7198 (3.63); 7.7159 (2.53); 7.5663 (0.50); 7.5631 (0.32); 7.5548 (0.36); 7.5478 (1.81); 7.5421 (0.52); 7.5331 (0.98); 7.5298 (1.58); 7.5264 (0.80); 7.5034 (2.72); 7.5001 (1.16); 7.4881 (1.77); 7.4842 (3.37); 7.4708 (0.52); 7.4667 (1.29); 7.4633 (0.74); 7.3461 (4.72); 7.3312 (1.70); 7.3279 (0.56); 7.3102 (2.36); 7.3037 (0.33); 7.2889 (1.57); 7.0250 (3.80); 7.0214 (3.46); 7.0153 (1.44); 7.0057 (1.38); 7.0028 (0.89); 6.9097 (1.02); 6.9063 (1.14); 6.9017 (0.93); 6.8874 (1.05); 6.8824 (0.99); 5.3439 (6.21); 5.1257 (0.41); 5.1093 (1.54); 5.0928 (1.56); 5.0763 (0.42); 3.3415 (50.51); 3.0153 (16.00); 2.8911 (7.51); 2.7325 (6.13); 2.5269 (0.35); 2.5136 (7.04); 2.5091 (14.06); 2.5046 (18.55); 2.5000 (13.49); 2.4955 (6.47); 1.5507 (6.03); 1.5342 (5.92); −0.0002 (4.06)
Example 322, Solvent: DMSO, Spectrometer: 400.13 MHz 7.7379 (2.94); 7.7200 (3.52); 7.7163 (2.56); 7.5694 (0.52); 7.5578 (0.44); 7.5510 (1.74); 7.5455 (0.60); 7.5361 (1.02); 7.5330 (1.53); 7.5064 (2.70); 7.4872 (3.32); 7.4736 (0.59); 7.4697 (1.24); 7.3255 (5.12); 7.3002 (1.89); 7.2954 (0.97); 7.2820 (4.64); 7.2606 (4.97); 7.2472 (0.96); 7.2425 (2.28); 6.9589 (1.11); 6.9404 (2.25); 6.9183 (5.27); 6.8990 (3.84); 6.8659 (3.36); 6.8462 (3.04); 5.7584 (1.12); 5.3394 (6.42); 4.8693 (0.96); 4.8533 (1.96); 4.8379 (0.96); 4.5790 (1.00); 4.5662 (1.20); 4.5616 (1.30); 4.5487 (1.00); 3.3932 (4.87); 3.2928 (2.26); 3.1888 (0.79); 3.0122 (16.00); 2.9105 (0.57); 2.8929 (1.41); 2.8748 (1.43); 2.8568 (0.56); 2.5111 (24.58); 2.5067 (32.65); 2.5024 (23.72); 1.9635 (0.42); 1.9451 (1.56); 1.9272 (2.16); 1.9105 (1.87); 1.8889 (1.18); 1.8759 (0.93); 1.8691 (1.52); 1.8572 (0.92); 1.8503 (1.66); 1.8322 (1.13); 1.8149 (0.58); 1.1116 (2.12); 1.0936 (4.34); 1.0754 (2.05); 1.0080 (4.98); 0.9896 (10.27); 0.9710 (4.87)
Example 323, Solvent: DMSO, Spectrometer: 399.95 MHz 10.6044 (0.99); 10.4354 (1.93); 8.0787 (0.63); 8.0580 (0.75); 7.9790 (1.43); 7.9572 (2.24); 7.8334 (0.64); 7.8142 (0.90); 7.7970 (1.39); 7.7780 (1.69); 7.7576 (1.12); 7.7265 (3.64); 7.7135 (1.07); 7.7087 (4.56); 7.7050 (3.21); 7.5689 (0.38); 7.5658 (0.68); 7.5626 (0.43); 7.5539 (0.51); 7.5475 (2.35); 7.5418 (0.67); 7.5326 (1.26); 7.5293 (2.03); 7.5259 (1.02); 7.4989 (3.43); 7.4957 (1.48); 7.4834 (2.33); 7.4797 (4.36); 7.4661 (0.67); 7.4621 (1.68); 7.4589 (0.96); 7.1395 (0.90); 7.1202 (1.06); 7.1163 (1.76); 7.0977 (1.65); 6.1620 (2.27); 6.1552 (1.74); 6.1486 (1.15); 6.1410 (1.11); 5.8283 (1.01); 5.8213 (1.02); 5.8143 (0.95); 5.8072 (0.92); 5.3617 (7.82); 3.3316 (117.10); 3.3079 (1.30); 3.1502 (0.43); 3.1402 (0.78); 3.1296 (0.66); 3.1178 (0.78); 3.1077 (0.45); 3.0716 (16.00); 3.0612 (8.68); 2.9179 (0.75); 2.8908 (12.80); 2.8643 (1.07); 2.7320 (10.02); 2.7309 (9.50); 2.6718 (0.34); 2.5251 (1.02); 2.5202 (1.58); 2.5117 (20.05); 2.5072 (39.90); 2.5026 (52.31); 2.4980 (37.67); 2.4935 (17.75); 2.4637 (0.34); 2.4537 (0.38); 2.4430 (0.36); 2.4321 (0.34); 2.3294 (0.33); 1.8768 (0.37); 1.8476 (0.40); 1.8195 (0.41); 1.8102 (0.44); 1.7966 (0.50); 1.7909 (0.69); 1.7876 (0.62); 1.7818 (0.53); 1.7683 (0.48); 1.7591 (0.44); 1.6280 (0.52); 1.6081 (0.56); 1.4122 (0.47); 1.4063 (0.58); 1.4017 (0.54); 1.3956 (0.51); 1.3836 (0.42); 1.3778 (0.51); 1.3732 (0.47); 1.3672 (0.45); 1.3235 (0.41); 1.3186 (0.37); 1.3031 (1.18); 1.2983 (1.30); 1.2931 (0.81); 1.2835 (1.60); 1.2685 (0.70); 1.2634 (0.79); 1.2409 (0.35); 1.2349 (0.43); 1.2254 (0.47); 1.2056 (0.37); 0.0080 (0.34); −0.0002 (10.51)

NMR Peak List Table 1

Example 324, Solvent: CDCl3, Spectrometer: 300.16 MHz 8.1893 (1.90); 8.1624 (2.14); 7.8514 (2.74); 7.7462 (1.30); 7.7201 (2.44); 7.6936 (1.39); 7.6449 (3.76); 7.6305 (2.84); 7.3211 (1.25); 7.2968 (3.76); 7.2671 (5.70); 7.2520 (6.74); 7.2466 (6.67); 7.2265 (4.57); 7.1382 (2.37); 7.1101 (4.43); 7.0754 (3.73); 7.0471 (2.34); 5.2736 (9.20); 3.0797 (16.00); 3.0368 (2.87); 2.7426 (2.75); 2.7168 (4.45); 2.6922 (2.18); 2.0047 (1.07); −0.0002 (1.49)

Example 325, Solvent: DMSO, Spectrometer: 400.13 MHz 10.2707 (2.81); 7.8308 (0.57); 7.8098 (1.73); 7.7927 (2.57); 7.7903 (2.20); 7.7861 (2.23); 7.7689 (0.62); 7.7653 (0.39); 7.4220 (1.01); 7.4021 (2.17); 7.3820 (1.57); 7.3181 (8.50); 7.3071 (9.73); 7.2974 (0.48); 7.2844 (1.53); 7.2809 (1.28); 7.2673 (0.83); 7.2636 (1.20); 7.2614 (1.02); 7.2457 (1.76); 7.2391 (2.78); 7.2361 (2.05); 7.2272 (1.18); 7.2151 (0.58); 7.1442 (1.07); 7.1425 (1.11); 7.1379 (0.99); 7.1363 (0.95); 7.1237 (0.96); 7.1218 (0.93); 7.1173 (0.94); 7.1153 (0.89); 7.1100 (1.38); 7.1063 (1.37); 7.0932 (1.28); 7.0894 (1.28); 5.7672 (6.91); 5.3371 (5.77); 4.3097 (1.63); 4.2924 (3.64); 4.2752 (1.67); 3.7886 (16.00); 3.4026 (1.13); 3.3522 (124.45); 3.3013 (1.15); 3.0531 (14.26); 2.9572 (1.57); 2.9399 (3.30); 2.9227 (1.50); 2.5599 (0.39); 2.5322 (0.61); 2.5187 (13.05); 2.5143 (27.08); 2.5099 (36.73); 2.5054 (26.27); 2.5010 (12.20); 2.4589 (0.37); 1.9964 (0.46); 1.2499 (0.40); 0.8639 (0.57)

Example 326, Solvent: DMSO, Spectrometer: 400.13 MHz 7.6240 (3.18); 7.6034 (3.68); 7.3073 (2.91); 7.2872 (2.56); 6.9984 (3.45); 6.6183 (3.43); 5.0954 (6.06); 4.0425 (0.33); 4.0247 (0.34); 3.4017 (1.53); 3.3515 (96.15); 3.3014 (1.20); 3.0355 (16.00); 2.5304 (0.36); 2.5256 (0.58); 2.5170 (6.14); 2.5125 (12.69); 2.5080 (17.18); 2.5035 (12.15); 2.4990 (5.59); 2.3549 (9.06); 1.9942 (1.50); 1.1971 (0.40); 1.1793 (0.82); 1.1615 (0.39)

Example 327, Solvent: DMSO, Spectrometer: 399.95 MHz 10.7598 (2.34); 8.1621 (1.47); 8.1418 (1.74); 7.9523 (0.98); 7.9060 (1.29); 7.8865 (1.81); 7.8664 (1.19); 7.7321 (2.68); 7.7283 (1.36); 7.7194 (0.80); 7.7143 (3.48); 7.7106 (2.42); 7.5659 (0.50); 7.5540 (0.35); 7.5475 (1.69); 7.5418 (0.49); 7.5326 (0.92); 7.5293 (1.50); 7.5259 (0.79); 7.4993 (2.48); 7.4961 (1.07); 7.4839 (1.67); 7.4802 (3.16); 7.4666 (0.48); 7.4593 (0.71); 7.2973 (2.07); 7.2141 (1.91); 7.1964 (2.13); 7.1806 (1.75); 7.1771 (1.76); 7.1659 (2.86); 7.1464 (0.75); 5.3763 (6.18); 3.3460 (124.75); 3.0868 (16.00); 3.0776 (0.82); 3.0723 (0.46); 2.8906 (7.90); 2.7321 (6.17); 2.7312 (6.26); 2.5257 (0.61); 2.5209 (0.95); 2.5124 (11.99); 2.5078 (24.04); 2.5032 (31.79); 2.4986 (23.03); 2.4941 (10.93); 2.3341 (9.59); 2.3055 (8.92); −0.0002 (7.13)

Example 328, Solvent: DMSO, Spectrometer: 400.13 MHz 10.5372 (1.96); 8.1004 (1.32); 8.0797 (1.57); 7.8440 (1.17); 7.8248 (1.62); 7.8045 (1.12); 7.4238 (1.00); 7.4038 (2.12); 7.3837 (1.56); 7.2895 (1.00); 7.2872 (1.33); 7.2857 (1.36); 7.2834 (1.26); 7.2702 (0.77); 7.2662 (1.16); 7.2640 (0.97); 7.2452 (1.47); 7.2393 (1.90); 7.2352 (1.40); 7.1517 (1.79); 7.1472 (1.25); 7.1450 (1.25); 7.1406 (1.14); 7.1384 (1.15); 7.1264 (1.04); 7.1243 (1.00); 7.1200 (0.96); 7.1179 (0.86); 5.7690 (1.09); 5.3659 (5.52); 3.7891 (16.00); 3.7678 (0.41); 3.7601 (0.43); 3.3995 (1.96); 3.3494 (140.76); 3.3261 (1.70); 3.2996 (2.16); 3.0471 (14.86); 2.6932 (0.51); 2.6836 (0.59); 2.6792 (0.72); 2.6624 (0.37); 2.5603 (0.44); 2.5326 (0.44); 2.5191 (12.00); 2.5147 (25.85); 2.5102 (36.06); 2.5057 (26.73); 2.5013 (13.49); 2.4697 (0.68); 2.4650 (0.73); 2.4604 (0.75); 2.4559 (0.56); 1.5933 (0.43); 1.5889 (0.37); 1.5792 (0.46); 1.5728 (0.51); 1.5673 (0.39); 1.5579 (0.53); 1.3672 (0.69); 1.3318 (0.38); 1.3200 (0.47); 1.3065 (0.70); 1.2871 (0.87); 1.2728 (1.30); 1.2621 (0.71); 1.2528 (1.16); 1.2374 (0.92); 1.2198 (0.48); 1.2125 (0.34); 1.0700 (5.63); 1.0530 (5.66); 0.8844 (2.63); 0.8665 (5.38); 0.8485 (2.16)

Example 329, Solvent: DMSO, Spectrometer: 399.95 MHz 10.9504 (2.41); 8.1344 (1.61); 8.1145 (1.96); 7.9535 (0.81); 7.9139 (1.31); 7.8946 (1.80); 7.8744 (1.20); 7.8248 (0.88); 7.8223 (1.15); 7.8187 (0.93); 7.8054 (1.03); 7.8017 (1.31); 7.7993 (1.00); 7.7325 (2.04); 7.7299 (2.67); 7.7261 (1.32); 7.7173 (0.87); 7.7122 (3.49); 7.7084 (2.44); 7.6280 (1.50); 7.6227 (1.93); 7.6180 (1.45); 7.5681 (0.33); 7.5652 (0.52); 7.5620 (0.35); 7.5532 (0.44); 7.5459 (2.53); 7.5413 (0.65); 7.5319 (1.02); 7.5283 (1.87); 7.5252 (3.14); 7.5053 (1.57); 7.4975 (2.43); 7.4941 (1.07); 7.4821 (1.69); 7.4784 (3.11); 7.4648 (0.56); 7.4607 (1.40); 7.4577 (1.09); 7.4524 (1.98); 7.4471 (0.73); 7.4397 (0.59); 7.4338 (2.83); 7.4310 (2.69); 7.4252 (0.43); 7.4173 (0.96); 7.4123 (2.43); 7.2653 (1.04); 7.2632 (1.12); 7.2590 (1.03); 7.2570 (1.01); 7.2449 (1.04); 7.2428 (0.96); 7.2386 (0.96); 7.2365 (0.90); 7.2256 (1.85); 7.2072 (2.89); 7.1887 (1.90); 7.1728 (0.47); 7.1702 (0.82); 7.1676 (0.47); 7.0967 (2.58); 7.0940 (3.16); 7.0887 (0.87); 7.0797 (0.94); 7.0775 (1.54); 7.0749 (2.73); 7.0726 (2.29); 7.0661 (0.33); 5.4049 (5.99); 3.3296 (62.97); 3.0799 (0.33); 3.0675 (16.00); 2.8906 (6.62); 2.7320 (5.17); 2.7311 (5.11); 2.5251 (0.76); 2.5202 (1.21); 2.5118 (13.85); 2.5073 (27.56); 2.5027 (36.33); 2.4980 (26.37); 2.4935 (12.57); 1.2898 (0.51); 0.0079 (0.34); −0.0002 (9.72)

Example 331, Solvent: DMSO, Spectrometer: 399.95 MHz 11.0401 (2.57); 8.1582 (0.66); 8.1381 (0.77); 7.9294 (1.25); 7.9093 (3.59); 7.8888 (3.02); 7.7294 (2.91); 7.7115 (3.66); 7.7079 (2.66); 7.5630 (0.53); 7.5599 (0.34); 7.5511 (0.42); 7.5447 (1.75); 7.5390 (0.56); 7.5295 (1.03); 7.5264 (1.53); 7.5231 (0.82); 7.4958 (2.72); 7.4925 (1.51); 7.4766 (3.79); 7.4733 (2.64); 7.4625 (2.88); 7.4558 (4.95); 7.4439 (0.57); 7.2371 (1.95); 7.2265 (1.08); 7.2191 (2.64); 7.2111 (1.03); 7.2067 (1.10); 7.2040 (0.98); 7.1992 (0.81); 7.1916 (0.81); 7.1840 (0.73); 5.3767 (5.29); 3.3329 (31.64); 3.3266 (39.78); 3.0858 (16.00); 2.8898 (1.00); 2.7302 (0.83); 2.5237 (1.02); 2.5102 (18.01); 2.5060 (33.96); 2.5015 (43.58); 2.4970 (31.82); 2.4926 (15.48); 0.0079 (0.55); −0.0002 (13.09); −0.0085 (0.46)

Example 332, Solvent: DMSO, Spectrometer: 399.95 MHz 11.1771 (2.60); 8.1574 (0.59); 8.1376 (0.68); 7.9524 (1.45); 7.9370 (1.28); 7.9174 (1.90); 7.8975 (1.13); 7.7298 (3.63); 7.7255 (5.59); 7.7129 (0.96); 7.7078 (3.66); 7.7042 (2.65); 7.6147 (2.05); 7.5941 (3.25); 7.5646 (0.56); 7.5526 (0.41); 7.5463 (1.80); 7.5407 (0.60); 7.5305 (3.04); 7.5283 (2.43); 7.5255 (2.83); 7.5099 (1.44); 7.5048 (1.56); 7.4967 (2.71); 7.4810 (1.91); 7.4774 (3.38); 7.4638 (0.56); 7.4598 (1.29); 7.4568 (0.80); 7.2497 (1.89); 7.2311 (1.80); 5.3772 (4.44); 3.3362 (67.00); 3.3337 (97.23); 3.0721 (16.00); 2.8904 (10.48); 2.7309 (8.65); 2.5248 (0.74); 2.5114 (14.81); 2.5071 (29.40); 2.5025 (38.83); 2.4980 (28.68); 2.4936 (14.10); −0.0002 (4.73)

Example 333, Solvent: DMSO, Spectrometer: 300.16 MHz 9.8162 (1.07); 7.7866 (0.39); 7.7457 (0.73); 7.7216 (1.07); 7.7077 (3.99); 7.6938 (0.53); 7.6806 (0.38); 7.4843 (1.39); 7.4549 (1.52); 7.1399 (0.67); 7.1177 (0.73); 7.0930 (0.35); 7.0560 (7.69); 6.9663 (1.52); 6.9368 (1.35); 5.3862 (0.48); 5.1534 (2.18); 4.0814 (0.50); 4.0577 (1.53); 4.0339 (1.56); 4.0103 (0.53); 3.8358 (1.09); 3.7949 (0.46); 3.7814 (5.68); 2.5266 (1.11); 2.5211 (1.47); 2.5156 (1.09); 2.0068 (6.43); 1.4777 (16.00); 1.2146 (1.68); 1.1909 (3.31); 1.1672 (1.64)

Example 334, Solvent: DMSO, Spectrometer: 399.95 MHz 10.5735 (2.04); 8.0370 (0.83); 8.0163 (1.06); 7.9528 (0.46); 7.8839 (1.29); 7.8647 (1.75); 7.8444 (1.10); 7.7311 (1.91); 7.7284 (2.51); 7.7246 (1.20); 7.7159 (0.74); 7.7107 (3.37); 7.7070 (2.34); 7.5670 (0.48); 7.5551 (0.34); 7.5488 (1.60); 7.5430 (0.47); 7.5338 (0.85); 7.5304 (1.40); 7.5270 (0.69); 7.4991 (2.30); 7.4956 (0.97); 7.4837 (1.59); 7.4800 (3.00); 7.4664 (0.46); 7.4623 (1.22); 7.4591 (0.67); 7.2044 (1.70); 7.1861 (1.78); 7.1704 (1.78); 7.1497 (1.05); 6.7869 (3.05); 6.7701 (1.09); 6.7687 (1.09); 6.7526 (0.84); 6.7489 (0.89); 6.7449 (0.60); 6.7315 (0.85);

| NMR Peak List Table 1 |
| --- |
| 6.7251 (0.69); 5.3834 (5.94); 4.7651 (6.17); 3.3380 (87.86); 3.0675 (16.00); 2.8905 (3.90); 2.7320 (3.13); 2.7309 (2.98); 2.5254 (0.60); 2.5206 (0.95); 2.5120 (11.85); 2.5075 (23.70); 2.5029 (31.15); 2.4983 (22.41); 2.4937 (10.52); 2.2718 (9.63); −0.0002 (1.06)<br>Example 335, Solvent: DMSO, Spectrometer: 399.95 MHz |
| 10.8446 (1.99); 8.0209 (0.87); 8.0003 (1.08); 7.9528 (1.10); 7.8447 (1.33); 7.8255 (1.79); 7.8052 (1.17); 7.7315 (2.67); 7.7275 (1.28); 7.7186 (0.82); 7.7136 (3.47); 7.7098 (2.40); 7.6157 (1.48); 7.6129 (1.48); 7.5958 (1.67); 7.5929 (1.61); 7.5688 (0.49); 7.5570 (0.35); 7.5504 (1.67); 7.5448 (0.49); 7.5356 (0.89); 7.5323 (1.44); 7.5290 (0.73); 7.5017 (2.41); 7.4984 (1.04); 7.4862 (1.66); 7.4825 (3.09); 7.4689 (0.49); 7.4648 (1.21); 7.4617 (0.68); 7.4224 (0.86); 7.4180 (0.95); 7.4034 (1.69); 7.3990 (1.61); 7.3695 (0.98); 7.3666 (0.97); 7.3511 (1.61); 7.3481 (1.51); 7.3324 (0.74); 7.3294 (0.69); 7.2373 (0.91); 7.2327 (0.91); 7.2178 (1.21); 7.2135 (1.15); 7.1990 (0.69); 7.1945 (0.62); 7.1670 (1.82); 7.1491 (1.74); 5.3809 (6.19); 3.9370 (5.68); 3.3354 (140.14); 3.3090 (0.35); 3.0674 (16.00); 2.8904 (9.16); 2.7313 (7.18); 2.5251 (0.83); 2.5201 (1.35); 2.5117 (15.68); 2.5072 (30.91); 2.5026 (40.50); 2.4980 (29.29); 2.4935 (13.85); −0.0002 (3.42)<br>Example 336, Solvent: DMSO, Spectrometer: 399.95 MHz |
| 12.4786 (2.21); 7.9529 (1.52); 7.7420 (3.01); 7.7242 (3.76); 7.7204 (2.69); 7.5661 (0.54); 7.5629 (0.38); 7.5547 (0.48); 7.5478 (1.81); 7.5419 (0.65); 7.5330 (1.19); 7.5297 (1.68); 7.5263 (0.91); 7.5052 (2.78); 7.4900 (2.12); 7.4862 (3.46); 7.4726 (0.75); 7.4686 (1.41); 7.4651 (0.85); 7.3748 (2.53); 7.3540 (4.70); 7.2546 (0.81); 7.2351 (1.91); 7.2324 (1.87); 7.2090 (2.85); 7.1895 (1.17); 5.3579 (6.69); 3.3459 (152.72); 3.0510 (16.00); 2.8913 (11.04); 2.7325 (9.33); 2.5123 (16.67); 2.5080 (29.40); 2.5035 (36.54); 2.4990 (26.79); 2.4947 (13.64); 2.3392 (10.84); 2.3099 (10.35); −0.0002 (2.20)<br>Example 337, Solvent: DMSO, Spectrometer: 399.95 MHz |
| 10.1862 (2.95); 7.9534 (0.44); 7.8307 (0.54); 7.8097 (2.03); 7.7940 (4.41); 7.7908 (3.18); 7.7744 (0.63); 7.7236 (2.85); 7.7058 (3.61); 7.7022 (2.59); 7.5629 (0.52); 7.5598 (0.34); 7.5510 (0.40); 7.5446 (1.72); 7.5390 (0.54); 7.5295 (1.01); 7.5264 (1.50); 7.5231 (0.80); 7.4960 (2.59); 7.4802 (1.94); 7.4769 (3.32); 7.4630 (0.58); 7.4592 (1.29); 7.4561 (0.78); 7.1029 (1.46); 7.0983 (1.45); 7.0869 (1.36); 7.0823 (1.38); 5.3351 (6.99); 3.9970 (0.94); 3.9821 (0.97); 3.9705 (1.49); 3.9556 (1.54); 3.8991 (1.51); 3.8821 (0.91); 3.8727 (0.96); 3.8555 (0.95); 3.3407 (108.77); 3.0658 (16.00); 2.8913 (3.20); 2.7327 (2.69); 2.7319 (2.63); 2.5258 (0.67); 2.5124 (11.47); 2.5082 (21.72); 2.5037 (27.88); 2.4992 (20.48); 2.4948 (10.09); 1.8031 (0.35); 1.7862 (0.53); 1.7707 (0.54); 1.7555 (0.38); 1.3887 (0.65); 1.3765 (1.06); 1.3689 (1.10); 1.3600 (1.18); 1.3549 (0.95); 1.3473 (0.96); 1.3411 (0.84); 1.3345 (0.66); 1.3259 (0.53); 1.3165 (0.44); 1.3110 (0.38); 1.3081 (0.37); 1.2857 (0.50); 1.2815 (0.60); 1.2746 (0.44); 1.2636 (0.60); 1.2456 (0.39); 1.2348 (0.43); 1.1501 (0.42); 1.1284 (0.70); 1.1131 (0.48); 1.1082 (0.69); 1.0886 (0.35); 0.9151 (7.35); 0.8982 (7.21); 0.8915 (3.49); 0.8735 (5.28); 0.8561 (2.17); −0.0002 (1.69)<br>Example 338, Solvent: DMSO, Spectrometer: 400.13 MHz |
| 12.5513 (1.17); 7.6263 (1.09); 7.6205 (1.13); 7.6179 (1.06); 7.6144 (1.30); 7.6111 (0.95); 7.6054 (0.98); 7.5949 (3.13); 7.5701 (0.78); 7.5561 (0.92); 7.5500 (1.21); 7.5357 (1.22); 7.5307 (0.75); 7.5149 (0.53); 7.4333 (0.56); 7.4307 (0.65); 7.4271 (0.60); 7.4245 (0.57); 7.4095 (1.05); 7.4052 (0.93); 7.3912 (0.51); 7.3881 (0.52); 7.3824 (0.41); 7.3566 (4.83); 7.3044 (1.84); 7.2858 (2.87); 7.2829 (2.93); 7.2643 (2.36); 6.9620 (1.09); 6.9437 (1.94); 6.9250 (1.40); 6.9166 (3.31); 6.8969 (2.97); 5.3601 (6.34); 5.0709 (0.44); 5.0545 (1.58); 5.0379 (1.60); 5.0215 (0.46); 3.3929 (2.83); 3.3899 (2.70); 3.3520 (253.47); 3.3140 (2.34); 3.3114 (2.50); 3.0141 (16.00); 2.5491 (0.83); 2.5451 (0.86); 2.5302 (1.04); 2.5166 (19.07); 2.5124 (38.30); 2.5080 (51.33); 2.5036 (37.65); 2.4711 (0.82); 2.4670 (0.79); 2.3348 (0.32); 1.9940 (1.18); 1.5532 (6.01); 1.5367 (6.00); 1.2496 (0.83); 1.1969 (0.34); 1.1791 (0.64); 0.8790 (0.36); 0.8623 (1.06); 0.8446 (0.43)<br>Example 339, Solvent: DMSO, Spectrometer: 400.13 MHz |
| 11.7047 (1.36); 9.3587 (0.63); 7.6178 (3.59); 7.5972 (4.11); 7.3051 (3.39); 7.2849 (3.06); 7.2361 (4.24); 7.0024 (0.53); 6.9802 (1.03); 6.9581 (0.62); 6.7544 (0.67); 6.7430 (0.69); 6.7373 (0.37); 6.7318 (0.56); 6.7204 (0.53); 5.7642 (5.42); 5.2561 (6.14); 4.7129 (0.43); 4.6996 (0.53); 4.6901 (0.80); 4.6805 (0.61); 4.6677 (0.42); 3.3989 (0.92); 3.3491 (61.31); 3.2987 (1.04); 3.2816 (0.37); 3.0239 (16.00); 2.5579 (0.41); 2.5534 (0.34); 2.5167 (11.74); 2.5124 (23.24); 2.5080 (31.00); 2.5035 (22.77); 2.4993 (11.62); 2.4669 (0.67); 2.4622 (0.71); 2.4576 (0.72); 2.3524 (10.31); 1.9943 (0.57); 1.9148 (0.85); 1.8958 (0.91); 1.8832 (1.04); 1.8713 (1.12); 1.8640 (1.12); 1.7223 (0.91); 1.7130 (0.98); 1.7003 (1.04); 1.6924 (1.00); 1.5303 (0.48); 1.5199 (0.51); 1.5002 (0.57); 1.4660 (0.54); 1.4594 (0.44); 1.4340 (1.01); 1.4095 (1.30); 1.3838 (1.40); 1.3571 (1.24); 1.3311 (0.97); 1.3251 (1.05); 1.3055 (0.47); 1.2982 (0.56); 1.2685 (0.47); 1.2593 (0.41); 1.2389 (0.78); 1.2120 (0.47); 1.1969 (0.39); 1.1791 (0.45)<br>Example 340, Solvent: DMSO, Spectrometer: 399.95 MHz |
| 10.5036 (1.94); 8.0858 (1.31); 8.0652 (1.55); 7.8345 (1.28); 7.8151 (1.77); 7.7949 (1.20); 7.7260 (2.01); 7.7236 (2.59); 7.7197 (1.30); 7.7108 (0.81); 7.7057 (3.49); 7.7019 (2.40); 7.5644 (0.49); 7.5525 (0.37); 7.5461 (1.64); 7.5404 (0.49); 7.5311 (0.88); 7.5278 (1.42); 7.5245 (0.73); 7.4967 (2.43); 7.4933 (1.06); 7.4813 (1.66); 7.4776 (3.09); 7.4640 (0.49); 7.4593 (1.23); 7.4558 (0.68); 7.1437 (1.77); 7.1261 (1.72); 5.3567 (6.33); 3.3291 (56.94); 3.0541 (16.00); 2.8910 (2.50); 2.7322 (1.97); 2.5254 (0.55); 2.5120 (11.03); 2.5075 (21.92); 2.5029 (28.90); 2.4983 (21.10); 2.4938 (10.12); 2.2770 (3.50); 2.2591 (4.27); 2.0961 (0.39); 2.0792 (0.72); 2.0623 (0.85); 2.0452 (0.66); 2.0279 (0.33); 0.9218 (14.86); 0.9052 (14.47); 0.8759 (0.48); −0.0002 (5.49)<br>Example 341, Solvent: DMSO, Spectrometer: 399.95 MHz |
| 10.7964 (1.97); 8.0347 (1.30); 8.0140 (1.60); 7.9532 (0.78); 7.8342 (1.32); 7.8150 (1.85); 7.7947 (1.20); 7.7226 (2.72); 7.7187 (1.40); 7.7097 (0.90); 7.7047 (3.49); 7.7010 (2.45); 7.5644 (0.52); 7.5613 (0.36); 7.5524 (0.39); 7.5460 (1.75); 7.5404 (0.59); 7.5311 (0.99); 7.5278 (1.53); 7.5244 (0.86); 7.4962 (2.57); 7.4930 (1.19); 7.4807 (1.81); 7.4770 (3.25); 7.4634 (0.56); 7.4593 (1.32); 7.4562 (0.78); 7.3568 (0.70); 7.3519 (1.12); 7.3465 (0.58); 7.3357 (4.33); 7.3312 (6.36); 7.3133 (3.71); 7.3088 (1.21); 7.2984 (0.72); 7.2939 (1.35); 7.2627 (0.47); 7.2586 (0.87); 7.2539 (1.12); 7.2487 (0.64); 7.2437 (0.69); 7.2370 (1.15); 7.2302 (0.38); 7.2245 (0.35); 7.2202 (0.50); 7.1578 (1.86); 7.1399 (1.81); 5.3691 (6.42); 3.7173 (6.49); 3.5605 (0.68); 3.3349 (84.22); 3.2182 (0.39); 3.0879 (0.37); 3.0505 (16.00); 3.0168 (0.34); 2.8902 (5.85); 2.7315 (4.65); 2.5252 (0.64); 2.5118 (13.25); 2.5074 (26.44); 2.5028 (34.90); 2.4982 (25.49); 2.4937 (12.32); 1.2348 (0.41); −0.0002 (8.23)<br>Example 342, Solvent: DMSO, Spectrometer: 400.13 MHz |
| 10.4822 (4.13); 7.8668 (0.86); 7.8466 (2.31); 7.8282 (2.23); 7.8111 (3.59); 7.7906 (1.43); 7.7318 (4.01); 7.7129 (4.58); 7.5700 (0.66); 7.5519 (2.01); 7.5335 (1.91); 7.5035 (3.37); 7.4843 (4.28); 7.4660 (1.59); 7.1433 (2.51); 7.1258 (2.41); 5.7680 (0.34); 5.3517 (8.92); 4.7808 (6.78); 4.7769 (7.14); 3.5835 (3.23); 3.3459 (39.30); 3.0750 (16.00); 2.5109 (30.31); 1.9974 (0.61); 1.2506 (1.30); 1.1818 (0.33); 0.8802 (0.47); 0.8650 (1.04); 0.8478 (0.49)<br>Example 343, Solvent: DMSO, Spectrometer: 400.13 MHz |
| 10.3290 (2.95); 7.8459 (0.69); 7.8250 (1.97); 7.8078 (2.49); 7.8025 (2.32); 7.7990 (2.59); 7.7816 (0.86); 7.7780 (0.57); 7.5391 (2.24); 7.5239 (0.69); 7.5151 (1.06); 7.5118 (1.10); 7.5063 (0.62); 7.5024 (0.90); 7.4979 (0.68); 7.3894 (0.41); 7.3699 (2.39); 7.3643 (1.61); 7.3582 (3.22); 7.3558 (3.08); 7.1130 (1.48); 7.1096 (1.50); 7.0959 (1.43); 7.0925 (1.38); 5.7689 (2.85); 5.3584 (0.35); 5.3325 (6.35); 4.1952 (2.12); 4.1785 (4.56); 4.1618 (2.09); 3.3706 (1.83); 3.3438 (51.96); 3.3167 (1.57); 3.0893 (0.64); 3.0769 (0.49); 3.0625 (16.00); 3.0354 (0.54); 2.9238 (1.38); |

NMR Peak List Table 1

2.9172 (3.15); 2.9106 (1.46); 2.5792 (1.30); 2.5725 (1.38); 2.5625 (2.74); 2.5558 (2.68); 2.5456 (2.18); 2.5380 (3.34); 2.5326 (3.29); 2.5278 (3.13); 2.5187 (19.36); 2.5143 (38.86); 2.5099 (52.05); 2.5054 (37.06); 2.5010 (17.23); 2.4865 (2.10); 2.4827 (2.22); 2.3644 (0.57); 2.3383 (10.64); 2.3121 (0.49); 1.9970 (0.58)
Example 344, Solvent: DMSO, Spectrometer: 399.95 MHz 10.7868 (2.09); 8.1713 (1.58); 8.1514 (1.87); 7.9532 (0.61); 7.9195 (1.28); 7.9001 (1.74); 7.8799 (1.20); 7.8640 (1.84); 7.8250 (0.59); 7.8210 (0.85); 7.8161 (0.47); 7.8139 (0.42); 7.8089 (0.71); 7.8046 (0.99); 7.7995 (0.54); 7.7405 (1.85); 7.7379 (2.49); 7.7340 (1.17); 7.7254 (0.73); 7.7202 (3.32); 7.7164 (2.24); 7.5674 (0.47); 7.5556 (0.34); 7.5490 (1.58); 7.5433 (0.46); 7.5342 (0.84); 7.5308 (1.39); 7.5274 (0.69); 7.5011 (2.32); 7.4977 (0.95); 7.4859 (1.53); 7.4820 (2.96); 7.4685 (0.45); 7.4644 (1.19); 7.4611 (0.64); 7.4030 (3.39); 7.3871 (1.65); 7.3683 (0.40); 7.2243 (1.73); 7.2067 (1.66); 5.4161 (6.03); 3.3297 (54.18); 3.0852 (16.00); 2.8903 (5.08); 2.7319 (3.93); 2.7309 (4.00); 2.5249 (0.63); 2.5201 (0.99); 2.5115 (11.45); 2.5070 (22.78); 2.5024 (29.99); 2.4978 (21.53); 2.4932 (10.10); 2.3876 (10.11); −0.0002 (1.26)
Example 345, Solvent: DMSO, Spectrometer: 399.95 MHz 10.4697 (2.08); 8.1064 (1.50); 8.0868 (1.86); 7.9533 (0.64); 7.8958 (1.24); 7.8765 (1.68); 7.8563 (1.12); 7.7348 (1.87); 7.7321 (2.43); 7.7281 (1.15); 7.7195 (0.73); 7.7144 (3.31); 7.7106 (2.26); 7.5668 (0.47); 7.5549 (0.34); 7.5485 (1.59); 7.5427 (0.51); 7.5323 (2.61); 7.5310 (2.82); 7.5237 (2.16); 7.4998 (2.27); 7.4963 (0.95); 7.4846 (1.53); 7.4807 (2.93); 7.4672 (0.44); 7.4631 (1.20); 7.4598 (0.64); 7.1991 (1.65); 7.1980 (1.66); 7.1806 (1.63); 6.3325 (1.53); 6.3301 (1.53); 6.3240 (1.54); 6.3216 (1.45); 5.4021 (5.83); 3.3378 (106.36); 3.3155 (0.35); 3.0735 (16.00); 2.8911 (5.51); 2.7324 (4.38); 2.7312 (4.18); 2.5258 (0.64); 2.5210 (0.99); 2.5124 (11.87); 2.5079 (23.75); 2.5033 (31.29); 2.4986 (22.51); 2.4941 (10.49); 2.3698 (8.46); −0.0002 (3.20)
Example 346, Solvent: DMSO, Spectrometer: 399.95 MHz 10.5880 (2.15); 8.0620 (1.14); 8.0412 (1.37); 7.9531 (0.72); 7.8386 (1.27); 7.8192 (1.77); 7.7990 (1.15); 7.7201 (2.60); 7.7164 (1.25); 7.7075 (0.79); 7.7024 (3.39); 7.6987 (2.36); 7.5642 (0.48); 7.5522 (0.35); 7.5458 (1.63); 7.5402 (0.48); 7.5308 (0.86); 7.5276 (1.41); 7.5242 (0.72); 7.4959 (2.41); 7.4926 (1.02); 7.4804 (1.67); 7.4767 (3.09); 7.4631 (0.49); 7.4591 (1.22); 7.4559 (0.70); 7.3427 (2.55); 7.3377 (0.98); 7.3267 (1.32); 7.3214 (5.36); 7.3158 (0.80); 7.2799 (4.54); 7.2748 (1.20); 7.2635 (0.97); 7.2586 (2.31); 7.1451 (1.80); 7.1272 (1.72); 5.3493 (6.15); 3.3324 (100.44); 3.0448 (16.00); 2.9063 (1.07); 2.8903 (7.38); 2.8683 (1.61); 2.7319 (4.73); 2.7310 (4.74); 2.7178 (1.73); 2.6980 (2.37); 2.6797 (1.18); 2.6720 (0.37); 2.5251 (0.80); 2.5117 (14.73); 2.5073 (29.28); 2.5027 (38.54); 2.4981 (27.95); 2.4936 (13.25); −0.0002 (6.71)
Example 347, Solvent: DMSO, Spectrometer: 400.13 MHz 10.6002 (3.59); 8.0852 (1.89); 8.0645 (2.24); 7.8484 (1.48); 7.8288 (2.54); 7.8089 (1.33); 7.7306 (3.99); 7.7117 (4.54); 7.5715 (0.67); 7.5536 (2.01); 7.5355 (1.89); 7.5043 (3.34); 7.4851 (4.28); 7.4668 (1.60); 7.3025 (1.13); 7.2837 (3.96); 7.2569 (6.77); 7.2397 (2.08); 7.1962 (1.30); 7.1790 (1.87); 7.1537 (2.83); 7.1350 (2.53); 5.3585 (8.79); 4.0629 (0.89); 4.0452 (2.68); 4.0274 (2.71); 4.0095 (0.92); 3.3444 (33.26); 3.0515 (16.00); 2.9208 (1.78); 2.9022 (3.80); 2.8826 (2.74); 2.7336 (2.73); 2.7137 (3.81); 2.6952 (1.83); 2.5108 (27.61); 1.9971 (10.87); 1.1994 (2.84); 1.1816 (5.58); 1.1639 (2.80)
Example 348, Solvent: DMSO, Spectrometer: 399.95 MHz 12.1340 (1.33); 8.0098 (0.92); 7.9897 (1.70); 7.9704 (1.43); 7.8942 (1.77); 7.8742 (1.25); 7.7286 (1.89); 7.7260 (2.42); 7.7221 (1.15); 7.7133 (0.75); 7.7082 (3.32); 7.7045 (2.30); 7.5683 (0.49); 7.5562 (0.35); 7.5500 (1.57); 7.5444 (0.46); 7.5350 (0.82); 7.5316 (1.36); 7.5283 (0.67); 7.4979 (2.26); 7.4943 (0.94); 7.4824 (1.60); 7.4787 (2.99); 7.4650 (0.46); 7.4609 (1.22); 7.4578 (0.67); 7.3792 (1.59); 7.3606 (1.55); 5.4394 (5.96); 3.3379 (128.50); 3.0662 (16.00); 2.8915 (2.29); 2.7327 (1.82); 2.7315 (1.75); 2.5259 (0.67); 2.5212 (1.10); 2.5126 (13.63); 2.5081 (27.26); 2.5034 (35.89); 2.4988 (25.83); 2.4943 (12.10); −0.0002 (7.61)
Example 349, Solvent: DMSO, Spectrometer: 399.95 MHz 10.2543 (2.68); 7.9532 (0.70); 7.8227 (0.67); 7.8017 (1.71); 7.7843 (2.07); 7.7746 (1.94); 7.7716 (2.20); 7.7538 (0.80); 7.7506 (0.60); 7.7248 (1.94); 7.7223 (2.60); 7.7185 (1.26); 7.7097 (0.79); 7.7046 (3.41); 7.7008 (2.38); 7.5633 (0.50); 7.5514 (0.38); 7.5449 (1.63); 7.5392 (0.50); 7.5300 (0.88); 7.5267 (1.42); 7.5233 (0.73); 7.4959 (2.39); 7.4925 (1.02); 7.4805 (1.63); 7.4768 (3.06); 7.4632 (0.48); 7.4591 (1.22); 7.4559 (0.69); 7.3997 (0.43); 7.3784 (0.92); 7.3728 (0.59); 7.3708 (0.47); 7.3646 (0.39); 7.3502 (11.60); 7.3482 (10.51); 7.3394 (0.61); 7.3357 (0.98); 7.3248 (0.51); 7.3145 (0.42); 7.2606 (1.89); 7.2443 (2.11); 7.1051 (1.44); 7.1020 (1.46); 7.0877 (1.40); 7.0846 (1.37); 5.3312 (6.08); 4.4282 (0.33); 4.4117 (0.75); 4.3952 (0.34); 4.2926 (1.54); 4.2759 (3.53); 4.2592 (1.60); 3.3372 (126.35); 3.0610 (16.00); 2.9947 (0.56); 2.9453 (1.49); 2.9287 (3.14); 2.9120 (1.42); 2.8908 (5.74); 2.7323 (4.49); 2.7313 (4.48); 2.5256 (0.73); 2.5208 (1.20); 2.5123 (13.89); 2.5078 (27.62); 2.5032 (36.45); 2.4986 (26.54); 2.4940 (12.71); −0.0002 (3.57)
Example 350, Solvent: DMSO, Spectrometer: 399.95 MHz 10.1864 (3.02); 7.9534 (0.57); 7.8312 (0.56); 7.8101 (2.19); 7.7945 (4.46); 7.7756 (0.82); 7.7707 (0.43); 7.7238 (2.98); 7.7058 (3.78); 7.7021 (2.84); 7.5630 (0.54); 7.5600 (0.40); 7.5510 (0.49); 7.5446 (1.81); 7.5389 (0.75); 7.5296 (1.11); 7.5265 (1.59); 7.4962 (2.76); 7.4805 (2.13); 7.4770 (3.51); 7.4634 (0.83); 7.4593 (1.45); 7.1028 (1.50); 7.0980 (1.55); 7.0870 (1.47); 7.0822 (1.53); 5.3350 (7.21); 4.0014 (0.95); 3.9861 (1.00); 3.9749 (1.68); 3.9595 (1.75); 3.9165 (1.66); 3.8997 (1.68); 3.8900 (1.07); 3.8731 (1.01); 3.3788 (0.32); 3.3388 (105.68); 3.0660 (16.00); 2.8913 (4.01); 2.8852 (0.59); 2.7321 (3.34); 2.5122 (12.39); 2.5080 (23.10); 2.5035 (30.13); 2.4990 (23.51); 2.4948 (13.50); 1.7201 (0.47); 1.7041 (0.77); 1.6875 (0.83); 1.6713 (0.59); 1.4677 (0.46); 1.4535 (0.61); 1.4490 (0.57); 1.4345 (0.96); 1.4200 (0.66); 1.4154 (0.78); 1.4014 (0.58); 1.3968 (0.34); 1.2034 (0.60); 1.1845 (0.95); 1.1662 (0.81); 1.1507 (0.82); 1.1321 (0.54); 0.9153 (8.10); 0.9093 (2.02); 0.8987 (9.35); 0.8827 (8.44); 0.8640 (3.59); −0.0002 (2.41)
Example 351, Solvent: CDCl3, Spectrometer: 300.16 MHz 7.9367 (2.19); 7.9094 (2.80); 7.7273 (1.51); 7.7010 (2.68); 7.6738 (3.71); 7.6503 (4.21); 7.6298 (2.91); 7.3598 (3.09); 7.2657 (3.71); 7.1381 (2.56); 7.1102 (4.82); 7.0824 (2.43); 7.0175 (2.74); 6.9931 (2.57); 5.2887 (10.20); 4.7665 (1.61); 3.1025 (16.00); 2.0103 (1.78); 1.9000 (2.89); 1.7612 (2.38); 1.7329 (2.66); 1.6600 (1.31); 1.5381 (2.17); 1.5043 (2.70); 1.4667 (2.95); 1.4382 (3.08); 1.4133 (2.78); 1.3737 (2.38); 1.3325 (1.78); 1.2914 (1.31); 1.2566 (1.36); −0.0002 (1.31)
Example 352, Solvent: DMSO, Spectrometer: 399.95 MHz 11.1247 (2.29); 8.2819 (3.02); 8.2767 (3.08); 8.1528 (1.61); 8.1327 (1.99); 7.9901 (1.54); 7.9848 (1.44); 7.9691 (1.89); 7.9638 (1.89); 7.9541 (0.84); 7.9401 (1.33); 7.9207 (1.83); 7.9005 (1.20); 7.8033 (3.39); 7.7823 (2.78); 7.7390 (1.93); 7.7366 (2.53); 7.7327 (1.21); 7.7239 (0.72); 7.7188 (3.37); 7.7150 (2.34); 7.5684 (0.48); 7.5566 (0.34); 7.5501 (1.65); 7.5444 (0.46); 7.5352 (0.85); 7.5318 (1.41); 7.5284 (0.70); 7.5017 (2.36); 7.4982 (0.97); 7.4863 (1.56); 7.4825 (3.06); 7.4690 (0.46); 7.4649 (1.22); 7.4616 (0.66); 7.2556 (1.79); 7.2375 (1.74); 5.4211 (6.09); 3.3313 (38.37); 3.0778 (16.00); 2.8913 (6.82); 2.7325 (5.36); 2.5261 (0.44); 2.5213 (0.70); 2.5127 (8.87); 2.5082 (17.81); 2.5036 (23.56); 2.4990 (16.98); 2.4944 (8.00); −0.0002 (0.96)

NMR Peak List Table 1

Example 353, Solvent: DMSO, Spectrometer: 400.13 MHz 9.8641 (1.93); 7.8004 (0.48); 7.7793 (1.24); 7.7622 (1.72); 7.7578 (1.49); 7.7541 (1.65); 7.7368 (0.71); 7.7321 (1.59); 7.7293 (1.89); 7.7255 (0.93); 7.7166 (0.58); 7.7115 (2.42); 7.7078 (1.70); 7.5676 (0.35); 7.5493 (1.16); 7.5436 (0.35); 7.5344 (0.63); 7.5311 (1.03); 7.5276 (0.53); 7.5004 (1.70); 7.4971 (0.75); 7.4851 (1.17); 7.4813 (2.18); 7.4678 (0.35); 7.4637 (0.87); 7.4604 (0.50); 7.0788 (0.97); 7.0752 (0.98); 7.0619 (0.92); 7.0583 (0.92); 5.3244 (4.26); 3.3896 (0.47); 3.3397 (41.48); 3.2899 (0.41); 3.0675 (11.33); 2.5304 (0.45); 2.5256 (0.75); 2.5169 (8.87); 2.5124 (18.25); 2.5079 (24.61); 2.5034 (17.32); 2.4989 (7.90); 1.7635 (0.58); 1.7461 (0.73); 1.7234 (0.82); 1.4389 (16.00); 1.3560 (0.38); 1.3488 (0.38); 1.3420 (0.50); 1.3322 (0.55); 1.3257 (0.57); 1.3174 (0.75); 1.3034 (0.99); 1.2877 (0.84); 1.2722 (0.64); 1.2522 (0.34); 0.9024 (1.88); 0.8850 (3.91); 0.8671 (1.36)

Example 354, Solvent: DMSO, Spectrometer: 400.13 MHz 7.5870 (0.36); 7.5372 (1.48); 7.5179 (2.69); 7.4986 (1.54); 7.4596 (1.32); 7.4401 (2.73); 7.4203 (1.72); 7.2590 (2.93); 7.2373 (5.70); 7.1701 (2.39); 7.1499 (2.05); 6.6317 (2.81); 6.6140 (2.67); 6.5162 (2.85); 6.4956 (2.72); 6.3123 (0.60); 6.2567 (0.53); 5.8756 (0.50); 5.8170 (0.73); 5.7902 (0.56); 5.7836 (0.56); 5.7699 (0.56); 5.2813 (9.40); 3.8363 (16.00); 2.5626 (19.23)

Example 355, Solvent: DMSO, Spectrometer: 400.13 MHz 10.5306 (2.21); 8.0790 (1.28); 8.0583 (1.51); 7.8391 (1.28); 7.8197 (1.77); 7.7996 (1.16); 7.5405 (2.15); 7.5254 (0.63); 7.5216 (0.55); 7.5165 (0.97); 7.5134 (0.96); 7.5083 (0.59); 7.5039 (0.86); 7.4994 (0.65); 7.3715 (2.45); 7.3666 (1.59); 7.3602 (3.09); 7.3577 (3.11); 7.1366 (1.85); 7.1189 (1.73); 5.3526 (6.21); 3.3938 (0.48); 3.3440 (44.99); 3.2942 (0.40); 3.0464 (16.00); 2.5642 (0.42); 2.5597 (0.57); 2.5552 (0.45); 2.5322 (1.20); 2.5188 (17.84); 2.5144 (36.19); 2.5099 (48.86); 2.5055 (35.26); 2.5011 (16.57); 2.4647 (0.35); 2.4602 (0.45); 2.4556 (0.35); 2.3971 (1.70); 2.3787 (3.20); 2.3601 (1.92); 2.3385 (10.36); 1.6135 (0.39); 1.5951 (1.12); 1.5767 (1.56); 1.5588 (1.08); 1.5405 (0.36); 1.3257 (0.40); 1.3094 (0.87); 1.2930 (1.76); 1.2855 (2.58); 1.2781 (2.17); 1.2682 (1.76); 1.2583 (1.31); 1.2477 (0.78); 0.8868 (2.57); 0.8697 (6.50); 0.8520 (2.62)

Example 356, Solvent: DMSO, Spectrometer: 399.95 MHz 12.4055 (0.86); 7.9526 (0.97); 7.7416 (1.96); 7.7391 (2.66); 7.7351 (1.30); 7.7266 (0.78); 7.7214 (3.44); 7.7176 (2.41); 7.5662 (0.47); 7.5548 (0.33); 7.5478 (1.66); 7.5420 (0.49); 7.5332 (0.91); 7.5298 (1.50); 7.5263 (0.75); 7.5042 (2.51); 7.5008 (1.08); 7.4892 (1.59); 7.4851 (3.10); 7.4718 (0.48); 7.4677 (1.21); 7.4641 (0.68); 7.3329 (4.75); 7.1872 (0.57); 7.1682 (1.82); 7.1475 (1.01); 6.7907 (3.25); 6.7723 (1.16); 6.7526 (0.88); 6.7489 (0.93); 6.7314 (0.91); 6.7253 (0.75); 5.3425 (5.89); 4.8140 (7.72); 3.3331 (69.47); 3.0202 (16.00); 2.8901 (8.02); 2.7316 (6.28); 2.7308 (6.36); 2.5248 (0.60); 2.5199 (0.94); 2.5114 (12.08); 2.5069 (24.17); 2.5023 (31.84); 2.4977 (23.01); 2.4932 (10.92); 2.2687 (10.20); −0.0002 (9.31)

Example 357, Solvent: DMSO, Spectrometer: 399.95 MHz 10.8133 (2.49); 8.1659 (1.62); 8.1458 (1.95); 8.0943 (0.48); 8.0872 (3.90); 8.0821 (1.24); 8.0702 (1.31); 8.0650 (4.12); 8.0579 (0.47); 7.9137 (1.27); 7.8944 (1.78); 7.8742 (1.19); 7.7353 (2.62); 7.7315 (1.35); 7.7228 (0.88); 7.7176 (3.44); 7.7139 (2.43); 7.5662 (0.49); 7.5631 (0.33); 7.5554 (0.38); 7.5480 (1.68); 7.5423 (0.55); 7.5330 (0.92); 7.5297 (1.48); 7.5263 (0.79); 7.4998 (2.53); 7.4963 (1.37); 7.4893 (2.12); 7.4843 (2.40); 7.4807 (3.39); 7.4706 (3.07); 7.4679 (3.14); 7.4630 (1.77); 7.4599 (0.98); 7.4543 (1.00); 7.4493 (2.50); 7.4436 (0.39); 7.2677 (0.71); 7.2650 (1.21); 7.2624 (0.74); 7.2465 (1.90); 7.2306 (0.55); 7.2280 (0.91); 7.2253 (0.59); 7.2181 (1.82); 7.2002 (1.78); 7.1452 (2.67); 7.1424 (3.27); 7.1373 (1.02); 7.1260 (1.59); 7.1234 (2.80); 7.1211 (2.39); 7.0606 (0.63); 7.0533 (4.09); 7.0482 (1.25); 7.0413 (0.43); 7.0362 (1.26); 7.0311 (3.97); 7.0240 (0.40); 5.4142 (5.96); 3.3293 (61.05); 3.1567 (0.32); 3.0799 (16.00); 3.0545 (0.34); 2.8905 (0.51); 2.7320 (0.41); 2.7309 (0.41); 2.5250 (0.84); 2.5116 (14.83); 2.5071 (29.04); 2.5025 (37.92); 2.4979 (27.39); 2.4934 (12.99); 1.3070 (0.44); 0.8796 (0.73); 0.0080 (0.38); −0.0002 (9.88)

Example 358, Solvent: DMSO, Spectrometer: 400.13 MHz 10.5367 (2.33); 8.0813 (1.35); 8.0606 (1.61); 7.8411 (1.25); 7.8216 (1.86); 7.8016 (1.16); 7.4233 (1.04); 7.4034 (2.27); 7.3833 (1.63); 7.2856 (1.58); 7.2660 (1.27); 7.2454 (1.65); 7.2397 (2.17); 7.2356 (1.50); 7.1459 (3.06); 7.1398 (1.36); 7.1265 (2.45); 7.1191 (1.10); 5.3603 (6.33); 3.7888 (16.00); 3.7596 (0.70); 3.3985 (0.35); 3.3486 (43.41); 3.2984 (0.45); 3.0441 (14.87); 2.5600 (0.36); 2.5319 (0.79); 2.5141 (28.51); 2.5097 (38.02); 2.5054 (27.97); 2.4638 (0.48); 2.4596 (0.54); 2.4055 (1.86); 2.3872 (3.47); 2.3686 (2.04); 1.5944 (0.48); 1.5762 (1.43); 1.5576 (2.01); 1.5390 (1.52); 1.5201 (0.60); 1.3663 (1.57); 1.3482 (0.34); 1.3296 (1.15); 1.3108 (1.88); 1.2920 (1.88); 1.2738 (1.12); 1.2556 (0.37); 0.9049 (4.05); 0.8867 (8.05); 0.8682 (3.41)

Example 359, Solvent: DMSO, Spectrometer: 399.95 MHz 10.2837 (2.70); 7.9529 (0.61); 7.8240 (0.70); 7.8030 (1.72); 7.7855 (2.06); 7.7745 (1.96); 7.7717 (2.20); 7.7537 (0.82); 7.7508 (0.65); 7.7206 (2.64); 7.7168 (1.31); 7.7080 (0.83); 7.7029 (3.46); 7.6991 (2.45); 7.5630 (0.50); 7.5598 (0.32); 7.5511 (0.38); 7.5447 (1.65); 7.5390 (0.52); 7.5298 (0.90); 7.5265 (1.45); 7.5231 (0.76); 7.4955 (2.45); 7.4921 (1.70); 7.4800 (1.70); 7.4763 (3.15); 7.4627 (0.51); 7.4586 (1.25); 7.4555 (0.73); 7.4144 (1.30); 7.4101 (2.22); 7.4064 (1.41); 7.3538 (0.61); 7.3448 (0.32); 7.3383 (0.78); 7.3309 (1.48); 7.3162 (2.37); 7.2947 (2.87); 7.2931 (2.90); 7.2901 (3.18); 7.2784 (1.27); 7.2731 (1.52); 7.2677 (0.91); 7.2600 (1.27); 7.2437 (1.56); 7.1062 (1.48); 7.1034 (1.52); 7.0889 (1.49); 7.0859 (1.43); 5.3320 (6.22); 4.4341 (0.54); 4.3114 (1.59); 4.2948 (3.64); 4.2783 (1.67); 3.3484 (195.53); 3.0598 (16.00); 3.0114 (0.40); 2.9615 (1.41); 2.9449 (2.93); 2.9285 (1.37); 2.8911 (4.89); 2.7326 (3.85); 2.7316 (3.88); 2.5263 (0.82); 2.5129 (15.31); 2.5085 (30.23); 2.5039 (39.71); 2.4993 (28.97); 2.4947 (13.99); 1.2345 (0.38); −0.0002 (1.72)

Example 360, Solvent: DMSO, Spectrometer: 499.93 MHz 8.6977 (5.13); 7.6370 (4.31); 7.6207 (4.47); 7.4018 (4.84); 7.3731 (0.38); 7.3568 (0.34); 7.3117 (4.27); 7.2955 (3.73); 7.0151 (0.49); 6.6708 (0.35); 5.3552 (8.40); 5.3273 (0.42); 5.1904 (0.78); 3.8201 (0.43); 3.5097 (15.51); 3.3228 (20.07); 3.2996 (0.64); 3.2803 (0.69); 3.0748 (16.00); 3.0403 (0.51); 2.5163 (2.66); 2.5132 (3.23); 2.3805 (1.26); 2.3747 (1.77); 2.3602 (13.33); 1.9994 (0.39); 1.2548 (0.41); 0.8685 (0.45)

Example 361, Solvent: DMSO, Spectrometer: 400.13 MHz 7.8582 (0.57); 5.3915 (0.63); 4.1510 (0.45); 3.8436 (1.74); 3.4133 (16.00); 3.1114 (1.61); 2.9519 (0.35); 2.5740 (0.97); 2.5696 (2.00); 2.5650 (2.71); 2.5605 (1.91); 2.5561 (0.87); 0.9860 (0.43); 0.9676 (0.88); 0.9491 (0.36)

Example 362, Solvent: DMSO, Spectrometer: 300.16 MHz 10.5351 (2.08); 8.1083 (1.37); 8.0811 (1.69); 7.8613 (1.22); 7.8356 (1.74); 7.8086 (1.11); 7.4422 (0.88); 7.4159 (2.15); 7.3892 (1.62); 7.3001 (1.49); 7.2728 (1.17); 7.2575 (1.54); 7.2497 (1.95); 7.2442 (1.31); 7.1632 (2.71); 7.1541 (1.14); 7.1403 (1.87); 7.1269 (0.92); 5.7807 (0.43); 5.3737 (5.71); 3.8222 (0.34); 3.8008 (16.00); 3.7716 (0.49); 3.3520 (75.07); 3.0552 (14.49); 2.5332 (8.46); 2.5272 (17.99); 2.5212 (24.66); 2.5152 (17.79); 2.5093 (8.39); 2.2963 (3.23); 2.2725 (4.11); 2.1237 (0.35); 2.1014 (0.69); 2.0787 (0.80); 2.0562 (0.59); 1.3779 (0.98); 0.9412 (14.50); 0.9191 (14.05)

NMR Peak List Table 1

Example 363, Solvent: DMSO, Spectrometer: 399.95 MHz 10.2058 (2.43); 7.8309 (0.51); 7.8099 (2.06); 7.7968 (2.75); 7.7941 (3.85); 7.7762 (0.59); 7.7248 (2.08); 7.7224 (2.63); 7.7185 (1.25); 7.7097 (0.84); 7.7046 (3.45); 7.7009 (2.35); 7.5621 (0.50); 7.5502 (0.39); 7.5438 (1.68); 7.5381 (0.49); 7.5289 (0.92); 7.5256 (1.45); 7.5221 (0.73); 7.4951 (2.45); 7.4917 (1.04); 7.4797 (1.71); 7.4760 (3.13); 7.4624 (0.50); 7.4583 (1.23); 7.4551 (0.68); 7.1052 (1.36); 7.1002 (1.37); 7.0896 (1.21); 7.0845 (1.27); 5.8636 (0.62); 5.8548 (0.33); 5.8378 (0.95); 5.8207 (0.99); 5.8117 (0.36); 5.8038 (0.36); 5.7949 (0.75); 5.7781 (0.35); 5.3311 (6.55); 5.1709 (0.49); 5.1670 (1.16); 5.1623 (1.23); 5.1584 (0.51); 5.1278 (0.45); 5.1239 (1.03); 5.1191 (1.09); 5.1153 (0.45); 5.0897 (0.60); 5.0870 (1.17); 5.0845 (0.98); 5.0821 (1.01); 5.0792 (0.49); 5.0641 (0.55); 5.0614 (1.08); 5.0589 (0.90); 5.0565 (0.94); 5.0536 (0.44); 4.1605 (2.18); 4.1436 (4.67); 4.1267 (2.22); 3.3294 (51.59); 3.0657 (16.00); 2.8907 (1.00); 2.7320 (0.79); 2.7311 (0.79); 2.5251 (0.60); 2.5118 (10.47); 2.5073 (20.50); 2.5027 (26.80); 2.4981 (19.33); 2.4936 (9.13); 2.4081 (0.71); 2.4050 (0.48); 2.3945 (1.33); 2.3913 (2.11); 2.3881 (1.33); 2.3777 (1.36); 2.3745 (2.08); 2.3712 (1.27); 2.3608 (0.50); 2.3576 (0.69); 0.9336 (0.63); −0.0002 (8.80)

Example 364, Solvent: DMSO, Spectrometer: 399.95 MHz 10.9348 (2.13); 8.1578 (1.55); 8.1380 (1.90); 8.1219 (1.89); 8.1165 (0.74); 8.1082 (2.06); 8.0996 (2.10); 8.0914 (0.76); 8.0859 (1.94); 7.9532 (0.70); 7.9258 (1.27); 7.9065 (1.73); 7.8863 (1.16); 7.7387 (1.86); 7.7360 (2.47); 7.7321 (1.19); 7.7234 (0.75); 7.7183 (3.30); 7.7145 (2.28); 7.5684 (0.47); 7.5566 (0.33); 7.5501 (1.60); 7.5444 (0.48); 7.5352 (0.87); 7.5319 (1.43); 7.5284 (0.73); 7.5021 (2.30); 7.4986 (1.02); 7.4868 (1.54); 7.4829 (3.00); 7.4694 (0.47); 7.4653 (1.23); 7.4620 (0.70); 7.3623 (2.08); 7.3570 (0.63); 7.3452 (0.74); 7.3401 (3.94); 7.3349 (0.72); 7.3232 (0.64); 7.3179 (1.93); 7.2351 (1.69); 7.2167 (1.66); 5.4185 (5.92); 3.3521 (65.03); 3.3478 (91.92); 3.0808 (16.00); 2.8914 (5.86); 2.7327 (4.71); 2.7318 (4.45); 2.5266 (0.55); 2.5219 (0.86); 2.5133 (11.02); 2.5088 (22.14); 2.5041 (29.22); 2.4995 (21.11); 2.4950 (9.92); −0.0002 (0.99)

Example 365, Solvent: DMSO, Spectrometer: 399.95 MHz 10.4916 (1.94); 8.0771 (1.31); 8.0565 (1.55); 7.9535 (0.37); 7.8305 (1.26); 7.8112 (1.74); 7.7909 (1.19); 7.7260 (1.96); 7.7235 (2.58); 7.7196 (1.29); 7.7109 (0.81); 7.7057 (3.49); 7.7020 (2.37); 7.5641 (0.49); 7.5522 (0.37); 7.5458 (1.63); 7.5401 (0.49); 7.5309 (0.87); 7.5275 (1.43); 7.5241 (0.72); 7.4964 (2.42); 7.4929 (1.04); 7.4810 (1.65); 7.4772 (3.08); 7.4596 (1.24); 7.4564 (0.69); 7.1404 (1.74); 7.1230 (1.68); 5.3549 (6.16); 3.3289 (49.21); 3.0551 (16.00); 2.8908 (3.03); 2.7323 (2.37); 2.7312 (2.39); 2.5254 (0.56); 2.5205 (0.88); 2.5120 (10.34); 2.5075 (20.59); 2.5029 (27.23); 2.4983 (19.80); 2.4937 (9.46); 2.3940 (3.07); 2.3755 (3.88); 2.2278 (0.67); 2.2090 (0.83); 2.1898 (0.63); 1.7463 (0.62); 1.7344 (0.86); 1.7166 (0.92); 1.7061 (0.68); 1.7036 (0.69); 1.6962 (0.37); 1.6881 (0.42); 1.6193 (0.36); 1.6130 (0.56); 1.6045 (0.82); 1.5924 (1.07); 1.5852 (0.66); 1.5811 (0.68); 1.5752 (0.82); 1.5689 (0.49); 1.5648 (0.42); 1.5597 (0.38); 1.5521 (0.38); 1.5359 (0.40); 1.5197 (0.49); 1.5173 (0.50); 1.5104 (0.79); 1.5011 (0.83); 1.4927 (0.96); 1.4806 (0.80); 1.4739 (0.54); 1.2029 (0.32); 1.1844 (0.80); 1.1707 (0.73); 1.1652 (0.88); 1.1538 (0.81); 1.1456 (0.59); 1.1350 (0.66); 0.8757 (0.47); −0.0002 (9.08)

Example 366, Solvent: DMSO, Spectrometer: 399.95 MHz 12.5689 (0.71); 7.9536 (0.80); 7.7420 (1.98); 7.7394 (2.76); 7.7355 (1.39); 7.7269 (0.78); 7.7218 (3.54); 7.7180 (2.54); 7.5676 (0.49); 7.5561 (0.35); 7.5492 (1.73); 7.5434 (0.51); 7.5345 (0.95); 7.5311 (1.58); 7.5276 (0.79); 7.5052 (2.60); 7.5019 (1.14); 7.4901 (1.63); 7.4862 (3.19); 7.4728 (0.53); 7.4686 (1.41); 7.4641 (1.72); 7.4599 (1.63); 7.4443 (1.37); 7.4403 (1.71); 7.3470 (4.63); 7.2809 (0.73); 7.2769 (0.72); 7.2619 (1.14); 7.2605 (1.14); 7.2572 (1.38); 7.2416 (0.98); 7.2375 (0.92); 6.9949 (0.82); 6.9916 (1.12); 6.9760 (1.25); 6.9723 (3.41); 6.9565 (0.65); 6.9530 (1.52); 6.9507 (1.71); 5.3432 (5.84); 5.1284 (0.38); 5.1120 (1.40); 5.0953 (1.41); 5.0788 (0.38); 3.3436 (52.87); 3.0291 (16.00); 3.0209 (0.61); 3.0145 (0.82); 2.8910 (6.58); 2.7328 (5.23); 2.7318 (5.12); 2.5267 (0.40); 2.5218 (0.61); 2.5133 (7.53); 2.5088 (15.09); 2.5042 (19.94); 2.4996 (14.42); 2.4950 (6.79); 1.5950 (5.61); 1.5785 (5.57); 1.5502 (0.34); −0.0002 (2.09)

Example 367, Solvent: DMSO, Spectrometer: 399.95 MHz 10.1886 (1.49); 7.9742 (1.03); 7.9533 (1.86); 7.8599 (0.98); 7.8409 (1.25); 7.8204 (0.78); 7.7249 (1.38); 7.7222 (1.84); 7.7184 (0.88); 7.7096 (0.56); 7.7045 (2.43); 7.7008 (1.68); 7.5637 (0.35); 7.5454 (1.15); 7.5397 (0.34); 7.5304 (0.61); 7.5271 (1.00); 7.5237 (0.51); 7.4954 (1.70); 7.4919 (0.73); 7.4799 (1.18); 7.4762 (2.17); 7.4626 (0.35); 7.4585 (0.88); 7.4554 (0.49); 7.1829 (1.23); 7.1657 (1.17); 5.3786 (4.29); 3.3399 (87.21); 3.0540 (11.56); 2.8907 (3.99); 2.7321 (3.20); 2.7308 (3.19); 2.5254 (0.51); 2.5205 (0.82); 2.5120 (9.20); 2.5075 (18.19); 2.5029 (23.84); 2.4983 (17.24); 2.4937 (8.10); 2.0474 (11.49); 1.5590 (16.00); −0.0002 (1.91)

Example 368, Solvent: DMSO, Spectrometer: 399.95 MHz 12.4336 (0.66); 7.9525 (1.16); 7.7388 (2.80); 7.7349 (1.38); 7.7263 (0.82); 7.7211 (3.54); 7.7173 (2.48); 7.5670 (0.48); 7.5638 (0.32); 7.5557 (0.35); 7.5487 (1.73); 7.5428 (0.53); 7.5340 (0.95); 7.5306 (1.56); 7.5272 (0.81); 7.5051 (2.64); 7.5019 (1.16); 7.4901 (1.67); 7.4861 (3.22); 7.4727 (0.50); 7.4686 (1.25); 7.4651 (0.71); 7.3431 (5.06); 7.3246 (2.70); 7.3042 (1.76); 7.0929 (1.38); 7.0875 (2.46); 7.0820 (1.79); 7.0472 (1.17); 7.0455 (1.36); 7.0425 (1.07); 7.0407 (1.04); 7.0274 (1.05); 7.0256 (1.13); 7.0226 (1.00); 7.0208 (0.90); 6.9708 (1.10); 6.9692 (1.16); 6.9647 (1.05); 6.9631 (1.01); 6.9499 (1.01); 6.9483 (1.01); 6.9437 (0.97); 6.9421 (0.90); 5.3456 (5.96); 4.8919 (7.46); 3.3483 (158.79); 3.0350 (0.40); 3.0221 (16.00); 2.8908 (9.32); 2.7319 (7.35); 2.7314 (7.37); 2.5259 (0.72); 2.5126 (14.07); 2.5081 (27.94); 2.5035 (36.92); 2.4989 (26.94); 2.4945 (12.93); 2.2231 (0.42); −0.0002 (0.60)

Example 369, Solvent: DMSO, Spectrometer: 399.95 MHz 10.2328 (2.72); 7.9531 (0.61); 7.8207 (0.61); 7.7997 (1.83); 7.7827 (3.03); 7.7763 (2.46); 7.7591 (0.69); 7.7554 (0.41); 7.7231 (2.73); 7.7053 (3.53); 7.7016 (2.50); 7.5627 (0.50); 7.5595 (0.32); 7.5507 (0.38); 7.5444 (1.68); 7.5387 (0.52); 7.5293 (0.97); 7.5261 (1.48); 7.5228 (0.77); 7.4954 (2.50); 7.4798 (1.84); 7.4763 (3.22); 7.4625 (0.55); 7.4586 (1.28); 7.4555 (0.75); 7.2587 (1.38); 7.2423 (1.85); 7.1920 (2.44); 7.1721 (4.14); 7.1597 (0.80); 7.1392 (0.66); 7.1156 (3.70); 7.1024 (2.04); 7.0996 (2.85); 7.0861 (1.52); 7.0823 (1.42); 5.3304 (6.54); 4.3815 (0.70); 4.3646 (0.32); 4.2681 (1.69); 4.2507 (3.80); 4.2334 (1.75); 3.3295 (63.37); 3.0624 (16.00); 2.9435 (0.52); 2.8990 (1.52); 2.8903 (5.03); 2.8817 (3.06); 2.8646 (1.38); 2.7319 (3.79); 2.7310 (3.61); 2.5247 (0.75); 2.5113 (14.79); 2.5069 (28.69); 2.5023 (37.13); 2.4978 (27.13); 2.4933 (13.12); 2.2794 (1.68); 2.2636 (10.00); 1.2348 (0.33); 0.0079 (0.33); −0.0002 (9.04)

Example 370, Solvent: DMSO, Spectrometer: 400.13 MHz 12.1253 (2.00); 7.6237 (1.13); 7.6171 (1.49); 7.6135 (1.37); 7.6026 (0.98); 7.5961 (2.56); 7.5930 (3.18); 7.5691 (0.79); 7.5550 (0.89); 7.5489 (1.24); 7.5346 (1.15); 7.5300 (0.75); 7.5137 (0.48); 7.4304 (0.58); 7.4277 (0.63); 7.4242 (0.58); 7.4214 (0.54); 7.4069 (1.04); 7.4025 (0.92); 7.3882 (0.48); 7.3845 (0.49); 7.3793 (0.37); 7.2839 (4.74); 5.7615 (0.39); 5.3434 (6.68); 3.4016 (3.20); 3.3516 (203.75); 3.3016 (2.30); 3.0126 (16.00); 2.5620 (0.58); 2.5577 (0.74); 2.5532 (0.65); 2.5163 (15.04); 2.5122 (28.70); 2.5078 (37.42); 2.5034 (26.78); 2.4624 (0.40); 2.4577 (0.45); 2.4532 (0.37); 2.4321 (2.08); 2.4137 (3.72); 2.3950 (2.20); 1.6063 (0.54); 1.5880 (1.54); 1.5694 (2.11); 1.5508 (1.58); 1.5318 (0.61); 1.3402 (0.36); 1.3216 (1.22); 1.3028 (1.98); 1.2841 (1.97); 1.2658 (1.18); 1.2477 (0.39); 0.8961 (4.28); 0.8778 (8.45); 0.8593 (3.56)

Example 371, Solvent: DMSO, Spectrometer: 399.95 MHz 10.6146 (2.17); 8.0199 (1.49); 8.0000 (1.97); 7.9530 (1.33); 7.8761 (1.36); 7.8569 (1.80); 7.8366 (1.14); 7.7192 (2.63); 7.7155 (1.24); 7.7064 (0.87); 7.7015 (3.46); 7.6978 (2.36); 7.5628 (0.51); 7.5596 (0.33); 7.5507 (0.40); 7.5445 (1.65); 7.5389 (0.49); 7.5295 (0.89); 7.5262 (1.41); 7.5228 (0.70); 7.4927 (2.39); 7.4893 (1.01); 7.4771 (1.74); 7.4735 (3.10); 7.4598 (0.51); 7.4558 (1.24); 7.4527 (0.68); 7.2076 (1.78); 7.1900

NMR Peak List Table 1

(1.69); 5.3794 (6.02); 3.3328 (126.76); 3.0495 (16.00); 2.8911 (10.81); 2.7323 (8.42); 2.7313 (8.66); 2.5253 (0.91); 2.5120 (16.93); 2.5075 (32.95); 2.5029 (42.83); 2.4983 (30.77); 2.4937 (14.35); 2.1610 (1.78); 2.1401 (1.87); 1.7355 (0.68); 1.7206 (2.55); 1.7002 (2.42); 1.2522 (5.41); 1.2352 (5.18); 1.0915 (4.77); 1.0742 (4.48); 0.0080 (0.45); −0.0002 (12.06); −0.0085 (0.35)
Example 372, Solvent: DMSO, Spectrometer: 399.95 MHz 10.2150 (1.04); 7.8145 (0.82); 7.7973 (1.51); 7.7918 (1.11); 7.7284 (0.90); 7.7257 (1.13); 7.7219 (0.55); 7.7131 (0.36); 7.7080 (1.50); 7.7043 (1.05); 7.5454 (0.73); 7.5304 (0.40); 7.5270 (0.64); 7.4967 (1.06); 7.4932 (0.45); 7.4813 (0.74); 7.4776 (1.36); 7.4599 (0.55); 7.1047 (0.61); 7.1007 (0.62); 7.0881 (0.59); 7.0841 (0.57); 5.3430 (2.80); 3.7969 (4.10); 3.3291 (22.59); 3.0627 (7.19); 2.8911 (1.94); 2.7323 (1.60); 2.7311 (1.49); 2.5204 (0.44); 2.5119 (4.93); 2.5074 (9.74); 2.5028 (12.79); 2.4982 (9.24); 2.4937 (4.38); 0.9337 (16.00); 0.9052 (0.49); −0.0002 (4.50)
Example 373, Solvent: DMSO, Spectrometer: 399.95 MHz 12.8166 (1.73); 8.0306 (0.53); 8.0246 (3.75); 8.0201 (1.32); 8.0077 (1.43); 8.0031 (4.57); 7.9973 (0.64); 7.9532 (1.72); 7.7729 (4.38); 7.7684 (1.48); 7.7513 (4.17); 7.7453 (3.35); 7.7325 (0.91); 7.7275 (3.54); 7.7237 (2.55); 7.5677 (0.47); 7.5646 (0.34); 7.5564 (0.36); 7.5492 (1.74); 7.5435 (0.55); 7.5346 (0.97); 7.5313 (1.57); 7.5279 (0.85); 7.5067 (2.68); 7.4914 (1.72); 7.4875 (3.28); 7.4741 (0.52); 7.4700 (1.24); 7.4665 (0.78); 7.3919 (3.72); 5.3835 (6.09); 3.3302 (82.54); 3.0168 (16.00); 2.8909 (13.13); 2.7316 (10.91); 2.5252 (0.87); 2.5118 (16.23); 2.5074 (31.73); 2.5029 (41.54); 2.4984 (30.46); 2.4939 (14.82); 0.0078 (0.53); −0.0002 (13.09); −0.0085 (0.43)
Example 374, Solvent: DMSO, Spectrometer: 399.95 MHz 10.5338 (2.12); 8.0745 (1.30); 8.0537 (1.55); 7.8361 (1.30); 7.8168 (1.83); 7.7966 (1.19); 7.7234 (2.66); 7.7105 (0.83); 7.7055 (3.46); 7.7017 (2.39); 7.5648 (0.48); 7.5528 (0.28); 7.5464 (1.69); 7.5408 (0.47); 7.5315 (0.91); 7.5282 (1.41); 7.5249 (0.71); 7.4974 (2.46); 7.4818 (1.72); 7.4781 (3.15); 7.4645 (0.49); 7.4605 (1.23); 7.4572 (0.69); 7.1438 (1.86); 7.1256 (1.78); 5.3553 (6.54); 3.5493 (2.35); 3.5325 (5.06); 3.5157 (2.42); 3.3346 (104.02); 3.0721 (0.33); 3.0543 (16.00); 2.8910 (2.52); 2.7319 (2.05); 2.5253 (0.71); 2.5204 (1.10); 2.5119 (14.07); 2.5074 (27.95); 2.5029 (36.72); 2.4983 (26.58); 2.4938 (12.60); 2.4108 (1.52); 2.3926 (3.02); 2.3741 (1.66); 1.8517 (0.47); 1.8347 (1.35); 1.8168 (1.56); 1.7975 (1.43); 1.7806 (0.54); 1.6361 (0.36); 1.6177 (1.09); 1.5990 (1.53); 1.5801 (1.22); 1.5613 (0.48); 1.4378 (0.49); 1.4239 (0.68); 1.4180 (1.11); 1.4079 (0.65); 1.4001 (1.50); 1.3863 (0.57); 1.3797 (0.77); −0.0002 (4.11)
Example 375, Solvent: DMSO, Spectrometer: 399.95 MHz 10.7390 (1.95); 8.0257 (1.22); 8.0050 (1.51); 7.9529 (0.71); 7.8287 (1.27); 7.8095 (1.74); 7.7891 (1.15); 7.7214 (2.53); 7.7176 (1.21); 7.7088 (0.75); 7.7037 (3.38); 7.6999 (2.36); 7.5638 (0.47); 7.5519 (0.34); 7.5455 (1.60); 7.5399 (0.46); 7.5305 (0.84); 7.5272 (1.38); 7.5238 (0.69); 7.4953 (2.34); 7.4918 (0.98); 7.4798 (1.61); 7.4761 (3.06); 7.4625 (0.48); 7.4584 (1.23); 7.4552 (0.68); 7.2292 (2.44); 7.2092 (3.60); 7.1518 (1.74); 7.1328 (1.91); 7.1252 (3.15); 7.1056 (2.16); 5.3645 (6.09); 3.6570 (5.26); 3.3287 (60.75); 3.0473 (16.00); 2.8901 (5.80); 2.7316 (4.56); 2.7307 (4.56); 2.5247 (0.55); 2.5199 (0.94); 2.5114 (13.05); 2.5069 (26.19); 2.5023 (34.53); 2.4976 (24.97); 2.4931 (11.82); 2.2637 (9.60); 0.0080 (0.53); −0.0002 (15.92); −0.0086 (0.47)
Example 376, Solvent: DMSO, Spectrometer: 400.13 MHz 10.5833 (2.13); 8.1412 (1.25); 8.1205 (1.46); 7.8987 (1.25); 7.8794 (1.75); 7.8591 (1.15); 7.6809 (0.63); 7.6768 (0.94); 7.6712 (0.89); 7.6656 (0.68); 7.6624 (1.10); 7.6588 (0.88); 7.6560 (0.93); 7.6516 (1.17); 7.6454 (2.31); 7.6427 (2.11); 7.6216 (0.72); 7.6074 (0.82); 7.6015 (1.08); 7.5870 (1.18); 7.5819 (0.55); 7.5664 (0.51); 7.4921 (0.50); 7.4892 (0.56); 7.4857 (0.49); 7.4828 (0.46); 7.4679 (0.86); 7.4642 (0.75); 7.4498 (0.40); 7.4469 (0.41); 7.4438 (0.38); 7.2126 (1.79); 7.1949 (1.71); 5.8243 (2.54); 5.4358 (6.17); 3.4481 (0.51); 3.3982 (42.17); 3.3482 (0.41); 3.1093 (16.00); 2.6199 (0.41); 2.6154 (0.58); 2.6109 (0.43); 2.5880 (0.82); 2.5833 (1.32); 2.5744 (16.94); 2.5700 (35.55); 2.5655 (48.62); 2.5610 (34.80); 2.5567 (16.18); 2.5201 (0.38); 2.5155 (0.49); 2.5110 (0.80); 2.4528 (1.36); 2.4344 (3.10); 2.4158 (1.79); 1.6686 (0.36); 1.6502 (1.06); 1.6318 (1.48); 1.6139 (1.03); 1.5956 (0.34); 1.3808 (0.37); 1.3648 (0.79); 1.3481 (1.60); 1.3406 (2.40); 1.3333 (2.01); 1.3233 (1.64); 1.3135 (1.18); 1.3028 (0.62); 1.2954 (0.48); 0.9418 (2.45); 0.9247 (6.33); 0.9069 (2.54)
Example 377, Solvent: DMSO, Spectrometer: 399.95 MHz 10.5486 (2.09); 8.0769 (1.15); 8.0562 (1.36); 7.9534 (0.40); 7.8355 (1.28); 7.8162 (1.74); 7.7960 (1.17); 7.7238 (2.56); 7.7199 (1.23); 7.7111 (0.75); 7.7060 (3.41); 7.7022 (2.36); 7.5630 (0.48); 7.5511 (0.34); 7.5447 (1.65); 7.5390 (0.47); 7.5298 (0.85); 7.5264 (1.40); 7.5230 (0.71); 7.4954 (2.37); 7.4919 (1.01); 7.4799 (1.61); 7.4762 (3.08); 7.4626 (0.46); 7.4585 (1.21); 7.4553 (0.68); 7.2984 (1.10); 7.2945 (0.45); 7.2799 (2.65); 7.2661 (0.85); 7.2616 (2.54); 7.2105 (3.24); 7.1929 (2.59); 7.1743 (1.40); 7.1691 (0.35); 7.1597 (0.35); 7.1563 (0.55); 7.1434 (1.77); 7.1255 (1.71); 5.3532 (6.15); 3.3283 (54.14); 3.0539 (16.00); 2.8904 (3.35); 2.7316 (2.62); 2.6157 (1.44); 2.5970 (1.93); 2.5770 (1.62); 2.5249 (0.68); 2.5202 (1.04); 2.5116 (12.85); 2.5071 (25.62); 2.5025 (33.69); 2.4979 (24.30); 2.4933 (11.46); 2.4397 (1.45); 2.4214 (2.77); 2.4029 (1.64); 1.9101 (0.44); 1.8910 (1.21); 1.8719 (1.51); 1.8530 (1.12); 1.8344 (0.35); 0.0080 (0.35); −0.0002 (10.62)
Example 378, Solvent: DMSO, Spectrometer: 399.95 MHz 12.4210 (2.01); 7.9530 (1.04); 7.7377 (1.93); 7.7351 (2.62); 7.7311 (1.25); 7.7227 (0.78); 7.7175 (3.41); 7.7136 (2.33); 7.5639 (0.46); 7.5525 (0.33); 7.5456 (1.65); 7.5397 (0.48); 7.5309 (0.91); 7.5275 (1.49); 7.5240 (0.74); 7.5017 (2.48); 7.4983 (1.05); 7.4867 (1.59); 7.4826 (3.05); 7.4693 (0.48); 7.4651 (1.20); 7.4616 (0.66); 7.3453 (0.34); 7.3315 (0.52); 7.3262 (3.12); 7.3209 (3.45); 7.3124 (12.83); 7.3042 (0.57); 7.2996 (0.69); 7.2771 (4.45); 7.2657 (0.78); 7.2633 (0.69); 7.2597 (0.55); 7.2542 (0.62); 7.2508 (0.78); 7.2458 (0.53); 7.2405 (0.34); 7.2370 (0.39); 5.3279 (5.95); 3.7498 (7.45); 3.3295 (25.43); 3.3275 (36.79); 3.0163 (16.00); 2.8900 (8.57); 2.7315 (6.74); 2.5246 (0.63); 2.5198 (0.98); 2.5114 (11.58); 2.5068 (22.97); 2.5022 (30.18); 2.4976 (21.76); 2.4931 (10.27); 0.0080 (0.42); −0.0002 (11.84); −0.0085 (0.35)
Example 379, Solvent: DMSO, Spectrometer: 399.95 MHz 10.0901 (1.67); 8.0496 (1.08); 8.0289 (1.34); 7.8809 (1.28); 7.8615 (1.78); 7.8414 (1.10); 7.7331 (0.32); 7.7276 (1.93); 7.7249 (2.49); 7.7211 (1.26); 7.7124 (0.82); 7.7072 (3.43); 7.7035 (2.32); 7.5652 (0.48); 7.5533 (0.36); 7.5469 (1.58); 7.5412 (0.48); 7.5320 (0.86); 7.5286 (1.39); 7.5252 (0.71); 7.4976 (2.35); 7.4941 (1.03); 7.4822 (1.61); 7.4785 (2.99); 7.4649 (0.47); 7.4608 (1.20); 7.4576 (0.66); 7.1874 (1.70); 7.1700 (1.64); 5.3671 (6.32); 4.0642 (8.62); 3.3601 (19.81); 3.3284 (43.74); 3.0675 (16.00); 2.5251 (0.60); 2.5202 (0.98); 2.5117 (10.28); 2.5072 (20.13); 2.5026 (26.35); 2.4980 (19.02); 2.4935 (8.98); 0.8758 (0.53); 0.0080 (0.32); −0.0002 (8.55)
Example 380, Solvent: DMSO, Spectrometer: 399.95 MHz 11.0468 (2.33); 8.2087 (1.47); 8.2042 (2.62); 8.1998 (1.55); 8.1544 (1.61); 8.1345 (1.97); 8.0191 (0.91); 8.0166 (1.21); 8.0128 (0.93); 7.9996 (1.03); 7.9969 (1.25); 7.9958 (1.26); 7.9932 (0.98); 7.9531 (0.92); 7.9344 (1.31); 7.9151 (1.83); 7.8949 (1.17); 7.8119 (0.91); 7.8095 (1.05); 7.8070 (0.99); 7.8046 (0.90); 7.7919 (1.07); 7.7895 (1.12); 7.7870 (1.15); 7.7846 (0.98); 7.7390 (1.93); 7.7365 (2.57); 7.7326 (1.26); 7.7239 (0.76); 7.7187 (3.37); 7.7150 (2.37); 7.5684 (0.47); 7.5565 (0.33); 7.5500 (1.61); 7.5443 (0.48); 7.5351 (0.86); 7.5318 (1.42); 7.5284 (0.74); 7.5015 (3.00); 7.4867 (1.68); 7.4810 (4.00); 7.4694 (0.53); 7.4653 (1.29); 7.4609 (1.73); 7.2472 (1.78); 7.2293 (1.72); 5.4193 (6.15); 3.3474 (79.23); 3.3440 (115.92); 3.0810 (16.00); 2.8912 (7.35); 2.7325 (5.82); 2.7316 (5.74); 2.5262 (0.60); 2.5215 (0.91); 2.5129 (12.27); 2.5084 (24.79); 2.5038 (32.90); 2.4992 (24.02); 2.4947 (11.54); −0.0002 (7.80)

NMR Peak List Table 1

Example 381, Solvent: DMSO, Spectrometer: 399.95 MHz 10.8881 (1.89); 8.0482 (1.10); 8.0275 (1.34); 7.9534 (1.17); 7.8927 (2.02); 7.8861 (1.51); 7.8778 (2.27); 7.8692 (2.28); 7.8581 (2.00); 7.8435 (1.97); 7.8362 (1.41); 7.8169 (1.65); 7.7965 (1.12); 7.7256 (1.87); 7.7229 (2.46); 7.7190 (1.18); 7.7103 (0.75); 7.7051 (3.35); 7.7014 (2.30); 7.5624 (0.48); 7.5504 (0.35); 7.5441 (1.59); 7.5384 (0.47); 7.5291 (0.90); 7.5257 (1.53); 7.5217 (1.95); 7.5170 (1.62); 7.5052 (1.46); 7.4996 (2.24); 7.4952 (4.17); 7.4886 (2.90); 7.4813 (1.57); 7.4780 (2.28); 7.4744 (3.58); 7.4566 (1.36); 7.4538 (0.79); 7.1606 (1.66); 7.1431 (1.61); 5.3758 (5.74); 3.9037 (4.99); 3.3314 (84.48); 3.0547 (16.00); 2.8902 (9.91); 2.7319 (7.85); 2.7308 (7.61); 2.5251 (0.76); 2.5204 (1.22); 2.5118 (14.47); 2.5073 (28.90); 2.5027 (38.06); 2.4980 (27.38); 2.4935 (12.84); −0.0002 (8.50)

Example 382, Solvent: DMSO, Spectrometer: 399.95 MHz 10.6884 (2.06); 8.0222 (0.67); 8.0016 (0.87); 7.8850 (1.29); 7.8658 (1.69); 7.8455 (1.07); 7.7315 (1.88); 7.7287 (2.48); 7.7249 (1.18); 7.7162 (0.74); 7.7110 (3.35); 7.7073 (2.30); 7.5671 (0.48); 7.5552 (0.34); 7.5488 (1.58); 7.5431 (0.46); 7.5339 (0.84); 7.5305 (1.39); 7.5271 (0.69); 7.4993 (2.27); 7.4958 (0.95); 7.4839 (1.56); 7.4802 (2.95); 7.4666 (0.46); 7.4625 (1.21); 7.4593 (0.65); 7.2827 (1.19); 7.2625 (2.51); 7.2421 (1.92); 7.2081 (1.68); 7.1996 (1.41); 7.1945 (2.27); 7.1891 (3.17); 7.1695 (1.29); 7.1673 (1.51); 7.1652 (1.12); 7.1629 (1.00); 7.1498 (0.92); 7.1476 (0.93); 7.1453 (0.86); 7.1432 (0.68); 6.9984 (1.00); 6.9963 (1.04); 6.9922 (0.98); 6.9901 (0.93); 6.9776 (0.91); 6.9755 (0.88); 6.9713 (0.88); 6.9693 (0.78); 5.3865 (5.76); 4.8406 (5.38); 3.3339 (77.04); 3.0689 (16.00); 2.8905 (0.35); 2.5253 (0.71); 2.5205 (1.15); 2.5119 (13.10); 2.5074 (26.04); 2.5027 (34.22); 2.4981 (24.64); 2.4935 (11.54); −0.0002 (2.40)

Example 383, Solvent: CDCl3, Spectrometer: 300.16 MHz 7.9456 (2.10); 7.9178 (2.65); 7.7269 (1.43); 7.7001 (2.53); 7.6728 (3.34); 7.6472 (3.04); 7.6295 (2.57); 7.2642 (9.28); 7.1378 (2.26); 7.1118 (4.37); 7.0844 (2.20); 7.0178 (2.62); 6.9930 (2.44); 5.2842 (9.93); 5.0332 (0.71); 5.0110 (1.22); 4.9903 (1.22); 4.9702 (0.68); 3.1054 (16.00); 1.7335 (0.39); 1.7115 (0.86); 1.6900 (1.19); 1.6663 (1.21); 1.6532 (1.29); 1.6116 (8.38); 1.5884 (1.39); 1.5662 (0.71); 1.3629 (0.77); 1.3428 (1.15); 1.3207 (1.40); 1.2955 (8.48); 1.2748 (8.38); 0.9369 (14.57); 0.9159 (13.90); −0.0002 (2.87)

Example 384, Solvent: DMSO, Spectrometer: 400.13 MHz 10.5328 (2.13); 8.0787 (1.28); 8.0580 (1.52); 7.8384 (1.28); 7.8190 (1.79); 7.7988 (1.19); 7.5405 (2.14); 7.5253 (0.63); 7.5209 (0.53); 7.5165 (0.93); 7.5132 (0.95); 7.5079 (0.57); 7.5038 (0.87); 7.4993 (0.64); 7.3901 (0.41); 7.3711 (2.32); 7.3656 (1.55); 7.3595 (3.13); 7.3570 (3.09); 7.1364 (1.83); 7.1186 (1.74); 5.3530 (6.22); 4.0613 (0.50); 4.0455 (1.53); 4.0257 (1.55); 4.0079 (0.51); 3.3952 (0.54); 3.3452 (30.65); 3.2949 (0.53); 3.0474 (16.00); 2.5596 (0.38); 2.5320 (0.53); 2.5273 (0.87); 2.5186 (8.94); 2.5142 (18.43); 2.5097 (24.98); 2.5052 (17.82); 2.5008 (8.22); 2.4593 (0.39); 2.4548 (0.33); 2.4071 (1.81); 2.3888 (3.41); 2.3702 (1.98); 2.3381 (10.37); 1.9963 (6.81); 1.5958 (0.46); 1.5776 (1.34); 1.5589 (1.85); 1.5405 (1.38); 1.5215 (0.57); 1.3308 (1.10); 1.3119 (1.73); 1.2931 (1.73); 1.2750 (1.05); 1.2569 (0.32); 1.1984 (1.83); 1.1806 (3.67); 1.1628 (1.79); 0.9054 (4.10); 0.8871 (8.36); 0.8768 (0.37); 0.8686 (3.44)

Example 385, Solvent: CDCl3, Spectrometer: 300.16 MHz 9.2433 (0.89); 8.5283 (0.54); 8.5013 (0.59); 7.7846 (1.15); 7.7590 (1.66); 7.7317 (1.19); 7.6522 (1.59); 7.6480 (2.15); 7.6425 (1.14); 7.6325 (0.78); 7.6254 (2.72); 7.6199 (2.23); 7.5104 (0.33); 7.4857 (1.22); 7.4771 (0.6); 7.4676 (0.95); 7.4626 (1.50); 7.4572 (0.85); 7.4521 (0.64); 7.4443 (2.50); 7.4397 (1.17); 7.4262 (1.22); 7.4244 (1.23); 7.4197 (2.46); 7.4025 (0.49); 7.3968 (0.87); 7.3907 (0.58); 7.2636 (2.74); 7.1610 (1.64); 7.1363 (1.53); 5.3624 (6.90); 3.3141 (2.09); 3.2896 (2.97); 3.2648 (2.24); 3.1101 (16.00); 1.7511 (0.39); 1.7274 (1.01); 1.7022 (1.79); 1.6935 (0.93); 1.6770 (2.45); 1.6520 (0.70); 1.4949 (0.98); 1.4698 (1.45); 1.4442 (1.46); 1.4203 (0.90); 0.9759 (3.50); 0.9516 (7.07); 0.9272 (2.94); −0.0002 (1.15)

Example 386, Solvent: DMSO, Spectrometer: 399.95 MHz 10.7418 (1.97); 8.0578 (1.25); 8.0371 (1.50); 7.9533 (0.93); 7.8227 (1.27); 7.8033 (1.72); 7.7831 (1.15); 7.7071 (2.56); 7.7033 (1.22); 7.6943 (0.75); 7.6893 (3.36); 7.6856 (2.33); 7.5568 (0.49); 7.5446 (0.37); 7.5385 (1.60); 7.5329 (0.47); 7.5234 (0.83); 7.5201 (1.35); 7.5168 (0.68); 7.4857 (2.36); 7.4821 (0.99); 7.4700 (1.63); 7.4664 (3.04); 7.4527 (0.48); 7.4487 (1.21); 7.4457 (0.68); 7.4087 (1.51); 7.4052 (2.08); 7.3875 (2.96); 7.3314 (1.73); 7.3269 (0.57); 7.3132 (3.23); 7.2939 (1.65); 7.2470 (0.67); 7.2438 (1.17); 7.2406 (0.66); 7.2308 (0.50); 7.2256 (1.51); 7.2202 (0.37); 7.2106 (0.33); 7.2075 (0.53); 7.1365 (1.76); 7.1187 (1.70); 5.3438 (5.95); 3.8183 (0.56); 3.8019 (0.77); 3.7968 (0.75); 3.7803 (0.59); 3.3264 (38.18); 3.0233 (16.00); 2.8902 (7.74); 2.7317 (6.02); 2.7308 (6.16); 2.5248 (0.79); 2.5115 (14.43); 2.5070 (28.64); 2.5024 (37.59); 2.4977 (27.04); 2.4932 (12.69); 2.0947 (0.34); 2.0765 (0.43); 2.0730 (0.39); 2.0612 (0.49); 2.0548 (0.43); 2.0429 (0.48); 2.0395 (0.48); 2.0212 (0.39); 1.7198 (0.40); 1.7031 (0.61); 1.6854 (0.73); 1.6680 (0.53); 1.6514 (0.36); 0.8610 (2.77); 0.8427 (6.03); 0.8244 (2.55); 0.0079 (0.53); −0.0002 (15.46); −0.0086 (0.44)

Example 387, Solvent: DMSO, Spectrometer: 400.13 MHz 9.8767 (0.82); 8.0246 (0.58); 8.0043 (0.73); 7.8474 (0.47); 7.8280 (0.64); 7.8078 (0.40); 7.5412 (0.75); 7.5163 (0.33); 7.5132 (0.33); 7.3712 (0.86); 7.3598 (1.08); 7.3575 (1.05); 7.1489 (0.66); 7.1306 (0.62); 5.7689 (2.10); 5.3786 (2.23); 3.3443 (11.96); 3.0684 (5.46); 2.5321 (0.36); 2.5186 (5.00); 2.5143 (10.13); 2.5098 (13.61); 2.5053 (9.71); 2.5010 (4.51); 2.3374 (3.68); 1.2399 (16.00)

Example 388, Solvent: DMSO, Spectrometer: 399.95 MHz 10.5007 (1.97); 8.0764 (1.46); 8.0557 (1.74); 7.9532 (0.33); 7.8306 (1.27); 7.8113 (1.80); 7.7910 (1.17); 7.7230 (2.63); 7.7193 (1.31); 7.7103 (0.84); 7.7053 (3.41); 7.7016 (2.43); 7.5650 (0.49); 7.5532 (0.38); 7.5468 (1.58); 7.5410 (0.50); 7.5318 (0.90); 7.5285 (1.38); 7.5251 (0.74); 7.4978 (2.44); 7.4945 (1.10); 7.4824 (1.70); 7.4787 (3.12); 7.4650 (0.51); 7.4610 (1.24); 7.4578 (0.73); 7.1384 (1.81); 7.1201 (1.76); 5.3573 (6.42); 3.3418 (105.76); 3.0589 (16.00); 2.9544 (0.50); 2.9354 (0.75); 2.9162 (0.61); 2.8913 (2.56); 2.7326 (2.09); 2.7315 (2.00); 2.6341 (0.39); 2.5260 (0.69); 2.5126 (12.21); 2.5082 (23.81); 2.5036 (31.00); 2.4991 (22.64); 2.4946 (10.96); 1.8666 (0.36); 1.8464 (0.93); 1.8260 (1.13); 1.8167 (0.76); 1.8120 (0.85); 1.8005 (0.55); 1.7931 (0.35); 1.7859 (0.42); 1.7809 (0.42); 1.7151 (0.80); 1.7092 (0.57); 1.6964 (1.13); 1.6900 (1.00); 1.6813 (1.32); 1.6776 (1.38); 1.6644 (1.97); 1.6524 (1.31); 1.6464 (1.13); 1.6329 (0.81); 1.6272 (0.68); 1.6138 (0.43); 1.6069 (0.55); 1.5839 (0.50); 1.5754 (0.57); 1.5717 (0.55); 1.5470 (1.08); 1.5376 (1.16); 1.5304 (1.34); 1.5186 (1.09); 1.5118 (0.88); 1.4909 (0.36)

Example 389, Solvent: DMSO, Spectrometer: 399.95 MHz 10.5069 (1.95); 8.0631 (1.20); 8.0424 (1.43); 7.8301 (1.26); 7.8108 (1.73); 7.7905 (1.14); 7.7318 (0.34); 7.7262 (2.03); 7.7237 (2.61); 7.7199 (1.27); 7.7110 (0.83); 7.7059 (3.46); 7.7022 (2.40); 7.5643 (0.50); 7.5611 (0.90); 7.5524 (0.38); 7.5460 (1.67); 7.5403 (0.50); 7.5311 (0.90); 7.5278 (1.45); 7.5243 (0.73); 7.4967 (2.44); 7.4933 (1.05); 7.4813 (1.69); 7.4776 (3.13); 7.4640 (0.49); 7.4599 (1.24); 7.4567 (0.69); 7.1397 (1.75); 7.1213 (1.70); 5.3531 (6.21); 3.3287 (43.18); 3.0720 (0.45); 3.0539 (16.00); 2.8908 (2.58); 2.7322 (2.01); 2.7312 (2.01); 2.5253 (0.61); 2.5204 (0.97); 2.5119 (10.42); 2.5074 (20.51); 2.5028 (26.96); 2.4982 (19.56); 2.4937 (9.34); 2.3033 (1.58); 2.2849 (2.51); 2.2656 (1.81); 2.2574 (0.75); 2.2377 (0.96); 2.2183 (0.80); 2.1989 (0.38); 2.0272 (0.36); 2.0171 (0.40); 2.0086 (0.62); 2.0066 (0.63); 2.0027 (0.64); 1.9984 (0.94); 1.9880 (0.83); 1.9843 (0.77); 1.9778 (0.93); 1.9744 (0.77); 1.9695 (0.66); 1.9660 (0.70); 1.9607 (0.43); 1.9550 (0.34); 1.9491 (0.43); 1.8059 (0.48); 1.8029 (0.64); 1.8012 (0.64); 1.7871 (0.58); 1.7820 (1.15); 1.7676 (0.89); 1.7584 (0.90); 1.7470 (0.55); 1.7403 (0.55); 1.7364

NMR Peak List Table 1

(0.35); 1.6892 (0.93); 1.6702 (2.13); 1.6514 (2.03); 1.6328 (0.83); 1.6254 (0.43); 1.6188 (0.33); 1.6034 (1.04); 1.5967 (0.79); 1.5799 (1.13); 1.5744 (1.16); 1.5587 (0.66); 1.5535 (0.90); 0.8622 (0.71); −0.0002 (8.05)
Example 390, Solvent: DMSO, Spectrometer: 399.95 MHz 10.0026 (2.06); 8.0726 (1.55); 8.0521 (1.93); 7.8842 (1.32); 7.8649 (1.90); 7.8448 (1.16); 7.7254 (2.72); 7.7127 (0.89); 7.7076 (3.54); 7.7039 (2.49); 7.5647 (0.51); 7.5615 (0.32); 7.5527 (0.40); 7.5464 (1.71); 7.5408 (0.51); 7.5314 (0.96); 7.5281 (1.45); 7.5247 (0.75); 7.4964 (2.47); 7.4808 (1.78); 7.4771 (3.21); 7.4635 (0.52); 7.4594 (1.29); 7.4563 (0.77); 7.1984 (1.85); 7.1801 (1.80); 5.3767 (6.51); 4.1631 (0.45); 4.1464 (1.65); 4.1298 (1.67); 4.1132 (0.47); 3.3329 (83.44); 3.3215 (1.62); 3.3124 (1.81); 3.2953 (1.74); 3.2809 (1.67); 3.2635 (1.68); 3.2554 (0.80); 3.2376 (0.81); 3.0797 (16.00); 3.0659 (0.37); 2.8913 (0.54); 2.7325 (0.44); 2.5256 (0.68); 2.5123 (11.39); 2.5079 (22.13); 2.5033 (28.90); 2.4987 (21.01); 2.4942 (10.08); 1.3121 (6.45); 1.2955 (6.33); 1.0487 (0.43); 1.0463 (0.44); 1.0409 (0.41); 1.0370 (0.35); 1.0289 (0.75); 1.0207 (0.35); 1.0167 (0.45); 1.0116 (0.44); 1.0090 (0.44); 0.4849 (0.73); 0.4779 (1.04); 0.4735 (1.56); 0.4706 (1.10); 0.4639 (1.32); 0.4594 (1.00); 0.4575 (1.01); 0.4533 (1.43); 0.4475 (0.82); 0.4433 (0.78); 0.2019 (0.81); 0.1930 (1.81); 0.1895 (2.21); 0.1808 (2.16); 0.1776 (1.65); 0.1682 (0.67); −0.0002 (4.96)
Example 391, Solvent: DMSO, Spectrometer: 400.13 MHz 11.0276 (2.51); 8.1691 (1.68); 8.1490 (2.03); 7.9445 (1.33); 7.9250 (1.90); 7.9049 (1.26); 7.8944 (1.33); 7.8919 (1.10); 7.8750 (1.67); 7.8724 (1.49); 7.8636 (1.00); 7.8600 (0.66); 7.8448 (0.82); 7.8387 (0.91); 7.8346 (0.67); 7.6024 (0.58); 7.5877 (0.69); 7.5821 (1.09); 7.5675 (1.27); 7.5618 (1.30); 7.5539 (2.26); 7.5489 (1.48); 7.5387 (0.67); 7.5339 (0.60); 7.5303 (0.95); 7.5268 (0.99); 7.5174 (0.93); 7.5129 (0.69); 7.4866 (0.58); 7.4845 (0.63); 7.4801 (0.57); 7.4781 (0.56); 7.4631 (0.96); 7.4580 (0.85); 7.4442 (0.43); 7.4419 (0.44); 7.4376 (0.40); 7.4355 (0.37); 7.3955 (0.33); 7.3764 (2.22); 7.3703 (1.53); 7.3644 (3.16); 7.3619 (3.11); 7.2441 (1.78); 7.2261 (1.78); 5.4218 (6.20); 3.3943 (1.10); 3.3445 (54.95); 3.2947 (0.83); 3.0750 (16.00); 2.6789 (0.33); 2.5688 (0.39); 2.5643 (0.77); 2.5598 (1.05); 2.5553 (0.76); 2.5508 (0.39); 2.5323 (1.05); 2.5188 (19.92); 2.5144 (40.84); 2.5099 (55.29); 2.5055 (39.65); 2.5011 (18.54); 2.4693 (0.34); 2.4648 (0.57); 2.4602 (0.76); 2.4556 (0.55); 2.3407 (10.44); 1.9970 (1.24); 1.2523 (0.92); 1.1992 (0.36); 1.1814 (0.67); 1.1636 (0.32); 0.8812 (0.42); 0.8645 (1.36); 0.8469 (0.52)
Example 392, Solvent: DMSO, Spectrometer: 400.13 MHz 12.5733 (1.72); 7.6261 (3.54); 7.6055 (4.12); 7.3568 (4.66); 7.3091 (3.37); 7.2889 (2.96); 7.0152 (1.30); 6.9964 (1.75); 6.9942 (1.67); 6.9157 (0.67); 6.9082 (0.88); 6.9009 (0.96); 6.8934 (1.47); 6.8892 (0.62); 6.8812 (0.75); 6.8742 (1.83); 6.8629 (4.80); 6.8586 (3.14); 6.8477 (1.14); 6.8438 (0.93); 5.3230 (6.03); 5.1546 (1.11); 5.1461 (2.10); 5.1364 (1.16); 4.4546 (2.33); 4.4323 (2.52); 4.4261 (2.87); 4.0421 (0.58); 4.0242 (0.58); 3.3970 (0.66); 3.3471 (67.02); 3.2973 (0.68); 2.9986 (16.00); 2.5578 (0.39); 2.5301 (0.75); 2.5165 (14.60); 2.5123 (29.33); 2.5078 (39.11); 2.5034 (28.35); 2.4994 (13.71); 2.4626 (0.40); 2.4580 (0.46); 2.4536 (0.35); 2.3547 (10.22); 2.3350 (0.40); 1.9948 (2.54); 1.1969 (0.68); 1.1791 (1.35); 1.1613 (0.67)
Example 393, Solvent: DMSO, Spectrometer: 399.95 MHz 12.5563 (0.44); 8.1105 (0.44); 8.1034 (3.66); 8.0984 (1.15); 8.0861 (1.23); 8.0811 (3.92); 8.0737 (0.41); 7.9532 (0.76); 7.9040 (1.39); 7.8988 (0.43); 7.8868 (0.45); 7.8817 (1.47); 7.7487 (2.00); 7.7461 (2.66); 7.7422 (1.30); 7.7337 (0.82); 7.7285 (3.41); 7.7247 (2.38); 7.5681 (0.47); 7.5568 (0.34); 7.5498 (1.63); 7.5438 (0.50); 7.5351 (0.94); 7.5317 (1.51); 7.5282 (0.77); 7.5076 (2.49); 7.5042 (1.10); 7.4926 (1.61); 7.4886 (3.05); 7.4753 (0.51); 7.4711 (1.23); 7.4675 (0.73); 7.3845 (0.89); 7.3625 (0.94); 7.3443 (4.57); 7.0898 (0.44); 7.0825 (3.84); 7.0775 (1.19); 7.0650 (1.17); 7.0601 (3.68); 7.0526 (0.46); 7.0294 (1.51); 7.0243 (0.44); 7.0122 (0.43); 7.0071 (1.35); 6.9765 (0.91); 6.9546 (0.80); 5.3767 (5.61); 3.8453 (16.00); 3.8243 (6.22); 3.7997 (0.36); 3.7896 (3.84); 3.3424 (91.62); 3.0171 (15.48); 2.9458 (4.16); 2.8912 (6.02); 2.7850 (0.66); 2.7325 (4.75); 2.5262 (0.75); 2.5128 (14.48); 2.5084 (28.24); 2.5038 (36.64); 2.4992 (26.44); 2.4947 (12.48); −0.0002 (3.63)
Example 394, Solvent: DMSO, Spectrometer: 399.95 MHz 11.7925 (1.40); 7.9532 (0.38); 7.7322 (2.03); 7.7294 (2.72); 7.7254 (1.35); 7.7170 (0.97); 7.7118 (3.54); 7.7080 (2.39); 7.5623 (0.53); 7.5590 (0.35); 7.5509 (0.41); 7.5440 (1.74); 7.5381 (0.55); 7.5293 (1.01); 7.5259 (1.58); 7.5224 (0.80); 7.4997 (2.63); 7.4963 (1.17); 7.4847 (1.76); 7.4807 (3.26); 7.4673 (0.54); 7.4632 (1.31); 7.4597 (0.76); 7.2557 (0.55); 5.8452 (0.63); 5.8362 (0.33); 5.8193 (0.95); 5.8022 (0.98); 5.7931 (0.36); 5.7853 (0.36); 5.7764 (0.75); 5.7597 (0.35); 5.2821 (5.80); 5.1694 (0.50); 5.1655 (1.19); 5.1608 (1.28); 5.1569 (0.54); 5.1263 (0.45); 5.1224 (1.07); 5.1177 (1.17); 5.1139 (0.49); 5.0947 (0.62); 5.0919 (1.22); 5.0892 (0.99); 5.0870 (1.07); 5.0841 (0.52); 5.0691 (0.56); 5.0662 (1.11); 5.0637 (0.89); 5.0613 (0.99); 5.0585 (0.46); 4.2279 (0.54); 4.2217 (2.07); 4.2049 (4.40); 4.1882 (2.08); 3.3339 (96.70); 3.0302 (16.00); 2.9895 (0.64); 2.8907 (3.07); 2.7322 (2.36); 2.7311 (2.43); 2.5253 (0.63); 2.5205 (1.04); 2.5120 (11.75); 2.5075 (23.44); 2.5029 (30.95); 2.4982 (22.50); 2.4937 (10.74); 2.4225 (0.71); 2.4194 (0.50); 2.4090 (1.29); 2.4058 (2.07); 2.4026 (1.35); 2.3923 (1.29); 2.3890 (2.03); 2.3859 (1.30); 2.3754 (0.48); 2.3723 (0.69); 1.2348 (0.32); 1.1206 (0.53); 1.1054 (0.52); 0.9300 (1.12); 0.0080 (0.33); −0.0002 (9.72)
Example 395, Solvent: DMSO, Spectrometer: 399.95 MHz 10.1127 (2.58); 7.9532 (0.35); 7.8282 (0.49); 7.8071 (2.01); 7.7951 (2.36); 7.7914 (3.78); 7.7743 (0.55); 7.7257 (1.90); 7.7230 (2.58); 7.7191 (1.22); 7.7105 (0.77); 7.7053 (3.46); 7.7015 (2.34); 7.7005 (2.24); 7.5623 (0.49); 7.5439 (1.62); 7.5382 (0.47); 7.5291 (0.86); 7.5257 (1.44); 7.5222 (0.71); 7.4955 (2.38); 7.4921 (0.99); 7.4802 (1.59); 7.4764 (3.03); 7.4629 (0.46); 7.4588 (1.22); 7.4555 (0.66); 7.1012 (1.29); 7.0958 (1.29); 7.0857 (1.16); 7.0804 (1.21); 5.3305 (6.04); 4.8838 (0.40); 4.8703 (0.58); 4.8681 (0.58); 4.8650 (0.52); 4.8547 (0.58); 4.8513 (0.60); 4.8357 (0.41); 3.3290 (56.41); 3.0698 (16.00); 2.8906 (2.95); 2.7977 (1.23); 2.7910 (2.92); 2.7844 (1.24); 2.7321 (2.26); 2.7309 (2.29); 2.5250 (0.63); 2.5203 (1.02); 2.5117 (11.93); 2.5071 (23.85); 2.5025 (31.49); 2.4979 (22.71); 2.4933 (10.66); 2.2839 (0.80); 2.2773 (0.87); 2.2650 (1.70); 2.2584 (1.61); 2.2472 (1.00); 2.2406 (0.92); 1.7763 (0.54); 1.7588 (1.05); 1.7489 (0.36); 1.7405 (1.33); 1.7350 (0.84); 1.7218 (1.11); 1.7157 (0.41); 1.7017 (0.47); 1.2559 (6.32); 1.2403 (6.30); −0.0002 (1.30)
Example 396, Solvent: DMSO, Spectrometer: 400.13 MHz 9.8305 (1.11); 7.7772 (0.77); 7.7613 (1.78); 7.7574 (1.15); 7.6655 (1.58); 7.6603 (0.50); 7.6482 (0.52); 7.6430 (1.74); 7.0663 (0.55); 7.0619 (0.57); 7.0502 (0.54); 7.0455 (0.68); 7.0374 (1.69); 7.0322 (0.52); 7.0200 (0.49); 7.0149 (1.57); 5.2763 (2.54); 3.8139 (6.53); 3.3288 (12.65); 3.0511 (6.27); 2.5186 (2.23); 2.5142 (4.61); 2.5097 (6.28); 2.5052 (4.47); 2.5008 (2.09); 1.4705 (16.00)
Example 397, Solvent: DMSO, Spectrometer: 399.95 MHz 9.0453 (2.48); 8.1017 (1.76); 8.0810 (2.02); 7.8722 (1.32); 7.8528 (1.87); 7.8327 (1.26); 7.7023 (2.63); 7.6985 (1.27); 7.6895 (0.86); 7.6845 (3.61); 7.6807 (2.77); 7.6620 (0.49); 7.6582 (0.34); 7.5610 (0.55); 7.5577 (0.38); 7.5489 (1.00); 7.5427 (1.73); 7.5373 (0.65); 7.5276 (0.91); 7.5243 (1.52); 7.5209 (0.89); 7.4905 (2.49); 7.4868 (1.21); 7.4808 (0.42); 7.4749 (1.78); 7.4713 (3.26); 7.4576 (0.54); 7.4535 (1.29); 7.4505 (0.76); 7.4086 (0.42); 7.3884 (0.56); 7.2850 (2.35); 7.2654 (3.36); 7.2387 (0.35); 7.1763 (4.31); 7.1700 (2.44); 7.1562 (3.05); 7.1507 (2.41); 6.8849 (0.45); 6.8674 (1.97); 6.8497 (1.99); 6.8320 (0.46); 5.3154 (6.26); 5.2630 (0.88); 3.3290 (62.14); 2.9998 (16.00); 2.9549 (2.24); 2.8905 (2.33); 2.7319 (1.82); 2.7313 (1.81); 2.5251 (0.74); 2.5201 (1.19); 2.5117 (13.15); 2.5072 (25.84); 2.5026 (33.70); 2.4980 (24.25); 2.4935 (11.40); 2.3602 (9.97); 2.3417 (1.53); 1.6974 (6.56); 1.6797 (6.47); 1.5052 (0.40); 1.4977 (0.43); 1.1423 (0.43); 1.1347 (0.41); 0.0080 (0.34); −0.0002 (9.54)

NMR Peak List Table 1

Example 398, Solvent: DMSO, Spectrometer: 399.95 MHz 10.7213 (2.08); 8.0266 (1.24); 8.0060 (1.60); 7.9532 (0.59); 7.8650 (1.33); 7.8457 (1.81); 7.8254 (1.15); 7.7276 (2.02); 7.7250 (2.61); 7.7212 (1.27); 7.7123 (0.83); 7.7072 (3.48); 7.7035 (2.39); 7.5673 (0.50); 7.5553 (0.38); 7.5490 (1.68); 7.5434 (0.49); 7.5340 (0.89); 7.5307 (1.43); 7.5273 (0.72); 7.4981 (2.39); 7.4947 (1.01); 7.4827 (1.73); 7.4790 (3.12); 7.4653 (0.51); 7.4613 (1.27); 7.4581 (0.70); 7.1950 (1.77); 7.1774 (1.72); 7.1591 (1.06); 7.1409 (1.15); 7.1175 (0.50); 7.1143 (0.46); 7.0983 (1.07); 7.0783 (0.68); 7.0752 (0.59); 6.8510 (0.93); 6.8327 (1.64); 6.8167 (2.06); 6.7977 (1.42); 5.3797 (5.98); 5.0599 (1.08); 5.0435 (1.08); 3.3321 (65.01); 3.0608 (0.76); 3.0520 (16.00); 2.8904 (4.79); 2.7320 (3.80); 2.7309 (3.73); 2.5252 (0.63); 2.5118 (12.29); 2.5073 (24.36); 2.5027 (31.90); 2.4981 (23.00); 2.4936 (10.86); 2.2186 (9.97); 1.5536 (5.61); 1.5372 (5.60); −0.0002 (4.58)

Example 399, Solvent: DMSO, Spectrometer: 400.13 MHz 11.0289 (2.45); 8.1728 (1.63); 8.1526 (1.96); 7.9463 (1.26); 7.9268 (1.80); 7.9067 (1.19); 7.8936 (1.28); 7.8910 (1.07); 7.8741 (1.59); 7.8716 (1.41); 7.8624 (0.97); 7.8588 (0.65); 7.8435 (0.78); 7.8376 (0.89); 7.8335 (0.66); 7.6017 (0.52); 7.5871 (0.65); 7.5815 (1.03); 7.5669 (1.09); 7.5620 (0.77); 7.5472 (0.68); 7.4857 (0.57); 7.4837 (0.62); 7.4792 (0.56); 7.4773 (0.55); 7.4623 (0.95); 7.4573 (0.88); 7.4432 (0.43); 7.4411 (0.46); 7.4368 (0.43); 7.4347 (0.41); 7.4278 (1.03); 7.4079 (2.19); 7.3878 (1.58); 7.2994 (1.45); 7.2982 (1.46); 7.2959 (1.30); 7.2825 (0.77); 7.2787 (1.19); 7.2765 (0.99); 7.2595 (1.82); 7.2541 (3.75); 7.2500 (1.65); 7.2363 (1.73); 7.1494 (1.04); 7.1476 (1.12); 7.1431 (0.98); 7.1412 (0.97); 7.1288 (0.92); 7.1269 (0.92); 7.1225 (0.88); 7.1206 (0.79); 5.4295 (5.89); 3.7900 (16.00); 3.3955 (0.36); 3.3456 (29.34); 3.0728 (14.83); 2.5598 (0.39); 2.5323 (0.66); 2.5187 (11.27); 2.5144 (22.95); 2.5099 (30.99); 2.5054 (22.33); 2.5011 (10.50); 1.9966 (0.95); 1.2494 (0.59); 1.1809 (0.52); 0.8632 (0.82); 0.8455 (0.32)

Example 400, Solvent: DMSO, Spectrometer: 399.95 MHz 10.2652 (2.65); 7.9532 (0.51); 7.8332 (0.58); 7.8167 (0.44); 7.8122 (2.01); 7.7962 (4.69); 7.7920 (2.88); 7.7755 (0.67); 7.7227 (2.71); 7.7189 (1.30); 7.7100 (0.83); 7.7050 (3.50); 7.7012 (2.41); 7.5618 (0.49); 7.5499 (0.36); 7.5434 (1.68); 7.5377 (0.49); 7.5285 (0.90); 7.5252 (1.45); 7.5218 (0.74); 7.4951 (2.48); 7.4918 (1.06); 7.4797 (1.68); 7.4760 (3.16); 7.4624 (0.49); 7.4583 (1.24); 7.4551 (0.69); 7.1102 (1.40); 7.1058 (1.42); 7.0940 (1.30); 7.0896 (1.32); 5.3309 (6.64); 4.2254 (2.02); 4.2167 (1.77); 4.2138 (2.33); 4.2101 (1.66); 4.2018 (2.14); 3.6070 (2.19); 3.5988 (1.70); 3.5950 (2.32); 3.5921 (1.75); 3.5834 (2.00); 3.4983 (1.51); 3.4808 (4.76); 3.4633 (4.82); 3.4458 (1.57); 3.3406 (100.43); 3.0718 (16.00); 2.8910 (4.19); 2.7316 (3.26); 2.5259 (0.50); 2.5126 (9.41); 2.5081 (18.75); 2.5035 (24.77); 2.4989 (18.10); 2.4944 (8.73); 1.1268 (4.89); 1.1093 (9.87); 1.0918 (4.78); −0.0002 (0.94)

Example 401, Solvent: DMSO, Spectrometer: 399.95 MHz 10.6923 (2.12); 8.1675 (1.56); 8.1475 (1.87); 7.9531 (0.74); 7.9087 (1.25); 7.8894 (1.70); 7.8692 (1.19); 7.8525 (1.75); 7.8486 (1.79); 7.7784 (1.00); 7.7738 (0.87); 7.7589 (1.12); 7.7541 (0.99); 7.7393 (1.85); 7.7368 (2.47); 7.7328 (1.18); 7.7242 (0.71); 7.7190 (3.30); 7.7152 (2.27); 7.5668 (0.47); 7.5550 (0.33); 7.5484 (1.60); 7.5427 (0.45); 7.5336 (0.83); 7.5302 (1.39); 7.5268 (0.68); 7.5056 (0.43); 7.5004 (2.31); 7.4970 (0.96); 7.4851 (1.51); 7.4813 (2.96); 7.4678 (0.44); 7.4636 (1.20); 7.4603 (0.65); 7.2728 (1.66); 7.2529 (1.47); 7.2122 (1.71); 7.1945 (1.65); 5.4134 (5.91); 3.3294 (54.85); 3.0831 (16.00); 2.8904 (6.35); 2.7318 (4.93); 2.7309 (4.81); 2.5249 (0.62); 2.5201 (0.96); 2.5115 (12.18); 2.5070 (24.48); 2.5023 (32.36); 2.4977 (23.26); 2.4932 (10.91); 2.2935 (12.89); −0.0002 (1.32)

Example 402, Solvent: DMSO, Spectrometer: 399.95 MHz 10.6837 (2.17); 8.0205 (0.72); 8.0000 (0.94); 7.9529 (0.74); 7.8817 (1.31); 7.8624 (1.78); 7.8422 (1.10); 7.7283 (2.59); 7.7244 (1.27); 7.7156 (0.78); 7.7105 (3.40); 7.7068 (2.38); 7.5683 (0.48); 7.5564 (0.36); 7.5500 (1.61); 7.5443 (0.48); 7.5350 (0.87); 7.5317 (1.42); 7.5283 (0.73); 7.5005 (2.38); 7.4971 (1.03); 7.4851 (1.62); 7.4814 (3.05); 7.4678 (0.49); 7.4637 (1.22); 7.4605 (0.70); 7.3639 (0.36); 7.3549 (4.10); 7.3493 (1.24); 7.3380 (1.33); 7.3323 (4.70); 7.3234 (0.42); 7.2045 (1.75); 7.1867 (1.67); 7.0019 (0.42); 6.9930 (4.43); 6.9873 (1.29); 6.9760 (1.23); 6.9704 (3.94); 6.9614 (0.33); 5.3827 (6.08); 4.8101 (5.71); 3.3411 (108.47); 3.3105 (0.34); 3.0665 (16.00); 2.8907 (5.99); 2.7322 (4.69); 2.7312 (4.75); 2.5258 (0.62); 2.5210 (1.00); 2.5124 (12.35); 2.5079 (24.66); 2.5033 (32.54); 2.4987 (23.64); 2.4942 (11.28); −0.0002 (0.78)

Example 403, Solvent: DMSO, Spectrometer: 400.13 MHz 12.1396 (0.34); 10.6020 (5.21); 8.0801 (2.66); 8.0593 (3.18); 7.8492 (2.85); 7.8298 (4.09); 7.8096 (2.63); 7.7252 (6.00); 7.7123 (1.93); 7.7074 (7.71); 7.7037 (5.56); 7.5767 (1.06); 7.5736 (0.73); 7.5649 (0.87); 7.5583 (3.73); 7.5527 (1.20); 7.5435 (2.08); 7.5402 (3.28); 7.5369 (1.73); 7.5109 (5.58); 7.4955 (3.81); 7.4917 (7.02); 7.4782 (1.16); 7.4741 (2.74); 7.4709 (1.62); 7.3007 (2.23); 7.2969 (1.10); 7.2818 (6.98); 7.2700 (2.13); 7.2645 (9.09); 7.2571 (7.02); 7.2528 (9.59); 7.2367 (4.30); 7.2202 (0.72); 7.1994 (1.65); 7.1950 (2.14); 7.1902 (1.44); 7.1779 (3.18); 7.1718 (1.01); 7.1655 (0.85); 7.1607 (1.19); 7.1566 (0.70); 7.1426 (4.24); 7.1247 (4.03); 5.3626 (14.12); 4.0441 (0.58); 4.0264 (0.60); 3.4953 (1.84); 3.4772 (6.19); 3.4590 (6.30); 3.4409 (1.93); 3.3931 (0.43); 3.3431 (44.47); 3.2933 (0.42); 2.9174 (2.61); 2.8991 (5.31); 2.8790 (4.02); 2.8387 (0.55); 2.8198 (1.09); 2.8007 (0.68); 2.7299 (4.19); 2.7096 (5.67); 2.6912 (2.75); 2.6835 (0.93); 2.6786 (0.97); 2.6742 (0.70); 2.5639 (1.08); 2.5597 (1.42); 2.5520 (1.40); 2.5321 (4.02); 2.5184 (48.43); 2.5141 (98.74); 2.5096 (132.35); 2.5051 (94.84); 2.5008 (44.47); 2.4641 (1.30); 2.4597 (1.50); 2.4554 (1.06); 2.3408 (0.60); 2.3365 (0.82); 2.3319 (0.59); 1.9969 (2.54); 1.3714 (0.45); 1.2858 (0.43); 1.2512 (1.99); 1.1990 (0.75); 1.1812 (1.36); 1.1634 (0.67); 1.0448 (7.07); 1.0363 (1.50); 1.0268 (16.00); 1.0085 (6.83); 0.8816 (0.93); 0.8648 (2.88); 0.8472 (1.13)

Example 404, Solvent: DMSO, Spectrometer: 399.95 MHz 10.5534 (2.01); 8.0729 (1.22); 8.0522 (1.45); 7.8401 (1.30); 7.8208 (1.76); 7.8006 (1.19); 7.7322 (0.35); 7.7264 (2.00); 7.7240 (2.61); 7.7201 (1.31); 7.7113 (0.84); 7.7062 (3.52); 7.7024 (2.38); 7.5648 (0.50); 7.5616 (0.32); 7.5529 (0.39); 7.5465 (1.65); 7.5408 (0.49); 7.5316 (0.88); 7.5283 (1.43); 7.5249 (0.73); 7.4974 (2.45); 7.4940 (1.05); 7.4820 (1.67); 7.4782 (3.09); 7.4647 (0.48); 7.4606 (1.22); 7.4573 (0.68); 7.1481 (1.77); 7.1305 (1.70); 5.3570 (6.23); 3.6704 (1.67); 3.6549 (4.26); 3.6391 (2.08); 3.3331 (49.99); 3.0551 (16.00); 2.8909 (0.91); 2.7321 (0.72); 2.5253 (0.68); 2.5203 (1.12); 2.5120 (11.22); 2.5075 (22.00); 2.5029 (28.85); 2.4983 (20.85); 2.4937 (9.84); 2.4414 (1.44); 2.4237 (2.88); 2.4066 (1.29); 1.7634 (0.38); 1.7563 (0.57); 1.7500 (0.59); 1.7402 (1.08); 1.7339 (1.04); 1.7256 (1.73); 1.7232 (1.86); 1.7171 (1.69); 1.7098 (1.67); 1.7064 (1.63); 1.6982 (0.90); 1.6920 (0.97); 1.6895 (0.96); 1.6802 (0.51); 1.6756 (0.44); 1.6695 (0.40); 0.8758 (0.41); −0.0002 (5.70)

Example 405, Solvent: DMSO, Spectrometer: 400.13 MHz 10.3160 (6.78); 7.8533 (1.75); 7.8325 (4.32); 7.8148 (5.04); 7.8014 (6.46); 7.7829 (2.51); 7.6768 (6.98); 7.6588 (8.41); 7.6555 (6.62); 7.5450 (1.24); 7.5266 (4.04); 7.5086 (3.65); 7.4800 (6.49); 7.4607 (7.93); 7.4432 (3.06); 7.1375 (4.04); 7.1213 (3.91); 5.7628 (0.84); 5.7146 (0.63); 5.7002 (1.42); 5.6866 (1.08); 5.6732 (1.75); 5.6586 (1.71); 5.6455 (1.24); 5.6316 (1.73); 5.6172 (0.83); 5.3241 (16.00); 4.9940 (7.64); 4.9675 (3.49); 4.9519 (3.13); 4.1928 (5.00); 4.1762 (10.71); 4.1591 (9.33); 4.1408 (6.81); 4.0420 (0.33); 3.3307 (39.53); 3.3070 (2.64); 2.9096 (3.20); 2.9031 (6.76); 2.8966 (3.51); 2.6759 (0.36); 2.5735 (3.32); 2.5670 (3.62); 2.5569 (6.81); 2.5503 (6.79); 2.5403 (4.17); 2.5337 (4.19); 2.5107 (47.57); 2.5065 (62.01); 2.5024 (47.29); 2.3335 (0.43); 2.0786 (0.64); 1.9935 (1.09); 1.2831 (0.70); 1.2497 (2.51); 1.1964 (0.38); 1.1787 (0.61); 1.1609 (0.33); 0.8785 (1.09); 0.8709 (0.93); 0.8620 (2.78); 0.8444 (1.25)

NMR Peak List Table 1

Example 406, Solvent: DMSO, Spectrometer: 400.13 MHz 10.2539 (0.81); 7.8730 (0.64); 7.8671 (0.67); 7.8597 (1.50); 7.6428 (0.64); 7.6402 (0.60); 7.5831 (0.32); 7.1711 (0.34); 7.1636 (0.34); 7.1503 (0.33); 5.8222 (0.93); 5.4111 (1.74); 4.1580 (0.52); 4.1413 (1.13); 4.1245 (0.53); 3.4038 (16.00); 3.1203 (4.23); 2.5728 (2.56); 2.5685 (5.38); 2.5640 (7.36); 2.5595 (5.31); 2.5552 (2.49); 1.6679 (0.39); 1.3915 (0.48); 1.3839 (0.98); 1.3749 (0.74); 1.3659 (0.65); 0.9568 (0.49); 0.9394 (1.34); 0.9216 (0.41)

Example 407, Solvent: DMSO, Spectrometer: 400.13 MHz 9.8766 (0.83); 8.0274 (0.58); 8.0071 (0.73); 7.8498 (0.46); 7.8305 (0.64); 7.8103 (0.40); 7.4234 (0.37); 7.4035 (0.80); 7.3834 (0.57); 7.2852 (0.53); 7.2830 (0.47); 7.2657 (0.43); 7.2635 (0.35); 7.2446 (0.57); 7.2388 (0.73); 7.2346 (0.51); 7.1584 (0.67); 7.1440 (0.55); 7.1401 (0.99); 7.1257 (0.35); 7.1239 (0.34); 7.1194 (0.33); 5.3862 (2.20); 3.7878 (5.76); 3.3441 (14.78); 3.0656 (5.35); 2.5319 (0.41); 2.5186 (5.93); 2.5143 (11.80); 2.5099 (15.73); 2.5054 (11.28); 2.5011 (5.31); 1.2390 (16.00)

Example 410, Solvent: DMSO, Spectrometer: 400.13 MHz 7.7340 (3.19); 7.7162 (3.95); 7.7125 (2.78); 7.5658 (0.63); 7.5543 (0.55); 7.5475 (2.12); 7.5416 (0.66); 7.5327 (1.26); 7.5293 (1.89); 7.5259 (0.95); 7.5026 (3.16); 7.4874 (2.23); 7.4836 (3.92); 7.4701 (0.67); 7.4660 (1.58); 7.4626 (0.88); 7.3214 (0.66); 5.7573 (1.04); 5.3255 (5.92); 4.4343 (0.84); 3.4826 (0.32); 3.4596 (0.70); 3.4511 (0.36); 3.4434 (0.38); 3.4089 (16.00); 3.3931 (2.39); 3.3590 (1431.96); 3.3092 (15.32); 3.2880 (0.55); 3.2766 (0.48); 3.2700 (0.33); 3.2601 (0.65); 3.0287 (15.76); 2.6776 (0.63); 2.6730 (0.82); 2.6684 (0.60); 2.5583 (1.05); 2.5537 (1.42); 2.5494 (1.07); 2.5262 (2.40); 2.5128 (52.34); 2.5084 (105.57); 2.5039 (140.95); 2.4995 (100.24); 2.4951 (46.94); 2.4587 (1.33); 2.4540 (1.62); 2.4496 (1.24); 2.3351 (0.67); 2.3306 (0.88); 2.3262 (0.65); 1.6967 (0.98); 1.4294 (0.74); 1.4123 (1.33); 1.3936 (1.32); 1.3749 (0.77); 1.2340 (0.36); 0.9333 (4.56); 0.9150 (9.21); 0.8964 (3.99); −0.0002 (2.70)

Example 416, Solvent: DMSO, Spectrometer: 400.13 MHz 7.6661 (0.70); 7.6572 (0.72); 7.6498 (1.01); 7.6463 (0.99); 7.6407 (1.73); 7.6269 (1.33); 7.6212 (1.32); 7.6142 (1.04); 7.6031 (0.75); 7.5947 (0.69); 7.3986 (0.81); 7.3919 (3.33); 7.3785 (2.97); 7.3706 (8.67); 7.3610 (6.61); 7.3532 (7.71); 7.3396 (0.62); 6.4579 (4.46); 6.4401 (4.29); 6.3782 (4.59); 6.3578 (4.47); 6.0313 (0.38); 5.9906 (7.71); 5.7606 (0.92); 5.2246 (0.60); 5.1700 (16.00); 4.0378 (0.38); 4.0200 (0.39); 3.4003 (0.38); 3.3850 (0.48); 3.3506 (37.42); 3.3353 (40.85); 3.3010 (0.53); 3.2857 (0.54); 3.2129 (1.21); 2.5527 (0.39); 2.5253 (0.70); 2.5118 (15.44); 2.5074 (31.58); 2.5030 (42.53); 2.4985 (30.35); 2.4942 (14.22); 2.4623 (0.33); 2.4579 (0.49); 2.4534 (0.56); 2.4488 (0.37); 1.9898 (1.70); 1.1923 (0.47); 1.1745 (0.91); 1.1568 (0.46); −0.0002 (4.74)

Example 417, Solvent: DMSO, Spectrometer: 400.13 MHz 10.1117 (2.91); 7.8366 (0.35); 7.8154 (2.25); 7.8083 (2.37); 7.8015 (5.52); 7.7873 (0.42); 7.6835 (0.58); 7.6796 (0.68); 7.6743 (0.38); 7.6637 (0.42); 7.6587 (0.66); 7.6544 (0.57); 7.5521 (0.58); 7.5484 (0.39); 7.5360 (0.93); 7.5321 (0.99); 7.5162 (0.68); 7.3833 (0.42); 7.3796 (0.44); 7.3708 (0.42); 7.3671 (0.49); 7.3628 (0.66); 7.3592 (0.67); 7.3502 (0.62); 7.3469 (0.66); 7.3427 (0.35); 7.1168 (1.28); 7.1100 (1.26); 7.1029 (1.09); 7.0961 (1.23); 5.3771 (6.26); 4.6774 (0.38); 4.6647 (0.42); 4.6548 (0.71); 4.6453 (0.51); 4.6322 (0.34); 3.4011 (2.49); 3.3700 (0.51); 3.3509 (185.01); 3.3006 (1.44); 3.1931 (16.00); 2.5581 (0.40); 2.5304 (0.44); 2.5256 (0.73); 2.5169 (10.75); 2.5125 (22.54); 2.5080 (30.69); 2.5035 (21.63); 2.4990 (9.87); 1.8775 (0.68); 1.8646 (0.79); 1.8514 (0.82); 1.8457 (0.82); 1.7337 (0.68); 1.7241 (0.74); 1.7105 (0.78); 1.7033 (0.73); 1.5281 (0.35); 1.5188 (0.37); 1.4985 (0.42); 1.4331 (0.79); 1.4083 (1.04); 1.3840 (1.15); 1.3578 (0.93); 1.3513 (0.71); 1.3320 (0.69); 1.3257 (0.79); 1.2997 (0.40); 1.2754 (0.34); 1.2458 (0.53)

Example 420, Solvent: DMSO, Spectrometer: 400.13 MHz 10.5177 (1.98); 8.0906 (1.25); 8.0699 (1.48); 7.8464 (1.24); 7.8272 (1.69); 7.8069 (1.15); 7.6862 (0.58); 7.6823 (0.66); 7.6769 (0.37); 7.6664 (0.41); 7.6610 (0.64); 7.6569 (0.55); 7.5498 (0.32); 7.5460 (0.57); 7.5423 (0.38); 7.5300 (0.92); 7.5261 (0.99); 7.5138 (0.45); 7.5101 (0.69); 7.3844 (0.46); 7.3807 (0.47); 7.3719 (0.45); 7.3681 (0.49); 7.3639 (0.66); 7.3603 (0.67); 7.3513 (0.64); 7.3480 (0.65); 7.3436 (0.34); 7.1635 (1.74); 7.1461 (1.67); 5.4045 (6.13); 4.0421 (0.67); 4.0243 (0.68); 3.3924 (0.88); 3.3424 (77.23); 3.2925 (0.82); 3.1764 (16.00); 2.5304 (0.40); 2.5256 (0.66); 2.5169 (9.30); 2.5125 (19.45); 2.5080 (26.44); 2.5035 (18.66); 2.4990 (8.55); 2.4075 (1.74); 2.3892 (3.15); 2.3705 (1.92); 1.9943 (3.03); 1.5952 (0.45); 1.5770 (1.28); 1.5582 (1.78); 1.5400 (1.32); 1.5208 (0.55); 1.3307 (1.06); 1.3117 (1.65); 1.2930 (1.68); 1.2748 (1.04); 1.1968 (0.85); 1.1790 (1.70); 1.1612 (0.83); 0.9046 (4.01); 0.8864 (8.31); 0.8679 (3.39)

Example 442, Solvent: DMSO, Spectrometer: 400.13 MHz 12.5729 (2.54); 7.6843 (1.28); 7.6818 (2.35); 7.6792 (1.44); 7.6636 (2.21); 7.6618 (2.12); 7.6252 (0.49); 7.6156 (4.44); 7.6131 (4.76); 7.6066 (3.50); 7.6052 (3.44); 7.6030 (3.29); 7.5993 (2.30); 7.5827 (0.39); 7.5791 (0.37); 7.5308 (1.54); 7.5219 (1.39); 7.5179 (1.15); 7.5117 (1.39); 7.5091 (1.21); 7.5038 (1.15); 7.4978 (0.97); 7.4899 (0.84); 7.4050 (1.45); 7.0215 (1.56); 7.0200 (1.56); 7.0025 (2.18); 7.0003 (2.04); 6.9469 (0.32); 6.9258 (0.70); 6.9207 (1.10); 6.9131 (1.20); 6.9056 (1.32); 6.8982 (2.05); 6.8941 (0.82); 6.8861 (1.16); 6.8818 (1.70); 6.8789 (2.45); 6.8689 (6.04); 6.8643 (4.65); 6.8532 (1.58); 6.8490 (1.86); 6.8458 (1.21); 6.8400 (0.72); 6.8355 (0.63); 6.8294 (0.39); 6.8236 (0.41); 5.7632 (16.00); 5.3970 (7.78); 5.1698 (1.47); 5.1616 (2.59); 5.1515 (1.50); 5.0500 (0.32); 5.0416 (0.55); 5.0342 (0.34); 4.4778 (0.39); 4.4674 (0.34); 4.4480 (2.63); 4.4411 (3.44); 4.4380 (3.33); 4.4334 (3.02); 4.4121 (0.89); 4.2844 (0.43); 4.2773 (0.43); 4.2553 (0.33); 4.2483 (0.33); 3.4069 (2.55); 3.3569 (173.53); 3.3071 (2.33); 3.2639 (0.47); 3.2139 (21.67); 2.6774 (0.36); 2.5628 (0.49); 2.5583 (0.67); 2.5538 (0.49); 2.5307 (0.97); 2.5172 (22.00); 2.5128 (45.68); 2.5083 (61.93); 2.5038 (44.10); 2.4994 (20.54); 2.4674 (0.37); 2.4629 (0.57); 2.4585 (0.72); 2.4539 (0.53); 2.3351 (0.40)

Example 444, Solvent: DMSO, Spectrometer: 400.13 MHz 10.1810 (2.80); 7.8181 (2.56); 7.8134 (2.63); 7.8054 (5.69); 7.7925 (0.45); 7.7299 (0.60); 7.7257 (0.69); 7.7109 (1.14); 7.7065 (1.41); 7.6907 (0.69); 7.6868 (0.75); 7.6549 (0.36); 7.6505 (0.36); 7.6414 (0.42); 7.6366 (0.77); 7.6338 (0.61); 7.6321 (0.60); 7.6296 (0.52); 7.6217 (0.74); 7.6183 (0.64); 7.6157 (0.82); 7.6110 (0.48); 7.6019 (0.52); 7.5975 (0.45); 7.3961 (0.82); 7.3941 (0.90); 7.3751 (0.84); 7.3727 (0.97); 7.3679 (2.29); 7.3505 (1.85); 7.3480 (2.05); 7.3445 (0.95); 7.3320 (0.97); 7.3293 (0.82); 7.1218 (1.28); 7.1137 (1.33); 7.1092 (1.11); 7.1011 (1.26); 5.3642 (6.35); 4.1042 (1.90); 4.0874 (4.16); 4.0707 (1.98); 3.4274 (7.09); 3.4174 (0.61); 3.3778 (477.76); 3.3546 (4.45); 3.3452 (1.68); 3.3280 (8.75); 3.3155 (1.05); 3.1925 (16.00); 2.5576 (0.34); 2.5305 (0.76); 2.5257 (1.12); 2.5172 (10.43); 2.5127 (21.52); 2.5082 (29.41); 2.5037 (21.37); 2.4992 (10.64); 2.4677 (0.37); 2.4630 (0.47); 2.4584 (0.55); 2.4539 (0.42); 1.6310 (0.86); 1.6139 (1.40); 1.6083 (0.94); 1.5967 (1.04); 1.5798 (0.37); 1.3464 (1.11); 1.3436 (1.07); 1.3359 (1.79); 1.3284 (3.68); 1.3196 (2.75); 1.3104 (2.57); 1.2585 (0.32); 0.9005 (1.82); 0.8941 (1.10); 0.8831 (5.10); 0.8716 (1.24); 0.8651 (1.56)

Example 449, Solvent: DMSO, Spectrometer: 400.13 MHz 10.5144 (2.11); 8.1062 (1.48); 8.0856 (1.80); 7.8463 (1.28); 7.8270 (1.81); 7.8131 (0.35); 7.8067 (1.27); 7.7266 (0.62); 7.7224 (0.70); 7.7074 (1.16); 7.7032 (1.39); 7.6872 (0.61); 7.6834 (0.71); 7.6579 (0.36); 7.6536 (0.36); 7.6444 (0.42); 7.6396 (0.78); 7.6369 (0.66); 7.6246 (0.69); 7.6214 (0.70); 7.6188 (0.83); 7.6141 (0.47); 7.6049 (0.47); 7.6006 (0.42); 7.3978 (0.97); 7.3766 (0.95); 7.3706 (2.60); 7.3506 (2.78); 7.3332 (0.93); 7.3307 (0.81); 7.1678 (1.83); 7.1501 (1.76); 5.3952 (6.38); 5.3592 (0.36); 3.4051 (3.56); 3.3552 (250.07); 3.3152 (0.86); 3.3053 (2.59);

NMR Peak List Table 1

3.1977 (0.93); 3.1820 (16.00); 2.6938 (0.54); 2.6773 (0.70); 2.6628 (0.39); 2.5581 (0.37); 2.5306 (0.43); 2.5171 (10.44); 2.5127 (21.58); 2.5082 (29.22); 2.5038 (20.80); 2.4994 (9.69); 1.5945 (0.47); 1.5899 (0.40); 1.5804 (0.48); 1.5739 (0.56); 1.5686 (0.41); 1.5591 (0.55); 1.3328 (0.41); 1.3210 (0.50); 1.3149 (0.39); 1.3076 (0.76); 1.3029 (0.59); 1.2937 (0.84); 1.2881 (0.96); 1.2737 (1.49); 1.2599 (1.58); 1.2538 (1.55); 1.2444 (1.63); 1.2389 (1.27); 1.2256 (0.49); 1.2211 (0.53); 1.2136 (0.37); 1.0708 (6.10); 1.0538 (6.09); 0.8836 (2.90); 0.8657 (5.89); 0.8477 (2.34)
Example 460, Solvent: DMSO, Spectrometer: 400.13 MHz 9.8085 (1.01); 8.1598 (1.38); 7.7943 (0.33); 7.7736 (0.65); 7.7552 (0.64); 7.7280 (0.92); 7.7072 (0.43); 7.5742 (0.32); 7.3320 (0.36); 7.3130 (0.46); 7.3082 (0.34); 7.3009 (0.62); 7.2990 (0.64); 7.2891 (0.36); 7.2790 (0.44); 7.2649 (3.66); 7.2626 (3.50); 7.1349 (0.56); 7.1170 (0.55); 5.2629 (2.06); 5.2442 (0.60); 4.0426 (0.47); 4.0247 (0.48); 2.5628 (0.36); 2.5583 (0.43); 2.5305 (0.69); 2.5170 (11.70); 2.5127 (23.94); 2.5082 (32.26); 2.5038 (23.18); 2.4995 (10.88); 1.9948 (1.61); 1.4828 (0.57); 1.4639 (16.00); 1.3390 (0.76); 1.2383 (0.53); 1.1973 (0.45); 1.1795 (0.87); 1.1617 (0.43)
Example 464, Solvent: DMSO, Spectrometer: 400.13 MHz 10.5149 (2.05); 8.0915 (1.24); 8.0708 (1.47); 7.8463 (1.24); 7.8068 (1.69); 7.8068 (1.16); 7.6858 (0.58); 7.6819 (0.67); 7.6766 (0.38); 7.6661 (0.41); 7.6611 (0.64); 7.6566 (0.56); 7.6400 (0.32); 7.5497 (0.33); 7.5459 (0.58); 7.5422 (0.39); 7.5299 (0.93); 7.5260 (0.99); 7.5136 (0.45); 7.5100 (0.69); 7.3841 (0.48); 7.3804 (0.48); 7.3715 (0.46); 7.3678 (0.50); 7.3634 (0.66); 7.3599 (0.68); 7.3509 (0.64); 7.3475 (0.66); 7.3434 (0.35); 7.1638 (1.76); 7.1464 (1.67); 7.1452 (1.65); 5.4044 (6.09); 4.0421 (0.96); 4.0243 (0.98); 4.0065 (0.32); 3.3926 (0.75); 3.3426 (74.92); 3.2928 (0.83); 3.1761 (16.00); 2.5305 (0.35); 2.5257 (0.59); 2.5170 (8.84); 2.5125 (18.52); 2.5080 (25.27); 2.5035 (17.91); 2.4990 (8.28); 2.3976 (1.63); 2.3793 (3.06); 2.3607 (1.79); 1.9943 (4.35); 1.6128 (0.34); 1.5942 (1.04); 1.5758 (1.46); 1.5578 (1.01); 1.5396 (0.35); 1.3240 (0.36); 1.3086 (0.78); 1.2917 (1.62); 1.2842 (2.50); 1.2769 (2.04); 1.2664 (1.65); 1.2575 (1.21); 1.2468 (0.66); 1.2394 (0.48); 1.1968 (1.23); 1.1790 (2.42); 1.1612 (1.20); 0.8845 (2.40); 0.8674 (6.29); 0.8497 (2.53)
Example 480, Solvent: DMSO, Spectrometer: 400.13 MHz 10.5120 (2.13); 8.0883 (1.33); 8.0675 (1.61); 7.8429 (1.24); 7.8235 (1.79); 7.8034 (1.26); 7.7253 (0.60); 7.7211 (0.68); 7.7061 (1.13); 7.7019 (1.41); 7.6859 (0.66); 7.6822 (0.76); 7.6564 (0.37); 7.6521 (0.37); 7.6429 (0.42); 7.6381 (0.78); 7.6354 (0.69); 7.6232 (0.75); 7.6198 (0.71); 7.6173 (0.85); 7.6126 (0.50); 7.6034 (0.48); 7.5991 (0.44); 7.3963 (0.95); 7.3751 (0.97); 7.3695 (2.52); 7.3494 (2.60); 7.3327 (0.96); 7.3302 (0.81); 7.1621 (1.83); 7.1443 (1.75); 5.7601 (2.18); 5.3896 (6.41); 3.4083 (1.59); 3.3580 (127.96); 3.3120 (0.85); 3.3081 (1.79); 3.1982 (0.60); 3.1790 (16.00); 2.5167 (5.65); 2.5124 (11.37); 2.5079 (15.19); 2.5035 (10.91); 2.4992 (5.18); 2.4164 (0.34); 2.4071 (1.83); 2.3889 (3.28); 2.3702 (1.98); 1.5951 (0.46); 1.5769 (1.34); 1.5581 (1.88); 1.5397 (1.41); 1.5207 (0.57); 1.3301 (1.09); 1.3112 (1.76); 1.2924 (1.77); 1.2742 (1.06); 1.2589 (0.62); 1.2433 (0.54); 0.9031 (3.97); 0.8848 (8.04); 0.8664 (3.35); 0.7719 (0.53)
Example 481, Solvent: DMSO, Spectrometer: 400.13 MHz 12.1354 (3.63); 7.6863 (1.77); 7.6839 (3.15); 7.6813 (1.94); 7.6657 (2.98); 7.6640 (2.88); 7.6223 (0.63); 7.6130 (6.12); 7.6104 (6.40); 7.6038 (4.90); 7.6023 (4.91); 7.6005 (4.72); 7.5968 (3.22); 7.5801 (0.54); 7.5766 (0.51); 7.5407 (0.43); 7.5297 (2.12); 7.5205 (1.92); 7.5170 (1.59); 7.5105 (1.95); 7.5079 (1.63); 7.5025 (1.57); 7.4969 (1.34); 7.4888 (1.20); 7.2990 (8.24); 5.3716 (11.47); 4.0415 (0.41); 4.0237 (0.41); 3.4112 (0.57); 3.4046 (3.66); 3.3904 (0.45); 3.3547 (297.76); 3.3048 (3.10); 3.2635 (0.41); 3.2136 (29.99); 2.5624 (0.43); 2.5579 (0.57); 2.5533 (0.42); 2.5304 (0.77); 2.5169 (16.75); 2.5125 (34.20); 2.5080 (45.90); 2.5035 (32.38); 2.4990 (14.91); 2.4626 (0.45); 2.4579 (0.58); 2.4535 (0.51); 2.4428 (3.59); 2.4245 (6.31); 2.4057 (3.93); 1.9937 (1.83); 1.6132 (0.89); 1.5949 (2.58); 1.5905 (1.24); 1.5762 (3.50); 1.5577 (2.66); 1.5387 (1.12); 1.3472 (0.62); 1.3286 (2.09); 1.3097 (3.33); 1.2910 (3.44); 1.2728 (2.26); 1.2543 (1.20); 1.2490 (1.22); 1.1961 (0.56); 1.1783 (1.02); 1.1605 (0.51); 0.9016 (7.73); 0.8833 (16.00); 0.8648 (6.91); 0.8611 (2.73); 0.8432 (1.04)
Example 493, Solvent: DMSO, Spectrometer: 400.13 MHz 12.5522 (2.06); 7.6803 (3.75); 7.6777 (2.34); 7.6621 (3.55); 7.6602 (3.42); 7.6238 (0.78); 7.6142 (7.21); 7.6117 (7.59); 7.6052 (5.61); 7.6014 (5.09); 7.5977 (3.66); 7.5811 (0.63); 7.5775 (0.71); 7.5390 (0.52); 7.5277 (2.56); 7.5189 (2.26); 7.5147 (1.86); 7.5086 (2.32); 7.5060 (2.00); 7.5009 (1.88); 7.4946 (1.62); 7.4869 (1.47); 7.4742 (0.32); 7.4653 (0.32); 7.3691 (10.44); 7.3166 (0.70); 7.3107 (4.17); 7.3055 (1.91); 7.2991 (2.41); 7.2922 (6.41); 7.2891 (6.51); 7.2808 (2.88); 7.2770 (3.47); 7.2706 (5.57); 7.2644 (1.46); 7.2591 (2.02); 6.9692 (2.45); 6.9508 (4.41); 6.9365 (2.15); 6.9324 (3.27); 6.9265 (6.15); 6.9241 (7.08); 6.9189 (2.74); 6.9046 (6.50); 6.8958 (0.92); 6.8721 (1.91); 6.8696 (2.30); 6.8501 (2.05); 6.8480 (1.68); 5.7594 (16.00); 5.3876 (12.97); 5.2756 (0.34); 5.0820 (1.00); 5.0655 (3.48); 5.0490 (3.48); 5.0324 (0.97); 4.8317 (0.35); 4.8148 (1.18); 4.7978 (1.19); 4.7809 (0.37); 3.7201 (0.33); 3.4243 (1.78); 3.3745 (216.51); 3.3264 (4.65); 3.2665 (0.91); 3.2163 (35.02); 3.1665 (0.49); 3.0693 (0.41); 2.8342 (0.35); 2.6816 (0.32); 2.6771 (0.45); 2.6725 (0.34); 2.5627 (0.60); 2.5582 (0.78); 2.5537 (0.53); 2.5304 (1.08); 2.5256 (1.83); 2.5169 (26.82); 2.5125 (56.25); 2.5080 (76.63); 2.5035 (54.45); 2.4991 (25.21); 2.4674 (0.52); 2.4629 (0.71); 2.4583 (0.78); 2.4538 (0.51); 2.3393 (0.33); 2.3349 (0.47); 2.3302 (0.35); 1.9929 (1.17); 1.5613 (12.89); 1.5448 (13.20); 1.5181 (0.50); 1.5052 (5.79); 1.4882 (5.66); 1.2371 (0.52); 1.1954 (0.35); 1.1776 (0.65); 1.1598 (0.33)
Example 499, Solvent: DMSO, Spectrometer: 400.13 MHz 11.9277 (4.49); 7.6901 (4.46); 7.6877 (2.89); 7.6718 (4.46); 7.6704 (4.25); 7.6192 (0.96); 7.6102 (8.62); 7.6077 (9.21); 7.5988 (8.49); 7.5945 (4.78); 7.5777 (0.67); 7.5742 (0.66); 7.5382 (0.64); 7.5273 (2.96); 7.5167 (2.87); 7.5151 (2.48); 7.5081 (2.83); 7.5056 (2.41); 7.4997 (2.26); 7.4948 (1.95); 7.4864 (1.64); 7.3081 (11.76); 7.5719 (7.50); 5.3377 (16.00); 4.2889 (0.49); 4.2726 (0.33); 4.2568 (5.17); 4.2405 (11.56); 4.2242 (5.38); 3.4191 (0.55); 3.4134 (0.51); 3.4078 (3.57); 3.3872 (0.48); 3.3578 (290.56); 3.3254 (0.53); 3.3079 (2.91); 3.2915 (0.61); 3.2416 (40.76); 3.1915 (0.56); 3.1884 (0.70); 2.9337 (3.59); 2.9271 (8.15); 2.9205 (3.78); 2.6071 (3.14); 2.6005 (3.29); 2.5908 (6.69); 2.5842 (6.51); 2.5745 (3.35); 2.5679 (3.14); 2.5584 (0.83); 2.5540 (0.67); 2.5380 (0.50); 2.5309 (0.99); 2.5171 (15.11); 2.5128 (30.62); 2.5083 (41.00); 2.5038 (29.40); 2.4995 (13.88); 2.4628 (0.41); 2.4585 (0.47); 2.4540 (0.35); 1.9936 (1.06); 1.1779 (0.58)
Example 508, Solvent: DMSO, Spectrometer: 400.13 MHz 7.6971 (0.71); 7.6934 (0.75); 7.6763 (1.46); 7.6728 (1.69); 7.6675 (0.93); 7.6565 (1.04); 7.6514 (1.65); 7.6305 (0.77); 7.6270 (0.75); 7.5544 (1.38); 7.5383 (2.26); 7.5346 (2.37); 7.5185 (1.62); 7.4095 (2.84); 7.3911 (3.87); 7.3893 (3.82); 7.3810 (1.20); 7.3774 (1.28); 7.3707 (3.72); 7.3651 (1.37); 7.3606 (1.72); 7.3572 (1.69); 7.3478 (1.63); 7.3449 (1.68); 7.3366 (0.81); 7.3273 (0.73); 7.3245 (0.72); 6.5282 (4.45); 6.5105 (4.26); 6.4053 (4.50); 6.3848 (4.33); 6.0324 (7.56); 5.7609 (1.95); 5.2252 (16.00); 4.0204 (0.32); 3.3866 (0.69); 3.3361 (45.64); 3.2858 (0.58); 3.2638 (0.51); 3.2134 (34.60); 3.1630 (0.46); 2.9992 (0.44); 2.5586 (0.39); 2.5542 (0.53); 2.5497 (0.39); 2.5121 (15.31); 2.5081 (30.66); 2.5037 (40.81); 2.4993 (29.29); 2.4579 (0.41); 2.4534 (0.51); 2.4489 (0.36); 1.9903 (1.39); 1.2789 (0.45); 1.2453 (2.12); 1.1928 (0.44); 1.1750 (0.74); 1.1572 (0.37); 0.8748 (0.95); 0.8580 (2.85); 0.8404 (1.17); −0.0002 (5.13)
Example 510, Solvent: DMSO, Spectrometer: 400.13 MHz 7.8076 (0.58); 7.7990 (0.35); 7.7956 (0.33); 7.7338 (1.50); 7.7296 (1.66); 7.7147 (2.92); 7.7104 (3.29); 7.6947 (1.70); 7.6909 (1.72); 7.6457 (0.89); 7.6415 (0.89); 7.6321 (1.11); 7.6274 (1.95); 7.6248 (1.72); 7.6126 (1.82); 7.6092 (1.75); 7.6067 (2.02); 7.6020 (1.20); 7.5928 (1.16); 7.5885 (1.00); 7.5825 (0.35); 7.5790 (0.36); 7.4060 (2.96); 7.3877 (6.18); 7.3668 (6.66); 7.3460 (4.65); 7.3447 (4.64); 7.3277 (2.16); 7.3252 (1.85); 6.5268 (4.43); 6.5091 (4.24); 6.4031 (4.49); 6.3827 (4.29); 6.0269 (7.18); 5.9794 (0.51); 5.7555 (12.51); 5.3534 (0.71); 5.2080 (16.00);

-continued

NMR Peak List Table 1

5.1456 (0.70); 3.4050 (1.11); 3.3901 (0.72); 3.3537 (88.85); 3.3129 (0.65); 3.3041 (1.48); 3.2646 (0.43); 3.2135 (34.42); 3.1926 (1.86); 3.1638 (0.55); 3.1483 (0.33); 2.5057 (22.11); 2.5013 (28.75); 2.4970 (21.00); 2.4606 (0.32); 2.4560 (0.41); 2.4516 (0.45); 1.9867 (1.17); 1.5305 (2.66); 1.3700 (1.17); 1.3544 (1.16); 1.2528 (1.57); 1.2372 (1.62); 1.1889 (0.35); 1.1711 (0.65); 1.1533 (0.33)
Example 512, Solvent: CDCl3, Spectrometer: 300.16 MHz 7.6104 (2.40); 7.6053 (1.28); 7.5941 (0.85); 7.5874 (3.11); 7.5821 (2.41); 7.4879 (0.37); 7.4632 (1.44); 7.4550 (0.50); 7.4446 (0.99); 7.4398 (1.50); 7.4349 (0.83); 7.4170 (2.71); 7.3971 (1.53); 7.3918 (2.74); 7.3745 (0.52); 7.3689 (1.00); 7.3634 (0.63); 7.2621 (3.61); 6.9361 (4.17); 5.3797 (7.09); 3.3237 (2.13); 3.2992 (3.25); 3.2745 (2.30); 3.0246 (16.00); 1.7509 (0.48); 1.7274 (1.18); 1.7020 (1.98); 1.6940 (0.95); 1.6776 (1.39); 1.6519 (0.71); 1.5092 (0.36); 1.4846 (1.13); 1.4595 (1.71); 1.4341 (1.70); 1.4101 (1.04); 1.3862 (0.36); 1.3052 (1.25); 1.2531 (1.10); 0.9659 (3.84); 0.9416 (7.60); 0.9171 (3.27); −0.0002 (2.05)
Example 513, Solvent: DMSO, Spectrometer: 400.13 MHz 10.5079 (2.05); 8.0859 (1.25); 8.0652 (1.51); 7.8428 (1.24); 7.8236 (1.72); 7.8032 (1.24); 7.7233 (0.60); 7.7190 (0.68); 7.7042 (1.09); 7.6999 (1.35); 7.6839 (0.63); 7.6801 (0.70); 7.6564 (0.36); 7.6520 (0.36); 7.6429 (0.41); 7.6380 (0.76); 7.6354 (0.62); 7.6336 (0.60); 7.6312 (0.52); 7.6034 (0.71); 7.6197 (0.63); 7.6172 (0.79); 7.6125 (0.44); 7.6034 (0.45); 7.5990 (0.39); 7.3959 (0.92); 7.3747 (0.92); 7.3692 (2.44); 7.3491 (2.44); 7.3325 (0.93); 7.3299 (0.76); 7.1614 (1.74); 7.1440 (1.68); 5.3873 (6.13); 3.4294 (6.56); 3.4165 (0.47); 3.4126 (0.48); 3.4078 (0.68); 3.3795 (451.85); 3.3544 (1.07); 3.3478 (0.56); 3.3449 (0.47); 3.3384 (0.35); 3.3297 (5.58); 3.3100 (0.76); 3.1961 (0.72); 3.1769 (16.00); 2.5579 (0.33); 2.5304 (0.40); 2.5255 (0.72); 2.5169 (9.83); 2.5125 (20.41); 2.5080 (27.65); 2.5035 (19.57); 2.4990 (9.03); 2.4581 (0.33); 2.3954 (1.65); 2.3770 (3.07); 2.3584 (1.79); 1.6111 (0.33); 1.5925 (1.02); 1.5741 (1.45); 1.5562 (1.01); 1.5379 (0.34); 1.3218 (0.35); 1.3059 (0.77); 1.2896 (1.63); 1.2823 (2.54); 1.2749 (2.08); 1.2643 (1.74); 1.2579 (1.66); 1.2426 (1.10); 0.8822 (2.38); 0.8651 (6.24); 0.8475 (2.53); 0.7930 (0.33)
Example 519, Solvent: DMSO, Spectrometer: 400.13 MHz 11.7891 (2.69); 7.6904 (1.74); 7.6881 (3.03); 7.6856 (1.88); 7.6698 (2.90); 7.6682 (2.75); 7.6295 (0.53); 7.6269 (0.69); 7.6203 (1.05); 7.6117 (5.99); 7.6092 (6.15); 7.6022 (4.81); 7.6004 (5.39); 7.5958 (3.35); 7.5791 (0.62); 7.5756 (0.41); 7.5389 (0.45); 7.5280 (2.12); 7.5186 (1.96); 7.5157 (1.58); 7.5088 (1.91); 7.5063 (1.57); 7.5006 (1.51); 7.4954 (1.31); 7.4871 (1.11); 7.2904 (8.13); 7.2392 (0.69); 5.4325 (0.74); 5.3335 (10.81); 4.2500 (0.59); 4.1799 (3.66); 4.1634 (7.84); 4.1468 (3.74); 4.0693 (0.61); 3.4046 (5.19); 3.3914 (0.38); 3.3814 (0.61); 3.3547 (404.79); 3.3344 (1.04); 3.3229 (0.54); 3.3150 (0.34); 3.3047 (4.39); 3.2843 (0.43); 3.2345 (28.39); 3.1929 (2.23); 3.1846 (0.38); 2.6772 (0.34); 2.5627 (0.45); 2.5582 (0.64); 2.5537 (0.81); 2.5307 (0.81); 2.5259 (1.37); 2.5172 (20.14); 2.5128 (42.22); 2.5083 (57.50); 2.5038 (40.91); 2.4994 (19.00); 2.4675 (0.35); 2.4629 (0.54); 2.4584 (0.65); 2.4540 (0.48); 2.3350 (0.37); 1.9942 (0.96); 1.6517 (0.79); 1.6346 (2.47); 1.6280 (0.95); 1.6170 (3.20); 1.5975 (2.85); 1.5810 (1.38); 1.4156 (0.58); 1.3970 (2.04); 1.3780 (3.27); 1.3591 (3.36); 1.3409 (2.07); 1.3226 (0.66); 1.2811 (0.44); 1.2491 (1.92); 1.1967 (0.33); 1.1788 (0.55); 0.9310 (7.70); 0.9126 (16.00); 0.8941 (6.74); 0.8797 (1.73); 0.8708 (0.80); 0.8618 (3.82); 0.8442 (1.70)
Example 525, Solvent: DMSO, Spectrometer: 400.13 MHz 10.3136 (2.88); 7.8476 (0.58); 7.8266 (1.98); 7.8102 (4.65); 7.8058 (2.87); 7.7890 (0.77); 7.7846 (0.40); 7.7313 (0.61); 7.7271 (0.70); 7.7123 (1.18); 7.7079 (1.45); 7.6922 (0.68); 7.6883 (0.74); 7.6544 (0.35); 7.6500 (0.35); 7.6408 (0.42); 7.6360 (0.77); 7.6332 (0.63); 7.6212 (0.73); 7.6153 (0.83); 7.6105 (0.46); 7.6014 (0.51); 7.5972 (0.44); 7.3935 (0.94); 7.3675 (2.23); 7.3501 (1.89); 7.3482 (2.01); 7.3318 (0.92); 7.3293 (0.78); 7.1370 (1.39); 7.1328 (1.42); 7.1207 (1.31); 7.1164 (1.34); 5.7579 (1.89); 5.3679 (6.56); 4.1954 (2.03); 4.1788 (4.53); 4.1621 (2.09); 3.4791 (0.33); 3.4282 (6.97); 3.3788 (426.80); 3.3442 (0.56); 3.3295 (6.85); 3.3159 (0.86); 3.1958 (16.00); 2.9130 (1.33); 2.9064 (3.02); 2.8998 (1.41); 2.5794 (1.21); 2.5727 (1.29); 2.5627 (2.74); 2.5562 (2.81); 2.5463 (1.36); 2.5395 (1.30); 2.5303 (0.78); 2.5168 (10.27); 2.5125 (20.83); 2.5080 (27.94); 2.5035 (19.75); 2.4991 (9.11); 2.4631 (0.35); 2.4586 (0.43)
Example 530, Solvent: DMSO, Spectrometer: 400.13 MHz 11.7847 (4.18); 7.6882 (4.37); 7.6859 (2.81); 7.6699 (4.32); 7.6684 (4.17); 7.6264 (0.51); 7.6202 (1.08); 7.6114 (8.54); 7.6089 (8.99); 7.6000 (8.05); 7.5956 (4.71); 7.5787 (0.61); 7.5753 (0.61); 7.5387 (0.63); 7.5277 (2.92); 7.5186 (2.71); 7.5155 (2.34); 7.5085 (2.72); 7.5061 (2.33); 7.5003 (2.13); 7.4952 (1.86); 7.4869 (1.60); 7.2901 (11.92); 7.2385 (0.36); 5.7631 (1.84); 5.4332 (0.35); 5.3336 (16.00); 4.1711 (5.02); 4.1544 (10.81); 4.1377 (5.09); 3.4131 (0.38); 3.4046 (7.16); 3.3546 (450.31); 3.3182 (0.37); 3.3043 (3.32); 3.2855 (0.81); 3.2355 (40.34); 3.2071 (0.33); 3.1920 (1.08); 3.1851 (0.37); 2.6774 (0.41); 2.5626 (0.67); 2.5582 (1.01); 2.5537 (0.81); 2.5492 (0.50); 2.5307 (1.17); 2.5171 (25.22); 2.5128 (51.74); 2.5083 (69.75); 2.5039 (50.03); 2.4996 (23.67); 2.4624 (0.43); 2.4580 (0.58); 2.3398 (0.33); 2.3351 (0.45); 1.6687 (0.73); 1.6510 (2.53); 1.6337 (4.05); 1.6164 (2.91); 1.5993 (1.03); 1.3616 (0.67); 1.3464 (2.78); 1.3365 (5.10); 1.3284 (9.52); 1.3191 (8.57); 1.3102 (6.18); 1.3017 (2.54); 1.2779 (0.77); 0.9014 (5.01); 0.8840 (14.37); 0.8662 (4.55); 0.8519 (0.91); 0.8338 (0.41)
Example 534, Solvent: DMSO, Spectrometer: 400.13 MHz 10.3216 (2.76); 7.8511 (0.57); 7.8346 (0.44); 7.8301 (1.91); 7.8139 (4.58); 7.8096 (2.73); 7.7930 (0.64); 7.6835 (0.59); 7.6796 (0.68); 7.6743 (0.38); 7.6637 (0.42); 7.6590 (0.65); 7.6544 (0.55); 7.5530 (0.58); 7.5494 (0.39); 7.5370 (0.93); 7.5331 (0.99); 7.5208 (0.46); 7.5171 (0.67); 7.3835 (0.41); 7.3798 (0.44); 7.3708 (0.43); 7.3672 (0.49); 7.3629 (0.65); 7.3593 (0.67); 7.3503 (0.62); 7.3470 (0.66); 7.3428 (0.34); 7.1387 (1.35); 7.1343 (1.38); 7.1224 (1.27); 7.1180 (1.28); 5.7638 (7.80); 5.3856 (6.21); 4.1966 (1.45); 4.1800 (4.43); 4.1633 (2.01); 3.4009 (2.37); 3.3508 (229.28); 3.3194 (0.33); 3.3009 (2.19); 3.2434 (0.35); 3.1948 (16.00); 2.9199 (1.33); 2.9133 (3.15); 2.9066 (1.40); 2.5805 (1.16); 2.5738 (1.21); 2.5638 (2.74); 2.5572 (2.80); 2.5473 (1.29); 2.5406 (1.13); 2.5304 (0.63); 2.5256 (0.97); 2.5169 (13.21); 2.5125 (27.64); 2.5080 (37.59); 2.5034 (26.53); 2.4990 (12.15); 2.4625 (0.32); 2.4580 (0.41)
Example 538, Solvent: DMSO, Spectrometer: 400.13 MHz 12.1325 (5.11); 7.6841 (4.02); 7.6815 (2.50); 7.6658 (3.80); 7.6641 (3.72); 7.6228 (0.80); 7.6135 (7.73); 7.6109 (8.18); 7.6042 (6.16); 7.6027 (6.36); 7.6012 (6.15); 7.5974 (4.07); 7.5808 (0.61); 7.5772 (0.61); 7.5411 (0.54); 7.5301 (2.70); 7.5208 (2.44); 7.5174 (2.02); 7.5109 (2.45); 7.5083 (2.08); 7.5029 (1.95); 7.4973 (1.70); 7.4892 (1.50); 7.2994 (10.05); 5.3716 (14.60); 4.0419 (0.38); 4.0242 (0.38); 3.4109 (0.69); 3.4057 (6.88); 3.3899 (0.77); 3.3557 (585.31); 3.3258 (0.86); 3.3057 (7.09); 3.2629 (0.54); 3.2128 (38.11); 3.3.1628 (0.47); 2.6819 (0.38); 2.6773 (0.50); 2.6728 (0.37); 2.5629 (0.65); 2.5583 (0.90); 2.5539 (0.73); 2.5307 (1.29); 2.5172 (28.69); 2.5128 (59.14); 2.5083 (79.86); 2.5038 (56.71); 2.4994 (26.29); 2.4630 (0.79); 2.4583 (1.00); 2.4538 (0.78); 2.4491 (0.53); 2.4337 (4.29); 2.4152 (8.10); 2.3966 (4.66); 2.3397 (0.44); 2.3351 (0.70); 1.9941 (1.67); 1.6315 (0.86); 1.6130 (2.66); 1.5946 (3.69); 1.5766 (2.57); 1.5582 (0.88); 1.3214 (1.02); 1.3054 (2.15); 1.2890 (4.40); 1.2818 (7.02); 1.2742 (5.74); 1.2636 (5.22); 1.2547 (4.45); 1.2449 (3.99); 1.2168 (0.67); 1.1966 (0.68); 1.1788 (1.03); 1.1610 (0.51); 0.8840 (6.22); 0.8669 (16.00); 0.8619 (6.17); 0.8493 (6.72); 0.8444 (2.66); 0.8170 (0.36)
Example 539, Solvent: DMSO, Spectrometer: 400.13 MHz 12.4467 (0.49); 7.7288 (1.42); 7.7161 (0.46); 7.7111 (1.81); 7.7073 (1.24); 7.5464 (0.89); 7.5317 (0.52); 7.5283 (0.80); 7.5248 (0.41); 7.5019 (1.33); 7.4867 (0.89); 7.4828 (1.64); 7.4653 (0.62); 7.4618 (0.34); 7.2866 (1.15); 5.7567 (3.06); 5.3019 (2.79); 3.4665 (0.36); 3.4168 (6.80); 3.3669 (522.30); 3.3171 (5.64); 3.0140 (8.63); 2.5545 (0.43); 2.5271 (0.55); 2.5136 (14.16); 2.5092 (29.42); 2.5047 (39.85); 2.5002 (28.41); 2.4958 (13.26); 2.4594 (0.35); 2.4549 (0.44); 2.4503 (0.32); 2.0750 (0.62); 1.4895 (16.00)

NMR Peak List Table 1

Example 543, Solvent: DMSO, Spectrometer: 400.13 MHz 12.4396 (2.27); 7.6840 (1.99); 7.6815 (1.27); 7.6658 (1.92); 7.6640 (1.91); 7.6234 (0.41); 7.6138 (3.82); 7.6114 (4.07); 7.6047 (3.12); 7.6035 (3.11); 7.6013 (2.97); 7.5976 (2.08); 7.5810 (0.35); 7.5774 (0.34); 7.5292 (1.32); 7.5202 (1.21); 7.5163 (1.02); 7.5100 (1.26); 7.5075 (1.11); 7.5022 (1.00); 7.4962 (0.85); 7.4883 (0.78); 7.3600 (0.39); 7.3576 (0.47); 7.3533 (0.34); 7.3382 (4.24); 7.3337 (4.71); 7.3250 (16.00); 7.3185 (6.34); 7.3049 (0.38); 7.2988 (0.67); 7.2968 (0.67); 7.2840 (1.06); 7.2770 (1.13); 7.2747 (1.24); 7.2658 (1.37); 7.2626 (1.42); 7.2574 (0.86); 7.2490 (0.88); 7.2413 (0.41); 5.3809 (7.22); 4.0420 (0.87); 4.0242 (0.89); 3.7676 (8.88); 3.5650 (1.20); 3.4075 (1.86); 3.3955 (0.32); 3.3576 (152.35); 3.3076 (1.72); 3.2186 (18.39); 2.5306 (0.50); 2.5171 (10.66); 2.5128 (21.73); 2.5083 (29.16); 2.5038 (20.82); 2.4995 (9.74); 2.4584 (0.33); 1.9942 (3.82); 1.2476 (1.36); 1.1964 (1.07); 1.1786 (2.07); 1.1608 (1.01); 0.8782 (0.63); 0.8614 (2.01); 0.8437 (0.79)

Example 552, Solvent: DMSO, Spectrometer: 400.13 MHz 10.1835 (2.74); 7.8187 (2.69); 7.8149 (2.69); 7.8064 (5.53); 7.7299 (0.61); 7.7256 (0.69); 7.7109 (1.15); 7.7065 (1.41); 7.6907 (0.67); 7.6868 (0.72); 7.6548 (0.36); 7.6504 (0.35); 7.6413 (0.42); 7.6365 (0.77); 7.6338 (0.60); 7.6321 (0.58); 7.6296 (0.50); 7.6216 (0.73); 7.6181 (0.62); 7.6156 (0.80); 7.6109 (0.45); 7.6018 (0.50); 7.5975 (0.41); 7.3942 (0.93); 7.3727 (0.98); 7.3679 (2.34); 7.3504 (1.88); 7.3480 (2.11); 7.3319 (0.93); 7.3293 (0.78); 7.1218 (1.28); 7.1131 (1.37); 7.1097 (1.10); 7.1010 (1.21); 5.7587 (0.88); 5.3644 (6.44); 4.1131 (2.04); 4.0965 (4.36); 4.0799 (2.06); 3.4259 (4.59); 3.4205 (0.49); 3.4039 (0.64); 3.3759 (406.79); 3.3504 (0.68); 3.3259 (5.60); 3.3153 (0.88); 3.1924 (16.00); 2.5304 (0.42); 2.5255 (0.71); 2.5170 (9.17); 2.5125 (19.04); 2.5080 (25.79); 2.5035 (18.12); 2.4990 (8.26); 2.4579 (0.35); 1.6317 (0.42); 1.6145 (1.30); 1.6081 (0.52); 1.5972 (1.66); 1.5918 (1.07); 1.5776 (1.39); 1.5610 (0.58); 1.3981 (1.06); 1.3790 (1.65); 1.3653 (0.76); 1.3602 (1.72); 1.3421 (1.01); 1.2583 (0.82); 1.2427 (0.84); 0.9288 (4.20); 0.9104 (8.58); 0.8919 (3.51)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC. ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

The following table 2 illustrates in a non limiting manner examples of compounds of formula (V) according to the invention.

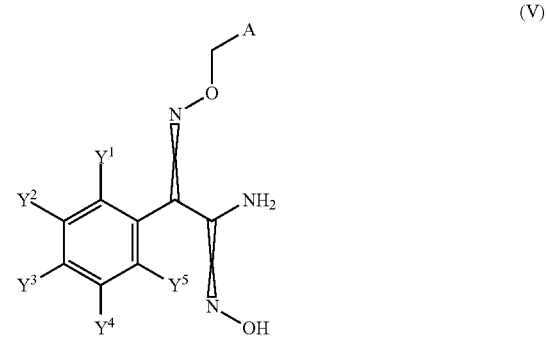

(V)

In table 2 we use the following abbreviations for specified claimed elements "$A^1$" and "$A^2$" of the generic structure (I) of the invention:

$A^1$

$A^2$

TABLE 2

| Ex-no | $Y^1$ | $Y^2$ | $Y^3$ | $Y^4$ | $Y^5$ | A | $Z^1$ | $Z^2$ | $Z^3$ | $Z^4$ | Stereo | LogP |
|---|---|---|---|---|---|---|---|---|---|---|---|---|
| V-1 | H | H | H | H | H | A1 | [(but-3-yn-1-yloxy)carbonyl]amino | H | H | H | Z, U | 2.1 [a] |
| V-2 | H | H | H | H | H | A2 | amino | H | | | Z, U | 0.43 [a] |
| V-3 | H | H | H | H | H | A1 | amino | H | H | H | Z, U | 0.41 [a] |
| V-5 | H | H | H | H | fluoro | A1 | (tert-butoxycarbonyl)amino | H | H | H | Z, U | 2.68 [a] |
| V-6 | H | methoxy | H | H | H | A1 | amino | H | H | H | U, U | 0.58 [a] |
| V-7 | H | $CH_3$ | H | H | H | A1 | amino | H | H | H | U, U | 0.75 [a] |
| V-8 | H | H | fluoro | H | H | A1 | (tert-butoxycarbonyl)amino | H | H | H | Z, U | 2.68 [a] |
| V-9 | H | H | H | H | H | A1 | amino | H | H | H | U, U | 0.39 [a] |
| V-10 | H | H | H | H | chloro | A2 | amino | H | | | Z, U | 0.73 [a] |
| V-11 | H | H | H | H | H | A1 | (tert-butoxycarbonyl)amino | H | H | H | Z, U | 2.54 [a] |
| V-12 | H | fluoro | H | H | H | A1 | amino | H | H | H | U, U | 0.56 [a] |
| V-13 | H | H | methoxy | H | H | A1 | (tert-butoxycarbonyl)amino | H | H | H | Z, U | 2.51 [a] |
| V-14 | H | H | H | H | H | A1 | (tert-butoxycarbonyl)amino | H | H | H | Z, U | 2.57 [a] |
| V-15 | H | H | $CH_3$ | H | H | A2 | amino | H | | | Z, U | 0.89 [a] |
| V-16 | fluoro | fluoro | H | H | H | A1 | (tert-butoxycarbonyl)amino | H | H | H | U, U | 2.9 [a] |

We describe the double bond geometry of the examples of table 2 as shown here:

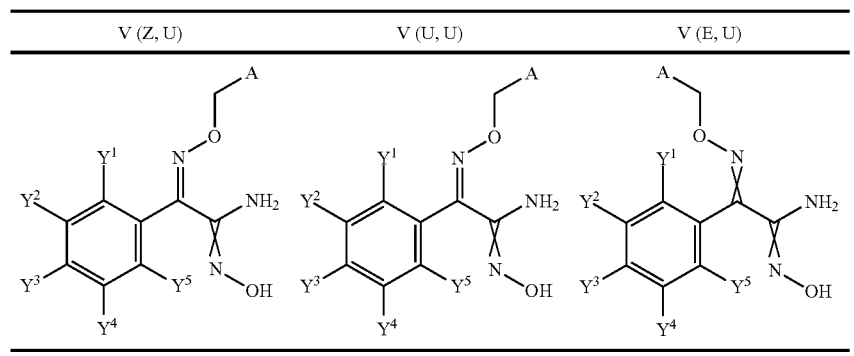

| V (Z, U) | V (U, U) | V (E, U) |
|---|---|---|

Measurement of log P values was performed according EEC directive 79/831 Annex V.A8 by HPLC (High Performance Liquid Chromatography) on reversed phase columns with the following methods: [a]Measurement of LC-MS was done at pH 2.7 with 0.1% formic acid in water and with acetonitrile (contains 0.1% formic acid) as eluent with a linear gradient from 10% acetonitrile to 95% acetonitrile. Calibration was done with not branched alkan2-ones (with 3 to 16 carbon atoms) with known log P-values (measurement of log P values using retention times with linear interpolation between successive alkanones). lambda-maX-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value-signal intensity pairs are semicolons as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$)

NMR Peak List Table 2

Example V-1, Solvent: DMSO, Spectrometer: 400.13 MHz 10.2384 (6.32); 9.5810 (13.93); 7.7909 (1.47); 7.7700 (3.84); 7.7525 (4.80); 7.7422 (5.37); 7.7243 (1.83); 7.5899 (3.91); 7.5855 (5.01); 7.5774 (2.97); 7.5723 (4.42); 7.5658 (5.73); 7.5505 (0.33); 7.4352 (0.38); 7.4304 (0.45); 7.4142 (2.59); 7.4070 (9.61); 7.4032 (8.91); 7.3964 (3.44); 7.3887 (5.02); 7.3806 (1.29); 7.3763 (1.37); 7.3706 (0.64); 7.3662 (0.71); 7.1661 (3.23); 7.1511 (3.03); 5.9854 (8.22); 5.4365 (0.34); 5.2038 (13.23); 4.1935 (4.30); 4.1769 (9.43); 4.1602 (4.47); 4.0603 (1.21); 4.0426 (3.71); 4.0247 (3.76); 4.0070 (1.26); 3.3392 (422.26); 3.3159 (2.65); 2.9149 (2.89); 2.9084 (6.35); 2.9018 (3.09); 2.6756 (0.55); 2.5771 (2.62); 2.5705 (2.80); 2.5605 (5.58); 2.5538 (5.57); 2.5438 (3.33); 2.5371 (3.44); 2.5112 (71.28); 2.5068 (94.61); 2.5024 (68.57); 2.3336 (0.58); 1.9937 (16.00); 1.2371 (0.41); 1.1971 (4.22); 1.1793 (8.32); 1.1615 (4.08); 1.0499 (0.39); 1.0347 (0.37)

Example V-2, Solvent: DMSO, Spectrometer: 400.13 MHz 9.5491 (15.10); 7.9561 (0.37); 7.5986 (4.12); 7.5934 (5.07); 7.5850 (5.16); 7.5742 (5.35); 7.4520 (0.37); 7.4455 (0.39); 7.4084 (10.73); 7.4033 (9.94); 7.3951 (6.17); 7.3911 (5.82); 7.3811 (1.82); 7.3677 (0.64); 6.9462 (8.98); 6.8974 (0.61); 6.5207 (7.46); 6.3354 (0.34); 5.8870 (8.21); 4.9797 (13.41); 4.9560 (0.57); 4.3672 (0.76); 4.3569 (0.84); 4.0593 (1.18); 4.0415 (3.66); 4.0237 (3.70); 4.0060 (1.27); 3.4971 (0.62); 3.3982 (1.44); 3.3500 (796.75); 3.3269 (13.02); 3.2172 (0.45); 2.8944 (2.41); 2.7352 (1.99); 2.6757 (0.62); 2.6716 (0.47); 2.5153 (42.64); 2.5110 (85.51); 2.5066 (115.29); 2.5022 (85.59); 2.4981 (44.52); 2.3379 (0.69); 2.3333 (0.85); 2.3289 (0.70); 1.9932 (16.00); 1.9289 (0.36); 1.1962 (4.25); 1.1784 (8.48); 1.1606 (4.28); 1.0489 (5.22); 1.0336 (5.22); 1.0068 (0.37); 0.9911 (0.33)

NMR Peak List Table 2

Example V-3, Solvent: DMSO, Spectrometer: 400.13 MHz 9.5835 (13.01); 8.3625 (0.37); 7.5882 (4.44); 7.5838 (5.66); 7.5713 (5.26); 7.5643 (6.24); 7.5507 (0.81); 7.4450 (1.04); 7.4381 (0.87); 7.4292 (0.89); 7.4020 (11.27); 7.3979 (10.91); 7.3843 (6.11); 7.3723 (1.96); 7.3655 (3.78); 7.3462 (4.70); 7.3268 (2.98); 6.5792 (4.56); 6.5611 (4.32); 6.3511 (4.77); 6.3307 (4.59); 6.0162 (8.57); 5.9407 (9.28); 5.0551 (15.24); 5.0194 (1.15); 4.0601 (1.27); 4.0423 (3.80); 4.0245 (3.84); 4.0068 (1.30); 3.3355 (29.82); 3.3117 (0.86); 2.6758 (0.36); 2.5103 (49.80); 2.5063 (63.64); 2.5024 (48.40); 2.3328 (0.40); 1.9941 (16.00); 1.4690 (1.60); 1.3672 (5.00); 1.3289 (0.43); 1.2469 (0.33); 1.2313 (0.41); 1.2153 (0.37); 1.1969 (4.20); 1.1791 (8.28); 1.1613 (4.14); 1.0497 (0.33); 1.0344 (0.36)

Example V-5, Solvent: DMSO, Spectrometer: 400.13 MHz 10.3501 (0.70); 10.0193 (2.28); 9.7981 (0.35); 9.7886 (0.39); 9.7751 (0.99); 7.7649 (0.78); 7.7561 (0.33); 7.7477 (1.00); 7.7414 (1.08); 7.7382 (1.21); 7.7232 (0.39); 7.7205 (0.46); 7.7172 (0.50); 7.4206 (0.38); 7.3712 (0.48); 7.3671 (0.46); 7.2552 (0.33); 7.2127 (0.96); 7.1934 (1.14); 7.1754 (0.35); 7.1727 (0.37); 7.1676 (0.35); 7.1176 (0.58); 7.1143 (0.59); 7.1004 (0.54); 7.0972 (0.53); 6.0190 (1.16); 5.4960 (0.40); 5.1917 (2.45); 5.1726 (0.78); 5.1364 (0.73); 4.3783 (0.63); 4.3679 (0.65); 3.4137 (1.17); 3.3637 (98.84); 3.3138 (0.97); 2.5167 (5.13); 2.5123 (10.50); 2.5078 (14.14); 2.5033 (10.05); 2.4989 (4.67); 1.4718 (16.00); 1.4676 (7.25); 1.4586 (5.96); 1.3449 (0.38); 1.0499 (4.29); 1.0346 (4.22)

Example V-6, Solvent: DMSO, Spectrometer: 400.13 MHz 9.6370 (0.70); 7.4196 (0.51); 7.4009 (0.49); 7.3688 (0.34); 7.2198 (0.33); 7.1966 (0.34); 7.1549 (0.44); 7.1048 (0.32); 6.6322 (0.45); 6.4048 (0.44); 6.3849 (0.41); 6.0589 (0.67); 6.0014 (0.88); 5.9870 (0.56); 5.1080 (0.97); 5.0737 (0.76); 3.8140 (1.62); 3.8037 (2.10); 3.4077 (16.00); 2.5607 (6.25); 2.0479 (1.01); 1.4147 (3.15); 1.2322 (0.54)

Example V-7, Solvent: DMSO, Spectrometer: 400.13 MHz 9.5760 (6.62); 8.3420 (0.76); 7.3883 (5.91); 7.3676 (4.96); 7.3485 (3.46); 7.3294 (2.43); 7.2979 (1.40); 7.2790 (3.12); 7.2604 (2.23); 7.2335 (2.92); 7.2149 (1.47); 6.6030 (0.53); 6.5779 (2.96); 6.5597 (2.73); 6.3537 (3.14); 6.3332 (3.03); 6.0066 (6.27); 5.9484 (6.83); 5.0527 (9.42); 5.0163 (2.00); 4.3786 (1.17); 4.3685 (1.22); 3.7863 (0.42); 3.7747 (0.41); 3.3618 (126.69); 2.5107 (33.34); 2.3242 (4.01); 2.3099 (16.00); 1.9974 (0.53); 1.3672 (8.64); 1.3273 (0.79); 1.0530 (6.86); 1.0378 (6.86)

Example V-8, Solvent: DMSO, Spectrometer: 400.13 MHz 9.8779 (0.56); 9.7865 (1.21); 9.6621 (0.57); 9.6336 (3.02); 7.7446 (0.65); 7.7337 (0.90); 7.7236 (0.59); 7.7166 (1.41); 7.7111 (1.06); 7.7047 (0.50); 7.6478 (0.53); 7.6268 (1.05); 7.6215 (0.35); 7.6129 (0.85); 7.6043 (0.88); 7.5961 (0.37); 7.5905 (0.80); 7.2696 (0.82); 7.2473 (1.52); 7.2251 (0.76); 7.1220 (0.58); 7.1180 (0.93); 7.1054 (0.53); 7.1013 (0.69); 6.0218 (1.41); 5.7691 (0.46); 5.3607 (0.38); 5.3461 (0.87); 5.3315 (0.40); 5.1883 (2.33); 4.4588 (0.94); 4.4442 (0.92); 3.3459 (5.83); 2.5274 (0.35); 2.5186 (5.01); 2.5143 (10.54); 2.5098 (14.40); 2.5053 (10.39); 2.5009 (4.90); 1.9970 (0.49); 1.4936 (3.04); 1.4707 (16.00); 1.4614 (12.40); 1.3492 (0.46)

Example V-9, Solvent: DMSO, Spectrometer: 400.13 MHz 11.6706 (0.57); 9.6437 (11.07); 9.6111 (0.83); 9.5063 (0.63); 8.4196 (0.59); 7.7923 (0.46); 7.7813 (0.37); 7.6999 (0.55); 7.6809 (0.65); 7.6363 (6.50); 7.6236 (6.88); 7.6173 (6.99); 7.5953 (1.26); 7.4949 (1.76); 7.4818 (2.21); 7.4494 (13.30); 7.4362 (7.91); 7.4173 (4.66); 7.3978 (5.09); 7.3783 (2.83); 6.6564 (0.54); 6.6317 (4.88); 6.6136 (4.56); 6.4035 (5.20); 6.3830 (5.05); 6.3504 (0.33); 6.3303 (0.35); 6.0740 (10.41); 5.9980 (11.15); 5.9375 (0.56); 5.8614 (0.66); 5.8221 (0.66); 5.1080 (16.00); 5.0728 (1.69); 4.3673 (0.40); 4.1097 (0.74); 4.0921 (2.21); 4.0743 (2.25); 4.0565 (0.76); 3.3989 (18.10); 2.5564 (28.20); 2.0442 (8.96); 1.5193 (0.74); 1.4187 (6.75); 1.4031 (1.13); 1.3796 (0.48); 1.2810 (0.33); 1.2463 (2.37); 1.2285 (4.62); 1.2108 (2.32); −0.0002 (0.88)

Example V-10, Solvent: DMSO, Spectrometer: 400.13 MHz 10.2843 (0.88); 10.2483 (5.58); 7.4351 (1.19); 7.4160 (2.67); 7.4015 (1.05); 7.3921 (1.16); 7.3889 (1.30); 7.3793 (1.59); 7.3704 (1.05); 7.3596 (1.06); 7.3517 (0.73); 7.3307 (1.08); 7.3211 (3.26); 7.3190 (2.88); 6.9883 (3.79); 6.9201 (0.65); 6.5519 (3.30); 6.4022 (0.49); 5.9548 (3.07); 5.4767 (0.50); 4.9653 (6.06); 4.9214 (0.91); 4.3712 (2.12); 4.3608 (2.23); 3.7995 (0.51); 3.7891 (0.53); 3.7843 (0.71); 3.7738 (0.69); 3.7691 (0.58); 3.7586 (0.53); 3.4075 (1.69); 3.3574 (108.93); 3.3075 (1.85); 2.8952 (0.74); 2.7366 (0.60); 2.5165 (8.02); 2.5124 (16.13); 2.5080 (21.76); 2.5036 (16.33); 2.4681 (0.61); 2.4630 (0.62); 2.4583 (0.61); 2.4540 (0.48); 1.9948 (1.32); 1.1979 (0.35); 1.1801 (0.69); 1.1623 (0.35); 1.0515 (15.90); 1.0362 (16.00); 1.0016 (0.39)

Example V-11, Solvent: DMSO, Spectrometer: 400.13 MHz 9.7597 (1.29); 9.5891 (2.61); 7.7312 (0.81); 7.7140 (1.69); 7.7093 (1.19); 7.6923 (0.33); 7.5921 (0.80); 7.5877 (1.04); 7.5796 (0.71); 7.5749 (0.94); 7.5681 (1.16); 7.4136 (0.58); 7.4068 (2.01); 7.4028 (1.90); 7.3955 (0.87); 7.3886 (1.12); 7.3807 (0.36); 7.3765 (0.36); 7.1311 (0.60); 7.1276 (0.63); 7.1145 (0.57); 7.1111 (0.59); 5.9845 (1.68); 5.1919 (2.69); 4.0430 (0.63); 4.0252 (0.64); 3.3402 (10.07); 2.5110 (2.83); 2.5067 (3.75); 2.5024 (2.84); 1.9938 (2.65); 1.4699 (16.00); 1.1970 (0.71); 1.1792 (1.39); 1.1614 (0.70); 1.0477 (1.52); 1.0326 (1.53)

Example V-12, Solvent: DMSO, Spectrometer: 400.13 MHz 9.7235 (1.91); 7.5204 (0.47); 7.5026 (0.54); 7.4753 (1.06); 7.4563 (0.44); 7.4266 (0.63); 7.4075 (0.95); 7.3883 (0.56); 7.3676 (0.70); 7.3429 (0.99); 7.3252 (0.62); 6.6247 (0.98); 6.6066 (0.84); 6.4128 (0.92); 6.3923 (0.89); 6.1293 (1.87); 6.0148 (2.03); 5.1290 (2.84); 5.0941 (0.50); 3.4120 (16.00); 2.5614 (6.29); 2.0478 (1.20); 1.4178 (1.98); 1.2497 (0.32); 1.2324 (0.62); 1.1034 (0.78); 1.0887 (0.78)

Example V-13, Solvent: DMSO, Spectrometer: 300.16 MHz 9.7890 (1.09); 9.5497 (0.53); 7.7369 (0.96); 7.7157 (2.18); 7.6911 (0.38); 7.5387 (1.69); 7.5096 (1.86); 7.1356 (0.79); 7.1181 (0.74); 6.9814 (1.86); 6.9522 (1.67); 5.9612 (2.01); 5.1652 (2.89); 3.7826 (6.20); 3.3647 (3.36); 2.5205 (2.59); 1.4805 (16.00); 1.0636 (0.71); 1.0434 (0.71)

Example V-15, Solvent: DMSO, Spectrometer: 300.16 MHz 9.5113 (5.70); 7.4915 (5.08); 7.4656 (6.21); 7.2124 (6.05); 7.1871 (5.11); 7.1412 (0.90); 6.9410 (8.68); 6.5056 (5.27); 5.8482 (7.91); 4.9567 (10.11); 4.8853 (0.43); 3.3439 (16.33); 2.5007 (4.74); 2.3105 (16.00); 1.0475 (0.84); 1.0272 (0.84)

NMR Peak List Table 2

Example V-16, Solvent: DMSO, Spectrometer: 400.13 MHz 10.6429 (0.37); 10.4140 (0.90); 10.1114 (2.88); 9.8002 (0.44); 9.7870 (1.15); 7.7905 (0.32); 7.7698 (0.84); 7.7522 (1.06); 7.7449 (0.92); 7.7419 (0.99); 7.7321 (0.33); 7.7240 (0.42); 7.7208 (0.38); 7.7149 (0.34); 7.4705 (0.44); 7.4655 (0.34); 7.4569 (0.34); 7.2216 (0.44); 7.2117 (0.90); 7.2034 (0.84); 7.1996 (0.71); 7.1929 (0.58); 7.1147 (0.70); 7.1117 (0.66); 7.0974 (0.62); 6.0780 (1.19); 5.5613 (0.42); 5.2094 (2.49); 5.1576 (0.79); 4.0425 (0.61); 4.0247 (0.62); 3.3406 (23.20); 2.8956 (0.34); 2.5577 (0.39); 2.5299 (0.75); 2.5165 (13.42); 2.5121 (27.31); 2.5076 (36.65); 2.5032 (26.10); 2.4989 (12.23); 2.4621 (0.34); 2.4575 (0.40); 1.9950 (2.71); 1.4723 (16.00); 1.4604 (7.39); 1.3451 (0.91); 1.3397 (0.46); 1.2392 (0.61); 1.1973 (0.75); 1.1795 (1.48); 1.1617 (0.74)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC. ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

The following table 3 illustrates in a non limiting manner examples of compounds of formula (VII) according to the invention.

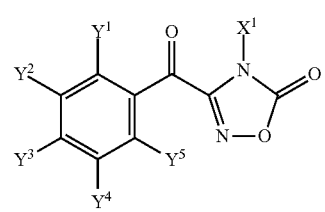

(VII)

TABLE 3

| Ex. | $Y^1$ | $Y^2$ | $Y^3$ | $Y^4$ | $Y^5$ | $X^1$ | LogP |
|---|---|---|---|---|---|---|---|
| VII-1 | H | H | H | H | H | Me | 3.21 [a] |

Measurement of log P values was performed according EEC directive 79/831 Annex V.A8 by HPLC (High Performance Liquid Chromatography) on reversed phase columns with the following methods:

[a]measurement of LC-MS was done at pH 2.7 with 0.1% formic acid in water and with acetonitrile (contains 0.1% formic acid) as eluent with a linear gradient from 10% acetonitrile to 95% acetonitrile.

Calibration was done with not branched alkan2-ones (with 3 to 16 carbon atoms) with known log P-values (measurement of log P values using retention times with linear interpolation between successive alkanones). lambda-maX-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the –value in ppm and the signal intensity in round brackets. Between the –value-signal intensity pairs are semicolons as delimiters.

The peak list of an example has therefore the form:

$\delta_1$ (intensity$_1$); $\delta_2$ (intensity$_2$); ... ; $\delta_i$ (intensity$_i$); ... ; $\delta_n$ (intensity$_n$)

NMR Peak List Table 3

Example V11-1, Solvent: DMSO, Spectrometer: 499.93 MHz 8.1468 (2.84); 8.1323 (3.08); 8.1301 (2.62); 7.8209 (0.72); 7.8061 (1.66); 7.7912 (1.01); 7.6541 (2.15); 7.6385 (3.33); 7.6228 (1.70); 3.3813 (16.00); 3.3525 (3.79); 2.5148 (0.84); 2.5115 (1.10); 2.5082 (0.84))

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC. ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

EXAMPLE A

*Phytophthora* Test (Tomato)/Preventive

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Phytophthora infestans*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Ex_no. | Eff. % |
|---|---|
| 2 | 100 |
| 3 | 98 |
| 5 | 95 |
| 6 | 98 |
| 7 | 95 |
| 8 | 98 |
| 9 | 95 |
| 10 | 95 |
| 11 | 100 |
| 12 | 95 |
| 13 | 95 |
| 14 | 95 |
| 15 | 98 |
| 16 | 98 |
| 17 | 98 |
| 18 | 95 |
| 19 | 95 |
| 20 | 95 |
| 21 | 97 |
| 26 | 93 |
| 58 | 80 |
| 70 | 84 |
| 74 | 95 |
| 86 | 90 |
| 104 | 93 |
| 111 | 95 |
| 136 | 95 |
| 148 | 97 |
| 154 | 95 |
| 163 | 95 |
| 168 | 92 |
| 198 | 95 |
| 199 | 97 |
| 226 | 92 |
| 282 | 92 |
| 322 | 75 |
| 342 | 92 |
| 347 | 92 |
| 405 | 95 |

EXAMPLE B

*Plasmopara* Test (Grapevines)/Preventive

Solvent: 24.5 parts by weight of acetone 24.5 parts by weight of dimethylacetamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the untreated control, while an efficacy of 100% means that no disease is observed.

In this test the following compounds according to the invention showed efficacy of 70% or even higher at a concentration of 10 ppm of active ingredient.

TABLE

Plasmopara test (grapevines)/preventive

| Ex_no. | Eff. % |
|---|---|
| 2 | 97 |
| 3 | 100 |
| 5 | 88 |
| 6 | 100 |
| 7 | 96 |
| 8 | 99 |
| 9 | 94 |
| 10 | 96 |
| 11 | 98 |
| 12 | 94 |
| 13 | 93 |
| 14 | 96 |
| 15 | 97 |
| 16 | 94 |
| 17 | 94 |
| 18 | 100 |
| 19 | 97 |
| 20 | 94 |
| 21 | 100 |
| 37 | 80 |
| 39 | 97 |
| 44 | 98 |
| 50 | 95 |
| 51 | 91 |
| 54 | 93 |
| 59 | 98 |
| 68 | 90 |
| 74 | 94 |
| 80 | 98 |
| 85 | 73 |
| 92 | 93 |
| 95 | 100 |
| 100 | 74 |
| 102 | 91 |
| 104 | 100 |
| 111 | 100 |
| 116 | 93 |
| 120 | 84 |
| 136 | 75 |
| 140 | 85 |
| 148 | 100 |
| 152 | 70 |
| 163 | 96 |
| 166 | 95 |
| 167 | 86 |
| 168 | 100 |
| 173 | 86 |
| 180 | 95 |
| 195 | 95 |
| 198 | 100 |
| 199 | 100 |
| 206 | 81 |
| 208 | 91 |
| 226 | 100 |
| 228 | 93 |
| 233 | 78 |
| 240 | 80 |
| 244 | 86 |
| 245 | 93 |
| 248 | 85 |
| 281 | 97 |
| 282 | 96 |
| 284 | 79 |
| 291 | 77 |
| 292 | 90 |
| 295 | 89 |
| 296 | 74 |
| 302 | 92 |
| 307 | 98 |
| 312 | 95 |
| 316 | 84 |
| 317 | 91 |
| 318 | 93 |
| 321 | 82 |
| 325 | 84 |
| 327 | 95 |
| 336 | 91 |
| 340 | 79 |
| 342 | 100 |
| 343 | 95 |
| 344 | 93 |
| 347 | 100 |
| 352 | 79 |
| 355 | 75 |
| 364 | 100 |
| 365 | 98 |
| 376 | 93 |
| 378 | 95 |
| 380 | 95 |
| 389 | 100 |
| 395 | 93 |
| 401 | 90 |
| 404 | 87 |
| 405 | 85 |
| 406 | 79 |

EXAMPLE C

Pythium Test (Cucumber)/Seed Treatment

The test is performed under greenhouse conditions.

Cucumber seeds, treated with the active compound or compound combinations, solved in N-methyl-2-pyrrolidon and diluted with water to the desired dosages, were sown in 6*6 cm pots containing 4 cm of a 1:1 mix of steamed field soil and sand.

Perlite was incubated with mycelium fragments of Pythium aphanidermatum. 5 ml of infected perlite was scattered between the treated cotton seeds. Seeds were then covered by the 1:1 mix of steamed field soil and sand. Pots were incubated in the greenhouse 7 days at 24° C. and 80% relative humidity. Assessment consisted of counting of emerged seedlings. 0% means an efficacy which corresponds to that of the control, while an efficacy of 100% means that all seedlings have emerged.

In this test the following compounds according to the invention showed an efficacy of 70% or even higher at a dosage of 10 g/dt seed of active ingredient.

| Ex_no. | Eff. % |
|---|---|
| 2 | 98 |
| 3 | 95 |
| 15 | 98 |
| 168 | 92 |
| 199 | 99 |
| 226 | 99 |
| 282 | 100 |
| 342 | 100 |

EXAMPLE D

Pythium Test (Cotton)/Seed Treatment

The test is performed under greenhouse conditions.

Cotton seeds, treated with the active compound or compound combinations, solved in N-methyl-2-pyrrolidon and diluted with water to the desired dosages, were sown in 6*6 cm pots containing 4 cm of a 1:1 mix of steamed field soil and sand.

Perlite was incubated with mycelium fragments of *Pythium ultimum*. 1 ml of infected perlite was scattered between the treated cotton seeds. Seeds were then covered by light expanded clay aggregate. Pots were incubated in the greenhouse 7 days at 20° C. and 80% relative humidity.

Assessment consisted of counting of emerged seedlings. 0% means an efficacy which corresponds to that of the control, while an efficacy of 100% means that all seedlings have emerged.

In this test the following compounds according to the invention showed an efficacy of 70% or even higher at a dosage of 10 g/dt seed of active ingredient.

| Ex_no. | Eff. % |
|---|---|
| 2 | 89 |
| 3 | 93 |
| 15 | 96 |
| 92 | 100 |
| 168 | 70 |
| 199 | 96 |
| 226 | 93 |
| 342 | 100 |

EXAMPLE E

*Pythium* Test (Corn)/Seed Treatment

The test is performed under greenhouse conditions.

Corn seeds, treated with the active compound or compound combinations, solved in N-methyl-2-pyrrolidon and diluted with water to the desired dosages, were sown in 6*6 cm pots containing 4 cm of a 1:1 mix of steamed field soil and sand.

Perlite was incubated with mycelium fragments of *Pythium irregulare*. 5 ml of infected perlite was scattered between the treated cotton seeds. Seeds were than covered by the 1:1 mix of steamed field soil and sand. Pots were incubated in the greenhouse 7 days at 10° C. and 80% relative humidity and then 14 days at 20° C. and 80% relative humidity.

Assessment consisted of counting of emerged seedlings. 0% means an efficacy which corresponds to that of the control, while an efficacy of 100% means that all seedlings have emerged.

In this test the following compounds according to the invention showed an efficacy of 70% or even higher at a dosage of 10 g/dt seed of active ingredient.

| Ex_no. | Eff. % |
|---|---|
| 2 | 100 |
| 3 | 100 |
| 15 | 100 |
| 168 | 100 |
| 199 | 100 |
| 226 | 90 |
| 282 | 90 |
| 342 | 100 |

EXAMPLE F

In Vivo Test on *Phytophthora Infestans* (Tomato Late Blight)

The active ingredients tested are prepared by homogenization in a mixture of acetone/Tween/DMSO, then diluted with water to obtain the desired active material concentration.

Tomato plants (Rentita variety) sown in started cups on a 50/50 peat soil-pozzolana substrate and grown at 20-25° C., are treated at stage Z12 by spraying with the aqueous suspension described above.

Plants, used as controls, are treated with an aqueous solution not containing the active material. After 24 hours, the plants are contaminated by spraying them with an aqueous suspension of *Phytophthora infestans* spores (20.000 spores per ml). The spores are collected from infected plants. The contaminated tomato plants are incubated for 5 days at 20° C., under a humid atmosphere. Grading is carried out 5 days after the contamination, in comparison with the control plants.

Under these conditions, good protection (at least 70%) is observed at a dose of 500 ppm with the following compounds:

| Ex_no. | Eff. % |
|---|---|
| 8 | 100 |
| 15 | 99 |
| 27 | 100 |
| 29 | 100 |
| 30 | 100 |
| 32 | 100 |
| 33 | 100 |
| 34 | 99 |
| 36 | 85 |
| 37 | 100 |
| 39 | 100 |
| 40 | 100 |
| 42 | 92 |
| 43 | 100 |
| 44 | 100 |
| 47 | 100 |
| 48 | 98 |
| 50 | 94 |
| 52 | 100 |
| 53 | 73 |
| 54 | 100 |
| 55 | 100 |
| 56 | 100 |
| 57 | 85 |
| 59 | 100 |
| 61 | 100 |
| 62 | 99 |
| 63 | 100 |
| 67 | 89 |
| 68 | 100 |
| 71 | 99 |
| 72 | 97 |
| 73 | 100 |
| 75 | 90 |
| 77 | 100 |
| 78 | 100 |
| 79 | 88 |
| 80 | 98 |
| 81 | 78 |
| 82 | 99 |
| 83 | 100 |
| 84 | 100 |
| 85 | 99 |
| 87 | 95 |
| 88 | 98 |
| 89 | 99 |
| 91 | 85 |
| 92 | 100 |
| 93 | 99 |
| 95 | 100 |
| 98 | 99 |
| 99 | 99 |
| 101 | 97 |
| 102 | 100 |
| 103 | 80 |
| 106 | 75 |
| 107 | 100 |
| 108 | 100 |
| 109 | 93 |
| 110 | 98 |

-continued

| Ex_no. | Eff. % |
|---|---|
| 111 | 100 |
| 112 | 73 |
| 113 | 90 |
| 114 | 100 |
| 118 | 100 |
| 119 | 97 |
| 120 | 100 |
| 123 | 98 |
| 124 | 99 |
| 127 | 100 |
| 130 | 100 |
| 131 | 100 |
| 132 | 97 |
| 133 | 88 |
| 134 | 99 |
| 137 | 98 |
| 138 | 97 |
| 139 | 100 |
| 140 | 100 |
| 142 | 100 |
| 143 | 75 |
| 144 | 95 |
| 145 | 83 |
| 146 | 93 |
| 147 | 100 |
| 148 | 100 |
| 151 | 85 |
| 152 | 95 |
| 153 | 100 |
| 155 | 92 |
| 158 | 85 |
| 161 | 92 |
| 165 | 70 |
| 166 | 99 |
| 167 | 98 |
| 168 | 99 |
| 170 | 100 |
| 171 | 100 |
| 172 | 100 |
| 173 | 100 |
| 175 | 93 |
| 176 | 100 |
| 177 | 100 |
| 178 | 99 |
| 180 | 98 |
| 182 | 100 |
| 184 | 99 |
| 185 | 83 |
| 186 | 83 |
| 187 | 80 |
| 188 | 99 |
| 190 | 100 |
| 191 | 95 |
| 192 | 100 |
| 197 | 100 |
| 200 | 98 |
| 201 | 100 |
| 202 | 98 |
| 206 | 100 |
| 207 | 100 |
| 208 | 100 |
| 209 | 84 |
| 210 | 75 |
| 211 | 91 |
| 212 | 73 |
| 215 | 98 |
| 216 | 95 |
| 218 | 80 |
| 219 | 85 |
| 221 | 100 |
| 224 | 93 |
| 225 | 99 |
| 226 | 100 |
| 227 | 100 |
| 228 | 100 |
| 229 | 100 |
| 230 | 95 |

-continued

| Ex_no. | Eff. % |
|---|---|
| 232 | 100 |
| 233 | 99 |
| 235 | 100 |
| 236 | 100 |
| 237 | 97 |
| 239 | 84 |
| 240 | 100 |
| 243 | 99 |
| 244 | 99 |
| 246 | 100 |
| 247 | 99 |
| 248 | 100 |
| 250 | 80 |
| 251 | 98 |
| 255 | 98 |
| 256 | 100 |
| 257 | 100 |
| 258 | 89 |
| 261 | 100 |
| 262 | 78 |
| 263 | 78 |
| 264 | 94 |
| 265 | 93 |
| 266 | 100 |
| 267 | 97 |
| 268 | 100 |
| 270 | 100 |
| 271 | 80 |
| 272 | 88 |
| 276 | 98 |
| 278 | 100 |
| 280 | 100 |
| 281 | 97 |
| 282 | 98 |
| 284 | 95 |
| 285 | 88 |
| 286 | 97 |
| 288 | 97 |
| 289 | 98 |
| 290 | 75 |
| 291 | 100 |
| 292 | 99 |
| 295 | 97 |
| 297 | 95 |
| 300 | 100 |
| 301 | 100 |
| 302 | 100 |
| 303 | 98 |
| 304 | 83 |
| 306 | 100 |
| 308 | 89 |
| 309 | 100 |
| 310 | 70 |
| 312 | 94 |
| 313 | 100 |
| 317 | 98 |
| 318 | 99 |
| 321 | 97 |
| 323 | 100 |
| 324 | 94 |
| 325 | 99 |
| 327 | 100 |
| 328 | 75 |
| 329 | 93 |
| 331 | 98 |
| 332 | 85 |
| 335 | 99 |
| 336 | 99 |
| 337 | 99 |
| 340 | 100 |
| 341 | 100 |
| 342 | 99 |
| 343 | 100 |
| 344 | 100 |
| 345 | 99 |
| 346 | 97 |
| 347 | 100 |

-continued

| Ex_no. | Eff. % |
|---|---|
| 348 | 100 |
| 350 | 98 |
| 351 | 93 |
| 352 | 100 |
| 355 | 100 |
| 357 | 92 |
| 358 | 100 |
| 361 | 90 |
| 362 | 71 |
| 363 | 99 |
| 364 | 98 |
| 365 | 100 |
| 366 | 94 |
| 367 | 100 |
| 369 | 70 |
| 372 | 100 |
| 373 | 97 |
| 374 | 100 |
| 375 | 97 |
| 376 | 100 |
| 377 | 99 |
| 378 | 100 |
| 379 | 100 |
| 380 | 93 |
| 381 | 75 |
| 383 | 70 |
| 384 | 100 |
| 386 | 80 |
| 387 | 100 |
| 388 | 100 |
| 389 | 99 |
| 390 | 100 |
| 394 | 90 |
| 395 | 99 |
| 396 | 73 |
| 400 | 100 |
| 401 | 99 |
| 403 | 100 |
| 404 | 98 |
| 406 | 94 |
| 407 | 95 |

EXAMPLE G

In Vivo Test on *Botrytis Cinerea* (Grey Mould)

The active ingredients tested are prepared by homogenization in a mixture of acetone/Tween/DMSO, then diluted with water to obtain the desired active material Gherkin plants (Vert petit de Paris variety), sown on a 50/50 peat soil-pozzolana substrate in starter cups and grown at 18-20° C., are treated at the cotyledon Z11 stage by spraying with the active ingredient prepared as described above.

Plants, used as controls, are treated with an aqueous solution not containing the active material. After 24 hours, the plants are contaminated by spraying them with an aqueous suspension of cryopreserved *Botrytis cinerea* spores (50.000 spores per ml) on upper surface of the leaves. The spores are suspended in a nutrient solution composed of:
  10 g/L of PDB;
  50 g/L of D-fructose;
  2 g/L of $NH_4NO_3$;
  1 g/L of $KH_2PO_4$.

The contaminated cucumber plants are settled for 4/5 days in a climatic room at 17° C. (day/night) and at 80% relative humidity.

Grading is carried out 4/5 days after the contamination, in comparison with the control plants.

Under these conditions, good (at least 70%) or total protection is observed at a dose of 500 ppm with the following compounds:

| Ex_no. | Eff. % |
|---|---|
| 35 | 71 |
| 36 | 86 |
| 67 | 80 |
| 83 | 73 |
| 180 | 83 |
| 211 | 84 |
| 278 | 78 |
| 332 | 71 |
| 354 | 71 |
| 373 | 85 |

EXAMPLE H

In Vivo Test on *Sphaerotheca fuliginea* (Cucurbits Powdery Mildew)

The active ingredients tested are prepared by homogenization in a mixture of acetone/tween/DMSO, then diluted with water to obtain the desired active material.

Gherkin plants (Vert petit de Paris variety) in starter cups, sown on a 50/50 peat soil-pozzolana substrate and grown at 20° C./23° C., are treated at the cotyledon Z10 stage by spraying with the aqueous suspension described above. Plants, used as controls, are treated with an aqueous solution not containing the active material.

After 24 hours, the plants are contaminated by spraying them with an aqueous suspension of *Sphaerotheca fuliginea* spores (100.000 spores per ml). The spores are collected from a contaminated plants. The contaminated gherkin plants are incubated at about 20° C./25° C. and at 60/70% relative humidity.

Grading (% of efficacy) is carried out 12 days after the contamination, in comparison with the control plants.

Under these conditions, good (at least 70%) or total protection is observed at a dose of 500 ppm with the following compounds:

| Ex_no. | Eff. % |
|---|---|
| 83 | 85 |
| 124 | 80 |
| 190 | 98 |
| 197 | 80 |
| 209 | 75 |
| 211 | 72 |
| 212 | 100 |

EXAMPLE I

In Vivo Test on *Uromyces Appendiculatus* (Brown Rust of Bean)

The active ingredients tested are prepared by homogenization in a mixture of acetone/tween/DMSO, then diluted with water to obtain the desired active material.

Wheat plants (Saxa variety) sown on 50/50 peat soil-pozzolana substrate in starter cups and grown at 24° C., are treated at the 2-leaf stage (9 cm tall) by spraying with the aqueous suspension described above.

Plants, used as controls, are treated with an aqueous solution not containing the active material.

After 24 hours, the plants are contaminated by spraying the leaves with an aqueous suspension of *Uromyces appendiculatus* spores (150.000 spores per ml). The spores are collected from a 10-day-old contaminated wheat and are suspended in water containing 2.5 ml/l of tween 80 10%. The contaminated wheat plants are incubated for 24 hours at 20° C. and at 100% relative humidity, and then for 10 days at 20° C. and at 70% relative humidity. Grading is carried out 10 days after the contamination, in comparison with the control plants.

Under these conditions, good (at least 70%) or total protection is observed at a dose of 500 ppm with the following compounds:

| Ex_no. | Eff. % |
|---|---|
| 39 | 81 |
| 43 | 75 |
| 62 | 71 |
| 83 | 75 |
| 99 | 71 |
| 111 | 72 |
| 113 | 79 |
| 140 | 73 |
| 171 | 82 |
| 185 | 75 |
| 190 | 83 |
| 197 | 89 |
| 206 | 91 |
| 212 | 100 |
| 216 | 71 |
| 228 | 70 |
| 258 | 93 |
| 276 | 89 |
| 280 | 83 |
| 295 | 70 |
| 400 | 94 |
| 406 | 79 |

EXAMPLE K

In Vivo Test on *Pyrenophora Teres* (Barley Net Blotch)

The active ingredients tested are prepared by homogenization in a mixture of acetone/Tween/DMSO, then diluted with water to obtain the desired active material concentration.

Barley plants (Plaisant variety), sown on a 50/50 peat soil-pozzolana substrate in starter cups and grown at 22° C. (12 h)/20° C. (12 h), are treated at the 1-leaf stage (10 cm tall) by spraying with the active ingredient prepared as described above.

Plants, used as controls, are treated with an aqueous solution not containing the active material.

After 24 hours, the plants are contaminated by spraying them with an aqueous suspension of *Pyrenophora teres* spores (12.000 spores per ml). The spores are collected from a 12-day-old culture.

The contaminated barley plants are incubated for 24 hours at about 20° C. and at 100% relative humidity, and then for 12 days at 80% relative humidity.

Grading is carried out 12 days after the contamination, in comparison with the control plants.

Under these conditions, good (at least 70%) is observed at a dose of 500 ppm with the following compounds:

| Ex_no. | Eff. % |
|---|---|
| 35 | 100 |
| 36 | 71 |
| 53 | 70 |
| 71 | 70 |
| 84 | 70 |
| 117 | 79 |
| 212 | 97 |
| 250 | 79 |
| 255 | 70 |
| 256 | 90 |
| 268 | 96 |
| 379 | 100 |

EXAMPLE I

In Vivo Test on *Mycosphaerella graminicola* (Wheat Leaf Spot)

The active ingredients tested are prepared by homogenization in a mixture of acetone/tween/DMSO, then diluted with water to obtain the desired active material concentration.

Wheat plants (Scipion variety), sown on a 50/50 peat soil-pozzolana substrate in starter cups and grown at 22° C. (12 h)/20° C. (12 h), are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of cryopreserved *Mycosphaerella graminicola* spores (500.000 spores per ml). The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds:

| Ex_no. | Eff. % |
|---|---|
| 30 | 86 |
| 43 | 91 |
| 57 | 79 |
| 67 | 90 |
| 71 | 88 |
| 77 | 71 |
| 83 | 93 |
| 108 | 71 |
| 111 | 100 |
| 117 | 90 |
| 130 | 86 |
| 151 | 92 |
| 158 | 80 |
| 172 | 86 |
| 173 | 73 |
| 190 | 100 |
| 197 | 96 |
| 207 | 79 |
| 212 | 100 |
| 223 | 80 |
| 248 | 86 |
| 250 | 96 |
| 255 | 88 |
| 270 | 86 |
| 308 | 100 |
| 330 | 83 |
| 341 | 70 |
| 384 | 70 |
| 406 | 79 |

EXAMPLE M

In Vivo Test on *Puccinia Recondita* (Brown Rust)

The active ingredients tested are prepared by homogenization in a mixture of acetone/tween/DMSO, then diluted with water to obtain the desired active material.

Wheat plants (Scipion variety) sown on 50/50 peat soil-pozzolana substrate in starter cups and grown at 22° C. (12 h)/20° C. (12 h), are treated at the 1-leaf stage (10 cm tall) by spraying with the aqueous suspension described above.

Plants, used as controls, are treated with an aqueous solution not containing the active material. After 24 hours, the plants are contaminated by spraying the leaves with an aqueous suspension of *Puccinia recondite* spores (100.000 spores per ml). The spores are collected from a 10-day-old contaminated wheat and are suspended in water containing 2.5 ml/l of tween 80 10%. The contaminated wheat plants are incubated for 24 hours at 20° C. and at 100% relative humidity, and then for 10 days at 20° C. and at 70% relative humidity. Grading is carried out 10 days after the contamination, in comparison with the control plants.

Under these conditions, good (at least 70%) or total protection is observed at a dose of 500 ppm with the following compounds:

| Ex_no. | Eff. % |
| --- | --- |
| 36 | 75 |
| 39 | 98 |
| 43 | 94 |
| 63 | 75 |
| 67 | 98 |
| 73 | 81 |
| 83 | 89 |
| 88 | 78 |
| 120 | 98 |
| 131 | 81 |
| 140 | 86 |
| 172 | 89 |
| 173 | 89 |
| 185 | 78 |
| 190 | 94 |
| 191 | 89 |
| 197 | 94 |
| 209 | 88 |
| 211 | 71 |
| 212 | 89 |
| 215 | 81 |
| 228 | 81 |
| 233 | 98 |
| 258 | 81 |
| 280 | 98 |
| 292 | 75 |
| 308 | 94 |
| 317 | 81 |
| 324 | 75 |
| 325 | 75 |
| 351 | 75 |
| 384 | 79 |
| 395 | 72 |
| 406 | 81 |

EXAMPLE N

In Vivo Test on *Alternaria brassicae* (Leaf Spot of Crucifers)

The active ingredients tested are prepared by homogenization in a mixture of acetone/tween/DMSO, then diluted with water to obtain the desired active material.

Radish plants (Pernot variety), sown on a 50/50 peat soil-pozzolana substrate in starter cups and grown at 18-20° C., are treated at the cotyledon stage by spraying with the active ingredient prepared as described above.

Plants, used as controls, are treated with the mixture of acetone/tween/water not containing the active material.

After 24 hours, the plants are contaminated by spraying them with an aqueous suspension of *Alternaria brassicae* spores (40,000 spores per $cm^3$). The spores are collected from a 12 to 13 days-old culture.

The contaminated radish plants are incubated for 6-7 days at about 18° C., under a humid atmosphere.

Grading is carried out 6 to 7 days after the contamination, in comparison with the control plants.

Under these conditions, good protection (at least 70%) is observed at a dose of 500 ppm with the following compounds:

| Ex_no. | Eff. % |
| --- | --- |
| 34 | 100 |
| 39 | 83 |
| 111 | 70 |
| 209 | 70 |
| 212 | 70 |
| 262 | 83 |
| 308 | 90 |
| 364 | 92 |

EXAMPLE O

In Vivo Test on *Pyricularia grisea* (Rice Blast)

The active ingredients tested are prepared by homogenization in a mixture of acetone/tween/DMSO, then diluted with water to obtain the desired active material concentration.

Rice plants (Koshihikari variety), sown on a 50/50 peat soil-pozzolana substrate in starter cups and grown at 25° C., are treated at the 2-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyricularia grisea* spores (40,000 spores per ml). The spores are collected from a 17-day-old culture and are suspended in water containing 2.5 g/l of gelatin. The contaminated Rice plants are incubated for 6 days at 25° C. and at 80% relative humidity.

Grading (% of efficacy) is carried out 6 days after the contamination, in comparison with the control plants.

Under these conditions, good (at least 70%) or total protection is observed at a dose of 500 ppm with the following compounds:

| Ex_no. | Eff. % |
| --- | --- |
| 42 | 71 |
| 95 | 70 |
| 109 | 70 |
| 167 | 96 |
| 171 | 80 |
| 227 | 96 |
| 265 | 70 |
| 306 | 90 |

Chemistry

The following examples illustrate in a non-limiting manner the preparation and efficacy of the compounds of formula (I) according to the invention.

PREPARATION EXAMPLE 1

3-[(Z)-{[(6-aminopyridin-2-yl)methoxy]imino}(phenyl)methyl]-4-methyl-1,2,4-oxadiazol-5(4H)-one (compound 1) according to process P1

Step 1

To a solution of (2Z)-(hydroxyimino)(phenyl)acetonitrile (2.5 g, 17.10 mmol, 1 eq.) in 100 ml of acetonitrile and 10 ml DMF was added tert-butyl [6-(chloromethyl)pyridin-2-yl]carbamate (4.15 g, 17.10 mmol, 1 eq.) followed by potassium iodide (283 mg, 1.71 mmol, 0.1 eq.) and caesium carbonate (8.36 g, 25.65 mmol, 1.5 eq.). The reaction was stirred overnight at room temperature. The solvent was than evaporated and the residue dissolved in EtOAc (100 ml). The organic layer was washed with $H_2O$ and dried over $MgSO_4$ then concentrated. tert-butyl {6-[({[(Z)-cyano(phenyl)methylene]amino}oxy)methyl]pyridin-2-yl}carbamate (5.39 g, 80% yield, only 1 oxime isomer) was obtained as a white solid.

Step 2

To a solution of tert-butyl {6-[({[(Z)-cyano(phenyl)methylene]amino}oxy)methyl]pyridin-2-yl}carbamate (5.4 g, 15.32 mmol, 1 eq.) in DCM (200 ml) was added TFA (17.47 g, 153 mmol, 10 eq.). The solution was refluxed for 12 h. The reaction was quenched by addition of aq. sat. $NaHCO_3$ and extracted with EtOAc (3×50 ml). The organics were combined, dried over $MgSO_4$ and concentrated to give (2Z)-{[(6-aminopyridin-2-yl)methoxy]imino}(phenyl)acétonitrile (3.86 g, 89% yield).

Step 3: Preparation of (Z)-2-{[(6-aminopyridin-2-yl)methoxy]imino}-N'-hydroxy-2-phenylethanimidamide (compound V-3) according to process P1

To a suspension of (2Z)-{[(6-aminopyridin-2-yl)methoxy]imino}(phenyl)acétonitrile (4 g, 15.85 mmol, 1 eq.) in iPrOH/$H_2O$ (10/1, 110 ml) were added hydroxylamine hydrochloride (3.30 g, 47.56 mmol, 3 eq.) and potassium carbonate (6.57 g, 47.56 mmol, 3 eq.). The reaction was heated to 80° C. for 6 h and the solvent was evaporated to ¾$^{th}$. The residue was extracted with EtOAc (3×50 ml) and washed with aq. sat. NaCl. The organics were combined, dried over $MgSO_4$ and concentrated to give (Z)-2-{[(6-aminopyridin-2-yl)methoxy]imino}-N'-hydroxy-2-phenylethanimidamide (5 g, 99% yield) as a white solid.

Step 4: Preparation of 3-[(Z)-{[(6-aminopyridin-2-yl)methoxy]imino}(phenyl)methyl]-1,2,4-oxadiazol-5(4H)-one (compound 23) according to process P1

To a solution of (1Z,2Z)-2-{[(6-aminopyridin-2-yl)methoxy]imino}-V-hydroxy-2-phenylethanimidamide (3 g, 10.51 mmol, 1 eq.) in DMF (50 ml) was added CDI (1.70 g, 10.51 mmol, 1 eq.) and stirring at room temperature was allowed for 30 min before heated to 80° C. for 6 h. The reaction was quenched by addition of water and extracted with EtOAc (3×50 ml). The organics were combined, washed with aq. sat. NaCl, dried over $MgSO_4$ and concentrated. The residue was triturated in MeCN and a white solid was isolated by filtration giving a first crop of 3-[(Z)-{[(6-aminopyridin-2-yl)methoxy]imino}(phenyl)methyl]-1,2,4-oxadiazol-5(4H)-one (1.36 g, 36% yield). The mother liquor was concentrated and purified by chromatography on silica gel to give a second crop (2.9 g, 50% purity, 40% yield).

Step 5: Preparation of 3-[(Z)-{[(6-aminopyridin-2-yl)methoxy]imino}(phenyl)methyl]-4-methyl-1,2,4-oxadiazol-5(4H)-one (compound I) according to process P1

To a solution of 3-[(Z)-{[(6-aminopyridin-2-yl)methoxy]imino}(phenyl)methyl]-1,2,4-oxadiazol-5(4H)-one (1 g, 3.21 mmol, 1 eq.) in MeCN (50 ml) and DMF (10 ml) was added potassium carbonate (532 mg, 3.85 mmol, 1.2 eq.) followed by iodomethane (547 mg, 3.85 mmol, 1.2 eq.). The reaction was stirred at room temperature overnight. The reaction was quenched by addition of water and extracted with EtOAc (3×50 ml). The organics were combined, washed with aq. sat. NaCl, dried over $MgSO_4$ and concentrated. The residue was purified by chromatography on silica gel to give 3-[(Z)-{[(6-aminopyridin-2-yl)methoxy]imino}(phenyl)methyl]-4-methyl-1,2,4-oxadiazol-5(4H)-one (906 mg, 85% yield) has a white solid.

PREPARATION EXAMPLE 2 butyl {6-[({[(Z)-(4-methyl-5-oxo-4,5-dihydro-1,2,4-oxadiazol-3-yl)(phenyl)methylene]amino}oxy)methyl]pyridin-2-yl}carbamate (compound 18) according to process P2

To a solution of 3-[(Z)-{[(6-aminopyridin-2-yl)methoxy]imino}(phenyl)methyl]-4-methyl-1,2,4-oxadiazol-5(4H)-one (60 mg, 0.184 mmol, 1 eq.) in pyridine (2 ml) was added butylcarbamoyl chloride (50.3 mg, 0.369 mmol, 2 eq.) and stirring was allowed overnight. The reaction was quenched by addition of water and concentrated to dryness. The residue was taken in EtOAc and 0.5 ml of 1N NaOH was added. The solution was filtered through a chemelut pad and washed with EtOAc. After concentration, the residue was purified by chromatography on silica gel to give butyl {6-[({[(Z)-(4-methyl-5-oxo-4,5-dihydro-1,2,4-oxadiazol-3-yl)(phenyl)methylene]amino}oxy)methyl]pyridin-2-yl}carbamate (60 mg, 75% yield).

PREPARATION EXAMPLE 3

3-[(Z)-{[(6-aminopyridin-2-yl)methoxy]imino}(phenyl)methyl]-4-methyl-1,2,4-oxadiazol-5(4H)-one (compound I) and 3-[(E)-{[(6-aminopyridin-2-yl)methoxy]imino}(phenyl)methyl]-4-methyl-1,2,4-oxadiazol-5(4H)-one (compound 25) according to process P5

Step 1: Preparation of 3-benzoyl-4-methyl-1,2,4-oxadiazol-5(4H)-one (compound VII-1) according to process P5

To a solution of 3-benzyl-4-methyl-1,2,4-oxadiazol-5(4H)-one (3.87 g, 20.34 mmol, 1 eq.) in acetic acid (120 ml) was added chromium(VI) oxide (6.10 g, 61.04 mmol, 3 eq.) and stirring was allowed overnight. The reaction was quenched by addition of water and extracted with $Et_2O$ (3×50 ml). The organics were combined, washed with aq. sat.

NaHCO₃, dried over MgSO₄ and concentrated to give 3-benzoyl-4-methyl-1,2,4-oxadiazol-5(4H)-one (3.85 g, 88% yield) as a white solid.

Step 2: Preparation of 3-[(Z)-{[(6-aminopyridin-2-yl)methoxy]imino}(phenyl)methyl]-4-methyl-1,2,4-oxadiazol-5(4H)-one (compound I) and 3-[(E)-{[(6-aminopyridin-2-yl)methoxy]imino}(phenyl)methyl]-4-methyl-1,2,4-oxadiazol-5(4H)-one (compound 25) according to process P5

In a microwave tube, to a solution of 3-benzoyl-4-methyl-1,2,4-oxadiazol-5(4H)-one (500 mg, 2.44 mmol, 1 eq.) in iPrOH (10 ml) were added 6-[(aminooxy)methyl]pyridin-2-amine (340 mg, 2.44 mmol, 1 eq.) followed by pTSA.H₂O (578 mg, 2.93 mmol, 1.2 eq.). The reaction was microwaved at 160° C. for 2 h then was quenched by addition of water and extracted with EtOAc (3×50 ml). The organics were combined, washed with aq. sat. NaHCO₃, dried over MgSO₄ and concentrated. The residue was purified by preparative HPLC to give 3-[(Z)-{[(6-aminopyridin-2-yl)methoxy]imino}(phenyl)methyl]-4-methyl-1,2,4-oxadiazol-5(4H)-one (200 mg, 25%) and 3-[(E)-{[(6-aminopyridin-2-yl)methoxy]imino}(phenyl)methyl]-4-methyl-1,2,4-oxadiazol-5(4H)-one (62 mg, 8%).

PREPARATION EXAMPLE 4

3-[(Z)-{[(2-amino-1,3-thiazol-4-yl)methoxy]imino}(phenyl)methyl]-1,2,4-oxadiazol-5(4H)-one (compound 4) according to process P1

Step 1

To a solution of (2Z)-(hydroxyimino)(phenyl)acetonitrile (2.5 g, 17.10 mmol, 1 eq.) in 100 ml of acetonitrile and 10 ml DMF was added 4-(chloromethyl)-1,3-thiazol-2-amine hydrochloride (3.79 g, 20.52 mmol, 1.2 eq.) followed by potassium iodide (283 mg, 1.71 mmol, 0.1 eq.) and caesium carbonate (13.37 g, 41.05 mmol, 2.4 eq.). The reaction was stirred overnight at room temperature. The solvent was then evaporated and the residue dissolved in EtOAc (100 ml). The organic layer was washed with H₂O and dried over MgSO₄ then concentrated. (2Z)-{[(2-amino-1,3-thiazol-4-yl)methoxy]imino}(phenyl)acetonitrile (4 g, 90% yield, only 1 oxime isomer) was obtained as a white solid.

Step 2: Preparation of (1Z,2Z)-2-{[(2-amino-1,3-thiazol-4-yl)methoxy]imino}-N'-hydroxy-2-phenylethanimidamide (compound V-2) according to process P1

To a suspension of (2Z)-{[(2-amino-1,3-thiazol-4-yl)methoxy]imino}(phenyl)acetonitrile (4.5 g, 17.42 mmol, 1 eq.) in iPrOH/H₂O (10/1, 110 ml) were added hydroxylamine hydrochloride (3.63 g, 52.26 mmol, 3 eq.) and potassium carbonate (7.22 g, 52.2 mmol, 3 eq.). The reaction was heated to 80° C. for 6 h and the solvent was evaporated to ¾ᵗʰ. The residue was extracted with EtOAc (3×50 ml) and washed with aq. sat. NaCl. The organics were combined, dried over MgSO₄ and concentrated to give (1Z,2Z)-2-{[(2-amino-1,3-thiazol-4-yl)methoxy]imino}-N'-hydroxy-2-phenylethanimidamide (5.86 g) as a white solid.

Step 3: Preparation of 3-[(Z)-{[(2-amino-1,3-thiazol-4-yl)methoxy]imino}(phenyl)methyl]-1,2,4-oxadiazol-5(4H)-one (compound 24) according to process P1

To a solution of (1Z,2Z)-2-{[(2-amino-1,3-thiazol-4-yl)methoxy]imino}-N'-hydroxy-2-phenylethanimidamide (3 g, 10.29 mmol, 1 eq.) in DMF (50 ml) was added CDI (1.66 g, 10.29 mmol, 1 eq.) and stirring at room temperature was allowed for 30 min before heated to 80° C. for 6 h. The reaction was quenched by addition of water and extracted with EtOAc (3×50 ml). The organics were combined, washed with aq. sat. NaCl, dried over MgSO₄ and concentrated. The residue was triturated in MeCN and a white solid was isolated by filtration giving 3-[(Z)-{[(2-amino-1,3-thiazol-4-yl)methoxy]imino}(phenyl)methyl]-1,2,4-oxadiazol-5(4H)-one (2.89 g, 50% purity, 43% yield).

Step 4: Preparation of 3-[(Z)-{[(2-amino-1,3-thiazol-4-yl)methoxy]imino}(phenyl)methyl]-1,2,4-oxadiazol-5(4H)-one (compound 4) according to process P1

To a solution of 3-[(Z)-{[(2-amino-1,3-thiazol-4-yl)methoxy]imino}(phenyl)methyl]-1,2,4-oxadiazol-5(4H)-one (2.89 g, 50% purity, 4.56 mmol, 1 eq.) in MeCN (50 ml) and DMF (10 ml) was added potassium carbonate (757 mg, 5.48 mmol, 1.2 eq.) followed by iodomethane (778 mg, 5.48 mmol, 1.2 eq.). The reaction was stirred at room temperature overnight. The reaction was quenched by addition of water and extracted with EtOAc (3×50 ml). The organics were combined, washed with aq. sat. NaCl, dried over MgSO₄ and concentrated. The residue was purified by chromatography on silica gel to give 3-[(Z)-{[(2-amino-1,3-thiazol-4-yl)methoxy]imino}(phenyl)methyl]-4-methyl-1,2,4-oxadiazol-5(4H)-one (930 mg, 61% yield) has a white solid.

PREPARATION EXAMPLE 5 butyl {4-[({[(Z)-(4-methyl-5-oxo-4,5-dihydro-1,2,4-oxadiazol-3-yl)(phenyl)methylene]amino}oxy)methyl]-1,3-thiazol-2-yl}carbamate (compound 14) according to process P2

To a solution of 3-[(Z)-{[(2-amino-1,3-thiazol-4-yl)methoxy]imino}(phenyl)methyl]-4-methyl-1,2,4-oxadiazol-5(4H)-one (60 mg, 0.181 mmol, 1 eq.) in pyridine (2 ml) was added butylcarbamoyl chloride (49.4 mg, 0.362 mmol, 2 eq.) and stirring was allowed overnight. The reaction was quenched by addition of water and concentrated to dryness. The residue was taken in EtOAc and 0.5 ml of 1N NaOH was added. The solution was filtered through a chemelut pad and washed with EtOAc. After concentration, the residue was purified by chromatography on silica gel to give butyl {4-[({[(Z)-(4-methyl-5-oxo-4,5-dihydro-1,2,4-oxadiazol-3-yl)(phenyl)methylene]amino}oxy)methyl]-1,3-thiazol-2-yl}carbamate (45 mg, 55% yield).

PREPARATION EXAMPLE 6 tert-butyl {6-[({[(Z)-(4-methyl-5-oxo-4,5-dihydro-1,2,4-oxadiazol-3-yl)(phenyl)methylene]amino}oxy)methyl]pyridin-2-yl}carbamate (compound 21) according to process P2

To a solution of 3-[(Z)-{[(6-aminopyridin-2-yl)methoxy]imino}(phenyl)methyl]-4-methyl-1,2,4-oxadiazol-5(4H)- one (100 mg, 0.307 mmol, 1 eq.) in tetrahydrofurane (5 ml) was added triethylamine (0.118 mL, 1.23 mmol, 4 eq.) followed by di-tert-butyl dicarbonate (201 mg, 0.922 mmol, 3 eq.) and stirring was allowed overnight. The reaction was quenched by addition of 1N HCl and extracted with EtOAc (3×20 ml). The organics were combined, dried over $MgSO_4$ and concentrated. The residue was taken in dichloromethane and trifluoroacetic acid (0.118 mL, 1.54 mmol, 5 eq.) was added. The solution was stirred for 2 h at room temperature, quenched by addition of aq. sat. $NaHCO_3$ and extracted with EtOAc (3×20 ml). The organics were combineddried over $MgSO_4$ and concentrated. After concentration, the residue was purified by chromatography on silica gel to give tert-butyl {6-[({[(Z)-(4-methyl-5-oxo-4,5-dihydro-1,2,4-oxadiazol-3-yl)(phenyl)methylene]amino}oxy)methyl]pyridin-2-yl}carbamate (110 mg, 83% yield).

PREPARATION EXAMPLE 7 tert-butyl (2-cyclohexylethyl){6-[({[(Z)-(4-methyl-5-oxo-4,5-dihydro-1,2,4-oxadiazol-3-yl)(phenyl)methylene]amino}oxy)methyl]pyridin-2-yl}carbamate (compound 279) according to process P6

A solution of tert-butyl {6-[({[(Z)-(4-methyl-5-oxo-4,5-dihydro-1,2,4-oxadiazol-3-yl)(phenyl)methylene]amino}oxy)methyl]pyridin-2-yl}carbamate (100 mg, 0.235 mmol, 1 eq.) in N,N-dimethylformamide (2 ml) was treated with sodium hydride (10 mg, 0.259 mmol, 1.1 eq.) and stirred at room temperature for 30 minutes. (2-Bromoethyl)cyclohexane (67 mg, 0.353 mmol, 1.5 eq.) was than added and stirring was allowed overnight. The reaction was quenched by addition of water and extracted with EtOAc (3×20 ml). The organics were combined, washed with aq. sat. NaCl, dried over $MgSO_4$ and concentrated to afford tert-butyl (2-cyclohexylethyl){6-[({[(Z)-(4-methyl-5-oxo-4,5-dihydro-1,2,4-oxadiazol-3-yl)(phenyl)methylene]amino}oxy)methyl]pyridin-2-yl}carbamate (108 mg, 86% yield) which was used in the next step without further purification.

PREPARATION EXAMPLE 8

3-[(Z)-[({6-[(2-cyclohexylethyl)amino]pyridin-2-yl}methoxy)imino](phenyl)methyl]-4-methyl-1,2,4-oxadiazol-5(4H)-one (compound 253) according to process P7

A solution of tert-butyl (2-cyclohexylethyl){6-[({[(Z)-(4-methyl-5-oxo-4,5-dihydro-1,2,4-oxadiazol-3-yl)(phenyl)methylene]amino}oxy)methyl]pyridin-2-yl}carbamate (100 mg, 0.187 mmol, 1 eq.) in dichloromethane (5 ml) was treated with trifluoroacetic acid (0.144 mL, 1.867 mmol, 10 eq.) and refluxed overnight. The reaction was quenched by addition of $NaHCO_3$ sat. aq. and extracted with EtOAc (3×20 ml). The organics were combined, washed with aq. sat. NaCl, dried over $MgSO_4$ and concentrated. After concentration, the residue was purified by chromatography on silica gel to give 3-[(Z)-[({6-[(2-cyclohexylethyl)amino]pyridin-2-yl}methoxy)imino](phenyl)methyl]-4-methyl-1,2,4-oxadiazol-5(4H)-one (52 mg, 63% yield).

PREPARATION EXAMPLE 9

3-[(Z)-({[6-(diethylamino)pyridin-2-yl]methoxy}imino)(phenyl)methyl]-4-methyl-1,2,4-oxadiazol-5(4H)-one (compound 197) and 4-methyl-3-{(Z)-phenyl[({6-[(1-phenylethyl)amino]pyridin-2-yl}methoxy)imino]methyl}-1,2,4-oxadiazol-5(4H)-one (compound 43) according to process P8

To a solution of 3-[(Z)-{[(6-aminopyridin-2-yl)methoxy]imino}(phenyl)methyl]-4-methyl-1,2,4-oxadiazol-5(4H)-one (200 mg, 0.615 mmol, 1 eq.) in dichloromethane (2.5 ml) was added under argon acetophenone (73.9 mg, 0.615 mmol, 1 eq.) followed by titanium(IV) chloride (0.615 mL, 0.615 mmol, 1 eq.) and stirring was allowed for 1 h at room temperature. Sodium triacetoxyborohydride (651.5 mg, 3.07 mmol, 5 eq.) was than added and stirring was allowed overnight at room temperature. The crude mixture was filtered through a chemelut pad and washed with EtOAc. After concentration, the residue was purified by chromatography on silica gel to give 3-[(Z)-({[6-(diethylamino)pyridin-2-yl]methoxy}imino)(phenyl)methyl]-4-methyl-1,2,4-oxadiazol-5(4H)-one (30 mg, 11% yield) and 4-methyl-3-{(Z)-phenyl[({6-[(1-phenylethyl)amino]pyridin-2-yl}methoxy)imino]methyl}-1,2,4-oxadiazol-5(4H)-one (60 mg, 23% yield).

PREPARATION EXAMPLE 10

2-methylpentan-2-yl {6-[({[(Z)-(4-methyl-5-oxo-4,5-dihydro-1,2,4-oxadiazol-3-yl)(phenyl)methylene]amino}oxy)methyl]pyridin-2-yl}carbamate (compound 233) according to process P10

To a solution of 3-[(Z)-{[(2-amino-1,3-thiazol-4-yl)methoxy]imino}(phenyl)methyl]-4-methyl-1,2,4-oxadiazol-5(4H)-one (120 mg, 0.369 mmol, 1 eq.) in acetonitrile (3 ml) was added 4-fluorophenylcarbonochloridate (70.8 mg, 0.406 mmol, 1.1 eq.), followed by pyridine (0.030 mL, 0.369 mmol, 1 eq.) and stirring was allowed for 2 hours at room temperature. 2-Methyl-4-pentan-2-ol (0.050 mL, 0.406 mmol, 1.1 eq.) was then added and the resulting mixture was refluxed for 5 h. After concentration, the residue was purified by chromatography on silica gel to give 2-methylpentan-2-yl {6-[({[(Z)-(4-methyl-5-oxo-4,5-dihydro-1,2,4-oxadiazol-3-yl)(phenyl)methylene]amino}oxy)methyl]pyridin-2-yl}carbamate (105 mg, 59% yield) as a transparent oil.

The invention claimed is:

1. A compound of formula (I)

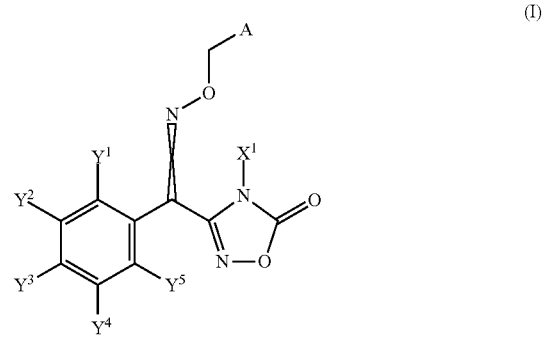

wherein $X^1$ is selected from the group consisting of a hydrogen atom, a formyl group, substituted or non-substituted $C_1$-$C_8$-alkyl, substituted or non-substituted $C_3$-$C_8$-cycloalkyl, a substituted or non-substituted $C_2$-$C_8$-alkenyl, substituted or non-substituted $C_2$-$C_8$-alkynyl, and a substituted or non-substituted $C_1$-$C_8$-alkylcarbonyl;

A is selected from $A^1$ or $A^2$:

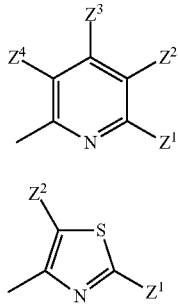

wherein
$Z^1$ is selected from the group consisting of a hydrogen atom, a halogen atom, a nitro group, an amino group, an hydroxyamino group, an hydroxy group, a cyano group, substituted or non-substituted $C_1$-$C_8$-alkoxyamino group, substituted or non-substituted $C_1$-$C_8$-alkylamino, substituted or non-substituted $C_2$-$C_8$-alkenylamino, substituted or non-substituted $C_2$-$C_8$-alkynylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, and a group of formula QC(=U)NR$^a$
wherein:
Q is selected from the group consisting of a hydrogen atom, substituted or non-substituted $C_1$-$C_8$-alkyl, substituted or non-substituted $C_3$-$C_8$-cycloalkyl, substituted or non-substituted $C_2$-$C_8$-alkenyl, substituted or non-substituted $C_3$-$C_8$-cycloalkenyl, substituted or non-substituted $C_2$-$C_8$-alkynyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylamino, substituted or non-substituted $C_1$-$C_8$-alkylsulfenyl, substituted or non-substituted $C_2$-$C_8$-alkenylsulfenyl, substituted or non-substituted $C_2$-$C_8$-alkynylsulfenyl, substituted or non-substituted arylsulfenyl, substituted or non-substituted aryl, substituted or non-substituted heterocyclyl, substituted or non-substituted $C_5$-$C_{12}$-fused bicycloalkyl, substituted or non-substituted $C_5$-$C_{12}$-fused bicycloalkenyl, substituted or non-substituted $C_5$-$C_{12}$-benzofused carbocyclyl, substituted or non-substituted $C_5$-$C_{12}$-benzofused heterocyclyl, substituted or non-substituted cycloalkoxy; substituted or non-substituted cycloalkenyloxy, substituted or non-substituted aryloxy; substituted or non-substituted heterocyclyloxy, substituted or non-substituted $C_5$-$C_{12}$-fused bicycloalkoxy, substituted or non-substituted $C_5$-$C_{12}$-fused bicycloalkenyloxy, substituted or non-substituted $C_5$-$C_{12}$-benzofused carbocyclyloxy, and substituted or non-substituted $C_5$-$C_{12}$-benzofused heterocyclyloxy;
U is an oxygen atom or a sulfur atom;
R$^a$ is selected from the group consisting of a hydrogen atom, a hydroxy group, substituted or non-substituted $C_1$-$C_8$-alkyl, substituted or non-substituted $C_3$-$C_8$-cycloalkyl, substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_3$-$C_{10}$-cycloalkenyl, substituted or non-substituted $C_5$-$C_{12}$-fused bicycloalkyl, substituted or non-substituted $C_5$-$C_{12}$-fused bicycloalkenyl, substituted or non-substituted aryl, substituted or non-substituted heterocyclyl, substituted or non-substituted $C_1$-$C_8$-alkylcarbonyl, substituted or non-substituted aryloxycarbonyl, and substituted or non-substituted $C_1$-$C_8$-alkoxycarbonyl;

$Z^2$, $Z^3$ and $Z^4$ independently are selected from the group consisting of a hydrogen atom, a halogen atom, substituted or non-substituted $C_1$-$C_8$-alkyl, substituted or non-substituted $C_3$-$C_8$-cycloalkyl, $C_2$-$C_8$-alkenyl, substituted or non-substituted $C_2$-$C_8$-alkynyl, and substituted or non-substituted $C_1$-$C_8$-alkoxy;

$Y^1$ to $Y^5$ independently are selected from the group consisting of a hydrogen atom, a halogen atom, a nitro group, a cyano group, substituted or non-substituted carbaldehyde O—($C_1$-$C_8$-alkyl)oxime, a pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted phenoxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, and substituted or non-substituted heterocyclyloxy;

salts, N-oxides, metallic complexes and metalloidic complexes thereof or (E) and (Z) isomers and mixtures thereof.

2. A compound according to claim 1 wherein $X^1$ is selected from the group consisting of a hydrogen atom, substituted or non-substituted $C_1$-$C_8$-alkyl, substituted or non-substituted $C_3$-$C_8$-cycloalkyl or and a substituted or non-substituted $C_2$-$C_8$-alkenyl.

3. A compound according to claim 2 wherein $X^1$ is selected from the group consisting of a hydrogen atom, a methyl group, an ethyl group, a n-propyl group, an isopropyl group Of and a cyclopropyl group.

4. A compound according to claim 1 wherein A is $A^1$.

5. A compound according to claim 1 wherein $Z^1$ is selected from the group consisting of a hydrogen atom, a halogen atom, a nitro group, an amino group, an hydroxyamino group, substituted or non-substituted $C_1$-$C_8$-alkoxyamino group, substituted or non-substituted $C_1$-$C_8$-alkylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, and a group of formula QC(=U)NR$^a$.

6. A compound according to claim 5 wherein $Z^1$ is an amino group, or a group of formula QC(=U)NR$^a$.

7. A compound according to claim 1 wherein U is an oxygen atom.

8. A compound according to claim 1 wherein R$^a$ is selected from the group consisting of a hydrogen atom, a hydroxy group, substituted or non-substituted $C_1$-$C_8$-alkyl, substituted or non-substituted $C_3$-$C_8$-cycloalkyl, and substituted or non-substituted $C_1$-$C_8$-alkoxy.

9. A compound according to claim 1 wherein Q is selected from the group consisting of a substituted or non-substituted $C_1$-$C_8$-alkyl, substituted or non-substituted $C_3$-$C_8$-cycloalkyl, substituted or non-substituted $C_2$-$C_8$-alkynyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylsulfenyl, substituted or non-substituted aryl, substituted or non-substituted heterocyclyl, and substituted or non-substituted $C_3$-$C_8$-cycloalkoxy.

10. A compound according to claim 1 wherein $Z^2$, $Z^3$ and $Z^4$ independently are selected from the group consisting of a hydrogen atom, a halogen atom, and substituted or non-substituted $C_1$-$C_8$-alkyl.

11. A compound according to claim 1 wherein $Y^1$ to $Y^5$ independently are selected from the group consisting of a hydrogen atom, a halogen atom, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, and substituted or non-substituted $C_1$-$C_8$-alkoxy.

12. A compound of formula (V)

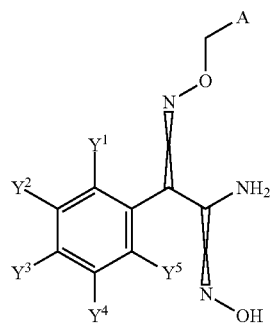

wherein
A is A$^1$ or A$^2$:

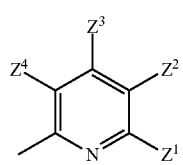

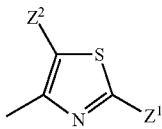

wherein
$Z^1$ is selected from the group consisting of a hydrogen atom, a halogen atom, a nitro group, an amino group, an hydroxyamino group, an hydroxy group, a cyano group, substituted or non-substituted $C_1$-$C_8$-alkoxyamino group, substituted or non-substituted $C_1$-$C_8$-alkylamino, substituted or non-substituted $C_2$-$C_8$-alkenylamino, substituted or non-substituted $C_2$-$C_8$-alkynylamino, substituted or non-substituted $C_3$-$C_{10}$-cycloalkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted heterocyclylamino, and a group of formula QC(=U)NR$^a$
wherein:
Q is selected from the group consisting of a hydrogen atom, substituted or non-substituted $C_1$-$C_8$-alkyl, substituted or non-substituted $C_3$-$C_8$-cycloalkyl, substituted or non-substituted $C_2$-$C_8$-alkenyl, substituted or non-substituted $C_3$-$C_8$-cycloalkenyl, substituted or non-substituted $C_2$-$C_8$-alkynyl, substituted or non-substituted $C_1$-$C_8$-alkoxy, substituted or non-substituted $C_2$-$C_8$-alkenyloxy, substituted or non-substituted $C_2$-$C_8$-alkynyloxy, substituted or non-substituted $C_1$-$C_8$-alkylamino, substituted or non-substituted $C_1$-$C_8$-alkylsulfenyl, substituted or non-substituted $C_2$-$C_8$-alkenylsulfenyl, substituted or non-substituted $C_2$-$C_8$-alkynylsulfenyl, substituted or non-substituted arylsulfenyl, substituted or non-substituted aryl, substituted or non-substituted heterocyclyl, substituted or non-substituted $C_5$-$C_{12}$-fused bicycloalkyl, substituted or non-substituted $C_5$-$C_{12}$-fused bicycloalkenyl, substituted or non-substituted $C_5$-$C_{12}$-benzofused carbocyclyl, substituted or non-substituted $C_5$-$C_{12}$-benzofused heterocyclyl, substituted or non-substituted cycloalkoxy; substituted or non-substituted cycloalkenyloxy, substituted or non-substituted aryloxy; substituted or non-substituted heterocyclyloxy, substituted or non-substituted $C_5$-$C_{12}$-fused bicycloalkoxy, substituted or non-substituted $C_5$-$C_{12}$-fused bicycloalkenyloxy, substituted or non-substituted $C_5$-$C_{12}$-benzofused carbocyclyloxy, and substituted or non-substituted $C_5$-$C_{12}$-benzofused heterocyclyloxy;
U is an oxygen atom or a sulfur atom;
R$^a$ is selected from the group consisting of a hydrogen atom, an hydroxy group, substituted or non-substituted $C_1$-$C_8$-alkyl, substituted or non-substituted $C_3$-$C_8$-cycloalkyl, substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_3$-$C_{10}$-cycloalkenyl, substituted or non-substituted $C_5$-$C_{12}$-fused bicycloalkyl, substituted or non-substituted $C_5$-$C_{12}$-fused bicycloalkenyl, substituted or non-substituted aryl, substituted or non-substituted heterocyclyl, substituted or non-substituted $C_1$-$C_8$-alkylcarbonyl, substituted or non-substituted aryloxycarbonyl, and substituted or non-substituted $C_1$-$C_8$-alkoxycarbonyl;

$Z^2$, $Z^3$ and $Z^4$ independently are selected from the group consisting of a hydrogen atom, a halogen atom, substituted or non-substituted $C_1$-$C_8$-alkyl, substituted or non-substituted $C_3$-$C_8$-cycloalkyl, $C_2$-$C_8$-alkenyl, substituted or non-substituted $C_2$-$C_8$-alkynyl, and substituted or non-substituted $C_1$-$C_8$-alkoxy;

$Y^1$ to $Y^5$ independently are selected from the group consisting of a hydrogen atom, a halogen atom, a nitro group, a cyano group, a substituted or non-substituted carbaldehyde O—($C_1$-$C_8$-alkyl)oxime, a pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted phenoxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, and substituted or non-substituted heterocyclyloxy.

13. A compound of formula (VII)

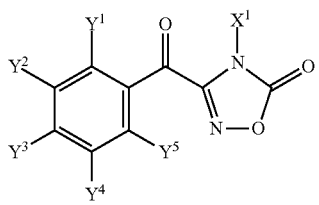

(VII)

wherein $Y^1$ to $Y^5$ independently are selected from the group consisting of a hydrogen atom, a halogen atom, a nitro group, a cyano group, substituted or non-substituted carbaldehyde O—($C_1$-$C_8$-alkyl)oxime, a pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted phenoxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, and substituted or non-substituted heterocyclyloxy;

and $X^1$ is substituted or non-substituted $C_1$-$C_8$-alkyl.

14. A fungicide composition comprising, as an active ingredient, an effective amount of a compound of formula (I) according to claim 1 and an agriculturally acceptable support, carrier or filler.

15. A fungicide composition according to claim 14 comprising at least one further active ingredient selected from the group of the insecticides, attractants, sterilants, bactericides, acaricides, nematicides, fungicides, growth regulators, herbicides, fertilizers, safeners, biologicals and semiochemicals.

16. A method for controlling phytopathogenic fungi of crops, wherein an agronomically effective and substantially non-phytotoxic quantity of a compound according to claim 1 is applied to the soil where plants grow or are capable of growing, to the leaves and/or the fruit of plants or to the seeds of plants.

17. A method for the control of phytopathogenic harmful fungi comprising the step of applying a compound of the formula (I) according to claim 1 to a location having said phytopathogenic harmful fungi.

18. A process for producing compositions for controlling phytopathogenic harmful fungi, comprising the step of mixing a compound of the formula (I) according to claim 1 with extenders and/or surfactants.

19. A method for the treatment transgenic plants comprising the step of applying a compound of the formula (I) according to claim 1 to a transgenic plant.

20. Use of compounds A method for treatment of seed or seed of transgenic plants comprising the step of applying a compound of the formula (I) according to claim 1 to said seed or seed of a transgenic plant.

21. A method for controlling phytopathogenic fungi of crops, characterized in that an agronomically effective and substantially non-phytotoxic quantity of a composition according to claim 14 is applied to the soil where plants grow or are capable of growing, to the leaves and/or the fruit of plants or to the seeds of plants.

* * * * *